United States Patent
Ishikawa et al.

(10) Patent No.: US 8,178,543 B2
(45) Date of Patent: *May 15, 2012

(54) BI- AND TRICYCLIC FUSED PYRIMIDINES AS TYROSINE KINASE INHIBITORS

(75) Inventors: Tomoyasu Ishikawa, Osaka (JP); Hiroshi Banno, Osaka (JP); Masaki Seto, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 750 days.

This patent is subject to a terminal disclaimer.

(21) Appl. No.: 12/172,631

(22) Filed: Jul. 14, 2008

(65) Prior Publication Data
US 2009/0029973 A1    Jan. 29, 2009

Related U.S. Application Data

(63) Continuation of application No. 10/592,812, filed as application No. PCT/JP2005/010451 on Jun. 1, 2005, now Pat. No. 7,507,740.

(30) Foreign Application Priority Data

Jun. 2, 2004   (JP) ................................. 2004-165050
Mar. 2, 2005   (JP) ................................. 2005-058231

(51) Int. Cl.
C07D 487/04    (2006.01)
A61K 31/519    (2006.01)
A61P 35/00     (2006.01)

(52) U.S. Cl. ................... 514/265.1; 514/262.1; 544/280; 544/262

(58) Field of Classification Search .................. 544/280; 514/265.1
See application file for complete search history.

(56) References Cited

U.S. PATENT DOCUMENTS

| | | | |
|---|---|---|---|
| 6,140,332 A | 10/2000 | Traxler et al. |
| 6,169,091 B1 | 1/2001 | Cockerill et al. |
| 6,180,636 B1 | 1/2001 | Traxler et al. |
| 6,187,777 B1 | 2/2001 | Norman et al. |
| 6,207,669 B1 | 3/2001 | Cockerill et al. |
| 6,265,410 B1 | 7/2001 | Bridges et al. |
| 6,284,764 B1 | 9/2001 | Kath et al. |
| 6,395,733 B1 | 5/2002 | Arnold et al. |
| 6,413,971 B1 | 7/2002 | Arnold et al. |
| 6,465,449 B1 | 10/2002 | Kath et al. |
| 6,541,481 B2 | 4/2003 | Kath et al. |
| 6,583,154 B1 | 6/2003 | Norman et al. |
| 6,734,180 B1 | 5/2004 | Nunokawa et al. |
| 6,867,201 B2 | 3/2005 | Kath et al. |
| 7,572,799 B2 | 8/2009 | Bell et al. |
| 8,097,621 B2 | 1/2012 | Bell et al. |
| 2001/0034351 A1 | 10/2001 | Kath et al. |
| 2002/0045630 A1 | 4/2002 | Arnold et al. |
| 2003/0055049 A1 | 3/2003 | Kath et al. |
| 2003/0186995 A1 | 10/2003 | Kath et al. |
| 2004/0209892 A1* | 10/2004 | Di Pietro et al. ......... 514/252.12 |
| 2004/0242604 A1 | 12/2004 | Bhattacharya et al. |
| 2005/0080097 A1 | 4/2005 | Moravcova et al. |
| 2005/0245544 A1 | 11/2005 | Bell et al. |
| 2009/0233937 A1 | 9/2009 | Ishikawa |
| 2009/0247539 A1 | 10/2009 | Bell et al. |
| 2010/0008912 A1 | 1/2010 | Ohta |
| 2010/0183604 A1 | 7/2010 | Ohta |
| 2010/0216788 A1 | 8/2010 | Ishikawa |
| 2012/0003152 A1 | 1/2012 | Arap et al. |

FOREIGN PATENT DOCUMENTS

| | | |
|---|---|---|
| BY | 001428 | 2/2001 |
| EP | 0 835 871 | 4/1998 |
| ES | 2 241 146 | 10/2005 |
| ES | 2 257 762 | 8/2006 |
| JP | 48-029796 | 4/1973 |
| PH | 1-2006-5020985 | 4/2011 |
| RU | 2003 134 646 | 4/2005 |

(Continued)

OTHER PUBLICATIONS

Sizova et. al. (Khimiko-Farmatsevticheskii Zhurnal, 1982, 16(11), pp. 1338-1343).* Supplementary European Search Report issued in European Application No. 05748463.6, mailed Apr. 26, 2010, 6 pages.
Database CA [Online] Chemical Abstracts Service, Columbus, Ohio, US; Database accession No. 1983:107247.
Database CA [Online] Chemical Abstracts Service, Columbus, Ohio, US; Database accession No. 1997:132775.
Database CA [Online] Chemical Abstracts Service, Columbus, Ohio, US; Database accession No. 2003:277531.

(Continued)

*Primary Examiner* — Susanna Moore
(74) *Attorney, Agent, or Firm* — Hamre, Schumann, Mueller & Larson, P.C.

(57) ABSTRACT

The present invention relates to a compound represented by the formula:

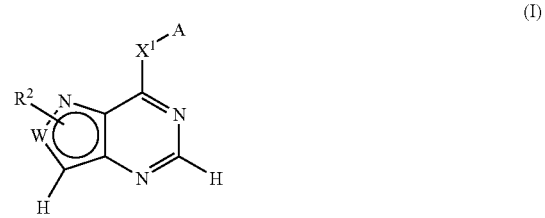

(I)

wherein W is $C(R^1)$ or N, each A is an optionally substituted aryl group or a heteroaryl group, $X^1$ is $-NR^3-Y^1-$, $-O-$, $-S-$, $-SO-$, $-SO_2-$ or $-CHR^3-$ wherein $R^3$ is a hydrogen atom or an optionally substituted aliphatic hydrocarbon group, or $R^3$ is optionally bonded to A to form an optionally substituted ring structure, $R^1$ is a hydrogen atom or an optionally substituted group bonded via a carbon atom, a nitrogen atom or an oxygen atom, $R^2$ is a hydrogen atom or optionally substituted group bonded via a carbon atom or a sulfur atom, or $R^1$ and $R^2$, or $R^2$ and $R^3$ are optionally bonded to form an optionally substituted ring structure, or a salt thereof, and a tyrosine kinase inhibitor or an agent for the prophylaxis or treatment of cancer, which contains this compound or a prodrug thereof.

2 Claims, No Drawings

FOREIGN PATENT DOCUMENTS

| | | |
|---|---|---|
| RU | 2004106783 | 7/2005 |
| WO | 95/19970 | 7/1995 |
| WO | 97/02266 | 1/1997 |
| WO | 97/38983 | 10/1997 |
| WO | 99/07703 | 2/1999 |
| WO | 00/43394 | 7/2000 |
| WO | 01/18170 | 3/2001 |
| WO | 02/088095 | 11/2002 |
| WO | 03/013541 | 2/2003 |
| WO | 03/051884 | 6/2003 |
| WO | 2004/096801 | 11/2004 |
| WO | 2006/010264 | 2/2006 |
| WO | 2007/054831 | 5/2007 |

OTHER PUBLICATIONS

Database CA [Online] Chemical Abstracts Service, Columbus, Ohio, US; Database accession No. 1973:418760.

Database CA [Online] Chemical Abstracts Service, Columbus, Ohio, US; Database accession No. 1972:95567.

Database CA [Online] Chemical Abstracts Service, Columbus, Ohio, US; Database accession No. 1992:490657.

Decision on Grant issued in corresponding Belarusian Patent Application No. a20061375 and mailed Oct. 26, 2009, with its English translation—22 pages.

Showalter, et al., "Tyrosine Kinase Inhibitors. 16. 6,5,6-Tricyclic Benzothieno[3,2-*d*] pyrimidines and Pyrimido[5,4-*b*]- and -[4,5-*b*]indoles as Potent Inhibitors of the Epidermal Growth Factor Receptor Tyrosine Kinase", J. Med. Chem., 1999, vol. 42, No. 26, 1999, pp. 5464-5474.

Federal Service for Intellectual Property, Patents and Trademarks (Rospatent), Decision on Grant issued in corresponding Russian Application No. 2006147267/04(051633) and mailed Nov. 29, 2009 with a full English Translation—24 pages.

Robins et al., "Potential Purine Antagonists. V. Synthesis of Some 3-Methyl-5, 7-substituted Pyrazolo [4,3-d] pyrimidines[1,2]" *The Journal of Organic Chemistry*: 1956, vol. 21 No. 8, pp. 833-836.

Moravcova et al., "Pyrazolo [4,3-d]pyrimidines as New Generation of Cyclin-Dependent Kinase Inhibitors" *BioorganicMedical Chemistry Letters*: 2003, pp. 2989-2992.

Capek et al., "A Facile Synthesis of 9-Deaza Analogue of Olomoucine", *Collect. Czech. Chem. Commun.*: 2003, vol. 68, pp. 779-791.

Sizova et al., " Pyrrolo [3,2-d] Pyrimidines. IV. Synthesis and Antibacterial and Antitumor Activity of 2,4,7-substituted pyrrolo [3,2-d] Pyrimidines" *Pharmaceutical Chemistry Journal*: 1982, vol. 16, No. 11, pp. 1338-1343.

Examiner Elia Bonnevalle, Supplementary European Search Report issued in European Application No. 05748463.6, mailed Apr. 26, 2010, 6 pages.

Database CA [Online] Chemical Abstracts Service, Columbus, Ohio, US; Database accession No. 1983:107247 (1982).

Database CA [Online] Chemical Abstracts Service, Columbus, Ohio, US; Database accession No. 1997:132775 (1996).

Database CA [Online] Chemical Abstracts Service, Columbus, Ohio, US; Database accession No. 2003:277531 (2003).

Database CA [Online] Chemical Abstracts Service, Columbus, Ohio, US; Database accession No. 1973:418760 (1973).

Database CA [Online] Chemical Abstracts Service, Columbus, Ohio, US; Database accession No. 1972:95567 (1971).

Database CA [Online] Chemical Abstracts Service, Columbus, Ohio, US; Database accession No. 1992:490657 (1992).

\* cited by examiner

BI- AND TRICYCLIC FUSED PYRIMIDINES AS TYROSINE KINASE INHIBITORS

CROSS-REFERENCE TO RELATED APPLICATIONS

This application is a Continuation of application Ser. No. 10/592,812, filed Sep. 14, 2006, which is a U.S. National Stage of PCT/JP2005/010451, filed Jun. 1, 2005, which applications are incorporated herein by reference.

TECHNICAL FIELD

The present invention relates to a fused pyrimidine compound having a growth factor receptor tyrosine kinase inhibitory activity, which is useful for the prophylaxis or treatment of cancer, a production method thereof and use thereof.

BACKGROUND ART

The gene of cell growth factor and growth factor receptor is called a protooncogene and plays a key role in the pathology of human tumor. The epithelial cell growth factor receptor family (erbB) includes EGFR, HER2, HER3 and HER4, which are type I receptor type tyrosine kinases. These erbB family express in various cell groups, and are deeply involved in the control of the growth and differentiation of cells and the control of suppression of cell death (apoptosis suppression). For example, high expression of EGFR and HER2, and homeostatic activation of receptors are empirically known to transform cells.

It is also known that high expression and simultaneous expression of each of these receptors are poor prognostic factors in various cancer patients.

These receptors are bound with many peptide ligands such as EGF, TGFα and the like, and binding of the ligand promotes homo- or heterodimerization of the receptors. This induces increase of kinase activity from self-phosphorylation or transphosphorylation of the receptors, and causes activation of downstream signaling pathway (MAPK, Akt) via a protein bound with a particular phosphorylated tyrosine residue. This is the mechanism of the receptor activity of the above-mentioned cell growth, differentiation, cell death suppression and the like, which is considered to be responsible for the high expression of receptor in cancer and malignant degeneration of cancer due to topical increase in the ligand concentration.

Many cancers are associated with the high expression of EGFR or HER2. For example, breast cancer (20-30%), ovarian cancer (20-40%), non-small cell lung cancer (30-60%), colorectal cancer (40-80%), prostate cancer (10-60%), bladder cancer (30-60%), kidney cancer (20-40%) and the like can be mentioned. Moreover, receptor expression and prognosis are correlated, and receptor expression is a poor prognostic factor in breast cancer, non-small cell lung cancer and the like.

In recent years, clinical use of a humanized anti-HER2 antibody (Trastuzumab) against HER2 highly expressing breast cancer, clinical trial of anti-EGFR antibody and clinical trials of several low molecular weight receptor enzyme inhibitors have demonstrated a potential of these drugs against HER2 or EGFR for therapeutic drugs for cancer. While these drugs show a tumor growth inhibitory action in clinical and non-clinical trials, they are known to induce inhibition of receptor enzyme activity and suppression of downstream signaling pathway. Therefore, a compound inhibiting EGFR or HER2 kinase, or inhibiting activation of EGFR or HER2 kinase is effective as a therapeutic drug for cancer.

As a compound that inhibits receptor type tyrosine kinases represented by HER2/EGFR kinase, fused heterocyclic compounds (e.g., WO97/13771, WO98/02437, WO00/44728), quinazoline derivatives (e.g., WO02/02552, WO01/98277, WO03/049740, WO03/050108), thienopyrimidine derivatives (e.g., WO03/053446), aromatic azole derivatives (e.g., WO98/03648, WO01/77107, WO03/031442) and the like are known; however, there is no HER2 kinase inhibitory substance to the present that has been marketed as a therapeutic drug for cancer.

As to pyrrolo[3,2-d]pyrimidine derivatives, the following compounds are known as compounds having a cell growth inhibitory activity (*Khim.-Farm. Zh.*, 1982, 16, 1338-1343; Collect. Czech. Chem. Commun., 2003, 68, 779-791).

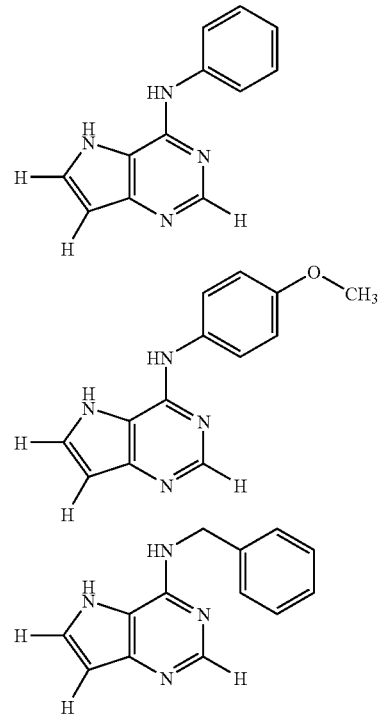

As a compound having a receptor type tyrosine kinase activity, the following pyrrolo[3,2-d]pyrimidine derivative is known (WO96/40142, WO98/23613).

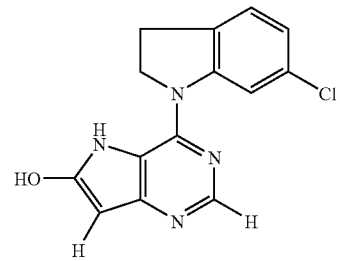

Furthermore, as to pyrazolo[4,3-d]pyrimidine derivatives, 3,5,7-trisubstituted pyrazolo[4,3-d]pyrimidine derivatives are known as compounds having a CDK inhibitory action, a cell growth inhibitory action and/or an apoptosis inducing action (EP-A-1348707), and 3-isopropylpyrazolo[4,3-d]pyrimidine derivatives are known as compounds having a CDK1/cyclin B inhibitory activity (*Bioorganic & Medicinal Chemistry Letters*, 2003, 13, 2989-2992). Furthermore, synthesis of 3-methylpyrazolo[4,3-d]pyrimidine derivatives has been reported (*The Journal of Organic Chemistry*, 1956, 21, 833-836).

DISCLOSURE OF THE INVENTION

The present invention aims at providing a compound having a superior tyrosine kinase inhibitory action, which is low toxic and highly satisfactory as a pharmaceutical product.

The present inventors have conducted intensive studies and found that a compound represented by the following formula (I) and a salt thereof (sometimes to be referred to as compound (I) in the present specification) have a superior tyrosine kinase inhibitory action. Further studies have resulted in the completion of the present invention.

Accordingly, the present invention provides
[1] a compound represented by the formula:

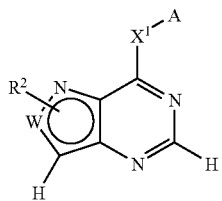

(I)

wherein W is $C(R^1)$ or N,

A is an optionally substituted aryl group or an optionally substituted heteroaryl group, $X^1$ is $-NR^3-Y^1-$, $-O-$, $-S-$, $-SO-$, $-SO_2-$ or $-CHR^3-$ wherein $R^3$ is a hydrogen atom or an optionally substituted aliphatic hydrocarbon group, or $R^3$ is optionally bonded to a carbon atom or a hetero atom on the aryl group or the heteroaryl group represented by A to form an optionally substituted ring structure, and $Y^1$ is a single bond or an optionally substituted $C_{1-4}$ alkylene or an optionally substituted $-O-(C_{1-4}$ alkylene)-, $R^1$ is a hydrogen atom or an optionally substituted group bonded via a carbon atom, a nitrogen atom or an oxygen atom, and $R^2$ is a hydrogen atom or an optionally substituted group bonded via a carbon atom or a sulfur atom, or $R^1$ and $R^2$, or $R^2$ and $R^3$ are optionally bonded to form an optionally substituted ring structure, provided that the compounds represented by the formulas

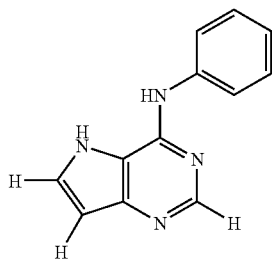

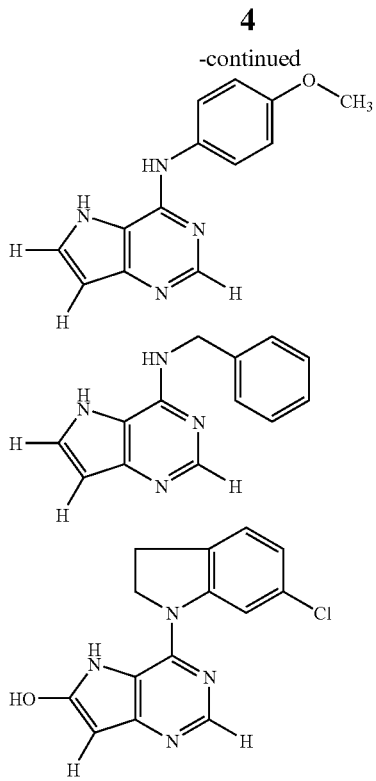

are excluded, or a salt thereof,

[2] a prodrug of the compound of the above-mentioned [1],

[3] the compound of the above-mentioned [1], wherein W is $C(R^1)$,

[4] the compound of the above-mentioned [3], wherein A is an aryl group substituted by a group of the formula $-Y^2-B$ and optionally further substituted, wherein $Y^2$ is a single bond, $-O-$, $-O-(C_{1-3}$ alkylene)-, $-NH-$ or $-S-$, and B is an aryl group, a heterocyclic group, a $C_{3-8}$ cycloalkyl group, a carbamoyl group, a ureido group, a $C_{6-18}$ aryl-carbonyl group or a $C_{6-18}$ aryl-$C_{1-4}$ alkyl-carbonyl group, each of which is optionally substituted,

[5] the compound of the above-mentioned [3], wherein $R^1$ is a group of the formula $-X^2-R^4$ wherein $X^2$ is a single bond, $-NH-$ or $-O-$, and $R^4$ is a hydrogen atom, a cyano group, or a $C_{1-8}$ alkyl group, a $C_{2-8}$ alkenyl group, a $C_{2-8}$ alkynyl group, a carbamoyl group, a $C_{1-8}$ alkyl-carbonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a heterocyclic group, a heterocycle-$C_{1-4}$ alkyl group, a heterocycle-carbonyl group or a heterocycle-$C_{1-4}$ alkyl-carbonyl group, each of which is optionally substituted,

[6] the compound of the above-mentioned [3], wherein $R^2$ is a hydrogen atom or a $C_{1-8}$ alkyl group, a $C_{2-8}$ alkenyl group, a $C_{2-8}$ alkynyl group, a carbamoyl group, a $C_{1-8}$ alkyl-carbonyl group, a $C_{1-8}$ alkylsulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocycle-$C_{1-4}$ alkyl group, a heterocycle-carbonyl group or a heterocycle-$C_{1-4}$ alkyl-carbonyl group, each of which is optionally substituted,

[7] the compound of the above-mentioned [3], wherein $X^1$ is $-NR^3-$ wherein $R^3$ is a hydrogen atom or an optionally substituted aliphatic hydrocarbon group,

[8] the compound of the above-mentioned [3], wherein A is an aryl group substituted by a group of the formula —Y$^2$—B and optionally further substituted, wherein Y$^2$ is a single bond, —O—, —O—(C$_{1-3}$ alkylene)-, —NH— or —S—, and B is an aryl group, a heterocyclic group, a C$_{3-8}$ cycloalkyl group, a carbamoyl group, a ureido group, a C$_{6-18}$ aryl-carbonyl group or a C$_{6-18}$ aryl-C$_{1-4}$ alkyl-carbonyl group, each of which is optionally substituted;

R$^1$ is a group of the formula —X$^2$—R$^4$ wherein X$^2$ is a single bond, —NH— or —O—, and R$^4$ is a hydrogen atom, a cyano group, or a C$_{1-8}$ alkyl group, a C$_{2-8}$ alkenyl group, a C$_{2-8}$ alkynyl group, a carbamoyl group, a C$_{1-8}$ alkyl-carbonyl group, a C$_{3-8}$ cycloalkyl group, a C$_{6-18}$ aryl group, a C$_{6-18}$ aryl-C$_{1-4}$ alkyl group, a C$_{6-18}$ aryl-carbonyl group, a C$_{6-18}$ aryl-C$_{1-4}$ alkyl-carbonyl group, a heterocyclic group, a heterocycle-C$_{1-4}$ alkyl group, a heterocycle-carbonyl group or a heterocycle-C$_{1-4}$ alkyl-carbonyl group, each of which is optionally substituted;

R$^2$ is a hydrogen atom or a C$_{1-8}$ alkyl group, a C$_{2-8}$ alkenyl group, a C$_{2-8}$ alkynyl group, a carbamoyl group, a C$_{1-8}$ alkyl-carbonyl group, a C$_{1-8}$ alkylsulfonyl group, a C$_{3-8}$ cycloalkyl group, a C$_{6-18}$ aryl group, a C$_{6-18}$ aryl-C$_{1-4}$ alkyl group, a C$_{6-18}$ aryl-carbonyl group, a C$_{6-18}$ aryl-C$_{1-4}$ alkyl-carbonyl group, a C$_{6-18}$ aryl-sulfonyl group, a heterocyclic group, a heterocycle-C$_{1-4}$ alkyl group, a heterocycle-carbonyl group or a heterocycle-C$_{1-4}$ alkyl-carbonyl group, each of which is optionally substituted; and X$^1$ is —NR$^3$— wherein R$^3$ is a hydrogen atom or an optionally substituted aliphatic hydrocarbon group,

[9] the compound of the above-mentioned [1], wherein W is N,

[10] the compound of the above-mentioned [9], wherein A is an aryl group substituted by a group of the formula —Y$^2$—B and optionally further substituted, wherein Y$^2$ is a single bond, —O—, —O—(C$_{1-3}$ alkylene)-, —NH— or —S—, and B is an aryl group, a heterocyclic group, a C$_{3-8}$ cycloalkyl group, a carbamoyl group, a ureido group, a C$_{6-18}$ aryl-carbonyl group or a C$_{6-18}$ aryl-C$_{1-4}$ alkyl-carbonyl group, each of which is optionally substituted,

[11] the compound of the above-mentioned [9], wherein R$^2$ is a hydrogen atom or a C$_{1-8}$ alkyl group, a C$_{2-8}$ alkenyl group, a C$_{2-8}$ alkynyl group, a carbamoyl group, a C$_{1-8}$ alkyl-carbonyl group, a C$_{1-8}$ alkylsulfonyl group, a C$_{3-8}$ cycloalkyl group, a C$_{6-18}$ aryl group, a C$_{6-18}$ aryl-C$_{1-4}$ alkyl group, a C$_{6-18}$ aryl-carbonyl group, a C$_{6-18}$ aryl-C$_{1-4}$ alkyl-carbonyl group, a C$_{6-18}$ aryl-sulfonyl group, a heterocyclic group, a heterocycle-C$_{1-4}$ alkyl group, a heterocycle-carbonyl group or a heterocycle-C$_{1-4}$ alkyl-carbonyl group, each of which is optionally substituted,

[12] the compound of the above-mentioned [9], wherein X$^1$ is —NR$^3$— wherein R$^3$ is a hydrogen atom or an optionally substituted aliphatic hydrocarbon group,

[13] the compound of the above-mentioned [9], wherein X$^1$ is —NR$^3$— wherein R$^3$ is a hydrogen atom or an optionally substituted aliphatic hydrocarbon group;

A is an aryl group substituted by a group of the formula —Y$^2$—B and optionally further substituted, wherein Y$^2$ is a single bond, —O—, —O—(C$_{1-3}$ alkylene)-, —NH— or —S—, and B is an aryl group, a heterocyclic group, a C$_{3-8}$ cycloalkyl group, a carbamoyl group, a ureido group, a C$_{6-18}$ aryl-carbonyl group or a C$_{6-18}$ aryl-C$_{1-4}$ alkyl-carbonyl group, each of which is optionally substituted;

R$^2$ is a hydrogen atom or a C$_{1-8}$ alkyl group, a C$_{2-8}$ alkenyl group, a C$_{2-8}$ alkynyl group, a carbamoyl group, a C$_{1-8}$ alkyl-carbonyl group, a C$_{1-8}$ alkylsulfonyl group, a C$_{3-8}$ cycloalkyl group, a C$_{6-18}$ aryl group, a C$_{6-18}$ aryl-C$_{1-4}$ alkyl group, a C$_{6-18}$ aryl-carbonyl group, a C$_{6-18}$ aryl-C$_{1-4}$ alkyl-carbonyl group, a C$_{6-18}$ aryl-sulfonyl group, a heterocyclic group, a heterocycle-C$_{1-4}$ alkyl group, a heterocycle-carbonyl group or a heterocycle-C$_{1-4}$ alkyl-carbonyl group, each of which is optionally substituted,

[14] the compound of the above-mentioned [9], wherein X$^1$ is —NR$^3$—;

A is an aryl group substituted by a group of the formula —Y$^2$—B and optionally further substituted, wherein Y$^2$ is a single bond, —O—, —O—(C$_{1-3}$ alkylene)-, —NH— or —S—, and B is an aryl group, a heterocyclic group, a C$_{3-8}$ cycloalkyl group, a carbamoyl group, a ureido group, a C$_{6-18}$ aryl-carbonyl group or a C$_{6-18}$ aryl-C$_{1-4}$ alkyl-carbonyl group, each of which is optionally substituted; and R$^2$ and R$^3$ are bonded to form an optionally substituted ring structure,

[15] a compound represented by the formula:

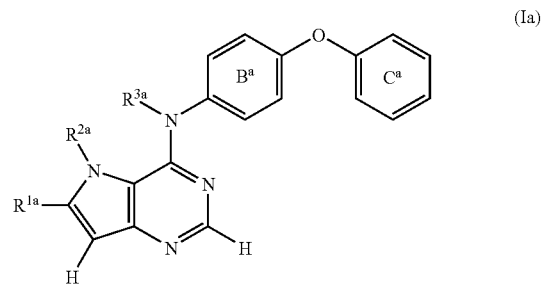

(Ia)

wherein R$^{1a}$ is a hydrogen atom or an optionally substituted group bonded via a carbon atom, a nitrogen atom or an oxygen atom, R$^{2a}$ is an optionally substituted group bonded via a carbon atom or a sulfur atom, or R$^{1a}$ and R$^{2a}$, or R$^{2a}$ and R$^{3a}$ are optionally bonded to form an optionally substituted ring structure, R$^{3a}$ is a hydrogen atom or an optionally substituted aliphatic hydrocarbon group, or R$^{3a}$ is optionally bonded to a carbon atom of the adjacent phenyl group to form an optionally substituted ring structure, B$^a$ is an optionally substituted benzene ring, and C$^a$ is an optionally substituted —C$_{6-18}$ aryl group, or a salt thereof,

[16] a compound represented by the formula:

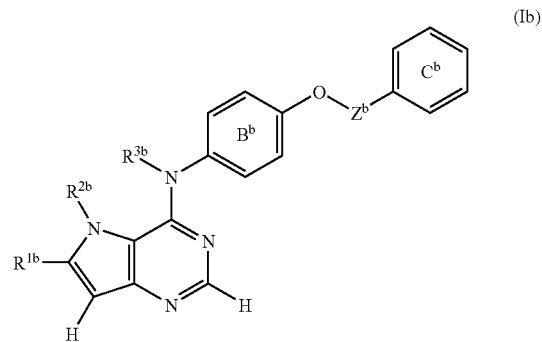

(Ib)

wherein R$^{1b}$ is a hydrogen atom or an optionally substituted group bonded via a carbon atom, a nitrogen atom or an oxygen atom, R$^{2b}$ is an optionally substituted group bonded via a carbon atom or a sulfur atom, or $R^{1b}$ and $R^{2b}$, or $R^{2b}$ and $R^{3b}$ are optionally bonded to form an optionally substituted ring structure, $R^{3b}$ is a hydrogen atom or an optionally substituted aliphatic hydrocarbon group, or $R^{3b}$ is optionally bonded to a carbon atom of the adjacent phenyl group to form an optionally substituted ring structure, $B^b$ is an optionally substituted benzene ring, $C^b$ is an optionally substituted $C_{6-18}$ aryl group, and $Z^b$ is an optionally substituted $C_{1-3}$ alkylene group, or a salt thereof,

[17] a compound represented by the formula:

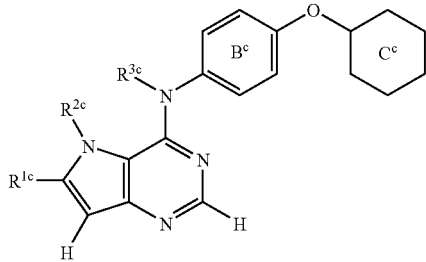

(Ic)

wherein $R^{1c}$ is a hydrogen atom or an optionally substituted group bonded via a carbon atom, a nitrogen atom or an oxygen atom, $R^{2c}$ is an optionally substituted group bonded via a carbon atom or a sulfur atom, or $R^{1c}$ and $R^{2c}$, or $R^{2c}$ and $R^{3c}$ are optionally bonded to form an optionally substituted ring structure, $R^{3c}$ is a hydrogen atom or an optionally substituted aliphatic hydrocarbon group, or $R^{3c}$ is optionally bonded to a carbon atom of the adjacent phenyl group to form an optionally substituted ring structure, $B^c$ is an optionally substituted benzene ring, and $C^c$ is an optionally substituted heterocyclic group, or a salt thereof,

[18] a compound represented by the formula:

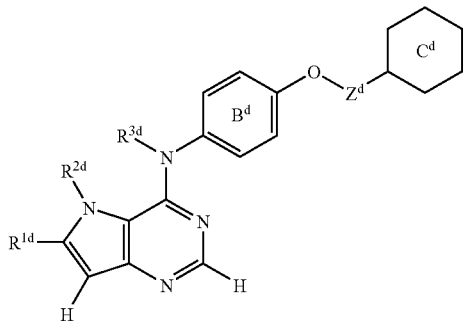

(Id)

wherein $R^{1d}$ is a hydrogen atom or an optionally substituted group bonded via a carbon atom, a nitrogen atom or an oxygen atom, $R^{2d}$ is an optionally substituted group bonded via a carbon atom or a sulfur atom, or $R^{1d}$ and $R^{2d}$, or $R^{2d}$ and $R^{3d}$ are optionally bonded to form an optionally substituted ring structure, $R^{3d}$ is a hydrogen atom or an optionally substituted aliphatic hydrocarbon group, or $R^{3d}$ is optionally bonded to a carbon atom of the adjacent phenyl group to form an optionally substituted ring structure, $B^d$ is an optionally substituted benzene ring, $C^d$ is an optionally substituted heterocyclic group, and $Z^d$ is an optionally substituted $C_{1-3}$ alkylene group, or a salt thereof,

[19] a compound represented by the formula:

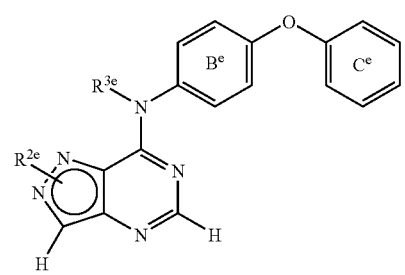

(Ie)

wherein $R^{2e}$ is an optionally substituted group bonded via a carbon atom or a sulfur atom, or $R^{2e}$ and $R^{3e}$ are optionally bonded to form an optionally substituted ring structure, $R^{3e}$ is a hydrogen atom or an optionally substituted aliphatic hydrocarbon group, or $R^{3e}$ is optionally bonded to a carbon atom of the adjacent phenyl group to form an optionally substituted ring structure, $B^e$ is an optionally substituted benzene ring, and $C^e$ is an optionally substituted $C_{6-18}$ aryl group, or a salt thereof,

[20] a compound represented by the formula:

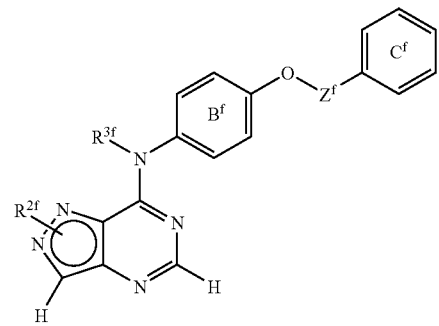

(If)

wherein $R^{2f}$ is an optionally substituted group bonded via a carbon atom or a sulfur atom, or $R^{2f}$ and $R^{3f}$ are optionally bonded to form an optionally substituted ring structure, $R^{3f}$ is a hydrogen atom or an optionally substituted aliphatic hydrocarbon group, or $R^{3f}$ is optionally bonded to a carbon atom of the adjacent phenyl group to form an optionally substituted ring structure, $B^f$ is an optionally substituted benzene ring, $C^f$ is an optionally substituted $C_{6-18}$ aryl group, and $Z^f$ is an optionally substituted $C_{1-3}$ alkylene group, or a salt thereof,

[21] a compound represented by the formula:

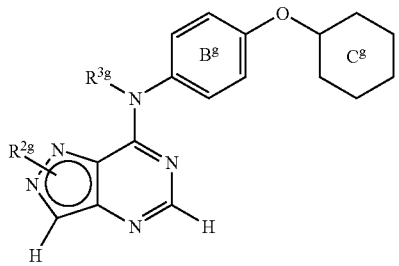
(Ig)

wherein $R^{2g}$ is an optionally substituted group bonded via a carbon atom or a sulfur atom, or $R^{2g}$ and $R^{3g}$ are optionally bonded to form an optionally substituted ring structure, $R^{3g}$ is a hydrogen atom or an optionally substituted aliphatic hydrocarbon group, or $R^{3g}$ is optionally bonded to a carbon atom of the adjacent phenyl group to form an optionally substituted ring structure, $B^g$ is an optionally substituted benzene ring, and $C^g$ is an optionally substituted heterocyclic group, or a salt thereof,

[22] (i) 2-{2-[4-({3-chloro-4-[(3-fluorobenzyl)oxy]phenyl}amino)-5H-pyrrolo[3,2-d]pyrimidin-5-yl]ethoxy}ethanol, (ii) 2-{2-[4-({3-chloro-4-[3-(trifluoromethyl)phenoxy]phenyl}amino)-5H-pyrrolo[3,2-d]pyrimidin-5-yl]ethoxy}ethanol, (iii) N-{2-[4-({3-chloro-4-[3-(trifluoromethyl)phenoxy]phenyl}amino)-5H-pyrrolo[3,2-d]pyrimidin-5-yl]ethyl}-3-hydroxy-3-methylbutanamide, (iv) N-{2-[4-({3-chloro-4-[3-(trifluoromethyl)phenoxy]phenyl}amino)-5H-pyrrolo[3,2-d]pyrimidin-5-yl]ethyl}-2-(methylsulfonyl)acetamide, (v) N-{2-[4-({3-chloro-4-[3-(trifluoromethyl)phenoxy]phenyl}amino)-5H-pyrrolo[3,2-d]pyrimidin-5-yl]ethyl}-2-methyl-2-(methylsulfonyl)propanamide, (vi) 5-{2-[2-(tert-butylsulfonyl)ethoxy]ethyl}-N-{3-chloro-4-[3-(trifluoromethyl)phenoxy]phenyl}-5H-pyrrolo[3,2-d]pyrimidin-4-amine, (vii) 2-(methylsulfonyl)-N-{2-[4-({3-methyl-4-[3-(trifluoromethoxy)phenoxy]phenyl}amino)-5H-pyrrolo[3,2-d]pyrimidin-5-yl]ethyl}acetamide, (viii) N-[2-(4-{[3-chloro-4-(3-chlorophenoxy)phenyl]amino}-5H-pyrrolo[3,2-d]pyrimidin-5-yl)ethyl]-2-(methylsulfonyl)acetamide, or (ix) N-{2-[4-({3-chloro-4-[3-(trifluoromethoxy)phenoxy]phenyl}amino)-5H-pyrrolo[3,2-d]pyrimidin-5-yl]ethyl}-2-(methylsulfonyl)acetamide, or a salt of any of them,

[23] a method of producing a compound represented by the formula:

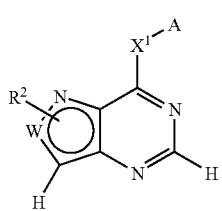
(I)

wherein each symbol is as defined in the above-mentioned [1], or a salt thereof, which comprises reacting a compound represented by the formula:

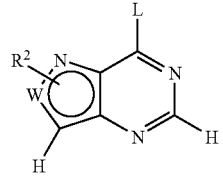
(II)

wherein L is a leaving group, and other symbols are as defined in the above-mentioned [1], or a salt thereof with a compound represented by the formula:

G-X$^1$-A (III)

wherein G is a hydrogen atom or a metal atom, and other symbols are as defined in the above-mentioned [1], or a salt thereof,

[24] a pharmaceutical agent comprising a compound represented by the formula:

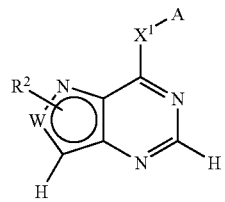
(I)

wherein W is C($R^1$) or N,

A is an optionally substituted aryl group or an optionally substituted heteroaryl group, $X^1$ is —NR$^3$—Y$^1$—, —O—, —S—, —SO—, —SO$_2$— or —CHR$^3$— wherein $R^3$ is a hydrogen atom or an optionally substituted aliphatic hydrocarbon group, or $R^3$ is optionally bonded to a carbon atom or a hetero atom on the aryl group or the heteroaryl group represented by A to form an optionally substituted ring structure, and $Y^1$ is a single bond or an optionally substituted $C_{1-4}$ alkylene or an optionally substituted —O—($C_{1-4}$ alkylene)-, $R^1$ is a hydrogen atom or an optionally substituted group bonded via a carbon atom, a nitrogen atom or an oxygen atom, and $R^2$ is a hydrogen atom or an optionally substituted group bonded via a carbon atom or a sulfur atom, or $R^1$ and $R^2$, or $R^2$ and $R^3$ are optionally bonded to form an optionally substituted ring structure, provided that the compounds represented by the formulas

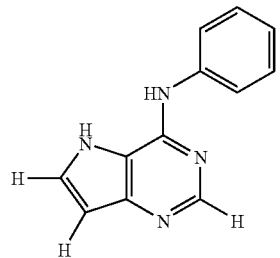

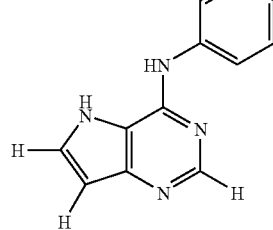

-continued

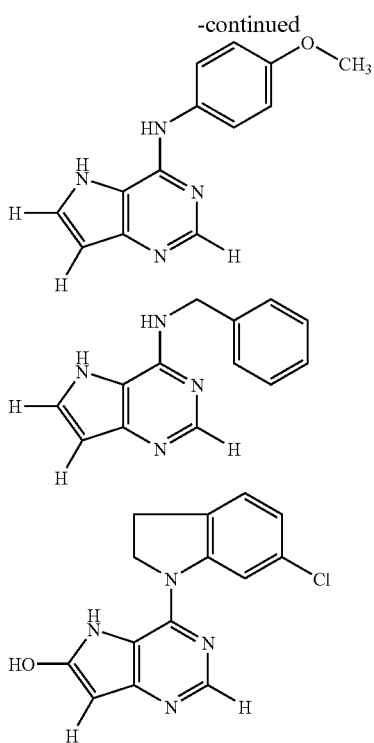

are excluded, or a salt thereof, or a prodrug thereof,

[25] the pharmaceutical agent of the above-mentioned [24] which is a tyrosine kinase inhibitor,

[26] the pharmaceutical agent of the above-mentioned [24] which is an agent for the prophylaxis or treatment of cancer,

[27] the pharmaceutical agent of the above-mentioned [26] wherein the cancer is breast cancer, prostate cancer, lung cancer, pancreatic cancer or kidney cancer,

[28] a method for the prophylaxis or treatment of cancer in a mammal, which comprises administering, to said mammal, an effective amount of a compound represented by the formula:

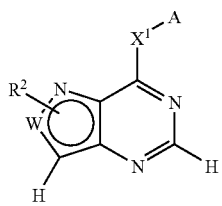

(I)

wherein W is C($R^1$) or N,

A is an optionally substituted aryl group or an optionally substituted heteroaryl group, $X^1$ is —$NR^3$—$Y^1$—, —O—, —S—, —SO—, —$SO_2$— or —$CHR^3$— wherein $R^3$ is a hydrogen atom or an optionally substituted aliphatic hydrocarbon group, or $R^3$ is optionally bonded to a carbon atom or a hetero atom on the aryl group or the heteroaryl group represented by A to form an optionally substituted ring structure, and $Y^1$ is a single bond or an optionally substituted $C_{1-4}$ alkylene or an optionally substituted —O—($C_{1-4}$ alkylene)-, $R^1$ is a hydrogen atom or an optionally substituted group bonded via a carbon atom, a nitrogen atom or an oxygen atom, and $R^2$ is a hydrogen atom or an optionally substituted group bonded via a carbon atom or a sulfur atom, or $R^1$ and $R^2$, or $R^2$ and $R^3$ are optionally bonded to form an optionally substituted ring structure, provided that the compounds represented by the formulas

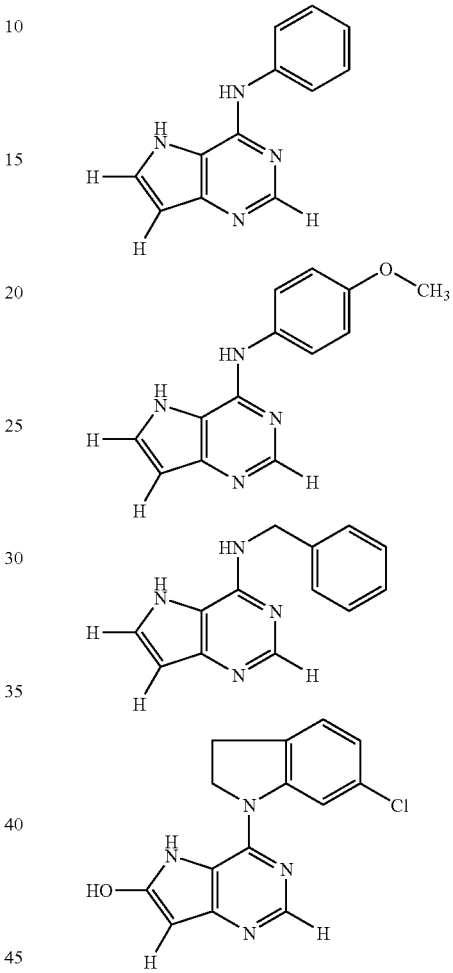

are excluded, or a salt thereof, or a prodrug thereof,

[29] use of a compound represented by the formula:

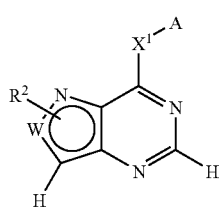

(I)

wherein W is C($R^1$) or N,

A is an optionally substituted aryl group or an optionally substituted heteroaryl group, $X^1$ is —$NR^3$—$Y^1$—, —O—, —S—, —SO—, —$SO_2$— or —$CHR^3$— wherein $R^3$ is a hydrogen atom or an optionally substituted aliphatic hydrocarbon group, or $R^3$ is optionally bonded to a carbon atom or a hetero atom on the aryl group or the heteroaryl group represented by A to form an optionally substituted ring structure, and Y$^1$ is a single bond or an optionally substituted C$_{1-4}$ alkylene or an optionally substituted —O—(C$_{1-4}$ alkylene)-, R$^1$ is a hydrogen atom or an optionally substituted group bonded via a carbon atom, a nitrogen atom or an oxygen atom, and R$^2$ is a hydrogen atom or an optionally substituted group bonded via a carbon atom or a sulfur atom, or R$^1$ and R$^2$, or R$^2$ and R$^3$ are optionally bonded to form an optionally substituted ring structure, provided that the compounds represented by the formulas

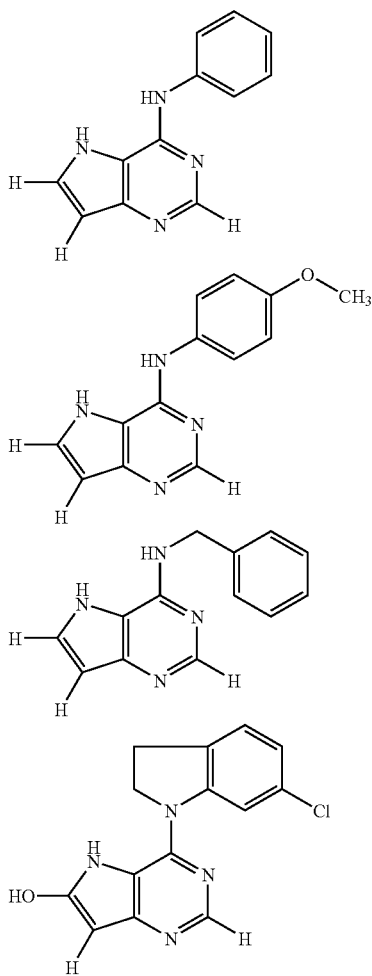

are excluded, or a salt thereof, or a prodrug thereof, for the production of an agent for the prophylaxis or treatment of cancer, and the like.

Furthermore, the present invention provides

[30] the compound of the above-mentioned [15], wherein R$^{2a}$ is (i) a C$_{1-8}$ alkyl group, a C$_{2-8}$ alkenyl group, a C$_{2-8}$ alkynyl group, a C$_{1-8}$ alkyl-carbonyl group, a C$_{1-8}$ alkylsulfonyl group, a C$_{3-8}$ cycloalkyl group, a C$_{6-18}$ aryl group, a C$_{6-18}$ aryl-C$_{1-4}$ alkyl group, a C$_{6-18}$ aryl-carbonyl group, a C$_{6-18}$ aryl-C$_{1-4}$ alkyl-carbonyl group, a C$_{6-18}$ aryl-sulfonyl group, a heterocyclic group, a heterocycle-C$_{1-4}$ alkyl group, a heterocycle-carbonyl group or a heterocycle-C$_{1-4}$ alkyl-carbonyl group, each of which is optionally substituted by 1 to 5 substituents selected from the group (substituent group T) consisting of (a) halogen,
(b) oxo,
(c) optionally halogenated C$_{1-4}$ alkyl,
(d) —(CH$_2$)$_m$-Q,
(e) —(CH$_2$)$_m$—Z$^1$-(optionally halogenated C$_{1-4}$ alkyl),
(f) —(CH$_2$)$_m$—Z$^1$—C$_{3-8}$ cycloalkyl,
(g) —(CH$_2$)$_m$—Z$^2$—(CH$_2$)$_n$-Q,
(h) —(CH$_2$)$_m$—Z$^2$—(CH$_2$)$_n$—Z$^1$-(optionally halogenated C$_{1-4}$ alkyl),
(i) —(CH$_2$)$_m$—Z$^2$—(CH$_2$)$_n$—Z$^1$—C$_{3-8}$ cycloalkyl,
(j) —(CH$_2$)$_m$—Z$^1$-(optionally substituted heterocyclic group)
(preferably, said heterocyclic group is a 5- to 8-membered heterocyclic group having 1 to 3 hetero atoms selected from a nitrogen atom, an oxygen atom and an optionally oxidized sulfur atom),
(k) —(CH$_2$)$_m$—Z$^2$—C$_{1-4}$ alkoxy, and
(l) —(CH$_2$)$_m$—Z$^2$—(CH$_2$)$_n$—Z$^1$—(CH$_2$)$_n$—Z$^1$—C$_{1-4}$ alkyl wherein m is an integer of 0 to 4,
n is an integer of 1 to 4,
Q is hydroxy, carboxy, cyano, nitro, —NR$^6$R$^7$, —CONR$^6$R$^7$, —OCONH$_2$ or —SO$_2$NR$^6$R$^7$,
Z$^1$ is —O—, —CO—, —C(OH)R$^8$—, —C(=N—OR$^8$)—, —S—, —SO—, —SO$_2$—, —N(COR$^8$)—, —N(CO$_2$R$^9$)—, —N(SO$_2$R$^9$)—, —CO—OC—, —O—CO—, —CO—NR$^8$—, —NR$^8$—CO—, —NR$^8$—CO$_2$—, —NR$^8$—CO—NH—, —NR$^8$—SO$_2$—, or —NR$^8$—C(=NH)—NH—,
Z$^2$ is —O—, —CO—, —C(OH)R$^8$—, —C(=N—OR$^8$)—, —S—, —SO—, —SO$_2$—, —NR$^8$—, —N(COR$^8$)—, —N(CO$_2$R$^9$)—, —N(SO$_2$R$^9$)—, —CO—O—, —O—CO—, —CO—NR$^8$—, —NR$^8$—CO—, —NR$^8$—CO$_2$—, —NR$^8$—CO—NH—, —NR$^8$—C(=NH)—NH—, —NR$^8$—SO$_2$—, or —SO$_2$—NR$^8$—,
(CH$_2$)$_m$ and (CH$_2$)$_n$ are optionally substituted by 1 to 5 substituents selected from halogen, optionally halogenated C$_{1-4}$ alkyl and hydroxy, and when m or n is not less than 2, a subset —CH$_2$CH$_2$— of (CH$_2$)$_m$ and (CH$_2$) is optionally replaced by —CH=CH— or —C≡C—,
R$^6$ and R$^7$ are the same or different and each is a hydrogen atom or a C$_{1-4}$ alkyl group, or R$^6$ and R$^7$ are bonded to form, together with a nitrogen atom, a 3- to 8-membered saturated or unsaturated aliphatic heterocyclic group,
R$^8$ is a hydrogen atom or a C$_{1-4}$ alkyl group, and
R$^9$ is a C$_{1-4}$ alkyl group, or
(ii) a carbamoyl group optionally having 1 or 2 C$_{1-8}$ alkyl group(s) optionally substituted by substituent(s) selected from substituent group T,
wherein said carbamoyl group has two substituents, which optionally form, together with the adjacent nitrogen atom, a 3- to 8-membered saturated or unsaturated aliphatic heterocyclic group optionally substituted by substituent(s) selected from substituent group T,
[31] the compound of the above-mentioned [15], wherein
B$^a$ is a benzene ring optionally substituted by 1 to 4 substituents selected from halogen, C$_{1-4}$ alkyl, hydroxy-C$_{1-4}$ alkyl and C$_{1-4}$ alkyloxy;
C$^a$ is a phenyl group optionally substituted by 1 to 5 substituents selected from
(i) halogen,
(ii) optionally halogenated C$_{1-4}$ alkyl,
(iii) hydroxy-C$_{1-4}$ alkyl,
(iv) heterocycle-C$_{1-4}$ alkyl (preferably, 5- to 8-membered heterocycle-C$_{1-4}$ alkyl, said 5- to 8-membered heterocycle has 1 to 3 hetero atoms selected from a nitrogen atom, an oxygen atom and an optionally oxidized sulfur atom, such as imidazolyl, triazolyl and the like),
(v) optionally halogenated $C_{1-4}$ alkyloxy,
(vi) $C_{1-4}$ alkyl-carbonyl,
(vii) cyano,
(viii) carbamoyl optionally substituted by $C_{1-8}$ alkyl, and
(ix) $C_{1-4}$ alkoxy-carbonyl;

$R^{1a}$ is
(i) a hydrogen atom,
(ii) a cyano group, or
(iii) a $C_{1-4}$ alkyl group or a $C_{2-4}$ alkenyl group, each of which is optionally substituted by —NR$^8$—CO—(CH$_2$)$_n$—NR$^6$R$^7$
wherein n is an integer of 1 to 4, $R^6$ and $R^7$ are the same or different and each is a hydrogen atom or a $C_{1-4}$ alkyl group, $R^8$ is a hydrogen atom or a $C_{1-4}$ alkyl group, and when n is not less than 2, a subset —CH$_2$CH$_2$— of (CH$_2$)$_n$ is optionally replaced by —CH=CH—; and $R^{2a}$ is a $C_{1-8}$ alkyl group, a $C_{2-8}$ alkenyl group or a $C_{2-8}$ alkynyl group, each of which is optionally substituted by substituent(s) selected from
(a) hydroxy,
(b) carboxy,
(c) cyano,
(d) optionally halogenated $C_{1-4}$ alkyloxy,
(e) —O—(CH$_2$)$_n$—OH,
(f) —O—(CH$_2$)$_n$—O—CO—NH$_2$,
(g) —O—(CH$_2$)$_n$—O-(optionally halogenated $C_{1-4}$ alkyl),
(h) —O—(CH$_2$)$_n$—SO$_2$-(optionally halogenated $C_{1-4}$ alkyl),
(i) —O—(CH$_2$)$_n$—SO$_2$—$C_{6-18}$ aryl,
(j) —O—(CH$_2$)$_n$—SO$_2$—(CH$_2$)$_n$—OH,
(k) —O—(CH$_2$)$_n$—NR$^8$—CO—$C_{1-4}$ alkyl,
(l) —O—(CH$_2$)$_n$—NR$^8$—CO—(CH$_2$)$_n$—SO$_2$—$C_{1-4}$ alkyl,
(m) —O—(CH$_2$)$_n$—NR$^8$—SO$_2$-(optionally halogenated $C_{1-4}$ alkyl),
(n) —CO—NR$^8$—(CH$_2$)$_n$—OH,
(o) —CO—NR$^8$—(CH$_2$)$_n$—SO$_2$-(optionally halogenated $C_{1-4}$ alkyl),
(p) —CO—NR$^8$—O—$C_{1-4}$ alkyl,
(q) —NR$^6$R$^7$,
(r) —NR$^8$—(CH$_2$)$_n$—OH,
(s) —NR$^8$—(CH$_2$)$_n$—SO$_2$—$C_{1-4}$ alkyl,
(t) —NR$^8$—CO-(optionally halogenated $C_{1-4}$ alkyl),
(u) —NR$^8$—CO—(CH$_2$)$_n$—OH,
(v) —NR$^8$—CO—(CH$_2$)$_n$—CN,
(w) —NR$^8$—CO—(CH$_2$)$_n$—NR$^6$R$^7$,
(x) —NR$^8$—CO—(CH$_2$)$_n$—O—$C_{1-4}$ alkyl,
(y) —NR$^8$—CO—(CH$_2$)$_n$—SO-(optionally halogenated $C_{1-4}$ alkyl),
(z) —NR$^8$—CO—(CH$_2$)$_n$—SO$_2$-(optionally halogenated $C_{1-4}$ alkyl),
(aa) —NR$^8$—CO—(CH$_2$)$_n$—SO$_2$—$C_{3-8}$ cycloalkyl,
(bb) —NR$^8$—CO—(CH$_2$)$_n$—NR$^8$—SO$_2$—$C_{1-4}$ alkyl,
(cc) —NR$^8$—CO$_2$—(CH$_2$)$_n$—SO$_2$—$C_{1-4}$ alkyl,
(dd) —NR$^8$—CO—NH—(CH$_2$)$_n$—SO$_2$—$C_{1-4}$ alkyl,
(ee) —NR$^8$—CO—NH—O—$C_{1-4}$ alkyl,
(ff) —NR$^8$—CO—NH—(CH$_2$)$_n$—O—$C_{1-4}$ alkyl,
(gg) —NR$^8$—C(=NH)—NH—$C_{1-4}$ alkyl,
(hh) —NR$^8$—SO$_2$—(CH$_2$)$_n$—SO$_2$—$C_{1-4}$ alkyl,
(ii) —S—(CH$_2$)$_n$—OH,
(jj) —SO—(CH$_2$)$_n$—OH,
(kk) —SO$_2$—(CH$_2$)$_n$—OH, and
(ll) —NR$^8$—CO-(optionally substituted heterocyclic group)
(preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—O—$C_{1-4}$ alkyl, —CO—NH—$C_{1-4}$ alkyl, —CONH$_2$, —SO$_2$—$C_{1-4}$ alkyl, —SO$_2$—NH—$C_{1-4}$ alkyl, —SO$_2$NH$_2$ and the like)
wherein n is an integer of 1 to 4, $R^6$ and $R^7$ are the same or different and each is a hydrogen atom or a $C_{1-4}$ alkyl group, $R^8$ is a hydrogen atom or a $C_{1-4}$ alkyl group, (CH$_2$)$_n$ are optionally substituted by halogenated $C_{1-4}$ alkyl or hydroxy, and when n is not less than 2, a subset —CH$_2$CH$_2$— of (CH$_2$)$_n$ is optionally replaced by —CH=CH—;

$R^{3a}$ is a hydrogen atom or a $C_{1-6}$ alkyl group; or
$R^{1a}$ and $R^{2a}$ are optionally bonded to form $R^{2a}$ and $R^{3a}$ are optionally bonded to form $C_{2-4}$ alkylene optionally substituted by an imino group, particularly preferably, $R^{2a}$ is a $C_{1-8}$ alkyl group, a $C_{2-8}$ alkenyl group or a $C_{2-8}$ alkynyl group (particularly, a $C_{1-8}$ alkyl group), each of which is optionally substituted by substituent(s) selected from
(a) hydroxy,
(b) carboxy,
(c) cyano,
(d) optionally halogenated $C_{1-4}$ alkyloxy,
(e) —O—(CH$_2$)$_n$—OH (wherein (CH$_2$)$_n$ is optionally substituted by hydroxy),
(f) —O—(CH$_2$)$_n$—O—CO—NH$_2$,
(g) —O—(CH$_2$)$_n$—O-(optionally halogenated $C_{1-4}$ alkyl),
(h) —O—(CH$_2$)$_n$—SO$_2$-(optionally halogenated $C_{1-4}$ alkyl),
(i) —O—(CH$_2$)$_n$—SO$_2$—$C_{6-18}$ aryl,
(j) —O—(CH$_2$)$_n$—SO$_2$—(CH$_2$)$_n$—OH,
(k) —O—(CH$_2$)$_n$—NR$^8$—CO—$C_{1-4}$ alkyl,
(l) —O—(CH$_2$)$_n$—NR$^8$—CO—(CH$_2$)$_n$—SO$_2$—$C_{1-4}$ alkyl,
(m) —O—(CH$_2$)$_n$—NR$^8$—SO$_2$-(optionally halogenated $C_{1-4}$ alkyl),
(n) —CO—NR$^8$—(CH$_2$)$_n$—OH,
(o) —CO—NR$^8$—(CH$_2$)$_n$—SO$_2$-(optionally halogenated $C_{1-4}$ alkyl),
(p) —CO—NR$^8$—O—$C_{1-4}$ alkyl,
(q) —NR$^6$R$^7$,
(r) —NR$^8$—(CH$_2$)$_n$—OH,
(s) —NR$^8$—(CH$_2$)$_n$—SO$_2$—$C_{1-4}$ alkyl,
(t) —NR$^8$—CO-(optionally halogenated $C_{1-4}$ alkyl),
(u) —NR$^8$—CO—(CH$_2$)$_n$—OH (wherein (CH$_2$)$_n$ is optionally substituted by optionally halogenated $C_{1-4}$ alkyl or hydroxy),
(v) —NR$^8$—CO—(CH$_2$)$_n$—CN,
(w) —NR$^8$—CO—(CH$_2$)$_n$—NR$^6$R$^7$ (when n is not less than 2, a subset —CH$_2$CH$_2$— of (CH$_2$)$_n$ is optionally replaced by —CH=CH—),
(x) —NR$^8$—CO—(CH$_2$)$_n$—O—$C_{1-4}$ alkyl,
(y) —NR$^8$—CO—(CH$_2$)$_n$—SO-(optionally halogenated $C_{1-4}$ alkyl),
(z) —NR$^8$—CO—(CH$_2$)$_n$—SO$_2$-(optionally halogenated $C_{1-4}$ alkyl)
(wherein (CH$_2$)$_n$ is optionally substituted by $C_{1-4}$ alkyl),
(aa) —NR$^8$—CO—(CH$_2$)$_n$—SO$_2$—$C_{3-8}$ cycloalkyl,
(bb) —NR$^8$—CO—(CH$_2$)$_n$—NR$^8$—SO$_2$—$C_{1-4}$ alkyl, (cc) —NR$^8$—CO$_2$—(CH$_2$)$_n$—SO$_2$—C$_{1-4}$ alkyl,
(dd) —NR$^8$—CO—NH—(CH$_2$)$_n$—SO$_2$—C$_{1-4}$ alkyl,
(ee) —NR$^8$—CO—NH—O—C$_{1-4}$ alkyl,
(ff) —NR$^8$—CO—NH(CH$_2$)$_n$—O—C$_{1-4}$ alkyl,
(gg) —NR$^8$—C(=NH)—NH—C$_{1-4}$ alkyl,
(hh) —NR$^8$—SO$_2$—(CH$_2$)$_n$—SO$_2$—C$_{1-4}$ alkyl,
(ii) —S—(CH$_2$)$_n$—OH,
(jj) —SO—(CH$_2$)$_n$—OH,
(kk) —SO$_2$—(CH$_2$)$_n$—OH, and
(ll) —NR$^8$—CO-(optionally substituted heterocyclic group) (preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, C$_{1-4}$ alkyl, optionally oxidized C$_{1-4}$ alkylthio, —CO—C$_{1-4}$ alkyl, —CO—O—C$_{1-4}$ alkyl, —CO—NH—C$_{1-4}$ alkyl, —CONH$_2$, —SO$_2$—C$_{1-4}$ alkyl, —SO$_2$—NH—C$_{1-4}$ alkyl, —SO$_2$NH$_2$ and the like),
wherein n is an integer of 1 to 4, R$^6$ and R$^7$ are the same or different and each is a hydrogen atom or a C$_{1-4}$ alkyl group, R$^8$ is a hydrogen atom or a C$_{1-4}$ alkyl group,

[32] the compound of the above-mentioned [15], wherein
B$^a$ is a benzene ring optionally substituted by 1 to 4 substituents selected from halogen and optionally halogenated C$_{1-4}$ alkyl;
C$^a$ is a phenyl group substituted by 1 to 5 substituents selected from
(i) halogen,
(ii) optionally halogenated C$_{1-4}$ alkyl,
(iii) hydroxy-C$_{1-4}$ alkyl,
(iv) heterocycle-C$_{1-4}$ alkyl (preferably, 5- to 8-membered heterocycle-C$_{1-4}$ alkyl, said 5- to 8-membered heterocycle has 1 to 3 hetero atoms selected from a nitrogen atom, an oxygen atom and an optionally oxidized sulfur atom, such as imidazolyl and the like),
(v) optionally halogenated C$_{1-4}$ alkyloxy,
(vi) cyano, and
(vii) carbamoyl optionally substituted by C$_{1-8}$ alkyl;
R$^{1a}$ is a hydrogen atom;
R$^{2a}$ is a C$_{1-8}$ alkyl group, a C$_{2-8}$ alkenyl group or a C$_{2-8}$ alkynyl group, each of which is substituted by substituent(s) selected from
(a) hydroxy,
(b) optionally halogenated C$_{1-4}$ alkyloxy,
(c) —O—(CH$_2$)$_n$—OH,
(d) —O—(CH$_2$)$_n$—O—CO—NH$_2$,
(e) —O—(CH$_2$)$_n$—O—C$_{1-4}$ alkyl,
(f) —O—(CH$_2$)$_n$—SO$_2$-(optionally halogenated C$_{1-4}$ alkyl),
(g) —O—(CH$_2$)$_n$—SO$_2$—C$_{6-18}$ aryl,
(h) —O—(CH$_2$)$_n$—SO$_2$—(CH$_2$)$_n$—OH,
(i) —O—(CH$_2$)$_n$—NR$^8$—SO$_2$-(optionally halogenated C$_{1-4}$ alkyl),
(j) —CO—NR$^8$—(CH$_2$)$_n$—OH,
(k) —CO—NR$^8$—(CH$_2$)$_n$—SO$_2$-(optionally halogenated C$_{1-4}$ alkyl),
(l) —NR$^6$R$^7$,
(m) —NR$^8$—(CH$_2$)$_n$—OH,
(n) —NR$^8$—(CH$_2$)$_n$—SO$_2$—C$_{1-4}$ alkyl,
(o) —NR$^8$—CO(CH$_2$)$_n$—OH,
(p) —NR$^8$—CO—(CH$_2$)$_n$—O—C$_{1-4}$ alkyl,
(q) —NR$^8$—CO—(CH$_2$)$_n$—SO-(optionally halogenated C$_{1-4}$ alkyl),
(r) —NR$^8$—CO—(CH$_2$)$_n$—SO$_2$-(optionally halogenated C$_{1-4}$ alkyl),
(s) —NR$^8$—CO—(CH$_2$)$_n$—SO$_2$—C$_{3-8}$ cycloalkyl,
(t) —NR$^8$—CO$_2$—(CH$_2$)$_n$—SO$_2$—C$_{1-4}$ alkyl,
(u) —NR$^8$—CO—NH—(CH$_2$)$_n$—SO$_2$—C$_{1-4}$ alkyl,
(v) —NR$^8$—SO$_2$—(CH$_2$)$_n$—SO$_2$—C$_{1-4}$ alkyl,
(w) —S—(CH$_2$)$_n$—OH,
(x) —SO—(CH$_2$)$_n$—OH,
(y) —SO$_2$—(CH$_2$)$_n$—OH, and
(z) —NR$^8$—CO-(optionally substituted heterocyclic group)
(preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, C$_{1-4}$ alkyl, optionally oxidized C$_{1-4}$ alkylthio, —CO—C$_{1-4}$ alkyl, —CO—NH—C$_{1-4}$ alkyl, —CONH$_2$, —SO$_2$—C$_{1-4}$ alkyl, —SO$_2$—NH—C$_{1-4}$ alkyl, —SO$_2$NH$_2$ and the like),
wherein n is an integer of 1 to 4, R$^6$ and R$^7$ are the same or different and each is a hydrogen atom or a C$_{1-4}$ alkyl group, R$^8$ is a hydrogen atom or a C$_{1-4}$ alkyl group, and (CH$_2$)$_n$ is optionally substituted by C$_{1-4}$ alkyl or hydroxy;
R$^{3a}$ is a hydrogen atom or a C$_{1-6}$ alkyl group; or
R$^{1a}$ and R$^{2a}$ are optionally bonded to form

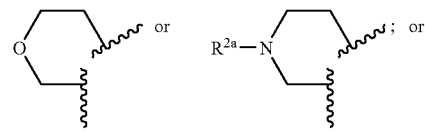

R$^{2a}$ and R$^{3a}$ are optionally bonded to form C$_{2-4}$ alkylene, particularly preferably, R$^{2a}$ is a C$_{1-8}$ alkyl group, a C$_{2-8}$ alkenyl group or a C$_{2-8}$ alkynyl group (particularly, a C$_{1-8}$ alkyl group), each of which is substituted by substituent(s) selected from
(a) hydroxy,
(b) optionally halogenated C$_{1-4}$ alkyloxy,
(c) —O—(CH$_2$)$_n$—OH (wherein (CH$_2$)$_n$ is optionally substituted by hydroxy),
(d) —O—(CH$_2$)$_n$—O—CO—NH$_2$,
(e) —O—(CH$_2$)$_n$—O—C$_{1-4}$ alkyl,
(f) —O—(CH$_2$)$_n$—SO$_2$-(optionally halogenated C$_{1-4}$ alkyl),
(g) —O—(CH$_2$)$_n$—SO$_2$—C$_{6-18}$ aryl,
(h) —O—(CH$_2$)$_n$—SO$_2$—(CH$_2$)$_n$—OH,
(i) —O—(CH$_2$)$_n$—NR$^8$—SO$_2$-(optionally halogenated C$_{1-4}$ alkyl),
(j) —CO—NR$^8$—(CH$_2$)$_n$—OH,
(k) —CO—NR$^8$—(CH$_2$)$_n$—SO$_2$-(optionally halogenated C$_{1-4}$ alkyl),
(l) —NR$^6$R$^7$,
(m) —NR$^8$—(CH$_2$)$_n$—OH,
(n) —NR$^8$—(CH$_2$)$_n$—SO$_2$—C$_{1-4}$ alkyl,
(o) —NR$^8$—CO—(CH$_2$)$_n$—OH (wherein CH$_2$)$_n$ is optionally substituted by C$_{1-4}$ alkyl),
(p) —NR$^8$—CO—(CH$_2$)$_n$—O—C$_{1-4}$ alkyl,
(q) —NR$^8$—CO—(CH$_2$)$_n$—SO-(optionally halogenated C$_{1-4}$ alkyl),
(r) —NR$^8$—CO—(CH$_2$)$_n$—SO$_2$-(optionally halogenated C$_{1-4}$ alkyl)
(wherein (CH$_2$)$_n$ is optionally substituted by C$_{1-4}$ alkyl),
(s) —NR$^8$—CO—(CH$_2$)$_n$—SO$_2$—C$_{3-8}$ cycloalkyl,
(t) —NR$^8$—CO$_2$—(CH$_2$)$_n$—SO$_2$—C$_{1-4}$ alkyl,
(u) —NR$^8$—CO—NH—(CH$_2$)$_n$—SO$_2$—C$_{1-4}$ alkyl,
(v) —NR$^8$—SO$_2$—(CH$_2$)$_n$—SO$_2$—C$_{1-4}$ alkyl,
(w) —S—(CH$_2$)$_n$—OH,
(x) —SO—(CH$_2$)$_n$—OH,
(y) —SO$_2$—(CH$_2$)$_n$—OH r and
(z) —NR$^8$—CO-(optionally substituted heterocyclic group)

(preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—NH—$C_{1-4}$ alkyl, —CONH$_2$, —SO$_2$—$C_{1-4}$ alkyl, —SO$_2$—NH—$C_{1-4}$ alkyl, —SO$_2$NH$_2$ and the like),
wherein n is an integer of 1 to 4, $R^6$ and $R^7$ are the same or different and each is a hydrogen atom or a $C_{1-4}$ alkyl group, and $R^8$ is a hydrogen atom or a $C_{1-4}$ alkyl group,

[33] the compound of the above-mentioned [31], wherein $R^{2a}$ is (i) a $C_{5-8}$ alkyl group substituted by hydroxy,
(ii) a $C_{1-8}$ alkyl group substituted by substituent(s) selected from
(a) halogenated $C_{1-4}$ alkyloxy,
(b) —O—(CH$_2$)$_n$—OH,
(c) —O—(CH$_2$)$_n$—O—CO—NH$_2$,
(d) —O—(CH$_2$)$_n$—O-(optionally halogenated $C_{1-4}$ alkyl),
(e) —O—(CH$_2$)$_n$—SO$_2$-(optionally halogenated $C_{1-4}$ alkyl),
(f) —O—(CH$_2$)$_n$—SO$_2$—$C_{6-18}$ aryl,
(g) —O—(CH$_2$)$_n$—NR$^8$—SO$_2$-(optionally halogenated $C_{1-4}$ alkyl),
(h) —CO—NR$^8$—(CH$_2$)$_n$—OH,
(i) —CO—NR$^8$—(CH$_2$)$_n$—SO$_2$-(optionally halogenated $C_{1-4}$ alkyl),
(j) —NR$^8$—(CH$_2$)$_n$—SO$_2$—$C_{1-4}$ alkyl,
(k) —NR$^8$—CO—(CH$_2$)$_n$—OH,
(l) —NR$^8$—CO—(CH$_2$)$_n$—O—$C_{1-4}$ alkyl,
(m) —NR$^8$—CO—(CH$_2$)$_n$—SO-(optionally halogenated $C_{1-4}$ alkyl),
(n) —NR$^8$—CO—(CH$_2$)$_n$—SO$_2$-(optionally halogenated $C_{1-4}$ alkyl),
(o) —NR$^8$—CO—(CH$_2$)$_n$—SO$_2$—$C_{3-8}$ cycloalkyl,
(p) —NR$^8$—CO$_2$—(CH$_2$)$_n$—SO$_2$—$C_{1-4}$ alkyl,
(q) —NR$^8$—CO—NH—(CH$_2$)$_n$—SO$_2$—$C_{1-4}$ alkyl,
(r) —NR$^8$—SO$_2$—(CH$_2$)$_n$—SO$_2$—$C_{1-4}$ alkyl,
(s) —S—(CH$_2$)$_n$—OH,
(t) —SO—(CH$_2$)$_n$—OH,
(u) —SO$_2$—(CH$_2$)$_n$—OH, and
(v) —NR$^8$—CO-(optionally substituted heterocyclic group)
(preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—NH—$C_{1-4}$ alkyl, —CONH$_2$, —SO$_2$—$C_{1-4}$ alkyl, —SO$_2$—NH—$C_{1-4}$ alkyl, —SO$_2$NH$_2$ and the like),
wherein n is an integer of 1 to 4, $R^8$ is a hydrogen atom or a $C_{1-4}$ alkyl group, and (CH$_2$)$_n$ is optionally substituted by $C_{1-4}$ alkyl or hydroxy,
(iii) a $C_{2-8}$ alkenyl group optionally substituted by hydroxy, or
(iv) a $C_{2-8}$ alkynyl group optionally substituted by hydroxy, particularly preferably, $R^{2a}$ is (i) a $C_{5-8}$ alkyl group substituted by hydroxy,
(ii) a $C_{1-8}$ alkyl group substituted by substituent(s) selected from
(a) halogenated $C_{1-4}$ alkyloxy,
(b) —O—(CH$_2$)$_n$—OH (wherein (CH$_2$)$_n$ is optionally substituted by hydroxy),
(c) —O—(CH$_2$)$_n$—O—CO—NH$_2$,
(d) —O—(CH$_2$)$_n$—O-(optionally halogenated $C_{1-4}$ alkyl),
(e) —O—(CH$_2$)$_n$—SO$_2$-(optionally halogenated $C_{1-4}$ alkyl),
(f) —O—(CH$_2$)$_n$—SO$_2$—$C_{6-18}$ aryl,
(g) —O—(CH$_2$)$_n$—NR$^8$—SO$_2$-(optionally halogenated $C_{1-4}$ alkyl),
(h) —CO—NR$^8$—(CH$_2$)$_n$—OH,
(i) —CO—NR$^8$—(CH$_2$)$_n$—SO$_2$-(optionally halogenated $C_{1-4}$ alkyl),
(j) —NR$^8$—(CH$_2$)$_n$—SO$_2$—$C_{1-4}$ alkyl,
(k) —NR$^8$—CO—(CH$_2$)$_n$—OH (wherein (CH$_2$)$_n$ is optionally substituted by $C_{1-4}$ alkyl),
(l) —NR$^8$—CO—(CH$_2$)$_n$—O—$C_{1-4}$ alkyl,
(m) —NR$^8$—CO—(CH$_2$)$_n$—SO-(optionally halogenated $C_{1-4}$ alkyl),
(n) —NR$^8$—CO—(CH$_2$)$_n$—SO$_2$-(optionally halogenated $C_{1-4}$ alkyl)
(wherein (CH$_2$)$_n$ is optionally substituted by $C_{1-4}$ alkyl),
(o) —NR$^8$—CO—(CH$_2$)$_n$—SO$_2$—$C_{3-8}$ cycloalkyl,
(p) —NR$^8$—CO$_2$—(CH$_2$)$_n$—SO$_2$—$C_{1-4}$ alkyl,
(q) —NR$^8$—CO—NH—(CH$_2$)$_n$—SO$_2$—$C_{1-4}$ alkyl,
(r) —NR$^8$—SO$_2$—(CH$_2$)$_n$—SO$_2$—$C_{1-4}$ alkyl,
(s) —S—(CH$_2$)$_n$—OH,
(t) —SO—(CH$_2$)$_n$—OH,
(u) —SO$_2$—(CH$_2$)$_n$—OH, and
(v) —NR$^8$—CO-(optionally substituted heterocyclic group)
(preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—NH—$C_{1-4}$ alkyl, —CONH$_2$, —SO$_2$—$C_{1-4}$ alkyl, —SO$_2$—NH—$C_{1-4}$ alkyl, —SO$_2$NH$_2$ and the like),
wherein n is an integer of 1 to 4, and $R^8$ is a hydrogen atom or a $C_{1-4}$ alkyl group,
(iii) a $C_{2-8}$ alkenyl group optionally substituted by hydroxy, or
(iv) a $C_{2-8}$ alkynyl group optionally substituted by hydroxy,

[34] the compound of the above-mentioned [16], wherein $R^{2b}$ is (i) a $C_{1-8}$ alkyl group, a $C_{2-8}$ alkenyl group, a $C_{2-8}$ alkynyl group, a $C_{1-8}$ alkyl-carbonyl group, a $C_{1-8}$ alkylsulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocycle-$C_{1-4}$ alkyl group, a heterocycle-carbonyl group or a heterocycle-$C_{1-4}$ alkyl-carbonyl group, each of which is optionally substituted by 1 to 5 substituents selected from the group (substituent group T) consisting of
(a) halogen,
(b) oxo,
(c) optionally halogenated $C_{1-4}$ alkyl,
(d) —(CH$_2$)$_m$-Q,
(e) —(CH$_2$)$_m$—$Z^1$-(optionally halogenated $C_{1-4}$ alkyl),
(f) —(CH$_2$)$_m$—$Z^1$—$C_{3-8}$ cycloalkyl,
(g) —(CH$_2$)$_m$—$Z^2$—(CH$_2$)$_n$-Q,
(h) —(CH$_2$)$_m$—$Z^2$—(CH$_2$)$_n$—$Z^1$-(optionally halogenated $C_{1-4}$ alkyl),
(i) —(CH$_2$)$_m$—$Z^2$—(CH$_2$)$_n$—$Z^1$—$C_{3-8}$ cycloalkyl,
(j) —(CH$_2$)$_m$—$Z^1$-(optionally substituted heterocyclic group)
(preferably, said heterocyclic group is a 5- to 8-membered heterocyclic group having 1 to 3 hetero atoms selected from a nitrogen atom, an oxygen atom and an optionally oxidized sulfur atom),
(k) —(CH$_2$)$_m$—$Z^2$—$C_{1-4}$ alkoxy, and
(l) —(CH$_2$)$_m$—$Z^2$—(CH$_2$)$_n$—$Z^1$—(CH$_2$)$_n$—$Z^1$—$C_{1-4}$ alkyl
wherein m is an integer of 0 to 4, n is an integer of 1 to 4,
Q is hydroxy, carboxy, cyano, nitro, —NR$^6$R$^7$, —CONR$^6$R$^7$, —OCONH$_2$ or —SO$_2$NR$^6$R$^7$,
$Z^1$ is —O—, —CO—, —C(OH)R$^8$—, —C(=N—OR$^8$)—, —S—, —SO—, —SO$_2$—, —N(COR$^8$)—, —N(CO$_2$R$^9$)—, —N(SO$_2$R$^9$)—, —CO—O—, —O—CO—, —CO—NR$^8$—, —NR$^8$—CO—, —NR$^8$—CO$_2$—, —NR$^8$—CO—NH—, —NR$^8$—SO$_2$—, or —NR$^8$—C(=NH)—NH—, Z$^2$ is —O—, —CO—, —C(OH)R$^8$—, —C(=N—OR$^8$)—, —S—, —SO—, —SO$_2$—, —NR$^8$—, —N(COR$^8$)—, —N(CO$_2$R$^9$)—, —N(SO$_2$R$^9$)—, —CO—O—, —O—CO—, —CO—NR$^8$—, —NR$^8$—CO—, —NR$^8$—CO$_2$—, —NR$^8$—CO—NH—, —NR$^8$—C(=NH)—NH—, —NR$^8$—SO$_2$—, or —SO$_2$—NR$^8$—, (CH$_2$)$_m$ and (CH$_2$)$_n$ are optionally substituted by 1 to 5 substituents selected from halogen, optionally halogenated C$_{1-4}$ alkyl and hydroxy, and when m or n is not less than 2, a subset —CH$_2$CH$_2$— of (CH$_2$)$_m$ and (CH$_2$)$_n$ is optionally replaced by —CH=CH— or —C≡C—, R$^6$ and R$^7$ are the same or different and each is a hydrogen atom or a C$_{1-4}$ alkyl group, or R$^6$ and R$^7$ are bonded to form, together with a nitrogen atom, a 3- to 8-membered saturated or unsaturated aliphatic heterocyclic group, R$^8$ is a hydrogen atom or a C$_{1-4}$ alkyl group, and R$^9$ is a C$_{1-4}$ alkyl group, or (ii) a carbamoyl group optionally having 1 or 2 C$_{1-8}$ alkyl group(s) optionally substituted by substituent(s) selected from substituent group T, wherein the carbamoyl group has two substituents, and they optionally form, together with the adjacent nitrogen atom, a 3- to 8-membered saturated or unsaturated aliphatic heterocyclic group optionally substituted by substituent(s) selected from substituent group T,

[35] the compound of the above-mentioned [16] wherein
B$^b$ is a benzene ring optionally substituted by halogen;
C$^b$ is a phenyl group optionally substituted by 1 to 5 substituents selected from halogen, optionally halogenated C$_{1-4}$ alkyl and cyano;
R$^{1b}$ is (i) a hydrogen atom, or
(ii) a C$_{2-4}$ alkenyl group optionally substituted by hydroxy;
R$^{2b}$ is
(i) a C$_{1-8}$ alkyl group optionally substituted by substituent(s) selected from
(a) halogen,
(b) hydroxy,
(c) C$_{1-4}$ alkyloxy,
(d) —O—(CH$_2$)$_n$—OH,
(e) —O—(CH$_2$)$_n$—O—C$_{1-4}$ alkyl,
(f) —CO—NR$^8$—(CH$_2$)$_n$—OH,
(g) —NR$^6$R$^7$, and
(h) —NR$^8$—(CH$_2$)$_n$—OH,
wherein n is an integer of 1 to 4, R$^6$ and R$^7$ are the same or different and each is a hydrogen atom or a C$_{1-4}$ alkyl group, and R$^8$ is a hydrogen atom or a C$_{1-4}$ alkyl group, (ii) a C$_{6-18}$ aryl-C$_{1-4}$ alkyl group optionally substituted by substituent(s) selected from
(a) C$_{1-4}$ alkyl optionally having hydroxy,
(b) carboxy,
(c) C$_{1-4}$ alkoxy-carbonyl,
(d) 5- to 8-membered heterocycle-carbonyl having 1 to 3 hetero atoms selected from a nitrogen atom, an oxygen atom and a sulfur atom, which optionally has substituent(s) selected from hydroxy and C$_{1-4}$ alkyl, and
(e) C$_{1-4}$ alkyl-carbamoyl optionally having substituent(s) selected from hydroxy and carbamoyl, (iii) a C$_{6-18}$ aryl-carbonyl group optionally substituted by C$_{1-4}$ alkoxy, (iv) a C$_{6-18}$ aryl-sulfonyl group optionally substituted by C$_{1-4}$ alkoxy, or (v) a 5- to 8-membered heterocycle-C$_{1-4}$ alkyl group having 1 to 3 hetero atoms selected from a nitrogen atom, an oxygen atom and a sulfur atom, which is optionally substituted by substituent(s) selected from
(a) carboxy, and
(b) C$_{1-4}$ alkoxy-carbonyl;
R$^{3b}$ is a hydrogen atom or a C$_{1-6}$ alkyl group; or
R$^{2b}$ and R$^{3b}$ are optionally bonded to form C$_{2-4}$ alkylene; and
Z$^b$ is a C$_{1-3}$ alkylene group,

[36] the compound of the above-mentioned [16], wherein
B$^b$ is a benzene ring optionally substituted by halogen;
C$^b$ is a phenyl group optionally substituted by 1 to 5 substituents selected from halogen and optionally halogenated C$_{1-4}$ alkyl;
R$^{1b}$ is a hydrogen atom;
R$^{2b}$ is a C$_{1-8}$ alkyl group optionally substituted by substituent(s) selected from
(a) hydroxy,
(b) —O—(CH$_2$)$_n$—OH,
(c) —O—(CH$_2$)$_n$—O—C$_{1-4}$ alkyl,
(d) —CO—NR$^8$—(CH$_2$)$_n$—OH,
(e) —NR$^6$R$^7$, and
(f) —NR$^8$—(CH$_2$)$_n$—OH,
wherein n is an integer of 1 to 4, R$^6$ and R$^7$ are the same or different and each is a hydrogen atom or a C$_{1-4}$ alkyl group, and R$^8$ is a hydrogen atom or a C$_{1-4}$ alkyl group;
R$^{3b}$ is a hydrogen atom or a C$_{1-6}$ alkyl group; and
Z$^b$ is a C$_{1-3}$ alkylene group,

[37] the compound of the above-mentioned [36], wherein
B$^b$ is a benzene ring optionally substituted by halogen;
C$^b$ is a phenyl group optionally substituted by 1 to 5 substituents selected from halogen and optionally halogenated C$_{1-4}$ alkyl;
R$^{1b}$ is a hydrogen atom;
R$^{2b}$ is a C$_{1-8}$ alkyl group substituted by substituent(s) selected from
(a) —O—(CH$_2$)$_n$—OH,
(b) —O—(CH$_2$)$_n$—O—C$_{1-4}$ alkyl, and
(c) —CO—NR$^8$—(CH$_2$)$_n$—OH,
wherein n is an integer of 1 to 4, and R$^8$ is a hydrogen atom or a C$_{1-4}$ alkyl group;
R$^{3b}$ is a hydrogen atom or a C$_{1-6}$ alkyl group; and
Z$^b$ is a methylene group,

[38] the compound of the above-mentioned [17], wherein
R$^{2c}$ is (i) a C$_{1-8}$ alkyl group, a C$_{2-8}$ alkenyl group, a C$_{2-8}$ alkynyl group, a C$_{1-8}$ alkyl-carbonyl group, a C$_{1-8}$ alkyl-sulfonyl group, a C$_{3-8}$ cycloalkyl group, a C$_{6-18}$ aryl group, a C$_{6-18}$ aryl-C$_{1-4}$ alkyl group, a C$_{6-18}$ aryl-carbonyl group, a C$_{6-18}$ aryl-C$_{1-4}$ alkyl-carbonyl group, a C$_{6-18}$ aryl-sulfonyl group, a heterocyclic group, a heterocycle-C$_{1-4}$ alkyl group, a heterocycle-carbonyl group or a heterocycle-C$_{1-4}$ alkyl-carbonyl group, each of which is optionally substituted by 1 to 5 substituents selected from the group (substituent group T) consisting of
(a) halogen,
(b) oxo,
(c) optionally halogenated C$_{1-4}$ alkyl,
(d) —(CH$_2$)$_m$-Q,
(e) —(CH$_2$)$_m$—Z$^1$-(optionally halogenated C$_{1-4}$ alkyl),
(f) —(CH$_2$)$_m$—Z$^1$—C$_{3-8}$ cycloalkyl,
(g) —(CH$_2$)$_m$—Z$^2$—(CH$_2$)$_n$-Q,
(h) —(CH$_2$)$_m$—Z$^2$—(CH$_2$)$_n$—Z$^1$-(optionally halogenated C$_{1-4}$ alkyl),
(i) —(CH$_2$)$_m$—Z$^2$—(CH$_2$)$_n$—Z$^1$—C$_{3-8}$ cycloalkyl,
(j) —(CH$_2$)$_m$—Z$^1$-(optionally substituted heterocyclic group)

(preferably, said heterocyclic group is a 5- to 8-membered heterocyclic group having 1 to 3 hetero atoms selected from a nitrogen atom, an oxygen atom and an optionally oxidized sulfur atom), (k) —$(CH_2)_m$—$Z^2$—$C_{1-4}$ alkoxy, and (l) —$(CH_2)_m$—$Z^2$—$(CH_2)_n$—$Z^1$—$(CH_2)_n$—$Z^1$—$C_{1-4}$ alkyl wherein m is an integer of 0 to 4, n is an integer of 1 to 4, Q is hydroxy, carboxy, cyano, nitro, —$NR^6R^7$, —$CONR^6R^7$ or —$SO_2NR^6R^7$, $Z^1$ is —O—, —CO—, —$C(OH)R^8$—, —$C(=N—OR^8)$—, —S—, —SO—, —$SO_2$—, —$N(COR^8)$—, —$N(CO_2R^9)$—, —$N(SO_2R^9)$—, —CO—O—, —O—CO—, —$CO—NR^8$—, —$NR^8$—CO—, —$NR^8$—$CO_2$—, —$NR^8$—CO—NH—, —$NR^8$—$SO_2$—, or —$NR^8$—C(=NH)—NH—, $Z^2$ is —O—, —CO—, —$C(OH)R^8$—, —$C(=N—OR^8)$—, —S—, —SO—, —$SO_2$—, —$NR^8$—, —$N(COR^8)$—, —$N(CO_2R^9)$—, —$N(SO_2R^9)$—, —CO—O—, —O—CO—, —$CO—NR^8$—, —$NR^8$—CO—, —$NR^8$—$CO_2$—, —$NR^8$—CO—NH—, —$NR^8$—C(=NH)—NH—, —$NR^8$—$SO_2$—, or —$SO_2$—$NR^8$—, $(CH_2)_m$ and $(CH_2)_n$ are optionally substituted by 1 to 5 substituents selected from halogen, optionally halogenated $C_{1-4}$ alkyl and hydroxy, and when m or n is not less than 2, a subset —$CH_2CH_2$— of $(CH_2)_m$ and $(CH_2)_n$ is optionally replaced by —CH=CH—, $R^6$ and $R^7$ are the same or different and each is a hydrogen atom or a $C_{1-4}$ alkyl group, or $R^6$ and $R^7$ are bonded to form, together with a nitrogen atom, a 3- to 8-membered saturated or unsaturated aliphatic heterocyclic group, $R^8$ is a hydrogen atom or a $C_{1-4}$ alkyl group, and $R^9$ is a $C_{1-4}$ alkyl group, or (ii) a carbamoyl group optionally having 1 or 2 $C_{1-8}$ alkyl group(s) optionally substituted by substituent(s) selected from substituent group T, wherein the carbamoyl group has two substituents, and they optionally form, together with the adjacent nitrogen atom, a 3- to 8-membered saturated or unsaturated aliphatic heterocyclic group optionally substituted by substituent(s) selected from substituent group T,

[39] the compound of the above-mentioned [17], wherein $B^c$ is a benzene ring optionally substituted by 1 to 4 substituents selected from halogen and optionally halogenated $C_{1-4}$ alkyl;

$C^c$ is a 5- to 8-membered heterocyclic group having 1 to 3 hetero atoms selected from a nitrogen atom, an oxygen atom and a sulfur atom (e.g., pyridyl, pyrimidinyl, 4-piperidyl), which is optionally substituted by 1 to 5 substituents selected from (i) halogen, (ii) $C_{1-4}$ alkyl, (iii) $C_{1-4}$ alkyl-carbonyl, (iv) optionally halogenated $C_{1-4}$ alkoxy-carbonyl, (v) $C_{3-8}$ cycloalkyl-carbonyl, and (vi) a carbamoyl group optionally substituted by substituent(s) selected from (a) optionally halogenated $C_{1-8}$ alkyl, (b) $C_{3-8}$ cycloalkyl, and (c) $C_{6-18}$ aryl optionally substituted by substituent(s) selected from halogen, $C_{1-4}$ alkyl and $C_{1-4}$ alkyloxy;

$R^{1c}$ is (i) a hydrogen atom, (ii) a $C_{2-4}$ alkenyl group optionally substituted by hydroxy, or (iii) a 5- to 8-membered heterocyclic group having 1 to 3 hetero atoms selected from a nitrogen atom, an oxygen atom and a sulfur atom;

$R^{2c}$ is (i) a $C_{1-4}$ alkyl group optionally substituted by substituent(s) selected from (a) halogen, (b) hydroxy, (c) $C_{1-4}$ alkyloxy, (d) carboxy, (e) $C_{1-4}$ alkoxy-carbonyl, (f) —O—$(CH_2)_n$—OH, (g) —O—$(CH_2)_n$—O—$C_{1-4}$ alkyl, (h) —CO—$NR^8$—$(CH_2)_n$—OH, and (i) —$NR^8$—CO—$(CH_2)_n$—$SO_2$—$C_{1-4}$ alkyl wherein n is an integer of 1 to 4, and $R^8$ is a hydrogen atom or a $C_{1-4}$ alkyl group, or (ii) a $C_{6-18}$ aryl-$C_{1-4}$ alkyl group optionally substituted by $C_{1-4}$ alkyl optionally having hydroxy;

$R^{3c}$ is a hydrogen atom or a $C_{1-6}$ alkyl group; or $R^{2c}$ and $R^{3c}$ are optionally bonded to form $C_{2-4}$ alkylene,

[40] the compound of the above-mentioned [17], wherein $B^c$ is a benzene ring optionally substituted by 1 to 4 substituents selected from halogen and $C_{1-4}$ alkyl;

$C^c$ is a 5- to 8-membered heterocyclic group having 1 to 3 hetero atoms selected from a nitrogen atom, an oxygen atom and a sulfur atom, which is optionally substituted by 1 to 5 substituents selected from (i) $C_{1-4}$ alkyl, (ii) $C_{1-4}$ alkyl-carbonyl, (iii) optionally halogenated $C_{1-4}$ alkoxy-carbonyl, (iv) $C_{3-8}$ cycloalkyl-carbonyl, and (v) a carbamoyl group optionally substituted by substituent(s) selected from (a) optionally halogenated $C_{1-8}$ alkyl, (b) $C_{3-8}$ cycloalkyl, and (c) $C_{6-18}$ aryl optionally substituted by halogen;

$R^{1c}$ is a hydrogen atom;

$R^{2c}$ is a $C_{1-4}$ alkyl group optionally substituted by substituent(s) selected from (a) hydroxy, (b) $C_{1-4}$ alkyloxy, (c) —O—$(CH_2)_n$—OH, (d) —O—$(CH_2)_n$—O—$C_{1-4}$ alkyl, and (e) —$NR^8$—CO—$(CH_2)_n$—$SO_2$—$C_{1-4}$ alkyl wherein n is an integer of 1 to 4, and $R^8$ is a hydrogen atom or a $C_{1-4}$ alkyl group;

$R^{3c}$ is a hydrogen atom or a $C_{1-6}$ alkyl group,

[41] the compound of the above-mentioned [40], wherein $R^{2c}$ is a $C_{1-4}$ alkyl group optionally substituted by substituent(s) selected from (a) —O—$(CH_2)_n$—OH, and (b) —O—$(CH_2)_n$—O—$C_{1-4}$ alkyl, wherein n is an integer of 1 to 4,

[42] the compound of the above-mentioned [18], wherein $B^d$ is a benzene ring optionally substituted by halogen;

$C^d$ is a 5- to 8-membered heterocyclic group having 1 to 3 hetero atoms selected from a nitrogen atom, an oxygen atom and a sulfur atom;

$R^{1d}$ is a hydrogen atom;

$R^{2d}$ is (i) $C_{1-4}$ alkyl optionally substituted by substituent(s) selected from (a) $C_{1-4}$ alkyloxy, (b) —O—$(CH_2)_n$—OH, and (c) —$NR^8$—CO—$(CH_2)_n$—$SO_2$—$C_{1-4}$ alkyl wherein n is an integer of 1 to 4, and $R^8$ is a hydrogen atom or a $C_{1-4}$ alkyl group, or (ii) a 5- to 8-membered heterocycle-$C_{1-4}$ alkyl group having 1 to 3 hetero atoms selected from a nitrogen atom, an oxygen atom and a sulfur atom, which is optionally substituted by substituent(s) selected from
(a) carboxy, and
(b) $C_{1-4}$ alkoxy-carbonyl;
$R^{3d}$ is a hydrogen atom or a $C_{1-6}$ alkyl group; and
$Z^d$ is a $C_{1-3}$ alkylene group,
[43] the compound of the above-mentioned [18], wherein
$B^d$ is a benzene ring optionally substituted by halogen;
$C^d$ is a 5- to 8-membered heterocyclic group having 1 to 3 hetero atoms selected from a nitrogen atom, an oxygen atom and a sulfur atom;
$R^{1d}$ is a hydrogen atom;
$R^{2d}$ is a $C_{1-4}$ alkyl group optionally substituted by $C_{1-4}$ alkyloxy;
$R^{3d}$ is a hydrogen atom or a $C_{1-6}$ alkyl group; and
$Z^d$ is a methylene group,
[44] the compound of the above-mentioned [19], wherein
$R^{2d}$ is (i) a $C_{1-8}$ alkyl group, a $C_{2-8}$ alkenyl group, a $C_{2-8}$ alkynyl group, a $C_{1-8}$ alkyl-carbonyl group, a $C_{1-8}$ alkyl-sulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocycle-$C_{1-4}$ alkyl group, a heterocycle-carbonyl group or a heterocycle-$C_{1-4}$ alkyl-carbonyl group, each of which is optionally substituted by 1 to 5 substituents selected from the group (substituent group T) consisting of
(a) halogen,
(b) oxo,
(c) optionally halogenated $C_{1-4}$ alkyl,
(d) —$(CH_2)_m$-Q,
(e) —$(CH_2)_m$—$Z^1$-(optionally halogenated $C_{1-4}$ alkyl),
(f) —$(CH_2)_m$—$Z^1$—$C_{3-8}$ cycloalkyl,
(g) —$(CH_2)_m$—$Z^2$—$(CH_2)_n$-Q,
(h) —$(CH_2)_m$—$Z^2$—$(CH_2)_n$—$Z^1$-(optionally halogenated $C_{1-4}$ alkyl),
(i) —$(CH_2)_m$—$Z^2$-$(CH_2)_n$—$Z^1$—$C_{3-8}$ cycloalkyl,
(j) —$(CH_2)_m$—$Z^1$-(optionally substituted heterocyclic group)
(preferably, said heterocyclic group is a 5- to 8-membered heterocyclic group having 1 to 3 hetero atoms selected from a nitrogen atom, an oxygen atom and an optionally oxidized sulfur atom),
(k) —$(CH_2)_m$—$Z^2$—$C_{1-4}$ alkoxy, and
(l) —$(CH_2)_m$—$Z^2$—$(CH_2)_n$—$Z^1$—$(CH_2)_n$—$Z^1$—$C_{1-4}$ alkyl
wherein m is an integer of 0 to 4, n is an integer of 1 to 4,
Q is hydroxy, carboxy, cyano, nitro, —$NR^6R^7$, —$CONR^6R^7$ or —$SO_2NR^6R^7$,
$Z^1$ is —O—, —CO—, —$C(OH)R^8$—, —$C(=N-OR^8)$—, —S—, —SO—, —$SO_2$—, —$N(COR^8)$—, —$N(CO_2R^9)$—, —$N(SO_2R^9)$—, —CO—O—, —O—CO—, —CO—$NR^8$—, —$NR^8$—CO—, —$NR^8$—$CO_2$—, —$NR^8$—CO—NH—, —$NR^8$—$SO_2$—, or —$NR^8$—$C(=NH)$—NH—,
$Z^2$ is —O—, —CO—, —$C(OH)R^8$—, —$C(=N-OR^8)$—, —S—, —SO—, —$SO_2$—, —$NR^8$—, —$N(COR^8)$—, —$N(CO_2R^9)$—, —$N(SO_2R^9)$—, —CO—O—, —O—CO—, —CO—$NR^8$—, —$NR^8$—CO—, —$NR^8$—$CO_2$—, —$NR^8$—CO—NH—, —$NR^8$—$C(=NH)$—NH—, —$NR^8$—$SO_2$—, or —$SO_2$—$NR^8$—,
$(CH_2)_m$ and $(CH_2)_n$ are optionally substituted by 1 to 5 substituents selected from halogen, optionally halogenated $C_{1-4}$ alkyl and hydroxy, and when m or n is not less than 2, a subset —$CH_2CH_2$— of $(CH_2)_m$ and $(CH_2)_n$ is optionally replaced by —CH=CH—, $R^6$ and $R^7$ are the same or different and each is a hydrogen atom or a $C_{1-4}$ alkyl group, or $R^6$ and $R^7$ are bonded to form, together with a nitrogen atom, a 3- to 8-membered saturated or unsaturated aliphatic heterocyclic group,
$R^8$ is a hydrogen atom or a $C_{1-4}$ alkyl group, and $R^9$ is a $C_{1-4}$ alkyl group, or
(ii) a carbamoyl group optionally having 1 or 2 $C_{1-8}$ alkyl group(s) optionally substituted by substituent(s) selected from substituent group T,
wherein the carbamoyl group has two substituents, and they optionally form, together with the adjacent nitrogen atom, a 3- to 8-membered saturated or unsaturated aliphatic heterocyclic group optionally substituted by substituent(s) selected from substituent group T,
[45] the compound of the above-mentioned [19], wherein
$B^e$ is a benzene ring optionally substituted by halogen;
$C^e$ is a phenyl group optionally substituted by optionally halogenated $C_{1-4}$ alkyl;
$R^{2e}$ is a $C_{1-4}$ alkyl group optionally substituted by —O—$(CH_2)_n$—OH
wherein n is an integer of 1 to 4,
[46] the compound of the above-mentioned [19], wherein
$B^e$ is a benzene ring optionally substituted by halogen;
$C^e$ is a phenyl group optionally substituted by optionally halogenated $C_{1-4}$ alkyl;
$R^{2e}$ is a $C_{1-4}$ alkyl group substituted by —O—$(CH_2)_n$—OH
wherein n is an integer of 1 to 4,
[47] the compound of the above-mentioned [20], wherein
$R^{2f}$ is (i) a $C_{1-8}$ alkyl group, a $C_{2-8}$ alkenyl group, a $C_{2-8}$ alkynyl group, a $C_{1-8}$ alkyl-carbonyl group, a $C_{1-8}$ alkyl-sulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocycle-$C_{1-4}$ alkyl group, a heterocycle-carbonyl group or a heterocycle-$C_{1-4}$ alkyl-carbonyl group, each of which is optionally substituted by 1 to 5 substituents selected from the group (substituent group T) consisting of
(a) halogen,
(b) oxo,
(c) optionally halogenated $C_{1-4}$ alkyl,
(d) —$(CH_2)_m$-Q,
(e) —$(CH_2)_m$—$Z^1$-(optionally halogenated $C_{1-4}$ alkyl),
(f) —$(CH_2)_m$—$Z^1$—$C_{3-8}$ cycloalkyl,
(g) —$(CH_2)_m$—$Z^2$—$(CH_2)_n$-Q,
(h) —$(CH_2)_m$—$Z^2$—$(CH_2)_n$—$Z^1$-(optionally halogenated $C_{1-4}$ alkyl),
(i) —$(CH_2)_m$—$Z^2$—$(CH_2)_n$—$Z^1$—$C_{3-8}$ cycloalkyl,
(j) —$(CH_2)_m$—$Z^1$-(optionally substituted heterocyclic group)
(preferably, said heterocyclic group is a 5- to 8-membered heterocyclic group having 1 to 3 hetero atoms selected from a nitrogen atom, an oxygen atom and an optionally oxidized sulfur atom),
(k) —$(CH_2)_m$—$Z^2$—$C_{1-4}$ alkoxy, and
(l) —$(CH_2)_m$—$Z^2$—$(CH_2)_n$—$Z^1$—$(CH_2)_n$—$Z^1$—$C_{1-4}$ alkyl
wherein m is an integer of 0 to 4, n is an integer of 1 to 4,
Q is hydroxy, carboxy, cyano, nitro, —$NR^6R^7$, —$CONR^6R^7$ or —$SO_2NR^6R^7$,
$Z^1$ is —O—, —CO—, —$C(OH)R^8$—, —$C(=N-OR^8)$—, —S—, —SO—, —$SO_2$—, —$N(COR^8)$—, —$N(CO_2R^9)$—, —$N(SO_2R^9)$—, —CO—O—, —O—CO—, —CO—$NR^8$—, —$NR^8$—CO—, —$NR^8$—$CO_2$—, —$NR^8$—CO—NH—, —$NR^8$—$SO_2$—, or —$NR^8$—$C(=NH)$—NH—,
$Z^2$ is —O—, —CO—, —$C(OH)R^8$—, —$C(=N-OR^8)$—, —S—, —SO—, —$SO_2$—, —$NR^8$—, —$N(COR^8)$—, —N(CO$_2$R$^9$)—, —N(SO$_2$R$^9$)—, —CO—O—, —O—CO—, —CO—NR$^8$—, —NR$^8$—CO—, —NR$^8$—CO$_2$—, —NR$^8$—CO—NH—, —NR$^8$—SO$_2$—, or —SO$_2$—NR$^8$—, (CH$_2$)$_m$ and (CH$_2$)$_n$ are optionally substituted by 1 to 5 substituents selected from halogen, optionally halogenated C$_{1-4}$ alkyl and hydroxy, and when m or n is not less than 2, a subset —CH$_2$CH$_2$— of (CH$_2$)$_m$ and (CH$_2$)$_n$ is optionally replaced by —CH=CH—, R$^6$ and R$^7$ are the same or different and each is a hydrogen atom or a C$_{1-4}$ alkyl group, or R$^6$ and R$^7$ are bonded to form, together with a nitrogen atom, a 3- to 8-membered saturated or unsaturated aliphatic heterocyclic group, R$^8$ is a hydrogen atom or a C$_{1-4}$ alkyl group, and R$^9$ is a C$_{1-4}$ alkyl group, or (ii) a carbamoyl group optionally having 1 or 2 C$_{1-8}$ alkyl group(s) optionally substituted by substituent(s) selected from substituent group T, wherein the carbamoyl group has two substituents, and they optionally form, together with the adjacent nitrogen atom, a 3- to 8-membered saturated or unsaturated aliphatic heterocyclic group optionally substituted by substituent(s) selected from substituent group T,

[48] the compound of the above-mentioned [20], wherein

B$^f$ is a benzene ring optionally substituted by halogen;

C$^f$ is a phenyl group optionally substituted by halogen;

R$^{2f}$ is (i) a C$_{1-4}$ alkyl group optionally substituted by 1 to 5 substituents selected from the group consisting of (a) hydroxy, (b) —O—(CH$_2$)$_n$—OH, (c) —NR$^8$—(CH$_2$)$_n$—O—C$_{1-4}$ alkyl, (d) —NR$^8$—(CH$_2$)$_n$-heterocyclic group (preferably, said heterocyclic group is a 5- to 8-membered heterocyclic group having 1 to 3 hetero atoms selected from a nitrogen atom, an oxygen atom and a sulfur atom), and (e) —NR$^8$—(CH$_2$)$_n$—SO$_2$—C$_{1-4}$ alkyl, wherein n is an integer of 1 to 4, and R$^8$ is a hydrogen atom or a C$_{1-4}$ alkyl group, (ii) a C$_{6-18}$ aryl group optionally substituted by 1 to 5 substituents selected from the group consisting of (a) C$_{1-4}$ alkyl optionally substituted by substituent(s) selected from hydroxy, —NR$^8$—(CH$_2$)$_n$—OH, —NR$^8$—(CH$_2$)$_n$—O—C$_{1-4}$ alkyl, —NR$^8$—(CH$_2$)$_n$-heterocyclic group (preferably, said heterocyclic group is a 5- to 8-membered heterocyclic group having 1 to 3 hetero atoms selected from a nitrogen atom, an oxygen atom and a sulfur atom) and —NR$^8$—(CH$_2$)$_n$—SO$_2$—C$_{1-4}$ alkyl, and (b) —CO—NR$^8$—(CH$_2$)$_n$—O—C$_{1-4}$ alkyl, wherein n is an integer of 1 to 4, and R$^8$ is a hydrogen atom or a C$_{1-4}$ alkyl group, or (iii) a C$_{6-18}$ aryl-C$_{1-4}$ alkyl group optionally substituted by 1 to 5 substituents selected from the group consisting of (a) carboxy, (b) C$_{1-4}$ alkoxy-carbonyl, and (c) —CO—NR$^8$—(CH$_2$)$_n$—O—C$_{1-4}$ alkyl, wherein n is an integer of 1 to 4, and R$^8$ is a hydrogen atom or a C$_{1-4}$ alkyl group;

R$^{3f}$ is a hydrogen atom or a C$_{1-6}$ alkyl group; or

R$^{2f}$ and R$^{3f}$ are optionally bonded to form C$_{2-4}$ alkylene; and

Z$^f$ is a C$_{1-3}$ alkylene group,

[49] the compound of the above-mentioned [20], wherein

B$^f$ is a benzene ring optionally substituted by halogen;

C$^f$ is a phenyl group optionally substituted by halogen;

R$^{2f}$ is a C$_{1-4}$ alkyl group optionally substituted by 1 to 5 substituents selected from the group consisting of (a) hydroxy, and (b) —O—(CH$_2$)$_n$—OH wherein n is an integer of 1 to 4;

R$^{3f}$ is a hydrogen atom or a C$_{1-6}$ alkyl group; and

Z$^f$ is methylene,

[50] the compound of the above-mentioned [49], wherein

R$^{2f}$ is a C$_{1-4}$ alkyl group substituted by —O—(CH$_2$)$_n$—OH wherein n is an integer of 1 to 4,

[51] the compound of the above-mentioned [21], wherein

R$^{2g}$ is (i) a C$_{1-8}$ alkyl group, a C$_{2-8}$ alkenyl group, a C$_{2-8}$ alkynyl group, a C$_{1-8}$ alkyl-carbonyl group, a C$_{1-8}$ alkyl-sulfonyl group, a C$_{3-8}$ cycloalkyl group, a C$_{6-18}$ aryl group, a C$_{6-18}$ aryl-C$_{1-4}$ alkyl group, a C$_{6-18}$ aryl-carbonyl group, a C$_{6-18}$ aryl-C$_{1-4}$ alkyl-carbonyl group, a C$_{6-18}$ aryl-sulfonyl group, a heterocyclic group, a heterocycle-C$_{1-4}$ alkyl group, a heterocycle-carbonyl group or a heterocycle-C$_{1-4}$ alkyl-carbonyl group, each of which is optionally substituted by 1 to 5 substituents selected from the group (substituent group T) consisting of (a) halogen, (b) oxo, (c) optionally halogenated C$_{1-4}$ alkyl, (d) —(CH$_2$)$_m$-Q, (e) —(CH$_2$)$_m$—Z$^1$-(optionally halogenated C$_{1-4}$ alkyl), (f) —(CH$_2$)$_m$—Z$^1$—C$_{3-8}$ cycloalkyl, (g) —(CH$_2$)$_m$—Z$^2$—(CH$_2$)$_n$-Q, (h) —(CH$_2$)$_m$—Z$^2$—(CH$_2$)$_n$—Z$^1$-(optionally halogenated C$_{1-4}$ alkyl), (i) —(CH$_2$)$_m$—Z$^2$—(CH$_2$)$_n$—Z$^1$—C$_{3-8}$ cycloalkyl, (j) —(CH$_2$)$_m$—Z$^1$-(optionally substituted heterocyclic group)

(preferably, said heterocyclic group is a 5- to 8-membered heterocyclic group having 1 to 3 hetero atoms selected from a nitrogen atom, an oxygen atom and an optionally oxidized sulfur atom), (k) —(CH$_2$)$_m$—Z$^2$—C$_{1-4}$ alkoxy, and (l) —(CH$_2$)$_m$—Z$^2$—(CH$_2$)$_n$—Z$^1$—(CH$_2$)$_n$—Z$^1$—C$_{1-4}$ alkyl wherein m is an integer of 0 to 4, n is an integer of 1 to 4, Q is hydroxy, carboxy, cyano, nitro, —NR$^6$R$^7$, —CONR$^6$R$^7$ or —SO$_2$NR$^6$R$^7$, Z$^1$ is —O—, —CO—, —C(OH)R$^8$—, —C(=N—OR$^8$)—, —S—, —SO—, —SO$_2$—, —N(COR$^8$)—, —N(CO$_2$R$^9$)—, —N(SO$_2$R$^8$)—, —CO—O—, —O—CO—, —CO—NR$^8$—, —NR$^8$—CO—, —NR$^8$—CO$_2$—, —NR$^8$—CO—NH—, —NR$^8$—SO$_2$—, or —NR$^8$—C(=NH)—NH—, Z$^2$ is —O—, —CO—, —C(OH)R$^8$—, —C(=N—OR$^8$)—, —S—, —SO—, —SO$_2$—, —NR$^8$—, —N(COR$^8$)—, —N(CO$_2$R$^9$)—, —N(SO$_2$R$^8$)—, —CO—O—, —O—CO—, —CO—NR$^8$—, —NR$^8$—CO—, —NR$^8$—CO$_2$—, —NR$^8$—CO—NH—, —NR$^8$—C(=NH)—NH—, —NR$^8$—SO$_2$—, or —SO$_2$—NR$^8$—, (CH$_2$)$_m$ and (CH$_2$)$_n$ are optionally substituted by 1 to 5 substituents selected from halogen, optionally halogenated C$_{1-4}$ alkyl and hydroxy, and when m or n is not less than 2, a subset —CH$_2$CH$_2$— of (CH$_2$)$_m$ and (CH$_2$)$_n$ is optionally replaced by —CH=CH—, R$^6$ and R$^7$ are the same or different and each is a hydrogen atom or a C$_{1-4}$ alkyl group, or R$^6$ and R$^7$ are bonded to form, together with a nitrogen atom, a 3- to 8-membered saturated or unsaturated aliphatic heterocyclic group, R$^8$ is a hydrogen atom or a C$_{1-4}$ alkyl group, and R$^9$ is a C$_{1-4}$ alkyl group, or (ii) a carbamoyl group optionally having 1 or 2 C$_{1-8}$ alkyl group(s) optionally substituted by substituent(s) selected from substituent group T, wherein the carbamoyl group has two substituents, and they optionally form, together with the adjacent nitrogen atom, a 3- to 8-membered saturated or unsaturated aliphatic heterocyclic group optionally substituted by substituent(s) selected from substituent group T,

[52] the compound of the above-mentioned [21], wherein
$B^g$ is a benzene ring optionally substituted by $C_{1-4}$ alkyl;
$C^g$ is a 5- to 8-membered heterocyclic group having 1 to 3 hetero atoms selected from a nitrogen atom, an oxygen atom and a sulfur atom, which is optionally substituted by $C_{1-4}$ alkyl $R^{2g}$ is
(i) a $C_{1-4}$ alkyl group optionally substituted by hydroxy,
(ii) a $C_{6-18}$ aryl group optionally substituted by substituent(s) selected from
(a) nitro,
(b) amino,
(c) —CO—$NR^8$—$(CH_2)_n$—O—$C_{1-4}$ alkyl,
(d) —$NR^8$—CO—$(CH_2)_n$—O—$C_{1-4}$ alkyl,
(e) —$NR^8$—CO—$(CH_2)_n$—$NR^6R^7$,
(f) —$NR^8$—CO—$(CH_2)_n$—COOH
(g) —$NR^8$—CO—$(CH_2)_n$—$CO_2$—$C_{1-4}$ alkyl, and
(h) —$NR^8$—CO—$(CH_2)_n$—O—$(CH_2)_n$—O—$C_{1-4}$ alkyl,
wherein m is an integer of 0 to 4, n is an integer of 1 to 4, $R^6$ and $R^7$ are the same or different and each is a hydrogen atom or a $C_{1-4}$ alkyl group, and $R^8$ is a hydrogen atom or a $C_{1-4}$ alkyl group, or
(iii) a $C_{6-18}$ aryl-$C_{1-4}$ alkyl group optionally substituted by substituent(s) selected from
(a) carboxy,
(b) $C_{1-4}$ alkoxy-carbonyl, and
(c) —CO—$NR^8$—$(CH_2)_n$—O—$C_{1-4}$ alkyl,
wherein n is an integer of 1 to 4, and $R^8$ is a hydrogen atom or a $C_{1-4}$ alkyl group;
$R^{3g}$ is a hydrogen atom or a $C_{1-6}$ alkyl group; or
$R^{2g}$ and $R^{3g}$ are optionally bonded to form $C_{2-4}$ alkylene,
[53] the compound of the above-mentioned [21], wherein $R^{2g}$ is
(i) a $C_{6-18}$ aryl group optionally substituted by substituent(s) selected from
(a) nitro,
(b) amino,
(c) —CO—$NR^8$—$(CH_2)_n$—O—$C_{1-4}$ alkyl,
(d) —$NR^8$—CO—$(CH_2)_n$—O—$C_{1-4}$ alkyl,
(e) —$NR^8$—CO—$(CH_2)_n$—$NR^6R^7$,
(f) —$NR^8$—CO—$(CH_2)_n$—COOH
(g) —$NR^8$—CO—$(CH_2)_n$—$CO_2$—$C_{1-4}$ alkyl, and
(h) —$NR^8$—CO—$(CH_2)_n$—O—$(CH_2)_n$—O—$C_{1-4}$ alkyl,
wherein m is an integer of 0 to 4, n is an integer of 1 to 4, $R^6$ and $R^7$ are the same or different and each is a hydrogen atom or a $C_{1-4}$ alkyl group, and $R^8$ is a hydrogen atom or a $C_{1-4}$ alkyl group, or
(ii) a $C_{6-18}$ aryl-$C_{1-4}$ alkyl group substituted by substituent(s) selected from
(a) carboxy,
(b) $C_{1-4}$ alkoxy-carbonyl, and
(c) —CO—$NR^8$—$(CH_2)_n$—O—$C_{1-4}$ alkyl,
wherein n is an integer of 1 to 4, and $R^8$ is a hydrogen atom or a $C_{1-4}$ alkyl group,
[54] the compound of the above-mentioned [1], wherein A is a $C_{6-18}$ aryl group substituted by substituent(s) selected from
(i) a phenyloxy group optionally substituted by 1 to 5 substituents selected from
(a) halogen,
(b) optionally halogenated $C_{1-4}$ alkyl,
(c) hydroxy-$C_{1-4}$ alkyl,
(d) heterocycle-$C_{1-4}$ alkyl (preferably, 5- to 8-membered heterocycle-$C_{1-4}$ alkyl, said 5- to 8-membered heterocycle has 1 to 3 hetero atoms selected from a nitrogen atom, an oxygen atom and an optionally oxidized sulfur atom, such as imidazolyl, triazolyl and the like),
(e) optionally halogenated $C_{1-4}$ alkyloxy,
(f) $C_{1-4}$ alkyl-carbonyl,
(g) cyano,
(h) carbamoyl optionally substituted by $C_{1-8}$ alkyl, and
(i) $C_{1-4}$ alkoxy-carbonyl,
(ii) a phenyl-$C_{1-3}$ alkyloxy group optionally substituted by 1 to 5 substituents selected from
(a) halogen,
(b) optionally halogenated $C_{1-4}$ alkyl,
(c) hydroxy-$C_{1-4}$ alkyl,
(d) heterocycle-$C_{1-4}$ alkyl (preferably, 5- to 8-membered heterocycle-$C_{1-4}$ alkyl, said 5- to 8-membered heterocycle has 1 to 3 hetero atoms selected from a nitrogen atom, an oxygen atom and an optionally oxidized sulfur atom, such as imidazolyl, triazolyl and the like),
(e) optionally halogenated $C_{1-4}$ alkyloxy,
(f) $C_{1-4}$ alkyl-carbonyl,
(g) cyano,
(h) carbamoyl optionally substituted by $C_{1-8}$ alkyl, and
(i) $C_{1-4}$ alkoxy-carbonyl,
(iii) a 5- to 8-membered heterocyclooxy group containing 1 to 3 hetero atoms selected from a nitrogen atom, an oxygen atom and a sulfur atom, which is optionally substituted by 1 to 5 substituents selected from
(a) halogen,
(b) optionally halogenated $C_{1-4}$ alkyl,
(c) hydroxy-$C_{1-4}$ alkyl,
(d) heterocycle-$C_{1-4}$ alkyl (preferably, 5- to 8-membered heterocycle-$C_{1-4}$ alkyl, said 5- to 8-membered heterocycle has 1 to 3 hetero atoms selected from a nitrogen atom, an oxygen atom and an optionally oxidized sulfur atom, such as imidazolyl, triazolyl and the like),
(e) optionally halogenated $C_{1-4}$ alkyloxy,
(f) $C_{1-4}$ alkyl-carbonyl,
(g) cyano,
(h) carbamoyl optionally substituted by $C_{1-8}$ alkyl, and
(i) $C_{1-4}$ alkoxy-carbonyl, and
(iv) 5- to 8-membered heterocycle-$C_{1-3}$ alkyloxy containing 1 to 3 hetero atoms selected from a nitrogen atom, an oxygen atom and a sulfur atom, which is optionally substituted by 1 to 5 substituents selected from
(a) halogen,
(b) optionally halogenated $C_{1-4}$ alkyl,
(c) hydroxy-$C_{1-4}$ alkyl,
(d) heterocycle-$C_{1-4}$ alkyl (preferably, 5- to 8-membered heterocycle-$C_{1-4}$ alkyl, said 5- to 8-membered heterocycle has 1 to 3 hetero atoms selected from a nitrogen atom, an oxygen atom and an optionally oxidized sulfur atom, such as imidazolyl, triazolyl and the like),
(e) optionally halogenated $C_{1-4}$ alkyloxy,
(f) $C_{1-4}$ alkyl-carbonyl,
(g) cyano,
(h) carbamoyl optionally substituted by $C_{1-8}$ alkyl, and
(i) $C_{1-4}$ alkoxy-carbonyl;
wherein the $C_{6-18}$ aryl group is optionally further substituted by 1 to 4 substituents selected from halogen, $C_{1-4}$ alkyl, hydroxy-$C_{1-4}$ alkyl and $C_{1-4}$ alkyloxy;
$R^1$ is
(i) a hydrogen atom,
(ii) a cyano group, or
(iii) a $C_{1-4}$ alkyl group or a $C_{2-4}$ alkenyl group, each of which is optionally substituted by —$NR^8$—CO—$(CH_2)_n$—$NR^6R^7$
wherein n is an integer of 1 to 4, $R^6$ and $R^7$ are the same or different and each is a hydrogen atom or a $C_{1-4}$ alkyl group, R⁸ is a hydrogen atom or a $C_{1-4}$ alkyl group, and when n is not less than 2, a subset —$CH_2CH_2$— of $(CH_2)_n$ is optionally replaced by —CH=CH—;

$R^2$ is a $C_{1-8}$ alkyl group, a $C_{2-8}$ alkenyl group or a $C_{2-8}$ alkynyl group, each of which is optionally substituted by substituent(s) selected from
(a) hydroxy,
(b) carboxy,
(c) cyano,
(d) optionally halogenated $C_{1-4}$ alkyloxy,
(e) —O—$(CH_2)_n$—OH,
(f) —O—$(CH_2)_n$—O—CO—$NH_2$,
(g) —O—$(CH_2)_n$—O-(optionally halogenated $C_{1-4}$ alkyl),
(h) —O—$(CH_2)_n$—$SO_2$-(optionally halogenated $C_{1-4}$ alkyl),
(i) —O—$(CH_2)_n$—$SO_2$—$C_{6-18}$ aryl,
(j) —O—$(CH_2)_n$—$SO_2$—$(CH_2)_n$—OH,
(k) —O—$(CH_2)_n$—$NR^8$—CO—$C_{1-4}$ alkyl,
(l) —O—$(CH_2)_n$—$NR^8$—CO—$(CH_2)_n$—$SO_2$—$C_{1-4}$ alkyl,
(m) —O—$(CH_2)_n$—$NR^8$—$SO_2$-(optionally halogenated $C_{1-4}$ alkyl),
(n) —CO—$NR^8$—$(CH_2)_n$—OH,
(o) —CO—$NR^8$—$(CH_2)_n$—$SO_2$-(optionally halogenated $C_{1-4}$ alkyl),
(p) —CO—$NR^8$—O—$C_{1-4}$ alkyl,
(q) —$NR^6R^7$,
(r) —$NR^8$—$(CH_2)_n$—OH,
(s) —$NR^8$—$(CH_2)_n$—$SO_2$—$C_{1-4}$ alkyl,
(t) —$NR^8$—CO-(optionally halogenated $C_{1-4}$ alkyl),
(u) —$NR^8$—CO—$(CH_2)_n$—OH,
(v) —$NR^8$—CO—$(CH_2)_n$—CN,
(w) —$NR^8$—CO—$(CH_2)_n$—$NR^6R^7$,
(x) —$NR^8$—CO—$(CH_2)_n$—O—$C_{1-4}$ alkyl,
(y) —$NR^8$—CO—$(CH_2)_n$—SO-(optionally halogenated $C_{1-4}$ alkyl),
(z) —$NR^8$—CO—$(CH_2)_n$—$SO_2$-(optionally halogenated $C_{1-4}$ alkyl),
(aa) —$NR^8$—CO—$(CH_2)_n$—$SO_2$—$C_{3-8}$ cycloalkyl,
(bb) —$NR^8$—CO—$(CH_2)_n$—$NR^8$—$SO_2$—$C_{1-4}$ alkyl,
(cc) —$NR^8$—$CO_2$—$(CH_2)_n$—$SO_2$—$C_{1-4}$ alkyl,
(dd) —$NR^8$—CO—NH—$(CH_2)_n$—$SO_2$—$C_{1-4}$ alkyl,
(ee) —$NR^8$—CO—NH—O—$C_{1-4}$ alkyl,
(ff) —$NR^8$—CO—NH—$(CH_2)_n$—O—$C_{1-4}$ alkyl,
(gg) —$NR^8$—C(=NH)—NH—$C_{1-4}$ alkyl,
(hh) —$NR^8$—$SO_2$—$(CH_2)_n$—$SO_2$—$C_{1-4}$ alkyl,
(ii) —S—$(CH_2)_n$—OH,
(jj) —SO—$(CH_2)_n$—OH,
(kk) —$SO_2$—$(CH_2)_n$—OH, and
(ll) —$NR^8$—CO-(optionally substituted heterocyclic group)
(preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—O—$C_{1-4}$ alkyl, —CO—NH—$C_{1-4}$ alkyl, —$CONH_2$, —$SO_2$—$C_{1-4}$ alkyl, —$SO_2$—NH—$C_{1-4}$ alkyl, —$SO_2NH_2$ and the like)
wherein n is an integer of 1 to 4, $R^6$ and $R^7$ are the same or different and each is a hydrogen atom or a $C_{1-4}$ alkyl group, $R^8$ is a hydrogen atom or a $C_{1-4}$ alkyl group, $(CH_2)_n$ is optionally substituted by halogenated $C_{1-4}$ alkyl or hydroxy, and when n is not less than 2, a subset —$CH_2CH_2$— of $(CH_2)_n$ is optionally replaced by —CH=CH—;
$R^3$ is a hydrogen atom or a $C_{1-6}$ alkyl group; or,
$R^1$ and $R^2$ are optionally bonded to form

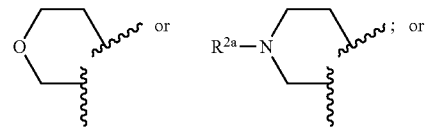

$R^2$ and $R^3$ are optionally bonded to form $C_{2-4}$ alkylene optionally substituted by an imino group.

Particularly preferably, $R^2$ is a $C_{1-8}$ alkyl group, a $C_{2-8}$ alkenyl group or a $C_{2-8}$ alkynyl group (particularly $C_{1-8}$ alkyl group), each of which is optionally substituted by substituent(s) selected from
(a) hydroxy,
(b) carboxy,
(c) cyano,
(d) optionally halogenated $C_{1-4}$ alkyloxy,
(e) —O—$(CH_2)_n$—OH (wherein $(CH_2)_n$ is optionally substituted by hydroxy),
(f) —O—$(CH_2)_n$—O—CO—$NH_2$,
(g) —O—$(CH_2)_n$—O-(optionally halogenated $C_{1-4}$ alkyl),
(h) —O—$(CH_2)_n$—$SO_2$-(optionally halogenated $C_{1-4}$ alkyl),
(i) —O—$(CH_2)_n$—$SO_2$—$C_{6-18}$ aryl,
(j) —O—$(CH_2)_n$—$SO_2$—$(CH_2)_n$—OH,
(k) —O—$(CH_2)_n$—$NR^8$—CO—$C_{1-4}$ alkyl,
(l) —O—$(CH_2)_n$—$NR^8$—CO—$(CH_2)_n$—$SO_2$—$C_{1-4}$ alkyl,
(m) —O—$(CH_2)_n$—$NR^8$—$SO_2$-(optionally halogenated $C_{1-4}$ alkyl),
(n) —CO—$NR^8$—$(CH_2)_n$—OH,
(o) —CO—$NR^8$—$(CH_2)_n$—$SO_2$-(optionally halogenated $C_{1-4}$ alkyl),
(p) —CO—$NR^8$—O—$C_{1-4}$ alkyl,
(q) —$NR^6R^7$,
(r) —$NR^8$—$(CH_2)_n$—OH,
(s) —$NR^8$—$(CH_2)_n$—$SO_2$—$C_{1-4}$ alkyl,
(t) —$NR^8$—CO-(optionally halogenated $C_{1-4}$ alkyl),
(u) —$NR^8$—CO—$(CH_2)_n$—OH (wherein $(CH_2)_n$ is optionally substituted by optionally halogenated $C_{1-4}$ alkyl or hydroxy),
(v) —$NR^8$—CO—$(CH_2)_n$—CN,
(w) —$NR^8$—CO—$(CH_2)_n$—$NR^6R^7$ (when n is not less than 2, a subset —$CH_2CH_2$— of $(CH_2)_n$ is optionally replaced by —CH=CH—),
(x) —$NR^8$—CO—$(CH_2)_n$—O—$C_{1-4}$ alkyl,
(y) —$NR^8$—CO—$(CH_2)_n$—SO-(optionally halogenated $C_{1-4}$ alkyl),
(z) —$NR^8$—CO—$(CH_2)_n$—$SO_2$-(optionally halogenated $C_{1-4}$ alkyl)
(wherein $(CH_2)_n$ is optionally substituted by $C_{1-4}$ alkyl),
(aa) —$NR^8$—CO—$(CH_2)_n$—$SO_2$—$C_{3-8}$ cycloalkyl,
(bb) —$NR^8$—CO—$(CH_2)_n$—$NR^8$—$SO_2$—$C_{1-4}$ alkyl,
(cc) —$NR^8$—$CO_2$—$(CH_2)_n$—$SO_2$—$C_{1-4}$ alkyl,
(dd) —$NR^8$—CO—NH—$(CH_2)_n$—$SO_2$—$C_{1-4}$ alkyl,
(ee) —$NR^8$—CO—NH—O—$C_{1-4}$ alkyl,
(ff) —$NR^8$—CO—NH—$(CH_2)_n$—O—$C_{1-4}$ alkyl,
(gg) —$NR^8$—C(=NH)—NH—$C_{1-4}$ alkyl,
(hh) —$NR^8$—$SO_2$—$(CH_2)_n$—$SO_2$—$C_{1-4}$ alkyl,
(ii) —S—$(CH_2)_n$—OH,
(jj) —SO—$(CH_2)_n$—OH,
(kk) —$SO_2$—$(CH_2)_n$—OH, and
(ll) —$NR^8$—CO-(optionally substituted heterocyclic group)
(preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—O—$C_{1-4}$ alkyl, —CO—NH—$C_{1-4}$ alkyl, —CONH$_2$, —SO$_2$—$C_{1-4}$ alkyl, —SO$_2$—NH—$C_{1-4}$ alkyl, —SO$_2$NH$_2$ and the like),
wherein n is an integer of 1 to 4, $R^6$ and $R^7$ are the same or different and each is a hydrogen atom or a $C_{1-4}$ alkyl group, and $R^8$ is a hydrogen atom or a $C_{1-4}$ alkyl group,

[55] the compound of the above-mentioned [1], wherein
A is a $C_{6-18}$ aryl group substituted by substituent(s) selected from
(i) a phenyloxy group substituted by 1 to 5 substituents selected from
(a) halogen,
(b) optionally halogenated $C_{1-4}$ alkyl,
(c) hydroxy-$C_{1-4}$ alkyl,
(d) heterocycle-$C_{1-4}$ alkyl (preferably, 5- to 8-membered heterocycle-$C_{1-4}$ alkyl, said 5- to 8-membered heterocycle has 1 to 3 hetero atoms selected from a nitrogen atom, an oxygen atom and an optionally oxidized sulfur atom, such as imidazolyl and the like),
(e) optionally halogenated $C_{1-4}$ alkyloxy,
(f) cyano,
(g) carbamoyl optionally substituted by $C_{1-8}$ alkyl, and
(h) $C_{1-4}$ alkoxy-carbonyl,
(ii) a phenyl-$C_{1-3}$ alkyloxy group substituted by 1 to 5 substituents selected from
(a) halogen,
(b) optionally halogenated $C_{1-4}$ alkyl,
(c) hydroxy-$C_{1-4}$ alkyl,
(d) heterocycle-$C_{1-4}$ alkyl (preferably, 5- to 8-membered heterocycle-$C_{1-4}$ alkyl, said 5- to 8-membered heterocycle has 1 to 3 hetero atoms selected from a nitrogen atom, an oxygen atom and an optionally oxidized sulfur atom, such as imidazolyl and the like),
(e) optionally halogenated $C_{1-4}$ alkyloxy,
(f) cyano,
(g) carbamoyl optionally substituted by $C_{1-8}$ alkyl, and
(h) $C_{1-4}$ alkoxy-carbonyl,
(iii) a 5- to 8-membered heterocyclooxy group containing 1 to 3 hetero atoms selected from a nitrogen atom, an oxygen atom and a sulfur atom, which is substituted by 1 to 5 substituents selected from
(a) halogen,
(b) optionally halogenated $C_{1-4}$ alkyl,
(c) hydroxy-$C_{1-4}$ alkyl,
(d) heterocycle-$C_{1-4}$ alkyl (preferably, 5- to 8-membered heterocycle-$C_{1-4}$ alkyl, said 5- to 8-membered heterocycle has 1 to 3 hetero atoms selected from a nitrogen atom, an oxygen atom and an optionally oxidized sulfur atom, such as imidazolyl and the like),
(e) optionally halogenated $C_{1-4}$ alkyloxy,
(f) cyano,
(g) carbamoyl optionally substituted by $C_{1-8}$ alkyl, and
(h) $C_{1-4}$ alkoxy-carbonyl, and
(iv) 5- to 8-membered heterocycle-$C_{1-3}$ alkyloxy containing 1 to 3 hetero atoms selected from a nitrogen atom, an oxygen atom and a sulfur atom, which is substituted by 1 to 5 substituents selected from
(a) halogen,
(b) optionally halogenated $C_{1-4}$ alkyl,
(c) hydroxy-$C_{1-4}$ alkyl,
(d) heterocycle-$C_{1-4}$ alkyl (preferably, 5- to 8-membered heterocycle-$C_{1-4}$ alkyl, said 5- to 8-membered heterocycle has 1 to 3 hetero atoms selected from a nitrogen atom, an oxygen atom and an optionally oxidized sulfur atom, such as imidazolyl and the like),
(e) optionally halogenated $C_{1-4}$ alkyloxy,
(f) cyano,
(g) carbamoyl optionally substituted by $C_{1-8}$ alkyl, and
(h) $C_{1-4}$ alkoxy-carbonyl;
wherein the $C_{6-18}$ aryl group is optionally further substituted by 1 to 4 substituents selected from halogen and optionally halogenated $C_{1-4}$ alkyl;
$R^1$ is a hydrogen atom;
$R^2$ is a $C_{1-8}$ alkyl group, a $C_{2-8}$ alkenyl group or a $C_{2-8}$ alkynyl group, each of which is substituted by substituent(s) selected from
(a) hydroxy,
(b) optionally halogenated $C_{1-4}$ alkyloxy,
(c) —O—$(CH_2)_n$—OH,
(d) —O—$(CH_2)_n$—O—CO—NH$_2$,
(e) —O—$(CH_2)_n$—O—$C_{1-4}$ alkyl,
(f) —O—$(CH_2)_n$—SO$_2$-(optionally halogenated $C_{1-4}$ alkyl),
(g) —O—$(CH_2)_n$—SO$_2$—$C_{6-18}$ aryl,
(h) —O—$(CH_2)_n$—SO$_2$—$(CH_2)_n$—OH,
(i) —O—$(CH_2)_n$—NR$^8$—SO$_2$-(optionally halogenated $C_{1-4}$ alkyl),
(j) —CO—NR$^8$—$(CH_2)_n$—OH,
(k) —CO—NR$^8$—$(CH_2)_n$—SO$_2$-(optionally halogenated $C_{1-4}$ alkyl),
(l) —NR$^6$R$^7$,
(m) —NR$^8$—$(CH_2)_n$—OH,
(n) —NR$^8$—$(CH_2)_n$—SO$_2$—$C_{1-4}$ alkyl,
(o) —NR$^8$—CO—$(CH_2)_n$—OH,
(p) —NR$^8$—CO—$(CH_2)_n$—O—$C_{1-4}$ alkyl,
(q) —NR$^8$—CO—$(CH_2)_n$—SO-(optionally halogenated $C_{1-4}$ alkyl),
(r) —NR$^8$—CO—$(CH_2)_n$—SO$_2$-(optionally halogenated $C_{1-4}$ alkyl),
(s) —NR$^8$—CO—$(CH_2)_n$—SO$_2$—$C_{3-8}$ cycloalkyl,
(t) —NR$^8$—CO$_2$—$(CH_2)_n$—SO$_2$—$C_{1-4}$ alkyl,
(u) —NR$^8$—CO—NH—$(CH_2)_n$—SO$_2$—$C_{1-4}$ alkyl,
(v) —NR$^8$—SO$_2$—$(CH_2)_n$—SO$_2$—$C_{1-4}$ alkyl,
(w) —S—$(CH_2)_n$—OH,
(x) —SO—$(CH_2)_n$—OH,
(y) —SO$_2$—$(CH_2)_n$—OH, and
(z) —NR$^8$—CO-(optionally substituted heterocyclic group) (preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—NH—$C_{1-4}$ alkyl, —CONH$_2$, —SO$_2$—$C_{1-4}$ alkyl, —SO$_2$—NH—$C_{1-4}$ alkyl, —SO$_2$NH$_2$ and the like),
wherein n is an integer of 1 to 4, $R^6$ and $R^7$ are the same or different and each is a hydrogen atom or a $C_{1-4}$ alkyl group, $R^8$ is a hydrogen atom or a $C_{1-4}$ alkyl group, and $(CH_2)_n$ is optionally substituted by $C_{1-4}$ alkyl or hydroxy);
$R^3$ is a hydrogen atom or a $C_{1-6}$ alkyl group; or,
$R^1$ and $R^2$ are optionally bonded to form

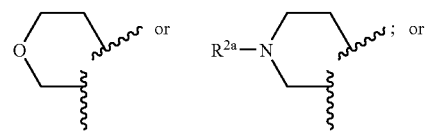

$R^2$ and $R^3$ are optionally bonded to form $C_{2-4}$ alkylene, particularly preferably, $R^2$ is a $C_{1-8}$ alkyl group, a $C_{2-8}$ alkenyl group or a $C_{2-8}$ alkynyl group (particularly, a $C_{1-8}$ alkyl group), each of which is substituted by substituent(s) selected from
(a) hydroxy,
(b) optionally halogenated $C_{1-4}$ alkyloxy,
(c) —O—$(CH_2)_n$—OH (wherein $(CH_2)_n$ is optionally substituted by hydroxy),
(d) —O—$(CH_2)_n$—O—CO—$NH_2$,
(e) —O—$(CH_2)_n$—O—$C_{1-4}$ alkyl,
(f) —O—$(CH_2)_n$—$SO_2$-(optionally halogenated $C_{1-4}$ alkyl),
(g) —O—$(CH_2)_n$—$SO_2$—$C_{6-18}$ aryl,
(h) —O—$(CH_2)_n$—$SO_2$—$(CH_2)_n$—OH,
(i) —O—$(CH_2)_n$—$NR^8$—$SO_2$-(optionally halogenated $C_{1-4}$ alkyl),
(j) —CO—$NR^8$—$(CH_2)_n$—OH,
(k) —CO—$NR^8$—$(CH_2)_n$—$SO_2$-(optionally halogenated $C_{1-4}$ alkyl),
(l) —$NR^6R^7$,
(m) —$NR^8$—$(CH_2)_n$—OH,
(n) —$NR^8$—$(CH_2)_n$—$SO_2$—$C_{1-4}$ alkyl,
(o) —$NR^8$—CO—$(CH_2)_n$—OH (wherein $(CH_2)_n$ is optionally substituted by $C_{1-4}$ alkyl),
(p) —$NR^8$—CO—$(CH_2)_n$—O—$C_{1-4}$ alkyl,
(q) —$NR^8$—CO—$(CH_2)_n$—SO-(optionally halogenated $C_{1-4}$ alkyl),
(r) —$NR^8$—CO—$(CH_2)_n$—$SO_2$-(optionally halogenated $C_{1-4}$ alkyl)
(wherein $(CH_2)_n$ is optionally substituted by $C_{1-4}$ alkyl),
(s) —$NR^8$—CO—$(CH_2)_n$—$SO_2$—$C_{3-8}$ cycloalkyl,
(t) —$NR^8$—$CO_2$—$(CH_2)_n$—$SO_2$—$C_{1-4}$ alkyl,
(u) —$NR^8$—CO—NH—$(CH_2)_n$—$SO_2$—$C_{1-4}$ alkyl,
(v) —$NR^8$—$SO_2$—$(CH_2)_n$—$SO_2$—$C_{1-4}$ alkyl,
(w) —S—$(CH_2)_n$—OH,
(x) —SO—$(CH_2)_n$—OH,
(y) —$SO_2$—$(CH_2)_n$—OH, and
(z) —$NR^8$—CO-(optionally substituted heterocyclic group)
(preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—NH—$C_{1-4}$ alkyl, —$CONH_2$, —$SO_2$—$C_{1-4}$ alkyl, —$SO_2$—NH—$C_{1-4}$ alkyl, —$SO_2NH_2$ and the like),
wherein n is an integer of 1 to 4, $R^6$ and $R^7$ are the same or different and each is a hydrogen atom or a $C_{1-4}$ alkyl group, and $R^8$ is a hydrogen atom or a $C_{1-4}$ alkyl group,
[56] the compound of the above-mentioned [55], wherein $R^2$ is (i) a $C_{5-8}$ alkyl group substituted by hydroxy,
(ii) a $C_{1-8}$ alkyl group substituted by substituent(s) selected from
(a) halogenated $C_{1-4}$ alkyloxy,
(b) —O—$(CH_2)_n$—OH,
(c) —O—$(CH_2)_n$—O—CO—$NH_2$,
(d) —O—$(CH_2)_n$—O-(optionally halogenated $C_{1-4}$ alkyl),
(e) —O—$(CH_2)_n$—$SO_2$-(optionally halogenated $C_{1-4}$ alkyl),
(f) —O—$(CH_2)_n$—$SO_2$—$C_{6-18}$ aryl,
(g) —O—$(CH_2)_n$—$NR^8$—$SO_2$-(optionally halogenated $C_{1-4}$ alkyl),
(h) —CO—$NR^8$—$(CH_2)_n$—OH,
(i) —CO—$NR^8$—$(CH_2)_n$—$SO_2$-(optionally halogenated $C_{1-4}$ alkyl),
(j) —$NR^8$—$(CH_2)_n$—$SO_2$—$C_{1-4}$ alkyl,
(k) —$NR^8$—CO—$(CH_2)_n$—OH,
(l) —$NR^8$—CO—$(CH_2)_n$—O—$C_{1-4}$ alkyl,
(m) —$NR^8$—CO—$(CH_2)_n$—SO-(optionally halogenated $C_{1-4}$ alkyl),
(n) —$NR^8$—CO—$(CH_2)_n$—$SO_2$-(optionally halogenated $C_{1-4}$ alkyl),
(o) —$NR^8$—CO—$(CH_2)_n$—$SO_2$—$C_{3-8}$ cycloalkyl,
(p) —$NR^8$—$CO_2$—$(CH_2)_n$—$SO_2$—$C_{1-4}$ alkyl,
(q) —$NR^8$—CO—NH—$(CH_2)_n$—$SO_2$—$C_{1-4}$ alkyl,
(r) —$NR^8$—$SO_2$—$(CH_2)_n$—$SO_2$—$C_{1-4}$ alkyl,
(s) —S—$(CH_2)_n$—OH,
(t) —SO—$(CH_2)_n$—OH,
(u) —$SO_2$—$(CH_2)_n$—OH, and
(v) —$NR^8$—CO-(optionally substituted heterocyclic group)
(preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—NH—$C_{1-4}$ alkyl, —$CONH_2$, —$SO_2$—$C_{1-4}$ alkyl, —$SO_2$—NH—$C_{1-4}$ alkyl, —$SO_2NH_2$ and the like),
wherein n is an integer of 1 to 4, $R^8$ is a hydrogen atom or a $C_{1-4}$ alkyl group, and $(CH_2)_n$ is optionally substituted by $C_{1-4}$ alkyl,
(iii) a $C_{2-8}$ alkenyl group optionally substituted by hydroxy, or
(iv) a $C_{2-8}$ alkynyl group optionally substituted by hydroxy,
particularly preferably, $R^2$ is
(i) a $C_{5-8}$ alkyl group substituted by hydroxy,
(ii) a $C_{1-8}$ alkyl group substituted by substituent(s) selected from
(a) halogenated $C_{1-4}$ alkyloxy,
(b) —O—$(CH_2)_n$—OH (wherein $(CH_2)_n$ is optionally substituted by hydroxy),
(c) —O—$(CH_2)_n$—O—CO—$NH_2$,
(d) —O—$(CH_2)_n$—O-(optionally halogenated $C_{1-4}$ alkyl),
(e) —O—$(CH_2)_n$—$SO_2$-(optionally halogenated $C_{1-4}$ alkyl),
(f) —O—$(CH_2)_n$—$SO_2$—$C_{6-18}$ aryl,
(g) —O—$(CH_2)_n$—$NR^8$—$SO_2$-(optionally halogenated $C_{1-4}$ alkyl),
(h) —CO—$NR^8$—$(CH_2)_n$—OH,
(i) —CO—$NR^8$—$(CH_2)_n$—$SO_2$-(optionally halogenated $C_{1-4}$ alkyl),
(j) —$NR^8$—$(CH_2)_n$—$SO_2$—$C_{1-4}$ alkyl,
(k) —$NR^8$—CO—$(CH_2)_n$—OH (wherein $(CH_2)_n$ is optionally substituted by $C_{1-4}$ alkyl),
(l) —$NR^8$—CO—$(CH_2)_n$—O—$C_{1-4}$ alkyl,
(m) —$NR^8$—CO—$(CH_2)_n$—SO-(optionally halogenated $C_{1-4}$ alkyl),
(n) —$NR^8$—$CO(CH_2)_n$—$SO_2$-(optionally halogenated $C_{1-4}$ alkyl)
(wherein $(CH_2)_n$ is optionally substituted by $C_{1-4}$ alkyl),
(o) —$NR^8$—$CO(CH_2)_n$—$SO_2$—$C_{3-8}$ cycloalkyl,
(p) —$NR^8$—$CO_2$—$(CH_2)_n$—$SO_2$—$C_{1-4}$ alkyl,
(q) —$NR^8$—CO—NH—$(CH_2)_n$—$SO_2$—$C_{1-4}$ alkyl,
(r) —$NR^8$—$SO_2$—$(CH_2)_n$—$SO_2$—$C_{1-4}$ alkyl,
(s) —S—$(CH_2)_n$—OH,
(t) —SO—$(CH_2)_n$—OH,
(u) —$SO_2$—$(CH_2)_n$—OH, and
(v) —$NR^8$—CO-(optionally substituted heterocyclic group)
(preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—NH—$C_{1-4}$ alkyl, —$CONH_2$, —$SO_2$—$C_{1-4}$ alkyl, —$SO_2$—NH—$C_{1-4}$ alkyl, —$SO_2NH_2$ and the like),
wherein n is an integer of 1 to 4, and $R^8$ is a hydrogen atom or a $C_{1-4}$ alkyl group,
(iii) a $C_{2-8}$ alkenyl group optionally substituted by hydroxy, or
(iv) a $C_{2-8}$ alkynyl group optionally substituted by hydroxy,

[57] the compound of the above-mentioned [1], which is selected from the following (A) to (H):

(A) a compound (I) wherein
W is $CR^1$;
A is a phenyloxy-$C_{6-18}$ aryl group wherein the phenyloxy moiety is optionally substituted by 1 to 5 substituents selected from
(i) halogen,
(ii) optionally halogenated $C_{1-4}$ alkyl,
(iii) hydroxy-$C_{1-4}$ alkyl,
(iv) heterocycle-$C_{1-4}$ alkyl (preferably, 5- to 8-membered heterocycle-$C_{1-4}$ alkyl, said 5- to 8-membered heterocycle has 1 to 3 hetero atoms selected from a nitrogen atom, an oxygen atom and an optionally oxidized sulfur atom, such as imidazolyl, triazolyl and the like),
(v) optionally halogenated $C_{1-4}$ alkyloxy,
(vi) $C_{1-4}$ alkyl-carbonyl,
(vii) cyano,
(viii) carbamoyl optionally substituted by $C_{1-8}$ alkyl, and
(ix) $C_{1-4}$ alkoxy-carbonyl, and
the $C_{6-18}$ aryl moiety is optionally further substituted by 1 to 4 substituents selected from halogen, $C_{1-4}$ alkyl, hydroxy-$C_{1-4}$ alkyl, $C_{1-4}$ alkyloxy, carboxy and $C_{1-4}$ alkoxy-carbonyl;
$X^1$ is —$NR^{3'}$— wherein $R^{3'}$ is a hydrogen atom or a $C_{1-6}$ alkyl group;
$R^1$ is
(i) a hydrogen atom,
(ii) a cyano group, or
(iii) a $C_{1-4}$ alkyl group or a $C_{2-4}$ alkenyl group, each of which is optionally substituted by —$NR^8$—CO—$(CH_2)_n$—$NR^6R^7$
wherein n is an integer of 1 to 4, $R^6$ and $R^7$ are the same or different and each is a hydrogen atom or a $C_{1-4}$ alkyl group, $R^8$ is a hydrogen atom or a $C_{1-4}$ alkyl group, and when n is not less than 2, a subset —$CH_2CH_2$— of $(CH_2)_n$ is optionally replaced by —CH=CH—; and
$R^2$ is (i) a hydrogen atom or
(ii) a $C_{1-8}$ alkyl group, a $C_{2-8}$ alkenyl group or a $C_{2-8}$ alkynyl group, each of which is optionally substituted by substituent(s) selected from
(a) hydroxy,
(b) carboxy,
(c) cyano,
(d) optionally halogenated $C_{1-4}$ alkyloxy,
(e) —O—$(CH_2)_n$—OH,
(f) —O—$(CH_2)_n$—O—CO—$NH_2$,
(g) —O—$(CH_2)_n$—O-(optionally halogenated $C_{1-4}$ alkyl),
(h) —O—$(CH_2)_n$—$SO_2$-(optionally halogenated $C_{1-4}$ alkyl),
(i) —O—$(CH_2)_n$—$SO_2$—$C_{6-18}$ aryl,
(j) —O—$(CH_2)_n$—$SO_2$—$(CH_2)_n$—OH,
(k) —O—$(CH_2)_n$—$NR^8$—CO—$C_{1-4}$ alkyl,
(l) —O—$(CH_2)_n$—$NR^8$—CO—$(CH_2)_n$—$SO_2$—$C_{1-4}$ alkyl,
(m) —O—$(CH_2)_n$—$NR^8$—$SO_2$-(optionally halogenated $C_{1-4}$ alkyl),
(n) —CO—$NR^8$—$(CH_2)_n$—OH,
(o) —CO—$NR^8$—$(CH_2)_n$—$SO_2$-(optionally halogenated $C_{1-4}$ alkyl),
(p) —CO—$NR^8$—O—$C_{1-4}$ alkyl,
(q) —$NR^6R^7$,
(r) —$NR^8$—$(CH_2)_n$—OH,
(s) —$NR^8$—$(CH_2)_n$—$SO_2$—$C_{1-4}$ alkyl,
(t) —$NR^8$—CO-(optionally halogenated $C_{1-4}$ alkyl),
(u) —$NR^8$—CO—$(CH_2)_n$—OH,
(v) —$NR^8$—CO—$(CH_2)_n$—CN,
(w) —$NR^8$—CO—$(CH_2)_n$—$NR^6R^7$,
(x) —$NR^8$—CO—$(CH_2)_n$—O—$C_{1-4}$ alkyl,
(y) —$NR^8$—CO—$(CH_2)_n$—SO-(optionally halogenated $C_{1-4}$ alkyl),
(z) —$NR^8$—CO—$(CH_2)_n$—$SO_2$-(optionally halogenated $C_{1-4}$ alkyl),
(aa) —$NR^8$—CO—$(CH_2)_n$—$SO_2$—$C_{3-8}$ cycloalkyl,
(bb) —$NR^8$—CO—$(CH_2)_n$—$NR^8$—$SO_2$—$C_{1-4}$ alkyl,
(cc) —$NR^8$—$CO_2$—$(CH_2)_n$—$SO_2$—$C_{1-4}$ alkyl,
(dd) —$NR^8$—CO—NH—$(CH_2)_n$—$SO_2$—$C_{1-4}$ alkyl,
(ee) —$NR^8$—CO—NH—O—$C_{1-4}$ alkyl,
(ff) —$NR^8$—CO—NH—$(CH_2)_n$—O—$C_{1-4}$ alkyl,
(gg) —$NR^8$—C(=NH)—NH—$C_{1-4}$ alkyl,
(hh) —$NR^8$—$SO_2$—$(CH_2)_n$—$SO_2$—$C_{1-4}$ alkyl,
(ii) —S—$(CH_2)_n$—OH,
(jj) —SO—$(CH_2)_n$—OH,
(kk) —$SO_2$—$(CH_2)_n$—OH, and
(ll) —$NR^8$—CO-(optionally substituted heterocyclic group)
(preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—O—$C_{1-4}$ alkyl, —CO—NH—$C_{1-4}$ alkyl, —$CONH_2$, —$SO_2$—$C_{1-4}$ alkyl, —$SO_2$—NH—$C_{1-4}$ alkyl, —$SO_2NH_2$ and the like),
wherein n is an integer of 1 to 4, $R^6$ and $R^7$ are the same or different and each is a hydrogen atom or a $C_{1-4}$ alkyl group, $R^8$ is a hydrogen atom or a $C_{1-4}$ alkyl group, $(CH_2)_n$ is optionally substituted by optionally halogenated $C_{1-4}$ alkyl or hydroxy, and when n is not less than 2, a subset —$CH_2CH_2$— of $(CH_2)_n$ is optionally replaced by —CH=CH—; or
$R^1$ and $R^2$ are optionally bonded to form

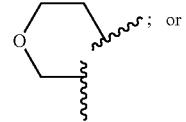

; or $R^2$ and $R^{3'}$ are optionally bonded to form $C_{2-4}$ alkylene optionally substituted by an imino group, particularly preferably, $R^{2a}$ is a $C_1$— alkyl group, a $C_{2-8}$ alkenyl group or a $C_{2-8}$ alkynyl group (particularly, $C_{1-8}$ alkyl group), each of which is optionally substituted by substituent(s) selected from
(a) hydroxy,
(b) carboxy,
(c) cyano,
(d) optionally halogenated $C_{1-4}$ alkyloxy,
(e) —O—$(CH_2)_n$—OH (wherein $(CH_2)_n$ is optionally substituted by hydroxy),
(f) —O—$(CH_2)_n$—O—CO—$NH_2$,
(g) —O—$(CH_2)_n$—O-(optionally halogenated $C_{1-4}$ alkyl),
(h) —O—$(CH_2)_n$—$SO_2$-(optionally halogenated $C_{1-4}$ alkyl),
(i) —O—$(CH_2)_n$—$SO_2$—$C_{6-18}$ aryl,
(j) —O—$(CH_2)_n$—$SO_2$—$(CH_2)_n$—OH,
(k) —O—$(CH_2)_n$—$NR^8$—CO—$C_{1-4}$ alkyl,
(l) —O—$(CH_2)_n$—$NR^8$—CO—$(CH_2)_n$—$SO_2$—$C_{1-4}$ alkyl,
(m) —O—$(CH_2)_n$—$NR^8$—$SO_2$-(optionally halogenated $C_{1-4}$ alkyl),
(n) —CO—$NR^8$—$(CH_2)_n$—OH,
(o) —CO—$NR^8$—$(CH_2)_n$—$SO_2$-(optionally halogenated $C_{1-4}$ alkyl),
(p) —CO—$NR^8$—O—$C_{1-4}$ alkyl, (q) —NR⁶R⁷,
(r) —NR⁸—(CH₂)ₙ—OH,
(s) —NR⁸—(CH₂)ₙ—SO₂—C₁₋₄ alkyl,
(t) —NR⁸—CO-(optionally halogenated C₁₋₄ alkyl),
(u) —NR⁸—CO—(CH₂)ₙ—OH (wherein (CH₂)ₙ is optionally substituted by optionally halogenated C₁₋₄ alkyl or hydroxy),
(v) —NR⁸—CO—(CH₂)ₙ—CN,
(w) —NR⁸—CO—(CH₂)ₙ—NR⁶R⁷ (when n is not less than 2, a subset —CH₂CH₂— of (CH₂)ₙ is optionally replaced by —CH=CH—),
(x) —NR⁸—CO—(CH₂)ₙ—O—C₁₋₄ alkyl,
(y) —NR⁸—CO—(CH₂)ₙ—SO-(optionally halogenated C₁₋₄ alkyl),
(z) —NR⁸—CO—(CH₂)ₙ—SO₂-(optionally halogenated C₁₋₄ alkyl)
(wherein (CH₂)ₙ is optionally substituted by C₁₋₄ alkyl),
(aa) —NR⁸—CO—(CH₂)ₙ—SO₂—C₃₋₈ cycloalkyl,
(bb) —NR⁸—CO—(CH₂)ₙ—NR⁸—SO₂—C₁₋₄ alkyl,
(cc) —NR⁸—CO₂—(CH₂)ₙ—SO₂—C₁₋₄ alkyl,
(dd) —NR⁸—CO—NH—(CH₂)ₙ—SO₂—C₁₋₄ alkyl,
(ee) —NR⁸—CO—NH—O—C₁₋₄ alkyl,
(ff) —NR⁸—CO—NH—(CH₂)ₙ—O—C₁₋₄ alkyl,
(gg) —NR⁸—C(=NH)—NH—C₁₋₄ alkyl,
(hh) —NR⁸—SO₂—(CH₂)ₙ—SO₂—C₁₋₄ alkyl,
(ii) —S—(CH₂)ₙ—OH,
(jj) —SO—(CH₂)ₙ—OH,
(kk) —SO₂—(CH₂)ₙ—OH, and
(ll) —NR⁸—CO-(optionally substituted heterocyclic group)
(preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, C₁₋₄ alkyl, optionally oxidized C₁₋₄ alkylthio, —CO—C₁₋₄ alkyl, —CO—O—C₁₋₄ alkyl, —CO—NH—C₁₋₄ alkyl, —CONH₂, —SO₂—C₁₋₄ alkyl, —SO₂—NH—C₁₋₄ alkyl, —SO₂NH₂ and the like),
wherein n is an integer of 1 to 4, R⁶ and R⁷ are the same or different and each is a hydrogen atom or a C₁₋₄ alkyl group, and R⁸ is a hydrogen atom or a C₁₋₄ alkyl group,
(B) a compound (I) wherein
W is CR¹;
A is phenyl-C₁₋₃ alkyloxy-C₆₋₁₈ aryl group wherein the phenyl moiety is optionally substituted by 1 to 5 substituents selected from halogen, optionally halogenated C₁₋₄ alkyl and cyano, and
the C₆₋₁₈ aryl moiety is optionally further substituted by 1 to 4 substituents selected from halogen, C₁₋₄ alkyl optionally having hydroxy and C₁₋₄ alkyloxy;
X¹ is —NR³'— wherein R³' is a hydrogen atom or a C₁₋₆ alkyl group;
R¹ is (i) a hydrogen atom,
(ii) a C₁₋₄ alkyl group or a C₂₋₄ alkenyl group, each of which is optionally substituted by substituent(s) selected from
(a) hydroxy,
(b) amino,
(c) —NR⁸—CO—(CH₂)ₙ—NR⁶R⁷, and
(d) —NR⁸—CO—(CH₂)ₙ—O—C₁₋₄ alkyl
wherein n is an integer of 1 to 4, R⁶ and R⁷ are the same or different and each is a hydrogen atom or a C₁₋₄ alkyl group, R⁸ is a hydrogen atom or a C₁₋₄ alkyl group, and when n is not less than 2, a subset —CH₂—CH₂ of (CH₂)ₙ is optionally replaced by —CH=CH—, or
(iii) a C₆₋₁₈ aryl group optionally substituted by substituent(s) selected from (a) amino,
(b) carboxy, and
(c) —NR⁸—CO—(CH₂)ₙ—O—C₁₋₄ alkyl
wherein n is an integer of 1 to 4, and R⁸ is a hydrogen atom or a C₁₋₄ alkyl group, or
(iv) a 5- to 8-membered heterocyclic group having 1 to 3 hetero atoms selected from a nitrogen atom, an oxygen atom and a sulfur atom; and
R² is (i) a hydrogen atom,
(ii) a C₁₋₈ alkyl group optionally substituted by substituent(s) selected from
(a) halogen,
(b) hydroxy,
(c) C₁₋₄ alkyloxy,
(d) —O—(CH₂)ₙ—OH,
(e) —O—(CH₂)ₙ—O—C₁₋₄ alkyl,
(f) —CO—NR⁸—(CH₂)ₙ—OH,
(g) —NR⁶R⁷, and
(h) —NR⁸—(CH₂)ₙ—OH
wherein n is an integer of 1 to 4, R⁶ and R⁷ are the same or different and each is a hydrogen atom or a C₁₋₄ alkyl group, and R⁸ is a hydrogen atom or a C₁₋₄ alkyl group,
(iii) a C₆₋₁₈ aryl-C₁₋₄ alkyl group optionally substituted by substituent(s) selected from
(a) C₁₋₄ alkyl optionally having hydroxy,
(b) carboxy,
(c) C₁₋₄ alkoxy-carbonyl,
(d) 5- to 8-membered heterocycle-carbonyl having 1 to 3 hetero atoms selected from a nitrogen atom, an oxygen atom and a sulfur atom, which optionally has substituent(s) selected from hydroxy and C₁₋₄ alkyl, and
(e) C₁₋₄ alkyl-carbamoyl optionally having substituent(s) selected from hydroxy and carbamoyl,
(iv) a C₆₋₁₈ aryl-carbonyl group optionally substituted by C₁₋₄ alkoxy,
(v) a C₆₋₁₈ aryl-sulfonyl group optionally substituted by C₁₋₄ alkoxy, or
(vi) a 5- to 8-membered heterocycle-C₁₋₄ alkyl group having 1 to 3 hetero atoms selected from a nitrogen atom, an oxygen atom and a sulfur atom, which is optionally substituted by substituent(s) selected from
(a) carboxy, and
(b) C₁₋₄ alkoxy-carbonyl; or
R² and R³' are optionally bonded to form C₂₋₄ alkylene,
(C) a compound (I) wherein W is CR¹;
A is a 5- to 8-membered heterocylooxy-C₆₋₁₈ aryl group containing 1 to 3 hetero atoms selected from a nitrogen atom, an oxygen atom and a sulfur atom, wherein the heterocylooxy moiety is optionally substituted by 1 to 5 substituents selected from
(i) halogen,
(ii) C₁₋₄ alkyl,
(iii) C₁₋₄ alkyl-carbonyl,
(iv) optionally halogenated C₁₋₄ alkoxy-carbonyl,
(v) C₃₋₈ cycloalkyl-carbonyl, and
(vi) a carbamoyl group optionally substituted by substituent(s) selected from
(a) optionally halogenated C₁₋₈ alkyl,
(b) C₃₋₈ cycloalkyl, and
(c) C₆₋₁₈ aryl optionally substituted by substituent(s) selected from halogen, C₁₋₄ alkyl and C₁₋₄ alkyloxy, and
the C₆₋₁₈ aryl moiety is optionally further substituted by 1 to 4 substituents selected from halogen and optionally halogenated C₁₋₄ alkyl;
X¹ is —NR³'— wherein R³' is a hydrogen atom or a C₁₋₆ alkyl group;

$R^1$ is (i) a hydrogen atom,
(ii) a $C_{1-4}$ alkyl group or a $C_{2-4}$ alkenyl group, each of which is optionally substituted by substituent(s) selected from
(a) hydroxy,
(b) amino,
(c) —$NR^8$—CO—$(CH_2)_n$—$NR^6R^7$, and
(d) —$NR^8$—CO—$(CH_2)_n$—O—$C_{1-4}$ alkyl,
wherein n is an integer of 1 to 4, $R^6$ and $R^7$ are the same or different and each is a hydrogen atom or a $C_{1-4}$ alkyl group, $R^8$ is a hydrogen atom or a $C_{1-4}$ alkyl group, and when n is not less than 2, a subset —$CH_2CH_2$— of $(CH_2)_n$ is optionally replaced by —CH=CH—,
(iii) a $C_{6-18}$ aryl group optionally substituted by substituent(s) selected from
(a) $C_{1-4}$ alkyl optionally substituted by substituent(s) selected from hydroxy, —$NR^8$—$(CH_2)_n$—$SO_2$—$C_{1-4}$ alkyl and —$NR^8$—CO—$(CH_2)_n$—O—$C_{1-4}$ alkyl,
(b) amino,
(c) $C_{1-4}$ alkyloxy,
(d) carboxy, and
(e) —$NR^8$—CO—$(CH_2)_n$—O—$C_{1-4}$ alkyl,
wherein n is an integer of 1 to 4, and $R^8$ is a hydrogen atom or a $C_{1-4}$ alkyl group, or
(iv) a 5- to 8-membered heterocyclic group having 1 to 3 hetero atoms selected from a nitrogen atom, an oxygen atom and a sulfur atom; and
$R^2$ is (i) a hydrogen atom,
(ii) a $C_{1-4}$ alkyl group optionally substituted by substituent(s) selected from
(a) halogen,
(b) hydroxy,
(c) $C_{1-4}$ alkyloxy,
(d) carboxy,
(e) $C_{1-4}$ alkoxy-carbonyl,
(f) —O—$(CH_2)_n$—OH,
(g) —O—$(CH_2)_n$—O—$C_{1-4}$ alkyl,
(h) —CO—$NR^8$—$(CH_2)_n$—OH, and
(i) —$NR^8$—CO—$(CH_2)_n$—$SO_2$—$C_{1-4}$ alkyl
wherein n is an integer of 1 to 4, and $R^8$ is a hydrogen atom or a $C_{1-4}$ alkyl group, or
(iii) a $C_{6-18}$ aryl-$C_{1-4}$ alkyl group optionally substituted by $C_{1-4}$ alkyl optionally having hydroxy; or
$R^2$ and $R^{3'}$ are optionally bonded to form $C_{2-4}$ alkylene,
(D) a compound (I) wherein
W is $CR^1$;
A is 5- to 8-membered heterocycle-$C_{1-3}$ alkyloxy-$C_{6-18}$ aryl group containing 1 to 3 hetero atoms selected from a nitrogen atom, an oxygen atom and a sulfur atom
wherein the $C_{6-18}$ aryl moiety is optionally further substituted by halogen;
$X^1$ is —$NR^{3'}$— wherein $R^{3'}$ is a hydrogen atom or a $C_{1-6}$ alkyl group;
$R^1$ is (i) a hydrogen atom or
(ii) a 5- to 8-membered heterocyclic group having 1 to 3 hetero atoms selected from a nitrogen atom, an oxygen atom and a sulfur atom; and
$R^2$ is (i) a hydrogen atom,
(ii) $C_{1-4}$ alkyl optionally substituted by substituent(s) selected from
(a) $C_{1-4}$ alkyloxy,
(b) —O—$(CH_2)_n$—OH, and
(c) —$NR^8$—CO—$(CH_2)_n$—$SO_2$—$C_{1-4}$ alkyl
wherein n is an integer of 1 to 4, and $R^8$ is a hydrogen atom or a $C_{1-4}$ alkyl group, or
(iii) a 5- to 8-membered heterocycle-$C_{1-4}$ alkyl group having 1 to 3 hetero atoms selected from a nitrogen atom, an oxygen atom and a sulfur atom, which is optionally substituted by substituent(s) selected from
(a) carboxy, and
(b) $C_{1-4}$ alkoxy-carbonyl,
(E) a compound (I) wherein
W is N;
A is a phenyloxy-$C_{6-18}$ aryl group wherein the phenyloxy moiety is optionally substituted by 1 to 5 substituents selected from optionally halogenated $C_{1-4}$ alkyl and cyano, and
the $C_{6-18}$ aryl moiety is optionally further substituted by 1 to 4 substituents selected from halogen and $C_{1-4}$ alkyl;
$X^1$ is —$NR^3$— wherein $R^3$ is a hydrogen atom or a $C_{1-6}$ alkyl group; and
$R^2$ is (i) a hydrogen atom or
(ii) a $C_{1-4}$ alkyl group optionally substituted by —O—$(CH_2)_n$—OH
wherein n is an integer of 1 to 4,
(F) a compound (I) wherein
W is N;
A is a phenyl-$C_{1-3}$ alkyloxy-$C_{6-18}$ aryl group wherein the phenyl moiety is optionally substituted by 1 to 5 substituents selected from halogen and cyano, and
the $C_{6-18}$ aryl moiety is optionally further substituted by 1 to 4 substituents selected from halogen and $C_{1-4}$ alkyl;
$X^1$ is —$NR^3$— wherein $R^3$ is a hydrogen atom or a $C_{1-6}$ alkyl group; and
$R^2$ is (i) a hydrogen atom,
(ii) a $C_{1-4}$ alkyl group optionally substituted by 1 to 5 substituents selected from the group consisting of
(a) hydroxy,
(b) —O—$(CH_2)_n$—OH,
(c) —$NR^8$—$(CH_2)_n$—O—$C_{1-4}$ alkyl,
(d) —$NR^8$—$(CH_2)_n$-heterocyclic group (preferably, said heterocyclic group is a 5- to 8-membered heterocyclic group having 1 to 3 hetero atoms selected from a nitrogen atom, an oxygen atom and a sulfur atom), and
(e) —$NR^8$—$(CH_2)_n$—$SO_2$—$C_{1-4}$ alkyl
wherein n is an integer of 1 to 4, and $R^8$ is a hydrogen atom or a $C_{1-4}$ alkyl group,
(iii) a $C_{6-18}$ aryl group optionally substituted by $C_{1-4}$ alkyl optionally substituted by substituent(s) selected from hydroxy, —$NR^8$—$(CH_2)_n$—OH, —$NR^8$—$(CH_2)_n$-heterocyclic group (preferably, said heterocyclic group is a 5- to 8-membered heterocyclic group having 1 to 3 hetero atoms selected from a nitrogen atom, an oxygen atom and a sulfur atom) and —$NR^8$—$(CH_2)_n$—$SO_2$—$C_{1-4}$ alkyl, or
(iv) a $C_{6-18}$ aryl-$C_{1-4}$ alkyl group optionally substituted by 1 to 5 substituents selected from the group consisting of
(a) carboxy,
(b) $C_{1-4}$ alkoxy-carbonyl, and
(c) —CO—$NR^8$—$(CH_2)_n$—O—$C_{1-4}$ alkyl
wherein n is an integer of 1 to 4, and $R^8$ is a hydrogen atom or a $C_{1-4}$ alkyl group; or
$R^2$ and $R^{3'}$ are optionally bonded to form $C_{2-4}$ alkylene,
(G) a compound (I) wherein
W is N;
A is a 5- to 8-membered heterocyclooxy-$C_{6-18}$ aryl group containing 1 to 3 hetero atoms selected from a nitrogen atom, an oxygen atom and a sulfur atom wherein the heterocyclooxy moiety is optionally substituted by $C_{1-4}$ alkyl, and
the $C_{6-18}$ aryl moiety is optionally further substituted by $C_{1-4}$ alkyl;
$X^1$ is —$NR^{3'}$— wherein $R^{3'}$ is a hydrogen atom or a $C_{1-6}$ alkyl group; and
$R^2$ is (i) a hydrogen atom,
(ii) a $C_{1-4}$ alkyl group optionally substituted by hydroxy, (iii) a $C_{6-18}$ aryl group optionally substituted by substituent(s) selected from
(a) nitro,
(b) amino,
(c) —CO—NR$^8$—(CH$_2$)$_n$—O—C$_{1-4}$ alkyl,
(d) —NR$^8$—CO—(CH$_2$)$_n$—O—C$_{1-4}$ alkyl,
(e) —NR$^8$—CO—(CH$_2$)$_n$—NR$^6$R$^7$,
(f) —NR$^8$—CO—(CH$_2$)$_n$—COOH
(g) —NR$^8$—CO—(CH$_2$)$_n$—CO$_2$—C$_{1-4}$ alkyl, and
(h) —NR$^8$—CO—(CH$_2$)$_m$—O—(CH$_2$)$_n$—O—C$_{1-4}$ alkyl
wherein m is an integer of 0 to 4, n is an integer of 1 to 4, R$^6$ and R$^7$ are the same or different and each is a hydrogen atom or a C$_{1-4}$ alkyl group, and R$^8$ is a hydrogen atom or a C$_{1-4}$ alkyl group, or
(iv) a $C_{6-18}$ aryl-C$_{1-4}$ alkyl group optionally substituted by substituent(s) selected from
(a) carboxy,
(b) C$_{1-4}$ alkoxy-carbonyl,
(c) —CO—NR$^8$—(CH$_2$)$_n$—O—C$_{1-4}$ alkyl,
wherein n is an integer of 1 to 4, and R$^8$ is a hydrogen atom or a C$_{1-4}$ alkyl group); or
R$^2$ and R$^{3'}$ are optionally bonded to form C$_{2-4}$ alkylene,
(H) a compound (I) wherein
W is CH;
A is a $C_{6-18}$ aryl group optionally substituted by substituent(s) selected from
(a) carboxy,
(b) C$_{1-4}$ alkoxy-carbonyl,
(c) a 5- to 8-membered heterocycle-carbonyl group containing 1 to 3 hetero atoms selected from a nitrogen atom, an oxygen atom and a sulfur atom (preferably, a 5- to 8-membered cyclic amino-carbonyl group optionally having 1 or 2 hetero atoms selected from a nitrogen atom, an oxygen atom and a sulfur atom), which is optionally substituted by $C_{6-18}$ aryl-C$_{1-4}$ alkyl;
(d) a carbamoyl group optionally substituted by $C_{6-18}$ aryl-C$_{1-4}$ alkyl, and
(e) a ureido group optionally substituted by $C_{6-18}$ aryl-C$_{1-4}$ alkyl;
X$^1$ is —NR$^{3'}$— wherein R$^{3'}$ is a hydrogen atom or a C$_{1-6}$ alkyl group; and R$^2$ is a hydrogen atom,
[58] the compound of the above-mentioned [1], wherein A is (i) a $C_{6-18}$ aryl group or (ii) a 5- to 8-membered heteroaryl group containing, as an atom (ring atom) constituting a ring system, 1 to 4 hetero atoms selected from an oxygen atom, an optionally oxidized sulfur atom and a nitrogen atom (preferably, an oxygen atom, a sulfur atom and a nitrogen atom), each of which is optionally substituted by 1 to 5 substituents selected from halogen, optionally halogenated C$_{1-4}$ alkyl, hydroxy, optionally halogenated C$_{1-4}$ alkyloxy, C$_{1-4}$ alkyloxymethyl, hydroxy-C$_{1-4}$ alkyl, C$_{1-4}$ alkyl-carbonyl, carboxy, C$_{1-4}$ alkoxy-carbonyl, cyano, carbamoyl, sulfamoyl, nitro, amino, C$_{1-4}$ alkyl-carbonylamino, C$_{1-4}$ alkoxy-carbonylamino, C$_{1-4}$ alkylsulfonylamino and a group of the formula —Y$^2$—B,
wherein Y$^2$ is a single bond, —O—, —O—(C$_{1-3}$ alkylene)-, —NH— or —S—,
B is
(A) (i) a $C_{6-18}$ aryl group, (ii) a 5- to 8-membered heteroaryl group containing, as an atom (ring atom) constituting a ring system, 1 to 4 hetero atoms selected from an oxygen atom, an optionally oxidized sulfur atom and a nitrogen atom (preferably, an oxygen atom, a sulfur atom and a nitrogen atom) or a saturated or unsaturated aliphatic heterocyclic group, (iii) a C$_{3-8}$ cycloalkyl group, (iv) a carbamoyl group, (v) a $C_{6-18}$ aryl-carbonyl group or (vi) a $C_{6-18}$ aryl-C$_{1-4}$ alkyl-carbonyl group, each of which is optionally substituted by 1 to 5 substituents selected from halogen, optionally halogenated C$_{1-4}$ alkyl, hydroxy, optionally halogenated C$_{1-4}$ alkyloxy, C$_{1-4}$ alkyloxymethyl, hydroxy-C$_{1-4}$ alkyl, C$_{1-4}$ alkyl-carbonyl, carboxy, C$_{1-4}$ alkoxy-carbonyl, cyano, carbamoyl, sulfamoyl, nitro, amino, C$_{1-4}$ alkyl-carbonylamino, C$_{1-4}$ alkoxy-carbonylamino and C$_{1-4}$ alkylsulfonylamino or
(B) a ureido group optionally having 1 or 2 C$_{1-8}$ alkyl group(s) optionally substituted by substituent(s) selected from substituent group T,
wherein the ureido group has two substituents, and they optionally form, together with the adjacent nitrogen atom, a 3- to 8-membered saturated or unsaturated aliphatic heterocyclic group optionally substituted by substituent(s) selected from substituent group T,
wherein the substituent group T is a group consisting of
(a) halogen,
(b) oxo,
(c) optionally halogenated C$_{1-4}$ alkyl,
(d) —(CH$_2$)$_m$-Q,
(e) —(CH$_2$)$_m$—Z$^1$-(optionally halogenated C$_{1-4}$ alkyl),
(f) —(CH$_2$)$_m$—Z$^1$—C$_{3-8}$ cycloalkyl,
(g) —(CH$_2$)$_m$—Z$^2$—(CH$_2$)$_n$-Q,
(h) —(CH$_2$)$_m$—Z$^2$—(CH$_2$)$_n$—Z$^1$-(optionally halogenated C$_{1-4}$ alkyl),
(i) —(CH$_2$)$_m$—Z$^2$-(CH$_2$)$_n$—Z$^1$—C$_{3-8}$ cycloalkyl,
(j) —(CH$_2$)$_m$—Z$^1$-(optionally substituted heterocyclic group)
(preferably, said heterocyclic group is a 5- to 8-membered heterocyclic group having 1 to 3 hetero atoms selected from a nitrogen atom, an oxygen atom and an optionally oxidized sulfur atom),
(k) —(CH$_2$)$_m$—Z$^2$—C$_{1-4}$ alkoxy, and
(l) —(CH$_2$)$_m$—Z$^2$-(CH$_2$)$_n$—Z$^1$—(CH$_2$)$_n$—Z$^1$—C$_{1-4}$ alkyl
wherein m is an integer of 0 to 4, n is an integer of 1 to 4,
Q is hydroxy, carboxy, cyano, nitro, —NR$^6$R$^7$, —CONR$^6$R$^7$, —OCONH$_2$ or —SO$_2$NR$^6$R$^7$,
Z$^1$ is —O—, —CO—, —C(OH)R$^8$—, —C(=N—OR$^8$)—, —S—, —SO—, —SO$_2$—, —N(COR$^8$)—, —N(CO$_2$R$^9$)—, —N(SO$_2$R$^9$)—, —CO—O—, —O—CO—, —CO—NR$^8$—, —NR$^8$—CO—, —NR$^8$—CO$_2$—, —NR$^8$—CO—NH—, —NR$^8$—SO$_2$—, or —NR$^8$—C(=NH)—NH—,
Z$^2$ is —O—, —CO—, —C(OH)R$^8$—, —C(=N—OR$^8$)—, —S—, —SO—, —SO$_2$—, —NR$^8$—, —N(COR$^8$)—, —N(CO$_2$R$^9$)—, —N(SO$_2$R$^9$)—, —CO—O—, —O—CO—, —CO—NR$^8$—, —NR$^8$—CO—, —NR$^8$—CO$_2$—, —NR$^8$—CO—NH—, —NR$^8$—C(=NH)—NH—, —NR$^8$—SO$_2$—, or —SO$_2$—NR$^8$—,
(CH$_2$)$_m$ and (CH$_2$)$_n$ are optionally substituted by 1 to 5 substituents selected from halogen, optionally halogenated C$_{1-4}$ alkyl and hydroxy, and when m or n is not less than 2, a subset —CH$_2$CH$_2$— of (CH$_2$)$_m$ and (CH$_2$)$_n$ is optionally replaced by —CH=CH— or —C≡C—,
R$^6$ and R$^7$ are the same or different and each is a hydrogen atom or a C$_{1-4}$ alkyl group, or R$^6$ and R$^7$ form, together with a nitrogen atom, a 3- to 8-membered saturated or unsaturated aliphatic heterocyclic group optionally substituted by 1 to 5 substituents selected from halogen, optionally halogenated C$_{1-4}$ alkyl, hydroxy, optionally halogenated C$_{1-4}$ alkyloxy, C$_{1-4}$ alkyloxymethyl, hydroxy C$_{1-4}$ alkyl, C$_{1-4}$ alkyl-carbonyl, carboxy, C$_{1-4}$ alkoxy-carbonyl, cyano, carbamoyl, sulfamoyl, nitro, amino, C$_{1-4}$ alkyl-carbonylamino, C$_{1-4}$ alkoxy-carbonylamino and C$_{1-4}$ alkylsulfonylamino,
R$^8$ is a hydrogen atom or C$_{1-4}$ alkyl, and R$^9$ is C$_{1-4}$ alkyl, R$^3$ is (i) a hydrogen atom, or
(ii) a C$_{1-8}$ alkyl group, a C$_{2-8}$ alkenyl group, a C$_{2-8}$ alkynyl group or a C$_{3-8}$ cycloalkyl group, each of which is optionally substituted by 1 to 3 substituents selected from halogen, hydroxy, C$_{1-4}$ alkyloxy, C$_{1-4}$ alkyl-carbonyl, carboxy, C$_{1-4}$ alkoxy-carbonyl, cyano, carbamoyl, sulfamoyl, nitro, amino, C$_{1-4}$ alkyl-carbonylamino, C$_{1-4}$ alkoxy-carbonylamino and C$_{1-4}$ alkylsulfonylamino, or
R$^3$ is optionally bonded to a carbon atom or a hetero atom on the aryl group or the heteroaryl group represented by A to form a saturated or unsaturated 4- to 8-membered nitrogen-containing heterocycle, which is optionally substituted by 1 to 3 substituents selected from halogen, hydroxy, C$_{1-4}$ alkyloxy, C$_{1-4}$ alkyl-carbonyl, carboxy, C$_{1-4}$ alkoxy-carbonyl, cyano, carbamoyl, sulfamoyl, nitro, amino, C$_{1-4}$ alkyl-carbonylamino, C$_{1-4}$ alkoxy-carbonylamino and C$_{1-4}$ alkylsulfonylamino, Y$^1$ is (i) a single bond or
(ii) C$_{1-4}$ alkylene or —O—(C$_{1-4}$ alkylene)-, each of which is optionally substituted by 1 to 3 substituents selected from halogen, hydroxy, C$_{1-4}$ alkyloxy, C$_{1-4}$ alkyl-carbonyl, carboxy, C$_{1-4}$ alkoxy-carbonyl, cyano, carbamoyl, sulfamoyl, nitro, amino, C$_{1-4}$ alkyl-carbonylamino, C$_{1-4}$ alkoxy-carbonylamino and C$_{1-4}$ alkylsulfonylamino,
R$^1$ is (i) a hydrogen atom or
(ii) a group represented by the formula —X$^2$—R$^4$,
wherein X$^2$ is a single bond, —NH— or —O—, and
R$^4$ is (i) a hydrogen atom,
(ii) a cyano group,
(iii) a C$_{1-8}$ alkyl group, a C$_{2-8}$ alkenyl group, a C$_{2-8}$ alkynyl group, a C$_{1-8}$ alkyl-carbonyl group, a C$_{3-8}$ cycloalkyl group, a C$_{6-18}$ aryl group, a C$_{6-18}$ aryl-C$_{1-4}$ alkyl group, a C$_{6-18}$ aryl-carbonyl group, a C$_{6-18}$ aryl-C$_{1-4}$ alkyl-carbonyl group, a heterocyclic group (e.g., a 5- to 8-membered heteroaryl group containing, as an atom (ring atom) constituting a ring system, 1 to 4 hetero atoms selected from an oxygen atom, an optionally oxidized sulfur atom and a nitrogen atom
(preferably, an oxygen atom, a sulfur atom and a nitrogen atom) or a saturated or unsaturated aliphatic heterocyclic group), a heterocycle-C$_{1-4}$ alkyl group, a heterocycle-carbonyl group or a heterocycle-C$_{1-4}$ alkyl-carbonyl group, each of which is optionally substituted by 1 to 5 substituents selected from substituent group T, or
(iv) a carbamoyl group optionally having 1 or 2 C$_{1-8}$ alkyl group(s) optionally substituted by substituent(s) selected from substituent group T,
wherein the carbamoyl group has two substituents, and they optionally form, together with the adjacent nitrogen atom, a 3- to 8-membered saturated or unsaturated aliphatic heterocyclic group optionally substituted by substituent(s) selected from substituent group T,
R$^2$ is (i) a hydrogen atom,
(ii) a C$_{1-8}$ alkyl group, a C$_{2-8}$ alkenyl group, a C$_{2-8}$ alkynyl group, a C$_{1-8}$ alkyl-carbonyl group, a C$_{1-8}$ alkylsulfonyl group, a C$_{3-8}$ cycloalkyl group, a C$_{6-18}$ aryl group, a C$_{6-18}$ aryl-C$_{1-4}$ alkyl group, a C$_{6-18}$ aryl-carbonyl group, a C$_{6-18}$ aryl-C$_{1-4}$ alkyl-carbonyl group, a C$_{6-18}$ aryl-sulfonyl group, a heterocyclic group, a heterocycle-C$_{1-4}$ alkyl group, a heterocycle-carbonyl group or a heterocycle-C$_{1-4}$ alkyl-carbonyl group, each of which is optionally substituted by 1 to 5 substituents selected from substituent group T, or
(iii) a carbamoyl group optionally having 1 or 2 C$_{1-8}$ alkyl group(s) optionally substituted by substituent(s) selected from substituent group T,
wherein the carbamoyl group has two substituents, and they optionally form, together with the adjacent nitrogen atom, a 3- to 8-membered saturated or an unsaturated aliphatic heterocyclic group, which is optionally substituted by substituent(s) selected from substituent group T, or
R$^1$ and R$^2$, or R$^2$ and R$^3$ are optionally bonded to form a saturated or unsaturated 4- to 8-membered heterocycle optionally substituted by 1 to 5 substituents selected from substituent group T,
[59] the compound of the above-mentioned [15], wherein
R$^{1a}$ is (i) a hydrogen atom or
(ii) a group represented by the formula —X$^2$—R$^4$,
wherein X$^2$ is a single bond, —NH— or —O—, and
R$^4$ is (i) a hydrogen atom,
(ii) a cyano group,
(iii) a C$_{1-8}$ alkyl group, a C$_{2-8}$ alkenyl group, a C$_{2-8}$ alkynyl group, a C$_{1-8}$ alkyl-carbonyl group, a C$_{3-8}$ cycloalkyl group, a C$_{6-18}$ aryl group, a C$_{6-18}$ aryl-C$_{1-4}$ alkyl group, a C$_{6-18}$ aryl-carbonyl group, a C$_{6-18}$ aryl-C$_{1-4}$ alkyl-carbonyl group, a heterocyclic group (e.g., a 5- to 8-membered heteroaryl group containing, as an atom (ring atom) constituting a ring system, 1 to 4 hetero atoms selected from an oxygen atom, an optionally oxidized sulfur atom and a nitrogen atom
(preferably, an oxygen atom, a sulfur atom and a nitrogen atom) or a saturated or unsaturated aliphatic heterocyclic group), a heterocycle-C$_{1-4}$ alkyl group, a heterocycle-carbonyl group or a heterocycle-C$_{1-4}$ alkyl-carbonyl group, each of which is optionally substituted by 1 to 5 substituents selected from substituent group T, or
(iv) a carbamoyl group optionally having 1 or 2 C$_{1-8}$ alkyl group(s) optionally substituted by substituent(s) selected from substituent group T,
wherein the carbamoyl group has two substituents, and they optionally form, together with the adjacent nitrogen atom, a 3- to 8-membered saturated or an unsaturated aliphatic heterocyclic group, which is optionally substituted by substituent(s) selected from substituent group T,
R$^{2a}$ is (i) a hydrogen atom,
(ii) a C$_{1-8}$ alkyl group, a C$_{2-8}$ alkenyl group, a C$_{2-8}$ alkynyl group, a C$_{1-8}$ alkyl-carbonyl group, a C$_{1-8}$ alkylsulfonyl group, a C$_{3-8}$ cycloalkyl group, a C$_{6-18}$ aryl group, a C$_{6-18}$ aryl-C$_{1-4}$ alkyl group, a C$_{6-18}$ aryl-carbonyl group, a C$_{6-18}$ aryl-C$_{1-4}$ alkyl-carbonyl group, a C$_{6-18}$ aryl-sulfonyl group, a heterocyclic group, a heterocycle-C$_{1-4}$ alkyl group, a heterocycle-carbonyl group or a heterocycle-C$_{1-4}$ alkyl-carbonyl group, each of which is optionally substituted by 1 to 5 substituents selected from substituent group T, or
(iii) a carbamoyl group optionally having 1 or 2 C$_{1-8}$ alkyl group(s) optionally substituted by substituent(s) selected from substituent group T,
wherein the carbamoyl group has two substituents, and they optionally form, together with the adjacent nitrogen atom, a 3- to 8-membered saturated or an unsaturated aliphatic heterocyclic group, which is optionally substituted by substituent(s) selected from substituent group T, or
R$^{1a}$ and R$^{2a}$, or R$^{2a}$ and R$^{3a}$ are optionally bonded to form a saturated or unsaturated 4- to 8-membered heterocycle optionally substituted by 1 to 5 substituents selected from substituent group T,
R$^{3a}$ is (i) a hydrogen atom, or
(ii) a C$_{1-8}$ alkyl group, a C$_{2-8}$ alkenyl group, a C$_{2-8}$ alkynyl group or a C$_{3-8}$ cycloalkyl group, each of which is optionally substituted by 1 to 3 substituents selected from halogen, hydroxy, C$_{1-4}$ alkyloxy, C$_{1-4}$ alkyl-carbonyl, carboxy, C$_{1-4}$ alkoxy-carbonyl, cyano, carbamoyl, sulfamoyl, nitro, amino, C$_{1-4}$ alkyl-carbonylamino, C$_{1-4}$ alkoxy-carbonylamino and C$_{1-4}$ alkylsulfonylamino, or $R^{3a}$ is optionally bonded to a carbon atom of the adjacent phenyl group to form a saturated or unsaturated 4- to 8-membered nitrogen-containing heterocycle, which is optionally substituted by 1 to 3 substituents selected from halogen, hydroxy, $C_{1-4}$ alkyloxy, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino, $B^a$ is a benzene ring optionally substituted by 1 to 5 substituents selected from halogen, optionally halogenated $C_{1-4}$ alkyl, hydroxy, optionally halogenated $C_{1-4}$ alkyloxy, $C_{1-4}$ alkyloxymethyl, hydroxy-$C_{1-4}$ alkyl, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino, and $C^a$ is a $C_{6-18}$ aryl group optionally substituted by 1 to 5 substituents selected from halogen, optionally halogenated $C_{1-4}$ alkyl, hydroxy, optionally halogenated $C_{1-4}$ alkyloxy, $C_{1-4}$ alkyloxymethyl, hydroxy-$C_{2-4}$ alkyl, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino,

[60] the compound of the above-mentioned [16], wherein $R^{1b}$ is (i) a hydrogen atom or
(ii) a group represented by the formula —$X^2$—$R^4$,
wherein $X^2$ is a single bond, —NH— or —O—, and
$R^4$ is (i) a hydrogen atom,
(ii) a cyano group,
(iii) a $C_{1-8}$ alkyl group, a $C_{2-8}$ alkenyl group, a $C_{2-8}$ alkynyl group, a $C_{1-8}$ alkyl-carbonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a heterocyclic group (e.g., a 5- to 8-membered heteroaryl group containing, as an atom (ring atom) constituting a ring system, 1-4 hetero atoms selected from an oxygen atom, an optionally oxidized sulfur atom and a nitrogen atom (preferably, an oxygen atom, a sulfur atom and a nitrogen atom) or a saturated or unsaturated aliphatic heterocyclic group), a heterocycle-$C_{1-4}$ alkyl group, a heterocycle-carbonyl group or a heterocycle-$C_{1-4}$ alkyl-carbonyl group, each of which is optionally substituted by 1 to 5 substituents selected from substituent group T, or
(iv) a carbamoyl group optionally having 1 or 2 $C_{1-8}$ alkyl group(s) optionally substituted by substituent(s) selected from substituent group T,
wherein the carbamoyl group has two substituents, and they optionally form, together with the adjacent nitrogen atom, a 3- to 8-membered saturated or an unsaturated aliphatic heterocyclic group, which is optionally substituted by substituent(s) selected from substituent group T, $R^{2b}$ is (i) a hydrogen atom,
(ii) a $C_{1-8}$ alkyl group, a $C_{2-8}$ alkenyl group, a $C_{2-8}$ alkynyl group, a $C_{1-8}$ alkyl-carbonyl group, a $C_{1-8}$ alkylsulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocycle-$C_{1-4}$ alkyl group, a heterocycle-carbonyl group or a heterocycle-$C_{1-4}$ alkyl-carbonyl group, each of which is optionally substituted by 1 to 5 substituents selected from substituent group T, or
(iii) a carbamoyl group optionally having 1 or 2 $C_{1-8}$ alkyl group(s) optionally substituted by substituent(s) selected from substituent group T,
wherein the carbamoyl group has two substituents, and they optionally form, together with the adjacent nitrogen atom, a 3- to 8-membered saturated or an unsaturated aliphatic heterocyclic group, which is optionally substituted by substituent(s) selected from substituent group T, or $R^{1b}$ and $R^{2b}$, or $R^{2b}$ and $R^{3b}$ are optionally bonded to form a saturated or unsaturated 4- to 8-membered heterocycle optionally substituted by 1 to 5 substituents selected from substituent group T, $R^{3b}$ is (i) a hydrogen atom, or
(ii) a $C_{1-8}$ alkyl group, a $C_{2-8}$ alkenyl group, a $C_{2-8}$ alkynyl group or a $C_{3-8}$ cycloalkyl group, each of which is optionally substituted by 1 to 3 substituents selected from halogen, hydroxy, $C_{1-4}$ alkyloxy, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino, or $R^{3b}$ is optionally bonded to a carbon atom of the adjacent phenyl group to form a saturated or unsaturated 4- to 8-membered nitrogen-containing heterocycle, which is optionally substituted by 1 to 3 substituents selected from halogen, hydroxy, $C_{1-4}$ alkyloxy, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino, $B^b$ is a benzene ring optionally substituted by 1 to 5 substituents selected from halogen, optionally halogenated $C_{1-4}$ alkyl, hydroxy, optionally halogenated $C_{1-4}$ alkyloxy, $C_{1-4}$ alkyloxymethyl, hydroxy-$C_{1-4}$ alkyl, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino, $C^b$ is a $C_{6-18}$ aryl group optionally substituted by 1 to 5 substituents selected from halogen, optionally halogenated $C_{1-4}$ alkyl, hydroxy, optionally halogenated $C_{1-4}$ alkyloxy, $C_{1-4}$ alkyloxymethyl, hydroxy-$C_{1-4}$ alkyl, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino, and $Z^b$ is a $C_{1-3}$ alkylene group optionally substituted by 1 to 3 substituents selected from halogen, hydroxy, $C_{1-4}$ alkyloxy, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino,

[61] the compound of the above-mentioned [17], wherein $R^{1c}$ is (i) a hydrogen atom or
(ii) a group represented by the formula —$X^2$—$R^4$,
wherein $X^2$ is a single bond, —NH— or —O—, and
$R^4$ is (i) a hydrogen atom,
(ii) a cyano group,
(iii) a $C_{1-8}$ alkyl group, a $C_{2-8}$ alkenyl group, a $C_{2-8}$ alkynyl group, a $C_{1-8}$ alkyl-carbonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a heterocyclic group (e.g., a 5- to 8-membered heteroaryl group containing, as an atom (ring atom) constituting a ring system, 1 to 4 hetero atoms selected from an oxygen atom, an optionally oxidized sulfur atom and a nitrogen atom
(preferably, an oxygen atom, a sulfur atom and a nitrogen atom) or a saturated or unsaturated aliphatic heterocyclic group), a heterocycle-$C_{1-4}$ alkyl group, a heterocycle-carbonyl group or a heterocycle-$C_{1-4}$ alkyl-carbonyl group, each of which is optionally substituted by 1 to 5 substituents selected from substituent group T, or
(iv) a carbamoyl group optionally having 1 or 2 $C_{1-8}$ alkyl group(s) optionally substituted by substituent(s) selected from substituent group T, wherein the carbamoyl group has two substituents, and they optionally form, together with the adjacent nitrogen atom, a 3- to 8-membered saturated or an unsaturated aliphatic heterocyclic group, which is optionally substituted by substituent(s) selected from substituent group T, $R^{2c}$ is (i) a hydrogen atom, (ii) a $C_{1-8}$ alkyl group, a $C_{2-8}$ alkenyl group, a $C_{2-8}$ alkynyl group, a $C_{1-8}$ alkyl-carbonyl group, a $C_{1-8}$ alkylsulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocycle-$C_{1-4}$ alkyl group, a heterocycle-carbonyl group or a heterocycle-$C_{1-4}$ alkyl-carbonyl group, each of which is optionally substituted by 1 to 5 substituents selected from substituent group T, or (iii) a carbamoyl group optionally having 1 or 2 $C_{1-8}$ alkyl group(s) optionally substituted by substituent(s) selected from substituent group T, wherein the carbamoyl group has two substituents, and they optionally form, together with the adjacent nitrogen atom, a 3- to 8-membered saturated or an unsaturated aliphatic heterocyclic group, which is optionally substituted by substituent(s) selected from substituent group T, or $R^{1c}$ and $R^{2c}$, or $R^{2c}$ and $R^{3c}$ are optionally bonded to form a saturated or unsaturated 4- to 8-membered heterocycle optionally substituted by 1 to 5 substituents selected from substituent group T, $R^{3c}$ is (i) a hydrogen atom, or (ii) a $C_{1-8}$ alkyl group, a $C_{2-8}$ alkenyl group, a $C_{2-8}$ alkynyl group or a $C_{3-8}$ cycloalkyl group, each of which is optionally substituted by 1 to 3 substituents selected from halogen, hydroxy, $C_{1-4}$ alkyloxy, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino, or $R^{3c}$ is optionally bonded to a carbon atom of the adjacent phenyl group to form a saturated or unsaturated 4- to 8-membered nitrogen-containing heterocycle, which is optionally substituted by 1 to 3 substituents selected from halogen, hydroxy, $C_{1-4}$ alkyloxy, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino, $B^c$ is a benzene ring optionally substituted by 1 to 5 substituents selected from halogen, optionally halogenated $C_{1-4}$ alkyl, hydroxy, optionally halogenated-$C_{1-4}$ alkyloxy, $C_{1-4}$ alkyloxymethyl, hydroxy-$C_{1-4}$ alkyl, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino, and $C^c$ is a 5- to 8-membered heterocyclic group having 1 to 3 hetero atoms selected from a nitrogen atom, an oxygen atom and an optionally oxidized sulfur atom, which is optionally substituted by 1 to 5 substituents selected from halogen, optionally halogenated $C_{1-4}$ alkyl, hydroxy, optionally halogenated $C_{1-4}$ alkyloxy, $C_{1-4}$ alkyloxymethyl, hydroxy-$C_{1-4}$ alkyl, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino,

[62] the compound of the above-mentioned [18], wherein $R^{1d}$ is (i) a hydrogen atom or (ii) a group represented by the formula —$X^2$—$R^4$, wherein $X^2$ is a single bond, —NH— or —O—, and $R^4$ is (i) a hydrogen atom, (ii) a cyano group, (iii) a $C_{1-8}$ alkyl group, a $C_{2-8}$ alkenyl group, a $C_{2-8}$ alkynyl group, a $C_{1-8}$ alkyl-carbonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a heterocyclic group (e.g., a 5- to 8-membered heteroaryl group containing, as an atom (ring atom) constituting a ring system, 1 to 4 hetero atoms selected from an oxygen atom, an optionally oxidized sulfur atom and a nitrogen atom (preferably, an oxygen atom, a sulfur atom and a nitrogen atom) or a saturated or unsaturated aliphatic heterocyclic group), a heterocycle-$C_{1-4}$ alkyl group, a heterocycle-carbonyl group or a heterocycle-$C_{1-4}$ alkyl-carbonyl group, each of which is optionally substituted by 1 to 5 substituents selected from substituent group T, or (iv) a carbamoyl group optionally having 1 or 2 $C_{1-8}$ alkyl group(s) optionally substituted by substituent(s) selected from substituent group T, wherein the carbamoyl group has two substituents, and they optionally form, together with the adjacent nitrogen atom, a 3- to 8-membered saturated or an unsaturated aliphatic heterocyclic group, which is optionally substituted by substituent(s) selected from substituent group T, $R^{2d}$ is (i) a hydrogen atom, (ii) a $C_{1-8}$ alkyl group, a $C_{2-8}$ alkenyl group, a $C_{2-8}$ alkynyl group, a $C_{1-8}$ alkyl-carbonyl group, a $C_{1-8}$ alkylsulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocycle-$C_{1-4}$ alkyl group, a heterocycle-carbonyl group or a heterocycle-$C_{1-4}$ alkyl-carbonyl group, each of which is optionally substituted by 1 to 5 substituents selected from substituent group T, or (iii) a carbamoyl group optionally having 1 or 2 $C_{1-8}$ alkyl group(s) optionally substituted by substituent(s) selected from substituent group T, wherein the carbamoyl group has two substituents, and they optionally form, together with the adjacent nitrogen atom, a 3- to 8-membered saturated or an unsaturated aliphatic heterocyclic group, which is optionally substituted by substituent(s) selected from substituent group T, or $R^{1d}$ and $R^{2d}$, or $R^{2d}$ and $R^{3d}$ are optionally bonded to form a saturated or unsaturated 4- to 8-membered heterocycle optionally substituted by 1 to 5 substituents selected from substituent group T, $R^{3d}$ is (i) a hydrogen atom, or (ii) a $C_{1-8}$ alkyl group, a $C_{2-8}$ alkenyl group, a $C_{2-8}$ alkynyl group or a $C_{3-8}$ cycloalkyl group, each of which is optionally substituted by 1 to 3 substituents selected from halogen, hydroxy, $C_{1-4}$ alkyloxy, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino, or $R^{3d}$ is optionally bonded to a carbon atom of the adjacent phenyl group to form a saturated or unsaturated 4- to 8-membered nitrogen-containing heterocycle, which is optionally substituted by 1 to 3 substituents selected from halogen, hydroxy, $C_{1-4}$ alkyloxy, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino, $B^d$ is a benzene ring optionally substituted by 1 to 5 substituents selected from halogen, optionally halogenated $C_{1-4}$ alkyl, hydroxy, optionally halogenated $C_{1-4}$ alkyloxy, $C_{1-4}$ alkyloxymethyl, hydroxy-$C_{1-4}$ alkyl, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino, $C^d$ is a 5- to 8-membered heterocyclic group having 1 to 3 hetero atoms selected from a nitrogen atom, an oxygen atom and an optionally oxidized sulfur atom, which is optionally substituted by 1 to 5 substituents selected from halogen, optionally halogenated $C_{1-4}$ alkyl, hydroxy, optionally halogenated $C_{1-4}$ alkyloxy, $C_{1-4}$ alkyloxymethyl, hydroxy-$C_{1-4}$ alkyl, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino, and $Z^d$ is a $C_{1-3}$ alkylene group optionally substituted by 1 to 3 substituents selected from halogen, hydroxy, $C_{1-4}$ alkyloxy, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino,

[63] the compound of the above-mentioned [19], wherein $R^{2e}$ is (i) a hydrogen atom, (ii) a $C_{1-8}$ alkyl group, a $C_{2-8}$ alkenyl group, a $C_{2-8}$ alkynyl group, a $C_{1-8}$ alkyl-carbonyl group, a $C_{1-8}$ alkylsulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocycle-$C_{1-4}$ alkyl group, a heterocycle-carbonyl group or a heterocycle-$C_{1-4}$ alkyl-carbonyl group, each of which is optionally substituted by 1 to 5 substituents selected from substituent group T, or (iii) a carbamoyl group optionally having 1 or 2 $C_{1-8}$ alkyl group(s) optionally substituted by substituent(s) selected from substituent group T, wherein the carbamoyl group has two substituents, and they optionally form, together with the adjacent nitrogen atom, a 3- to 8-membered saturated or an unsaturated aliphatic heterocyclic group, which is optionally substituted by substituent(s) selected from substituent group T, or $R^{2e}$ and $R^{3e}$ are optionally bonded to form a saturated or unsaturated 4- to 8-membered heterocycle optionally substituted by 1 to 5 substituents selected from substituent group T, $R^{3e}$ is (i) a hydrogen atom, or (ii) a $C_{1-8}$ alkyl group, a $C_{2-8}$ alkenyl group, a $C_{2-8}$ alkynyl group or a $C_{3-8}$ cycloalkyl group, each of which is optionally substituted by 1 to 3 substituents selected from halogen, hydroxy, $C_{1-4}$ alkyloxy, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino, or $R^{3e}$ is optionally bonded to a carbon atom of the adjacent phenyl group to form a saturated or unsaturated 4- to 8-membered nitrogen-containing heterocycle, which is optionally substituted by 1 to 3 substituents selected from halogen, hydroxy, $C_{1-4}$ alkyloxy, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino, $B^e$ is a benzene ring optionally substituted by 1 to 5 substituents selected from halogen, optionally halogenated $C_{1-4}$ alkyl, hydroxy, optionally halogenated $C_{1-4}$ alkyloxy, $C_{1-4}$ alkyloxymethyl, hydroxy-$C_{1-4}$ alkyl, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino, and $C^e$ is a $C_{6-18}$ aryl group optionally substituted by 1 to 5 substituents selected from halogen, optionally halogenated $C_{1-4}$ alkyl, hydroxy, optionally halogenated $C_{1-4}$ alkyloxy, $C_{1-4}$ alkyloxymethyl, hydroxy-$C_{1-4}$ alkyl, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino,

[64] the compound of the above-mentioned [20], wherein $R^{2f}$ is (i) a hydrogen atom, (ii) a $C_{1-8}$ alkyl group, a $C_{2-8}$ alkenyl group, a $C_{2-8}$ alkynyl group, a $C_{1-8}$ alkyl-carbonyl group, a $C_{1-8}$ alkylsulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocycle-$C_{1-4}$ alkyl group, a heterocycle-carbonyl group or a heterocycle-$C_{1-4}$ alkyl-carbonyl group, each of which is optionally substituted by 1 to 5 substituents selected from substituent group T, or (iii) a carbamoyl group optionally having 1 or 2 $C_{1-8}$ alkyl group(s) optionally substituted by substituent(s) selected from substituent group T, wherein the carbamoyl group has two substituents, and they optionally form, together with the adjacent nitrogen atom, a 3- to 8-membered saturated or an unsaturated aliphatic heterocyclic group, which is optionally substituted by substituent(s) selected from substituent group T, or $R^{2f}$ and $R^{3f}$ are optionally bonded to form a saturated or unsaturated 4- to 8-membered heterocycle optionally substituted by 1 to 5 substituents selected from substituent group T, $R^{3f}$ is (i) a hydrogen atom, or (ii) a $C_{1-8}$ alkyl group, a $C_{2-8}$ alkenyl group, a $C_{2-8}$ alkynyl group or a $C_{3-8}$ cycloalkyl group, each of which is optionally substituted by 1 to 3 substituents selected from halogen, hydroxy, $C_{1-4}$ alkyloxy, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino, or $R^{3f}$ is optionally bonded to a carbon atom of the adjacent phenyl group to form a saturated or unsaturated 4- to 8-membered nitrogen-containing heterocycle, which is optionally substituted by 1 to 3 substituents selected from halogen, hydroxy, $C_{1-4}$ alkyloxy, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino, $B^f$ is a benzene ring optionally substituted by 1 to 5 substituents selected from halogen, optionally halogenated $C_{1-4}$ alkyl, hydroxy, optionally halogenated $C_{1-4}$ alkyloxy, $C_{1-4}$ alkyloxymethyl, hydroxy-$C_{1-4}$ alkyl, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino, $C^f$ is a $C_{6-18}$ aryl group optionally substituted by 1 to 5 substituents selected from halogen, optionally halogenated $C_{1-4}$ alkyl, hydroxy, optionally halogenated $C_{1-4}$ alkyloxy, $C_{1-4}$ alkyloxymethyl, hydroxy-$C_{1-4}$ alkyl, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino, and $Z^f$ is a $C_{1-3}$ alkylene group optionally substituted by 1 to 3 substituents selected from halogen, hydroxy, $C_{1-4}$ alkyloxy, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino,

[65] the compound of the above-mentioned [21], wherein
R$^{2g}$ is (i) a hydrogen atom,
(ii) a $C_{1-8}$ alkyl group, a $C_{2-8}$ alkenyl group, a $C_{2-8}$ alkynyl group, a $C_{1-8}$ alkyl-carbonyl group, a $C_{1-8}$ alkylsulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocycle-$C_{1-4}$ alkyl group, a heterocycle-carbonyl group or a heterocycle-$C_{1-4}$ alkyl-carbonyl group, each of which is optionally substituted by 1 to 5 substituents selected from substituent group T, or
(iii) a carbamoyl group optionally having 1 or 2 $C_{1-8}$ alkyl group(s) optionally substituted by substituent(s) selected from substituent group T,
wherein the carbamoyl group has two substituents, and they optionally form, together with the adjacent nitrogen atom, a 3- to 8-membered saturated or an unsaturated aliphatic heterocyclic group, which is optionally substituted by substituent(s) selected from substituent group T, or
R$^{2g}$ and R$^{3g}$ are optionally bonded to form a saturated or unsaturated 4- to 8-membered heterocycle optionally substituted by 1 to 5 substituents selected from substituent group T,
R$^{3g}$ is (i) a hydrogen atom, or
(ii) a $C_{1-8}$ alkyl group, a $C_{2-8}$ alkenyl group, a $C_{2-8}$ alkynyl group or a $C_{3-8}$ cycloalkyl group, each of which is optionally substituted by 1 to 3 substituents selected from halogen, hydroxy, $C_{1-4}$ alkyloxy, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino, or
R$^{3g}$ is optionally bonded to a carbon atom of the adjacent phenyl group to form a saturated or unsaturated 4- to 8-membered nitrogen-containing heterocycle optionally substituted by 1 to 3 substituents selected from halogen, hydroxy, $C_{1-4}$ alkyloxy, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino,
B$^g$ is a benzene ring optionally substituted by 1 to 5 substituents selected from halogen, optionally halogenated $C_{1-4}$ alkyl, hydroxy, optionally halogenated $C_{1-4}$ alkyloxy, $C_{1-4}$ alkyloxymethyl, hydroxy-$C_{1-4}$ alkyl, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino,
C$^g$ is a 5- to 8-membered heterocyclic group having 1 to 3 hetero atoms selected from a nitrogen atom, an oxygen atom and an optionally oxidized sulfur atom, which is optionally substituted by 1 to 5 substituents selected from halogen, optionally halogenated $C_{1-4}$ alkyl, hydroxy, optionally halogenated $C_{1-4}$ alkyloxy, $C_{1-4}$ alkyloxymethyl, hydroxy-$C_{1-4}$ alkyl, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino, and the like.

According to the present invention, a fused pyrimidine compound having a superior tyrosine kinase inhibitory action, which is low toxic and highly satisfactory as a pharmaceutical product, a production method thereof and use thereof can be provided.

In the present specification, unless otherwise specified, the "aryl" in the "aryl group" and the substituents includes a monocyclic aryl group and a fused polycyclic aryl group. As the "aryl group", for example, a $C_{6-18}$ aryl group can be mentioned. As the "$C_{6-18}$ aryl group", for example, phenyl, biphenylyl, naphthyl, anthryl, phenanthryl and acenaphthylenyl can be mentioned.

In the present specification, as the "heterocyclic group" (and "heterocycle-" in the substituents), for example, a 5- to 8-membered heteroaryl group or a saturated or unsaturated aliphatic heterocyclic group containing, as an atom (ring atom) constituting a ring system, one or more (preferably 1 to 4, more preferably 1 or 2) hetero atoms selected from an oxygen atom, an optionally oxidized sulfur atom and a nitrogen atom and the like (preferably, an oxygen atom, a sulfur atom and a nitrogen atom etc.) can be mentioned.

In the present specification, unless otherwise specified, as the "aliphatic hydrocarbon group", a linear or branched aliphatic hydrocarbon group having 1 to 15 carbon atom (preferably, 1 to 8 carbon atom) can be mentioned. As such "aliphatic hydrocarbon group", for example, a $C_{1-8}$ alkyl group, a $C_{2-8}$ alkenyl group, a $C_{2-8}$ alkynyl group, a $C_{3-8}$ cycloalkyl group and the like can be mentioned.

In the present specification, unless otherwise specified, as the "heteroaryl group", an aromatic monocyclic heterocyclic group (e.g., 5- or 6-membered aromatic monocyclic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like) and an aromatic fused heterocyclic group (e.g., 8 to 12-membered aromatic fused heterocyclic group such as benzofuranyl, isobenzofuranyl, benzothienyl, indolyl, isoindolyl, 1H-indazolyl, benzindazolyl, benzoxazolyl, 1,2-benzisoxazolyl, benzothiazolyl, benzopyranyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acrydinyl, phenoxazinyl, phenothiazinyl, phenazinyl, phenoxathiinyl, thianthrenyl, phenathridinyl, phenathrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like) and the like can be mentioned. As the aromatic fused heterocyclic group, a heterocycle wherein the aforementioned 5- or 6-membered aromatic monocyclic heterocyclic group is fused with a benzene ring and a heterocycle wherein the same or different two heterocycles of the aforementioned 5- or 6-membered aromatic monocyclic heterocyclic group are fused are preferable.

In the present specification, unless otherwise specified, as the "aliphatic heterocyclic group", for example, a 3- to 8-membered (preferably 5- or 6-membered) saturated or unsaturated (preferably saturated) aliphatic heterocyclic group such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, dihydro-1,2,4-oxadiazolyl and the like, and the like can be mentioned.

In the present specification, unless otherwise specified, as the "$C_{1-8}$ alkyl group", for example, methyl, ethyl, n-propyl, i-propyl, n-butyl, i-butyl, s-butyl, t-butyl, n-pentyl, i-pentyl, t-pentyl, neopentyl, n-hexyl, i-hexyl, n-heptyl and n-octyl and the like can be mentioned, with preference given to a $C_{1-6}$ alkyl group. In the present specification, moreover, unless otherwise specified, as the "$C_{1-4}$ alkyl group", for example, methyl, ethyl, n-propyl, i-propyl, n-butyl and i-butyl can be mentioned.

In the present specification, unless otherwise specified, as the "$C_{2-8}$ alkenyl group", for example, vinyl, (1- or 2-)propenyl, (1-, 2- or 3-)butenyl, pentenyl, octenyl and (1,3-)butadienyl can be mentioned, with preference given to a $C_{2-4}$ alkenyl group.

In the present specification, unless otherwise specified, as the "$C_{2-8}$ alkynyl group", for example, ethynyl, (1- or 2-)propynyl, (1-, 2- or 3-)butynyl, pentynyl and octynyl can be mentioned, with preference given to a $C_{2-4}$ alkynyl group.

In the present specification, unless otherwise specified, as the "$C_{3-8}$ cycloalkyl group", for example, cyclopropyl, cyclobutyl, cyclopentyl, cyclohexyl, cycloheptyl and cyclooctyl can be mentioned, with preference given to a $C_{3-6}$ cycloalkyl group.

In the present specification, unless otherwise specified, as the "$C_{1-4}$ alkylene", for example, methylene, ethylene, trimethylene, tetramethylene and propylene and the like can be mentioned.

In the present specification, unless otherwise specified, as the "—O—($C_{1-4}$ alkylene)-", for example, —OCH$_2$—, —OCH$_2$CH$_2$—, —O—(CH$_2$)$_3$—, —O(CH$_2$)$_4$—, —OCH(CH$_3$)—, —OC(CH$_3$)$_2$—, —OCH(CH$_3$)CH$_2$—, —OCH$_2$CH(CH$_3$)—, —OC(CH$_3$)$_2$CH$_2$— and —OCH$_2$C(CH$_3$)$_2$— and the like can be mentioned.

In the present specification, unless otherwise specified, as the "$C_{6-18}$ aryl-carbonyl group", for example, benzoyl, naphthoyl, anthrylcarbonyl, phenanthrylcarbonyl and acenaphthylenylcarbonyl and the like can be mentioned.

In the present specification, unless otherwise specified, as the "$C_{6-18}$ aryl-$C_{1-4}$ alkyl-carbonyl group", for example, benzylcarbonyl, 3-phenylpropionyl, 2-phenylpropionyl, 4-phenylbutyryl and 5-phenylpentanoyl and the like can be mentioned.

In the present specification, unless otherwise specified, as the "halogen", fluorine, chlorine, bromine and iodine can be mentioned.

As the "5- to 8-membered heterocycle-carbonyl group containing 1 to 3 hetero atoms selected from a nitrogen atom, an oxygen atom and a sulfur atom", "a 5- to 8-membered cyclic amino-carbonyl group optionally having 1 or 2 hetero atoms selected from a nitrogen atom, an oxygen atom and a sulfur atom" is preferable, for example, pyrrolidin-1-ylcarbonyl, piperidin-1-ylcarbonyl, piperazin-1-ylcarbonyl, morpholin-4-ylcarbonyl, thiomorpholin-4-ylcarbonyl and the like can be mentioned.

In the above-mentioned formula, as the "aryl group" for A, a $C_{6-18}$ aryl group is preferable, and phenyl is more preferable.

The "aryl group" is optionally substituted by a group of the formula —Y$^2$—B, wherein Y$^2$ is a single bond, —O—, —O—($C_{1-3}$ alkylene)- (preferably —OCH$_2$—), —NH— or —S—, and B is an aryl group, a heterocyclic group, a $C_{3-8}$ cycloalkyl group, a carbamoyl group, a ureido group, a $C_{6-18}$ aryl-carbonyl group or a $C_{6-18}$ aryl-$C_{1-4}$ alkyl-carbonyl group, each of which is optionally substituted.

As Y$^2$, a single bond, —O— or —OCH$_2$— is preferable, and —O— or —OCH$_2$— is more preferable.

As the "aryl group" for B, a $C_{6-18}$ aryl group is preferable, and phenyl is more preferable.

As the "heterocyclic group" for B, the aforementioned "5 or 6-membered aromatic monocyclic heterocyclic group" is preferable, and pyridyl is more preferable.

The "aryl group", "heterocyclic group", "$C_{6-18}$ aryl-carbonyl group" or "$C_{6-18}$ aryl-$C_{1-4}$ alkyl-carbonyl group" for B may have, for example, 1 to 5, the same or different substituents selected from halogen, optionally halogenated $C_{1-4}$ alkyl, hydroxy, optionally halogenated $C_{1-4}$ alkyloxy, $C_{1-4}$ alkyloxymethyl, hydroxy-$C_{1-4}$ alkyl, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino, at any substitutable position(s).

The "aryl group" for A may have, besides a group of the above-mentioned formula —Y$^2$—B, 1 to 5, the same or different substituents at any substitutable position(s). As such substituent, substituents similar to those exemplified for "aryl group" or "heterocyclic group" for B can be mentioned.

As the "aliphatic hydrocarbon group" for R$^3$, a $C_{1-8}$ alkyl group, a $C_{2-8}$ alkenyl group, a $C_{2-8}$ alkynyl group and a $C_{3-8}$ cycloalkyl group are preferable.

The "aliphatic hydrocarbon group" for R$^3$ is optionally substituted by 1 to 3 substituents selected from halogen, hydroxy, $C_{1-4}$ alkyloxy, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino.

The "$C_{1-4}$ alkylene" and "—O—($C_{1-4}$ alkylene)-" for Y$^1$ are optionally substituted by 1 to 3 substituents selected from halogen, hydroxy, $C_{1-4}$ alkyloxy, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino.

As X$^1$, —NR$^3$— wherein R$^3$ is as defined above is preferable.

As the "optionally substituted group bonded via a carbon atom, a nitrogen atom or an oxygen atom" for R$^1$, a group of the formula —X$^2$—R$^4$ can be mentioned, wherein X$^2$ is a single bond, —NH— or —O—, and R$^4$ is a hydrogen atom, a cyano group, or a $C_{1-8}$ alkyl group, a $C_{2-8}$ alkenyl group, a $C_{2-8}$ alkynyl group, a carbamoyl group, a $C_{1-8}$ alkyl-carbonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a heterocyclic group, a heterocycle-$C_{1-4}$ alkyl group, a heterocycle-carbonyl group or a heterocycle-$C_{1-4}$ alkyl-carbonyl group, each of which is optionally substituted.

The "$C_{1-8}$ alkyl group", "$C_{2-8}$ alkenyl group", "$C_{2-8}$ alkynyl group", "$C_{1-8}$ alkyl-carbonyl group", "$C_{3-8}$ cycloalkyl group", "$C_{6-18}$ aryl group", "$C_{6-18}$ aryl-$C_{1-4}$ alkyl group", "$C_{6-18}$ aryl-carbonyl group", "$C_{6-18}$ aryl-$C_{1-4}$ alkyl-carbonyl group", "heterocyclic group", "heterocycle-$C_{1-4}$ alkyl group", "heterocycle-carbonyl group" and "heterocycle-$C_{1-4}$ alkyl-carbonyl group" are, for example, optionally substituted by one or more (preferably 1 to 5, more preferably 1 to 3) substituent(s) selected from (a) halogen,
(b) oxo,
(c) optionally halogenated $C_{1-4}$ alkyl,
(d) —(CH$_2$)$_m$-Q,
(e) —(CH$_2$)$_m$—Z$^1$-(optionally halogenated $C_{1-4}$ alkyl),
(f) —(CH$_2$)$_m$—Z$^1$—$C_{3-8}$ cycloalkyl,
(g) —(CH$_2$)$_m$—Z$^2$—(CH$_2$)$_n$-Q,
(h) —(CH$_2$)$_m$—Z$^2$—(CH$_2$)$_n$—Z$^1$-(optionally halogenated $C_{1-4}$ alkyl),
(i) —(CH$_2$)$_m$—Z$^2$—(CH$_2$)$_n$—Z$^1$—$C_{3-8}$ cycloalkyl,
(j) —(CH$_2$)$_m$—Z$^1$-(optionally substituted heterocyclic group)
(preferably, said heterocyclic group is a 5- to 8-membered heterocyclic group having 1 to 3 hetero atoms selected from a nitrogen atom, an oxygen atom and an optionally oxidized sulfur atom)
(k) —(CH$_2$)$_m$—Z$^2$—$C_{1-4}$ alkoxy, and (l) —$(CH_2)_m$—$Z^2$—$(CH_2)_n$—$Z^1$—$(CH_2)_n$—$Z^1$—$C_{1-4}$ alkyl (hereinafter to be sometimes to be referred to as substituent group T).

In these formulas, m is an integer of 0 to 4, n is an integer of 1 to 4, Q is hydroxy, carboxy, cyano, nitro, —$NR^6R^7$, —$CONR^6R^7$ or —$SO_2NR^6R^7$, $Z^1$ is —O—, —CO—, —C(OH)$R^8$—, —C(=N—$OR^8$)—, —S—, —SO—, —$SO_2$—, —N(COR$^8$)—, —N(CO$_2R^9$)—, —N(SO$_2R^9$)—, —CO—O—, —O—CO—, —CO—NR$^8$—, —NR$^8$—CO—, —NR$^8$—CO$_2$—, —NR$^8$—CO—NH—, —NR$^8$—SO$_2$—, or —NR$^8$—C(=NH)—NH—, and $Z^2$ is —O—, —CO—, —C(OH)$R^8$—, —C(=N—$OR^8$)—, —S—, —SO—, —$SO_2$—, —NR$^8$—, —N(COR$^8$)—, —N(CO$_2R^9$)—, —N(SO$_2R^9$)—, —CO—O—, —O—CO—, —CO—NR$^8$—, —NR$^8$—CO—, —NR$^8$—CO$_2$—, NR$^8$—CO—NH—, —NR$^8$—C(=NH)—NH—, —NR$^8$—SO$_2$—, or —SO$_2$—NR$^8$—. In these formulas, $(CH_2)_m$ and $(CH_2)_n$ are optionally substituted by one or more (preferably 1 to 5, more preferably 1 to 3) substituents selected from, for example, halogen, optionally halogenated $C_{1-4}$ alkyl and hydroxy, and when m or n is not less than 2, a subset —$CH_2CH_2$— of $(CH_2)_m$ and $(CH_2)_n$ is optionally replaced by —CH=CH— or —C≡C—.

In these formulas, $R^6$ and $R^7$ are the same or different and each is a hydrogen atom or $C_{1-4}$ alkyl, or $R^6$ and $R^7$ form a ring together with a nitrogen atom. In these formulas, moreover, $R^8$ is a hydrogen atom or $C_{1-4}$ alkyl and $R^9$ is $C_{1-4}$ alkyl. When $R^6$ and $R^7$ form a ring together with a nitrogen atom, as the nitrogen-containing heterocyclic group, for example, a 3 to 8-membered (preferably 5 or 6-membered) saturated or unsaturated (preferably saturated) aliphatic heterocyclic group such as azetidinyl, pyrrolidinyl, piperidinyl, homopiperidinyl, heptamethyleneimino, morpholinyl, thiomorpholinyl, piperazinyl, homopiperazinyl and the like, and the like can be mentioned.

As $X^2$, a single bond is preferable.

As $R^4$, a hydrogen atom or a $C_{1-8}$ alkyl group, a $C_{2-8}$ alkenyl group, a $C_{6-18}$ aryl group or heterocyclic group, each of which is optionally substituted is preferable. As the "$C_{6-18}$ aryl group" for $R^4$, phenyl is preferable. As the "heterocyclic group" for $R^4$, the aforementioned "5 or 6-membered aromatic monocyclic heterocyclic group" is preferable, and furyl is preferable.

As the "optionally substituted group bonded via a carbon atom or a sulfur atom" for $R^2$, a $C_{1-8}$ alkyl group, a $C_{2-8}$ alkenyl group, a $C_{2-8}$ alkynyl group, a carbamoyl group, a $C_{1-8}$ alkyl-carbonyl group, a $C_{1-8}$ alkylsulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocycle-$C_{1-4}$ alkyl group, a heterocycle-carbonyl group or a heterocycle-$C_{1-4}$ alkyl-carbonyl group, each of which is optionally substituted, can be mentioned.

The "$C_{1-8}$ alkyl group", "$C_{2-8}$ alkenyl group", "$C_{2-8}$ alkynyl group", "$C_{1-8}$ alkyl-carbonyl group", "$C_{1-8}$ alkylsulfonyl group", "$C_{3-8}$ cycloalkyl group", "$C_{6-18}$ aryl group", "$C_{6-18}$ aryl-$C_{1-4}$ alkyl group", "$C_{6-18}$ aryl-carbonyl group", "$C_{6-18}$ aryl-$C_{1-4}$ alkyl-carbonyl group", "$C_{6-18}$ aryl-sulfonyl group", "heterocyclic group", "heterocycle-$C_{1-4}$ alkyl group", "heterocycle-carbonyl group" and "heterocycle-$C_{1-4}$ alkyl-carbonyl group" are optionally substituted by, for example, one or more (preferably 1 to 5, more preferably 1 to 3) substituents selected from the above-mentioned substituent group T.

As $R^2$, a hydrogen atom or a $C_{1-8}$ alkyl group, a $C_{6-18}$ aryl group, a $C_{6-18}$ aryl-$C_{1-4}$ alkyl group, a $C_{6-18}$ aryl-carbonyl group, a $C_{6-18}$ aryl-sulfonyl group or heterocycle-$C_{1-4}$ alkyl group, each of which is optionally substituted, is preferable.

As the "$C_{6-18}$ aryl group" for $R^2$, phenyl is preferable. As the "$C_{6-18}$ aryl-$C_{1-4}$ alkyl group" for $R^2$, benzyl is preferable. As the "$C_{6-18}$ aryl-carbonyl group" for $R^2$, benzoyl is preferable. As the "$C_{6-18}$ aryl-sulfonyl group" for $R^2$, phenylsulfonyl is preferable. As the "heterocyclic group" or "heterocycle-" of "heterocycle-$C_{1-4}$ alkyl group", "heterocycle-carbonyl group" and "heterocycle-$C_{1-4}$ alkyl-carbonyl group" for $R^2$, the aforementioned "5 or 6-membered aromatic monocyclic heterocyclic group" or the aforementioned "aliphatic heterocyclic group" is preferable, and furyl or tetrahydrofuryl is preferable.

In the substituents that a group represented by $R^2$ may have, when $R^6$ and $R^7$ form a ring together with a nitrogen atom, the "ring" optionally further has 1 to 5 (preferably 1 to 3) the same or different substituents. As such substituents, substituents similar to those exemplified for "aryl group" or "heterocyclic group" for B can be mentioned.

The aforementioned "carbamoyl group" and "ureido group" optionally have 1 or 2 optionally substituted $C_{1-8}$ alkyl group(s). Alternatively, the "carbamoyl group" and "ureido group" may have two substituents and they may form an optionally substituted ring, together with the adjacent nitrogen atom. As the "ring" of the "optionally substituted ring", rings similar to those formed by $R^6$ and $R^7$ together with a nitrogen atom as exemplified above can be mentioned. As the "substituent" of the "optionally substituted $C_{1-8}$ alkyl group" and as the "substituent" of the "optionally substituted ring", groups similar to the substituents of the above-mentioned substituent group T can be mentioned.

As the "optionally substituted carbamoyl group", carbamoyl, $C_{1-8}$ alkylcarbamoyl, di($C_{1-8}$ alkyl)carbamoyl, $C_{6-18}$ aryl-$C_{1-4}$ alkylcarbamoyl, azetidin-1-ylcarbonyl, pyrrolidin-1-ylcarbonyl, piperidin-1-ylcarbonyl, piperazin-1-ylcarbonyl, morpholin-4-ylcarbonyl, thiomorpholin-4-ylcarbonyl, ($C_{1-4}$ alkyl)piperidin-1-ylcarbonyl, ($C_{6-18}$ aryl-$C_{1-4}$ alkyl)piperidin-1-ylcarbonyl and the like can be mentioned.

As the "optionally substituted ureido group", ureido, 3-($C_{1-8}$ alkyl)ureido, 3,3-di($C_{1-8}$ alkyl)ureido, 3-($C_{6-18}$ aryl-$C_{1-4}$ alkyl)ureido, azetidine-1-ylcarbonylamino, pyrrolidin-1-ylcarbonylamino, piperidin-1-ylcarbonylamino, piperazin-1-ylcarbonylamino, morpholin-4-ylcarbonylamino, thiomorpholin-4-ylcarbonylamino, ($C_{1-4}$ alkyl)piperidin-1-ylcarbonylamino, ($C_{6-18}$ aryl-$C_{1-4}$ alkyl)piperidin-1-ylcarbonylamino and the like can be mentioned.

As the "ring structure" of the optionally substituted ring structure formed by $R^3$ bonded to a carbon atom or a hetero atom on the aryl group or the heteroaryl group represented by A, a saturated or unsaturated (preferably saturated) 4- to 8-membered (preferably 5- or 6-membered) nitrogen-containing heterocycle can be mentioned. Specifically,

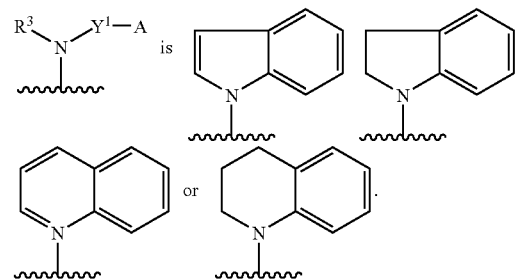

The "ring structure" may have 1 to 5 (preferably 1 to 3, more preferably 1 or 2) the same or different substituents at any substitutable position(s). As such substituents, substituents similar to those exemplified for "aryl group" or "heterocyclic group" for B can be mentioned.

As the "ring structure" of the optionally substituted ring structure formed by $R^1$ and $R^2$ bonded to each other, a saturated or unsaturated (preferably saturated) 4- to 8-membered (preferably 5- or 6-membered) heterocycle can be mentioned. When $R^1$ and $R^2$ are bonded to form an optionally substituted ring structure, for example,

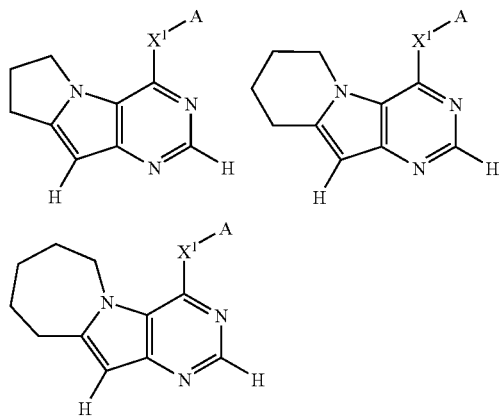

wherein each symbol is as defined above, and the like can be mentioned.

As the "ring structure" of the optionally substituted ring structure formed by $R^2$ and $R^3$ bonded to each other, a saturated or unsaturated (preferably saturated) 4- to 8-membered (preferably 5- to 7-membered) heterocycle can be mentioned. When $R^2$ and $R^3$ are bonded to form an optionally substituted ring structure, for example,

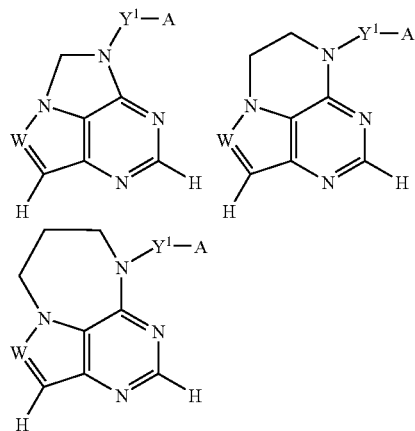

wherein each symbol is as defined above, and the like can be mentioned. The "ring structure" formed by $R^1$ and $R^2$, or $R^2$ and $R^3$ bonded to each other may have 1 to 5 (preferably 1 to 3, more preferably 1 or 2) the same or different substituents selected from the above-mentioned substituent group T at any substitutable position(s).

When W is $C(R^1)$, compound (I) is represented by the following formula (IA):

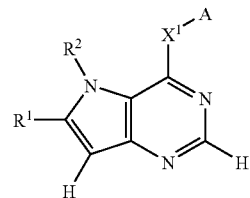

(IA)

wherein each symbol is as defined above.

When W is N, compound (I) is represented by the following formula (IB) or (IC):

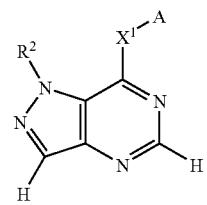

(IB)

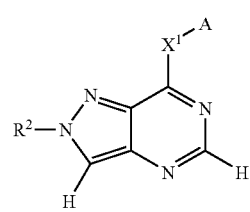

(IC)

wherein each symbol is as defined above.

Specifically, as compound (I), the following compounds (Ia)-(Ij) and the like are preferably used.

[compound (Ia)]

A compound represented by the formula:

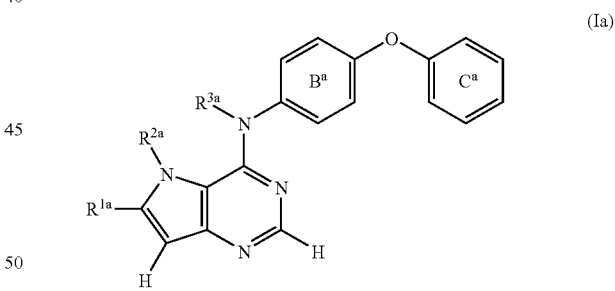

(Ia)

wherein $R^{1a}$ is a hydrogen atom or an optionally substituted group bonded via a carbon atom, a nitrogen atom or an oxygen atom, and $R^{2a}$ is an optionally substituted group bonded via a carbon atom or a sulfur atom, or $R^{1a}$ and $R^{2a}$, or $R^{2a}$ and $R^{3a}$ are optionally bonded to form an optionally substituted ring structure, $R^{3a}$ is a hydrogen atom or an optionally substituted aliphatic hydrocarbon group, or $R^{3a}$ is optionally bonded to a carbon atom of the adjacent phenyl group to form an optionally substituted ring structure, $B^a$ is an optionally substituted benzene ring, and $C^a$ is an optionally substituted $C_{6-18}$ aryl group, or a salt thereof.

As the "optionally substituted group bonded via a carbon atom, a nitrogen atom or an oxygen atom" for $R^{1a}$, those similar to the "optionally substituted group bonded via a carbon atom, a nitrogen atom or an oxygen atom" for $R^1$ can be used.

As the "optionally substituted group bonded via a carbon atom or a sulfur atom" for $R^{2a}$, those similar to the "optionally substituted group bonded via a carbon atom or a sulfur atom" for $R^2$ can be used.

As the "optionally substituted ring structure" formed by $R^{1a}$ and $R^{2a}$, or $R^{2a}$ and $R^{3a}$ bonded to each other, those similar to the "optionally substituted ring structure" formed by $R^1$ and $R^2$, or $R^2$ and $R^3$ bonded to each other can be used.

As the "optionally substituted aliphatic hydrocarbon group" for $R^{3a}$, those similar to the "optionally substituted aliphatic hydrocarbon group" for $R^3$ can be used.

As the "optionally substituted ring structure" for $R^{3a}$, which is formed by binding to a carbon atom of the adjacent phenyl group, those similar to the "optionally substituted ring structure" for $R^3$, which is formed by binding to a carbon atom of the adjacent phenyl group can be used.

As the substituent of the "optionally substituted benzene ring" for $B^a$, for example, 1 to 5, the same or different substituents selected from halogen, optionally halogenated $C_{1-4}$ alkyl, hydroxy, optionally halogenated $C_{1-4}$ alkyloxy, $C_{1-4}$ alkyloxymethyl, hydroxy-$C_{1-4}$ alkyl, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino can be used.

As the "$C_{6-18}$ aryl group" of the "optionally substituted $C_{6-18}$ aryl group" for $C^a$, for example, phenyl, biphenylyl, naphthyl, anthryl, phenanthryl, acenaphthylenyl and the like can be used, with preference given to a phenyl group.

As the "substituent" of the "optionally substituted $C_{6-18}$ aryl group" for $C^a$, those similar to the substituents of the "optionally substituted benzene ring" for $B^a$ can be used.

As $R^{2a}$, a $C_{1-8}$ alkyl group, a $C_{2-8}$ alkenyl group, a $C_{2-8}$ alkynyl group, a carbamoyl group, a $C_{1-8}$ alkyl-carbonyl group, a $C_{1-8}$ alkylsulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocycle-$C_{1-4}$ alkyl group, a heterocycle-carbonyl group or a heterocycle-$C_{1-4}$ alkyl-carbonyl group, each of which is optionally substituted by 1 to 5 substituents selected from
(a) halogen,
(b) oxo,
(c) optionally halogenated $C_{1-4}$ alkyl,
(d) —$(CH_2)_m$-Q,
(e) —$(CH_2)_m$—$Z^1$-(optionally halogenated $C_{1-4}$ alkyl),
(f) —$(CH_2)_m$—$Z^1$—$C_{3-8}$ cycloalkyl,
(g) —$(CH_2)_m$—$Z^2$—$(CH_2)_n$-Q,
(h) —$(CH_2)_m$—$Z^2$—$(CH_2)_n$—$Z^1$-(optionally halogenated $C_{1-4}$ alkyl),
(i) —$(CH_2)_m$—$Z^2$—$(CH_2)_m$—$Z^1$—$C_{3-8}$ cycloalkyl,
(j) —$(CH_2)_m$—$Z^1$-(optionally substituted heterocyclic group) (preferably, said heterocyclic group is a 5- to 8-membered heterocyclic group having 1 to 3 hetero atoms selected from a nitrogen atom, an oxygen atom and an optionally oxidized sulfur atom),
(k) —$(CH_2)_m$—$Z^2$—$C_{1-4}$ alkoxy, and
(l) —$(CH_2)_m$—$Z^2$—$(CH_2)_n$—$Z^1$—$(CH_2)_n$—$Z^1$—$C_{1-4}$ alkyl
wherein m is an integer of 0 to 4, n is an integer of 1 to 4,
Q is hydroxy, carboxy, cyano, nitro, —$NR^6R^7$, —$CONR^6R^7$, —$OCONH_2$ or —$SO_2NR^6R^7$,
$Z^1$ is —O—, —CO—, —$C(OH)R^8$—, —$C(=N-OR^8)$—, —S—, —SO—, —$SO_2$—, —$N(COR^8)$—, —$N(CO_2R^9)$—, —$N(SO_2R^9)$—, —CO—O—, —O—CO—, —CO—$NR^8$—, —$NR^8$—CO—, —$NR^8$—$CO_2$—, —$NR^8$—CO—NH—, —$NR^8$—$SO_2$—, or —$NR^8$—C(=NH)—NH—, $Z^2$ is —O—, —CO—, —$C(OH)R^8$—, —$C(=N-OR)$—, —S—, —SO—, —$SO_2$—, —$NR^8$—, —$N(COR^8)$—, —$N(CO_2R^9)$—, —$N(SO_2R^9)$—, —CO—O—, —O—CO—, —CO—$NR^8$—, —$NR^8$—CO—, —$NR^8$—$CO_2$—, —$NR^8$—CO—NH—, —$NR^8$—C(=NH)—NH—, —$NR^8$—$SO_2$—, or —$SO_2$—$NR^8$—, $(CH_2)_m$ and $(CH_2)_n$ are optionally substituted by 1 to 5 substituents selected from halogen, optionally halogenated $C_{1-4}$ alkyl and hydroxy, and when m or n is not less than 2, a subset —$CH_2CH_2$— of $(CH_2)_m$ and $(CH_2)_n$ is optionally replaced by —CH=CH— or —C≡C—, $R^6$ and $R^7$ are the same or different and each is a hydrogen atom or a $C_{1-4}$ alkyl group, or $R^6$ and $R^7$ are bonded to form, together with a nitrogen atom, a 3- to 8-membered saturated or unsaturated aliphatic heterocyclic group, $R^8$ is a hydrogen atom or $C_{1-4}$ alkyl, and $R^9$ is $C_{1-4}$ alkyl, is preferable.

As compound (Ia), a compound wherein
$B^a$ is a benzene ring optionally substituted by 1 to 4 substituents selected from halogen, $C_{1-4}$ alkyl, hydroxy-$C_{1-4}$ alkyl and $C_{1-4}$ alkyloxy;
$C^a$ is a phenyl group optionally substituted by 1 to 5 substituents selected from (i) halogen, (ii) optionally halogenated $C_{1-4}$ alkyl, (iii) hydroxy-$C_{1-4}$ alkyl, (iv) heterocycle-$C_{1-4}$ alkyl (preferably, 5- to 8-membered heterocycle-$C_{1-4}$ alkyl, said 5- to 8-membered heterocycle has 1 to 3 hetero atoms selected from a nitrogen atom, an oxygen atom and an optionally oxidized sulfur atom, such as imidazolyl, triazolyl and the like), (v) optionally halogenated $C_{1-4}$ alkyloxy, (vi) $C_{1-4}$ alkyl-carbonyl, (vii) cyano, (viii) carbamoyl optionally substituted by $C_{1-8}$ alkyl and (ix) $C_{1-4}$ alkoxy-carbonyl;
$R^{1a}$ is
(i) a hydrogen atom,
(ii) a cyano group, or
(iii) a $C_{1-4}$ alkyl group or a $C_{2-4}$ alkenyl group, each of which is optionally substituted by —$NR^8$—CO—$(CH_2)_n$—$NR^6R^7$ wherein n is an integer of 1 to 4, $R^6$ and $R^7$ are the same or different and each is a hydrogen atom or a $C_{1-4}$ alkyl group, $R^8$ is a hydrogen atom or a $C_{1-4}$ alkyl group, and when n is not less than 2, a subset —$CH_2CH_2$— of $(CH_2)_n$ is optionally replaced by —CH=CH—;

$R^{2a}$ is a $C_{1-8}$ alkyl group, a $C_{2-8}$ alkenyl group or a $C_{2-8}$ alkynyl group, each of which is optionally substituted by substituent(s) selected from
(a) hydroxy,
(b) carboxy,
(c) cyano,
(d) optionally halogenated $C_{1-4}$ alkyloxy,
(e) —O—$(CH_2)_n$—OH,
(f) —O—$(CH_2)_n$—O—CO—$NH_2$,
(g) —O—$(CH_2)_n$—O-(optionally halogenated $C_{1-4}$ alkyl),
(h) —O—$(CH_2)_n$—$SO_2$-(optionally halogenated $C_{1-4}$ alkyl),
(i) —O—$(CH_2)_n$—$SO_2$—$C_{6-18}$ aryl,
(j) —O—$(CH_2)_n$—$SO_2$—$(CH_2)_n$—OH,
(k) —O—$(CH_2)_n$—$NR^8$—CO—$C_{1-4}$ alkyl,
(l) —O—$(CH_2)_n$—$NR^8$—CO—$(CH_2)_n$—$SO_2$—$C_{1-4}$ alkyl,
(m) —O—$(CH_2)_n$—$NR^8$—$SO_2$-(optionally halogenated $C_{1-4}$ alkyl),
(n) —CO—$NR^8$—$(CH_2)_n$—OH,
(o) —CO—$NR^8$—$(CH_2)_n$—$SO_2$-(optionally halogenated $C_{1-4}$ alkyl),
(p) —CO—$NR^8$—O—$C_{1-4}$ alkyl, (q) —$NR^6R^7$,
(r) —$NR^8$—$(CH_2)_n$—OH,
(s) —$NR^8$—$(CH_2)_n$—$SO_2$—$C_{1-4}$ alkyl,
(t) —$NR^8$—CO-(optionally halogenated $C_{1-4}$ alkyl),
(u) —$NR^8$—CO—$(CH_2)_n$—OH,
(v) —$NR^8$—CO—$(CH_2)_n$—CN,
(w) —$NR^8$—CO—$(CH_2)_n$—$NR^6R^7$,
(x) —$NR^8$—CO—$(CH_2)_n$—O—$C_{1-4}$ alkyl,
(y) —$NR^8$—CO—$(CH_2)_n$—SO-(optionally halogenated $C_{1-4}$ alkyl),
(z) —$NR^8$—CO—$(CH_2)_n$—$SO_2$-(optionally halogenated $C_{1-4}$ alkyl),
(aa) —$NR^8$—CO—$(CH_2)_n$—$SO_2$—$C_{3-8}$ cycloalkyl,
(bb) —$NR^8$—CO—$(CH_2)_n$—$NR^8$—$SO_2$—$C_{1-4}$ alkyl,
(cc) —$NR^8$—$CO_2$—$(CH_2)_n$—$SO_2$—$C_{1-4}$ alkyl,
(dd) —$NR^8$—CO—NH—$(CH_2)_n$—$SO_2$—$C_{1-4}$ alkyl,
(ee) —$NR^8$—CO—NH—O—$C_{1-4}$ alkyl,
(ff) —$NR^8$—CO—NH—$(CH_2)_n$—O—$C_{1-4}$ alkyl,
(gg) —$NR^8$—C(=NH)—NH—$C_{1-4}$ alkyl,
(hh) —$NR^8$—$SO_2$—$(CH_2)_n$—$SO_2$—$C_{1-4}$ alkyl,
(ii) —S—$(CH_2)_n$—OH,
(jj) —SO—$(CH_2)_n$—OH,
(kk) —$SO_2$—$(CH_2)_n$—OH, and
(ll) —$NR^8$—CO-(optionally substituted heterocyclic group) (preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—O—$C_{1-4}$ alkyl, —CO—NH—$C_{1-4}$ alkyl, —$CONH_2$, —$SO_2$—$C_{1-4}$ alkyl, —$SO_2$—NH—$C_{1-4}$ alkyl, —$SO_2NH_2$ and the like),
wherein n is an integer of 1 to 4, $R^6$ and $R^7$ are the same or different and each is a hydrogen atom or a $C_{1-4}$ alkyl group, $R^8$ is a hydrogen atom or a $C_{1-4}$ alkyl group, $(CH_2)_n$ is optionally substituted by optionally halogenated $C_{1-4}$ alkyl or hydroxy, and when n is not less than 2, a subset —$CH_2CH_2$— of $(CH_2)_n$ is optionally replaced by —CH=CH—; and
$R^{3a}$ is a hydrogen atom or a $C_{1-6}$ alkyl group; or
$R^{1a}$ and $R^{2a}$ are optionally bonded to form

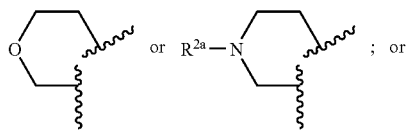

$R^{2a}$ and $R^{3a}$ are optionally bonded to form $C_{2-4}$ alkylene optionally substituted by an imino group is preferable.

As $R^8$, a hydrogen atom, methyl, ethyl and the like are preferable, and a hydrogen atom is particularly preferable.

As $R^{2a}$, a $C_{1-8}$ alkyl group, a $C_{2-8}$ alkenyl group or a $C_{2-8}$ alkynyl group, each of which is optionally substituted by substituent(s) selected from
(a) hydroxy,
(b) carboxy,
(c) cyano,
(d) optionally halogenated $C_{1-4}$ alkyloxy,
(e) —O—$(CH_2)_n$—OH (wherein $(CH_2)_n$ is optionally substituted by hydroxy),
(f) —O—$(CH_2)_n$—O—CO—$NH_2$,
(g) —O—$(CH_2)_n$—O-(optionally halogenated $C_{1-4}$ alkyl),
(h) —O—$(CH_2)_n$—$SO_2$-(optionally halogenated $C_{1-4}$ alkyl),
(i) —O—$(CH_2)_n$—$SO_2$—$C_{6-18}$ aryl,
(j) —O—$(CH_2)_n$—$SO_2$—$(CH_2)_n$—OH,
(k) —O—$(CH_2)_n$—$NR^8$—CO—$C_{1-4}$ alkyl,
(l) —O—$(CH_2)_n$—$NR^8$—CO—$(CH_2)_n$—$SO_2$—$C_{1-4}$ alkyl,
(m) —O—$(CH_2)_n$—$NR^8$—$SO_2$-(optionally halogenated $C_{1-4}$ alkyl),
(n) —CO—$NR^8$—$(CH_2)_n$—OH,
(o) —CO—$NR^8$—$(CH_2)_n$—$SO_2$-(optionally halogenated $C_{1-4}$ alkyl),
(p) —CO—$NR^8$—O—$C_{1-4}$ alkyl,
(q) —$NR^6R^7$,
(r) —$NR^8$—$(CH_2)_n$—OH,
(s) —$NR^8$—$(CH_2)_n$—$SO_2$—$C_{1-4}$ alkyl,
(t) —$NR^8$—CO-(optionally halogenated $C_{1-4}$ alkyl),
(u) —$NR^8$—CO—$(CH_2)_n$—OH (wherein $(CH_2)_n$ is optionally substituted by optionally halogenated $C_{1-4}$ alkyl or hydroxy),
(v) —$NR^8$—CO—$(CH_2)_n$—CN,
(w) —$NR^8$—CO—$(CH_2)_n$—$NR^6R^7$ (when n is not less than 2, a subset —$CH_2CH_2$— of $(CH_2)_n$ is optionally replaced by —CH=CH—),
(x) —$NR^8$—CO—$(CH_2)_n$—O—$C_{1-4}$ alkyl,
(y) —$NR^8$—CO—$(CH_2)_n$—SO-(optionally halogenated $C_{1-4}$ alkyl),
(z) —$NR^8$—CO—$(CH_2)_n$—$SO_2$-(optionally halogenated $C_{1-4}$ alkyl) (wherein $(CH_2)_n$ is optionally substituted by $C_{1-4}$ alkyl),
(aa) —$NR^8$—CO—$(CH_2)_n$—$SO_2$—$C_{3-8}$ cycloalkyl,
(bb) —$NR^8$—CO—$(CH_2)_n$—$NR^8$—$SO_2$—$C_{1-4}$ alkyl,
(cc) —$NR^8$—$CO_2$—$(CH_2)_n$—$SO_2$—$C_{1-4}$ alkyl,
(dd) —$NR^8$—CO—NH—$(CH_2)_n$—$SO_2$—$C_{1-4}$ alkyl,
(ee) —$NR^8$—CO—NH—O—$C_{1-4}$ alkyl,
(ff) —$NR^8$—CO—NH—$(CH_2)_n$—O—$C_{1-4}$ alkyl,
(gg) —$NR^8$—C(=NH)—NH—$C_{1-4}$ alkyl,
(hh) —$NR^8$—$SO_2$—$(CH_2)_n$—$SO_2$—$C_{1-4}$ alkyl,
(ii) —S—$(CH_2)_n$—OH,
(jj) —SO—$(CH_2)_n$—OH,
(kk) —$SO_2$—$(CH_2)_n$—OH, and
(ll) —$NR^8$—CO-(optionally substituted heterocyclic group) (preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—O—$C_{1-4}$ alkyl, —CO—NH—$C_{1-4}$ alkyl, —$CONH_2$, —$SO_2$—$C_{1-4}$ alkyl, —$SO_2$—NH—$C_{1-4}$ alkyl, —$SO_2NH_2$ and the like),
wherein n is an integer of 1 to 4, $R^6$ and $R^7$ are the same or different and each is a hydrogen atom or a $C_{1-4}$ alkyl group, and $R^8$ is a hydrogen atom or a $C_{1-4}$ alkyl group, is preferable.

As $R^8$, a hydrogen atom, methyl, ethyl and the like are preferable, and a hydrogen atom is particularly preferable.

As compound (Ia), moreover, a compound wherein
$B^a$ is a benzene ring optionally substituted by 1 to 4 substituents selected from halogen and optionally halogenated $C_{1-4}$ alkyl;
$C^a$ is a phenyl group substituted by 1 to 5 substituents selected from (i) halogen, (ii) optionally halogenated $C_{1-4}$ alkyl, (iii) hydroxy-$C_{1-4}$ alkyl, (iv) heterocycle-$C_{1-4}$ alkyl (preferably, 5- to 8-membered heterocycle-$C_{1-4}$ alkyl, said 5- to 8-membered heterocycle has 1 to 3 hetero atoms selected from a nitrogen atom, an oxygen atom and an optionally oxidized sulfur atom, such as imidazolyl and the like), (v) optionally halogenated $C_{1-4}$ alkyloxy, (vi) cyano, and (vii) carbamoyl optionally substituted by $C_{1-8}$ alkyl;

$R^{1a}$ is a hydrogen atom;

$R^{2a}$ is a $C_{1-8}$ alkyl group, a $C_{2-8}$ alkenyl group or a $C_{2-8}$ alkynyl group, each of which is substituted by substituent(s) selected from (a) hydroxy,
(b) optionally halogenated $C_{1-4}$ alkyloxy,
(c) —O—$(CH_2)_n$—OH,
(d) —O—$(CH_2)_n$—O—CO—$NH_2$,
(e) —O—$(CH_2)_n$—O—$C_{1-4}$ alkyl,
(f) —O—$(CH_2)_n$—$SO_2$-(optionally halogenated $C_{1-4}$ alkyl),
(g) —O—$(CH_2)_n$—$SO_2$—$C_{6-18}$ aryl,
(h) —O—$(CH_2)_n$—$SO_2$—$(CH_2)_n$—OH,
(i) —O—$(CH_2)_n$—$NR^8$—$SO_2$-(optionally halogenated $C_{1-4}$ alkyl),
(j) —CO—$NR^8$—$(CH_2)_n$—OH,
(k) —CO—$NR^8$—$(CH_2)_n$—$SO_2$-(optionally halogenated $C_{1-4}$ alkyl),
(l) —$NR^6R^7$,
(m) —$NR^8$—$(CH_2)_n$—OH,
(n) —$NR^8$—$(CH_2)_n$—$SO_2$—$C_{1-4}$ alkyl,
(o) —$NR^8$—CO—$(CH_2)_n$—OH,
(p) —$NR^8$—CO—$(CH_2)_n$—O—$C_{1-4}$ alkyl,
(q) —$NR^8$—CO—$(CH_2)_n$—SO-(optionally halogenated $C_{1-4}$ alkyl),
(r) —$NR^8$—CO—$(CH_2)_n$—$SO_2$-(optionally halogenated $C_{1-4}$ alkyl),
(s) —$NR^8$—CO—$(CH_2)_n$—$SO_2$—$C_{3-8}$ cycloalkyl,
(t) —$NR^8$—$CO_2$—$(CH_2)_n$—$SO_2$—$C_{1-4}$ alkyl,
(u) —$NR^8$—CO—NH—$(CH_2)_n$—$SO_2$—$C_{1-4}$ alkyl,
(v) —$NR^8$—$SO_2$—$(CH_2)_n$—$SO_2$—$C_{1-4}$ alkyl,
(w) —S—$(CH_2)_n$—OH,
(x) —SO—$(CH_2)_n$—OH,
(y) —$SO_2$—$(CH_2)_n$—OH, and
(z) —$NR^8$—CO-(optionally substituted heterocyclic group) (preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—NH—$C_{1-4}$ alkyl, —$CONH_2$, —$SO_2$—$C_{1-4}$ alkyl, —$SO_2$—NH—$C_{1-4}$ alkyl, —$SO_2NH_2$ and the like), wherein n is an integer of 1 to 4, $R^6$ and $R^7$ are the same or different and each is a hydrogen atom or a $C_{1-4}$ alkyl group, $R^8$ is a hydrogen atom or a $C_{1-4}$ alkyl group, and $(CH_2)_n$ is optionally substituted by $C_{1-4}$ alkyl or hydroxy;

$R^{3a}$ is a hydrogen atom or a $C_{1-6}$ alkyl group; or $R^{1a}$ and $R^{2a}$ are optionally bonded to form

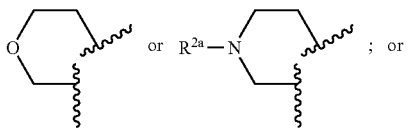

$R^{2a}$ and $R^{3a}$ are optionally bonded to form $C_{2-4}$ alkylene, is preferable.

Of these, as $R^{2a}$, a $C_{1-8}$ alkyl group, a $C_{2-8}$ alkenyl group or a $C_{2-8}$ alkynyl group (particularly, a $C_{1-8}$ alkyl group), each of which is substituted by substituent(s) selected from (a) hydroxy,
(b) optionally halogenated $C_{1-4}$ alkyloxy,
(c) —O—$(CH_2)_n$—OH (wherein $(CH_2)_n$ is optionally substituted by hydroxy),
(d) —O—$(CH_2)_n$—O—CO—$NH_2$,
(e) —O—$(CH_2)_n$—O—$C_{1-4}$ alkyl,
(f) —O—$(CH_2)_n$—$SO_2$-(optionally halogenated $C_{1-4}$ alkyl),
(g) —O—$(CH_2)_n$—$SO_2$—$C_{6-18}$ aryl,
(h) —O—$(CH_2)_n$—$SO_2$—$(CH_2)_n$—OH,
(i) —O—$(CH_2)_n$—$NR^8$—$SO_2$-(optionally halogenated $C_{1-4}$ alkyl),
(j) —CO—$NR^8$—$(CH_2)_n$—OH,
(k) —CO—$NR^8$—$(CH_2)_n$—$SO_2$-(optionally halogenated $C_{1-4}$ alkyl),
(l) —$NR^6R^7$,
(m) —$NR^8$—$(CH_2)_n$—OH,
(n) —$NR^8$—$(CH_2)_n$—$SO_2$—$C_{1-4}$ alkyl,
(o) —$NR^8$—CO—$(CH_2)_n$—OH (wherein $(CH_2)_n$ is optionally substituted by $C_{1-4}$ alkyl),
(p) —$NR^8$—CO—$(CH_2)_n$—O—$C_{1-4}$ alkyl,
(q) —$NR^8$—CO—$(CH_2)_n$—SO-(optionally halogenated $C_{1-4}$ alkyl),
(r) —$NR^8$—CO—$(CH_2)_n$—$SO_2$-(optionally halogenated $C_{1-4}$ alkyl)
(wherein $(CH_2)_n$ is optionally substituted by $C_{1-4}$ alkyl),
(s) —$NR^8$—CO—$(CH_2)_n$—$SO_2$—$C_{3-8}$ cycloalkyl,
(t) —$NR^8$—$CO_2$—$(CH_2)_n$—$SO_2$—$C_{1-4}$ alkyl,
(u) —$NR^8$—CO—NH—$(CH_2)_n$—$SO_2$—$C_{1-4}$ alkyl,
(v) —$NR^8$—$SO_2$—$(CH_2)_n$—$SO_2$—$C_{1-4}$ alkyl,
(w) —S—$(CH_2)_n$—OH,
(x) —SO—$(CH_2)_n$—OH,
(y) —$SO_2$—$(CH_2)_n$—OH, and
(z) —$NR^8$—CO-(optionally substituted heterocyclic group) (preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—NH—$C_{1-4}$ alkyl, —$CONH_2$, —$SO_2$—$C_{1-4}$ alkyl, —$SO_2$—NH—$C_{1-4}$ alkyl, —$SO_2NH_2$ and the like), wherein n is an integer of 1 to 4, $R^6$ and $R^7$ are the same or different and each is a hydrogen atom or a $C_{1-4}$ alkyl group, $R^8$ is a hydrogen atom or a $C_{1-4}$ alkyl group, is preferable.

As $R^{2a}$, (i) a $C_{5-8}$ alkyl group substituted by hydroxy,
(ii) a $C_{1-8}$ alkyl group substituted by substituent(s) selected from (a) halogenated $C_{1-4}$ alkyloxy,
(b) —O—$(CH_2)_n$—OH,
(c) —O—$(CH_2)_n$—O—CO—$NH_2$,
(d) —O—$(CH_2)_n$—O-(optionally halogenated $C_{1-4}$ alkyl),
(e) —O—$(CH_2)_n$—$SO_2$-(optionally halogenated $C_{1-4}$ alkyl),
(f) —O—$(CH_2)_n$—$SO_2$—$C_{6-18}$ aryl,
(g) —O—$(CH_2)_n$—$NR^8$—$SO_2$-(optionally halogenated $C_{1-4}$ alkyl),
(h) —CO—$NR^8$—$(CH_2)_n$—OH,
(i) —CO—$NR^8$—$(CH_2)_n$—$SO_2$-(optionally halogenated $C_{1-4}$ alkyl),
(j) —$NR^8$—$(CH_2)_n$—$SO_2$—$C_{1-4}$ alkyl,
(k) —$NR^8$—CO—$(CH_2)_n$—OH,
(l) —$NR^8$—CO—$(CH_2)_n$—O—$C_{1-4}$ alkyl,
(m) —$NR^8$—CO—$(CH_2)_n$—SO-(optionally halogenated $C_{1-4}$ alkyl),
(n) —$NR^8$—CO—$(CH_2)_n$—$SO_2$-(optionally halogenated $C_{1-4}$ alkyl),
(o) —$NR^8$—CO—$(CH_2)_n$—$SO_2$—$C_{3-8}$ cycloalkyl,
(p) —$NR^8$—$CO_2$—$(CH_2)_n$—$SO_2$—$C_{1-4}$ alkyl,
(q) —$NR^8$—CO—NH—$(CH_2)_n$—$SO_2$—$C_{1-4}$ alkyl,
(r) —$NR^8$—$SO_2$—$(CH_2)_n$—$SO_2$—$C_{1-4}$ alkyl,
(s) —S—$(CH_2)_n$—OH,
(t) —SO—$(CH_2)_n$—OH,
(u) —$SO_2$—$(CH_2)_n$—OH, and (v) —NR⁸—CO-(optionally substituted heterocyclic group) (preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—NH—$C_{1-4}$ alkyl, —CONH$_2$, —SO$_2$—$C_{1-4}$ alkyl, —SO$_2$—NH—$C_{1-4}$ alkyl, —SO$_2$NH$_2$ and the like), wherein n is an integer of 1 to 4, $R^8$ is a hydrogen atom or a $C_{1-4}$ alkyl group, and $(CH_2)_n$ is optionally substituted by $C_{1-4}$ alkyl or hydroxy, (iii) a $C_{2-8}$ alkenyl group optionally substituted by hydroxy, or (iv) a $C_{2-8}$ alkynyl group optionally substituted by hydroxy is preferable, and particularly, as $R^{2a}$, (i) a $C_{5-8}$ alkyl group substituted by hydroxy, (ii) a $C_{1-8}$ alkyl group substituted by substituent(s) selected from (a) halogenated $C_{1-4}$ alkyloxy, (b) —O—$(CH_2)_n$—OH (wherein $(CH_2)_n$ is optionally substituted by hydroxy), (c) —O—$(CH_2)_n$—O—CO—NH$_2$, (d) —O—$(CH_2)_n$—O-(optionally halogenated $C_{1-4}$ alkyl), (e) —O—$(CH_2)_n$—SO$_2$-(optionally halogenated $C_{1-4}$ alkyl), (f) —O—$(CH_2)_n$—SO$_2$—$C_{6-18}$ aryl, (g) —O—$(CH_2)_n$—NR⁸—SO$_2$-(optionally halogenated $C_{1-4}$ alkyl), (h) —CO—NR⁸—$(CH_2)_n$—OH, (i) —CO—NR⁸—$(CH_2)_n$—SO$_2$-(optionally halogenated $C_{1-4}$ alkyl), (j) —NR⁸—$(CH_2)_n$—SO$_2$—$C_{1-4}$ alkyl, (k) —NR⁸—CO—$(CH_2)_n$—OH (wherein $(CH_2)_n$ is optionally substituted by $C_{1-4}$ alkyl), (l) —NR⁸—CO—$(CH_2)_n$—O—$C_{1-4}$ alkyl, (m) —NR⁸—CO—$(CH_2)_n$—SO-(optionally halogenated $C_{1-4}$ alkyl), (n) —NR⁸—CO—$(CH_2)_n$—SO$_2$-(optionally halogenated $C_{1-4}$ alkyl) (wherein $(CH_2)_n$ is optionally substituted by $C_{1-4}$ alkyl), (o) —NR⁸—CO—$(CH_2)_n$—SO$_2$—$C_{3-8}$ cycloalkyl, (p) —NR⁸—CO$_2$—$(CH_2)_n$—SO$_2$—$C_{1-4}$ alkyl, (q) —NR⁸—CO—NH—$(CH_2)_n$—SO$_2$—$C_{1-4}$ alkyl, (r) —NR⁸—SO$_2$—$(CH_2)_n$—SO$_2$—$C_{1-4}$ alkyl, (s) —S—$(CH_2)_n$—OH, (t) —SO—$(CH_2)_n$—OH, (u) —SO$_2$—$(CH_2)_n$—OH, and (v) —NR⁸—CO-(optionally substituted heterocyclic group) (preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—NH—$C_{1-4}$ alkyl, —CONH$_2$, —SO$_2$—$C_{1-4}$ alkyl, —SO$_2$—NH—$C_{1-4}$ alkyl, —SO$_2$NH$_2$ and the like), wherein n is an integer of 1 to 4, and $R^8$ is a hydrogen atom or a $C_{1-4}$ alkyl group, (iii) a $C_{2-8}$ alkenyl group optionally substituted by hydroxy, or (iv) a $C_{2-8}$ alkynyl group optionally substituted by hydroxy is preferable, and as $R^8$, a hydrogen atom, methyl, ethyl and the like are preferable, and a hydrogen atom is particularly preferable.

[compound (Ib)]

A compound represented by the formula:

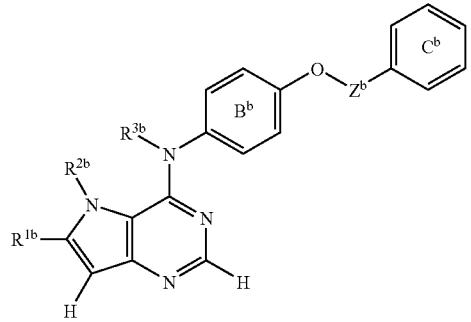

(Ib)

wherein $R^{1b}$ is a hydrogen atom or an optionally substituted group bonded via a carbon atom, a nitrogen atom or an oxygen atom, $R^{2b}$ is an optionally substituted group bonded via a carbon atom or a sulfur atom, or $R^{1b}$ and $R^{2b}$, or $R^{2b}$ and $R^{3b}$ are optionally bonded to form an optionally substituted ring structure, $R^{3b}$ is a hydrogen atom or an optionally substituted aliphatic hydrocarbon group, or $R^{3b}$ is optionally bonded to a carbon atom of the adjacent phenyl group to form an optionally substituted ring structure, $B^b$ is an optionally substituted benzene ring, $C^b$ is an optionally substituted $C_{6-18}$ aryl group, and $Z^b$ is an optionally substituted $C_{1-3}$ alkylene group, or a salt thereof.

As the "optionally substituted group bonded via a carbon atom, a nitrogen atom or an oxygen atom" for $R^{1b}$, those similar to the "optionally substituted group bonded via a carbon atom, a nitrogen atom or an oxygen atom" for $R^1$ can be used.

As the "optionally substituted group bonded via a carbon atom or a sulfur atom" for $R^{2b}$, those similar to the "optionally substituted group bonded via a carbon atom or a sulfur atom" for $R^2$ can be used.

As the "optionally substituted ring structure" formed by $R^{1b}$ and $R^{2b}$, or $R^{2b}$ and $R^{3b}$ bonded to each other, those similar to the "optionally substituted ring structure" formed by $R^1$ and $R^2$, or $R^2$ and $R^3$ bonded to each other can be used.

As the "optionally substituted aliphatic hydrocarbon group" for $R^{3b}$, those similar to the "optionally substituted aliphatic hydrocarbon group" for $R^3$ can be used.

As the "optionally substituted ring structure" formed by $R^{3b}$ and a carbon atom of the adjacent phenyl group, those similar to the "optionally substituted ring structure" formed by $R^3$ and a carbon atom of the adjacent phenyl group can be used.

As the "optionally substituted benzene ring" for $B^b$, those similar to the "optionally substituted benzene ring" for $B^a$ can be used.

As the "optionally substituted $C_{6-18}$ aryl group" for $C^b$, those similar to the "optionally substituted $C_{6-18}$ aryl group" for $C^a$ can be used.

As the "$C_{1-3}$ alkylene group" of the "optionally substituted $C_{1-3}$ alkylene group" for $Z^b$, methylene, ethylene, trimethylene and propylene can be used.

As the "substituent" of the "optionally substituted $C_{1-3}$ alkylene group" for $Z^b$, 1 to 3 substituents selected from halogen, hydroxy, $C_{1-4}$ alkyloxy, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkylsulfonylamino can be used.

As $R^{2b}$, a $C_{1-8}$ alkyl group, a $C_{2-8}$ alkenyl group, a $C_{2-8}$ alkynyl group, a carbamoyl group, a $C_{1-8}$ alkyl-carbonyl group, a $C_{1-8}$ alkylsulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocycle-$C_{1-4}$ alkyl group, a heterocycle-carbonyl group or a heterocycle-$C_{1-4}$ alkyl-carbonyl group, each of which is optionally substituted by 1 to 5 substituents selected from
(a) halogen,
(b) oxo,
(c) optionally halogenated $C_{1-4}$ alkyl,
(d) —$(CH_2)_m$-Q,
(e) —$(CH_2)_m$—$Z^1$-(optionally halogenated $C_{1-4}$ alkyl),
(f) —$(CH_2)_m$—$Z^1$—$C_{3-8}$ cycloalkyl,
(g) —$(CH_2)_m$—$Z^2$—$(CH_2)_n$-Q,
(h) —$(CH_2)_m$—$Z^2$—$(CH_2)_n$—$Z^1$-(optionally halogenated $C_{1-4}$ alkyl),
(i) —$(CH_2)_m$—$Z^2$—$(CH_2)_n$—$Z^1$—$C_{3-8}$ cycloalkyl,
(j) —$(CH_2)_m$—$Z^1$-(optionally substituted heterocyclic group) (preferably, said heterocyclic group is a 5- to 8-membered heterocyclic group having 1 to 3 hetero atoms selected from a nitrogen atom, an oxygen atom and an optionally oxidized sulfur atom),
(k) —$(CH_2)_m$—$Z^2$—$C_{1-4}$ alkoxy, and
(l) —$(CH_2)_m$—$Z^2$—$(CH_2)_n$—$Z^1$—$(CH_2)_n$—$C_{1-4}$ alkyl
wherein m is an integer of 0 to 4, n is an integer of 1 to 4,
Q is hydroxy, carboxy, cyano, nitro, —$NR^6R^7$, —$CONR^6R^7$, —$OCONH_2$ or —$SO_2NR^6R^7$,
$Z^1$ is —O—, —CO—, —C(OH)$R^8$—, —C(=N—OR$^8$)—, —S—, —O—, —SO$_2$—, —N(COR$^8$)—, —N(CO$_2$R$^9$)—, —N(SO$_2$R$^8$)—, —CO—O—, —O—CO—, —CO—NR$^8$—, —NR$^8$—CO—, —NR$^8$—CO$_2$—, —NR$^8$—CO—NH—, —NR$^8$—SO$_2$—, or —NR$^8$—C(=NH)—NH—,
$Z^2$ is —O—, —CO—, —C(OH)$R^8$—, —C(=N—OR$^8$)—, —S—, —SO—, —SO$_2$—, —NR$^8$—, —N(COR$^8$)—, —N(CO$_2$R$^9$)—, —N(SO$_2$R$^9$)—, —CO—O—, —O—CO—, —CO—NR$^8$—, —NR$^8$—CO—, —NR$^8$—CO$_2$—, —NR$^8$—CO—NH—, —NR$^8$—C(=NH)—NH—, —NR$^8$—SO$_2$—, or —SO$_2$—NR$^8$—,
$(CH_2)_m$ and $(CH_2)_n$ are optionally substituted by 1 to 5 substituents selected from halogen, optionally halogenated $C_{1-4}$ alkyl and hydroxy, and when m or n is not less than 2, a subset —CH$_2$CH$_2$— of $(CH_2)_m$ and $(CH_2)_n$ is optionally replaced by —CH=CH— or —C≡C—,
$R^6$ and $R^7$ are the same or different and each is a hydrogen atom or a $C_{1-4}$ alkyl group, or $R^6$ and $R^7$ are bonded to form, together with a nitrogen atom, a 3- to 8-membered saturated or unsaturated aliphatic heterocyclic group,
$R^8$ is a hydrogen atom or $C_{1-4}$ alkyl, and $R^9$ is $C_{1-4}$ alkyl is preferable.

As compound (Ib), a compound wherein
$B^b$ is a benzene ring optionally substituted by halogen;
$C^b$ is a phenyl group optionally substituted by 1 to 5 substituents selected from halogen, optionally halogenated $C_{1-4}$ alkyl and cyano;
$R^{1b}$ is (i) a hydrogen atom, or
(ii) a $C_{2-4}$ alkenyl group optionally substituted by hydroxy;
$R^{2b}$ is
(i) a $C_{1-8}$ alkyl group optionally substituted by substituent(s) selected from
(a) halogen,
(b) hydroxy,
(c) $C_{1-4}$ alkyloxy,
(d) —O—$(CH_2)_n$—OH,
(e) —O—$(CH_2)_n$—O—$C_{1-4}$ alkyl,
(f) —CO—NR$^8$—$(CH_2)_n$—OH,
(g) —NR$^6R^7$ and
(h) —NR$^8$—$(CH_2)_n$—OH,
wherein n is an integer of 1 to 4, $R^6$ and $R^7$ are the same or different and each is a hydrogen atom or a $C_{1-4}$ alkyl group, and $R^8$ is a hydrogen atom or a $C_{1-4}$ alkyl group,
(ii) a $C_{6-18}$ aryl-$C_{1-4}$ alkyl group optionally substituted by substituent(s) selected from
(a) $C_{1-4}$ alkyl optionally having hydroxy,
(b) carboxy,
(c) $C_{1-4}$ alkoxy-carbonyl,
(d) 5- to 8-membered heterocycle-carbonyl having 1 to 3 hetero atoms selected from a nitrogen atom, an oxygen atom and a sulfur atom, which optionally has substituent(s) selected from hydroxy and $C_{1-4}$ alkyl, and
(e) $C_{1-4}$ alkyl-carbamoyl optionally having substituent(s) selected from hydroxy and carbamoyl,
(iii) a $C_{6-18}$ aryl-carbonyl group optionally substituted by $C_{1-4}$ alkoxy,
(iv) a $C_{6-18}$ aryl-sulfonyl group optionally substituted by $C_{1-4}$ alkoxy, or
(v) a 5- to 8-membered heterocycle-$C_{1-4}$ alkyl group having 1 to 3 hetero atoms selected from a nitrogen atom, an oxygen atom and a sulfur atom, which is optionally substituted by substituent(s) selected from
(a) carboxy, and
(b) $C_{1-4}$ alkoxy-carbonyl;
$R^{3b}$ is a hydrogen atom or a $C_{1-6}$ alkyl group; or
$R^{2b}$ and $R^{3b}$ are optionally bonded to form $C_{2-4}$ alkylene; and
$Z^b$ is a $C_{1-3}$ alkylene group is preferable.

Moreover, as compound (Ib), a compound wherein
$B^b$ is a benzene ring optionally substituted by halogen;
$C^b$ is a phenyl group optionally substituted by 1 to 5 substituents selected from halogen and optionally halogenated $C_{1-4}$ alkyl;
$R^{1b}$ is a hydrogen atom;
$R^{2b}$ is a $C_{1-8}$ alkyl group optionally substituted by substituent(s) selected from
(a) hydroxy,
(b) —O—$(CH_2)_n$—OH,
(c) —O—$(CH_2)_n$—O—$C_{1-4}$ alkyl,
(d) —CO—NR$^8$—$(CH_2)_n$—OH,
(e) —NR$^6R^7$, and
(f) —NR$^8$—$(CH_2)_n$—OH,
wherein n is an integer of 1 to 4, $R^6$ and $R^7$ are the same or different and each is a hydrogen atom or a $C_{1-4}$ alkyl group, and $R^8$ is a hydrogen atom or a $C_{1-4}$ alkyl group;
$R^{3b}$ is a hydrogen atom or a $C_{1-6}$ alkyl group; and
$Z^b$ is a $C_{1-3}$ alkylene group is preferable.

Particularly, as compound (Ib), a compound wherein
$B^b$ is a benzene ring optionally substituted by halogen;
$C^b$ is a phenyl group optionally substituted by 1 to 5 substituents selected from halogen and optionally halogenated $C_{1-4}$ alkyl;
$R^{1b}$ is a hydrogen atom;
$R^{2b}$ is a $C_{1-8}$ alkyl group substituted by substituent(s) selected from
(a) —O—$(CH_2)_n$—OH,
(b) —O—$(CH_2)_n$—O—$C_{1-4}$ alkyl, and
(c) —CO—NR$^8$—$(CH_2)_n$—OH,
wherein n is an integer of 1 to 4, and $R^8$ is a hydrogen atom or a $C_{1-4}$ alkyl group;
$R^{3b}$ is a hydrogen atom or a $C_{1-6}$ alkyl group; and
$Z^b$ is a methylene group is preferable.

As $R^8$, a hydrogen atom, methyl, ethyl and the like are preferable, and a hydrogen atom is particularly preferable.

[compound (Ic)]

A compound represented by the formula:

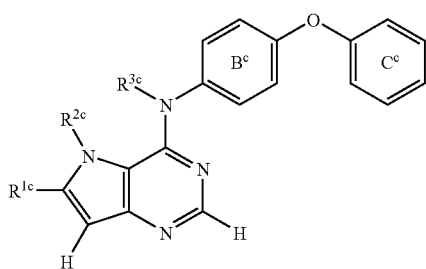

wherein $R^{1c}$ is a hydrogen atom or an optionally substituted group bonded via a carbon atom, a nitrogen atom or an oxygen atom, $R^{2c}$ is an optionally substituted group bonded via a carbon atom or a sulfur atom, or $R^{1c}$ and $R^{2c}$, or $R^{2c}$ and $R^{3c}$ are optionally bonded to form an optionally substituted ring structure, $R^{3c}$ is a hydrogen atom or an optionally substituted aliphatic hydrocarbon group, or $R^3$, is optionally bonded to a carbon atom of the adjacent phenyl group to form an optionally substituted ring structure, $B^c$ is an optionally substituted benzene ring, and cc is an optionally substituted heterocyclic group, or a salt thereof.

As the "optionally substituted group bonded via a carbon atom, a nitrogen atom or an oxygen atom" for $R^{1c}$, those similar to the "optionally substituted group bonded via a carbon atom, a nitrogen atom or an oxygen atom" for $R^1$ can be used.

As the "optionally substituted group bonded via a carbon atom or a sulfur atom" for $R^{2c}$, those similar to the "optionally substituted group bonded via a carbon atom or a sulfur atom" for $R^2$ can be used.

As the "optionally substituted ring structure" formed by $R^{1c}$ and $R^{2c}$, or $R^{2c}$ and $R^{3c}$ bonded to each other, those similar to the "optionally substituted ring structure" formed by $R^1$ and $R^2$, or $R^2$ and $R^3$ bonded to each other can be used.

As the "optionally substituted aliphatic hydrocarbon group" for $R^{3c}$, those similar to the "optionally substituted aliphatic hydrocarbon group" for $R^3$ can be used.

As the "optionally substituted ring structure" formed by $R^{3c}$ and a carbon atom of the adjacent phenyl group, those similar to the "optionally substituted ring structure" formed by $R^3$ and a carbon atom of the adjacent phenyl group can be used.

As the "optionally substituted benzene ring" for $B^c$, those similar to the "optionally substituted benzene ring" for $B^a$ can be used.

As the "heterocyclic group" of the "optionally substituted heterocyclic group" for Cc, the aforementioned "heterocyclic group" can be used, and a 5- to 8-membered heterocyclic group having 1 to 3 hetero atoms selected from a nitrogen atom, an oxygen atom and an optionally oxidized sulfur atom can be particularly preferably used. Specifically, 5 or 6-membered aromatic monocyclic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like, 3- to 8-membered (preferably 5- or 6-membered) saturated or unsaturated (preferably saturated) aliphatic heterocyclic groups such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, dihydro-1,2,4-oxadiazolyl and the like can be used, and particularly, pyridyl, pyrimidinyl, piperidyl (particularly, 4-piperidyl) and the like are preferable.

As the "substituent" of the "optionally substituted heterocyclic group" for $C^c$, those similar to the "substituent" of the "optionally substituted $C_{6-18}$ aryl group" for $C^a$ can be used.

As $R^{2c}$, a $C_{1-8}$ alkyl group, a $C_{2-8}$ alkenyl group, a $C_{2-8}$ alkynyl group, a carbamoyl group, a $C_{1-8}$ alkyl-carbonyl group, a $C_{1-8}$ alkylsulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocycle-$C_{1-4}$ alkyl group, a heterocycle-carbonyl group or a heterocycle-$C_{1-4}$ alkyl-carbonyl group, each of which is optionally substituted by 1 to 5 substituents selected from (a) halogen,
(b) oxo,
(c) optionally halogenated $C_{1-4}$ alkyl,
(d) —$(CH_2)_m$—Q,
(e) —$(CH_2)_m$—$Z^1$-(optionally halogenated $C_{1-4}$ alkyl),
(f) —$(CH_2)_m$—$Z^1$—$C_{3-8}$ cycloalkyl,
(g) —$(CH_2)_m$—$Z^2$—$(CH_2)_n$-Q,
(h) —$(CH_2)_m$—$Z^2$—$(CH_2)_n$—$Z^1$-(optionally halogenated $C_{1-4}$ alkyl),
(i) —$(CH_2)_m$—$Z^2$—$(CH_2)_n$—$Z^1$—$C_{3-8}$ cycloalkyl,
(j) —$(CH_2)_m$—$Z^1$-(optionally substituted heterocyclic group) (preferably, said heterocyclic group is a 5- to 8-membered heterocyclic group having 1 to 3 hetero atoms selected from a nitrogen atom, an oxygen atom and an optionally oxidized sulfur atom),
(k) —$(CH_2)_m$—$Z^2$—$C_{1-4}$ alkoxy, and
(l) —$(CH_2)_m$—$Z^2$—$(CH_2)_n$—$Z^1$—$(CH_2)_n$—$Z^1$—$C_{1-4}$ alkyl wherein m is an integer of 0 to 4, n is an integer of 1 to 4, Q is hydroxy, carboxy, cyano, nitro, —$NR^6R^7$, —$CONR^6R^7$ or —$SO_2NR^6R^7$, $Z^1$ is —O—, —CO—, —C(OH)$R^8$—, —C(=N—O$R^8$)—, —S—, —SO—, —$SO_2$—, —N(CO$R^8$)—, —N(CO$_2R^9$)—, —N(SO$_2R^9$)—, —CO—O—, —O—CO—, —CO—$NR^8$—, —$NR^8$—CO—, —$NR^8$—CO$_2$—, —$NR^8$—CO—NH—, —$NR^8$—SO$_2$—, or —$NR^8$—C(=NH)—NH—, $Z^2$ is —O—, —CO—, —C(OH)$R^8$—, —C(=N—O$R^8$)—, —S—, —SO—, SO$_2$—, —$NR^8$—, —N(CO$R^8$)—, —N(CO$_2R^9$)—, —N(SO$_2R^9$)—, —CO—O—, —O—CO—, —CO—$NR^8$—, —$NR^8$—CO—, —$NR^8$—CO$_2$—, —$NR^8$—CO—NH—, —$NR^8$—C(=NH)—NH—, —$NR^8$—SO$_2$—, or —SO$_2$—$NR^8$—, $(CH_2)_m$ and $(CH_2)_n$ are optionally substituted by 1 to 5 substituents selected from halogen, optionally halogenated $C_{1-4}$ alkyl and hydroxy, and when m or n is not less than 2, a subset —$CH_2CH_2$— of $(CH_2)_m$ and $(CH_2)_n$— is optionally replaced by —CH=CH—, $R^6$ and $R^7$ are the same or different and each is a hydrogen atom or a $C_{1-4}$ alkyl group, or $R^6$ and $R^7$ are bonded to form, together with a nitrogen atom, a 3- to 8-membered saturated or unsaturated aliphatic heterocyclic group, $R^8$ is a hydrogen atom or $C_{1-4}$ alkyl, and $R^9$ is $C_{1-4}$ alkyl is preferable.

As compound (Ic), a compound wherein $B^c$ is a benzene ring optionally substituted by 1 to 4 substituents selected from halogen and optionally halogenated $C_{1-4}$ alkyl;

$C^c$ is a 5- to 8-membered heterocyclic group having 1 to 3 hetero atoms selected from a nitrogen atom, an oxygen atom and a sulfur atom (e.g., pyridyl, pyrimidyl, 4-piperidyl), which is optionally substituted by 1 to 5 substituents selected from
(i) halogen,
(ii) $C_{1-4}$ alkyl,
(iii) $C_{1-4}$ alkyl-carbonyl,
(iv) optionally halogenated $C_{1-4}$ alkoxy-carbonyl,
(v) $C_{3-8}$ cycloalkyl-carbonyl, and
(vi) a carbamoyl group optionally substituted by substituent(s) selected from
(a) optionally halogenated $C_{1-8}$ alkyl,
(b) $C_{3-8}$ cycloalkyl, and
(c) $C_{6-18}$ aryl optionally substituted by substituent(s) selected from halogen, $C_{1-4}$ alkyl and $C_{1-4}$ alkyloxy;
$R^{1c}$ is (i) a hydrogen atom,
(ii) a $C_{2-4}$ alkenyl group optionally substituted by hydroxy, or
(iii) a 5- to 8-membered heterocyclic group having 1 to 3 hetero atoms selected from a nitrogen atom, an oxygen atom and a sulfur atom;
$R^{2c}$ is
(i) a $C_{1-4}$ alkyl group optionally substituted by substituent(s) selected from
(a) halogen,
(b) hydroxy,
(c) $C_{1-4}$ alkyloxy,
(d) carboxy,
(e) $C_{1-4}$ alkoxy-carbonyl,
(f) —O—$(CH_2)_n$—OH,
(g) —O—$(CH_2)_n$—O—$C_{1-4}$ alkyl,
(h) —CO—$NR^8$—$(CH_2)_n$—OH, and
(i) —$NR^8$—CO—$(CH_2)_n$—$SO_2$—$C_{1-4}$ alkyl
wherein n is an integer of 1 to 4, and $R^8$ is a hydrogen atom or a $C_{1-4}$ alkyl group, or
(ii) a $C_{6-18}$ aryl-$C_{1-4}$ alkyl group optionally substituted by $C_{1-4}$ alkyl optionally having hydroxy; and
$R^{3c}$ is a hydrogen atom or a $C_{1-6}$ alkyl group; or
$R^{2c}$ and $R^{3c}$ are optionally bonded to form $C_{2-4}$ alkylene is preferable.

Moreover, as compound (Ic), a compound wherein
$B^c$ is a benzene ring optionally substituted by 1 to 4 substituents selected from halogen and $C_{1-4}$ alkyl;
$C^c$ is a 5- to 8-membered heterocyclic group having 1 to 3 hetero atoms selected from a nitrogen atom, an oxygen atom and a sulfur atom, which is optionally substituted by 1 to 5 substituents selected from
(i) $C_{1-4}$ alkyl,
(ii) $C_{1-4}$ alkyl-carbonyl,
(iii) optionally halogenated $C_{1-4}$ alkoxy-carbonyl,
(iv) $C_{3-8}$ cycloalkyl-carbonyl, and
(v) a carbamoyl group optionally substituted by substituent(s) selected from
(a) optionally halogenated $C_{1-8}$ alkyl,
(b) $C_{3-8}$ cycloalkyl, and
(c) $C_{6-18}$ aryl optionally substituted by halogen;
$R^{1c}$ is a hydrogen atom;
$R^{2c}$ is a $C_{1-4}$ alkyl group optionally substituted by substituent(s) selected from
(a) hydroxy,
(b) $C_{1-4}$ alkyloxy,
(c) —O—$(CH_2)_n$—OH,
(d) —O—$(CH_2)_n$—O—$C_{1-4}$ alkyl, and
(e) —$NR^8$—$CO(CH_2)_n$—$SO_2$—$C_{1-4}$ alkyl
wherein n is an integer of 1 to 4, and $R^8$ is a hydrogen atom or a $C_{1-4}$ alkyl group; and
$R^{3c}$ is a hydrogen atom or a $C_{1-6}$ alkyl group is preferable, particularly, a compound wherein $R^{2c}$ is a $C_{1-4}$ alkyl group optionally substituted by substituent(s) selected from (a) —O—$(CH_2)_n$—OH, and
(b) —O—$(CH_2)_n$—O—$C_{1-4}$ alkyl,
wherein n is an integer of 1 to 4 is preferable.

[compound (Id)]

A compound represented by the formula

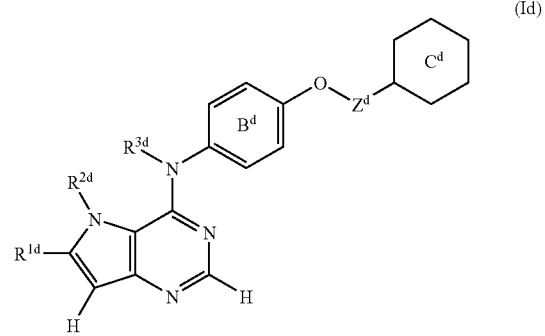

wherein $R^{1d}$ is a hydrogen atom or an optionally substituted group bonded via a carbon atom, a nitrogen atom or an oxygen atom,
$R^{2d}$ is an optionally substituted group bonded via a carbon atom or a sulfur atom, or
$R^{1d}$ and $R^{2d}$, or $R^{2d}$ and $R^{3d}$ are optionally bonded to form an optionally substituted ring structure,
$R^{3d}$ is a hydrogen atom or an optionally substituted aliphatic hydrocarbon group, or $R^{3d}$ is optionally bonded to a carbon atom of the adjacent phenyl group to form an optionally substituted ring structure,
$B^d$ is an optionally substituted benzene ring, $C^d$ is an optionally substituted heterocyclic group, and
$Z^d$ is an optionally substituted $C_{1-3}$ alkylene group, or a salt thereof.

As the "optionally substituted group bonded via a carbon atom, a nitrogen atom or an oxygen atom" for $R^{1d}$, those similar to the "optionally substituted group bonded via a carbon atom, a nitrogen atom or an oxygen atom" for $R^1$ can be used.

As the "optionally substituted group bonded via a carbon atom or a sulfur atom" for $R^{2d}$, those similar to the "optionally substituted group bonded via a carbon atom or a sulfur atom" for $R^2$ can be used.

As the "optionally substituted ring structure" formed by $R^{1d}$ and $R^{2d}$, or $R^{2d}$ and $R^{3d}$ bonded to each other, those similar to the "optionally substituted ring structure" formed by $R^1$ and $R^2$, or $R^2$ and $R^3$ bonded to each other can be used.

As the "optionally substituted aliphatic hydrocarbon group" for $R^{3d}$, those similar to the "optionally substituted aliphatic hydrocarbon group" for $R^3$ can be used.

As the "optionally substituted ring structure" formed by $R^{3d}$ and a carbon atom of the adjacent phenyl group, those similar to the "optionally substituted ring structure" formed by $R^3$ and a carbon atom of the adjacent phenyl group can be used.

As the "optionally substituted benzene ring" for $B^d$, those similar to the "optionally substituted benzene ring" for $B^a$ can be used.

As the "optionally substituted heterocyclic group" for $C^d$, those similar to the "optionally substituted heterocyclic group" for $C^c$ can be used.

As the "optionally substituted $C_{1-3}$ alkylene group" for $Z^d$, those similar to the "optionally substituted $C_{1-3}$ alkylene group" for $Z^b$ can be used.

As $R^{2d}$, a $C_{1-8}$ alkyl group, a $C_{2-8}$ alkenyl group, a $C_{2-8}$ alkynyl group, a carbamoyl group, a $C_{1-8}$ alkyl-carbonyl group, a $C_{1-8}$ alkylsulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocycle-$C_{1-4}$ alkyl group, a heterocycle-carbonyl group or a heterocycle-$C_{1-4}$ alkyl-carbonyl group, each of which is optionally substituted by 1 to 5 substituents selected from
(a) halogen,
(b) oxo,
(c) optionally halogenated $C_{1-4}$ alkyl,
(d) —$(CH_2)_m$-Q,
(e) —$(CH_2)_m$—$Z^1$-(optionally halogenated $C_{1-4}$ alkyl),
(f) —$(CH_2)_m$—$Z^1$—$C_{3-8}$ cycloalkyl,
(g) —$(CH_2)_m$—$Z^2$—$(CH_2)_n$-Q,
(h) —$(CH_2)_m$—$Z^2$—$(CH_2)_n$—$Z^2$-(optionally halogenated $C_{1-4}$ alkyl),
(i) —$(CH_2)_m$—$Z^2$—$(CH_2)_n$—$Z^1$—$C_{3-8}$ cycloalkyl,
(j) —$(CH_2)_m$—$Z^1$-(optionally substituted heterocyclic group) (preferably, said heterocyclic group is a 5- to 8-membered heterocyclic group having 1 to 3 hetero atoms selected from a nitrogen atom, an oxygen atom and an optionally oxidized sulfur atom),
(k) —$(CH_2)_m$—$Z^2$—$C_{1-4}$ alkoxy, and
(l) —$(CH_2)_m$—$Z^2$—$(CH_2)_n$—$Z^1$—$(CH_2)_n$—$Z^1$-$C_{1-4}$ alkyl
wherein m is an integer of 0 to 4, n is an integer of 1 to 4,
Q is hydroxy, carboxy, cyano, nitro, —$NR^6R^7$, —$CONR^6R^7$ or —$SO_2NR^6R^7$,
$Z^1$ is —O—, —CO—, —C(OH)$R^8$—, —C(=N—$OR^8$)—, —S—, —SO—, —$SO_2$—, —N(COR$^8$)—, —N(CO$_2R^9$)—, —N(SO$_2R^9$)—, —CO—O—, —O—CO—, —CO—$NR^8$—, —$NR^8$—CO—, —$NR^8$—CO$_2$—, —$NR^8$—CO—NH—, —$NR^8$—$SO_2$—, or —$NR^8$—C(=NH)—NH—,
$Z^2$ is —O—, —CO—, —C(OH)$R^8$—, —C(=N—$OR^8$)—, —S—, —SO—, —$SO_2$—, —$NR^8$—, —N(COR$^8$)—, —N(CO$_2R^9$)—, —N(SO$_2R^9$)—, —CO—O—, —O—CO—, —CO—$NR^8$—, —$NR^8$—CO—, —$NR^8$—CO$_2$—, —$NR^8$—CO—NH—, —$NR^8$—C(=NH)—NH—, —$NR^8$—$SO_2$—, or —$SO_2$—$NR^8$—,
$(CH_2)_m$ and $(CH_2)_n$ are optionally substituted by 1 to 5 substituents selected from halogen, optionally halogenated $C_{1-4}$ alkyl and hydroxy, and when m or n is not less than 2, a subset —$CH_2CH_2$— of $(CH_2)_m$ and $(CH_2)_n$ is optionally replaced by —CH=CH—,
$R^6$ and $R^7$ are the same or different and each is a hydrogen atom, or a $C_{1-4}$ alkyl group, or $R^6$ and $R^7$ are bonded to form, together with a nitrogen atom, a 3- to 8-membered saturated or unsaturated aliphatic heterocyclic group,
$R^8$ is a hydrogen atom or $C_{1-4}$ alkyl, and $R^9$ is $C_{1-4}$ alkyl, is preferable.

As compound (Id), a compound wherein
$B^d$ is a benzene ring optionally substituted by halogen;
$C^b$ is a 5- to 8-membered heterocyclic group having 1 to 3 hetero atoms selected from a nitrogen atom, an oxygen atom and a sulfur atom;
$R^{1d}$ is a hydrogen atom;
$R^{2d}$ is
(i) $C_{1-4}$ alkyl optionally substituted by substituent(s) selected from
(a) $C_{1-4}$ alkyloxy
(b) —O—$(CH_2)_n$—OH, and
(c) —$NR^8$—CO—$(CH_2)_n$—$SO_2$—$C_{1-4}$ alkyl
wherein n is an integer of 1 to 4, and $R^8$ is a hydrogen atom or a $C_{1-4}$ alkyl group, or (ii) a 5- to 8-membered heterocycle-$C_{1-4}$ alkyl group having 1 to 3 hetero atoms selected from a nitrogen atom, an oxygen atom and a sulfur atom, which is optionally substituted by substituent(s) selected from
(a) carboxy, and
(b) $C_{1-4}$ alkoxy-carbonyl;
$R^{3d}$ is a hydrogen atom or a $C_{1-6}$ alkyl group; and
$Z^d$ is a $C_{1-3}$ alkylene group is preferable.

Moreover, as compound (Id), a compound wherein
$B^d$ is a benzene ring optionally substituted by halogen;
$C^d$ is a 5- to 8-membered heterocyclic group having 1 to 3 hetero atoms selected from a nitrogen atom, an oxygen atom and a sulfur atom;
$R^{1d}$ is a hydrogen atom,
$R^{2d}$ is a $C_{1-4}$ alkyl group optionally substituted by $C_{1-4}$ alkyloxy,
$R^{3d}$ is a hydrogen atom or a $C_{1-6}$ alkyl group; and
$Z^d$ is a methylene group is preferable.

[compound (Ie)]
A compound represented by the formula:

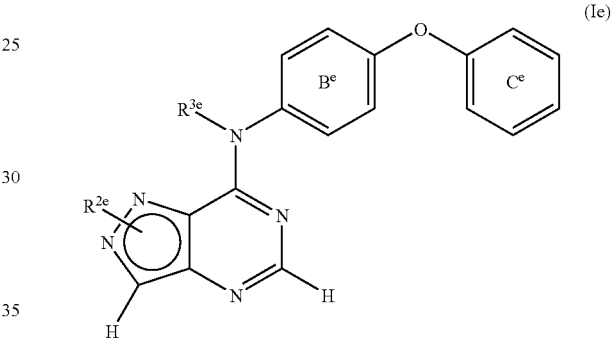

wherein $R^{2e}$ is an optionally substituted group bonded via a carbon atom or a sulfur atom, or
$R^{2e}$ and $R^{3e}$ are optionally bonded to form an optionally substituted ring structure,
$R^{3e}$ is a hydrogen atom or an optionally substituted aliphatic hydrocarbon group, or $R^{3e}$ is optionally bonded to a carbon atom of the adjacent phenyl group to form an optionally substituted ring structure,
$B^e$ is an optionally substituted benzene ring, and $C^e$ is an optionally substituted $C_{6-18}$ aryl group, or a salt thereof.

As the "optionally substituted group bonded via a carbon atom or a sulfur atoms" for $R^{2e}$, those similar to the "optionally substituted group bonded via a carbon atom or a sulfur atom" for $R^2$ can be used.

As the "optionally substituted ring structure" formed by $R^{2e}$ and $R^{3e}$ bonded to each other, those similar to the "optionally substituted ring structure" formed by $R^2$ and $R^3$ bonded to each other can be used.

As the "optionally substituted aliphatic hydrocarbon group" for $R^{3e}$, those similar to the "optionally substituted aliphatic hydrocarbon group" for $R^3$ can be used.

As the "optionally substituted ring structure" formed by $R^{3e}$ and a carbon atom of the adjacent phenyl group, those similar to the "optionally substituted ring structure" formed by $R^3$ and a carbon atom of the adjacent phenyl group can be used.

As the "optionally substituted benzene ring" for $B^e$, those similar to the "optionally substituted benzene ring" for $B^a$ can be used.

As the "optionally substituted $C_{6-18}$ aryl group" for $C^e$, those similar to the "optionally substituted $C_{6-18}$ aryl group" for $C^a$ can be used.

As $R^{2e}$, a $C_{1-8}$ alkyl group, a $C_{2-8}$ alkenyl group, a $C_{2-8}$ alkynyl group, a carbamoyl group, a $C_{1-8}$ alkyl-carbonyl group, a $C_{1-8}$ alkylsulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocycle-$C_{1-4}$ alkyl group, a heterocycle-carbonyl group or a heterocycle-$C_{1-4}$ alkyl-carbonyl group, each of which is optionally substituted by 1 to 5 substituents selected from
(a) halogen,
(b) oxo,
(c) optionally halogenated $C_{1-4}$ alkyl,
(d) —$(CH_2)_m$-Q,
(e) —$(CH_2)_m$—$Z^1$-(optionally halogenated $C_{1-4}$ alkyl),
(f) —$(CH_2)_m$—$Z^1$—$C_{3-8}$ cycloalkyl,
(g) —$(CH_2)_m$—$Z^2$—$(CH_2)_n$-Q,
(h) —$(CH_2)_m$—$Z^2$—$(CH_2)_n$—$Z^1$-optionally halogenated $C_{1-4}$ alkyl,
(i) —$(CH_2)_m$—$Z^2$—$(CH_2)_n$—$Z^1$—$C_{3-8}$ cycloalkyl,
(j) —$(CH_2)_m$—$Z^1$-(optionally substituted heterocyclic group) (preferably, said heterocyclic group is a 5- to 8-membered heterocyclic group having 1 to 3 hetero atoms selected from a nitrogen atom, an oxygen atom and an optionally oxidized sulfur atom),
(k) $(CH_2)_m$—$Z^2$—$C_{1-4}$ alkoxy, and
(l) —$(CH_2)_m$—$Z^2$—$(CH_2)_n$—$Z^1$—$(CH_2)_n$—$Z^1$-$C_{1-4}$ alkyl
wherein m is an integer of 0 to 4, n is an integer of 1 to 4, Q is hydroxy, carboxy, cyano, nitro, —$NR^6R^7$, —$CONR^6R^7$ or —$SO_2NR^6R^7$,
$Z^1$ is —O—, —CO—, —$C(OH)R^8$—, —$C(=N-OR^8)$—, —S—, —SO—, —$SO_2$—, —$N(COR^8)$—, —$N(CO_2R^9)$—, —$N(SO_2R^9)$—, —CO—O—, —O—CO—, —CO—$NR^8$—, —$NR^8$—CO—, —$NR^8$—$CO_2$—, —$NR^8$—CO—NH—, —$NR^8$—$SO_2$—, or —$NR^8$—C(=NH)—NH—,
$Z^2$ is —O—, —CO—, —$C(OH)R^8$—, —$C(=N-OR^8)$—, —S—, —SO—, —$SO_2$—, —$NR^8$—, —$N(COR^8)$—, —$N(CO_2R^9)$—, —$N(SO_2R^9)$—, —CO—O—, —O—CO—, —CO—$NR^8$—, —$NR^8$—CO—, —$NR^8$—$CO_2$—, —$NR^8$—CO—NH—, —$NR^8$—C(=NH)—NH—, —$NR^8$—$SO_2$—, or —$SO_2$—$NR^8$—,
$(CH_2)_m$ and $(CH_2)_n$ are optionally substituted by 1 to 5 substituents selected from halogen, optionally halogenated $C_{1-4}$ alkyl and hydroxy, and when m or n is not less than 2, a subset —$CH_2CH_2$— of $(CH_2)_m$ and $(CH_2)_n$ is optionally substituted by —CH=CH—,
$R^6$ and $R^7$ are the same or different and each is a hydrogen atom, or a $C_{1-4}$ alkyl group, or $R^6$ and $R^7$ are bonded to form, together with a nitrogen atom, a 3- to 8-membered saturated or unsaturated aliphatic heterocyclic group,
$R^8$ is a hydrogen atom or $C_{1-4}$ alkyl, and $R^9$ is $C_{1-4}$ alkyl is preferable.

As compound (Ie), a compound wherein
$B^e$ is a benzene ring optionally substituted by halogen;
$C^e$ is a phenyl group optionally substituted by optionally halogenated $C_{1-4}$ alkyl; and
$R^{2e}$ is a $C_{1-4}$ alkyl group optionally substituted by —O—$(CH_2)_n$—OH wherein n is an integer of 1 to 4 is preferable.
Moreover, as compound (Ie), a compound wherein
$B^e$ is a benzene ring optionally substituted by halogen;
$C^e$ is a phenyl group optionally substituted by optionally halogenated $C_{1-4}$ alkyl; and
$R^{2e}$ is a $C_{1-4}$ alkyl group substituted by —O—$(CH_2)_n$—OH wherein n is an integer of 1 to 4 is preferable.

[compound (If)]
A compound represented by the formula:

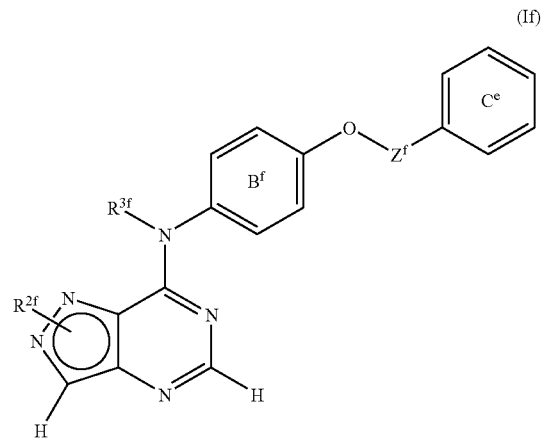

wherein $R^{2f}$ is an optionally substituted group bonded via a carbon atom or a sulfur atom, or
$R^{2f}$ and $R^{3f}$ are optionally bonded to form an optionally substituted ring structure,
$R^{3f}$ is a hydrogen atom or an optionally substituted aliphatic hydrocarbon group, or $R^{3f}$ is optionally bonded to a carbon atom of the adjacent phenyl group to form an optionally substituted ring structure,
$B^f$ is an optionally substituted benzene ring, $C^f$ is an optionally substituted $C_{6-18}$ aryl group, and
$Z^f$ is an optionally substituted $C_{1-3}$ alkylene group, or a salt thereof.

As the "optionally substituted group bonded via a carbon atom or a sulfur atom" for $R^{2f}$, those similar to the "optionally substituted group bonded via a carbon atom or a sulfur atom" for $R^2$ can be used.

As the "optionally substituted ring structure" formed by $R^{2f}$ and $R^{3f}$ bonded to each other, those similar to the "optionally substituted ring structure" formed by $R^2$ and $R^3$ bonded to each other can be used.

As the "optionally substituted aliphatic hydrocarbon group" for $R^3$, those similar to the "optionally substituted aliphatic hydrocarbon group" for $R^3$ can be used.

As the "optionally substituted ring structure" formed by $R^{3f}$ and a carbon atom of the adjacent phenyl group, those similar to the "optionally substituted ring structure" formed by $R^3$ and a carbon atom of the adjacent phenyl group can be used.

As the "optionally substituted benzene ring" for $B^f$, those similar to the "optionally substituted benzene ring" for $B^a$ can be used.

As the "optionally substituted $C_{6-18}$ aryl group" for $C^f$, those similar to the "optionally substituted $C_{6-18}$ aryl group" for $C^a$ can be used.

As the "optionally substituted $C_{1-3}$ alkylene group" for $Z^f$, those similar to the "optionally substituted $C_{1-3}$ alkylene group" for $Z^b$ can be used.

As $R^{2f}$, a $C_{1-8}$ alkyl group, a $C_{2-8}$ alkenyl group, a $C_{2-8}$ alkynyl group, a carbamoyl group, a $C_{1-8}$ alkyl-carbonyl group, a $C_{1-8}$ alkylsulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocycle-$C_{1-4}$ alkyl group, a heterocycle-carbonyl group or a heterocycle-$C_{1-4}$ alkyl-carbonyl group, each of which is optionally substituted by 1 to 5 substituents selected from
(a) halogen,
(b) oxo,
(c) optionally halogenated $C_{1-4}$ alkyl,
(d) —$(CH_2)_m$-Q,
(e) —$(CH_2)_m$—$Z^1$-(optionally halogenated $C_{1-4}$ alkyl),
(f) —$(CH_2)_m$—$Z^1$—$C_{3-8}$ cycloalkyl,
(g) —$(CH_2)_m$—$Z^2$—$(CH_2)_n$-Q,
(h) —$(CH_2)_m$—$Z^2$—$(CH_2)_n$—$Z^1$-optionally halogenated $C_{1-4}$ alkyl,
(i) —$(CH_2)_m$—$Z^2$—$(CH_2)_n$—$Z^1$—$C_{3-8}$ cycloalkyl,
(j) —$(CH_2)_m$—$Z^1$-(optionally substituted heterocyclic group) (preferably, said heterocyclic group is a 5- to 8-membered heterocyclic group having 1 to 3 hetero atoms selected from a nitrogen atom, an oxygen atom and an optionally oxidized sulfur atom),
(k) —$(CH_2)_m$—$Z^2$—$C_{1-4}$ alkoxy, and
(l) —$(CH_2)_m$—$Z^2$—$(CH_2)_n$—$Z^1$—$(CH_2)_n$—$Z^1$-$C_{1-4}$ alkyl
wherein m is an integer of 0 to 4, n is an integer of 1 to 4, Q is hydroxy, carboxy, cyano, nitro, —$NR^6R^7$, —$CONR^6R^7$ or —$SO_2NR^6R^7$,
$Z^1$ is —O—, —CO—, —C(OH)$R^8$—, —C(=N—O$R^8$)—, —S—, —SO—, —SO$_2$—, —N(CO$R^8$), —N(CO$_2R^9$)—, —N(SO$_2R^9$)—, —CO—O—, —O—CO—, —CO—$NR^8$—, —$NR^8$—CO—, —$NR^8$—CO$_2$—, —$NR^8$—CO—NH—, —$NR^8$—SO$_2$—, or —$NR^8$—C(=NH)—NH—,
$Z^2$ is —O—, —CO—, —C(OH)$R^8$—, —C(=N—O$R^8$)—, —S—, —SO—, —SO$_2$—, —$NR^8$—, —N(CO$R^8$)—, —N(CO$_2R^9$)—, —N(SO$_2R^9$)—, —CO—O—, —O—CO—, —CO—$NR^8$—, —$NR^8$—CO—, —$NR^8$—CO$_2$—, —$NR^8$—CO—NH—, —$NR^8$—C(=NH)—NH—, —$NR^8$—SO$_2$— or —SO$_2$—$NR^8$—,
$(CH_2)_m$ and $(CH_2)_n$ are optionally substituted by 1 to 5 substituents selected from halogen, optionally halogenated $C_{1-4}$ alkyl and hydroxy, and when m or n is not less than 2, a subset —CH$_2$CH$_2$— of $(CH_2)_m$ and $(CH_2)_n$ is optionally substituted by —CH=CH—,
$R^6$ and $R^7$ are the same or different and each is a hydrogen atom, or a $C_{1-4}$ alkyl group, or $R^6$ and $R^7$ are bonded to form, together with a nitrogen atom, a 3- to 8-membered saturated or unsaturated aliphatic heterocyclic group,
$R^8$ is a hydrogen atom or $C_{1-4}$ alkyl, and $R^9$ is $C_{1-4}$ alkyl, is preferable.

As compound (If), a compound wherein
$B^f$ is a benzene ring optionally substituted by halogen;
$C^f$ is a phenyl group optionally substituted by halogen;
$R^{2f}$ is
(i) a $C_{1-4}$ alkyl group optionally substituted by 1 to 5 substituents selected from the group consisting of
(a) hydroxy,
(b) —O—$(CH_2)_n$—OH,
(c) —$NR^8$—$(CH_2)_n$—O—$C_{1-4}$ alkyl,
(d) —$NR^8$—$(CH_2)_n$-heterocyclic group (preferably, said heterocyclic group is a 5- to 8-membered heterocyclic group having 1 to 3 hetero atoms selected from a nitrogen atom, an oxygen atom and a sulfur atom), and
(e) —$NR^8$—$(CH_2)_n$—SO$_2$—$C_{1-4}$ alkyl,
wherein n is an integer of 1 to 4, and $R^8$ is a hydrogen atom or a $C_{1-4}$ alkyl group,
(ii) a $C_{6-18}$ aryl group optionally substituted by 1 to 5 substituents selected from the group consisting of
(a) $C_{1-4}$ alkyl optionally substituted by substituent(s) selected from hydroxy, —$NR^8$—$(CH_2)_n$—OH, —$NR^8$—$(CH_2)_n$—O—$C_{1-4}$ alkyl, —$NR^8$—$(CH_2)_n$-heterocyclic group (preferably, said heterocyclic group is a 5- to 8-membered heterocyclic group having 1 to 3 hetero atoms selected from a nitrogen atom, an oxygen atom and a sulfur atom) and —$NR^8$—$(CH_2)_n$—SO$_2$—$C_{1-4}$ alkyl, and
(b) —CO—$NR^8$—$(CH_2)_n$—O—$C_{1-4}$ alkyl,
wherein n is an integer of 1 to 4, and $R^8$ is a hydrogen atom or a $C_{1-4}$ alkyl group, or
(iii) a $C_{6-18}$ aryl-$C_{1-4}$ alkyl group optionally substituted by 1 to 5 substituents selected from the group consisting of
(a) carboxy,
(b) $C_{1-4}$ alkoxy-carbonyl, and
(c) —CO—$NR^8$—$(CH_2)_n$—O—$C_{1-4}$ alkyl,
wherein n is an integer of 1 to 4, and $R^8$ is a hydrogen atom or a $C_{1-4}$ alkyl group,
$R^{3f}$ is a hydrogen atom or a $C_{1-6}$ alkyl group; and
$Z^f$ is a $C_{1-3}$ alkylene group; or
$R^{2f}$ and $R^{3f}$ are optionally bonded to form $C_{2-4}$ alkylene is preferable.

As $R^8$, a hydrogen atom, methyl, ethyl and the like are preferably, and a hydrogen atom is particularly preferable.

Moreover, as compound (If), a compound wherein
$B^f$ is a benzene ring optionally substituted by halogen;
$C^f$ is a phenyl group optionally substituted by halogen;
$R^{2f}$ is a $C_{1-4}$ alkyl group optionally substituted by 1 to 5 substituents selected from the group consisting of
(a) hydroxy, and
(b) —O—$(CH_2)_n$—OH wherein n is an integer of 1 to 4;
$R^{3f}$ is a hydrogen atom or a $C_{1-6}$ alkyl group;
$Z^f$ is methylene is preferable, and particularly, a compound wherein $R^{2f}$ is a $C_{1-4}$ alkyl group substituted by —O—$(CH_2)_n$—OH wherein n is an integer of 1 to 4 is preferable.

[compound (Ig)]

A compound represented by the formula:

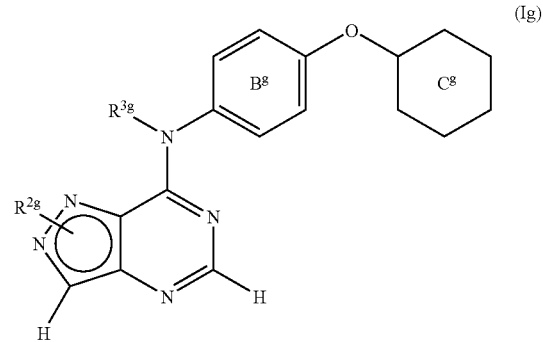

(Ig)

wherein $R^{2g}$ is an optionally substituted group bonded via a carbon atom or a sulfur atom, or
$R^{2g}$ and $R^{3g}$ are optionally bonded to form an optionally substituted ring structure,
$R^{3g}$ is a hydrogen atom or an optionally substituted aliphatic hydrocarbon group, or $R^{3g}$ is optionally bonded to a carbon atom of the adjacent phenyl group to form an optionally substituted ring structure,
$B^g$ is an optionally substituted benzene ring, and $C^g$ is an optionally substituted heterocyclic group, or a salt thereof.

As the "optionally substituted group bonded via a carbon atom or a sulfur atom" for $R^{2g}$, those similar to the "optionally substituted group bonded via a carbon atom or a sulfur atom" for $R^2$ can be used.

As the "optionally substituted ring structure" formed by $R^{2g}$ and $R^{3g}$ bonded to each other, those similar to the "optionally substituted ring structure" formed by $R^2$ and $R^3$ bonded to each other can be used.

As the "optionally substituted aliphatic hydrocarbon group" for $R^{3g}$, those similar to the "optionally substituted aliphatic hydrocarbon group" for $R^3$ can be used.

As the "optionally substituted ring structure" formed by $R^{3g}$ and a carbon atom of the adjacent phenyl group, those similar to the "optionally substituted ring structure" formed by $R^3$ and a carbon atom of the adjacent phenyl group can be used.

As the "optionally substituted benzene ring" for $B^g$, those similar to the "optionally substituted benzene ring" for $B^a$ can be used.

As the "optionally substituted heterocyclic group" for $C^g$, those similar to the "optionally substituted heterocyclic group" for $C^c$ can be used.

As $R^{2g}$, a $C_{1-8}$ alkyl group, a $C_{2-8}$ alkenyl group, a $C_{2-8}$ alkynyl group, a carbamoyl group, a $C_{1-8}$ alkyl-carbonyl group, a $C_{1-8}$ alkylsulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocycle-$C_{1-4}$ alkyl group, a heterocycle-carbonyl group or a heterocycle-$C_{1-4}$ alkyl-carbonyl group, each of which is optionally substituted by 1 to 5 substituents selected from
(a) halogen,
(b) oxo,
(c) optionally halogenated $C_{1-4}$ alkyl,
(d) —$(CH_2)_m$-Q,
(e) —$(CH_2)_m$—$Z^1$-(optionally halogenated $C_{1-4}$ alkyl),
(f) —$(CH_2)_m$—$Z^1$—$C_{3-8}$ cycloalkyl,
(g) —$(CH_2)_m$—$Z^2$—$(CH_2)_n$-Q,
(h) —$(CH_2)_m$—$Z^2$—$(CH_2)_n$—$Z^1$-(optionally halogenated $C_{1-4}$ alkyl),
(i) —$(CH_2)_m$—$Z^2$—$(CH_2)_n$—$Z^1$—$C_{3-8}$ cycloalkyl,
(j) —$(CH_2)_m$—$Z^1$-(optionally substituted heterocyclic group) (preferably, said heterocyclic group is a 5- to 8-membered heterocyclic group having 1 to 3 hetero atoms selected from a nitrogen atom, an oxygen atom and an optionally oxidized sulfur atom),
(k) —$(CH_2)_m$—$Z^2$—$C_{1-4}$ alkoxy, and
(l) —$(CH_2)_m$—$Z^2$—$(CH_2)_n$—$Z^1$—$(CH_2)_n$—$Z^1$—$C_{1-4}$ alkyl
wherein m is an integer of 0 to 4, n is an integer of 1 to 4, Q is hydroxy, carboxy, cyano, nitro, —$NR^6R^7$, —$CONR^6R^7$ or —$SO_2NR^6R^7$,
$Z^1$ is —O—, —CO—, —C(OH)$R^8$—, —C(=N—O$R^8$)—, —S—, —SO—, —$SO_2$—, —N(CO$R^8$)—, —N(CO$_2R^9$)—, —N(SO$_2R^9$)—, —CO—O—, —O—CO—, —CO—$NR^8$—, —$NR^8$—CO—, —$NR^8$—CO$_2$—, —$NR^8$—CO—NH—, —$NR^8$—$SO_2$—, or —$NR^8$—C(=NH)—NH—,
$Z^2$ is —O—, —CO—, —C(OH)$R^8$—, —C(=N—O$R^8$)—, —S—, —SO—, —$SO_2$—, —$NR^8$—, —N(CO$R^8$)—, —N(CO$_2R^9$)—, —N(SO$_2R^9$)—, —CO—O—, —O—CO—, —CO—$NR^8$—, —$NR^8$—CO—, —$NR^8$—CO$_2$—, —$NR^8$—CO—NH—, —$NR^8$—C(=NH)—NH—, —$NR^8$—$SO_2$—, or —$SO_2$—$NR^8$—,
$(CH_2)_m$ and $(CH_2)_n$ are optionally substituted by 1 to 5 substituents selected from halogen, optionally halogenated $C_{1-4}$ alkyl and hydroxy, and when m or n is not less than 2, a subset —$CH_2CH_2$— of $(CH_2)_m$ and $(CH_2)_n$ is optionally replaced by —CH=CH—.
$R^6$ and $R^7$ are the same or different and each is a hydrogen atom, or a $C_{1-4}$ alkyl group, or $R^6$ and $R^7$ are bonded to form, together with a nitrogen atom, a 3- to 8-membered saturated or unsaturated aliphatic heterocyclic group,
$R^8$ is a hydrogen atom or $C_{1-4}$ alkyl, and $R^9$ is $C_{1-4}$ alkyl, is preferable.

As compound (Ig), a compound wherein
$B^g$ is a benzene ring optionally substituted by $C_{1-4}$ alkyl;
$C^g$ is a 5- to 8-membered heterocyclic group having 1 to 3 hetero atoms selected from a nitrogen atom, an oxygen atom and a sulfur atom, which is optionally substituted by $C_{1-4}$ alkyl;
$R^{2g}$ is
(i) a $C_{1-4}$ alkyl group optionally substituted by hydroxy,
(ii) a $C_{6-18}$ aryl group optionally substituted by substituent(s) selected from
(a) nitro,
(b) amino,
(c) —CO—$NR^8$—$(CH_2)_n$—O—$C_{1-4}$ alkyl,
(d) —$NR^8$—CO—$(CH_2)_n$—O—$C_{1-4}$ alkyl,
(e) —$NR^8$—CO—$(CH_2)_n$—$NR^6R^7$,
(f) —$NR^8$—CO—$(CH_2)_n$—COOH,
(g) —$NR^8$—CO$(CH_2)_n$—$CO_2$—$C_{1-4}$ alkyl, and
(h) —$NR^8$—CO—$(CH_2)_n$—O—$(CH_2)_n$—O—$C_{1-4}$ alkyl,
wherein m is an integer of 0 to 4, n is an integer of 1 to 4, $R^6$ and $R^7$ are the same or different and each is a hydrogen atom or a $C_{1-4}$ alkyl group, and $R^8$ is a hydrogen atom or a $C_{1-4}$ alkyl group, or
(iii) a $C_{6-18}$ aryl-$C_{1-4}$ alkyl group optionally substituted by substituent(s) selected from
(a) carboxy,
(b) $C_{1-4}$ alkoxy-carbonyl, and
(c) —CO—$NR^8$—$(CH_2)_n$—O—$C_{1-4}$ alkyl,
wherein n is an integer of 1 to 4, and $R^8$ is a hydrogen atom or a $C_{1-4}$ alkyl group;
$R^{3g}$ is a hydrogen atom or a $C_{1-6}$ alkyl group; or
$R^{2g}$ and $R^{3g}$ are optionally bonded to form $C_{2-4}$ alkylene is preferable.

As compound (Ig), a compound wherein
$R^{2g}$ is
(i) a $C_{6-18}$ aryl group optionally substituted by substituent(s) selected from
(a) nitro,
(b) amino,
(c) —CO—$NR^8$—$(CH_2)_n$—O—$C_{1-4}$ alkyl,
(d) —$NR^8$—CO—$(CH_2)_n$—O—$C_{1-4}$ alkyl,
(e) —$NR^8$—CO—$(CH_2)_n$—$NR^6R^7$,
(f) —$NR^8$—CO—$(CH_2)_n$—COOH,
(g) —$NR^8$—CO—$(CH_2)_n$—$CO_2$—$C_{1-4}$ alkyl, and
(h) —$NR^8$—CO—$(CH_2)_n$—O—$(CH_2)_n$—O—$C_{1-4}$ alkyl,
wherein m is an integer of 0 to 4, n is an integer of 1 to 4, $R^6$ and $R^7$ are the same or different and each is a hydrogen atom or a $C_{1-4}$ alkyl group, and $R^8$ is a hydrogen atom or a $C_{1-4}$ alkyl group, or
(ii) a $C_{6-18}$ aryl-$C_{1-4}$ alkyl group substituted by substituent(s) selected from
(a) carboxy,
(b) $C_{1-4}$ alkoxy-carbonyl, and
(c) —CO—$NR^8$—$(CH_2)_n$—O—$C_{1-4}$ alkyl,
wherein n is an integer of 1 to 4, and $R^8$ is a hydrogen atom or a $C_{1-4}$ alkyl group, is preferable.

As $R^8$, a hydrogen atom, methyl, ethyl and the like are preferable, and a hydrogen atom is particularly preferable.
[compound (Ih)]
A compound (I) selected from the following (A) to (H).
(A) A compound (I) wherein W is $CR^1$;
A is a phenyloxy-$C_{6-18}$ aryl group wherein the phenyloxy moiety is optionally substituted by 1 to 5 substituents selected from
(i) halogen,
(ii) optionally halogenated $C_{1-4}$ alkyl,
(iii) hydroxy-$C_{1-4}$ alkyl,
(iv) heterocycle-$C_{1-4}$ alkyl (preferably, 5- to 8-membered heterocycle-$C_{1-4}$ alkyl, said 5- to 8-membered heterocycle has 1 to 3 hetero atoms selected from a nitrogen atom, an oxygen atom and an optionally oxidized sulfur atom, such as imidazolyl, triazolyl and the like),
(v) optionally halogenated $C_{1-4}$ alkyloxy,
(vi) $C_{1-4}$ alkyl-carbonyl,
(vii) cyano,
(viii) carbamoyl optionally substituted by $C_{1-8}$ alkyl, and
(ix) $C_{1-4}$ alkoxy-carbonyl, and
the $C_{6-18}$ aryl moiety is optionally further substituted by 1 to 4 substituents selected from halogen, $C_{1-4}$ alkyl, hydroxy-$C_{1-4}$ alkyl, $C_{1-4}$ alkyloxy, carboxy and $C_{1-4}$ alkoxy-carbonyl;
$X^1$ is —$NR^{3'}$— wherein $R^{3'}$ is a hydrogen atom or a $C_{1-6}$ alkyl group;
$R^1$ is
(i) a hydrogen atom,
(ii) a cyano group, or
(iii) a $C_{1-4}$ alkyl group or a $C_{2-4}$ alkenyl group, each of which is optionally substituted by —$NR^8$—CO—$(CH_2)_n$—$NR^6R^7$
wherein n is an integer of 1 to 4, $R^6$ and $R^7$ are the same or different and each is a hydrogen atom or a $C_{1-4}$ alkyl group, $R^8$ is a hydrogen atom or a $C_{1-4}$ alkyl group, and when n is not less than 2, a subset —$CH_2CH_2$— of $(CH_2)_n$ is optionally replaced by —CH=CH—;
$R^2$ is (i) a hydrogen atom or
(ii) a $C_{1-8}$ alkyl group, a $C_{2-8}$ alkenyl group or a $C_{2-8}$ alkynyl group, each of which is optionally substituted by substituent(s) selected from
(a) hydroxy,
(b) carboxy,
(c) cyano,
(d) optionally halogenated $C_{1-4}$ alkyloxy,
(e) —O—$(CH_2)_n$—OH,
(f) —O—$(CH_2)_n$—O—CO—$NH_2$,
(g) —O—$(CH_2)_n$—O-(optionally halogenated $C_{1-4}$ alkyl),
(h) —O—$(CH_2)_n$—$SO_2$-(optionally halogenated $C_{1-4}$ alkyl),
(i) —O—$(CH_2)_n$—$SO_2$—$C_{6-18}$ aryl,
(j) —O—$(CH_2)_n$—$SO_2$—$(CH_2)_n$—OH,
(k) —O—$(CH_2)_n$—$NR^8$—CO—$C_{1-4}$ alkyl,
(l) —O—$(CH_2)_n$—$NR^8$—CO—$(CH_2)_n$—$SO_2$—$C_{1-4}$ alkyl,
(m) —O—$(CH_2)_n$—$NR^8$—$SO_2$-(optionally halogenated $C_{1-4}$ alkyl),
(n) —CO—$NR^8$—$(CH_2)_n$—OH,
(o) —CO—$NR^8$—$(CH_2)_n$—$SO_2$-(optionally halogenated $C_{1-4}$ alkyl),
(p) —CO—$NR^8$—O—$C_{1-4}$ alkyl,
(q) —$NR^6R^7$,
(r) —$NR^8$—$(CH_2)_n$—OH,
(s) —$NR^8$—$(CH_2)_n$—$SO_2$—$C_{1-4}$ alkyl,
(t) —$NR^8$—CO-(optionally halogenated $C_{1-4}$ alkyl),
(u) —$NR^8$—CO—$(CH_2)_n$—OH,
(v) —$NR^8$—CO—$(CH_2)_n$—CN,
(w) —$NR^8$—CO—$(CH_2)_n$—$NR^6R^7$,
(x) —$NR^8$—CO—$(CH_2)_n$—O—$C_{1-4}$ alkyl,
(y) —$NR^8$—CO—$(CH_2)_n$—SO-(optionally halogenated $C_{1-4}$ alkyl),
(z) —$NR^8$—CO—$(CH_2)_n$—$SO_2$-(optionally halogenated $C_{1-4}$ alkyl),
(aa) —$NR^8$—CO—$(CH_2)_n$—$SO_2$—$C_{3-8}$ cycloalkyl,
(bb) —$NR^8$—CO—$(CH_2)_n$—$NR^8$—$SO_2$—$C_{1-4}$ alkyl,
(cc) —$NR^8$—$CO_2$—$(CH_2)_n$—$SO_2$—$C_{1-4}$ alkyl,
(dd) —$NR^8$—CO—NH—$(CH_2)_n$—$SO_2$—$C_{1-4}$ alkyl,
(ee) —$NR^8$—CO—NH—O—$C_{1-4}$ alkyl,
(ff) —$NR^8$—CO—NH—$(CH_2)_n$—O—$C_{1-4}$ alkyl,
(gg) —$NR^8$—C(=NH)—NH—$C_{1-4}$ alkyl,
(hh) —$NR^8$—$SO_2$—$(CH_2)_n$—$SO_2$—$C_{1-4}$ alkyl,
(ii) —S—$(CH_2)_n$—OH,
(jj) —SO—$(CH_2)_n$—OH,
(kk) —$SO_2$—$(CH_2)_n$—OH, and
(ll) —$NR^8$—CO-(optionally substituted heterocyclic group) (preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—O—$C_{1-4}$ alkyl, —CO—NH—$C_{1-4}$ alkyl, —$CONH_2$, —$SO_2$—$C_{1-4}$ alkyl, —$SO_2$—NH—$C_{1-4}$ alkyl, —$SO_2NH_2$ and the like)
wherein n is an integer of 1 to 4, $R^6$ and $R^7$ are the same or different and each is a hydrogen atom or a $C_{1-4}$ alkyl group, $R^8$ is a hydrogen atom or a $C_{1-4}$ alkyl group, $(CH_2)_n$ is optionally substituted by optionally halogenated $C_{1-4}$ alkyl or hydroxy, and when n is not less than 2, and a subset —$CH_2CH_2$— of $(CH_2)_n$ is optionally replaced by —CH=CH—; or
$R^1$ and $R^2$ are optionally bonded to form

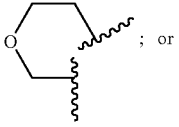

$R^2$ and $R^{3'}$ are optionally bonded to form $C_{2-4}$ alkylene optionally substituted by an imino group, particularly preferably, $R^{2a}$ is a $C_{1-8}$ alkyl group, a $C_{2-8}$ alkenyl group or a $C_{2-8}$ alkynyl group (particularly, $C_{1-8}$ alkyl group), each of which is optionally substituted by substituent(s) selected from
(a) hydroxy,
(b) carboxy,
(c) cyano,
(d) optionally halogenated $C_{1-4}$ alkyloxy,
(e) —O—$(CH_2)_n$—OH (wherein $(CH_2)_n$ is optionally substituted by hydroxy),
(f) —O—$(CH_2)_n$—O—CO—$NH_2$,
(g) —O—$(CH_2)_n$—O-(optionally halogenated $C_{1-4}$ alkyl),
(h) —O—$(CH_2)_n$—$SO_2$-(optionally halogenated $C_{1-4}$ alkyl),
(i) —O—$(CH_2)_n$—$SO_2$—$C_{6-18}$ aryl,
(j) —O—$(CH_2)_n$—$SO_2$—$(CH_2)_n$—OH,
(k) —O—$(CH_2)_n$—$NR^8$—CO—$C_{1-4}$ alkyl,
(l) —O—$(CH_2)_n$—$NR^8$—CO—$(CH_2)_n$—$SO_2$—$C_{1-4}$ alkyl,
(m) —O—$(CH_2)_n$—$NR^8$—$SO_2$-(optionally halogenated $C_{1-4}$ alkyl),
(n) —CO—$NR^8$—$(CH_2)_n$—OH,
(o) —CO—$NR^8$—$(CH_2)_n$—$SO_2$-(optionally halogenated $C_{1-4}$ alkyl),
(p) —CO—$NR^8$—O—$C_{1-4}$ alkyl,
(q) —$NR^6R^7$,
(r) —$NR^8$—$(CH_2)_n$—OH,
(s) —$NR^8$—$(CH_2)_n$—$SO_2$—$C_{1-4}$ alkyl,
(t) —$NR^8$—CO-(optionally halogenated $C_{1-4}$ alkyl),
(u) —$NR^8$—CO—$(CH_2)_n$—OH (wherein $(CH_2)_n$ is optionally substituted by optionally halogenated $C_{1-4}$ alkyl or hydroxy),
(v) —$NR^8$—CO—$(CH_2)_n$—CN,
(w) —$NR^8$—CO—$(CH_2)_n$—$NR^6R^7$ (when n is not less than 2, a subset —$CH_2CH_2$— of $(CH_2)_n$ is optionally replaced by —CH=CH—),
(x) —$NR^8$—CO—$(CH_2)_n$—O—$C_{1-4}$ alkyl, (y) —NR$^8$—CO—(CH$_2$)$_n$—SO-(optionally halogenated C$_{1-4}$ alkyl),
(z) —NR$^8$—CO—(CH$_2$)$_n$—SO$_2$-(optionally halogenated C$_{1-4}$ alkyl) (wherein (CH$_2$)$_n$ is optionally substituted by C$_{1-4}$ alkyl),
(aa) —NR$^8$—CO—(CH$_2$)$_n$—SO$_2$—C$_{3-8}$ cycloalkyl,
(bb) —NR$^8$—CO—(CH$_2$)$_n$—NR$^8$—SO$_2$—C$_{1-4}$ alkyl,
(cc) —NR$^8$—CO$_2$—(CH$_2$)$_n$—SO$_2$—C$_{1-4}$ alkyl,
(dd) —NR$^8$—CO—NH—(CH$_2$)$_n$—SO$_2$—C$_{1-4}$ alkyl,
(ee) —NR$^8$—CO—NH—O—C$_{1-4}$ alkyl,
(ff) —NR$^8$—CO—NH—(CH$_2$)$_n$—O—C$_{1-4}$ alkyl,
(gg) —NR$^8$—C(=NH)—NH—C$_{1-4}$ alkyl,
(hh) —NR$^8$—SO$_2$—(CH$_2$)$_n$—SO$_2$—C$_{1-4}$ alkyl,
(ii) —S—(CH$_2$)$_n$—OH,
(jj) —SO—(CH$_2$)$_n$—OH,
(kk) —SO$_2$—(CH$_2$)$_n$—OH, and
(ll) —NR$^8$—CO-(optionally substituted heterocyclic group) (preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, C$_{1-4}$ alkyl, optionally oxidized C$_{1-4}$ alkylthio, —CO—C$_{1-4}$ alkyl, —CO—O—C$_{1-4}$ alkyl, —CO—NH—C$_{1-4}$ alkyl, —CONH$_2$, —SO$_2$—C$_{1-4}$ alkyl, —SO$_2$—NH—C$_{1-4}$ alkyl, —SO$_2$NH$_2$ and the like)
wherein n is an integer of 1 to 4, R$^6$ and R$^7$ are the same or different and each is a hydrogen atom or a C$_{1-4}$ alkyl group, and R$^8$ is a hydrogen atom or a C$_{1-4}$ alkyl group.
(B) A compound (I) wherein W is CR$^1$;
A is a phenyl-C$_{1-3}$ alkyloxy-C$_{6-18}$ aryl group wherein the phenyl moiety is optionally substituted by 1 to 5 substituents selected from halogen, optionally halogenated C$_{1-4}$ alkyl and cyano, and
the C$_{6-18}$ aryl moiety is optionally further substituted by 1 to 4 substituents selected from halogen, C$_{1-4}$ alkyl optionally having hydroxy and C$_{1-4}$ alkyloxy;
X$^1$ is —NR$^{3'}$— wherein R$^{3'}$ is a hydrogen atom or a C$_{1-6}$ alkyl group;
R$^1$ is (i) a hydrogen atom, or
(ii) a C$_{1-4}$ alkyl group or a C$_{2-4}$ alkenyl group, each of which is optionally substituted by substituent(s) selected from
(a) hydroxy,
(b) amino, and
(c) —NR$^8$—CO—(CH$_2$)$_n$—NR$^6$R$^7$,
wherein n is an integer of 1 to 4, R$^6$ and R$^7$ are the same or different and each is a hydrogen atom or a C$_{1-4}$ alkyl group, and R$^8$ is a hydrogen atom or a C$_{1-4}$ alkyl group,
(iii) a C$_{6-18}$ aryl group optionally substituted by substituent(s) selected from
(a) amino,
(b) carboxy,
(c) —NR$^8$—CO—(CH$_2$)$_n$—O—C$_{1-4}$ alkyl, and
(d) —NR$^8$—CO—(CH$_2$)$_n$—O—C$_{1-4}$ alkyl,
wherein n is an integer of 1 to 4, and R$^8$ is a hydrogen atom or a C$_{1-4}$ alkyl group, and when n is not less than 2, a subset —CH$_2$—CH$_2$ of (CH$_2$)$_n$ is optionally replaced by —CH=CH—, or
(iv) a 5- to 8-membered heterocyclic group having 1 to 3 hetero atoms selected from a nitrogen atom, an oxygen atom and a sulfur atom;
R$^2$ is (i) a hydrogen atom,
(ii) a C$_{1-8}$ alkyl group optionally substituted by substituent(s) selected from
(a) halogen,
(b) hydroxy,
(c) C$_{1-4}$ alkyloxy,
(d) —O—(CH$_2$)$_n$—OH,
(e) —O—(CH$_2$)$_n$—O—C$_{1-4}$ alkyl,
(f) —CO—NR$^8$—(CH$_2$)$_n$—OH,
(g) —NR$^6$R$^7$, and
(h) —NR$^8$—(CH$_2$)$_n$—OH,
wherein n is an integer of 1 to 4, R$^6$ and R$^7$ are the same or different and each is a hydrogen atom or a C$_{1-4}$ alkyl group, and R$^8$ is a hydrogen atom or a C$_{1-4}$ alkyl group,
(iii) a C$_{6-18}$ aryl-C$_{1-4}$ alkyl group optionally substituted by substituent(s) selected from
(a) C$_{1-4}$ alkyl optionally having hydroxy,
(b) carboxy,
(c) C$_{1-4}$ alkoxy-carbonyl,
(d) 5- to 8-membered heterocycle-carbonyl having 1 to 3 hetero atoms selected from a nitrogen atom, an oxygen atom and a sulfur atom, which optionally has substituent(s) selected from hydroxy and C$_{1-4}$ alkyl, and
(e) C$_{1-4}$ alkyl-carbamoyl optionally having substituent(s) selected from hydroxy and carbamoyl,
(iv) a C$_{6-18}$ aryl-carbonyl group optionally substituted by C$_{1-4}$ alkoxy,
(v) a C$_{6-18}$ aryl-sulfonyl group optionally substituted by C$_{1-4}$ alkoxy, or
(vi) a 5- to 8-membered heterocycle-C$_{1-4}$ alkyl group having 1 to 3 hetero atoms selected from a nitrogen atom, an oxygen atom and a sulfur atom, which is optionally substituted by substituent(s) selected from
(a) carboxy, and
(b) C$_{1-4}$ alkoxy-carbonyl; or
R$^2$ and R$^{3'}$ are optionally bonded to form C$_{2-4}$ alkylene.
(C) A compound (I) wherein W is CR$^1$;
A is a 5- to 8-membered heterocyclooxy-C$_{6-18}$ aryl group containing 1 to 3 hetero atoms selected from a nitrogen atom, an oxygen atom and a sulfur atom, wherein the heterocyclooxy moiety is optionally substituted by 1 to 5 substituents selected from
(i) halogen,
(ii) C$_{1-4}$ alkyl,
(iii) C$_{1-4}$ alkyl-carbonyl,
(iv) optionally halogenated C$_{1-4}$ alkoxy-carbonyl,
(v) C$_{3-8}$ cycloalkyl-carbonyl, and
(vi) a carbamoyl group optionally substituted by substituent(s) selected from
(a) optionally halogenated C$_{1-8}$ alkyl,
(b) C$_{3-8}$ cycloalkyl, and
(c) C$_{6-18}$ aryl optionally substituted by substituent(s) selected from halogen, C$_{1-4}$ alkyl and C$_{1-4}$ alkyloxy, and
the C$_{6-18}$ aryl moiety is optionally further substituted by 1 to 4 substituents selected from halogen and optionally halogenated C$_{1-4}$ alkyl;
X$^1$ is —NR$^{3'}$— wherein R$^{3'}$ is a hydrogen atom or a C$_{1-6}$ alkyl group;
R$^1$ is (i) a hydrogen atom,
(ii) a C$_{1-4}$ alkyl group or a C$_{2-4}$ alkenyl group, each of which is optionally substituted by substituent(s) selected from
(a) hydroxy,
(b) amino,
(c) —NR$^8$—CO—(CH$_2$)$_n$—NR$^6$R$^7$, and
(d) —NR$^8$—CO—(CH$_2$)$_n$—O—C$_{1-4}$ alkyl,
wherein n is an integer of 1 to 4, R$^6$ and R$^7$ are the same or different and each is a hydrogen atom or a C$_{1-4}$ alkyl group, R$^8$ is a hydrogen atom or a C$_{1-4}$ alkyl group, and when n is not less than 2, a subset —CH$_2$CH$_2$— of (CH$_2$)$_n$ is optionally replaced by —CH=CH—, (iii) a $C_{6-18}$ aryl group optionally substituted by substituent(s) selected from
(a) $C_{1-4}$ alkyl optionally substituted by substituent(s) selected from hydroxy, —$NR^8$—$(CH_2)_n$—$SO_2$—$C_{1-4}$ alkyl and —$NR^8$—CO—$(CH_2)_n$—O—$C_{1-4}$ alkyl,
(b) amino,
(c) $C_{1-4}$ alkyloxy,
(d) carboxy, and
(e) —$NR^8$—CO—$(CH_2)_n$—O—$C_{1-4}$ alkyl,
wherein n is an integer of 1 to 4, and $R^8$ is a hydrogen atom or a $C_{1-4}$ alkyl group, or
(iv) a 5- to 8-membered heterocyclic group having 1 to 3 hetero atoms selected from a nitrogen atom, an oxygen atom and a sulfur atom;
$R^2$ is (i) a hydrogen atom,
(ii) a $C_{1-4}$ alkyl group optionally substituted by substituent(s) selected from
(a) halogen,
(b) hydroxy,
(c) $C_{1-4}$ alkyloxy,
(d) carboxy,
(e) $C_{1-4}$ alkoxy-carbonyl,
(f) —O—$(CH_2)_n$—OH,
(g) —O—$(CH_2)_n$—O—$C_{1-4}$ alkyl,
(h) —CO—$NR^8$—$(CH_2)_n$—OH, and
(i) —$NR^8$—CO—$(CH_2)_n$—$SO_2$—$C_{1-4}$ alkyl
wherein n is an integer of 1 to 4, and $R^8$ is a hydrogen atom or a $C_{1-4}$ alkyl group, or
(iii) a $C_{6-18}$ aryl-$C_{1-4}$ alkyl group optionally substituted by $C_{1-4}$ alkyl optionally having hydroxy; or
$R^2$ and $R^{3'}$ are optionally bonded to form $C_{2-4}$ alkylene.
(D) A compound (I) wherein W is $CR^1$;
A is 5- to 8-membered heterocycle-$C_{1-3}$ alkyloxy-$C_{6-18}$ aryl group containing 1 to 3 hetero atoms selected from a nitrogen atom, an oxygen atom and a sulfur atom;
wherein the $C_{6-18}$ aryl moiety is optionally further substituted by halogen;
$X^1$ is —$NR^{3'}$— wherein $R^{3'}$ is a hydrogen atom or a $C_{1-6}$ alkyl group;
$R^1$ is (i) a hydrogen atom or
(ii) a 5- to 8-membered heterocyclic group having 1 to 3 hetero atoms selected from a nitrogen atom, an oxygen atom and a sulfur atom;
$R^2$ is (i) a hydrogen atom,
(ii) $C_{1-4}$ alkyl optionally substituted by substituent(s) selected from
(a) $C_{1-4}$ alkyloxy,
(b) —O—$(CH_2)_n$—OH, and
(c) —$NR^8$—CO—$(CH_2)_n$—$SO_2$—$C_{1-4}$ alkyl,
wherein n is an integer of 1 to 4, and $R^8$ is a hydrogen atom or a $C_{1-4}$ alkyl group, or
(iii) a 5- to 8-membered heterocycle-$C_{1-4}$ alkyl group having 1 to 3 hetero atoms selected from a nitrogen atom, an oxygen atom and a sulfur atom, which is optionally substituted by substituent(s) selected from
(a) carboxy, and
(b) $C_{1-4}$ alkoxy-carbonyl.
(E) A compound (I) wherein W is N;
A is a phenyloxy-$C_{6-18}$ aryl group wherein the phenyloxy moiety is optionally substituted by 1 to 5 substituents selected from optionally halogenated $C_{1-4}$ alkyl and cyano, and
the $C_{6-18}$ aryl moiety is optionally further substituted by 1 to 4 substituents selected from halogen and $C_{1-4}$ alkyl;
$X^1$ is —$NR^{3'}$— wherein $R^{3'}$ is a hydrogen atom or a $C_{1-6}$ alkyl group;
$R^2$ is (i) a hydrogen atom or
(ii) a $C_{1-4}$ alkyl group optionally substituted by —O—$(CH_2)_n$—OH wherein n is an integer of 1 to 4.

(F) A compound (I) wherein W is N;
A is a phenyl-$C_{1-3}$ alkyloxy-$C_{6-18}$ aryl group wherein the phenyl moiety is optionally substituted by 1 to 5 substituents selected from halogen and cyano, and
the $C_{6-18}$ aryl moiety is optionally further substituted by 1 to 5 substituents selected from halogen and $C_{1-4}$ alkyl;
$X^1$ is —$NR^{3'}$— wherein $R^{3'}$ is a hydrogen atom or a $C_{1-6}$ alkyl group;
$R^2$ is (i) a hydrogen atom,
(ii) a $C_{1-4}$ alkyl group optionally substituted by 1 to 5 substituents selected from the group consisting of
(a) hydroxy,
(b) —O—$(CH_2)_n$—OH,
(c) —$NR^8$—$(CH_2)_n$—O—$C_{1-4}$ alkyl,
(d) —$NR^8$—$(CH_2)_n$-heterocyclic group (preferably, said heterocyclic group is a 5- to 8-membered heterocyclic group having 1 to 3 hetero atoms selected from a nitrogen atom, an oxygen atom and a sulfur atom), and
(e) —$NR^8$—$(CH_2)_n$—$SO_2$—$C_{1-4}$ alkyl,
wherein n is an integer of 1 to 4, and $R^8$ is a hydrogen atom or a $C_{1-4}$ alkyl group,
(iii) a $C_{6-18}$ aryl group optionally substituted by $C_{1-4}$ alkyl optionally substituted by substituent(s) selected from hydroxy, —$NR^8$—$(CH_2)_n$—OH, —$NR^8$—$(CH_2)_n$-heterocyclic group (preferably, said heterocyclic group is a 5- to 8-membered heterocyclic group having 1 to 3 hetero atoms selected from a nitrogen atom, an oxygen atom and a sulfur atom) and —$NR^8$—$(CH_2)_n$—$SO_2$—$C_{1-4}$ alkyl, or
(iv) a $C_{6-18}$ aryl-$C_{1-4}$ alkyl group optionally substituted by 1 to 5 substituents selected from the group consisting of
(a) carboxy,
(b) $C_{1-4}$ alkoxy-carbonyl, and
(c) —CO—$NR^8$—$(CH_2)_n$—O—$C_{1-4}$ alkyl,
wherein n is an integer of 1 to 4, and $R^8$ is a hydrogen atom or a $C_{1-4}$ alkyl group; or
$R^2$ and $R^3$ are optionally bonded to form $C_{2-4}$ alkylene.
(G) A compound (I) wherein W is N;
A is a 5- to 8-membered heterocyclooxy-$C_{6-18}$ aryl group containing 1 to 3 hetero atoms selected from a nitrogen atom, an oxygen atom and a sulfur atom, wherein the heterocyclooxy moiety is optionally substituted by $C_{1-4}$ alkyl, and
the $C_{6-18}$ aryl moiety is optionally further substituted by $C_{1-4}$ alkyl;
$X^1$ is —$NR^{3'}$— wherein $R^{3'}$ is a hydrogen atom or a $C_{1-6}$ alkyl group;
$R^2$ is (i) a hydrogen atom,
(ii) a $C_{1-4}$ alkyl group optionally substituted by hydroxy,
(iii) a $C_{6-18}$ aryl group optionally substituted by substituent(s) selected from
(a) nitro,
(b) amino,
(c) —CO—$NR^8$—$(CH_2)_n$—O—$C_{1-4}$ alkyl,
(d) —$NR^8$—CO—$(CH_2)_n$—O—$C_{1-4}$ alkyl,
(e) —$NR^8$—CO—$(CH_2)_n$—$NR^6R^7$,
(f) —$NR^8$—CO—$(CH_2)_n$—COOH,
(g) —$NR^8$—CO—$(CH_2)_n$—$CO_2$—$C_{1-4}$ alkyl, and
(h) —$NR^8$—CO—$(CH_2)_n$—O—$(CH_2)_n$—O—$C_{1-4}$ alkyl,
wherein m is an integer of 0 to 4, n is an integer of 1 to 4,
$R^6$ and $R^7$ are the same or different and each is a hydrogen atom or a $C_{1-4}$ alkyl group, and $R^8$ is a hydrogen atom or a $C_{1-4}$ alkyl group, or
(iv) a $C_{6-19}$ aryl-$C_{1-4}$ alkyl group optionally substituted by substituent(s) selected from
(a) carboxy,
(b) $C_{1-4}$ alkoxy-carbonyl, and
(c) —CO—$NR^8$—$(CH_2)_n$—O—$C_{1-4}$ alkyl, wherein n is an integer of 1 to 4, and $R^8$ is a hydrogen atom or a $C_{1-4}$ alkyl group; and
$R^2$ and $R^{3'}$ are optionally bonded to form $C_{2-4}$ alkylene.
(H) A compound (I) wherein W is CH;
A is a $C_{6-18}$ aryl group optionally substituted by substituent(s) selected from
(a) carboxy,
(b) $C_{1-4}$ alkoxy-carbonyl,
(c) a 5- to 8-membered heterocycle-carbonyl group containing 1 to 3 hetero atoms selected from a nitrogen atom, an oxygen atom and a sulfur atom (preferably, a 5- to 8-membered cyclic amino-carbonyl group optionally having 1 or 2 hetero atoms selected from a nitrogen atom, an oxygen atom and a sulfur atom), which is optionally substituted by $C_{6-18}$ aryl-$C_{1-4}$ alkyl,
(d) a carbamoyl group optionally substituted by $C_{6-18}$ aryl-$C_{1-4}$ alkyl, and
(e) a ureido group optionally substituted by $C_{6-18}$ aryl-$C_{1-4}$ alkyl;
$X^1$ is —$NR^{3'}$— wherein $R^{3'}$ is a hydrogen atom or a $C_{1-6}$ alkyl group; and
$R^2$ is a hydrogen atom.
[compound (Ii)]
A compound (I) wherein A is a $C_{6-18}$ aryl group substituted by substituent(s) selected from
(i) a phenyloxy group substituted by 1 to 5 substituents selected from
(a) halogen,
(b) optionally halogenated $C_{1-4}$ alkyl,
(c) hydroxy-$C_{1-4}$ alkyl,
(d) heterocycle-$C_{1-4}$ alkyl (preferably, 5- to 8-membered heterocycle-$C_{1-4}$ alkyl, said 5- to 8-membered heterocycle has 1 to 3 hetero atoms selected from a nitrogen atom, an oxygen atom and an optionally oxidized sulfur atom, such as imidazolyl, triazolyl and the like),
(e) optionally halogenated $C_{1-4}$ alkyloxy,
(f) $C_{1-4}$ alkyl-carbonyl,
(g) cyano,
(h) carbamoyl optionally substituted by $C_{1-8}$ alkyl, and
(i) $C_{1-4}$ alkoxy-carbonyl,
(ii) a phenyl-$C_{1-3}$ alkyloxy group substituted by 1 to 5 substituents selected from
(a) halogen,
(b) optionally halogenated $C_{1-4}$ alkyl,
(c) hydroxy-$C_{1-4}$ alkyl,
(d) heterocycle-$C_{1-4}$ alkyl (preferably, 5- to 8-membered heterocycle-$C_{1-4}$ alkyl, said 5- to 8-membered heterocycle has 1 to 3 hetero atoms selected from a nitrogen atom, an oxygen atom and an optionally oxidized sulfur atom, such as imidazolyl, triazolyl and the like),
(e) optionally halogenated $C_{1-4}$ alkyloxy,
(f) $C_{1-4}$ alkyl-carbonyl,
(g) cyano,
(h) carbamoyl optionally substituted by $C_{1-8}$ alkyl, and
(i) $C_{1-4}$ alkoxy-carbonyl,
(iii) a 5- to 8-membered heterocyclooxy group containing 1 to 3 hetero atoms selected from a nitrogen atom, an oxygen atom and a sulfur atom, which is substituted by 1 to 5 substituents selected from
(a) halogen,
(b) optionally halogenated $C_{1-4}$ alkyl,
(c) hydroxy-$C_{1-4}$ alkyl,
(d) heterocycle-$C_{1-4}$ alkyl (preferably, 5- to 8-membered heterocycle-$C_{1-4}$ alkyl, said 5- to 8-membered heterocycle has 1 to 3 hetero atoms selected from a nitrogen atom, an oxygen atom and an optionally oxidized sulfur atom, such as imidazolyl, triazolyl and the like),
(e) optionally halogenated $C_{1-4}$ alkyloxy,
(f) $C_{1-4}$ alkyl-carbonyl,
(g) cyano,
(h) carbamoyl optionally substituted by $C_{1-8}$ alkyl, and
(i) $C_{1-4}$ alkoxy-carbonyl, and
(iv) 5- to 8-membered heterocycle-$C_{1-3}$ alkyloxy containing 1 to 3 hetero atoms selected from a nitrogen atom, an oxygen atom and a sulfur atom, which is substituted by 1 to 5 substituents selected from
(a) halogen,
(b) optionally halogenated $C_{1-4}$ alkyl,
(c) hydroxy-$C_{1-4}$ alkyl,
(d) heterocycle-$C_{1-4}$ alkyl (preferably, 5- to 8-membered heterocycle-$C_{1-4}$ alkyl, said 5- to 8-membered heterocycle has 1 to 3 hetero atoms selected from a nitrogen atom, an oxygen atom and an optionally oxidized sulfur atom, such as imidazolyl, triazolyl and the like),
(e) optionally halogenated $C_{1-4}$ alkyloxy,
(f) $C_{1-4}$ alkyl-carbonyl,
(g) cyano,
(h) carbamoyl optionally substituted by $C_{1-8}$ alkyl, and
(i) $C_{1-4}$ alkoxy-carbonyl;
wherein the $C_{6-18}$ aryl group is optionally further substituted by 1 to 4 substituents selected from halogen and optionally halogenated $C_{1-4}$ alkyl;
$R^1$ is a hydrogen atom;
$R^2$ is a $C_{1-8}$ alkyl group, a $C_{2-8}$ alkenyl group or a $C_{2-8}$ alkynyl group, each of which is substituted by substituent(s) selected from
(a) hydroxy,
(b) carboxy,
(c) cyano,
(d) optionally halogenated $C_{1-4}$ alkyloxy,
(e) —O—$(CH_2)_n$—OH,
(f) —O—$(CH_2)_n$—O—CO—$NH_2$,
(g) —O—$(CH_2)_n$—O-(optionally halogenated $C_{1-4}$ alkyl),
(h) —O—$(CH_2)_n$—$SO_2$-(optionally halogenated $C_{1-4}$ alkyl),
(i) —O—$(CH_2)_n$—$SO_2$—$C_{6-18}$ aryl,
(j) —O—$(CH_2)_n$—$SO_2$—$(CH_2)_n$—OH,
(k) —O—$(CH_2)_n$—$NR^8$—CO—$C_{1-4}$ alkyl,
(l) —O—$(CH_2)_n$—$NR^8$—CO—$(CH_2)_n$—$SO_2$—$C_{1-4}$ alkyl,
(m) —O—$(CH_2)_n$—$NR^8$—$SO_2$-(optionally halogenated $C_{1-4}$ alkyl),
(n) —CO—$NR^8$—$(CH_2)_n$—OH,
(o) —CO—$NR^8$—$(CH_2)_n$—$SO_2$-(optionally halogenated $C_{1-4}$ alkyl),
(p) —CO—$NR^8$—O—$C_{1-4}$ alkyl,
(q) —$NR^6R^7$,
(r) —$NR^8$—$(CH_2)_n$—OH,
(s) —$NR^8$—$(CH_2)_n$—$SO_2$—$C_{1-4}$ alkyl,
(t) —$NR^8$—CO-(optionally halogenated $C_{1-4}$ alkyl),
(u) —$NR^8$—CO—$(CH_2)_n$—OH,
(v) —$NR^8$—CO—$(CH_2)_n$—CN,
(w) —$NR^8$—CO—$(CH_2)_n$—$NR^6R^7$,
(x) —$NR^8$—CO—$(CH_2)_n$—O—$C_{1-4}$ alkyl,
(y) —$NR^8$—CO—$(CH_2)_n$—SO-(optionally halogenated $C_{1-4}$ alkyl),
(z) —$NR^8$—CO—$(CH_2)_n$—$SO_2$-(optionally halogenated $C_{1-4}$ alkyl),
(aa) —$NR^8$—CO—$(CH_2)_n$—$SO_2$—$C_{3-8}$ cycloalkyl,
(bb) —$NR^8$—CO—$(CH_2)_n$—$NR^8$—$SO_2$—$C_{1-4}$ alkyl,
(cc) —$NR^8$—$CO_2$—$(CH_2)_n$—$SO_2$—$C_{1-4}$ alkyl,
(dd) —$NR^8$—CO—NH—$(CH_2)_n$—$SO_2$—$C_{1-4}$ alkyl,
(ee) —$NR^8$—CO—NH—O—$C_{1-4}$ alkyl,
(ff) —$NR^8$—CO—NH—$(CH_2)_n$—O—$C_{1-4}$ alkyl,
(gg) —$NR^8$—C(=NH)—NH—$C_{1-4}$ alkyl,
(hh) —$NR^8$—$SO_2$—$(CH_2)_n$—$SO_2$—$C_{1-4}$ alkyl, (ii) —S—(CH$_2$)$_n$—OH,
(jj) —SO—(CH$_2$)$_n$—OH,
(kk) —SO$_2$—(CH$_2$)$_n$—OH, and
(ll) —NR$^8$—CO-(optionally substituted heterocyclic group) (preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, C$_{1-4}$ alkyl, optionally oxidized C$_{1-4}$ alkylthio, —CO—C$_{1-4}$ alkyl, —CO—O—C$_{1-4}$ alkyl, —CO—NH—C$_{1-4}$ alkyl, —CONH$_2$, —SO$_2$—C$_{1-4}$ alkyl, —SO$_2$—NH—C$_{1-4}$ alkyl, —SO$_2$NH$_2$ and the like), wherein n is an integer of 1 to 4, R$^6$ and R$^7$ are the same or different and each is a hydrogen atom or a C$_{1-4}$ alkyl group, R$^8$ is a hydrogen atom or a C$_{1-4}$ alkyl group, (CH$_2$)$_n$ is optionally substituted by optionally halogenated C$_{1-4}$ alkyl or hydroxy, and when n is not less than 2, a subset —CH$_2$CH$_2$— of (CH$_2$)$_n$ is optionally replaced by —CH=CH—;

R$^3$ is a hydrogen atom or a C$_{1-6}$ alkyl group; or
R$^1$ and R$^2$ are optionally bonded to form

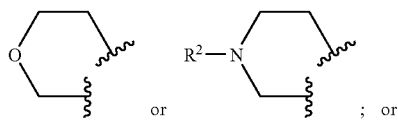

R$^2$ and R$^3$ are optionally bonded to form C$_{2-4}$ alkylene optionally substituted by an imino group, particularly preferably, R$^2$ is a C$_{1-8}$ alkyl group, a C$_{2-8}$ alkenyl group or a C$_{2-8}$ alkynyl group (particularly, C$_{1-8}$ alkyl group), each of which is optionally substituted by substituent(s) selected from
(a) hydroxy,
(b) carboxy,
(c) cyano,
(d) optionally halogenated C$_{1-4}$ alkyloxy,
(e) —O—(CH$_2$)$_n$—OH (wherein (CH$_2$)$_n$ is optionally substituted by hydroxy),
(f) —O—(CH$_2$)$_n$—O—CO—NH$_2$,
(g) —O—(CH$_2$)$_n$—O-(optionally halogenated C$_{1-4}$ alkyl),
(h) —O—(CH$_2$)$_n$—SO$_2$-(optionally halogenated C$_{1-4}$ alkyl),
(i) —O—(CH$_2$)$_n$—SO$_2$—C$_{6-18}$ aryl,
(j) —O—(CH$_2$)$_n$—SO$_2$—(CH$_2$)$_n$—OH,
(k) —O—(CH$_2$)$_n$—NR$^8$—CO—C$_{1-4}$ alkyl,
(l) —O—(CH$_2$)$_n$—NR$^8$—CO—(CH$_2$)$_n$—SO$_2$—C$_{1-4}$ alkyl,
(m) —O—(CH$_2$)$_n$—NR$^8$—SO$_2$-(optionally halogenated C$_{1-4}$ alkyl),
(n) —CO—NR$^8$—(CH$_2$)$_n$—OH,
(o) —CO—NR$^8$—(CH$_2$)$_n$—SO$_2$-(optionally halogenated C$_{1-4}$ alkyl),
(p) —CO—NR$^8$—O—C$_{1-4}$ alkyl,
(q) —NR$^6$R$^7$,
(r) —NR$^8$—(CH$_2$)$_n$—OH,
(s) —NR$^8$—(CH$_2$)$_n$—SO$_2$—C$_{1-4}$ alkyl,
(t) —NR$^8$—CO-(optionally halogenated C$_{1-4}$ alkyl),
(u) —NR$^8$—CO—(CH$_2$)$_n$—OH (wherein (CH$_2$)$_n$ is optionally substituted by optionally halogenated C$_{1-4}$ alkyl or hydroxy),
(v) —NR$^8$—CO—(CH$_2$)$_n$—CN,
(w) —NR$^8$—CO—(CH$_2$)$_n$—NR$^6$R$^7$ (when n is not less than 2, a subset —CH$_2$CH$_2$— of (CH$_2$)$_n$ is optionally replaced by —CH=CH—),
(x) —NR$^8$—CO—(CH$_2$)$_n$—O—C$_{1-4}$ alkyl,
(y) —NR$^8$—CO—(CH$_2$)$_n$—SO-(optionally halogenated C$_{1-4}$ alkyl),
(z) —NR$^8$—CO—(CH$_2$)$_n$—SO$_2$-(optionally halogenated C$_{1-4}$ alkyl) (wherein (CH$_2$)$_n$ is optionally substituted by C$_{1-4}$ alkyl),
(aa) —NR$^8$—CO—(CH$_2$)$_n$—SO$_2$—C$_{3-8}$ cycloalkyl,
(bb) —NR$^8$—CO—(CH$_2$)$_n$—NR$^8$—SO$_2$—C$_{1-4}$ alkyl,
(cc) —NR$^8$—CO$_2$—(CH$_2$)$_n$—SO$_2$—C$_{1-4}$ alkyl,
(dd) —NR$^8$—CO—NH—(CH$_2$)$_n$—SO$_2$—C$_{1-4}$ alkyl,
(ee) —NR$^8$—CO—NH—O—C$_{1-4}$ alkyl,
(ff) —NR$^8$—CO—NH—(CH$_2$)$_n$—O—C$_{1-4}$ alkyl,
(gg) —NR$^8$—C(=NH)—NH—C$_{1-4}$ alkyl,
(hh) —NR$^8$—SO$_2$—(CH$_2$)$_n$—SO$_2$—C$_{1-4}$ alkyl,
(ii) —S—(CH$_2$)$_n$—OH,
(jj) —SO—(CH$_2$)$_n$—OH,
(kk) —SO$_2$—(CH$_2$)$_n$—OH, and
(ll) —NR$^8$—CO-(optionally substituted heterocyclic group) (preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, C$_{1-4}$ alkyl, optionally oxidized C$_{1-4}$ alkylthio, —CO—C$_{1-4}$ alkyl, —CO—O—C$_{1-4}$ alkyl, —CO—NH—C$_{1-4}$ alkyl, —CONH$_2$, —SO$_2$—C$_{1-4}$ alkyl, —SO$_2$—NH—C$_{1-4}$ alkyl, —SO$_2$NH$_2$ and the like), wherein n is an integer of 1 to 4, R$^6$ and R$^7$ are the same or different and each is a hydrogen atom or a C$_{1-4}$ alkyl group, and R$^8$ is a hydrogen atom or a C$_{1-4}$ alkyl group.

[compound (Ij)]
A compound (I) wherein
A is a C$_{6-18}$ aryl group substituted by substituent(s) selected from
(i) a phenyloxy group substituted by 1 to 5 substituents selected from
(a) halogen,
(b) optionally halogenated C$_{1-4}$ alkyl,
(c) hydroxy-C$_{1-4}$ alkyl,
(d) heterocycle-C$_{1-4}$ alkyl (preferably, 5- to 8-membered heterocycle-C$_{1-4}$ alkyl, said 5- to 8-membered heterocycle has 1 to 3 hetero atoms selected from a nitrogen atom, an oxygen atom and an optionally oxidized sulfur atom, such as imidazolyl and the like),
(e) optionally halogenated C$_{1-4}$ alkyloxy,
(f) cyano,
(g) carbamoyl optionally substituted by C$_{1-8}$ alkyl, and
(h) C$_{1-4}$ alkoxy-carbonyl,
(ii) a phenyl-C$_{1-3}$ alkyloxy group substituted by 1 to 5 substituents selected from
(a) halogen,
(b) optionally halogenated C$_{1-4}$ alkyl,
(c) hydroxy-C$_{1-4}$ alkyl,
(d) heterocycle-C$_{1-4}$ alkyl (preferably, 5- to 8-membered heterocycle-C$_{1-4}$ alkyl, said 5- to 8-membered heterocycle has 1 to 3 hetero atoms selected from a nitrogen atom, an oxygen atom and an optionally oxidized sulfur atom, such as imidazolyl and the like),
(e) optionally halogenated C$_{1-4}$ alkyloxy,
(f) cyano,
(g) carbamoyl optionally substituted by C$_{1-8}$ alkyl, and
(h) C$_{1-4}$ alkoxy-carbonyl,
(iii) a 5- to 8-membered heterocyclooxy group containing 1 to 3 hetero atoms selected from a nitrogen atom, an oxygen atom and a sulfur atom, which is substituted by 1 to 5 substituents selected from
(a) halogen,
(b) optionally halogenated C$_{1-4}$ alkyl, (c) hydroxy-$C_{1-4}$ alkyl,
(d) heterocycle-$C_{1-4}$ alkyl (preferably, 5- to 8-membered heterocycle-$C_{1-4}$ alkyl, said 5- to 8-membered heterocycle has 1 to 3 hetero atoms selected from a nitrogen atom, an oxygen atom and an optionally oxidized sulfur atom, such as imidazolyl and the like),
(e) optionally halogenated $C_{1-4}$ alkyloxy,
(f) cyano,
(g) carbamoyl optionally substituted by $C_{1-8}$ alkyl, and
(h) $C_{1-4}$ alkoxy-carbonyl, and
(iv) 5- to 8-membered heterocycle-$C_{1-3}$ alkyloxy containing 1 to 3 hetero atoms selected from a nitrogen atom, an oxygen atom and a sulfur atom, which is substituted by 1 to 5 substituents selected from
(a) halogen,
(b) optionally halogenated $C_{1-4}$ alkyl,
(c) hydroxy-$C_{1-4}$ alkyl,
(d) heterocycle-$C_{1-4}$ alkyl (preferably, 5- to 8-membered heterocycle-$C_{1-4}$ alkyl having 1 to 3 hetero atoms selected from a nitrogen atom, an oxygen atom and an optionally oxidized sulfur atom, such as imidazolyl and the like),
(e) optionally halogenated $C_{1-4}$ alkyloxy,
(f) cyano,
(g) carbamoyl optionally substituted by $C_{1-8}$ alkyl, and
(h) $C_{1-4}$ alkoxy-carbonyl;
wherein the $C_{6-18}$ aryl group is optionally further substituted by 1 to 4 substituents selected from halogen and optionally halogenated $C_{1-4}$ alkyl;
$R^1$ is a hydrogen atom;
$R^2$ is a $C_{1-8}$ alkyl group, a $C_{2-8}$ alkenyl group or a $C_{2-8}$ alkynyl group, each of which is substituted by substituent(s) selected from
(a) hydroxy,
(b) optionally halogenated $C_{1-4}$ alkyloxy,
(c) —O—$(CH_2)_n$—OH,
(d) —O—$(CH_2)_n$—O—CO—$NH_2$,
(e) —O—$(CH_2)_n$—O—$C_{1-4}$ alkyl,
(f) —O—$(CH_2)_n$—$SO_2$-(optionally halogenated $C_{1-4}$ alkyl),
(g) —O—$(CH_2)_n$—$SO_2$—$C_{6-18}$ aryl,
(h) —O—$(CH_2)_n$—$SO_2$—$(CH_2)_n$—OH,
(i) —O—$(CH_2)_n$—$NR^8$—$SO_2$-(optionally halogenated $C_{1-4}$ alkyl),
(j) —CO—$NR^8$—$(CH_2)_n$—OH,
(k) —CO—$NR^8$—$(CH_2)_n$—$SO_2$-(optionally halogenated $C_{1-4}$ alkyl),
(l) —$NR^6R^7$,
(m) —$NR^8$—$(CH_2)_n$—OH,
(n) —$NR^8$—$(CH_2)_n$—$SO_2$—$C_{1-4}$ alkyl,
(o) —$NR^8$—CO—$(CH_2)_n$—OH,
(p) —$NR^8$—CO—$(CH_2)_n$—O—$C_{1-4}$ alkyl,
(q) —$NR^8$—CO—$(CH_2)_n$—SO-(optionally halogenated $C_{1-4}$ alkyl),
(r) —$NR^8$—CO—$(CH_2)_n$—$SO_2$-(optionally halogenated $C_{1-4}$ alkyl),
(s) —$NR^8$—CO—$(CH_2)_n$—$SO_2$—$C_{3-8}$ cycloalkyl,
(t) —$NR^8$—$CO_2$—$(CH_2)_n$—$SO_2$—$C_{1-4}$ alkyl,
(u) —$NR^8$—CO—NH—$(CH_2)_n$—$SO_2$—$C_{1-4}$ alkyl,
(v) —$NR^8$—$SO_2$—$(CH_2)_n$—$SO_2$—$C_{1-4}$ alkyl,
(w) —S—$(CH_2)_n$—OH,
(x) —SO—$(CH_2)_n$—OH,
(y) —$SO_2$—$(CH_2)_n$—OH, and
(z) —$NR^8$—CO-(optionally substituted heterocyclic group) (preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—NH—$C_{1-4}$ alkyl, —$CONH_2$, —$SO_2$—$C_{1-4}$ alkyl, —$SO_2$—NH—$C_{1-4}$ alkyl, —$SO_2NH_2$ and the like),
wherein n is an integer of 1 to 4, $R^6$ and $R^7$ are the same or different and each is a hydrogen atom or a $C_{1-4}$ alkyl group, $R^8$ is a hydrogen atom or a $C_{1-4}$ alkyl group, and $(CH_2)_n$ is optionally substituted by $C_{1-4}$ alkyl or hydroxy;
$R^3$ is a hydrogen atom or a $C_{1-6}$ alkyl group; or
$R^1$ and $R^2$ are optionally bonded to form or ; or $R^2$ and $R^3$ are optionally bonded to form $C_{2-4}$ alkylene.
Particularly preferably, $R^2$ is a $C_{1-8}$ alkyl group, a $C_{2-8}$ alkenyl group or a $C_{2-8}$ alkynyl group (particularly, a $C_{1-8}$ alkyl group), each of which is substituted by substituent(s) selected from
(a) hydroxy,
(b) optionally halogenated $C_{1-4}$ alkyloxy,
(c) —O—$(CH_2)_n$—OH (wherein $(CH_2)_n$ is optionally substituted by hydroxy),
(d) —O—$(CH_2)_n$—O—CO—$NH_2$,
(e) —O—$(CH_2)_n$—O—$C_{1-4}$ alkyl,
(f) —O—$(CH_2)_n$—$SO_2$-(optionally halogenated $C_{1-4}$ alkyl),
(g) —O—$(CH_2)_n$—$SO_2$—$C_{6-18}$ aryl,
(h) —O—$(CH_2)_n$—$SO_2$—$(CH_2)_n$—OH,
(i) —O—$(CH_2)_n$—$NR^8$—$SO_2$-(optionally halogenated $C_{1-4}$ alkyl),
(j) —CO—$NR^8$—$(CH_2)_n$—OH,
(k) —CO—$NR^8$—$(CH_2)_n$—$SO_2$-(optionally halogenated $C_{1-4}$ alkyl),
(l) —$NR^6R^7$,
(m) —$NR^8$—$(CH_2)_n$—OH,
(n) —$NR^8$—$(CH_2)_n$—$SO_2$—$C_{1-4}$ alkyl,
(o) —$NR^8$—CO—$(CH_2)_n$—OH (wherein $(CH_2)_n$ is optionally substituted by $C_{1-4}$ alkyl),
(p) —$NR^8$—CO—$(CH_2)_n$—O—$C_{1-4}$ alkyl,
(q) —$NR^8$—CO—$(CH_2)_n$—SO-(optionally halogenated $C_{1-4}$ alkyl),
(r) —$NR^8$—CO—$(CH_2)_n$—$SO_2$-(optionally halogenated $C_{1-4}$ alkyl) (wherein $(CH_2)_n$ is optionally substituted by $C_{1-4}$ alkyl),
(s) —$NR^8$—CO—$(CH_2)_n$—$SO_2$—$C_{3-8}$ cycloalkyl,
(t) —$NR^8$—$CO_2$—$(CH_2)_n$—$SO_2$—$C_{1-4}$ alkyl,
(u) —$NR^8$—CO—NH—$(CH_2)_n$—$SO_2$—$C_{1-4}$ alkyl,
(v) —$NR^8$—$SO_2$—$(CH_2)_n$—$SO_2$—$C_{1-4}$ alkyl,
(w) —S—$(CH_2)_n$—OH,
(x) —SO—$(CH_2)_n$—OH,
(y) —$SO_2$—$(CH_2)_n$—OH, and
(z) —$NR^8$—CO-(optionally substituted heterocyclic group) (preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—NH—$C_{1-4}$ alkyl, —$CONH_2$, —$SO_2$—$C_{1-4}$ alkyl, —$SO_2$—NH—$C_{1-4}$ alkyl, —$SO_2NH_2$ and the like),
wherein n is an integer of 1 to 4, $R^6$ and $R^7$ are the same or different and each is a hydrogen atom or a $C_{1-4}$ alkyl group, and $R^8$ is a hydrogen atom or a $C_{1-4}$ alkyl group, and the like is preferable.

[compound (Ik)]

A compound (I) wherein $R^2$ is (i) a $C_{5-8}$ alkyl group substituted by hydroxy, (ii) a $C_{1-8}$ alkyl group substituted by substituent(s) selected from (a) halogenated $C_{1-4}$ alkyloxy,
(b) —O—$(CH_2)_n$—OH,
(c) —O—$(CH_2)_n$—O—CO—$NH_2$,
(d) —O—$(CH_2)_n$—O-(optionally halogenated $C_{1-4}$ alkyl),
(e) —O—$(CH_2)_n$—$SO_2$-(optionally halogenated $C_{1-4}$ alkyl),
(f) —O—$(CH_2)_n$—$SO_2$—$C_{6-18}$ aryl,
(g) —O—$(CH_2)_n$—$NR^8$—$SO_2$-(optionally halogenated $C_{1-4}$ alkyl),
(h) —CO—$NR^8$—$(CH_2)_n$—OH,
(i) —CO—$NR^8$—$(CH_2)$, —$SO_2$-(optionally halogenated $C_{1-4}$ alkyl),
(j) —$NR^8$—$(CH_2)_n$—$SO_2$—$C_{1-4}$ alkyl,
(k) —$NR^8$—CO—$(CH_2)_n$—OH,
(l) —$NR^8$—CO—$(CH_2)_n$—O—$C_{1-4}$ alkyl,
(m) —$NR^8$—CO—$(CH_2)_n$—SO-(optionally halogenated $C_{1-4}$ alkyl),
(n) —$NR^8$—CO—$(CH_2)_n$—$SO_2$-(optionally halogenated $C_{1-4}$ alkyl),
(o) —$NR^8$—CO—$(CH_2)_n$—$SO_2$—$C_{3-8}$ cycloalkyl,
(p) —$NR^8$—$CO_2$—$(CH_2)_n$—$SO_2$—$C_{1-4}$ alkyl,
(q) —$NR^8$—CO—NH—$(CH_2)_n$—$SO_2$—$C_{1-4}$ alkyl,
(r) —$NR^8$—$SO_2$—$(CH_2)_n$—$SO_2$—$C_{1-4}$ alkyl,
(s) —S—$(CH_2)_n$—OH,
(t) —SO—$(CH_2)_n$—OH,
(u) —$SO_2$—$(CH_2)_n$—OH, and
(v) —$NR^8$—CO-(optionally substituted heterocyclic group) (preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—NH—$C_{1-4}$ alkyl, —$CONH_2$, —$SO_2$—$C_{1-4}$ alkyl, —$SO_2$—NH—$C_{1-4}$ alkyl, —$SO_2NH_2$ and the like), wherein n is an integer of 1 to 4, $R^8$ is a hydrogen atom or a $C_{1-4}$ alkyl group, and $(CH_2)_n$ is optionally substituted by $C_{1-4}$ alkyl, (iii) a $C_{2-8}$ alkenyl group optionally substituted by hydroxy, or
(iv) a $C_{2-8}$ alkynyl group optionally substituted by hydroxy.

Particularly preferably, $R^2$ is (i) a $C_{5-8}$ alkyl group substituted by hydroxy, (ii) a $C_{1-8}$ alkyl group substituted by substituent(s) selected from (a) halogenated $C_{1-4}$ alkyloxy,
(b) —O—$(CH_2)_n$—OH (wherein $(CH_2)_n$ is optionally substituted by hydroxy),
(c) —O—$(CH_2)_n$—O—CO—$NH_2$,
(d) —O—$(CH_2)_n$—O-(optionally halogenated $C_{1-4}$ alkyl),
(e) —O—$(CH_2)_n$—$SO_2$-(optionally halogenated $C_{1-4}$ alkyl),
(f) —O—$(CH_2)_n$—$SO_2$—$C_{6-18}$ aryl,
(g) —O—$(CH_2)_n$—$NR^8$—$SO_2$-(optionally halogenated $C_{1-4}$ alkyl),
(h) —CO—$NR^8$—$(CH_2)_n$—OH,
(i) —CO—$NR^8$—$(CH_2)_n$—$SO_2$-(optionally halogenated $C_{1-4}$ alkyl),
(j) —$NR^8$—$(CH_2)_n$—$SO_2$—$C_{1-4}$ alkyl,
(k) —$NR^8$—CO—$(CH_2)_n$—OH (wherein $(CH_2)_n$ is optionally substituted by $C_{1-4}$ alkyl),
(l) —$NR^8$—CO—$(CH_2)_n$—O—$C_{1-4}$ alkyl,
(m) —$NR^8$—CO—$(CH_2)_n$—SO-(optionally halogenated $C_{1-4}$ alkyl),
(n) —$NR^8$—CO—$(CH_2)_n$—$SO_2$-(optionally halogenated $C_{1-4}$ alkyl) (wherein $(CH_2)_n$ is optionally substituted by $C_{1-4}$ alkyl),
(o) —$NR^8$—CO—$(CH_2)_n$—$SO_2$—$C_{3-8}$ cycloalkyl,
(p) —$NR^8$—$CO_2$—$(CH_2)_n$—$SO_2$—$C_{1-4}$ alkyl,
(q) —$NR^8$—CO—NH—$(CH_2)_n$—$SO_2$—$C_{1-4}$ alkyl,
(r) —$NR^8$—$SO_2$—$(CH_2)_n$—$SO_2$—$C_{1-4}$ alkyl,
(s) —S—$(CH_2)_n$—OH,
(t) —SO—$(CH_2)_n$—OH,
(u) —$SO_2$—$(CH_2)_n$—OH A and
(v) —$NR^8$—CO-(optionally substituted heterocyclic group) (preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—NH—$C_{1-4}$ alkyl, —$CONH_2$, —$SO_2$—$C_{1-4}$ alkyl, —$SO_2$—NH—$C_{1-4}$ alkyl, —$SO_2NH_2$ and the like), wherein n is an integer of 1 to 4, and $R^8$ is a hydrogen atom or a $C_{1-4}$ alkyl group, (iii) a $C_{2-8}$ alkenyl group optionally substituted by hydroxy, or
(iv) a $C_{2-8}$ alkynyl group optionally substituted by hydroxy.

As the salts of the compound represented by the formula (I), for example, metal salt, ammonium salt, salts with organic base, salts with inorganic acid, salts with organic acid, salts with basic or acidic amino acid and the like can be mentioned. As preferable examples of the metal salt, for example, alkali metal salts such as sodium salt, potassium salt and the like; alkaline earth metal salts such as calcium salt, magnesium salt, barium salt and the like; aluminum salt and the like can be mentioned. As preferable examples of the salts with organic base, for example, salts with trimethylamine, triethylamine, pyridine, picoline, 2,6-lutidine, ethanolamine, diethanolamine, triethanolamine, tromethamine [tris(hydroxymethyl)methylamine], t-butylamine, cyclohexylamine, dicyclohexylamine, N,N'-dibenzylethylenediamine and the like can be mentioned. As preferable examples of salts with inorganic acid, for example, salts with hydrochloric acid, hydrobromic acid, nitric acid, sulfuric acid, phosphoric acid and the like can be mentioned. As preferable examples of the salts with organic acid, for example, salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like can be mentioned. As preferable examples of the salts with basic amino acid, for example, salts with arginine, lysine, ornithine and the like can be mentioned, and as preferable examples of the salts with acidic amino acid, for example, salts with aspartic acid, glutamic acid and the like can be mentioned.

Of these, pharmaceutically acceptable salts are preferable. For example, when a compound contains an acidic functional group, inorganic salts such as alkali metal salts (e.g., sodium salt, potassium salt etc.), alkaline earth metal salts (e.g., calcium salt, magnesium salt, barium salt etc.) and the like, ammonium salt and the like, and when a compound contains a basic functional group, for example, salts with inorganic acid such as hydrochloric acid, hydrobromic acid, nitric acid, sulfuric acid, phosphoric acid and the like, or salts with organic acid such as acetic acid, phthalic acid, fumaric acid, oxalic acid, tartaric acid, maleic acid, citric acid, succinic acid, methanesulfonic acid, p-toluenesulfonic acid and the like can be mentioned.

As compound (I), preferred is a compound wherein A is an aryl group substituted by a group of the formula —$Y^2$—B and optionally further substituted, wherein $Y^2$ is a single bond, —O—, —OCH$_2$—, —NH— or —S—, and B is an aryl group, a heterocyclic group, a C$_{3-8}$ cycloalkyl group, a carbamoyl group, a ureido group, a C$_{6-18}$ aryl-carbonyl group or a C$_{6-18}$ aryl-C$_{1-4}$ alkyl-carbonyl group, each of which is optionally substituted.

As a preferable embodiment of compound (I), a compound wherein W is C(R$^1$);

A is an aryl group substituted by a group of the formula —Y$^2$—B, and optionally further substituted, wherein Y$^2$ is a single bond, —O—, —OCH$_2$—, —NH— or —S—, and B is an aryl group, a heterocyclic group, a C$_{3-8}$ cycloalkyl group, a carbamoyl group, a ureido group, a C$_{6-18}$ aryl-carbonyl group or a C$_{6-18}$ aryl-C$_{1-4}$ alkyl-carbonyl group, each of which is optionally substituted;

R$^1$ is a group of the formula —X$^2$—R$^4$ wherein X$^2$ is a single bond, —NH— or —O—, and R$^4$ is hydrogen atom or a C$_{1-8}$ alkyl group, a C$_{2-8}$ alkenyl group, a C$_{2-8}$ alkynyl group, a carbamoyl group, a C$_{1-8}$ alkyl-carbonyl group, a C$_{3-8}$ cycloalkyl group, a C$_{6-18}$ aryl group, a C$_{6-18}$ aryl-C$_{1-4}$ alkyl group, a C$_{6-18}$ aryl-carbonyl group, a C$_{6-18}$ aryl-C$_{1-4}$ alkyl-carbonyl group, a heterocyclic group, a heterocycle-C$_{1-4}$ alkyl group, a heterocycle-carbonyl group or a heterocycle-C$_{1-4}$ alkyl-carbonyl group, each of which is optionally substituted;

R$^2$ is hydrogen atom or a C$_{1-8}$ alkyl group, a C$_{2-8}$ alkenyl group, a C$_{2-8}$ alkynyl group, a carbamoyl group, a C$_{1-8}$ alkyl-carbonyl group, a C$_{1-8}$ alkylsulfonyl group, a C$_{3-8}$ cycloalkyl group, a C$_{6-18}$ aryl group, a C$_{6-18}$ aryl-C$_{1-4}$ alkyl group, a C$_{6-18}$ aryl-carbonyl group, a C$_{6-18}$ aryl-C$_{1-4}$ alkyl-carbonyl group, a C$_{6-18}$ aryl-sulfonyl group, a heterocyclic group, a heterocycle-C$_{1-4}$ alkyl group, a heterocycle-carbonyl group or a heterocycle-C$_{1-4}$ alkyl-carbonyl group, each of which is optionally substituted; and X$^1$ is —NR$^3$— wherein R$^3$ is a hydrogen atom or an optionally substituted aliphatic hydrocarbon group can be mentioned.

As another preferable embodiment of compound (I), a compound wherein W is N;

X$^1$ is —NR$^3$— wherein R$^3$ is a hydrogen atom or an optionally substituted aliphatic hydrocarbon group;

A is an aryl group substituted by a group of the formula —Y$^2$—B and optionally further substituted wherein Y$^2$ is a single bond, —O—, —OCH$_2$—, —NH— or —S—, and B is an aryl group, a heterocyclic group, a C$_{3-8}$ cycloalkyl group, a carbamoyl group, a ureido group, a C$_{6-18}$ aryl-carbonyl group or a C$_{6-18}$ aryl-C$_{1-4}$ alkyl-carbonyl group, each of which is optionally substituted; and R$^2$ is a hydrogen atom or a C$_{1-8}$ alkyl group, a C$_{2-8}$ alkenyl group, a C$_{2-8}$ alkynyl group, a carbamoyl group, a C$_{1-8}$ alkyl-carbonyl group, a C$_{1-8}$ alkylsulfonyl group, a C$_{3-8}$ cycloalkyl group, a C$_{6-18}$ aryl group, a C$_{6-18}$ aryl-C$_{1-4}$ alkyl group, a C$_{6-18}$ aryl-carbonyl group, a C$_{6-18}$ aryl-C$_{1-4}$ alkyl-carbonyl group, a C$_{6-18}$ aryl-sulfonyl group, a heterocyclic group, a heterocycle-C$_{1-4}$ alkyl group, a heterocycle-carbonyl group or a heterocycle-C$_{1-4}$ alkyl-carbonyl group, each of which is optionally substituted can be mentioned.

As a yet another preferable embodiment of compound (I), a compound wherein W is N;

X$^1$ is —NR$^3$—;

A is an aryl group substituted by a group of the formula —Y$^2$—B and optionally further substituted wherein Y$^2$ is a single bond, —O—, —OCH$_2$—, —NH— or —S—, and B is an aryl group, a heterocyclic group, a C$_{3-8}$ cycloalkyl group, a carbamoyl group, a ureido group, a C$_{6-18}$ aryl-carbonyl group or a C$_{6-18}$ aryl-C$_{1-4}$ alkyl-carbonyl group, each of which is optionally substituted; and R$^2$ and R$^3$ are bonded to form an optionally substituted ring structure can be mentioned.

[Production Methods]

The production methods of compound (I) of the present invention are described in the following.

The compound (I) of the present invention the present invention can be obtained by, for example, the method shown by in the following schemes or a method analogous thereto and the like.

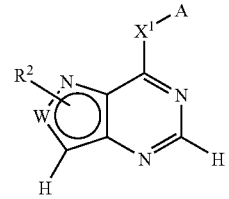
(I)

The compounds (II)-(VIII) in the schemes include salts, and as such salts, for example, those similar to the salts of compound (I) and the like can be used.

The compound obtained in each step can be used as a reaction mixture or as a crude product in the next reaction. In addition, the compound can be isolated from a reaction mixture according to a conventional method, and can be easily purified by a separation means such as recrystallization, distillation, chromatography and the like.

A schematic reaction formulas are shown in the following, wherein each symbol of the compounds is as defined above.

The compound (I) of the present invention can be produced by, for example, reacting a compound represented by the formula:

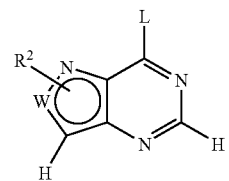
(II)

wherein L is a leaving group and other symbols are as defined above, or a salt thereof with a compound represented by the formula:

G-X$^1$-A    (III)

wherein G is a hydrogen atom or a metal atom, and other symbols are as defined above, or a salt thereof.

When X$^1$ is —NR$^3$—Y$^1$—, —O— or —S—, G is mainly a hydrogen atom, but may be an alkali metal such as lithium, sodium, potassium, cesium and the like, or an alkaline earth metal such as magnesium, calcium and the like. When X$^1$ is —CHR$^3$—, G is preferably a metal such as lithium, halogenated magnesium, copper, zinc and the like.

The compound (III) or a salt thereof is preferably used in an amount of 1-5 equivalents, preferably 1-2 equivalents, relative to compound (II) and the reaction is preferably carried out in a solvent. In addition, a base or an ammonium salt may be used in an amount of about 1-10 equivalents, preferably 1-2 equivalents.

In the aforementioned formula, as a leaving group represented by L, a halogen atom such as chlorine, bromine, iodine and the like, a group of the formula: —S(O)$_k$R$^a$ wherein k is 0, 1 or 2, and $R^a$ is a lower ($C_{1-4}$)alkyl group such as methyl, ethyl, propyl and the like, benzyl group, a $C_{6-10}$ aryl group such as, phenyl, tolyl and the like, or a group of the formula: —$OR^a$ wherein $R^a$ is as defined above, and the like can be used.

As a solvent in the aforementioned reaction, for example, halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, t-butanol, phenol and the like, ethers such as diethyl ether, tetrahydrofuran, dioxane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

As a base in the aforementioned reaction, an inorganic base, an organic base and the like can be used. Specifically, for example, sodium hydroxide, potassium hydroxide, sodium carbonate, potassium carbonate, sodium hydrogen carbonate, potassium hydrogen carbonate, triethylamine, N-ethyldiisopropylamine, pyridine, N,N-dimethylaminopyridine, sodium methoxide, sodium ethoxide, potassium t-butoxide, sodium hydride, sodium amide, diazabicycloundecene (DBU) and the like can be used.

As an ammonium salt in the aforementioned reaction, pyridine hydrochloride, pyridine hydrobromide, pyridine p-toluenesulfonate, quinoline hydrochloride, isoquinoline hydrochloride, pyrimidine hydrochloride, pyrazine hydrochloride, triazine hydrochloride, trimethylamine hydrochloride, triethylamine hydrochloride, N-ethyldiisopropylamine hydrochloride and the like can be used.

The aforementioned reaction can be carried under cooling, at room temperature or under heating (about 40-200° C., preferably about 40-160° C.), the reaction time is generally about 1-30 hr, preferably about 1-20 hr, more preferably about 1-10 hr.

A compound (I) wherein $X^1$ is —SO— or —$SO_2$— can be produced by subjecting a compound (I) wherein $X^1$ is —S— to an oxidation reaction. As an oxidizing agent therefor, for example, m-chloroperbenzoic acid, hydrogen peroxide, peracetic acid, t-butyl hydroperoxide, potassium peroxysulfate, potassium permanganate, sodium perborate, sodium periodate, sodium hypochlorite, halogen and the like can be used. When a compound (I) wherein $X^1$ is —SO— is produced, an oxidizing agent is used in an amount of about 1-1.5 equivalents relative to a starting compound, and when a compound (I) wherein $X^1$ is —$SO_2$— is produced, it is used in an amount of about 2-3 equivalents relative to a starting compound. The reaction solvent is not particularly limited as long as it does not react with the oxidizing agent and, for example, halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, t-butanol and the like, ethers such as diethyl ether, tetrahydrofuran, dioxane and the like, carboxylic acids such as acetic acid, trifluoroacetic acid and the like, acetonitrile, ethyl acetate, N,N-dimethylformamide, N,N-dimethylacetamide, 1-methyl-2-pyrrolidone, dimethyl sulfoxide, water or a mixed solvent thereof and the like can be used. The reaction is carried out under cooling, at room temperature or under heating, and the reaction time is generally about 1-20 hr, preferably about 1-10 hr.

A compound within the scope of the present invention can be also produced by applying means known per se to the obtained compound of the present invention (I) for introduction of substituents and conversion of functional groups. For conversion of substituents, a known conventional method can be used. For example, conversion to carboxy group by hydrolysis of ester, conversion to carbamoyl group by amidation of carboxy group, conversion to hydroxymethyl group by reduction of carboxy group, conversion to alcohol compound by reduction or alkylation of carbonyl group, reductive amination of carbonyl group, oximation of carbonyl group, acylation of amino group, alkylation of amino group, substitution and amination of active halogen by amine, alkylation of hydroxy group, substitution and amination of hydroxy group and the like can be mentioned. When a reactive substituent that causes non-object reaction is present during the introduction of substituents and conversion of functional groups, a protecting group is introduced in advance as necessary into the reactive substituent by a means known per se, and the protecting group is removed by a means known per se after the object reaction, whereby the compound within the scope of the present invention can be also produced.

The compound (I), which is a product of the reaction, may be produced as a single compound or as a mixture.

The compound (I) of the present invention thus obtained can be subjected to a means known per se, such as solvent extraction, concentration, neutralization, filtration, crystallization, recrystallization, column chromatography, high performance liquid chromatography and the like, whereby the object compound can be isolated and purified at high purity from a reaction mixture.

As the starting compound (III) of this production method, a commercially available one is used or can be produced by a means known per se.

The starting compound (II) of this production method can be produced by, for example, a method shown by the following scheme. Here, compounds (IIa), (IIb), (IIc), (IId) and (IIe) are encompassed in compound (II).

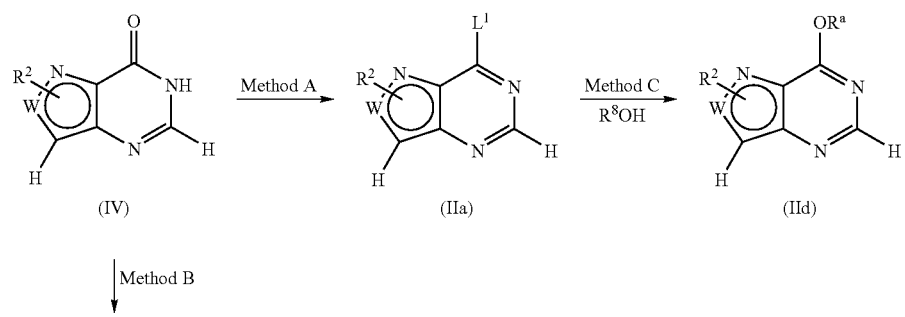

-continued

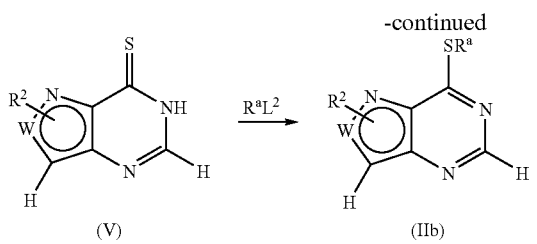 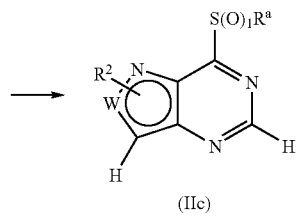

wherein L¹ and L² are halogen atoms, $R^a$ is as defined above and t is 1 or 2.

As Method A, compound (IIa) can be produced by reacting compound (IV) with a halogenating agent. As Method B, compound (1V) is reacted with an thionating agent to give compound (V), which is then reacted with a compound represented by $R^aL^2$ in the presence of a base to give compound (IIb), which is further subjected to an oxidation reaction to give compound (IIc). As Method C, compound (IIa) is reacted with a compound represented by $R^aOH$ in the presence of a base to give compound (IId).

As the halogenating agent in Method A, for example, about 1-100 equivalents of phosphorus oxychloride, phosphorus pentachloride, phosphorus trichloride, thionyl chloride, sulfuryl chloride, phosphorus tribromide and the like can be used. In this case, the reaction may be carried out in the presence of a base such as diethylaniline, dimethylaniline, pyridine and the like. While the reaction may be carried out without solvent, as a reaction solvent, for example, halogenated hydrocarbons such as dichloromethane, chloroform, carbon tetrachloride, 1,2-dichloroethane and the like, aromatic hydrocarbons such as benzene, toluene, xylene and the like, ethers such as diethyl ether, tetrahydrofuran, dioxane and the like, acetonitrile, ethyl acetate and the like may be used. The reaction is carried out under cooling, at room temperature or under heating, and the reaction time is generally about 1-20 hr, preferably about 1-10 hr.

As the thionating agent used in the production step from compound (IV) to compound (V) in Method B, for example, about 1-5 equivalents of a Lawesson reagent, phosphorus pentasulfide and the like can be used. As the reaction solvent, for example, halogenated hydrocarbons such as dichloromethane, chloroform, carbon tetrachloride, 1,2-dichloroethane and the like, aromatic hydrocarbons such as benzene, toluene, xylene and the like, ethers such as diethyl ether, tetrahydrofuran, dioxane and the like, and the like can be used. The reaction is carried out at room temperature or under heating, and the reaction time is generally about 1-20 hr, preferably about 1-10 hr.

As $R^aL^2$ in the production step from compound (V) to compound (IIb) in Method B, for example, about 1-5 equivalents of methyl iodide, benzyl chloride, benzyl bromide and the like can be used, and as the base, for example, sodium hydroxide, potassium hydroxide, sodium carbonate, potassium carbonate, sodium hydrogen carbonate, potassium hydrogen carbonate, triethylamine, N-ethyldiisopropylamine, pyridine, N,N-dimethylaminopyridine, sodium methoxide, sodium ethoxide, potassium t-butoxide, sodium hydride, sodium amide, diazabicycloundecene (DBU) and the like can be used. As the reaction solvent, for example, halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, t-butanol and the like, ethers such as diethyl ether, tetrahydrofuran, dioxane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used. The reaction is carried out under cooling, at room temperature or under heating, and the reaction time is generally about 1-20 hr, preferably about 1-10 hr.

As the oxidizing agent in the production step from compound (IIb) to compound (IIc) in Method B, for example, m-chloroperbenzoic acid, hydrogen peroxide, peracetic acid, t-butyl hydroperoxide, potassium peroxysulfate, potassium permanganate, sodium perborate, sodium periodate, sodium hypochlorite, halogen and the like can be used. When compound (IIc) wherein t=1 is produced, an oxidizing agent is used in about 1-1.5 equivalents relative to compound (IIb), and when compound (IIc) wherein t=2 is produced, it is used in about 2-3 equivalents relative to compound (IIb). The reaction solvent is not particularly limited as long as it does not react with the oxidizing agent and, for example, halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, t-butanol and the like, ethers such as diethyl ether, tetrahydrofuran, dioxane and the like, carboxylic acids such as acetic acid, trifluoroacetic acid and the like, acetonitrile, ethyl acetate, N,N-dimethylformamide, N,N-dimethylacetamide, 1-methyl-2-pyrrolidone, dimethyl sulfoxide, water or a mixed solvent thereof and the like can be used. The reaction is carried out under cooling, at room temperature or under heating, and the reaction time is generally about 1-20 hr, preferably about 1-10 hr.

As $R^aOH$ in the production step from compound (IIa) to compound (IId) in Method C, for example, about 1-10 equivalents of methanol, ethanol, phenol and the like can be used, and as a base, for example, sodium hydroxide, potassium hydroxide, sodium carbonate, potassium carbonate, sodium hydrogen carbonate, potassium hydrogen carbonate, triethylamine, N-ethyldiisopropylamine, pyridine, N,N-dimethylaminopyridine, sodium methoxide, sodium ethoxide, potassium t-butoxide, sodium hydride, sodium amide, diazabicycloundecene (DBU) and the like can be used. As a reaction solvent, for example, halogenated hydrocarbons such as dichloromethane, chloroform, carbon tetrachloride, 1,2-dichloroethane and the like, aromatic hydrocarbons such as benzene, toluene, xylene and the like, ethers such as diethyl ether, tetrahydrofuran, dioxane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used. The reaction is carried out under cooling, at room temperature or under heating, and the reaction time is generally about 1-20 hr, preferably about 1-10 hr.

Furthermore, compound (IV) can be produced by, for example, a method shown by the following formula:

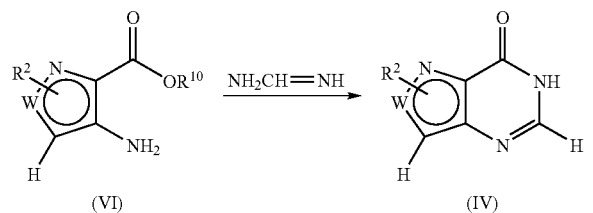

wherein $R^{10}$ is a $C_{1-4}$ alkyl group, and other symbols are as defined above.

That is, compound (VI) is reacted in the presence of about 1-4 equivalents of formamidine or a salt thereof, whereby compound (IV) can be produced. As the reaction solvent, for example, alcohols such as methanol, ethanol, isopropanol, t-butanol and the like, halogenated hydrocarbons such as dichloromethane, chloroform, carbon tetrachloride, 1,2-dichloroethane and the like, aromatic hydrocarbons such as benzene, toluene, xylene and the like, ethers such as diethyl ether, tetrahydrofuran, dioxane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used. The reaction is carried out under cooling, at room temperature or under heating, and the reaction time is generally about 1-20 hr, preferably about 1-10 hr.

When W is $C(R^1)$, compound (II) can be also produced by, for example, a method shown by the following formula:

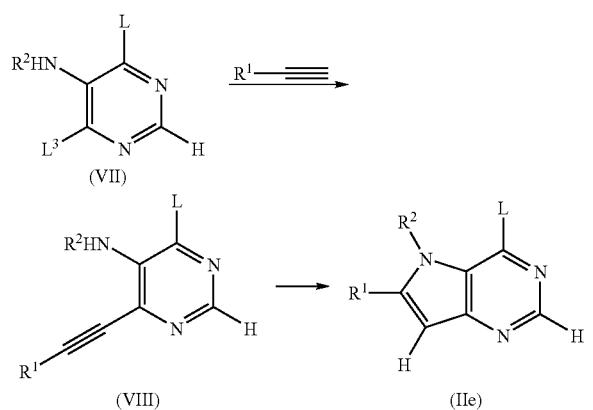

wherein $L^3$ is a halogen atom, and other symbols are as defined above.

For a step in this method to produce compound (VIII) from compound (VII), a reaction generally known as a Sonogashira reaction or a reaction analogous thereto can be used and generally, compound (VIII) can be produced by reacting compound (VII) with about 1-3 equivalents of a compound represented by the formula

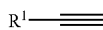

in the presence of a base, about 0.01-1 equivalent of a palladium catalyst and copper iodide. As the base, for example, triethylamine, N-ethyldiisopropylamine, diisopropylamine, pyridine, N,N-dimethylaminopyridine, diazabicycloundecene (DBU), sodium carbonate, potassium carbonate, sodium hydrogen carbonate, potassium hydrogen carbonate and the like can be used. As the palladium catalyst, for example, dichlorobis(triphenylphosphine)palladium(II), palladium on carbon, palladium(II) diacetate, bis(benzonitrile) dichloropalladium(II) and the like can be used. This reaction may be carried out in the co-presence of a tertiary phosphine compound such as triphenylphosphine, tributylphosphine and the like as a ligand. As the reaction solvent, for example, halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, t-butanol and the like, ethers such as diethyl ether, tetrahydrofuran, dioxane, 1,2-dimethoxyethane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used. This reaction is carried out at room temperature or under heating and the reaction time is generally about 1-50 hr, preferably about 1-20 hr.

For a step in this method to produce compound (IIe) from compound (VIII), generally, cyclization reaction is conducted in the presence of about 1-3 equivalents of base or about 0.01-1 equivalent of copper iodide to give compound (IIe). As the base, for example, potassium t-butoxide, sodium t-butoxide, cesium t-butoxide, sodium ethoxide, potassium hydride, sodium hydride, cesium hydroxide, sodium hydroxide, potassium hydroxide, sodium carbonate, potassium carbonate, sodium hydrogen carbonate, potassium hydrogen carbonate, triethylamine, N-ethyldiisopropylamine, diisopropylamine, pyridine, N,N-dimethylaminopyridine, diazabicycloundecene (DBU) and the like can be used. As the reaction solvent, for example, halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, t-butanol and the like, ethers such as diethyl ether, tetrahydrofuran, dioxane, 1,2-dimethoxyethane and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used. The reaction is carried out at low temperature, at room temperature or under heating and the reaction time is generally about 1-50 hr, preferably about 1-20 hr.

Depending on the kind of the substituent of starting compound (II), a starting compound (II) having a different substituent can be produced by substituent conversion from, as a starting material, a compound produced by the above-mentioned production method. For the substituent conversion, a known general method can be used. For example, conversion to carbamoyl group by hydrolysis and amidation of ester, conversion to hydroxymethyl group by reduction of carboxy group, conversion to alcohol compound by reduction or alkylation of carbonyl group, reductive amination of carbonyl group, oximation of carbonyl group, acylation of amino group, alkylation of amino group, substitution and amination of active halogen by amine, alkylation of hydroxy group, substitution and amination of hydroxy group and the like can be mentioned. When a reactive substituent that causes non-object reaction is present during the introduction of substituents and conversion of functional groups, a protecting group is introduced in advance as necessary into the reactive substituent by a means known per se, and the protecting group is removed by a means known per se after the object reaction, whereby the starting compound (II) can be also produced.

Thus-obtained compound (I) can be isolated and purified by a separation means known per se, such as concentration, concentration under reduced pressure, solvent extraction, crystallization, recrystallization, phase transfer, chromatography and the like.

If compound (I) is obtained as a free form, it can be converted into a desired salt by a method known per se or a modification thereof; conversely, if compound (I) is obtained as a salt, it can be converted into a free form or another desired salt by a method known per se or a modification thereof.

When compound (I) has isomers such as optical isomer, stereoisomer, positional isomer, rotational isomer and the like, and any isomers and mixtures are encompassed in the compound (I). For example, when compound (I) has an optical isomer, an optical isomer separated from a racemate is also encompassed in the compound (I). These isomers can be obtained as independent products by a synthesis means or a separation means (concentration, solvent extraction, column chromatography, recrystallization and the like) known per se.

The compound (I) may be a crystal, and both a single crystal and crystal mixtures are encompassed in the compound (I). Crystals can be produced by crystallization according to crystallization methods known per se.

The compound (I) may be a solvate (e.g., hydrate etc.) or a non-solvate, both of which are encompassed in the compound (I).

A compound labeled with an isotope (e.g., $^3$H, $^{14}$C, $^{35}$S, $^{125}$I and the like) is also encompassed in the compound (I).

A prodrug of the compound (I) or a salt thereof (hereinafter referred to as compound (I)) means a compound which is converted to the compound (I) with a reaction due to an enzyme, an gastric acid, etc. under the physiological condition in the living body, that is, a compound which is converted to the compound (I) with oxidation, reduction, hydrolysis, etc. according to an enzyme; a compound which is converted to the compound (I) by hydrolysis etc. due to gastric acid, etc. A prodrug for compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation, dimethylaminomethylcarbonylation, etc.); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I) by a method known per se.

A prodrug for compound (I) may also be one which is converted into compound (I) under a physiological condition, such as those described in *IYAKUHIN no KAIHATSU* (*Development of Pharmaceuticals*), Vol. 7, Design of Molecules, p. 163-198, Published by HIROKAWA SHOTEN (1990).

The compound (I) of the present invention, or a salt thereof or a prodrug thereof (hereinafter referred to as the compound of the present invention) possesses tyrosine kinase-inhibiting activity and can be used for the prophylaxis or treatment of treat tyrosine kinase-dependent diseases in mammals. Tyrosine kinase-dependent diseases include diseases characterized by increased cell proliferation due to abnormal tyrosine kinase enzyme activity. Furthermore, the compound of the present invention specifically inhibits HER2 kinase and/or EGFR kinase and is therefore also useful as a therapeutic agent for suppressing the growth of HER2 and/or EGFR kinase-expressing cancer, or a preventive agent for preventing the transition of hormone-dependent cancer to hormone-independent cancer. In addition, the compound is useful as a pharmaceutical agent because it shows low toxicity (e.g., acute toxicity, chronic toxicity, genetic toxicity, reproductive toxicity, cardiotoxicity, drug interaction, carcinogenicity and the like), high water solubility, and is superior in stability, pharmacokinetics (absorption, distribution, metabolism, excretion and the like) and efficacy expression.

Accordingly, the compound of the present invention can be used as a safe agent for the prophylaxis or treatment of diseases due to abnormal cell proliferation such as various cancers (particularly breast cancer, prostate cancer, pancreatic cancer, gastric cancer, lung cancer, colon cancer, rectal cancer, esophagus cancer, duodenal cancer, cancer of the tongue, cancer of pharynx, cerebral tumor, neurilemoma, non-small cell lung cancer, small cell lung cancer, liver cancer, kidney cancer, cancer of the bile duct, cancer of the uterine body, cancer of the uterine cervix, ovarian cancer, urinary bladder cancer, skin cancer, hemangioma, malignant lymphoma, malignant melanoma, thyroid cancer, bone tumors, vascular fibroma, retinoblastoma, penile cancer, solid cancer in childhood, Kaposi's sarcoma, Kaposi's sarcoma derived from AIDS, maxillary tumor, fibrous histiocytoma, leiomyosarcoma, rhabdomyosarcoma, leukemia, etc.), atherosclerosis, angiogenesis (e.g., angiogenesis associated with growth of solid cancer and sarcoma, angiogenesis associated with tumor metastasis, and angiogenesis associated with diabetic retinopathy, etc.), and viral diseases (HIV infection etc.).

Tyrosine kinase-dependent diseases further include cardiovascular diseases associated with abnormal tyrosine kinase enzyme activity. The compound of the present invention can therefore be used as an agent for prophylaxis or treatment of cardiovascular diseases such as restenosis.

The compound of the present invention is useful as an anticancer agent for the prophylaxis or treatment of cancer, especially e.g., breast cancer, prostate cancer, pancreatic cancer, gastric cancer, lung cancer, colon cancer, colorectal cancer, kidney cancer and the like.

The compound of the present invention shows low toxicity and can be used as a pharmaceutical agent as it is, or as a pharmaceutical composition in admixture with a commonly known pharmaceutically acceptable carrier etc. in mammals (e.g., humans, horses, bovines, dogs, cats, rats, mice, rabbits, pigs, monkeys, and the like).

In addition to the compound of the present invention, said pharmaceutical composition may contain other active ingredients, e.g., the following hormonal therapeutic agents, anticancer agent (e.g., chemotherapeutic agents, immunotherapeutic agents, or pharmaceutical agents inhibiting the action of cell growth factors or cell growth factor receptors), and the like.

As a pharmaceutical agent for mammals such as humans, the compound of the present invention can be administered orally in the form of, for example, tablets, capsules (including soft capsules and microcapsules), powders, granules and the like, or parenterally in the form of injections, suppositories, pellets and the like. Examples of the "parenteral administration route" include intravenous, intramuscular, subcutaneous, intra-tissue, intranasal, intradermal, instillation, intracerebral, intrarectal, intravaginal, intraperitoneal, intratumoral, juxtaposition of tumor and administration directly to the lesion.

The dose of the compound of the present invention varies depending on the route of administration, symptoms, etc. For example, when it is administered orally as an anticancer agent to a patient (body weight 40 to 80 kg) with breast cancer or prostate cancer, its dose is, for example, 0.5 to 100 mg/kg body weight per day, preferably 1 to 50 mg/kg body weight per day, and more preferably 1 or 25 mg/kg body weight per day. This amount may be administered once or in 2 to 3 divided portions daily.

The compound of the present invention can be safely administered orally or parenterally (e.g., topical, rectal, intravenous administrations etc.) as a single agent, or a pharmaceutical composition containing a pharmacologically acceptable carrier according to a conventional method (e.g., a method described in the Japanese Pharmacopoeia etc.), such as tablet (including sugar-coated tablet, film-coated tablet), powder, granule, capsule, liquid, emulsion, suspension, injection, suppository, sustained release preparation, plaster and the like.

And a combination of (1) administering an effective amount of a compound of the present invention and (2) 1 to 3 selected from the group consisting of (i) administering an effective amount of other anticancer agents, (ii) administering an effective amount of hormonal therapeutic agents and (iii) non-drug therapy can prevent and/or treat cancer more effectively. As the non-drug therapy, for example, surgery, radiotherapy, gene therapy, thermotherapy, cryotherapy, laser cauterization, and the like are exemplified and two or more of these may be combined.

For example, the compound of the present invention can be administered to the same subject simultaneously with hormonal therapeutic agents, anticancer agents (e.g., chemotherapeutic agents, immunotherapeutic agents, or pharmaceutical agents inhibiting the action of cell growth factors or cell growth factor receptors) (hereafter, these are referred to as a concomitant drug).

Although the compound of the present invention exhibits excellent anticancer action even when used as a simple agent, its effect can be enhanced by using it in combination with one or more of the concomitant drug(s) mentioned above (multi-agent co-administration).

As examples of said "hormonal therapeutic agents," there may be mentioned fosfestrol, diethylstylbestrol, chlorotrianisene, medroxyprogesterone acetate, megestrol acetate, chlormadinone acetate, cyproterone acetate, danazol, dienogest, asoprisnil, allylestrenol, gestrinone, nomegestrol, Tadenan, mepartricin, raloxifene, ormeloxifene, levormeloxifene, anti-estrogens (e.g., tamoxifen citrate, toremifene citrate, and the like), ER down regulator (e.g., fulvestrant, and the like), human menopausal gonadotrophin, follicle stimulating hormone, pill preparations, mepitiostane, testrolactone, aminoglutethimide, LH-RH agonists (e.g., goserelin acetate, buserelin, leuprorelin, and the like), droloxifene, epitiostanol, ethinylestradiol sulfonate, aromatase inhibitors (e.g., fadrozole hydrochloride, anastrozole, retrozole, exemestane, vorozole, formestane, and the like), anti-androgens (e.g., flutamide, bicartamide, nilutamide, and the like), 5α-reductase inhibitors (e.g., finasteride, dutasteride, epristeride, and the like), adrenocorticohormone drugs (e.g., dexamethasone, prednisolone, betamethasone, triamcinolone, and the like), androgen synthesis inhibitors (e.g., abiraterone, and the like), retinoid and drugs that retard retinoid metabolism (e.g., liarozole, and the like), etc. and LH-RH agonists (e.g., goserelin acetate, buserelin, leuprorelin) are preferable.

As examples of said "chemotherapeutic agents", there may be mentioned alkylating agents, antimetabolites, anticancer antibiotics, plant-derived anticancer agents, and the like.

As examples of "alkylating agents", there may be mentioned nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin, and the like.

As examples of "antimetabolites", there may be mentioned mercaptopurine, 6-mercaptopurine riboside, thioinosine, methotrexate, enocitabine, cytarabine, cytarabine ocfosfate, ancitabine hydrochloride, 5-FU drugs (e.g., fluorouracil, tegafur, UFT, doxifluridine, carmofur, gallocitabine, emmitefur, and the like), aminopterine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, ambamustine, and the like.

As examples of "anticancer antibiotics", there may be mentioned actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, and the like.

As examples of "plant-derived anticancer agents", there may be mentioned etoposide, etoposide phosphate, vinblastine sulfate, vincristine sulfate, vindesine sulfate, teniposide, paclitaxel, docetaxel, vinorelbine, and the like.

As examples of said "immunotherapeutic agents (BRM)", there may be mentioned picibanil, krestin, sizofuran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, procodazole, and the like.

The "growth factor" in said "pharmaceutical agents inhibiting the action of cell growth factors or cell growth factor receptors", there may be mentioned any substances that promote cell proliferation, which are normally peptides having a molecular weight of not more than 20,000 that are capable of exhibiting their activity at low concentrations by binding to a receptor, including (1) EGF (epidermal growth factor) or substances possessing substantially the same activity as it [e.g., EGF, heregulin (HER2 ligand), and the like], (2) insulin or substances possessing substantially the same activity as it [e.g., insulin, IGF (insulin-like growth factor)-1, IGF-2, and the like], (3) FGF (fibroblast growth factor) or substances possessing substantially the same activity as it [e.g., acidic FGF, basic FGF, KGF (keratinocyte growth factor), FGF-10, and the like], (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), and the like], and the like.

As examples of said "growth factor receptors", there may be mentioned any receptors capable of binding to the aforementioned growth factors, including EGF receptor, heregulin receptor (HER2), insulin receptor, IGF receptor, FGF receptor-1 or FGF receptor-2, and the like.

As examples of said "pharmaceutical agents inhibiting the action of cell growth factor", there may be mentioned trastuzumab (Herceptin (trade mark): HER2 antibody), imatinib mesilate, ZD1839 or cetuximab, antibody to VEGF (e.g., bevacizumab), antibody to VEGF receptor, gefitinib, erlotinib, and the like.

In addition to the aforementioned drugs, L-asparaginase, aceglatone, procarbazine hydrochloride, protoporphyrin-cobalt complex salt, mercuric hematoporphyrin-sodium, topoisomerase I inhibitors (e.g., irinotecan, topotecan, and the like), topoisomerase II inhibitors (e.g., sobuzoxane, and the like), differentiation inducers (e.g., retinoid, vitamin D, and the like), angiogenesis inhibitors (e.g., thalidomide, SU11248, and the like), α-blockers (e.g., tamsulosin hydrochloride, naftopidil, urapidil, alfuzosin, terazosin, prazosin, silodosin, and the like), serine/threonine kinase inhibitor, endothelin receptor antagonist (e.g., atrasentan, and the like), proteasome inhibitor (e.g., bortezomib, and the like), Hsp 90 inhibitor (e.g., 17-AAG, and the like), spironolactone, minoxidil, 11α-hydroxyprogesterone, bone resorption inhibiting/metastasis suppressing agent (e.g., zoledronic acid, alendronic acid, pamidronic acid, etidronic acid, ibandronic acid, clodronic acid) and the like can be used.

Of those mentioned above, LH-RH agonist (e.g., goserelin acetate, buserelin, leuprorelin, and the like), trastuzumab (HER2 antibody) and the like are preferable as concomitant drugs.

In combination of the compound of the present invention and the concomitant drug, the administration time of the compound of the present invention and the concomitant drug is not restricted, and the compound of the present invention and the concomitant drug can be administered to the administration subject simultaneously, or may be administered at different times. The dosage of the concomitant drug may be determined according to the administration amount clinically used, and can be appropriately selected depending on the administration subject, administration route, disease, combination and the like.

The administration mode of the compound of the present invention and the concomitant drug is not particularly restricted, and it is sufficient that the compound of the present invention and the concomitant drug are combined in administration. Examples of such administration mode include the following methods:

(1) The compound of the present invention and the concomitant drug are simultaneously produced to give a single preparation which is administered. (2) The compound of the present invention and the concomitant drug are separately produced to give two kinds of preparations which are administered simultaneously by the same administration route. (3) The compound of the present invention and the concomitant drug are separately produced to give two kinds of preparations which are administered by the same administration route only at the different times. (4) The compound of the present invention and the concomitant drug are separately produced to give two kinds of preparations which are administered simultaneously by different administration routes. (5) The compound of the present invention and the concomitant drug are separately produced to give two kinds of preparations which are administered by different administration routes at different times (for example, the compound of the present invention and the concomitant drug are administered in this order, or in the reverse order).

EXAMPLES

The present invention is explained in detail by way of the following Reference Examples, Examples, Formulation Examples and Experimental Examples but these do not limit the present invention.

The elution in column chromatography in Reference Examples and Examples was performed under observation by TLC (thin-layer chromatography). In the TLC observation, Kieselgel 60$F_{254}$ plate (Merck) or NH TLC plate manufactured by Fuji Silysia Chemical Ltd. was used as a TLC plate, the solvent used as an elution solvent in the column chromatography was used as a developing solvent, and the means of detection used was an UV detector. As silica gel for column, Kieselgel 60$F_{254}$ (70-230 mesh) manufactured by Merck or Chromatorex NH DM1020 (basic silica gel, 100-200 mesh) manufactured by Fuji Silysia Chemical Ltd. was used. The ratio of solvents in silica gel chromatography is a volume ratio of the solvents mixed. In addition, % means percentage by weight unless otherwise specified.

NMR spectra are shown by proton NMR with tetramethylsilane as the internal standard, using VARIAN Gemini-200 (200 MHz type spectrometer) or Gemini-300 (300 MHz type spectrometer) or BRUKER AVANCE300 (300 MHz type spectrometer); δ values are expressed in ppm.

The abbreviations used in Reference Examples and Examples mean the following:
s: singlet, br: broad, d: doublet, t: triplet, q: quartet, dd: double doublet, m: multiplet, J: coupling constant, Hz: hertz, DMSO: dimethyl sulfoxide Genetic manipulation methods described in Experimental Examples below are based on the methods described in Maniatis et al., *Molecular Cloning*, Cold Spring Harbor Laboratory, 1989, and the appended protocol.

Reference Example 1

Production of
2-[(2-chloro-4-nitrophenoxy)methyl]benzonitrile

To a solution of 2-chloro-4-nitrophenol (3.5 g) and 2-(bromomethyl)benzonitrile (4.0 g) in N,N-dimethylformamide (50 mL) was added potassium carbonate (3.7 g), and the mixture was stirred at room temperature for 30 min. After the completion of the reaction, water (50 mL) was added, and the mixture was stirred for 10 min. The resultant pale-yellow solid was collected by filtration. The residue was washed with diisopropyl ether, and dried to give the title compound (5.04 g) as pale-yellow crystals.

$^1$H-NMR (CDCl$_3$) δ 5.44 (2H, s), 7.13 (1H, d, J=9.0 Hz), 7.51 (1H, dt, J=1.2, 7.2 Hz), 7.68-7.80 (3H, m), 8.19 (1H, dd, J=2.7, 9.0 Hz), 8.35 (1H, d, J=2.7 Hz).

Reference Example 2

Production of
2-[(4-amino-2-chlorophenoxy)methyl]benzonitrile

To a solution of 2-[(2-chloro-4-nitrophenoxy)methyl]benzonitrile (2.0 g) in ethanol/water (9:1, 40 mL) was added calcium chloride (90%, 427 mg), and the mixture was stirred at 100° C. for 10 min. Reduced iron (90%, 2.6 g) was added at room temperature, and the mixture was stirred at 100° C. for 3 hrs. After the completion of the reaction, the reaction mixture was filtered (celite), and the filtrate was concentrated under reduced pressure. Water was added to the residue and the mixture was diluted with ethyl acetate and washed with water and saturated brine. The organic layer was dried over anhydrous magnesium sulfate, filtered and concentrated under reduced pressure. The residue was purified by silica gel column chromatography (hexane:ethyl acetate:methylene chloride=2:1:1) to give the title compound (1.2 g) as a white solid.

$^1$H-NMR (CDCl$_3$) δ 3.53 (2H, br s), 5.23 (2H, s), 6.54 (1H, dd, J=2.7, 8.7 Hz), 6.76 (1H, d, J=2.7 Hz), 6.88 (1H, d, J=8.7 Hz), 7.42 (1H, dt, J=0.9, 7.8 Hz), 7.62-7.70 (2H, m), 7.81 (1H, d, J=7.8 Hz).

Reference Example 3

Production of 2-[(2-methyl-4-nitrophenoxy)methyl]benzonitrile

The title compound (8.2 g) was obtained as a pale-yellow solid by the reaction in the same manner as in Reference Example 1 using 2-methyl-4-nitrophenol (5.0 g) and 2-(bromomethyl)benzonitrile (6.4 g).

$^1$H-NMR (CDCl$_3$) δ 2.37 (3H, s), 5.36 (2H, s), 6.97 (1H, d, J=8.4 Hz), 7.50 (1H, m), 7.65-7.69 (2H, m), 7.76 (1H, td, J=0.9, 7.5 Hz), 8.09-8.14 (2H, m).

Reference Example 4

Production of 2-[(4-amino-2-methylphenoxy)methyl]benzonitrile

The title compound (3.7 g) was obtained as a white solid by the reaction in the same manner as in Reference Example 2 using 2-[(2-methyl-4-nitrophenoxy)methyl]benzonitrile (6.0 g), calcium chloride (90%, 1.3 g) and reduced iron (90%, 8.3 g).

$^1$H-NMR (CDCl$_3$) δ 2.24 (3H, s), 3.41 (2H, br s), 5.17 (2H, s), 6.48 (1H, dd, J=3.0, 8.4 Hz), 6.56 (1H, d, J=3.0 Hz), 6.73 (1H, d, J=8.4 Hz), 7.40 (1H, dt, J=1.2, 7.5 Hz), 7.59-7.71 (3H, m).

Reference Example 5

Production of 3-(2-chloro-4-nitrophenoxy)benzonitrile

To a solution of 2-chloro-1-fluoro-4-nitrobenzene (3.7 g) and 3-hydroxybenzonitrile (2.5 g) in N,N-dimethylformamide (50 mL) was added potassium carbonate (4.4 g), and the mixture was stirred at 60° C. for 4 hrs. After the completion of the reaction, water (50 mL) was added, and the mixture was stirred for 10 min. The resultant pale-yellow solid was collected by filtration, washed with diisopropyl ether, and dried to give the title compound (5.3 g) as pale-yellow crystals.

$^1$H-NMR (CDCl$_3$) δ 7.03 (1H, d, J=9.0 Hz), 7.27-7.33 (2H, m), 7.55-7.56 (2H, m), 8.15 (1H, dd, J=2.7, 9.0 Hz), 8.42 (1H, d, J=2.7 Hz).

Reference Example 6

Production of 3-(4-amino-2-chlorophenoxy)benzonitrile

To a solution of 3-(2-chloro-4-nitrophenoxy)benzonitrile (2.0 g) in ethanol/water (9:1, 40 mL) was added calcium chloride (90%, 449 mg), and the mixture was stirred at 100° C. for 10 min. Reduced iron (90%, 2.7 g) was added at room temperature, and the mixture was stirred at 100° C. for 5 hrs.

After the completion of the reaction, the reaction mixture was filtered (celite), and the filtrate was concentrated under reduced pressure. Water was added to the residue and the mixture was diluted with ethyl acetate and washed with water and saturated brine. The organic layer was dried over anhydrous magnesium sulfate, filtered and concentrated under reduced pressure. The residue was purified by silica gel column chromatography (hexane:ethyl acetate=3:1) to give the title compound (1.25 g) as a white solid.

$^1$H-NMR (CDCl$_3$) δ 3.75 (2H, br s), 6.60 (1H, dd, J=2.7, 8.4 Hz), 6.80 (1H, d, J=2.7 Hz), 6.92 (1H, d, J=8.4 Hz), 7.06 (1H, m), 7.14 (1H, m), 7.30 (1H, td, J=1.2, 7.5 Hz), 7.37 (1H, d, J=7.5 Hz).

Reference Example 7

Production of ethyl 2-fluoro-5-nitrobenzoate

Under ice-cooling, thionyl chloride (8.02 mL) was added dropwise to ethanol (200 mL), and 2-fluoro-5-nitrobenzoic acid (13.81 g) was added. This mixture was stirred at 80° C. for 4 hrs. and concentrated under reduced pressure. A saturated aqueous sodium hydrogen carbonate solution was added to the reaction mixture and the mixture was extracted with ethyl acetate. The extract was washed with saturated brine and dried over anhydrous magnesium sulfate. The solvent was evaporated under reduced pressure to give the title compound (15.77 g) as a pale-yellow oil.

$^1$H-NMR (CDCl$_3$) δ: 1.43 (3H, t, J=7.2 Hz), 4.46 (2H, q, J=7.2 Hz), 7.32 (1H, t, J=9.1 Hz), 8.41 (1H, ddd, J=9.1, 4.3, 3.0 Hz), 8.85 (1H, dd, J=6.1, 3.0 Hz).

Reference Example 8

Production of ethyl 5-amino-2-phenoxybenzoate

A mixture of ethyl 2-fluoro-5-nitrobenzoate (1.07 g), phenol (565 mg), potassium carbonate (1.38 g) and N,N-dimethylformamide (20 mL) was stirred at 80° C. for 4 hrs. The reaction mixture was concentrated under reduced pressure. Water was added to the residue and the mixture was extracted with ethyl acetate. The extract was washed with saturated brine and dried over anhydrous magnesium sulfate. The solvent was evaporated under reduced pressure, and the obtained residue was purified by silica gel column chromatography (eluent, ethyl acetate:hexane=20:80→30:70). The object fraction was concentrated under reduced pressure and ethanol (20 mL) and 10% palladium on carbon (1.5 g) were added to the residue (1.54 g). The mixture was stirred overnight under a hydrogen stream. The catalyst was filtered off, and the filtrate was concentrated. The obtained residue was purified by silica gel column chromatography (eluent, ethyl acetate:hexane=20:80→50:50) and recrystallized from diisopropyl ether-hexane to give the title compound (1.07 g) as a pale-brown powder.

$^1$H-NMR (CDCl$_3$) δ: 1.12 (3H, t, J=7.2 Hz), 3.71 (2H, s), 4.17 (2H, q, J=7.2 Hz), 6.80-6.87 (3H, m), 6.91 (1H, d, J=8.5 Hz), 6.97 (1H, t, J=7.3 Hz), 7.21-7.30 (3H, m).

Reference Example 9

Production of methyl 4-{[7-(methylthio)-1H-pyrazolo[4,3-d]pyrimidin-1-yl]methyl}benzoate and methyl 4-{[7-(methylthio)-2H-pyrazolo[4,3-d]pyrimidin-2-yl]methyl}benzoate To a solution of 7-(methylthio)-1H-pyrazolo[4,3-d]pyrimidine (400 mg) in N,N-dimethylformamide (8 mL) was added 60% sodium hydride (98 mg) under ice-cooling, and the mixture was stirred at room temperature for 10 min. Then, methyl 4-(bromomethyl)benzoate (606 mg) was added under ice-cooling, and the mixture was stirred at room temperature for 30 min. After the completion of the reaction, the mixture was diluted with ethyl acetate and washed with saturated aqueous sodium hydrogen carbonate and saturated brine. The organic layer was concentrated under reduced pressure, and the residue was subjected to silica gel column chromatography (hexane:ethyl acetate=2:1→1:2) to give methyl 4-{[7-(methylthio)-1H-pyrazolo[4,3-d]pyrimidin-1-yl]methyl}benzoate (251 mg) and methyl 4-{[7-(methylthio)-2H-pyrazolo[4,3-d]pyrimidin-2-yl]methyl}benzoate (450 mg) both as pale-yellow solids.

methyl 4-{[7-(methylthio)-1H-pyrazolo[4,3-d]pyrimidin-1-yl]methyl}benzoate: $^1$H-NMR (CDCl$_3$) δ 2.71 (3H, s), 3.89 (3H, s), 5.93 (2H, s), 7.22 (2H, d, J=8.1 Hz), 7.98 (2H, d, J=8.1 Hz), 8.23 (1H, s), 8.80 (1H, s).

methyl 4-{[7-(methylthio)-2H-pyrazolo[4,3-d]pyrimidin-2-yl]methyl}benzoate: $^1$H-NMR (CDCl$_3$) δ 2.73 (3H, s), 3.92 (3H, s), 5.69 (2H, s), 7.34 (2H, d, J=8.4 Hz), 8.03 (2H, d, J=8.4 Hz), 8.04 (1H, s), 8.73 (1H, s).

Reference Example 10

Production of 2-[7-(methylthio)-1H-pyrazolo[4,3-d]pyrimidin-1-yl]ethyl benzoate and 2-[7-(methylthio)-2H-pyrazolo[4,3-d]pyrimidin-2-yl]ethyl benzoate To a solution of 7-(methylthio)-1H-pyrazolo[4,3-d]pyrimidine (300 mg) and 2-iodoethyl benzoate (548 mg) in N,N-dimethylformamide (10 mL) was added potassium carbonate (374 mg), and the mixture was stirred at 60° C. for 1 hr. After the completion of the reaction, water was added to the reaction mixture. The mixture was diluted with ethyl acetate and washed with water and saturated brine. The organic layer was dried over anhydrous magnesium sulfate, filtered and concentrated under reduced pressure. The residue was purified by silica gel column chromatography (hexane:ethyl acetate=3:2) to give 2-[7-(methylthio)-1H-pyrazolo[4,3-d]pyrimidin-1-yl]ethyl benzoate (266 mg) and 2-[7-(methylthio)-2H-pyrazolo[4,3-d]pyrimidin-2-yl]ethyl benzoate (191 mg) both as pale-yellow solids.

2-[7-(methylthio)-1H-pyrazolo[4,3-d]pyrimidin-1-yl]ethyl benzoate: $^1$H-NMR (CDCl$_3$) δ 2.66 (3H, s), 4.78 (2H, t, J=5.4 Hz), 5.06 (2H, t, J=5.4 Hz), 7.27-7.40 (2H, m), 7.53 (1H, m), 7.85-7.89 (2H, m), 8.20 (1H, s), 8.79 (1H, s).

2-[7-(methylthio)-2H-pyrazolo[4,3-d]pyrimidin-2-yl]ethyl benzoate: $^1$H-NMR (CDCl$_3$) δ 2.73 (3H, s), 4.80-4.86 (4H, m), 7.40-7.46 (2H, m), 7.58 (1H, m), 7.94-7.97 (2H, m), 8.20 (1H, s), 8.73 (1H, s).

Reference Example 11

Production of 3-[7-(methylthio)-1H-pyrazolo[4,3-d]pyrimidin-1-yl]propyl benzoate and 3-[7-(methylthio)-2H-pyrazolo[4,3-d]pyrimidin-2-yl]propyl benzoate 3-[7-(Methylthio)-1H-pyrazolo[4,3-d]pyrimidin-1-yl]propyl benzoate (623 mg) and 3-[7-(methylthio)-2H-pyrazolo[4,3-d]pyrimidin-2-yl]propyl benzoate (556 mg) were obtained both as pale-yellow solids by the reaction in the same manner as in Reference Example 10 using 7-(methylthio)-1H-pyrazolo[4,3-d]pyrimidine (600 mg), 3-iodopropyl benzoate (1.15 g) and potassium carbonate (748 mg).

3-[7-(methylthio)-1H-pyrazolo[4,3-d]pyrimidin-1-yl]propyl benzoate: $^1$H-NMR (CDCl$_3$) δ 2.40-2.47 (2H, m), 2.66 (3H, s), 4.42 (2H, t, J=5.7 Hz), 4.88 (2H, t, J=7.2 Hz), 7.42-7.46 (2H, m), 7.57 (1H, m), 7.98-8.02 (2H, m), 8.15 (1H, s), 8.73 (1H, s).

3-[7-(methylthio)-2H-pyrazolo[4,3-d]pyrimidin-2-yl]propyl benzoate: $^1$H-NMR (CDCl$_3$) δ 2.52-2.58 (2H, m), 2.72 (3H, s), 4.39 (2H, t, J=6.0 Hz), 4.65 (2H, t, J=6.9 Hz), 7.40-7.46 (2H, m), 7.57 (1H, m), 7.96-8.02 (2H, m), 8.14 (1H, s), 8.71 (1H, s).

Example 1

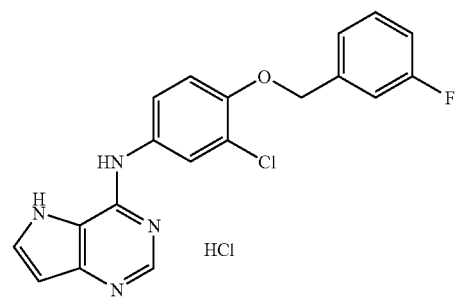

Production of N-{3-chloro-4-[(3-fluorobenzyl)oxy]phenyl}-5H-pyrrolo[3,2-d]pyrimidin-4-amine hydrochloride 4-Chloro-5H-pyrrolo[3,2-d]pyrimidine (770 mg) and 3-chloro-4-[(3-fluorobenzyl)oxy]aniline (2.52 g) were dissolved in 1-methyl-2-pyrrolidone (10 mL), and the mixture was stirred with heating at 140° C. for 2.5 hrs. After cooling to room temperature, the mixture was diluted with ethyl acetate (300 mL), and stirred at room temperature for 1 hr. The precipitated powder was collected by filtration, washed with ethyl acetate (30 mL), and dried under reduced pressure to give the title compound (1.62 g).

$^1$H-NMR (DMSO-d$_6$) δ: 5.27 (2H, s), 6.63 (1H, d, J=3 Hz), 7.0-7.5 (5H, m), 7.78 (1H, dd, J=3 Hz, 9 Hz), 8.00 (1H, m), 8.15 (1H, d, J=3 Hz), 8.79 (1H, s), 11.79 (1H, br s).

Example 2

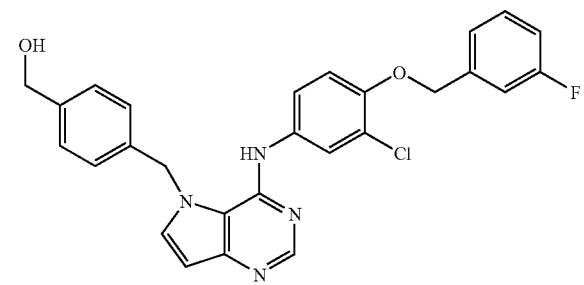

Production of (4-{[4-({3-chloro-4-[(3-fluorobenzyl)oxy]phenyl}amino)-5H-pyrrolo[3,2-d]pyrimidin-5-yl]methyl}phenyl)methanol (i) Production of {4-[(4-chloro-5H-pyrrolo[3,2-d]pyrimidin-5-yl)methyl]phenyl}methanol 4-Chloro-5H-pyrrolo[3,2-d]pyrimidine (307 mg) was dissolved in N,N-dimethylformamide (2 mL), potassium carbonate (304 mg) was added, and the mixture was stirred at room temperature for 30 min. 4-Hydroxymethylbenzyl chloride (377 mg) was added, and the mixture was stirred at room temperature for 16 hrs. After diluting with water (30 mL), the mixture was extracted with ethyl acetate/tetrahydrofuran (3:1, 80 mL×2). The organic layer was dried over magnesium sulfate and concentrated under reduced pressure. The residue was separated and purified by silica gel column chromatography (eluent, hexane:ethyl acetate=80:20→0:100) to give the title compound (383 mg) as a powder.

$^1$H-NMR (CDCl$_3$) δ: 2.15 (1H, br s), 4.69 (2H, d, J=4 Hz), 5.71 (2H, s), 6.76 (1H, m), 7.06 (2H, d, J=8 Hz), 7.34 (2H, d, J=8 Hz), 7.50 (1H, d, J=3 Hz), 8.69 (1H, s).

(ii) Production of (4-{[4-({3-chloro-4-[(3-fluorobenzyl)oxy]phenyl}amino)-5H-pyrrolo[3,2-d]pyrimidin-5-yl]methyl}phenyl)methanol {4-[(4-Chloro-5H-pyrrolo[3,2-d]pyrimidin-5-yl)methyl]phenyl}methanol (354 mg) and 3-chloro-4-[(3-fluorobenzyl)oxy]aniline (488 mg) were dissolved in 1-methyl-2-pyrrolidone (2.58 mL), and the mixture was stirred with heating at 140° C. for 2 hrs. After cooling to room temperature, the reaction mixture was diluted with ethyl acetate (80 mL) and partitioned with saturated aqueous sodium hydrogen carbonate (30 mL). The organic layer was washed with saturated brine (30 mL), dried over magnesium sulfate and concentrated under reduced pressure. The residue was separated and purified by silica gel column chromatography (eluent, hexane:ethyl acetate=80:20→0:100) to give the title compound (588 mg) as a powder.

$^1$H-NMR (CDCl$_3$) δ: 4.77 (2H, s), 5.07 (2H, s), 5.52 (2H, s), 6.26 (2H, s), 6.64 (1H, d, J=3 Hz), 6.81 (1H, d, J=9 Hz), 6.9-7.4 (8H, m), 7.49 (2H, d, J=8 Hz), 8.44 (1H, s).

Example 3

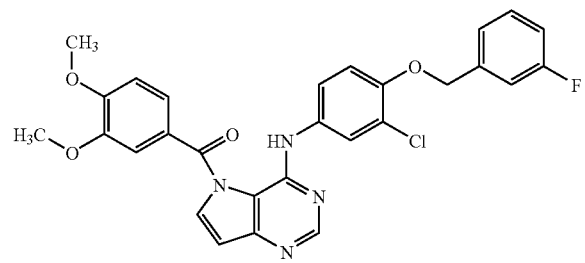

Production of N-{3-chloro-4-[(3-fluorobenzyl)oxy]phenyl}-5-(3,4-dimethoxybenzoyl)-5H-pyrrolo[3,2-d]pyrimidin-4-amine Under ice-cooling, to a suspension of N-{3-chloro-4-[(3-fluorobenzyl)oxy]phenyl}-5H-pyrrolo[3,2-d]pyrimidin-4-amine hydrochloride (150 mg) and potassium carbonate (102 mg) in N,N-dimethylformamide (1.5 mL) was added 3,4-dimethoxybenzoyl chloride (82 mg), and the mixture was stirred under ice-cooling, for 1 hr. The mixture was partitioned between ethyl acetate (50 mL) and water (30 mL). The organic layer was washed with saturated brine (30 mL), dried over magnesium sulfate and concentrated under reduced pressure. The residue was separated and purified by silica gel column chromatography (eluent, hexane:ethyl acetate=80: 20→ethyl acetate:methanol=80:20), and crystallized from diisopropyl ether to give the title compound (104 mg).

$^1$H-NMR (CDCl$_3$) δ: 3.97 (3H, s), 4.01 (3H, s), 5.14 (2H, s), 6.72 (1H, d, J=3 Hz), 6.9-7.6 (10H, m), 7.88 (2H, d, J=3 Hz), 8.63 (1H, s), 9.75 (1H, br s).

Example 4

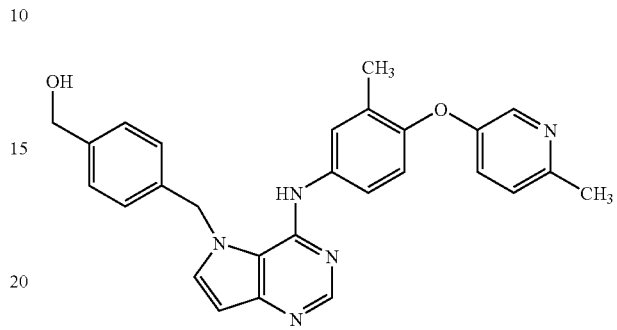

Production of (4-{[4-({3-methyl-4-[(6-methylpyridin-3-yl)oxy]phenyl}amino)-5H-pyrrolo[3,2-d]pyrimidin-5-yl]methyl}phenyl)methanol The title compound (242 mg) was obtained as crystals by the reaction in the same manner as in Example 2 (ii) using {4-[(4-chloro-5H-pyrrolo[3,2-d]pyrimidin-5-yl)methyl]phenyl}methanol (200 mg), 3-methyl-4-[(6-methylpyridin-3-yl)oxy]aniline (235 mg) and 1-methyl-2-pyrrolidone (1.46 mL).

$^1$H-NMR (CDCl$_3$) δ: 2.14 (3H, s), 2.50 (3H, s), 3.01 (1H, br s), 4.75 (2H, s), 5.53 (2H, s), 6.38 (1H, br s), 6.64 (1H, d, J=3 Hz), 6.75 (1H, d, J=9 Hz), 6.8-7.2 (6H, m), 7.34 (2H, d, J=3 Hz), 7.47 (1H, d, J=9 Hz), 8 09 (1H, m), 8.46 (1H, s).

Example 5

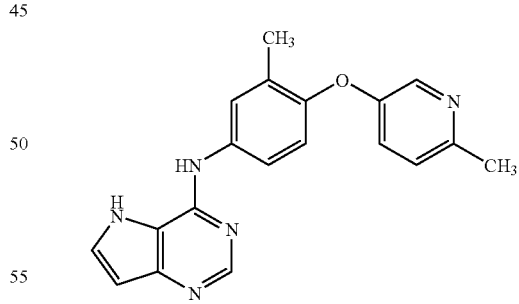

Production of N-{3-methyl-4-[(6-methylpyridin-3-yl)oxy]phenyl}-5H-pyrrolo[3,2-d]pyrimidin-4-amine The title compound (283 mg) was obtained as crystals by the reaction in the same manner as in Example 2 (ii) using 4-chloro-5H-pyrrolo[3,2-d]pyrimidine (200 mg), 3-methyl-4-[(6-methylpyridin-3-yl)oxy]aniline (418 mg) and 1-methyl-2-pyrrolidone (2.6 mL).

¹H-NMR (CDCl₃) δ: 2.16 (3H, s), 2.51 (3H, s), 6.56 (1H, d, J=3 Hz), 6.80 (1H, d, J=9 Hz), 7.0-7.6 (5H, m), 8 17 (1H, m), 8.59 (1H, s), 8.76 (1H, br s), 11.08 (1H, br s).

Example 6

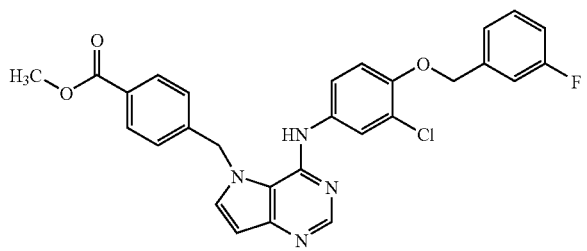

Production of methyl 4-{[4-({3-chloro-4-[(3-fluorobenzyl)oxy]phenyl}amino)-5H-pyrrolo[3,2-d]pyrimidin-5-yl]methyl}benzoate (i) Production of methyl 4-[(4-chloro-5H-pyrrolo[3,2-d]pyrimidin-5-yl)methyl]benzoate The title compound (1.0 g) was obtained as a powder by the reaction in the same manner as in Example 2 (i) using 4-chloro-5H-pyrrolo[3,2-d]pyrimidine (710 mg), methyl 4-(bromomethyl)benzoate (1.27 g), potassium carbonate (703 mg) and N,N-dimethylformamide (9.2 mL).

¹H-NMR (CDCl₃) δ: 3.90 (3H, s), 5.77 (2H, s), 6.83 (1H, d, J=3 Hz), 7.08 (2H, d, J=8 Hz), 7.53 (1H, d, J=3 Hz), 8.00 (2H, d, J=8 Hz), 8.73 (1H, s).

(ii) Production of methyl 4-{[4-({3-chloro-4-[(3-fluorobenzyl)oxy]phenyl}amino)-5H-pyrrolo[3,2-d]pyrimidin-5-yl]methyl}benzoate The title compound (1.35 g) was obtained as a powder by the reaction in the same manner as in Example 2 (ii) using methyl 4-[(4-chloro-5H-pyrrolo[3,2-d]pyrimidin-5-yl)methyl]benzoate (1.0 g), 3-chloro-4-[(3-fluorobenzyl)oxy]aniline (1.25 g) and 1-methyl-2-pyrrolidone (6.63 mL).

¹H-NMR (CDCl₃) δ: 3.93 (3H, s), 5.07 (2H, s), 5.57 (2H, s), 6.10 (2H, br s), 6.68 (1H, d, J=3 Hz), 6.7-7.4 (10H, m), 8.11 (2H, d, J=9 Hz), 8.47 (1H, s).

Example 7

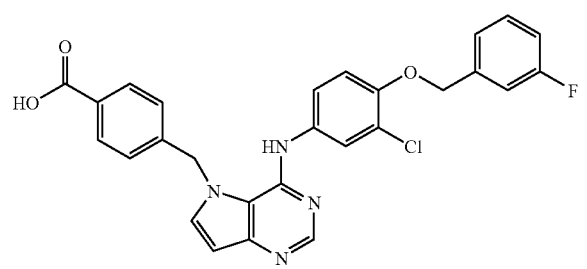

Production of 4-{[4-({3-chloro-4-[(3-fluorobenzyl)oxy]phenyl}amino)-5H-pyrrolo[3,2-d]pyrimidin-5-yl]methyl}benzoic acid Methyl 4-{[4-({3-chloro-4-[(3-fluorobenzyl)oxy]phenyl}amino)-5H-pyrrolo[3,2-d]pyrimidin-5-yl]methyl}benzoate (850 mg) was dissolved in a mixed solvent of ethanol (3.29 mL)/tetrahydrofuran (3.29 mL), 1N aqueous sodium hydroxide solution (3.29 mL) was added, and the mixture was stirred at room temperature for 20 hrs. 1N Hydrochloric acid (3.29 mL) was added to the reaction mixture and the mixture was diluted with water (20 mL). The precipitated crystals were collected by filtration, washed with water (10 mL), and dried under reduced pressure to give the title compound (738 mg).

¹H-NMR (DMSO-d₆) δ: 5.21 (2H, s), 5.94 (2H, s), 6.62 (1H, d, J=3 Hz), 7.0-7.6 (9H, m), 7.84 (2H, d, J=9 Hz), 7.91 (1H, d, J=3 Hz), 8.40 (1H, s), 8.81 (1H, br s), 12.88 (1H, br s).

Example 8

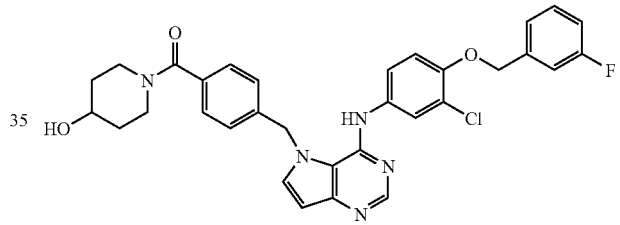

Production of 1-(4-{[4-({3-chloro-4-[(3-fluorobenzyl)oxy]phenyl}amino)-5H-pyrrolo[3,2-d]pyrimidin-5-yl]methyl}benzoyl)piperidin-4-ol To a mixture of 4-{[4-({3-chloro-4-[(3-fluorobenzyl)oxy]phenyl}amino)-5H-pyrrolo[3,2-d]pyrimidin-5-yl]methyl}benzoic acid (150 mg), 4-hydroxypiperidine (33.2 mg) and 1-hydroxybenzotriazole monohydrate (60 mg) in N,N-dimethylformamide (3 mL) were added 1-ethyl-3-(3-dimethylaminopropyl)carbodiimide hydrochloride (86 mg) and triethylamine (0.208 mL) at room temperature and the mixture was stirred overnight at room temperature. The mixture was partitioned between ethyl acetate (50 mL) and water (30 mL). The organic layer was washed with saturated brine (30 mL), dried over magnesium sulfate, and concentrated under reduced pressure. The residue was separated and purified by basic silica gel column chromatography (eluent, ethyl acetate:methanol=100:0→ethyl acetate:methanol=80:20), and crystallized from diisopropyl ether to give the title compound (168 mg).

¹H-NMR (CDCl₃) δ: 1.4-2.1 (5H, m), 3.0-3.7 (3H, m), 3.97 (1H, m), 4.16 (1H, m), 5.08 (2H, s), 5.55 (2H, s), 6.33 (1H, br s), 6.66 (1H, d, J=3 Hz), 6.82 (1H, d, J=9 Hz), 6.9-7.5 (11H, m), 8.47 (1H, s).

Example 9

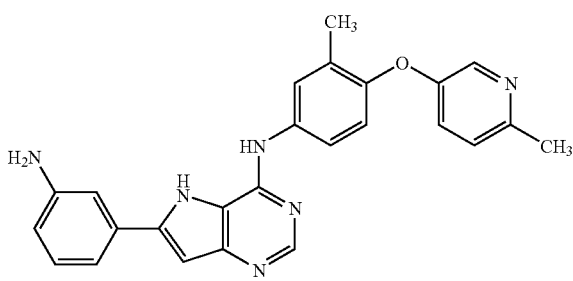

Production of 6-(3-aminophenyl)-N-{3-methyl-4-[(6-methylpyridin-3-yl)oxy]phenyl}-5H-pyrrolo[3,2-d]pyrimidin-4-amine

(i) Production of 6-chloro-N-{3-methyl-4-[(6-methylpyridin-3-yl)oxy]phenyl}-5-nitropyrimidin-4-amine hydrochloride 4,6-Dichloro-5-nitropyrimidine (9.7 g) was dissolved in 1-methyl-2-pyrrolidone (25.7 mL), a solution of 3-methyl-4-[(6-methylpyridin-3-yl)oxy]aniline (5.35 g) in 1-methyl-2-pyrrolidone (10 mL) was added dropwise under cooling at −15° C., and the mixture was stirred at −10° C. to 0° C. for 1 hr. The mixture was diluted with ethyl acetate (100 mL) and stirred at 0° C. for 15 min. The precipitated crystals were collected by filtration, washed with ethyl acetate (30 mL), and dried under reduced pressure to give the title compound (7.34 g).

$^1$H-NMR (DMSO-$d_6$) δ: 2.20 (3H, s), 2.67 (3H, s), 7.0-8.0 (5H, m), 8.44 (1H, m), 8.55 (1H, s), 10.14 (1H, br s).

(ii) Production of 6-chloro-N4-{3-methyl-4-[(6-methylpyridin-3-yl)oxy]phenyl}pyrimidine-4,5-diamine 6-Chloro-N-{3-methyl-4-[(6-methylpyridin-3-yl)oxy]phenyl}-5-nitropyrimidin-4-amine hydrochloride (2.04 g) was suspended in diethyl ether (9.45 mL) and a solution of tin(IV) chloride dihydrate (9.1 g) in conc. hydrochloric acid (20.17 mL) was added under ice-cooling. After stirring at room temperature for 3 hrs, the reaction mixture was poured into ice water (400 mL). A 50% aqueous sodium hydroxide solution (18 mL) was added dropwise to adjust pH to 8. Ethyl acetate (300 mL) was added and the mixture was filtered through celite. The organic layer was dried over magnesium sulfate and concentrated under reduced pressure to give the title compound (1.30 g).

$^1$H-NMR (CDCl$_3$) δ: 2.23 (3H, s), 2.52 (3H, s), 6.85 (1H, d, J=9 Hz), 7.0-7.5 (4H, m), 8.16 (1H, s), 8.21 (1H, d, J=3 Hz).

(iii) Production of 6-iodo-N4-{3-methyl-4-[(6-methylpyridin-3-yl)oxy]phenyl}pyrimidine-4,5-diamine hydriodide 6-Chloro-N4-{3-methyl-4-[(6-methylpyridin-3-yl)oxy]phenyl}pyrimidine-4,5-diamine (400 mg) was suspended in 55% hydriodic acid (6.16 mL), sodium iodide (878 mg) was added, and the mixture was stirred with heating at 70° C. for 10 min. After cooling to room temperature, water (40 mL)/ethyl acetate (30 mL) was added. After adjusting its pH to not less than 7 with aqueous sodium hydrogen carbonate, and the mixture was stirred at room temperature for 15 min. The organic layer was dried over magnesium sulfate and concentrated under reduced pressure to give the title compound (626 mg).

$^1$H-NMR (CDCl$_3$) δ: 2.19 (3H, s), 2.52 (3H, s), 4.23 (2H, br s), 6.81 (1H, d, J=9 Hz), 7.0-7.5 (5H, m), 7.97 (1H, s), 8.18 (1H, d, J=3 Hz).

(iv) Production of 6-[(3-aminophenyl)ethynyl]-N4-{3-methyl-4-[(6-methylpyridin-3-yl)oxy]phenyl}pyrimidine-4,5-diamine 6-Iodo-N4-{3-methyl-4-[(6-methylpyridin-3-yl)oxy]phenyl}pyrimidine-4,5-diamine hydriodide (200 mg) was dissolved in a mixed solvent of acetonitrile (7.6 mL)/triethylamine (5.72 mL), 3-ethynylaniline (0.0574 mL), trans-dichlorobis(triphenylphosphine)palladium(II) (15.4 mg) and copper(I) iodide (5.3 mg) were sequentially added, and the mixture was stirred under a nitrogen stream at room temperature for 1.5 hrs. The reaction mixture was concentrated under reduced pressure and the residue was separated and purified by silica gel column chromatography (eluent, hexane:ethyl acetate=80:20→ethyl acetate:methanol=80:20) to give the title compound (157 mg).

$^1$H-NMR (CDCl$_3$) δ: 2.19 (3H, s), 2.51 (3H, s), 3.65 (2H, br s), 4.37 (2H, br s), 6.6-7.5 (9H, m), 7.50 (1H, br s), 8.19 (1H, d, J=3 Hz), 8.29 (1H, s).

(v) Production of 6-(3-aminophenyl)-N-{3-methyl-4-[(6-methylpyridin-3-yl)oxy]phenyl}-5H-pyrrolo[3,2-d]pyrimidin-4-amine 6-[(3-Aminophenyl)ethynyl]-4-{3-methyl-4-[(6-methylpyridin-3-yl)oxy]phenyl}pyrimidine-4,5-diamine (140 mg) was dissolved in N,N-dimethylformamide (0.82 mL), copper(I) iodide (6.3 mg) was added and the mixture was stirred under a nitrogen stream with heating at 110° C. for 16 hrs. After cooling to room temperature, the reaction mixture was diluted with dichloromethane (20 mL), and filtered through celite. The filtrate was concentrated under reduced pressure, and the residue was separated and purified by basic silica gel column chromatography (eluent, ethyl acetate:methanol=100:0→85:15) and crystallized from diisopropyl ether to give the title compound (76 mg).

$^1$H-NMR (DMSO-$d_6$) δ: 2.22 (3H, s), 2.44 (3H, s), 5.32 (2H, br s), 6.65 (1H, d, J=7 Hz), 6.76 (1H, d, J=2 Hz), 6.9-7.3 (6H, m), 7.75 (1H, dd, J=3 Hz, 9 Hz), 7.83 (1H, d, J=2 Hz), 8.18 (1H, d, J=3 Hz), 8.34 (1H, s), 9.14 (1H, br s), 11.47 (1H, br s).

Example 10

Production of 6-(4-aminophenyl)-N-{3-methyl-4-[(6-methylpyridin-3-yl)oxy]phenyl}-5H-pyrrolo[3,2-d]pyrimidin-4-amine

(i) Production of 6-[(4-aminophenyl)ethynyl]-N4-{3-methyl-4-[(6-methylpyridin-3-yl)oxy]phenyl}pyrimidine-4,5-diamine 6-Iodo-N4-{3-methyl-4-[(6-methylpyridin-3-yl)oxy]phenyl}pyrimidine-4,5-diamine hydriodide (270 mg) was dissolved in a mixed solvent of acetonitrile (10.3 mL)/triethylamine (7.72 mL), and 4-ethynylaniline (80.3 mg), trans-dichlorobis(triphenylphosphine)palladium(II) (20.8 mg) and copper(I) iodide (7.16 mg) were sequentially added. The title compound (134 mg) was obtained as a powder by the reaction in the same manner as in Example 9 (iv).

¹H-NMR (CDCl₃) δ: 2.20 (3H, s), 2.51 (3H, s), 4.00 (4H, br s), 6.60 (2H, d, J=9 Hz), 6.83 (1H, d, J=9 Hz), 7.0-7.5 (6H, m), 8.21 (1H, m), 8.29 (1H, s).

(ii) Production of 6-(4-aminophenyl)-N-{3-methyl-4-[(6-methylpyridin-3-yl)oxy]phenyl}-5H-pyrrolo[3,2-d]pyrimidin-4-amine The title compound (68 mg) was obtained as a powder by the reaction in the same manner as in Example 9 (v) using 6-[(4-aminophenyl)ethynyl]-N4-{3-methyl-4-[(6-methylpyridin-3-yl)oxy]phenyl}pyrimidine-4,5-diamine (160 mg) and copper(I) iodide (7.2 mg).

¹H-NMR (DMSO-d₆) δ: 2.21 (3H, s), 2.44 (3H, s), 5.58 (2H, br s), 6.70 (2H, d, J=9 Hz), 6.99 (1H, d, J=2 Hz), 7.20 (2H, m), 7.56 (1H, d, J=9 Hz), 7.75 (1H, dd, J=2 Hz, 9 Hz), 7.81 (1H, d, J=2 Hz), 8.18 (1H, d, J=2 Hz), 8.32 (1H, s), 9.12 (1H, br s), 11.38 (1H, br s).

Example 11

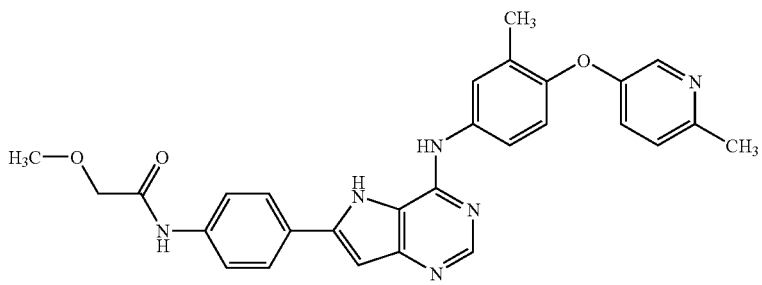

Production of 2-methoxy-N-{4-[4-({3-methyl-4-[(6-methylpyridin-3-yl)oxy]phenyl}amino)-5H-pyrrolo[3,2-d]pyrimidin-6-yl]phenyl}acetamide To a mixture of 6-(4-aminophenyl)-N-{3-methyl-4-[(6-methylpyridin-3-yl)oxy]phenyl}-5H-pyrrolo[3,2-d]pyrimidin-4-amine (40 mg), methoxyacetic acid (0.0145 mL) and 1-hydroxybenzotriazole monohydrate (38 mg) in N,N-dimethylformamide (1.9 mL) were added 1-ethyl-3-(3-dimethylaminopropyl)carbodiimide hydrochloride (54 mg) and triethylamine (0.079 mL) at room temperature. After stirring overnight at room temperature, the reaction mixture was diluted with dichloromethane (10 mL). The residue was separated and purified by basic silica gel column chromatography (eluent, ethyl acetate:methanol=100:0→ethyl acetate:methanol=85:15) and crystallized from diisopropyl ether to give the title compound (24 mg).

¹H-NMR (DMSO-d₆) δ: 2.21 (3H, s), 2.43 (3H, s), 3.39 (3H, s), 4.04 (2H, s), 6.91 (1H, d, J=2 Hz), 6.99 (1H, d, J=9 Hz), 7.20 (2H, m), 7.7-7.9 (6H, m), 8.17 (1H, d, J=3 Hz), 8.33 (1H, s), 9.07 (1H, br s), 9.97 (1H, br s), 11.52 (1H, br s).

Example 12

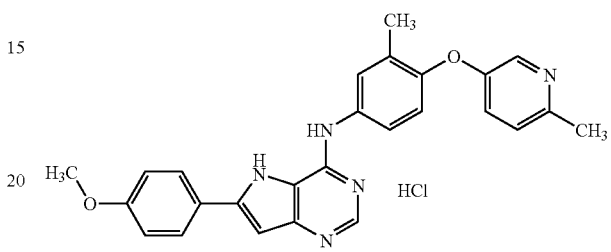

Production of 6-(4-methoxyphenyl)-N-{3-methyl-4-[(6-methylpyridin-3-yl)oxy]phenyl}-5H-pyrrolo[3,2-d]pyrimidin-4-amine hydrochloride (i) Production of 6-(4-methoxyphenyl)-5H-pyrrolo[3,2-d]pyrimidin-4-ol Ethyl 3-amino-5-(4-methoxyphenyl)-1H-pyrrole-2-carboxylate (7.2 g) was dissolved in tetrahydrofuran (16 mL)/ethanol (32 mL), formamidine (3.46 g) was added, and the mixture was stirred at 90° C. for 16 hrs. After cooling to room temperature, tetrahydrofuran was evaporated under reduced pressure. The residue was diluted with ethanol (20 mL), and the precipitated powder was collected by filtration, washed with ethanol (15 mL) and dried under reduced pressure to give the title compound (769 mg).

¹H-NMR (DMSO-d₆) δ: 3.80 (3H, s), 6.76 (1H, s), 6.9-7.1 (3H, m), 7.7-8.0 (2H, m), 11.83 (1H, br s).

(ii) Production of 4-chloro-6-(4-methoxyphenyl)-5H-pyrrolo[3,2-d]pyrimidine 6-(4-Methoxyphenyl)-5H-pyrrolo[3,2-d]pyrimidin-4-ol (500 mg) was suspended in N,N-diethylaniline (1.11 mL)/1,2-dichloroethane (3.73 mL), phosphorus oxychloride (2.29 mL) was added, and the mixture was stirred with heating at 110° C. for 2 hrs. After cooling to room temperature, the reaction mixture was treated with ice water (20 mL), and adjusted to pH 7 or above with aqueous ammonia. After diluting with tetrahydrofuran (500 mL), the mixture was washed with saturated brine (50 mL). The organic layer was dried over magnesium sulfate and concentrated under reduced pressure. The residue was separated and purified by silica gel column chromatography (eluent, hexane:ethyl acetate=80:20→20:80) to give the title compound (25 mg).
$^1$H-NMR (CDCl$_3$) δ: 3.90 (3H, s), 6.92 (1H, s), 7.05 (2H, d, J=9 Hz), 7.71 (2H, d, J=9 Hz), 8.73 (1H, s).

(iii) Production of 6-(4-methoxyphenyl)-N-{3-methyl-4-[(6-methylpyridin-3-yl)oxy]phenyl}-5H-pyrrolo[3,2-d]pyrimidin-4-amine hydrochloride The title compound (11 mg) was obtained as crystals by the reaction in the same manner as in Example 1 using 4-chloro-6-(4-methoxyphenyl)-5H-pyrrolo[3,2-d]pyrimidine (13 mg), 3-methyl-4-[(6-methylpyridin-3-yl)oxy]aniline (16 mg) and 1-methyl-2-pyrrolidone (0.2 mL).
$^1$H-NMR (DMSO-d$_6$) δ: 2.24 (3H, s), 2.46 (3H, s), 3.86 (3H, s), 7.02 (1H, s), 7.14 (2H, d, J=9 Hz), 7.26 (2H, m), 7.80 (1H, dd, J=3 Hz, 9 Hz), 7.90 (1H, d, J=3 Hz), 8.11 (2H, d, J=9 Hz), 8.22 (1H, d, J=3 Hz), 8.72 (1H, s), 11.54 (1H, br s).

Example 13

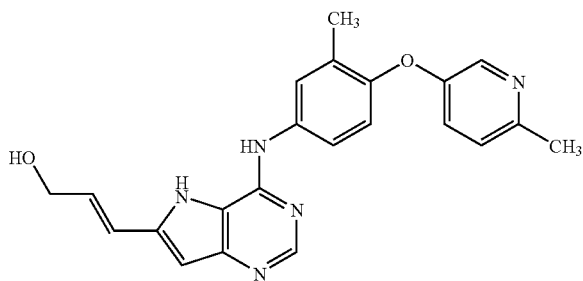

Production of (2E)-3-[4-({3-methyl-4-[(6-methylpyridin-3-yl)oxy]phenyl}amino)-5H-pyrrolo[3,2-d]pyrimidin-6-yl]-2-propen-1-ol (i) Production of (2E)-5-[5-amino-6-({3-methyl-4-[(6-methylpyridin-3-yl)oxy]phenyl}amino)pyrimidin-4-yl]-2-penten-4-yn-1-ol 6-Iodo-N4-{3-methyl-4-[(6-methylpyridin-3-yl)oxy]phenyl}pyrimidine-4,5-diamine hydriodide (507 mg) was dissolved in a mixed solvent of acetonitrile (19.4 mL)/triethylamine (14.5 mL), 2-penten-4-yn-1-ol (106 mg), trans-dichlorobis(triphenylphosphine)palladium(II) (38.8 mg) and copper(I) iodide (13.4 mg) were sequentially added. The title compound (373 mg) was obtained as a powder by the reaction in the same manner as in Example 9 (iv).
$^1$H-NMR (DMSO-d$_6$) δ: 2.17 (3H, s), 2.43 (3H, s), 4.12 (2H, m), 5.52 (2H, br s), 6.05 (1H, dt, J=2 Hz, 16 Hz), 6.53 (1H, dt, J=5 Hz, 16 Hz), 6.93 (1H, d, J=9 Hz), 7.20 (2H, m), 7.63 (2H, m), 7.96 (1H, s), 8.15 (1H, d, J=3 Hz), 8.57 (1H, br s).

(ii) Production of (2E)-3-[4-({3-methyl-4-[(6-methylpyridin-3-yl)oxy]phenyl}amino)-5H-pyrrolo[3,2-d]pyrimidin-6-yl]-2-propen-1-ol The title compound (59 mg) was obtained by the reaction in the same manner as in Example 9 (v) using (2E)-5-[5-amino-6-({3-methyl-4-[(6-methylpyridin-3-yl)oxy]phenyl}amino)pyrimidin-4-yl]-2-penten-4-yn-1-ol (200 mg), copper(I) iodide (9.8 mg) and N,N-dimethylformamide (1.29 mL), and crystallization from diisopropyl ether.
$^1$H-NMR (DMSO-d$_6$) δ: 2.20 (3H, s), 2.43 (3H, s), 4.22 (2H, d, J=3 Hz), 6.45 (1H, m), 6.50 (1H, s), 6.67 (1H, dt, J=16 Hz), 6.98 (1H, d, J=9 Hz), 7.19 (2H, m), 7.72 (1H, dd, J=3 Hz, 9 Hz), 7.80 (1H, d, J=2 Hz), 8.17 (1H, d, J=2 Hz), 8.30 (1H, s), 9.02 (1H, br s), 11.30 (1H, br s).

Example 14

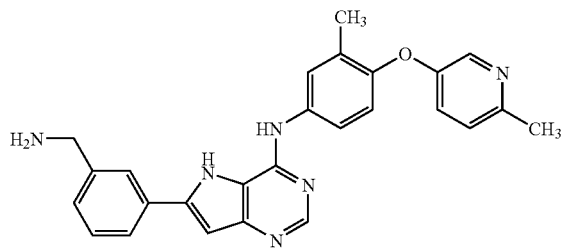

Production of 6-[3-(aminomethyl)phenyl]-N-{3-methyl-4-[(6-methylpyridin-3-yl)oxy]phenyl}-5H-pyrrolo[3,2-d]pyrimidin-4-amine (i) Production of tert-butyl 3-{[5-amino-6-({3-methyl-4-[(6-methylpyridin-3-yl)oxy]phenyl}amino)pyrimidin-4-yl]ethynyl}benzylcarbamate 6-Iodo-N4-{3-methyl-4-[(6-methylpyridin-3-yl)oxy]phenyl}pyrimidine-4,5-diamine hydriodide (500 mg) was dissolved in a mixed solvent of acetonitrile (14.8 mL)/triethylamine (11.0 mL), and tert-butyl 3-ethynylbenzylcarbamate (247 mg), trans-dichlorobis(triphenylphosphine)palladium (II) (31.3 mg) and copper(I) iodide (10.2 mg) were sequentially added. The title compound (376 mg) was obtained as a powder by the reaction in the same manner as in Example 9 (iv).
$^1$H-NMR (CDCl$_3$) δ: 1.47 (9H, s), 2.24 (3H, s), 2.53 (3H, s), 4.00 (2H, br s), 4.32 (2H, d, J=6 Hz), 5.04 (1H, br s), 6.87 (1H, d, J=9 Hz), 7.01 (1H, br s), 7.09-7.5 (9H, m), 8.22 (1H, d, J=2 Hz), 8.34 (1H, s).

(ii) Production of tert-butyl 3-[4-({3-methyl-4-[(6-methylpyridin-3-yl)oxy]phenyl}amino)-5H-pyrrolo[3,2-d]pyrimidin-6-yl]benzylcarbamate The title compound (287 mg) was obtained as a powder by the reaction in the same manner as in Example 9 (v) using tert-butyl 3-{[5-amino-6-({3-methyl-4-[(6-methylpyridin-3-yl)oxy]phenyl}amino)pyrimidin-4-yl]ethynyl}benzylcarbamate (363 mg) and copper(I) iodide (12.9 mg).
$^1$H-NMR (CDCl$_3$) δ: 1.49 (9H, s), 2.17 (3H, s), 2.51 (3H, s), 4.23 (2H, br s), 5.67 (1H, br s), 6.72 (1H, s), 6.82 (1H, d, J=8 Hz), 6.9-7.7 (8H, m), 8.16 (1H, br s), 8.60 (1H, s), 8.66 (1H, br s), 10.64 (1H, br s).

(iii) Production of 6-[3-(aminomethyl)phenyl]-N-{3-methyl-4-[(6-methylpyridin-3-yl)oxy]phenyl}-5H-pyrrolo[3,2-d]pyrimidin-4-amine tert-Butyl 3-[4-({3-methyl-4-[(6-methylpyridin-3-yl)oxy]phenyl}amino)-5H-pyrrolo[3,2-d]pyrimidin-6-yl]benzylcarbamate (230 mg) was suspended in tetrahydrofuran (2.3 mL), 2N hydrochloric acid (2.3 mL) was added, and the mixture was stirred with heating at 60° C. for 3 hrs. After cooling to room temperature, 1N aqueous sodium hydroxide solution (4.6 mL) was added, and the mixture was stirred at room temperature for 5 min. The solvent was removed by decantation, and the residue was dissolved in tetrahydrofuran (30 mL), dried over potassium carbonate, and concentrated under reduced pressure. The residue was triturated with diisopropyl ether, collected by filtration and dried under reduced pressure to give the title compound (164 mg).

$^1$H-NMR (DMSO-d$_6$) δ: 2.18 (3H, s), 2.41 (3H, s), 3.92 (2H, br s), 4.86 (2H, br s), 6.9-8.2 (11H, m), 8.33 (1H, s), 9.62 (1H, br s), 12.13 (1H, br s).

Example 15

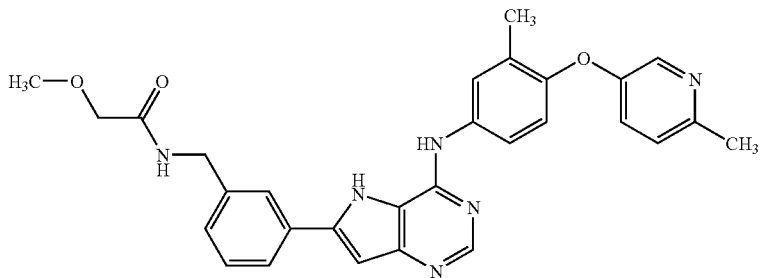

Production of 2-methoxy-N-{3-[4-({3-methyl-4-[(6-methylpyridin-3-yl)oxy]phenyl}amino)-5H-pyrrolo[3,2-d]pyrimidin-6-yl]benzyl}acetamide The title compound (56 mg) was obtained by the reaction in the same manner as in Example 11 using 6-[3-(aminomethyl)phenyl]-N-{3-methyl-4-[(6-methylpyridin-3-yl)oxy]phenyl}-5H-pyrrolo[3,2-d]pyrimidin-4-amine (50 mg), methoxyacetic acid (0.01055 mL), 1-hydroxybenzotriazole monohydrate (23.2 mg), N,N-dimethylformamide (2.3 ml), 1-ethyl-3-(3-dimethylaminopropyl)carbodiimide hydrochloride (32.9 mg) and triethylamine (0.080 mL).

$^1$H-NMR (DMSO-d$_6$) δ: 2.27 (3H, s), 2.52 (3H, s), 3.44 (3H, s), 3.98 (2H, s), 4.56 (2H, d, J=6 Hz), 6.65 (1H, s), 6.82 (1H, d, J=2 Hz), 6.93 (1H, d, J=8 Hz), 7.11 (2H, m), 7.3-7.9 (6H, m), 8.22 (1H, m), 8.47 (1H, s), 8.82 (1H, br s), 11.26 (1H, br s).

Example 16

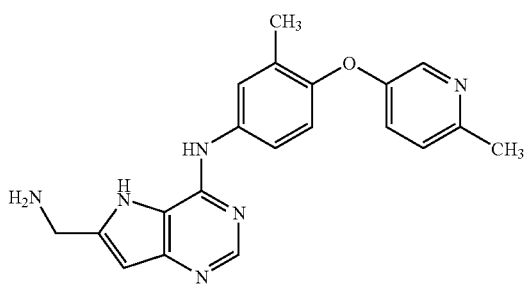

Production of 6-(aminomethyl)-N-{3-methyl-4-[(6-methylpyridin-3-yl)oxy]phenyl}-5H-pyrrolo[3,2-d]pyrimidin-4-amine (i) Production of tert-butyl 3-[5-amino-6-({3-methyl-4-[(6-methylpyridin-3-yl)oxy]phenyl}amino)pyrimidin-4-yl]-2-propynylcarbamate 6-Iodo-N4-{3-methyl-4-[(6-methylpyridin-3-yl)oxy]phenyl}pyrimidine-4,5-diamine hydriodide (500 mg) was dissolved in a mixed solvent of acetonitrile (14.8 mL)/triethylamine (11.0 mL), and tert-butyl 2-propynylcarbamate (166 mg), trans-dichlorobis(triphenylphosphine)palladium(II) (31.3 mg) and copper(I) iodide (10.2 mg) were sequentially added. The title compound (303 mg) was obtained as a powder by the reaction in the same manner as in Example 9 (iv).

$^1$H-NMR (CDCl$_3$) δ: 1.46 (9H, s), 2.22 (3H, s), 2.52 (3H, s), 4.06 (2H, br s), 4.17 (2H, d, J=6 Hz), 5.09 (1H, br s), 6.84 (1H, d, J=9 Hz), 7.0-7.5 (4H, m), 8.20 (1H, d, J=3 Hz), 8.25 (1H, s).

(ii) Production of tert-butyl [4-({3-methyl-4-[(6-methylpyridin-3-yl)oxy]phenyl}amino)-5H-pyrrolo[3,2-d]pyrimidin-6-yl]methylcarbamate The title compound (212 mg) was obtained as a powder by the reaction in the same manner as in Example 9 (v) using tert-butyl 3-[5-amino-6-({3-methyl-4-[(6-methylpyridin-3-yl)oxy]phenyl}amino)pyrimidin-4-yl]-2-propynylcarbamate (286 mg) and copper(I) iodide (11.8 mg).

$^1$H-NMR (CDCl$_3$) δ: 1.38 (9H, s), 2.20 (3H, s), 2.52 (3H, s), 4.30 (2H, d, J=6 Hz), 5.38 (1H, t, J=6 Hz), 6.32 (1H, br s), 6.83 (1H, d, J=9 Hz), 7.07 (1H, d, J=9 Hz), 7.1-7.4 (4H, m), 7.84 (1H, br s), 8.20 (1H, d, J=2 Hz), 8.50 (1H, s), 9.95 (1H, br s).

(iii) Production of 6-(aminomethyl)-N-{3-methyl-4-[(6-methylpyridin-3-yl)oxy]phenyl}-5H-pyrrolo[3,2-d]pyrimidin-4-amine The title compound (160 mg) was obtained as a powder by the reaction in the same manner as in Example 14 (iii) using tert-butyl [4-({3-methyl-4-[(6-methylpyridin-3-yl)oxy]phenyl}amino)-5H-pyrrolo[3,2-d]pyrimidin-6-yl]methylcarbamate (165 mg), 2N hydrochloric acid (1.92 mL) and tetrahydrofuran (1.92 mL).

$^1$H-NMR (DMSO-d$_6$) δ: 2.17 (3H, s), 2.42 (3H, s), 3.59 (2H, t, J=6 Hz), 3.95 (2H, s), 6.25 (1H, s), 6.86 (1H, s), 6.94 (1H, d, J=8 Hz), 7.1-7.3 (2H, m), 7.78 (2H, m), 8.14 (1H, d, J=3 Hz), 8.26 (1H, s), 9.46 (1H, br s), 11.50 (1H, br s).

Example 17

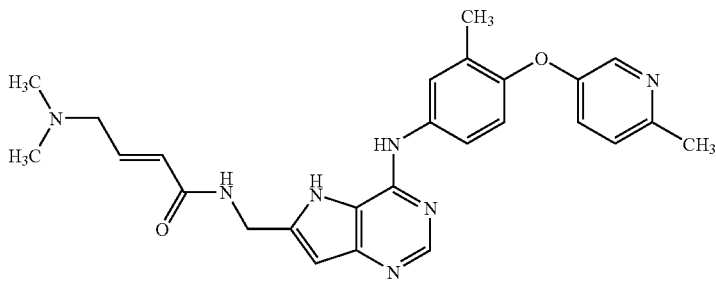

Production of (2E)-4-(dimethylamino)-N-{[4-({3-methyl-4-[(6-methylpyridin-3-yl)oxy]phenyl}amino)-5H-pyrrolo[3,2-d]pyrimidin-6-yl]methyl}-2-butenamide The title compound (32 mg) was obtained by the reaction in the same manner as in Example 11 using 6-(aminomethyl)-N-{3-methyl-4-[(6-methylpyridin-3-yl)oxy]phenyl}-5H-pyrrolo[3,2-d]pyrimidin-4-amine (40 mg), (2E)-4-(dimethylamino)-2-butenoic acid hydrochloride (22 mg), 1-hydroxybenzotriazole monohydrate (22.5 mg), N,N-dimethylformamide (2.2 mL), 1-ethyl-3-(3-dimethylaminopropyl)carbodiimide hydrochloride (31.9 mg) and triethylamine (0.0928 mL).

$^1$H-NMR (DMSO-d$_6$) δ: 2.15 (6H, s), 2.19 (3H, s), 2.43 (3H, s), 3.01 (2H, d, J=5 Hz), 4.55 (2H, d, J=5 Hz), 6.12 (1H, d, J=16 Hz), 6.36 (1H, d, J=1 Hz), 6.68 (1H, m), 6.96 (1H, d, J=8 Hz), 7.18 (2H, m), 7.74 (2H, m), 8.16 (1H, d, J=3 Hz), 8.30 (1H, s), 8.70 (1H, t, J=5 Hz), 9.30 (1H, br s), 11.03 (1H, br s).

Example 18

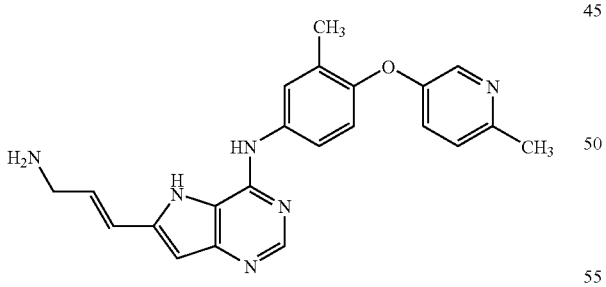

Production of 6-[(1E)-3-amino-1-propen-1-yl]-N-{3-methyl-4-[(6-methylpyridin-3-yl)oxy]phenyl}-5H-pyrrolo[3,2-d]pyrimidin-4-amine (i) Production of tert-butyl (2E)-5-[5-amino-6-({3-methyl-4-[(6-methylpyridin-3-yl)oxy]phenyl}amino)pyrimidin-4-yl]-2-penten-4-yn-1-ylcarbamate 6-Iodo-N4-{3-methyl-4-[(6-methylpyridin-3-yl)oxy]phenyl}pyrimidine-4,5-diamine hydroiodide (500 mg) was dissolved in a mixed solvent of acetonitrile (14.8 mL)/triethylamine (11.0 mL), and tert-butyl (2E)-2-penten-4-yn-1-ylcarbamate (194 mg), trans-dichlorobis(triphenylphosphine)palladium(II) (31.3 mg) and copper(I) iodide (10.2 mg) were sequentially added. The title compound (199 mg) was obtained as a powder by the reaction in the same manner as in Example 9 (iv).

$^1$H-NMR (CDCl$_3$) δ: 1.46 (9H, s), 2.20 (3H, s), 2.52 (3H, s), 3.85 (2H, m), 4.22 (2H, br s), 5.02 (1H, br s), 5.84 (1H, d, J=16 Hz), 6.29 (1H, m), 6.84 (1H, d, J=9 Hz), 7.0-7.5 (5H, m), 8.19 (1H, d, J=2 Hz), 8.26 (1H, s).

(ii) Production of tert-butyl (2E)-3-[4-({3-methyl-4-[(6-methylpyridin-3-yl)oxy]phenyl}amino)-5H-pyrrolo[3,2-d]pyrimidin-6-yl]-2-propenylcarbamate The title compound (66 mg) was obtained as a powder by the reaction in the same manner as in Example 9 (v) using tert-butyl (2E)-5-[5-amino-6-({3-methyl-4-[(6-methylpyridin-3-yl)oxy]phenyl}amino)pyrimidin-4-yl]-2-penten-4-yn-1-ylcarbamate (195 mg) and copper(I) iodide (7.63 mg).

$^1$H-NMR (CDCl$_3$) δ: 1.44 (9H, s), 2.12 (3H, s), 2.49 (3H, s), 3.82 (2H, br s), 5.53 (1H, br s), 6.00 (1H, d, J=16 Hz), 6.36 (1H, m), 6.77 (1H, d, J=9 Hz), 7.0-7.5 (4H, m), 8.09 (1H, s), 8.43 (1H, br s), 8.51 (1H, br s), 11.00 (1H, br s).

(iii) Production of 6-[(1E)-3-amino-1-propen-1-yl]-N-{3-methyl-4-[(6-methylpyridin-3-yl)oxy]phenyl}-5H-pyrrolo[3,2-d]pyrimidin-4-amine The title compound (41 mg) was obtained as a powder by the reaction in the same manner as in Example 14 (iii) using tert-butyl (2E)-3-[4-({3-methyl-4-[(6-methylpyridin-3-yl)oxy]phenyl}amino)-5H-pyrrolo[3,2-d]pyrimidin-6-yl]-2-propenylcarbamate (65 mg), 2N hydrochloric acid (0.755 mL) and tetrahydrofuran (0.755 mL).

$^1$H-NMR (DMSO-d$_6$) δ: 2.17 (3H, s), 2.42 (3H, s), 3.41 (2H, m), 6.40 (1H, s), 6.62 (2H, m), 6.96 (1H, d, J=8 Hz), 7.17 (2H, m), 7.95 (2H, m), 8.16 (1H, d, J=3 Hz), 8.28 (1H, s), 10.09 (1H, br s), 12.43 (1H, br s).

Example 19

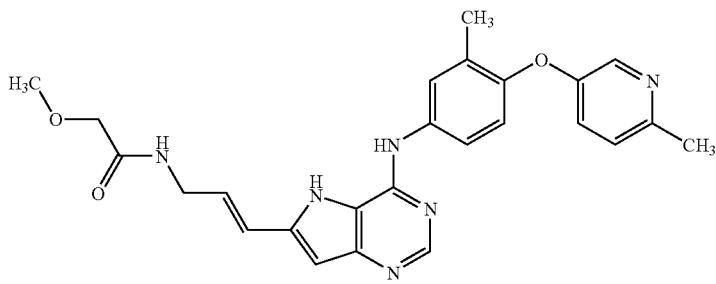

Production of 2-methoxy-N-{(2E)-3-[4-({3-methyl-4-[(6-methylpyridin-3-yl)oxy]phenyl}amino)-5H-pyrrolo[3,2-d]pyrimidin-6-yl]-2-propenyl}acetamide The title compound (15 mg) was obtained by the reaction in the same manner as in Example 11 using 6-[(1E)-3-aminopropen-1-yl]-N-{3-methyl-4-[(6-methylpyridin-3-yl)oxy]phenyl}-5H-pyrrolo[3,2-d]pyrimidin-4-amine (50 mg), methoxyacetic acid (0.0119 mL), 1-hydroxybenzotriazole monohydrate (26.2 mg), N,N-dimethylformamide (2.56 mL), 1-ethyl-3-(3-dimethylaminopropyl)carbodiimide hydrochloride (37.2 mg) and triethylamine (0.090 mL).
$^1$H-NMR (DMSO-$d_6$) δ: 2.20 (3H, s), 2.43 (3H, s), 3.36 (3H, s), 3.88 (2H, s), 3.97 (2H, t, J=5 Hz), 6.32 (1H, m), 6.49 (1H, d, J=1 Hz), 6.56 (1H, d, J=17 Hz), 6.97 (1H, d, J=9 Hz), 7.19 (2H, m), 7.75 (2H, m), 8.15 (1H, d, J=2 Hz), 8.24 (1H, t, J=5 Hz), 8.29 (1H, s), 9.04 (1H, br s), 11.33 (1H, br s).

Example 20

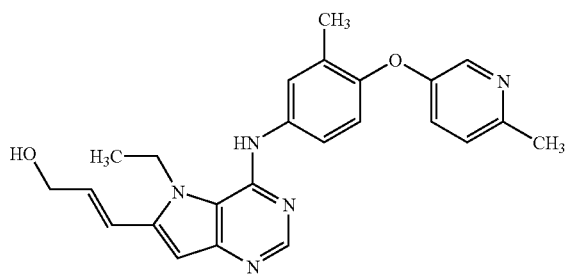

Production of (2E)-3-[5-ethyl-4-({3-methyl-4-[(6-methylpyridin-3-yl)oxy]phenyl}amino)-5H-pyrrolo[3,2-d]pyrimidin-6-yl]-2-propen-1-ol (i) Production of 4-iodo-6-phenoxypyrimidin-5-amine 4,6-Diiodopyrimidin-5-amine (2.2 g) was dissolved in 1-methyl-2-pyrrolidone (11.5 mL), phenol (656 mg) and potassium carbonate (964 mg) were added, and the mixture was stirred at 100° C. for 16 hrs. After cooling to room temperature, the mixture was diluted with ethyl acetate (200 mL) and washed successively with water (100 mL) and saturated brine (100 mL). The organic layer was dried over magnesium sulfate and concentrated under reduced pressure. The residue was separated and purified by silica gel column chromatography (eluent, hexane:ethyl acetate=80:20→20:80) to give the title compound (2.0 g) as an oil.
$^1$H-NMR (CDCl$_3$) δ: 4.34 (2H, br s), 7.1-7.5 (5H, m), 7.87 (1H, s).

(ii) Production of 4-((3E)-5-{[tert-butyl(dimethyl)silyl]oxy}-3-penten-1-ynyl)-6-phenoxypyrimidin-5-amine 4-Iodo-6-phenoxypyrimidin-5-amine (1.0 g) was dissolved in a mixed solvent of acetonitrile (53 mL)/triethylamine (39 mL), and tert-butyl(dimethyl)[(2E)-2-penten-4-ynyloxy]silane (753 mg), trans-dichlorobis(triphenylphosphine)palladium(II) (112 mg) and copper(I) iodide (36.5 mg) were sequentially added. The title compound (1.07 g) was obtained as crystals by the reaction in the same manner as in Example 9 (iv).
$^1$H-NMR (CDCl$_3$) δ: 0.09 (6H, s), 0.93 (9H, s), 4.32 (2H, m), 4.42 (2H, br s), 6.08 (1H, dt, J=16 Hz, 3 Hz), 6.48 (1H, dt, J=16 Hz, 4 Hz), 7.1-7.5 (5H, m), 8.11 (1H, s).

(iii) Production of 6-((1E)-3-{[tert-butyl(dimethyl)silyl]oxy}-1-propenyl)-4-phenoxy-5H-pyrrolo[3,2-d]pyrimidine The title compound (409 mg) was obtained as a powder by the reaction in the same manner as in Example 9 (v) using 4-((3E)-5-{[tert-butyl(dimethyl)silyl]oxy}-3-penten-1-ynyl)-6-phenoxypyrimidin-5-amine (950 mg) and copper(I) iodide (47.4 mg).
$^1$H-NMR (CDCl$_3$) δ: 0.12 (6H, s), 0.95 (9H, s), 4.39 (2H, m), 6.44 (1H, dt, J=16 Hz, 4 Hz), 6.67 (2H, m), 7.1-7.5 (5H, m), 8.48 (1H, s), 9.07 (1H, br s).

(iv) Production of 6-((1E)-3-{[tert-butyl(dimethyl)silyl]oxy}-1-propenyl)-5-ethyl-4-phenoxy-5H-pyrrolo[3,2-d]pyrimidine 6-((1E)-3-{[tert-Butyl(dimethyl)silyl]oxy}-1-propenyl)-4-phenoxy-5H-pyrrolo[3,2-d]pyrimidine (100 mg) was dissolved in N,N-dimethylformamide (0.786 mL), cesium carbonate (102.6 mg) was added, and the mixture was stirred at room temperature for 20 min. Iodoethane (0.0231 mL) was added and the mixture was stirred at room temperature for 2 hrs and at 40° C. for 4 hrs. After cooling to room temperature, the reaction mixture was diluted with ethyl acetate (50 mL) and washed successively with water (30 mL) and saturated brine (30 mL). The organic layer was dried over magnesium sulfate and concentrated under reduced pressure. The residue was separated and purified by silica gel column chromatography (eluent, hexane:ethyl acetate=80:20→50:50) to give the title compound (79 mg) as an oil.

¹H-NMR (CDCl₃) δ: 0.14 (6H, s), 0.97 (9H, s), 1.44 (3H, t, J=7 Hz), 4.44 (2H, m), 4.52 (2H, q, J=7 Hz), 6.58 (1H, dt, J=15 Hz, 4 Hz), 6.74 (1H, s), 6.78 (1H, m), 7.2-7.5 (5H, m), 8.41 (1H, s).

(v) Production of (2E)-3-[5-ethyl-4-({3-methyl-4-[(6-methylpyridin-3-yl)oxy]phenyl}amino)-5H-pyrrolo[3,2-d]pyrimidin-6-yl]-2-propen-1-ol A mixture of 6-((1E)-3-{[tert-butyl(dimethyl)silyl]oxy}-1-propenyl)-5-ethyl-4-phenoxy-5H-pyrrolo[3,2-d]pyrimidine (78 mg), 3-methyl-4-[(6-methylpyridin-3-yl)oxy]aniline (61.2 mg), pyridine hydrochloride (26 mg) and phenol (122 mg) was stirred with heating at 120° C. for 16 hrs. After cooling to room temperature, the mixture was diluted with dichloromethane (30 mL), and washed with saturated aqueous sodium hydrogen carbonate (20 mL). The organic layer was dried over magnesium sulfate and concentrated under reduced pressure. The residue was separated and purified by basic silica gel column chromatography (eluent, ethyl acetate:methanol=100:0→80:20) to give the title compound (32 mg) as a powder.
¹H-NMR (CDCl₃) δ: 1.46 (3H, t, J=7 Hz), 2.24 (3H, s), 2.53 (3H, s), 4.31 (2H, q, J=7 Hz), 4.42 (1H, dd, J=5 Hz, 2 Hz), 6.54 (1H, dt, J=15 Hz, 5 Hz), 6.66 (1H, s), 6.70 (1H, d, J=15 Hz), 6.88 (1H, d, J=8 Hz), 7.0-7.4 (4H, m), 8.20 (1H, d, J=2 Hz), 8.46 (1H, s).

Example 21

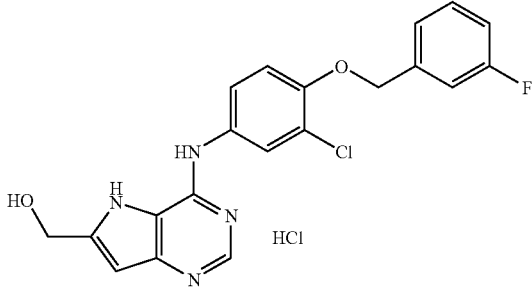

Production of [4-({3-chloro-4-[(3-fluorobenzyl)oxy]phenyl}amino)-5H-pyrrolo[3,2-d]pyrimidin-6-yl]methanol hydrochloride (i) Production of 3-(5-amino-6-phenoxypyrimidin-4-yl)-2-propyn-1-ol 4-Iodo-6-phenoxypyrimidin-5-amine (3.0 g) was dissolved in a mixed solvent of acetonitrile (159 mL)/triethylamine (117 mL), and 2-propyn-1-ol (0.669 mL), trans-dichlorobis(triphenylphosphine)palladium(II) (336 mg) and copper(I) iodide (109.5 mg) were sequentially added. The title compound (2.02 g) was obtained as crystals by the reaction in the same manner as in Example 9 (iv).
¹H-NMR (CDCl₃) δ: 3.53 (1H, br s), 4.52 (2H, br s), 4.63 (2H, br s), 7.1-7.5 (5H, m), 8.09 (1H, s).

(ii) Production of (4-phenoxy-5H-pyrrolo[3,2-d]pyrimidin-6-yl)methanol

The title compound (1.31 g) was obtained as crystals by the reaction in the same manner as in Example 9 (v) using 3-(5-amino-6-phenoxypyrimidin-4-yl)-2-propyn-1-ol (1.98 g) and copper(I) iodide (156 mg).
¹H-NMR (DMSO-d₆) δ: 4.67 (2H, d, J=5 Hz), 5.45 (1H, t, J=5 Hz), 6.50 (1H, s), 7.2-7.5 (5H, m), 8.26 (1H, s), 12.15 (1H, br s).

(iii) Production of [4-({3-chloro-4-[(3-fluorobenzyl)oxy]phenyl}amino)-5H-pyrrolo[3,2-d]pyrimidin-6-yl]methanol hydrochloride The title compound (142 mg) was obtained as crystals by the reaction in the same manner as in Example 1 using (4-phenoxy-5H-pyrrolo[3,2-d]pyrimidin-6-yl)methanol (100 mg), 3-chloro-4-[(3-fluorobenzyl)oxy]aniline (156 mg), pyridine hydrochloride (56.7 mg) and 1-methyl-2-pyrrolidone (0.828 mL).
¹H-NMR (DMSO-d₆) δ: 4.76 (2H, s), 5.27 (2H, s), 6.50 (1H, d, J=2 Hz), 7.1-7.6 (5H, m), 7.73 (1H, dd, J=3 Hz, 9 Hz), 8.12 (1H, d, J=3 Hz), 8.77 (1H, s), 11.50 (1H, br s).

Example 22

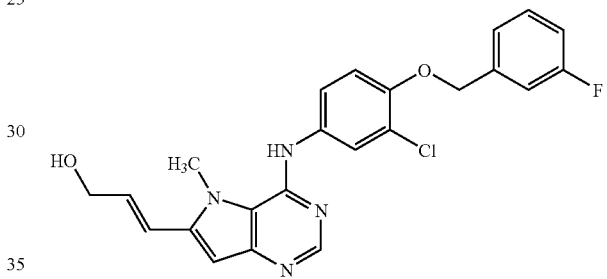

Production of (2E)-3-[4-({3-chloro-4-[(3-fluorobenzyl)oxy]phenyl}amino)-5-methyl-5H-pyrrolo[3,2-d]pyrimidin-6-yl]-2-propen-1-ol (i) Production of (2E)-5-(5-amino-6-phenoxypyrimidin-4-yl)-2-penten-4-yn-1-ol 4-Iodo-6-phenoxypyrimidin-5-amine (3.5 g) was dissolved in a mixed solvent of acetonitrile (185 mL)/triethylamine (136 mL), and 2-penten-4-yn-1-ol (1.1 g), trans-dichlorobis(triphenylphosphine)palladium(II) (392 mg) and copper(I) iodide (127 mg) were sequentially added. The title compound (1.79 g) was obtained as a powder by the reaction in the same manner as in Example 9 (iv).
¹H-NMR (CDCl₃) δ: 2.48 (1H, br s), 4.33 (2H, dd, J=5 Hz, 2 Hz), 4.45 (2H, br s), 6.12 (1H, dt, J=2 Hz, 16 Hz), 6.54 (1H, dt, J=16 Hz, 5 Hz), 7.1-7.5 (5H, m), 8.11 (1H, s).

(ii) Production of (2E)-3-(4-phenoxy-5H-pyrrolo[3,2-d]pyrimidin-6-yl)-2-propen-1-ol The title compound (1.25 g) was obtained as crystals by the reaction in the same manner as in Example 9 (v) using (2E)-5-(5-amino-6-phenoxypyrimidin-4-yl)-2-penten-4-yn-1-ol (1.7 g) and copper(I) iodide (268 mg).
¹H-NMR (CDCl₃) δ: 2.38 (1H, br s), 4.41 (2H, d, J=4 Hz), 6.58 (1H, dt, J=3 Hz, 16 Hz), 6.66 (1H, s), 6.75 (1H, d, J=16 Hz), 7.2-7.5 (5H, m), 8.48 (1H, s), 9.73 (1H, br s).

(iii) Production of (2E)-3-(4-phenoxy-5H-pyrrolo[3,2-d]pyrimidin-6-yl)-2-propenyl benzoate (2E)-3-(4-Phenoxy-5H-pyrrolo[3,2-d]pyrimidin-6-yl)-2-propen-1-ol (1.0 g) was suspended in tetrahydrofuran (20 mL), and triethylamine (0.651 mL) and benzoyl chloride (0.86 mL) were sequentially added under ice-cooling. The mixture was stirred under ice-cooling for 2 hrs, diluted with ethyl acetate (200 mL) and washed with water (50 mL). The organic layer was dried over magnesium sulfate and concentrated under reduced pressure. The residue was separated and purified by basic silica gel column chromatography (eluent, hexane:ethyl acetate=80:20→0:100) to give the title compound (1.08 g) as crystals.

$^1$H-NMR (CDCl$_3$) δ: 5.03 (2H, d, J=6 Hz), 6.52 (1H, m), 6.72 (1H, dt, J=16 Hz, 2 Hz), 6.80 (1H, d, J=16 Hz), 7.1-7.7 (8H, m), 8.08 (2H, m), 8.50 (1H, s), 9.27 (1H, br s).

(iv) Production of (2E)-3-(5-methyl-4-phenoxy-5H-pyrrolo[3,2-d]pyrimidin-6-yl)-2-propenyl benzoate (2E)-3-(4-Phenoxy-5H-pyrrolo[3,2-d]pyrimidin-6-yl)-2-propenyl benzoate (500 mg) was dissolved in N,N-dimethylformamide (4 mL), and potassium carbonate (279 mg) and iodomethane (0.1 mL) were sequentially added. After stirring at room temperature for 4 hrs, water (30 mL) was added to the reaction mixture and the mixture was extracted with ethyl acetate (100 mL), dried over magnesium sulfate and concentrated under reduced pressure. The residue was separated and purified by basic silica gel column chromatography (eluent, hexane:ethyl acetate=80:20→50:50) to give the title compound (301 mg) as crystals.

$^1$H-NMR (CDCl$_3$) δ: 4.14 (3H, s), 5.08 (2H, dd, J=6 Hz, 1 Hz), 6.66 (1H, m), 6.84 (1H, s), 6.85 (1H, d, J=16 Hz), 7.2-7.7 (8H, m), 8.10 (2H, d, J=9 Hz), 8.42 (1H, s).

(v) Production of (2E)-3-[4-({3-chloro-4-[(3-fluorobenzyl)oxy]phenyl}amino)-5-methyl-5H-pyrrolo[3,2-d]pyrimidin-6-yl]-2-propen-1-ol A mixture of (2E)-3-(5-methyl-4-phenoxy-5H-pyrrolo[3,2-d]pyrimidin-6-yl)-2-propenyl benzoate (100 mg), 3-chloro-4-[(3-fluorobenzyl)oxy]aniline (130 mg), pyridine hydrochloride (36 mg) and 1-methyl-2-pyrrolidone (0.518 mL) was stirred with heating at 140° C. for 4 hrs. After cooling to room temperature, aqueous sodium hydrogen carbonate (20 mL) was added to the reaction mixture and the mixture was extracted with ethyl acetate (100 mL). The organic layer was dried over magnesium sulfate and concentrated under reduced pressure. The residue was dissolved in tetrahydrofuran (0.518 mL)/ethanol (0.518 mL), 1N aqueous sodium hydroxide solution (0.518 mL) was added, and the mixture was stirred at room temperature for 2 hrs. Tetrahydrofuran/ethyl acetate (1:1, 50 mL) and saturated brine (30 mL) were added, and the mixture was extracted. The organic layer was dried over magnesium sulfate and concentrated under reduced pressure. The residue was separated and purified by basic silica gel column chromatography (eluent, ethyl acetate:methanol=100:0→85:15) to give the title compound (45 mg) as crystals.

$^1$H-NMR (DMSO-d$_6$) δ: 4.00 (3H, s), 4.21 (2H, t, J=4 Hz), 5.07 (1H, t, J=5 Hz), 5.23 (2H, s), 6.58 (1H, m), 6.68 (1H, s), 6.80 (1H, d, J=16 Hz), 7.1-7.8 (7H, m), 8.21 (1H, s), 8.49 (1H, br s).

Example 23

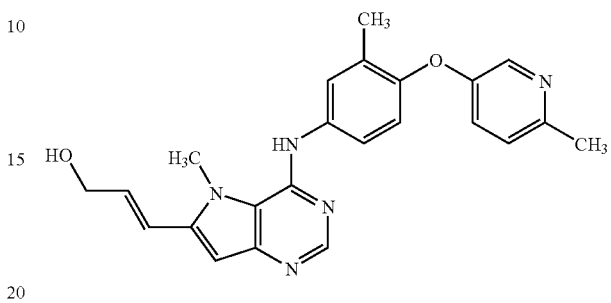

Production of (2E)-3-[5-methyl-4-({3-methyl-4-[(6-methylpyridin-3-yl)oxy]phenyl}amino)-5H-pyrrolo[3,2-d]pyrimidin-6-yl]-2-propen-1-ol The title compound (60 mg) was obtained as crystals by the reaction in the same manner as in Example 22 (v) using (2E)-3-(5-methyl-4-phenoxy-5H-pyrrolo[3,2-d]pyrimidin-6-yl)-2-propenyl benzoate (100 mg), 3-methyl-4-[(6-methylpyridin-3-yl)oxy]aniline (111 mg), pyridine hydrochloride (36 mg) and 1-methyl-2-pyrrolidone (0.518 mL).

$^1$H-NMR (DMSO-d$_6$) δ: 2.16 (3H, s), 2.43 (3H, s), 4.02 (3H, s), 4.22 (2H, br s), 5.07 (1H, t, J=5 Hz), 6.60 (1H, m), 6.69 (1H, s), 6.80 (1H, d, J=16 Hz), 6.93 (1H, d, J=9 Hz), 7.1-7.6 (5H, m), 8.16 (1H, d, J=2 Hz), 8.23 (1H, s), 8.54 (1H, br s).

Example 24

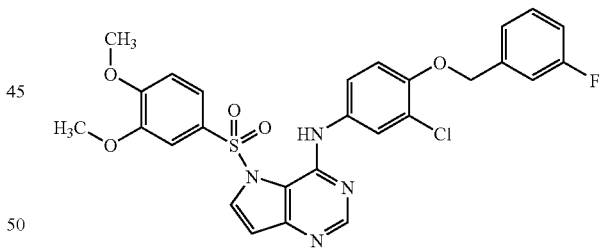

Production of N-{3-chloro-4-[(3-fluorobenzyl)oxy]phenyl}-5-[(3,4-dimethoxyphenyl)sulfonyl]-5H-pyrrolo[3,2-d]pyrimidin-4-amine N-{3-Chloro-4-[(3-fluorobenzyl)oxy]phenyl}-5H-pyrrolo[3,2-d]pyrimidin-4-amine hydrochloride (150 mg) was dissolved in N,N-dimethylformamide (1.5 mL), and potassium carbonate (102 mg) and (3,4-dimethoxyphenyl)sulfonyl chloride (96.9 mg) were sequentially added under ice-cooling. The mixture was stirred under ice-cooling for 2 hrs, and at room temperature for 1 hr. The mixture was diluted with ethyl acetate (50 mL) and washed twice with water (30 mL). The organic layer was dried over magnesium sulfate and concentrated under reduced pressure. The residue was separated and purified by silica gel column chromatography (eluent, hexane:ethyl acetate=80:20→0:100) to give the title compound (95 mg) as a powder.

$^1$H-NMR (CDCl$_3$) δ: 3.68 (3H, s), 3.86 (3H, s), 5.16 (2H, s), 6.76 (1H, d, J=4 Hz), 6.82 (1H, d, J=9 Hz), 6.97 (1H, d, J=9 Hz), 7.02 (1H, m), 7.1-7.4 (5H, m), 7.55 (1H, dd, J=9 Hz, 3 Hz), 7.79 (1H, d, J=4 Hz), 7.94 (1H, d, J=3 Hz), 8.52 (1H, s), 9.39 (1H, br s).

Example 25

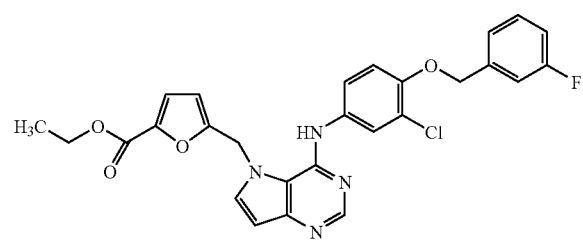

Production of ethyl 5-{[4-({3-chloro-4-[(3-fluorobenzyl)oxy]phenyl}amino)-5H-pyrrolo[3,2-d]pyrimidin-5-yl]methyl}-2-furoate (i) Production of ethyl 5-[(4-chloro-5H-pyrrolo[3,2-d]pyrimidin-5-yl)methyl]-2-furoate To a suspension of 4-chloro-5H-pyrrolo[3,2-d]pyrimidine (500 mg) in N,N-dimethylformamide (6.5 mL) was added potassium carbonate (541 mg) under ice-cooling, and the mixture was stirred for 15 min. while warming to room temperature. Ethyl 5-(chloromethyl)-2-furoate (737 mg) was added to the reaction mixture, and the mixture was stirred at room temperature for 16 hrs. The reaction mixture was diluted with water (20 mL), and extracted with a mixed solvent (40 mL×3) of ethyl acetate/tetrahydrofuran (1/1). The organic layer was washed with saturated brine (20 mL×3) and dried over anhydrous magnesium sulfate. The solvent was evaporated under reduced pressure, and the obtained residue was subjected to silica gel column chromatography (silica gel, eluent:hexane/ethyl acetate=80/20→10/90). The object fraction was concentrated under reduced pressure and dried to give the title compound (825 mg) as a pale-yellow solid.

$^1$H-NMR (CDCl$_3$) δ 1.37 (3H, t, J=7.2 Hz), 4.36 (2H, q, J=7.2 Hz), 5.75 (2H, s), 6.30 (1H, ddd, J=0.9, 2.1, 2.7 Hz), 6.80 (1H, t, J=3.9 Hz), 7.10 (1H, t, J=3.3 Hz), 7.63 (1H, dd, J=2.7, 3.3 Hz), 8.73 (1H, d, J=3.9 Hz).

(ii) Production of ethyl 5-{[4-({3-chloro-4-[(3-fluorobenzyl)oxy]phenyl}amino)-5H-pyrrolo[3,2-d]pyrimidin-5-yl]methyl}-2-furoate To a solution of ethyl 5-[(4-chloro-5H-pyrrolo[3,2-d]pyrimidin-5-yl)methyl]-2-furoate (200 mg) in 1-methyl-2-pyrrolidone (1.3 mL) was added 3-chloro-4-[(3-fluorobenzyl)oxy]aniline (247 mg), and the mixture was heated to 140° C. and stirred for 2 hrs. The reaction mixture was allowed to cool to room temperature, diluted with 5% aqueous sodium hydrogen carbonate solution (20 mL) and extracted with ethyl acetate (20 mL×3). The organic layer was washed with saturated brine and dried over anhydrous magnesium sulfate. The solvent was evaporated under reduced pressure, and the obtained residue was subjected to silica gel column chromatography (silica gel, eluent:ethyl acetate/methanol=10/0→8/2). The object fraction was concentrated under reduced pressure and dried to give the title compound (307 mg) as a pale-yellow solid.

$^1$H-NMR (CDCl$_3$) δ 1.34 (3H, t, J=7.2 Hz), 4.38 (2H, q, J=7.2 Hz), 5.14 (2H, s), 5.49 (2H, s), 6.45 (1H, d, J=3.4 Hz), 6.63 (1H, d, J=3.0 Hz), 6.94 (1H, d, J=8.8 Hz), 7.03 (1H, d, J=9.6 Hz), 7.26-7.38 (6H, m), 7.43 (1H, dd, J=2.6, 8.8 Hz), 7.65 (1H, d, J=3.0 Hz), 8.50 (1H, s).

Example 26

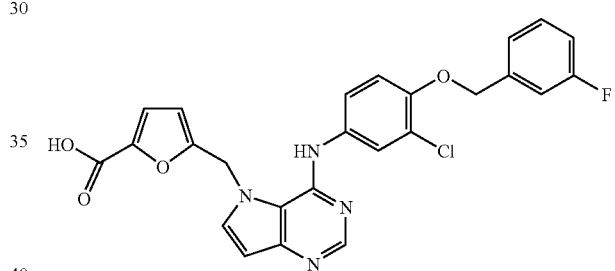

Production of 5-{[4-({3-chloro-4-[(3-fluorobenzyl)oxy]phenyl}amino)-5H-pyrrolo[3,2-d]pyrimidin-5-yl]methyl}-2-furancarboxylic acid To a solution of ethyl 5-{[4-({3-chloro-4-[(3-fluorobenzyl)oxy]phenyl}amino)-5H-pyrrolo[3,2-d]pyrimidin-5-yl]methyl}-2-furoate (280 mg) in a mixed solvent of tetrahydrofuran (1.34 mL) and ethanol (1.34 mL) was added 1N aqueous sodium hydroxide solution (1.34 mL) and the mixture was stirred at room temperature for 14 hrs. 1N Hydrochloric acid (1.34 mL) and water (10 mL) were added to the reaction mixture and the mixture was stirred at room temperature for 30 min. The resultant precipitate was collected by filtration, washed with water (10 mL×3) and diisopropyl ether (10 mL×3) and dried under reduced pressure (80° C.) to give the title compound (178 mg) as a white powder.

$^1$H-NMR (DMSO-d$_6$) δ 5.24 (2H, s), 5.89 (2H, s), 6.37 (1H, d, J=3.3 Hz), 6.54 (1H, d, J=2.7 Hz), 7.10 (1H, d, J=3.3 Hz), 7.21 (2H, d, J=9.0 Hz), 7.32 (2H, t, J=6.6 Hz), 7.48 (2H, t, J=8.1 Hz), 7.73 (2H, d, J=9.6 Hz), 8.29 (1H, s), 8.57 (1H, br s).

Example 27

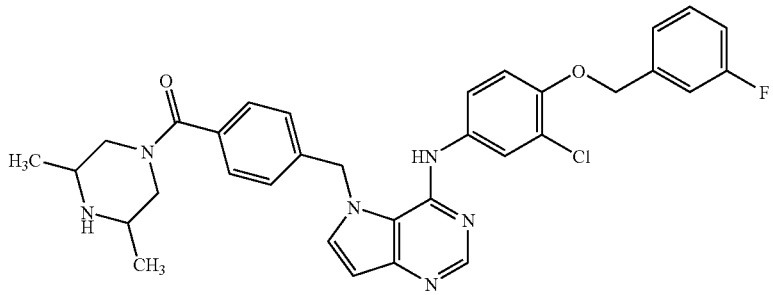

Production of N-{3-chloro-4-[(3-fluorobenzyl)oxy]phenyl}-5-{4-[(cis-3,5-dimethylpiperazin-1-yl)carbonyl]benzyl}-5H-pyrrolo[3,2-d]pyrimidin-4-amine To a solution of 4-{[4-({3-chloro-4-[(3-fluorobenzyl)oxy]phenyl}amino)-5H-pyrrolo[3,2-d]pyrimidin-5-yl]methyl}benzoic acid (120 mg) in N,N-dimethylformamide (2.4 mL) were added cis-2,6-dimethylpiperazine (95 mg) and 1H-1,2,3-benzotriazol-1-ol (65 mg), and the mixture was stirred at room temperature for 15 min. N-[3-(Dimethylamino)propyl]-N'-ethylcarbodiimide hydrochloride (92 mg) and triethylamine (0.2 mL) were added, and the mixture was stirred at room temperature for 12 hrs. The reaction mixture was diluted with water (20 mL) and extracted with ethyl acetate (25 mL×3). The organic layer was washed with saturated brine (20 mL×3) and dried over anhydrous magnesium sulfate. The solvent was evaporated under reduced pressure, and the obtained residue was subjected to silica gel column chromatography (basic silica gel, eluent:ethyl acetate/methanol=10/0→9/1). The object fraction was concentrated under reduced pressure. Chloroform/diisopropyl ether (3/7) was added to the residue and the resultant precipitate was collected by filtration and dried under reduced pressure to give the title compound (85 mg) as white powder crystals.

$^1$H-NMR (CDCl$_3$) δ 1.13 (6H, d, J=6.6 Hz), 1.66 (4H, br s), 2.69 (2H, br), 3.41 (1H, brd, J=6.6 Hz), 4.60 (1H, brd, J=13.5 Hz), 5.08 (2H, s), 5.56 (2H, s), 6.28 (1H, s), 6.68 (1H, dd, J=2.1, 5.4 Hz), 6.82 (1H, d, J=9.3 Hz), 7.00 (2H, dt, J=2.1, 8.7 Hz), 7.15-7.21 (4H, m), 7.25 (1H, d, J=2.4 Hz), 7.30-7.38 (4H, m), 7.48 (2H, d, J=8.4 Hz), 8.48 (1H, s).

Example 28

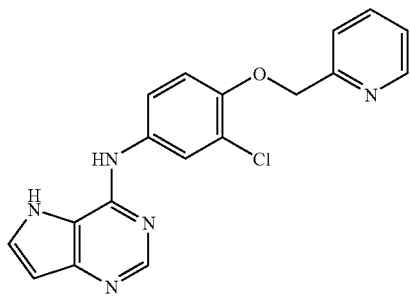

Production of N-[3-chloro-4-(pyridin-2-ylmethoxy)phenyl]-5H-pyrrolo[3,2-d]pyrimidin-4-amine To a solution of 4-chloro-5H-pyrrolo[3,2-d]pyrimidine (63 mg) in 1-methyl-2-pyrrolidone (0.8 mL), was added 3-chloro-4-(pyridin-2-ylmethoxy)aniline (149 mg), and the mixture was heated to 140° C. and stirred for 2 hrs. The reaction mixture was allowed to cool to room temperature, diluted with 5% aqueous sodium hydrogen carbonate solution (20 mL) and extracted with a mixed solvent (25 mL×3) of ethyl acetate/tetrahydrofuran (1/1). The organic layer was washed with saturated brine and dried over anhydrous magnesium sulfate. The solvent was evaporated under reduced pressure, and the obtained residue was subjected to silica gel column chromatography (basic silica gel, eluent:ethyl acetate/methanol=10/0→8/2). The object fraction was concentrated under reduced pressure. Chloroform/diisopropyl ether (1/9) was added to the residue, and the resultant precipitate was collected by filtration and dried under reduced pressure to give the title compound (112 mg) as pale-yellow powder crystals.

$^1$H-NMR (DMSO-d$_6$) δ 5.27 (2H, s), 6.48 (1H, d, J=2.4 Hz), 7.25 (1H, d, J=8.7 Hz), 7.37 (1H, dd, J=5.1, 7.5 Hz), 7.55-7.60 (2H, m), 7.66 (1H, s), 7.89 (1H, t, J=7.5 Hz), 8.20 (1H, dd, J=1.5, 2.4 Hz), 8.35 (1H, d, J=1.5 Hz), 8.60 (1H, dd, J=0.6, 4.8 Hz), 9.25 (1H, s), 12.78 (1H, s).

Example 29

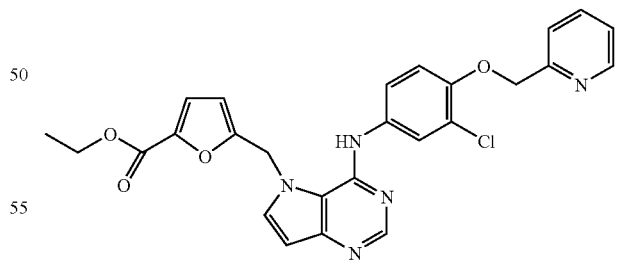

Production of ethyl 5-[(4-{[3-chloro-4-(pyridin-2-ylmethoxy)phenyl]amino}-5H-pyrrolo[3,2-d]pyrimidin-5-yl)methyl]-2-furoate To a solution of ethyl 5-[(4-chloro-5H-pyrrolo[3,2-d]pyrimidin-5-yl)methyl]-2-furoate (300 mg) in 1-methyl-2-pyrrolidone (2.0 mL) was added 3-chloro-4-(pyridin-2-ylmethoxy)aniline (360 mg), and the mixture was heated to 140° C. and stirred for 1.5 hrs. The reaction mixture was allowed to cool to room temperature, diluted with 5% aqueous sodium hydrogen carbonate solution (30 mL) and extracted with a mixed solvent (45 mL×3) of ethyl acetate/tetrahydrofuran (1/1). The organic layer was washed with saturated brine and dried over anhydrous magnesium sulfate. The solvent was evaporated under reduced pressure, and the obtained residue was subjected to silica gel column chromatography (basic silica gel, eluent:ethyl acetate/methanol=10/0→8/2). The object fraction was concentrated under reduced pressure. Chloroform/diisopropyl ether (1/9) was added to the residue, and the resultant precipitate was collected by filtration and dried under reduced pressure to give the title compound (440 mg) as pale-yellow powder crystals.

$^1$H-NMR (CDCl$_3$) δ 1.37 (3H, t, J=7.2 Hz), 4.36 (2H, q, J=7.2 Hz), 5.33 (2H, s), 5.91 (2H, s), 6.39 (1H, d, J=3.4 Hz), 6.57 (1H, d, J=2.6 Hz), 7.12 (1H, d, J=3.4 Hz), 7.23 (1H, d, J=9.0 Hz), 7.43 (1H, dd, J=4.8, 7.8 Hz), 7.50 (1H, dd, J=2.2, 9.2 Hz), 7.61 (1H, d, J=7.8 Hz), 7.75 (2H, s), 7.90 (1H, dt, J=1.2, 7.8 Hz), 8.14 (1H, d, J=4.8 Hz), 8.30 (1H, s), 8.55 (1H, br s).

Example 30

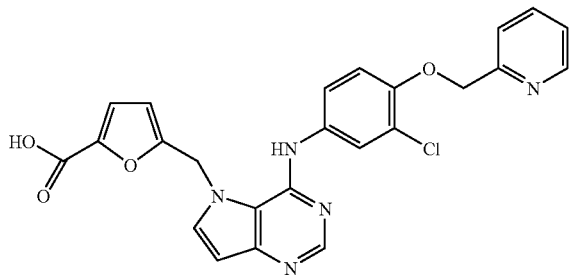

Production of 5-[(4-{[3-chloro-4-(pyridin-2-ylmethoxy)phenyl]amino}-5H-pyrrolo[3,2-d]pyrimidin-5-yl)methyl]-2-furancarboxylic acid To a solution of ethyl 5-[(4-{[3-chloro-4-(pyridin-2-ylmethoxy)phenyl]amino}-5H-pyrrolo[3,2-d]pyrimidin-5-yl) methyl]-2-furoate (440 mg) in a mixed solvent of tetrahydrofuran (2.0 mL) and ethanol (2.0 mL) was added 1N aqueous sodium hydroxide solution (2.0 mL), and the mixture was stirred at room temperature for 5 hrs. 1N Hydrochloric acid (2.0 mL) and water (25 mL) were added to the reaction mixture, and the mixture was stirred at room temperature for 30 min. The resultant precipitate was collected by filtration, washed with water (10 mL×3) and diisopropyl ether (10 mL×3), and dried under reduced pressure (80° C.) to give the title compound (310 mg) as white powder crystals.

$^1$H-NMR (DMSO-d$_6$) δ 5.27 (2H, s), 5.88 (2H, s), 6.35 (1H, d, J=3.4 Hz), 6.53 (1H, d, J=2.6 Hz), 7.08 (1H, d, J=3.4 Hz), 7.20 (1H, d, J=9.0 Hz), 7.37 (1H, dd, J=4.8, 7.8 Hz), 7.47 (1H, dd, J=2.2, 9.2 Hz), 7.58 (1H, d, J=7.8 Hz), 7.73 (2H, s), 7.88 (1H, t, J=1.2, 7.8 Hz), 8.27 (1H, s), 8.53 (1H, br s), 8.59 (1H, d, J=4.8 Hz).

Example 31

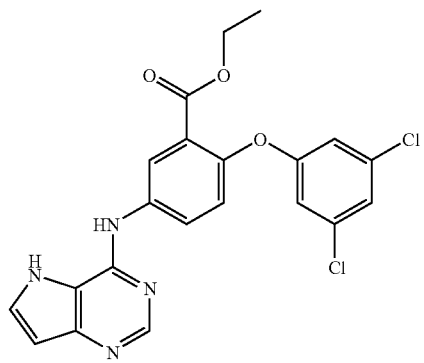

Production of ethyl 2-(3,5-dichlorophenoxy)-5-(5H-pyrrolo[3,2-d]pyrimidin-4-ylamino)benzoate To a solution of 4-chloro-5H-pyrrolo[3,2-d]pyrimidine (61 mg) in 1-methyl-2-pyrrolidone (0.8 mL), was added ethyl 5-amino-2-(3,5-dichlorophenoxy)benzoate (186 mg), and the mixture was heated to 140° C. and stirred for 2.5 hrs. The reaction mixture was allowed to cool to room temperature, diluted with 5% aqueous sodium hydrogen carbonate solution (20 mL), and extracted with a mixed solvent (25 mL×3) of ethyl acetate/tetrahydrofuran (1/1). The organic layer was washed with saturated brine and dried over anhydrous magnesium sulfate. The solvent was evaporated under reduced pressure, and the obtained residue was subjected to silica gel column chromatography (basic silica gel, eluent:hexane/ethyl acetate=8/2→0/10). The object fraction was concentrated under reduced pressure. Ethyl acetate was added to the residue, and the resultant precipitate was collected by filtration and dried under reduced pressure to give the title compound (149 mg) as pale-yellow powder crystals.

$^1$H-NMR (DMSO-d$_6$) δ 1.10 (3H, t, J=7.2 Hz), 4.18 (2H, q, J=7.2 Hz), 6.52 (1H, d, J=2.8 Hz), 6.90 (2H, t, J=3.0 Hz), 7.28 (1H, dd, J=1.8, 2.8 Hz), 7.33 (1H, dd, J=8.8 Hz), 7.71 (1H, d, J=2.8 Hz), 8.36 (2H, d, J=8.8 Hz), 8.39 (1H, d, J=1.8 Hz), 9.60 (1H, s), 11.15 (1H, s).

Example 32

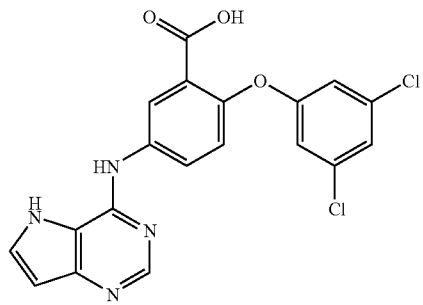

Production of 2-(3,5-dichlorophenoxy)-5-(5H-pyrrolo[3,2-d]pyrimidin-4-ylamino)benzoic acid To a solution of ethyl 2-(3,5-dichlorophenoxy)-5-(5H-pyrrolo[3,2-d]pyrimidin-4-ylamino)benzoate (100 mg) in a mixed solvent of tetrahydrofuran (0.68 mL) and ethanol (0.68 mL) was added 1N aqueous sodium hydroxide solution (0.68 mL), and the mixture was stirred at room temperature for 16 hrs. 1N Hydrochloric acid (0.68 mL) and water (5 mL) were added to the reaction mixture, and the mixture was stirred at room temperature for 30 min. The resultant precipitate was collected by filtration, washed with water (10 mL×3) and diisopropyl ether (10 mL×3) and dried under reduced pressure (80° C.) to give the title compound (76 mg) as white powder crystals.

$^1$H-NMR (DMSO-$d_6$) δ 6.52 (1H, d, J=1.2 Hz), 6.90 (2H, t, J=1.2 Hz), 7.28 (2H, dt, J=3.0, 5.1 Hz), 7.71 (1H, t, J=2.7 Hz), 8.29 (1H, dd, J=2.7, 8.7 Hz), 8.37 (1H, d, J=2.7 Hz), 8.40 (1H, d, J=1.2 Hz), 9.59 (1H, s), 11.18 (1H, br s).

Example 33

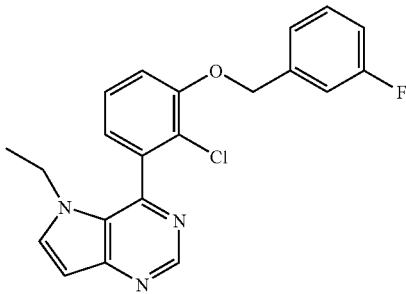

Production of N-{3-chloro-4-[(3-fluorobenzyl)oxy]phenyl}-5-ethyl-5H-pyrrolo[3,2-d]pyrimidin-4-amine (i) Production of 4-chloro-5-ethyl-5H-pyrrolo[3,2-d]pyrimidine To a suspension of 4-chloro-5H-pyrrolo[3,2-d]pyrimidine (200 mg) in N,N-dimethylformamide (1.3 mL) was added potassium carbonate (269 mg) under ice-cooling, and the mixture was stirred while warming to room temperature for 15 min. Iodoethane (305 mg) was added to the reaction mixture, and the mixture was stirred at room temperature for 3 hrs. The reaction mixture was diluted with water (20 mL) and extracted with ethyl acetate (30 mL×3). The organic layer was washed with saturated brine (20 mL×3) and dried over anhydrous magnesium sulfate. The solvent was evaporated under reduced pressure, and the obtained residue was subjected to silica gel column chromatography (silica gel, eluent:hexane/ethyl acetate=80/20→10/90). The object fraction was concentrated under reduced pressure and dried to give the title compound (187 mg) as a pale-yellow solid.

$^1$H-NMR (CDCl$_3$) δ 1.52 (3H, t, J=7.2 Hz), 4.55 (2H, q, J=7.2 Hz), 6.73 (1H, d, J=3.2 Hz), 7.51 (1H, d, J=3.2 Hz), 8.70 (1H, s).

(ii) Production of N-{3-chloro-4-[(3-fluorobenzyl)oxy]phenyl}-5-ethyl-5H-pyrrolo[3,2-d]pyrimidin-4-amine To a solution of 4-chloro-5-ethyl-5H-pyrrolo[3,2-d]pyrimidine (85 mg) in 1-methyl-2-pyrrolidone (0.94 mL) was added 3-chloro-4-[(3-fluorobenzyl)oxy]aniline (177 mg). The title compound (98 mg) was obtained as a pale-purple powder crystals by the reaction in the same manner as in Example 29.

$^1$H-NMR (CDCl$_3$) δ 1.56 (3H, t, J=7.4 Hz), 4.33 (2H, q, J=7.4 Hz), 5.15 (2H, s), 6.51 (1H, br s), 6.58 (1H, d, J=3.0 Hz), 6.72 (2H, s), 6.95 (1H, d, J=8.7 Hz), 7.02 (1H, m), 7.21 (1H, d, J=8.5 Hz), 7.25 (1H, d, J=3.0 Hz), 7.33-7.40 (2H, m), 7.60 (1H, d, J=2.5 Hz), 8.49 (1H, br s).

Example 34

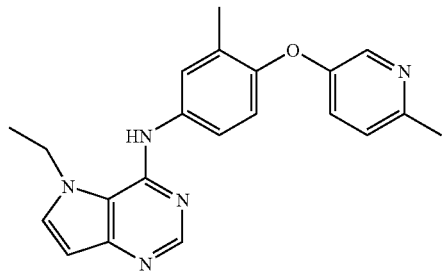

Production of 5-ethyl-N-{3-methyl-4-[(6-methylpyridin-3-yl)oxy]phenyl}-5H-pyrrolo[3,2-d]pyrimidin-4-amine To a solution of 4-chloro-5-ethyl-5H-pyrrolo[3,2-d]pyrimidine (85 mg) in 1-methyl-2-pyrrolidone (0.94 mL) was added 3-methyl-4-[(6-methylpyridin-3-yl)oxy]aniline (150 mg).

The title compound (67 mg) was obtained as white powder crystals by the reaction in the same manner as in Example 29.

$^1$H-NMR (CDCl$_3$) δ 1.57 (3H, t, J=7.4 Hz), 2.25 (3H, s), 2.53 (3H, s), 4.35 (2H, q, J=7.4 Hz), 6.58 (1H, d, J=3.0 Hz), 6.67 (1H, br s), 6.89 (1H, d, J=8.7 Hz), 7.08 (1H, d, J=8.5 Hz), 7.13 (1H, dd, J=3.0, 8.7 Hz), 7.25 (1H, d, J=3.0 Hz), 7.34 (1H, dd, J=2.6, 8.7 Hz), 7.42 (1H, d, J=2.5 Hz), 8.23 (1H, d, 1H, J=2.5 Hz), 8.50 (1H, s).

Example 35

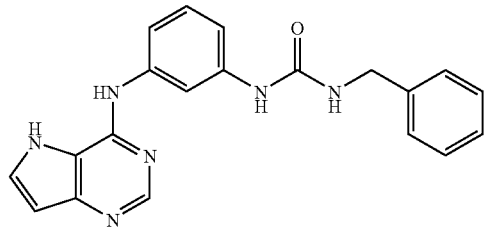

Production of N-benzyl-N'-[3-(5H-pyrrolo[3,2-d]pyrimidin-4-ylamino)phenyl]urea

To a solution of 4-chloro-5H-pyrrolo[3,2-d]pyrimidine (100 mg) in 1-methyl-2-pyrrolidone (1.3 mL), was added N-(3-aminophenyl)-N'-benzylurea (220 mg), and the mixture was heated to 140° C. and stirred for 1.5 hrs. The reaction mixture was allowed to cool to room temperature, diluted with 5% aqueous sodium hydrogen carbonate solution (20 mL), and extracted with a mixed solvent (30 mL×3) of ethyl acetate/tetrahydrofuran (1/1). The organic layer was washed with saturated brine and dried over anhydrous magnesium sulfate. The solvent was evaporated under reduced pressure, and the obtained residue was subjected to silica gel column chromatography (basic silica gel, eluent:ethyl acetate/methanol=100/0→85/15). The object fraction was concentrated under reduced pressure. Ethyl acetate was added to the residue, and the resultant precipitate was collected by filtration and dried under reduced pressure to give the title compound (97 mg) as pale-yellow powder crystals.

$^1$H-NMR (DMSO-$d_6$) δ 4.32 (2H, d, J=5.8 Hz), 6.47 (1H, s), 6.63 (1H, t, J=5.8 Hz), 7.02 (1H, d, J=8.4 Hz), 7.16-7.32 (6H, m), 7.62 (2H, d, J=8.4 Hz), 7.98 (1H, s), 8.33 (1H, s), 8.63 (1H, s), 9.15 (1H, s), 11.22 (1H, s).

Example 36

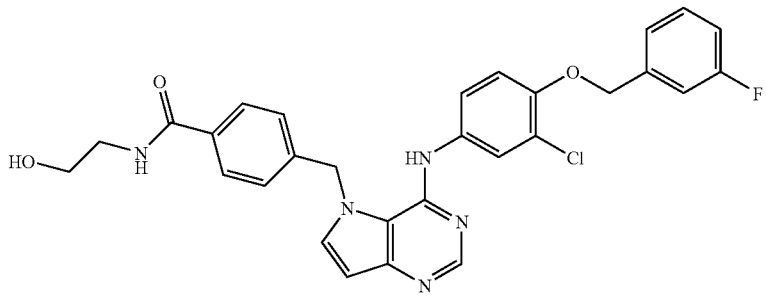

Production of 4-{[4-({3-chloro-4-[(3-fluorobenzyl)oxy]phenyl}amino)-5H-pyrrolo[3,2-d]pyrimidin-5-yl]methyl}-N-(2-hydroxyethyl)benzamide To a solution of 4-{[4-({3-chloro-4-[(3-fluorobenzyl)oxy]phenyl}amino)-5H-pyrrolo[3,2-d]pyrimidin-5-yl]methyl}benzoic acid (126 mg) in N,N-dimethylformamide (1.2 mL) were added N-[3-(dimethylamino)propyl]-N'-ethylcarbodiimide hydrochloride (72 mg) and 1-hydroxypyrrolidine-2,5-dione (43 mg), and the mixture was stirred at room temperature for 3 hrs. To this reaction mixture was added dropwise a solution of 2-aminoethanol (23 mg) in a mixed solvent of N,N-dimethylformamide (1.2 mL) and 10% aqueous sodium hydrogen carbonate (1.2 mL), and the mixture was stirred at room temperature for 48 hrs. The reaction mixture was diluted with water (25 mL) and extracted with ethyl acetate (25 mL×3). The organic layer was washed with saturated brine (25 mL×3), and dried over anhydrous magnesium sulfate. The solvent was evaporated under reduced pressure, and the obtained residue was subjected to silica gel column chromatography (basic silica gel, eluent:ethyl acetate/methanol=10/0→8/2). The object fraction was concentrated under reduced pressure. Chloroform/diisopropyl ether (1/4) was added to the residue, and the resultant precipitate was collected by filtration and dried under reduced pressure to give the title compound (105 mg) as white powder crystals.

$^1$H-NMR (DMSO-$d_6$) δ 3.27 (2H, t, J=5.9 Hz), 3.41-3.48 (2H, m), 4.68 (1H, t, J=5.9 Hz), 5.21 (2H, s), 5.84 (2H, s), 6.56 (1H, d, J=3.0 Hz), 7.06 (2H, d, J=8.1 Hz), 7.08 (2H, t, J=7.5 Hz), 7.27-7.35 (3H, m), 7.46 (1H, dt, J=5.8, 8.1 Hz), 7.64 (1H, d, J=2.5 Hz), 7.73 (2H, d, J=8.3 Hz), 7.82 (1H, d, J=3.0 Hz), 8.27 (2H, s), 8.33 (1H, t, J=5.4 Hz).

Example 37

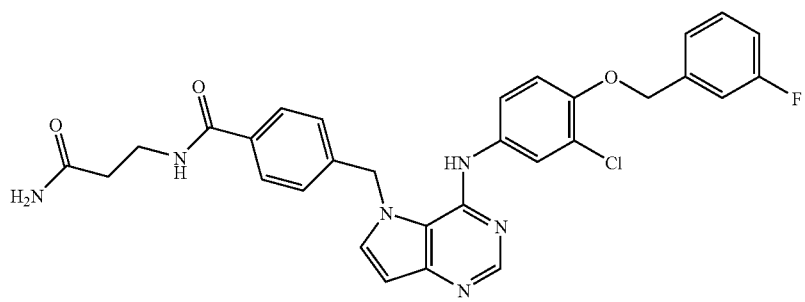

Production of N-(3-amino-3-oxopropyl)-4-{[4-({3-chloro-4-[(3-fluorobenzyl)oxy]phenyl}amino)-5H-pyrrolo[3,2-d]pyrimidin-5-yl]methyl}benzamide The title compound (83 mg) was obtained as white powder crystals by the reaction in the same manner as in Example 27 using 4-{[4-({3-chloro-4-[(3-fluorobenzyl)oxy]phenyl}amino)-5H-pyrrolo[3,2-d]pyrimidin-5-yl]methyl}benzoic acid (120 mg) and β-alaninamide hydrochloride (45 mg).

$^1$H-NMR (DMSO-$d_6$) δ 2.29 (1H, t, J=7.2 Hz), 3.37-3.42 (4H, m), 5.21 (2H, s), 5.83 (2H, s), 6.56 (1H, d, J=3.3 Hz), 6.80 (1H, br s), 7.06 (2H, d, J=8.3 Hz), 7.18 (2H, t, J=9.0 Hz), 7.29-7.34 (4H, m), 7.46 (1H, dt, J=5.8, 7.9 Hz), 7.63 (1H, d, J=2.4 Hz), 7.71 (2H, d, J=8.3 Hz), 7.81 (1H, d, J=3.2 Hz), 8.26 (1H, d, J=3.3 Hz), 8.40 (1H, t, J=5.7 Hz).

Example 38

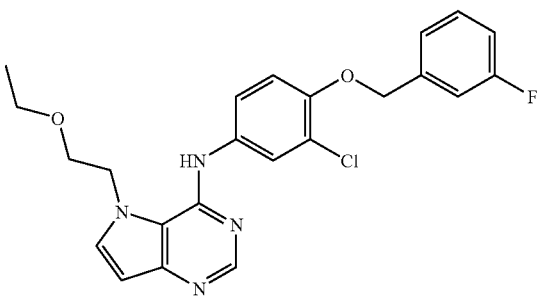

Production of N-{3-chloro-4-[(3-fluorobenzyl)oxy]phenyl}-5-(2-ethoxyethyl)-5H-pyrrolo[3,2-d]pyrimidin-4-amine (i) Production of 4-chloro-5-(2-ethoxyethyl)-5H-pyrrolo[3,2-d]pyrimidine To a suspension of 4-chloro-5H-pyrrolo[3,2-d]pyrimidine (500 mg) in N,N-dimethylformamide (4.5 mL) was added cesium carbonate (1324 mg) under ice-cooling, and the mixture was stirred while warming to room temperature for 15 min. 1-Bromo-2-ethoxyethane (1016 mg) was added to the reaction mixture, and the mixture was stirred at room temperature for 14 hrs. The reaction mixture was diluted with water (100 mL) and extracted with ethyl acetate (120 mL×3). The organic layer was washed with saturated brine (100 mL×3) and dried over anhydrous magnesium sulfate. The solvent was evaporated under reduced pressure, and the obtained residue was subjected to silica gel column chromatography (silica gel, eluent:hexane/ethyl acetate=85/15→20/80). The object fraction was concentrated under reduced pressure and dried to give the title compound (697 mg) as a pale-yellow oil.

$^1$H-NMR (CDCl$_3$) δ 1.13 (3H, t, J=6.9 Hz), 3.43 (2H, q, J=6.9 Hz), 3.78 (2H, t, J=5.1 Hz), 4.67 (2H, t, J=5.1 Hz), 6.71 (1H, d, J=3.0 Hz), 7.59 (1H, d, J=3.0 Hz), 8.70 (1H, s).

(ii) Production of N-{3-chloro-4-[(3-fluorobenzyl)oxy]phenyl}-5-(2-ethoxyethyl)-5H-pyrrolo[3,2-d]pyrimidin-4-amine To a solution of 4-chloro-5-(2-ethoxyethyl)-5H-pyrrolo[3,2-d]pyrimidine (90 mg) in 1-methyl-2-pyrrolidone (0.7 mL), 3-chloro-4-[(3-fluorobenzyl)oxy]aniline (151 mg) was added, and the mixture was heated to 140° C. and stirred for 7 hrs. The reaction mixture was allowed to cool to room temperature. The reaction mixture was diluted with 5% aqueous sodium hydrogen carbonate solution (20 mL) and extracted with ethyl acetate (25 mL×3). The organic layer was washed with saturated brine and dried over anhydrous magnesium sulfate. The solvent was evaporated under reduced pressure, and the obtained residue was subjected to silica gel column chromatography (basic silica gel, eluent:ethyl acetate/methanol=10/0→8/2). The object fraction was concentrated under reduced pressure. The residue was recrystallized from diisopropyl ether, collected by filtration and dried under reduced pressure to give the title compound (90 mg) as pale-yellow needle crystals.

$^1$H-NMR (CDCl$_3$) δ 1.22 (3H, t, J=7.0 Hz), 3.63 (2H, q, J=7.0 Hz), 3.90 (2H, t, J=4.4 Hz), 4.50 (2H, t, J=4.4 Hz), 5.13 (2H, s), 6.61 (1H, d, J=3.2 Hz), 6.94 (1H, d, J=8.9 Hz), 7.01 (1H, t, J=8.1 Hz), 7.17-7.25 (3H, m), 7.35 (1H, dt, J=5.6, 7.9 Hz), 7.47 (1H, dd, J=1.3, 8.9 Hz), 7.64 (1H, d, J=2.6 Hz), 8.48 (1H, s), 8.79 (1H, s).

Example 39

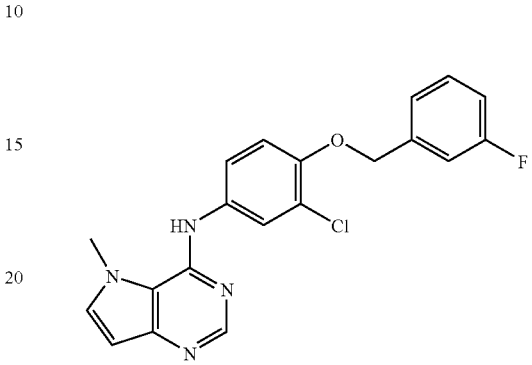

Production of N-{3-chloro-4-[(3-fluorobenzyl)oxy]phenyl}-5-methyl-5H-pyrrolo[3,2-d]pyrimidin-4-amine (i) Production of 4-chloro-5-methyl-5H-pyrrolo[3,2-d]pyrimidine To a suspension of 4-chloro-5H-pyrrolo[3,2-d]pyrimidine (320 mg) in N,N-dimethylformamide (2.0 mL), was added potassium carbonate (452 mg) under ice-cooling, and the mixture was stirred while warming to room temperature for 15 min. Iodomethane (444 mg) was added to the reaction mixture, and the mixture was stirred at room temperature for 3 hrs. The reaction mixture was diluted with water (25 mL) and extracted with ethyl acetate (30 mL×3). The organic layer was washed with saturated brine (20 mL×3) and dried over anhydrous magnesium sulfate. The solvent was evaporated under reduced pressure, and the obtained residue was subjected to silica gel column chromatography (silica gel, eluent: hexane/ethyl acetate=80/20→10/90). The object fraction was concentrated under reduced pressure and dried to give the title compound (325 mg) as a pale-yellow solid.

$^1$H-NMR (CDCl$_3$) δ 4.16 (3H, s), 6.70 (1H, d, J=3.9 Hz), 7.42 (1H, d, J=3.9 Hz), 8.69 (1H, s).

(ii) Production of N-{3-chloro-4-[(3-fluorobenzyl)oxy]phenyl}-5-methyl-5H-pyrrolo[3,2-d]pyrimidin-4-amine To a solution of 4-chloro-5-methyl-5H-pyrrolo[3,2-d]pyrimidine (100 mg) in 1-methyl-2-pyrrolidone (1.0 mL) was added 3-chloro-4-[(3-fluorobenzyl)oxy]aniline (225 mg), and the mixture was heated to 140° C. and stirred for 1.5 hrs. The reaction mixture was allowed to cool to room temperature, diluted with 5% aqueous sodium hydrogen carbonate solution (25 mL), and extracted with ethyl acetate (30 mL×3). The organic layer was washed with saturated brine and dried over anhydrous magnesium sulfate. The solvent was evaporated under reduced pressure, and the obtained residue was subjected to silica gel column chromatography (eluent:hexane/ethyl acetate=95/5→0/100). The object fraction was concentrated under reduced pressure. The residue was recrystallized from a mixed solvent of diisopropyl ether and chloroform, collected by filtration and dried under reduced pressure to give the title compound (121 mg) as a pale-purple powder crystals.

$^1$H-NMR (DMSO-$d_6$) δ 4.14 (3H, s), 5.24 (2H, s), 6.42 (1H, d, J=3.0 Hz), 7.16-7.23 (2H, m), 7.29-7.34 (2H, m), 7.44-7.56 (3H, m), 7.78 (1H, d, J=2.4 Hz), 8.24 (1H, s), 8.36 (1H, s).

Example 40

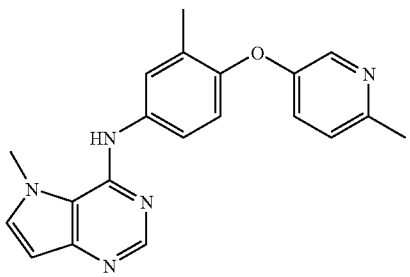

Production of 5-methyl-N-{3-methyl-4-[(6-methylpyridin-3-yl)oxy]phenyl}-5H-pyrrolo[3,2-d]pyrimidin-4-amine To a solution of 4-chloro-5-methyl-5H-pyrrolo[3,2-d]pyrimidine (100 mg) in 1-methyl-2-pyrrolidone (1.0 mL) was added 3-methyl-4-[(6-methylpyridin-3-yl)oxy]aniline (192 mg).

The title compound (106 mg) was obtained as white powder crystals by the reaction in the same manner as in Example 39 (ii).

$^1$H-NMR (DMSO-$d_6$) δ 2.17 (3H, s), 2.44 (3H, s), 4.15 (3H, s), 6.43 (1H, dd, J=0.9, 3.0 Hz), 6.94 (1H, d, J=8.4 Hz), 7.18 (1H, dd, J=3.0, 8.4 Hz), 7.24 (1H, d, J=8.7 Hz), 7.51 (1H, d, J=8.7 Hz), 7.56 (1H, d, J=3.0 Hz), 8.17 (1H, d, J=3.0 Hz), 8.25 (1H, d, J=0.9 Hz), 8.40 (1H, s), 8.63 (1H, s).

Example 41

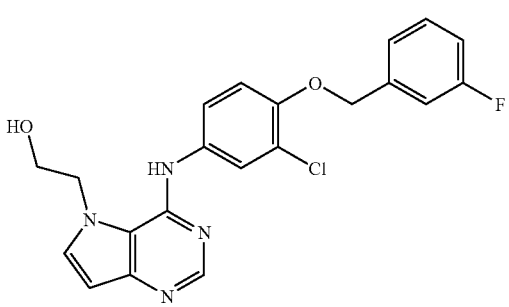

Production of 2-[4-({3-chloro-4-[(3-fluorobenzyl)oxy]phenyl}amino)-5H-pyrrolo[3,2-d]pyrimidin-5-yl]ethanol (i) Production of 5-(2-{[tert-butyl(dimethyl)silyl]oxy}ethyl)-4-chloro-5H-pyrrolo[3,2-d]pyrimidine To a suspension of 4-chloro-5H-pyrrolo[3,2-d]pyrimidine (307 mg) in N,N-dimethylformamide (2.0 mL) was added cesium carbonate (977 mg) under ice-cooling, and the mixture was stirred while warming to room temperature for 15 min. To the reaction mixture was added tert-butyl(2-iodoethoxy)dimethylsilane (839 mg), and the mixture was stirred at room temperature for 16 hrs. The reaction mixture was diluted with water (20 mL) and extracted with ethyl acetate (30 mL×3). The organic layer was washed with saturated brine (30 mL×3) and dried over anhydrous magnesium sulfate. The solvent was evaporated under reduced pressure, and the obtained residue was subjected to silica gel column chromatography (silica gel, eluent:hexane/ethyl acetate=85/15→10/90). The object fraction was concentrated under reduced pressure and dried to give the title compound (591 mg) as a white solid.

$^1$H-NMR (DMSO-$d_6$) δ 0.95 (9H, s), 4.10 (2H, t, J=5.2 Hz), 4.76 (2H, t, J=5.2 Hz), 6.87 (1H, d, J=3.0 Hz), 7.57 (1H, d, J=3.0 Hz), 8.85 (1H, s).

(ii) Production of 2-(4-chloro-5H-pyrrolo[3,2-d]pyrimidin-5-yl)ethanol

To a solution of 5-(2-{[tert-butyl(dimethyl)silyl]oxy}ethyl)-4-chloro-5H-pyrrolo[3,2-d]pyrimidine (560 mg) in tetrahydrofuran (1.7 mL), was added tetrabutylammonium fluoride (1M tetrahydrofuran solution) (2.69 mL) under ice-cooling, and the mixture was stirred for 4 hrs. The reaction mixture was diluted with water (20 mL) and extracted with ethyl acetate (30 mL×3). The organic layer was washed with saturated brine (30 mL×3) and dried over anhydrous magnesium sulfate. The solvent was evaporated under reduced pressure, and the obtained residue was subjected to silica gel column chromatography (silica gel, eluent:ethyl acetate/methanol=10/0→9/1). The object fraction was concentrated under reduced pressure and dried to give the title compound (391 mg) as a white solid.

$^1$H-NMR (CDCl$_3$) δ 2.13 (2H, td, J=6.3, 12.6 Hz), 4.66 (2H, t, J=6.3 Hz), 6.72 (1H, d, J=3.0 Hz), 7.57 (1H, d, J=3.0 Hz), 8.70 (1H, s).

(iii) Production of 2-[4-({3-chloro-4-[(3-fluorobenzyl)oxy]phenyl}amino)-5H-pyrrolo[3,2-d]pyrimidin-5-yl]ethanol To a solution of 2-(4-chloro-5H-pyrrolo[3,2-O]pyrimidin-5-yl)ethanol (130 mg) in 1-methyl-2-pyrrolidone (1.3 mL) was added 3-chloro-4-[(3-fluorobenzyl)oxy]aniline (193 mg), and the reaction mixture was stirred at 120° C. for 2 hrs. The reaction mixture was allowed to cool to room temperature and ethyl acetate (20 mL) was added. The resultant precipitate was recrystallized from a mixed solvent of hexane/methanol (3/7), collected by filtration and dried under reduced pressure to give the title compound (206 mg) as pale purple crystals.

$^1$H-NMR (DMSO-$d_6$) δ 3.86 (2H, t, J=4.3 Hz), 4.54 (2H, m), 5.24 (2H, s), 6.23 (1H, br s), 6.53 (1H, d, J=3.2 Hz), 7.18 (1H, dt, J=2.6, 8.1 Hz), 7.25 (1H, d, J=9.0 Hz), 7.29-7.34 (2H, m), 7.43-7.51 (2H, m), 7.70 (1H, d, J=3.2 Hz), 7.78 (1H, d, J=2.6 Hz), 8.37 (1H, br s), 9.82 (1H, br s).

Example 42

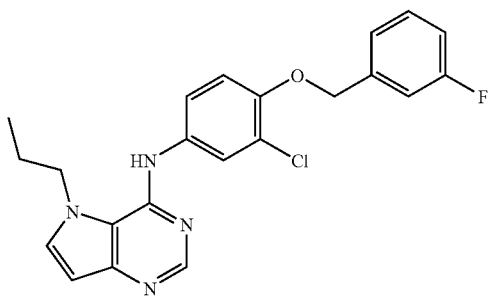

Production of N-{3-chloro-4-[(3-fluorobenzyl)oxy]phenyl}-5-propyl-5H-pyrrolo[3,2-d]pyrimidin-4-amine

(i) Production of 4-chloro-5-propyl-5H-pyrrolo[3,2-d]pyrimidine

To a suspension of 4-chloro-5H-pyrrolo[3,2-d]pyrimidine (150 mg) in N,N-dimethylformamide (1.6 mL) was added cesium carbonate (798 mg) under ice-cooling, and the mixture was stirred while warming to room temperature for 15 min. To the reaction mixture was added 1-bromopropane (301 mg), and the mixture was stirred at room temperature for 15 hrs. The reaction mixture was diluted with water (20 mL) and extracted with ethyl acetate (30 mL×3). The organic layer was washed with saturated brine (30 mL×3) and dried over anhydrous magnesium sulfate. The solvent was evaporated under reduced pressure, and the obtained residue was subjected to silica gel column chromatography (silica gel, eluent:hexane/ethyl acetate=90/10→20/80). The object fraction was concentrated under reduced pressure and dried to give the title compound (161 mg) as a white solid.

$^1$H-NMR (CDCl$_3$) δ 0.96 (3H, t, J=7.5 Hz), 1.86-1.98 (2H, m), 4.44 (2H, t, J=7.5 Hz), 6.73 (1H, t, J=3.3 Hz), 7.48 (1H, d, J=3.3 Hz), 8.70 (1H, s).

(ii) Production of N-{3-chloro-4-[(3-fluorobenzyl)oxy]phenyl}-5-propyl-5H-pyrrolo[3,2-d]pyrimidin-4-amine To a solution of 4-chloro-5-propyl-5H-pyrrolo[3,2-d]pyrimidine (80 mg) in 1-methyl-2-pyrrolidone (0.8 mL) was added 3-chloro-4-[(3-fluorobenzyl)oxy]aniline (193 mg), and the reaction mixture was stirred at 120° C. for 2 hrs. The reaction mixture was allowed to cool to room temperature, diluted with 5% aqueous sodium hydrogen carbonate solution (25 mL), and extracted with ethyl acetate (30 mL×3). The organic layer was washed with saturated brine and dried over anhydrous magnesium sulfate. The solvent was evaporated under reduced pressure, and the obtained residue was subjected to silica gel column chromatography (eluent:ethyl acetate/methanol=100/0→95/5). The object fraction was concentrated under reduced pressure. To the residue was added a mixed solvent of diisopropyl ether and chloroform. The resultant precipitate was collected by filtration and dried under reduced pressure to give the title compound (96 mg) as a pale-purple powder.

$^1$H-NMR (DMSO-d$_6$) δ 0.85 (3H, t, J=6.0 Hz), 1.81 (2H, q, J=6.9 Hz), 4.42 (2H, t, J=6.9 Hz), 5.18 (2H, s), 6.47 (1H, dd, J=1.8, 3.0 Hz), 7.02 (1H, d, J=8.7 Hz), 7.06 (1H, d, J=2.4 Hz), 7.21-7.49 (4H, m), 7.71 (1H, d, J=2.4 Hz), 7.77 (1H, br s), 8.07 (1H, br s), 8.34 (1H, d, J=2.1 Hz).

Example 43

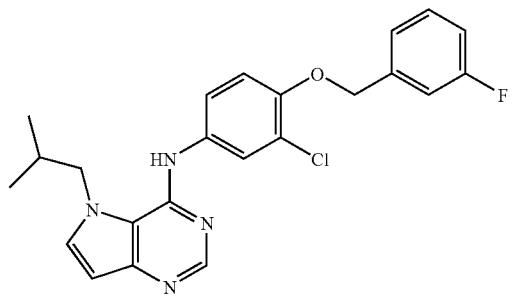

Production of N-{3-chloro-4-[(3-fluorobenzyl)oxy]phenyl}-5-isobutyl-5H-pyrrolo[3,2-d]pyrimidin-4-amine

(i) Production of 4-chloro-5-isobutyl-5H-pyrrolo[3,2-d]pyrimidine

To a suspension of 4-chloro-5H-pyrrolo[3,2-d]pyrimidine (150 mg) in N,N-dimethylformamide (1.6 mL) was added cesium carbonate (478 mg) under ice-cooling, and the mixture was stirred while warming to room temperature for 15 min. To the reaction mixture was added 1-bromo-2-methylpropane (336 mg), and the mixture was stirred at room temperature for 19 hrs. The reaction mixture was diluted with water (20 mL) and extracted with ethyl acetate (30 mL×3). The organic layer was washed with saturated brine (30 mL×3) and dried over anhydrous magnesium sulfate. The solvent was evaporated under reduced pressure, and the obtained residue was subjected to silica gel column chromatography (silica gel, eluent:hexane/ethyl acetate=90/10→20/80). The object fraction was concentrated under reduced pressure and dried to give the title compound (210 mg) as a white solid.

$^1$H-NMR (CDCl$_3$) δ 0.94 (6H, d, J=6.6 Hz), 2.14-2.27 (1H, m), 4.26 (2H, d, J=7.5 Hz), 6.72 (1H, d, J=2.4 Hz), 7.46 (1H, d, J=2.4 Hz), 8.70 (1H, s).

(ii) Production of N-{3-chloro-4-[(3-fluorobenzyl)oxy]phenyl}-5-isobutyl-5H-pyrrolo[3,2-d]pyrimidin-4-amine The title compound (89 mg) was obtained as a pale-purple powder by the reaction in the same manner as in Example 42 (ii) using a solution of 4-chloro-5-isobutyl-5H-pyrrolo[3,2-d]pyrimidine (90 mg) in 1-methyl-2-pyrrolidone (0.8 mL).

$^1$H-NMR (DMSO-d$_6$) δ 0.83 (6H, d, J=6.3 Hz), 2.08 (1H, m), 4.24 (2H, d, J=7.5 Hz), 5.17 (2H, s), 6.47 (1H, d, J=2.7 Hz), 7.02 (2H, d, J=8.7 Hz), 7.22-7.29 (2H, m), 7.32 (1H, d,

J=3.0 Hz), 7.40 (1H, dt, J=6.0, 8.1 Hz), 7.46 (1H, dd, J=2.7, 9.0 Hz), 7.73 (1H, d, J=2.7 Hz), 7.79 (1H, s), 8.09 (1H, br s).

Example 44

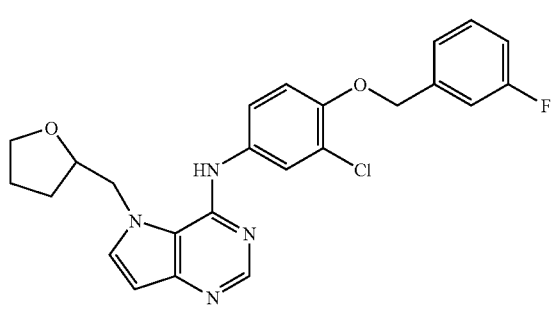

Production of N-{3-chloro-4-[(3-fluorobenzyl)oxy]phenyl}-5-(tetrahydrofuran-2-ylmethyl)-5H-pyrrolo[3,2-d]pyrimidin-4-amine (i) Production of 4-chloro-5-(tetrahydrofuran-2-ylmethyl)-5H-pyrrolo[3,2-d]pyrimidine To a suspension of 4-chloro-5H-pyrrolo[3,2-d]pyrimidine (150 mg) in N,N-dimethylformamide (1.0 mL) was added cesium carbonate (478 mg) under ice-cooling, and the mixture was stirred while warming to room temperature for 15 min. To the reaction mixture was added 2-(bromomethyl)tetrahydrofuran (242 mg), and the mixture was stirred at room temperature for 26 hrs. The reaction mixture was diluted with water (20 mL) and extracted with ethyl acetate (30 mL×3). The organic layer was washed with saturated brine (30 mL×3) and dried over anhydrous magnesium sulfate. The solvent was evaporated under reduced pressure, and the obtained residue was subjected to silica gel column chromatography (silica gel, eluent:hexane/ethyl acetate=90/10→20/80). The object fraction was concentrated under reduced pressure and dried to give the title compound (200 mg) as a colorless oil.

$^1$H-NMR (CDCl$_3$) δ 1.47-1.64 (1H, m), 1.85-2.17 (3H, m), 3.75-3.90 (2H, m), 4.18-4.31 (1H, m), 4.42-4.53 (1H, m), 4.71 (1H, dd, J=3.4, 14.6 Hz), 6.74 (1H, d, J=3.0 Hz), 7.63 (1H, d, J=3.0 Hz), 8.70 (1H, s).

(ii) Production of N-{3-chloro-4-[(3-fluorobenzyl)oxy]phenyl}-5-(tetrahydrofuran-2-ylmethyl)-5H-pyrrolo[3,2-d]pyrimidin-4-amine The title compound (139 mg) was obtained as white powder by the reaction in the same manner as in Example 42 (ii) using a solution of 4-chloro-5-(tetrahydrofuran-2-ylmethyl)-5H-pyrrolo[3,2-d]pyrimidine (200 mg) in 1-methyl-2-pyrrolidone (1.6 mL).

$^1$H-NMR (DMSO-d$_6$) δ 1.56-1.65 (2H, m), 1.78-1.80 (1H, m), 1.97-2.07 (1H, m), 3.70 (2H, m), 4.17-4.19 (1H, m), 4.43 (1H, dd, J=6.0, 15.0 Hz), 4.67 (1H, d, J=13.8 Hz), 5.21 (2H, s), 7.14 (1H, dd, J=8.1 Hz), 7.20 (1H, d, J=8.1 Hz), 7.27-7.48 (4H, m), 7.61 (1H, d, J=2.1 Hz), 7.78 (1H, d, J=1.5 Hz), 8.25 (1H, d, J=1.2 Hz), 8.60 (1H, d, J=1.2 Hz), 9.03 (1H, s).

Example 45

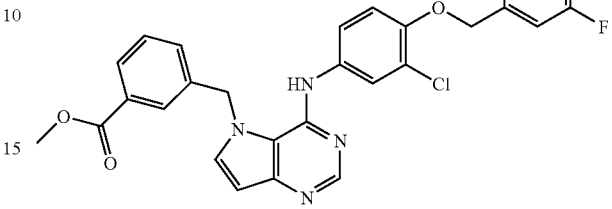

Production of methyl 3-{[4-({3-chloro-4-[(3-fluorobenzyl)oxy]phenyl}amino)-5H-pyrrolo[3,2-d]pyrimidin-5-yl]methyl}benzoate (i) Production of methyl 3-[(4-chloro-5H-pyrrolo[3,2-d]pyrimidin-5-yl)methyl]benzoate To a suspension of 4-chloro-5H-pyrrolo[3,2-d]pyrimidine (300 mg) in N,N-dimethylformamide (2.0 mL) was added cesium carbonate (955 mg) under ice-cooling, and the mixture was stirred while warming to room temperature for 15 min. To the reaction mixture was added methyl 3-(bromomethyl)benzoate (671 mg), and the mixture was stirred at room temperature for 4 hrs. The reaction mixture was diluted with water (40 mL), and extracted with a mixed solvent (40 mL×3) of ethyl acetate/tetrahydrofuran (1/1). The organic layer was washed with saturated brine (120 mL×3) and dried over anhydrous magnesium sulfate. The solvent was evaporated under reduced pressure, and the obtained residue was subjected to silica gel column chromatography (silica gel, eluent:hexane/ethyl acetate=80/20→10/90). The object fraction was concentrated under reduced pressure. Chloroform/diisopropyl ether (4/1) was added to the residue, and the resultant precipitate was collected by filtration, washed and dried under reduced pressure to give the title compound (319 mg) as a pale-brown powder.

$^1$H-NMR (CDCl$_3$) δ 3.90 (3H, s), 5.77 (2H, s), 6.82 (1H, d, J=3.4 Hz), 7.19 (1H, dd, J=1.2, 7.8 Hz), 7.41 (1H, t, J=7.8 Hz), 7.54 (1H, d, J=3.4 Hz), 7.82 (1H, s), 7.98 (1H, dt, J=1.2, 7.8 Hz), 8.73 (1H, s).

(ii) Production of methyl 3-{[4-({3-chloro-4-[(3-fluorobenzyl)oxy]phenyl}amino)-5H-pyrrolo[3,2-d]pyrimidin-5-yl]methyl}benzoate To a solution of methyl 3-[(4-chloro-5H-pyrrolo[3,2-d]pyrimidin-5-yl)methyl]benzoate (670 mg) in 1-methyl-2-pyrrolidone (3.0 mL) was added 3-chloro-4-[(3-fluorobenzyl)oxy]aniline (549 mg), and the reaction mixture was stirred at 120° C. for 1.5 hrs. The reaction mixture was allowed to cool to room temperature, diluted with 5% aqueous sodium hydrogen carbonate solution (50 mL), and extracted with ethyl acetate (50 mL×3). The organic layer was washed with saturated brine and dried over anhydrous magnesium sulfate. The solvent was evaporated under reduced pressure, and the obtained residue was subjected to silica gel column chromatography (basic silica gel, eluent:hexane/ethyl acetate=9/1→0/10). The object fraction was concentrated under reduced pressure and dried to give the title compound (1010 mg) as a yellow oil.

¹H-NMR (CDCl₃) δ 3.93 (3H, s), 5.08 (2H, s), 5.60 (2H, s), 6.39 (1H, s), 6.67 (1H, d, J=3.4 Hz), 6.82 (1H, d, J=9.2 Hz), 7.01 (2H, dd, J=2.6, 8.8 Hz), 7.16-7.40 (3H, m), 7.56 (1H, t, J=7.8 Hz), 7.94 (1H, s), 8.09 (1H, d, J=7.8 Hz), 8.47 (1H, s).

Example 46

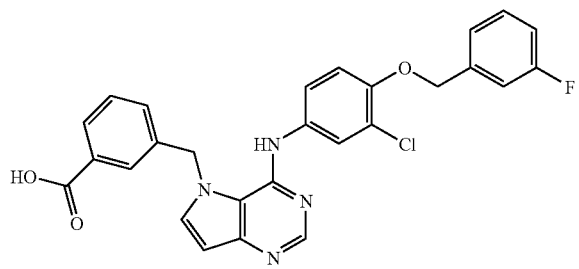

Production of 3-{[4-({3-chloro-4-[(3-fluorobenzyl)oxy]phenyl}amino)-5H-pyrrolo[3,2-d]pyrimidin-5-yl]methyl}benzoic acid To a solution of methyl 3-{[4-({3-chloro-4-[(3-fluorobenzyl)oxy]phenyl}amino)-5H-pyrrolo[3,2-d]pyrimidin-5-yl]methyl}benzoate (800 mg) in a mixed solvent of tetrahydrofuran (4.0 mL) and methanol (4.0 mL) was added 1N aqueous sodium hydroxide solution (4.0 mL), and the mixture was stirred at room temperature for 12 hrs. 1N Hydrochloric acid (4.0 mL) and water (15 mL) were added to the reaction mixture, and the mixture was stirred at room temperature for 30 min. The resultant precipitate was collected by filtration, washed with water (10 mL×3) and diisopropyl ether (10 mL×3) and dried under reduced pressure (80° C.) to give the title compound (610 mg) as a white powder.

¹H-NMR (DMSO-d₆) δ 5.21 (2H, s), 5.86 (2H, s), 6.57 (1H, dd, J=1.5, 3.3 Hz), 7.14-7.51 (8H, m), 7.58 (1H, dd, J=1.5, 2.4 Hz), 7.69 (1H, s), 7.78 (1H, d, J=6.3 Hz), 7.84 (1H, d, J=1.8 Hz), 8.27 (1H, d, J=1.5 Hz), 8.30 (1H, s).

Example 47

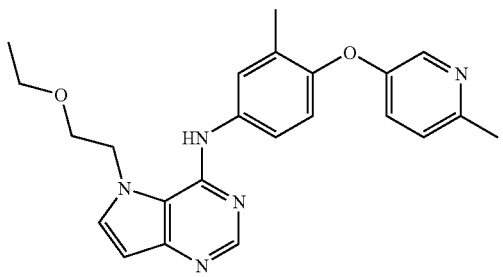

Production of 5-(2-ethoxyethyl)-N-{3-methyl-4-[(6-methylpyridin-3-yl)oxy]phenyl}-5H-pyrrolo[3,2-d]pyrimidin-4-amine To a solution of 4-chloro-5-(2-ethoxyethyl)-5H-pyrrolo[3,2-d]pyrimidine (160 mg) in 1-methyl-2-pyrrolidone (1.4 mL) was added 3-methyl-4-[(6-methylpyridin-3-yl)oxy]aniline (228 mg), and the reaction mixture was stirred at 120° C. for 2 hrs. The reaction mixture was allowed to cool to room temperature, diluted with 5% aqueous sodium hydrogen carbonate solution (25 mL), and extracted with ethyl acetate (40 mL×3). The organic layer was washed with saturated brine and dried over anhydrous magnesium sulfate. The solvent was evaporated under reduced pressure, and the obtained residue was subjected to silica gel column chromatography (eluent:hexane/ethyl acetate=90/10→0/100). The object fraction was concentrated under reduced pressure and dried to give the title compound (191 mg) as a colorless transparent oil.

¹H-NMR (CDCl₃) δ 1.25 (3H, dt, J=2.1, 7.2 Hz), 2.14 (3H, s), 2.52 (3H, s), 3.65 (2H, q, J=7.2 Hz), 3.92 (2H, t, J=4.5 Hz), 4.54 (2H, t, J=4.5 Hz), 6.62 (1H, d, J=3.0 Hz), 6.91 (1H, d, J=8.4 Hz), 7.11 (1H, dd, J=2.7, 8.4 Hz), 7.20 (1H, d, J=3.0 Hz), 7.40 (1H, dd, J=2.7, 8.4 Hz), 7.51 (1H, d, J=3.0 Hz), 8.26 (1H, dd, J=0.6, 2.7 Hz), 8.50 (1H, s), 8.84 (1H, br s).

Example 48

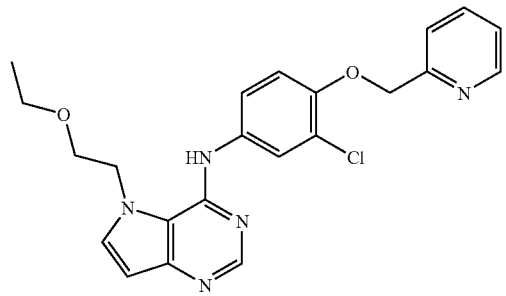

Production of N-[3-chloro-4-(pyridin-2-ylmethoxy)phenyl]-5-(2-ethoxyethyl)-5H-pyrrolo[3,2-d]pyrimidin-4-amine To a solution of 4-chloro-5-(2-ethoxyethyl)-5H-pyrrolo[3, 2-d]pyrimidine (160 mg) in 1-methyl-2-pyrrolidone (1.4 mL) was added 3-chloro-4-(pyridin-2-ylmethoxy)aniline (250 mg). The title compound (160 mg) was obtained as pale-yellow needle crystals by the reaction in the same manner as in Example 42 (ii).

¹H-NMR (CDCl₃) δ 1.23 (3H, t, J=7.2 Hz), 3.64 (2H, q, J=7.2 Hz), 3.91 (2H, t, J=7.2 Hz), 4.51 (2H, t, J=7.2 Hz), 5.27 (2H, s), 6.12 (1H, s), 6.61 (1H, d, J=3.3 Hz), 6.97 (1H, d, J=8.7 Hz), 7.18 (1H, d, J=3.3 Hz), 7.42 (1H, dd, J=2.7, 8.7 Hz), 7.66 (1H, s), 7.69 (1H, d, J=2.1 Hz), 7.76 (1H, dt, J=1.5, 8.7 Hz), 8.49 (1H, s), 8.60 (1H, d, J=4.5 Hz), 8.81 (1H, s).

Example 49

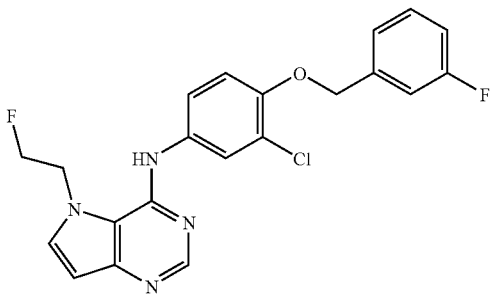

Production of N-{3-chloro-4-[(3-fluorobenzyl)oxy]phenyl}-5-(2-fluoroethyl)-5H-pyrrolo[3,2-d]pyrimidin-4-amine

(i) Production of 4-chloro-5-(2-fluoroethyl)-5H-pyrrolo[3,2-d]pyrimidine

To a suspension of 4-chloro-5H-pyrrolo[3,2-d]pyrimidine (100 mg) in N,N-dimethylformamide (0.6 mL) was added cesium carbonate (281 mg) under ice-cooling, and the mixture was stirred while warming to room temperature for 15 min. To the reaction mixture was added 1-bromo-2-fluoroethane (124 mg), and the mixture was stirred at room temperature for 5 hrs. The reaction mixture was diluted with water (20 mL) and extracted with ethyl acetate (20 mL×3). The organic layer was washed with saturated brine (20 mL×3) and dried over anhydrous magnesium sulfate. The solvent was evaporated under reduced pressure, and the obtained residue was subjected to silica gel column chromatography (silica gel, eluent:hexane/ethyl acetate=90/10→0/10). The object fraction was concentrated under reduced pressure and dried to give the title compound (110 mg) as a colorless transparent oil.

$^1$H-NMR (CDCl$_3$) δ 4.64-4.69 (1H, m), 4.75-4.79 (1H, m), 4.91 (2H, d, J=5.1 Hz), 6.77 (1H, dd, J=1.4, 3.4 Hz), 7.57 (1H, d, J=3.4 Hz), 8.73 (1H, s).

(ii) Production of N-{3-chloro-4-[(3-fluorobenzyl)oxy]phenyl}-5-(2-fluoroethyl)-5H-pyrrolo[3,2-d]pyrimidin-4-amine The title compound (124 mg) was obtained as white powder crystals by the reaction in the same manner as in Example 39 (ii) using a solution of 4-chloro-5-(2-fluoroethyl)-5H-pyrrolo[3,2-d]pyrimidine (110 mg) in 1-methyl-2-pyrrolidone (1.0 mL).

$^1$H-NMR (CDCl$_3$) δ 4.65 (2H, dt, J=4.0, 29.0 Hz), 4.90 (2H, dt, J=4.0, 47.2 Hz), 5.14 (2H, s), 6.65 (1H, d, J=3.0 Hz), 6.93 (1H, d, J=8.8 Hz), 7.04 (1H, d, J=8.8 Hz), 7.21-7.41 (6H, m), 7.55 (1H, s), 8.48 (1H, s).

Example 50

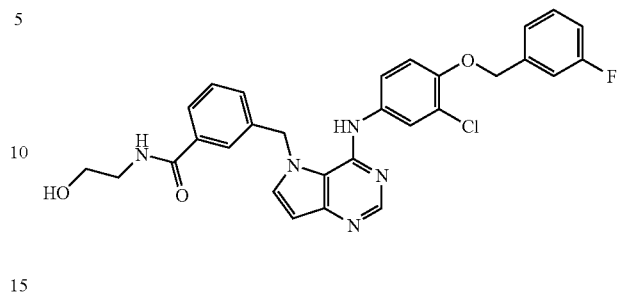

Production of 3-{[4-({3-chloro-4-[(3-fluorobenzyl)oxy]phenyl}amino)-5H-pyrrolo[3,2-d]pyrimidin-5-yl]methyl}-N-(2-hydroxyethyl)benzamide The title compound (93 mg) was obtained as white powder crystals by the reaction in the same manner as in Example 36 using 3-{[4-({3-chloro-4-[(3-fluorobenzyl)oxy]phenyl}amino)-5H-pyrrolo[3,2-d]pyrimidin-5-yl]methyl}benzoic acid (126 mg).

$^1$H-NMR (DMSO-d$_6$) δ 3.26-3.48 (4H, m), 4.71 (1H, t, J=5.6 Hz), 5.21 (2H, s), 5.83 (2H, s), 6.55 (1H, d, J=2.6 Hz), 7.06-7.52 (7H, m), 7.61-7.72 (4H, m), 7.80 (1H, d, J=3.2 Hz), 8.26 (2H, s), 8.39 (1H, m).

Example 51

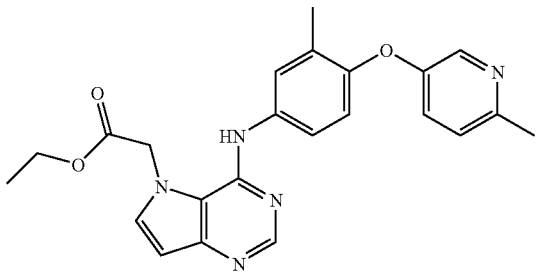

Production of ethyl [4-({3-methyl-4-[(6-methylpyridin-3-yl)oxy]phenyl}amino)-5H-pyrrolo[3,2-d]pyrimidin-5-yl]acetate

(i) Production of ethyl (4-chloro-5H-pyrrolo[3,2-d]pyrimidin-5-yl)acetate

To a suspension of 4-chloro-5H-pyrrolo[3,2-d]pyrimidine (200 mg) in N,N-dimethylformamide (1.3 mL) was added cesium carbonate (615 mg) under ice-cooling, and the mixture was stirred while warming to room temperature for 15 min. To the reaction mixture was added ethyl bromoacetate (326 mg), and the mixture was stirred at room temperature for 2.5 hrs. The reaction mixture was diluted with water (20 mL) and extracted with ethyl acetate (20 mL×3). The organic layer was washed with saturated brine (20 mL×3) and dried over anhydrous magnesium sulfate. The solvent was evaporated under reduced pressure, and the obtained residue was subjected to silica gel column chromatography (silica gel, eluent: hexane/ethyl acetate=90/10→0/10). The object fraction was concentrated under reduced pressure and dried to give the title compound (210 mg) as white powder crystals.

$^1$H-NMR (DMSO-d$_6$) δ 1.29 (3H, t, J=7.2 Hz), 4.27 (2H, q, J=7.2 Hz), 5.21 (2H, s), 6.80 (1H, d, J=3.3 Hz), 7.45 (1H, d, J=3.3 Hz), 8.74 (1H, s).

(ii) Production of ethyl [4-({3-methyl-4-[(6-methylpyridin-3-yl)oxy]phenyl}amino)-5H-pyrrolo[3,2-d]pyrimidin-5-yl]acetate To a solution of ethyl (4-chloro-5H-pyrrolo[3,2-d]pyrimidin-5-yl)acetate (140 mg) in isopropyl alcohol (0.6 mL) was added 3-methyl-4-[(6-methylpyridin-3-yl)oxy]aniline (188 mg), and the mixture was stirred in an oil bath at a temperature of 110° C. for 2 hrs. The reaction mixture was allowed to cool to room temperature, diluted with 5% aqueous sodium hydrogen carbonate solution (20 mL) and extracted with ethyl acetate (25 mL×3). The organic layer was washed with saturated brine and dried over anhydrous magnesium sulfate. The solvent was evaporated under reduced pressure, and the obtained residue was subjected to silica gel column chromatography (basic silica gel, eluent:ethyl acetate/methanol=10/0→9/1). The object fraction was concentrated under reduced pressure. Diisopropyl ether was added to the residue, and the resultant precipitate was collected by filtration and dried under reduced pressure to give the title compound (210 mg) as white powder crystals.

$^1$H-NMR (CDCl$_3$) δ 1.35 (3H, t, J=7.0 Hz), 2.25 (3H, s), 2.53 (3H, s), 4.35 (2H, q, J=7.0 Hz), 4.96 (2H, s), 6.64 (1H, d, J=3.4 Hz), 6.90 (1H, d, J=8.8 Hz), 7.08 (1H, d, J=1.8 Hz), 7.09 (1H, d, J=2.6 Hz), 7.22 (1H, d, J=3.4 Hz), 7.37 (1H, d, J=8.8 Hz), 7.44 (1H, d, J=2.6 Hz), 8.17 (1H, br s), 8.26 (1H, d, J=1.8 Hz), 8.53 (1H, s).

Example 52

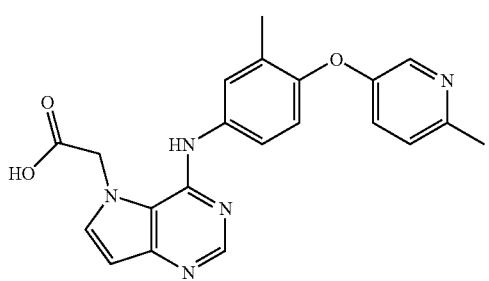

Production of [4-({3-methyl-4-[(6-methylpyridin-3-yl)oxy]phenyl}amino)-5H-pyrrolo[3,2-d]pyrimidin-5-yl]acetic acid The title compound (101 mg) was obtained as white powder by the reaction in the same manner as in Example 46 using ethyl [4-({3-methyl-4-[(6-methylpyridin-3-yl)oxy]phenyl}amino)-5H-pyrrolo[3,2-d]pyrimidin-5-yl]acetate (200 mg).

$^1$H-NMR (DMSO-d$_6$) δ 2.43 (3H, s), 2.51 (3H, s), 5.30 (2H, s), 6.49 (1H, s), 6.92 (1H, d, J=8.8 Hz), 7.20-7.25 (2H, m), 7.37-7.44 (2H, m), 7.62 (1H, s), 8.17 (1H, s), 8.31 (1H, s).

Example 53

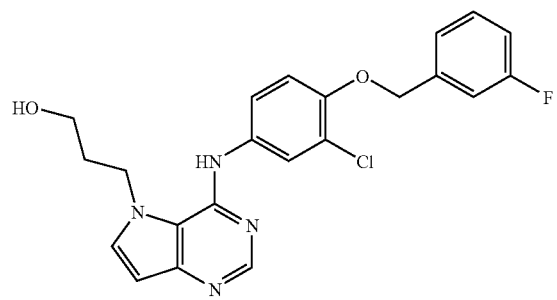

Production of 3-[4-({3-chloro-4-[(3-fluorobenzyl)oxy]phenyl}amino)-5H-pyrrolo[3,2-d]pyrimidin-5-yl]propan-1-ol (i) Production of 5-(3-{[tert-butyl(dimethyl)silyl]oxy}propyl)-4-chloro-5H-pyrrolo[3,2-d]pyrimidine To a suspension of 4-chloro-5H-pyrrolo[3,2-d]pyrimidine (400 mg) in N,N-dimethylformamide (2.6 mL) was added cesium carbonate (957 mg) under ice-cooling, and the mixture was stirred while warming to room temperature for 15 min. To the reaction mixture was added (3-bromopropoxy)(tert-butyl)dimethylsilane (979 mg), and the mixture was stirred at room temperature for 16 hrs. The reaction mixture was diluted with water (20 mL) and extracted with ethyl acetate (30 mL×3). The organic layer was washed with saturated brine (30 mL×3) and dried over anhydrous magnesium sulfate. The solvent was evaporated under reduced pressure, and the obtained residue was subjected to silica gel column chromatography (silica gel, eluent:hexane/ethyl acetate=85/15→10/90). The object fraction was concentrated under reduced pressure and dried to give the title compound (630 mg) as a white solid.

$^1$H-NMR (CDCl$_3$) δ 0.95 (9H, s), 2.83 (2H, t, J=5.2 Hz), 4.10 (2H, t, J=5.2 Hz), 4.76 (2H, t, J=5.2 Hz), 6.87 (1H, d, J=2.8 Hz), 7.71 (1H, d, J=2.8 Hz), 8.85 (1H, s).

(ii) Production of 3-(4-chloro-5H-pyrrolo[3,2-d]pyrimidin-5-yl)propan-1-ol

The title compound (320 mg) was obtained as white powder crystals by the reaction in the same manner as in Example 41 (ii) using 5-(3-{[tert-butyl(dimethyl)silyl]oxy}propyl)-4-chloro-5H-pyrrolo[3,2-d]pyrimidine (600 mg).

$^1$H-NMR (CDCl$_3$) δ 2.13 (2H, dt, J=6.3, 12.6 Hz), 3.65 (2H, dd, J=6.3, 10.2 Hz), 4.66 (2H, t, J=6.3 Hz), 6.72 (1H, d, J=3.0 Hz), 7.57 (1H, d, J=3.0 Hz), 8.70 (1H, s).

(iii) Production of 3-[4-({3-chloro-4-[(3-fluorobenzyl)oxy]phenyl}amino)-5H-pyrrolo[3,2-d]pyrimidin-5-yl]propan-1-ol The title compound (180 mg) was obtained as pale purple crystals by the reaction in the same manner as in Example 41 (iii) using 3-(4-chloro-5H-pyrrolo[3,2-d]pyrimidin-5-yl)propan-1-ol (100 mg).

¹H-NMR (DMSO-d₆) δ 1.98 (2H, t, J=6.0 Hz), 3.39 (2H, t, J=6.0 Hz), 4.66 (2H, t, J=6.0 Hz), 5.30 (2H, s), 6.66 (1H, d, J=3.2 Hz), 7.19 (1H, dt, J=1.9, 8.3 Hz), 7.29-7.34 (3H, m), 7.44-7.52 (2H, m), 7.72 (1H, d, J=2.6 Hz), 8.00 (1H, d, J=3.2 Hz), 8.66 (1H, s), 9.97 (1H, s).

Example 54

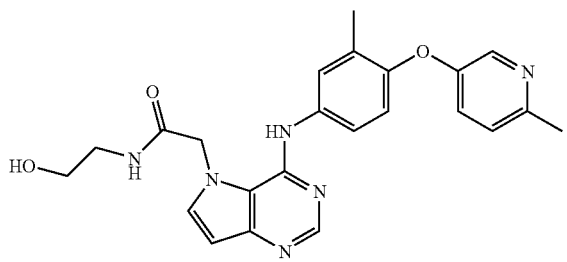

Production of N-(2-hydroxyethyl)-2-[4-({3-methyl-4-[(6-methylpyridin-3-yl)oxy]phenyl}amino)-5H-pyrrolo[3,2-d]pyrimidin-5-yl]acetamide The title compound (38 mg) was obtained as white powder by the reaction in the same manner as in Example 36 using [4-({3-methyl-4-[(6-methylpyridin-3-yl)oxy]phenylamino}-5H-pyrrolo[3,2-d]pyrimidin-5-yl)acetic acid (70 mg).

¹H-NMR (DMSO-d₆) δ 2.17 (3H, s), 2.43 (3H, s), 3.24 (2H, dd, J=5.6, 11.3 Hz), 3.47 (2H, dd, J=5.6, 11.3 Hz), 4.86 (1H, t, J=5.3 Hz), 5.04 (2H, s), 6.49 (1H, d, J=3.0 Hz), 6.97 (1H, d, J=8.5 Hz), 7.15 (1H, dd, J=2.8, 8.5 Hz), 7.22 (1H, d, J=8.5 Hz), 7.54-7.57 (3H, m), 8.16 (1H, d, J=2.5 Hz), 8.30 (1H, s), 8.91 (1H, t, J=5.6 Hz), 10.10 (1H, s).

Example 55

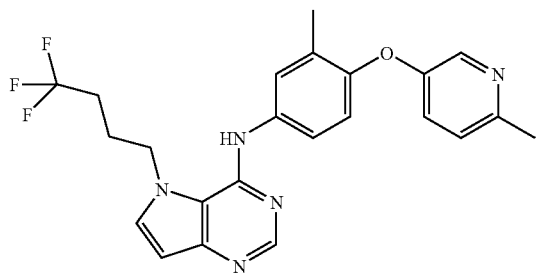

Production of N-{3-methyl-4-[(6-methylpyridin-3-yl)oxy]phenyl}-5-(4,4,4-trifluorobutyl)-5H-pyrrolo[3,2-d]pyrimidin-4-amine (i) Production of 4-chloro-5-(4,4,4-trifluorobutyl)-5H-pyrrolo[3,2-d]pyrimidine To a suspension of 4-chloro-5H-pyrrolo[3,2-d]pyrimidine (250 mg) in N,N-dimethylformamide (1.6 mL) was added cesium carbonate (675 mg) under ice-cooling, and the mixture was stirred while warming to room temperature for 15 min. To the reaction mixture was added 4-bromo-1,1,1-trifluorobutane (466 mg), and the mixture was stirred at room temperature for 15 hrs. The reaction mixture was diluted with water (20 mL) and extracted with ethyl acetate (20 mL×3). The organic layer was washed with saturated brine (20 mL×3) and dried over anhydrous magnesium sulfate. The solvent was evaporated under reduced pressure, and the obtained residue was subjected to silica gel column chromatography (silica gel, eluent:hexane/ethyl acetate=9/1→0/10). The object fraction was concentrated under reduced pressure and dried to give the title compound (440 mg) as a colorless transparent oil.

¹H-NMR (CDCl₃) δ 2.17 (4H, m), 4.57 (2H, t, J=6.6 Hz), 6.76 (1H, d, J=3.3 Hz), 7.47 (1H, d, J=3.3 Hz), 8.72 (1H, s).

(ii) Production of N-{3-methyl-4-[(6-methylpyridin-3-yl)oxy]phenyl}-5-(4,4,4-trifluorobutyl)-5H-pyrrolo[3,2-d]pyrimidin-4-amine The title compound (171 mg) was obtained as colorless oil by the reaction in the same manner as in Example 38 using 4-chloro-5-(4,4,4-trifluorobutyl)-5H-pyrrolo[3,2-d]pyrimidine (150 mg).

¹H-NMR (CDCl₃) δ 2.00-2.17 (4H, m), 2.25 (3H, s), 2.53 (3H, s), 4.29 (2H, t, J=6.9 Hz), 6.54 (1H, br s), 6.63 (1H, d, J=3.2 Hz), 6.88 (1H, d, J=8.5 Hz), 7.09 (1H, d, J=8.5 Hz), 7.13 (1H, dd, J=2.6, 8.5 Hz), 7.20 (1H, d, J=2.6 Hz), 7.23 (1H, d, J=3.2 Hz), 7.26 (1H, s), 7.32 (1H, d, J=2.6 Hz), 8.23 (1H, d, J=2.6 Hz), 8.54 (1H, s).

Example 56

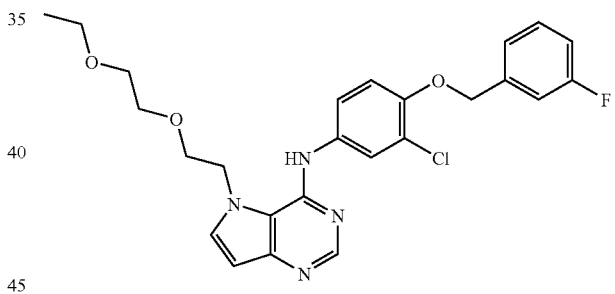

Production of N-{3-chloro-4-[(3-fluorobenzyl)oxy]phenyl}-5-[2-(2-ethoxyethoxy)ethyl]-5H-pyrrolo[3,2-d]pyrimidin-4-amine (i) Production of 4-chloro-5-[2-(2-ethoxyethoxy)ethyl]-5H-pyrrolo[3,2-d]pyrimidine To a suspension of 4-chloro-5H-pyrrolo[3,2-d]pyrimidine (300 mg) in N,N-dimethylformamide (2.0 mL) was added cesium carbonate (728 mg) under ice-cooling, and the mixture was stirred while warming to room temperature for 15 min. To the reaction mixture was added 1-bromo-2-(2-ethoxyethoxy)ethane (496 mg), and the mixture was stirred at room temperature for 20 hrs. The reaction mixture was diluted with water (20 mL) and extracted with ethyl acetate (20 mL×3). The organic layer was washed with saturated brine (20 mL×3) and dried over anhydrous magnesium sulfate. The solvent was evaporated under reduced pressure, and the obtained residue was subjected to silica gel column chromatography (silica gel, eluent:hexane/ethyl acetate=9/1→0/

10). The object fraction was concentrated under reduced pressure and dried to give the title compound (440 mg) as a colorless transparent oil.

¹H-NMR (CDCl₃) δ 1.17 (3H, t, J=7.1 Hz), 3.40-3.58 (6H, m), 3.87 (2H, t, J=5.1 Hz), 4.69 (2H, t, J=5.1 Hz), 6.70 (1H, d, J=3.3 Hz), 7.63 (1H, d, J=3.3 Hz), 8.69 (1H, s).

(ii) Production of N-{3-chloro-4-[(3-fluorobenzyl)oxy]phenyl}-5-[2-(2-ethoxyethoxy)ethyl]-5H-pyrrolo[3,2-d]pyrimidin-4-amine To a solution of 4-chloro-5-[2-(2-ethoxyethoxy)ethyl]-5H-pyrrolo[3,2-d]pyrimidine (150 mg) in 1-methyl-2-pyrrolidone (1.1 mL) was added 3-chloro-4-[(3-fluorobenzyl)oxy]aniline (189 mg), and the reaction mixture was stirred at 120° C. for 1 hr. The reaction mixture was allowed to cool to room temperature, diluted with 5% aqueous sodium hydrogen carbonate solution (25 mL), and extracted with ethyl acetate (30 mL×3). The organic layer was washed with saturated brine and dried over anhydrous magnesium sulfate. The solvent was evaporated under reduced pressure, and the obtained residue was subjected to silica gel column chromatography (basic silica gel, eluent:ethyl acetate/methanol=100/0→95/5). The object fraction was concentrated under reduced pressure and dried to give the title compound (146 mg) as a colorless oil.

¹H-NMR (CDCl₃) δ 1.09 (3H, t, J=6.9 Hz), 3.36 (2H, q, J=6.9 Hz), 3.51 (2H, t, J=4.2 Hz), 3.71 (2H, t, J=4.5 Hz), 3.98 (2H, t, J=4.5 Hz), 4.51 (2H, t, J=4.2 Hz), 5.24 (2H, s), 6.60 (1H, d, J=3.0 Hz), 6.91 (2H, d, J=8.8 Hz), 7.00 (2H, t, J=7.2 Hz), 7.17-7.37 (2H, m), 7.50 (1H, dd, J=2.7, 8.8 Hz), 7.68 (1H, d, J=3.0 Hz), 8.47 (1H, s), 8.68 (1H, s).

Example 57

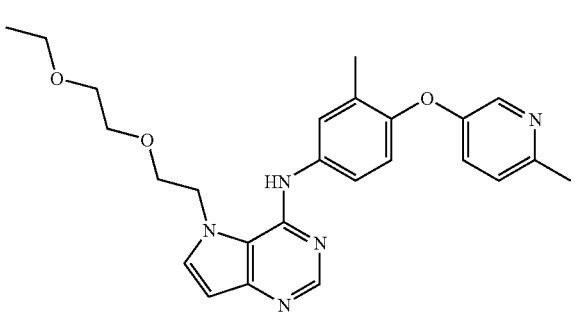

Production of 5-[2-(2-ethoxyethoxy)ethyl]-N-{3-methyl-4-[(6-methylpyridin-3-yl)oxy]phenyl}-5H-pyrrolo[3,2-d]pyrimidin-4-amine The title compound (98 mg) was obtained as colorless oil by the reaction in the same manner as in Example 47 using 4-chloro-5-[2-(2-ethoxyethoxy)ethyl]-5H-pyrrolo[3,2-d]pyrimidine (150 mg).

¹H-NMR (DMSO-d₆) δ 0.93 (3H, t, J=7.0 Hz), 2.24 (3H, s), 2.74 (3H, s), 3.23 (2H, q, J=7.0 Hz), 3.37-3.40 (2H, m), 3.56-3.59 (2H, m), 3.86 (2H, t, J=4.5 Hz), 4.89 (2H, t, J=4.5 Hz), 6.72 (1H, d, J=3.0 Hz), 7.22 (1H, d, J=8.7 Hz), 7.58-7.66 (2H, m), 7.91 (1H, d, J=8.7 Hz), 8.05 (1H, t, J=3.0 Hz), 8.09 (1H, d, J=3.0 Hz), 8.36 (1H, d, J=2.8 Hz), 8.73 (1H, s), 10.07 (1H, br s).

Example 58

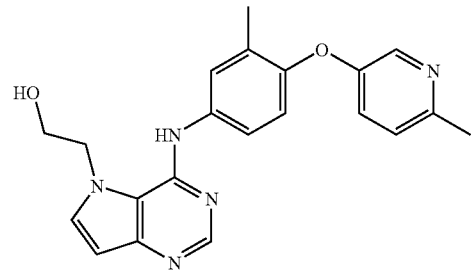

Production of 2-[4-({3-methyl-4-[(6-methylpyridin-3-yl)oxy]phenyl}amino)-5H-pyrrolo[3,2-d]pyrimidin-5-yl]ethanol The title compound (241 mg) was obtained as white powder crystals by the reaction in the same manner as in Example 47 using 2-(4-chloro-5H-pyrrolo[3,2-d]pyrimidin-5-yl)ethanol (250 mg).

¹H-NMR (DMSO-d₆) δ 2.17 (3H, s), 2.43 (3H, s), 3.87 (2H, t, J=4.5 Hz), 4.52 (2H, t, J=4.5 Hz), 6.27 (1H, br s), 6.48 (1H, dd, J=1.6, 3.0 Hz), 6.97 (1H, d, J=9.6 Hz), 7.16 (1H, ddd, J=1.6, 3.0, 8.7 Hz), 7.23 (1H, d, J=8.4 Hz), 7.53 (2H, br s), 7.63 (1H, dd, J=1.6, 3.0 Hz), 8.17 (1H, d, J=3.0 Hz), 8.28 (1H, d, J=1.6 Hz), 9.66 (1H, br s).

Example 59

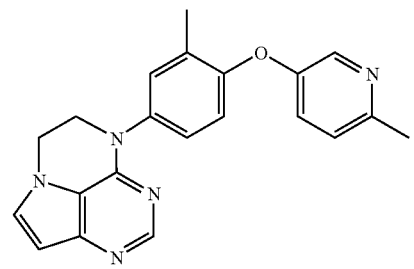

Production of 4-{3-methyl-4-[(6-methylpyridin-3-yl)oxy]phenyl}-5,6-dihydro-4H-pyrrolo[3,2,1-de]pteridine To a suspension of 2-[4-({3-methyl-4-[(6-methylpyridin-3-yl)oxy]phenyl}amino)-5H-pyrrolo[3,2-d]pyrimidin-5-yl]ethanol (50 mg) and tributylphosphine (54 mg) in toluene (2.5 mL) was added 1,1'-[(E)-diazene-1,2-diyldicarbonyl]dipiperidine (67 mg), and the mixture was stirred at room temperature for 3 hrs. The reaction mixture was diluted with water (15 mL) and extracted with ethyl acetate (20 mL×3). The organic layer was washed with saturated brine and dried over anhydrous magnesium sulfate. The solvent was evaporated under reduced pressure, and the obtained residue was subjected to silica gel column chromatography (basic silica gel, eluent:

ethyl acetate/methanol=100/0→90/10). The object fraction was concentrated under reduced pressure and dried to give the title compound (36 mg) as a white powder.

$^1$H-NMR (CDCl$_3$) δ 2.29 (3H, s), 2.54 (3H, s), 4.21 (2H, t, J=5.1 Hz), 4.41 (2H, t, J=5.1 Hz), 6.59 (1H, d, J=2.7 Hz), 6.92 (1H, d, J=8.4 Hz), 7.11 (1H, d, J=8.4 Hz), 7.18 (1H, dd, J=2.7, 8.4 Hz), 7.23-7.27 (2H, m), 7.38 (1H, d, J=2.7 Hz), 8.26 (1H, d, J=2.7 Hz), 8.49 (1H, s).

Example 60

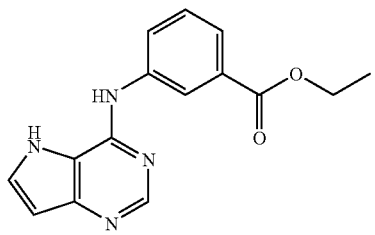

Production of ethyl 3-(5H-pyrrolo[3,2-d]pyrimidin-4-ylamino)benzoate

A mixture of 4-chloro-5H-pyrrolo[3,2-d]pyrimidine (2.78 g), ethyl 3-aminobenzoate (4.49 g) and 1-methyl-2-pyrrolidone (20 mL) was stirred at 120° C. for 1.5 hrs. To the reaction mixture were added ethyl acetate, water and saturated aqueous sodium hydrogen carbonate solution. The insoluble material was filtered off, and the ethyl acetate layer was separated. The aqueous layer was extracted with ethyl acetate, and the mixed ethyl acetate layer was washed with saturated brine and dried over anhydrous magnesium sulfate. The filtered insoluble material was suspended in methanol and ethyl acetate and saturated brine were added. The ethyl acetate layer was separated. The ethyl acetate layer was washed with saturated brine and dried over anhydrous magnesium sulfate. The mixed ethyl acetate layer was concentrated under reduced pressure and the obtained residue was purified by silica gel column chromatography (eluent, ethyl acetate) and crystallized from methanol-acetone-diisopropyl ether to give the title compound (2.85 g) as a pale-brown powder.

$^1$H-NMR (CDCl$_3$) δ: 1.39 (3H, t, J=7.2 Hz), 4.37 (2H, q, J=7.2 Hz), 6.51 (1H, d, J=3.3 Hz), 7.28-7.32 (1H, m), 7.42 (1H, t, J=8.0 Hz), 7.70 (1H, d, J=7.8 Hz), 8.09 (1H, s), 8.29 (1H, d, J=8.1 Hz), 8.49 (1H, m).

Example 61

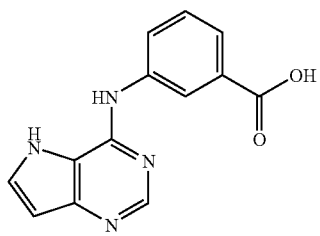

Production of 3-(5H-pyrrolo[3,2-d]pyrimidin-4-ylamino)benzoic acid

A mixture of ethyl 3-(5H-pyrrolo[3,2-d]pyrimidin-4-ylamino)benzoate (3.34 g), 1N aqueous sodium hydroxide solution (25 mL) and methanol (50 mL) was stirred overnight at room temperature. To the reaction mixture was added 1N hydrochloric acid (25 mL), and methanol was evaporated under reduced pressure. The precipitated crystals were collected by filtration and washed with water to give the title compound (3.09 g) as a pale-brown powder.

$^1$H-NMR (DMSO-d$_6$) δ: 6.50 (1H, m), 7.49 (1H, t, J=7.8 Hz), 7.60 (1H, d, J=7.8 Hz), 7.69 (1H, t, J=2.7 Hz), 8.25 (1H, d, J=7.8 Hz), 8.39 (1H, s), 8.43 (1H, s), 9.54 (1H, s), 11.24 (1H, s), 13.01 (1H, br).

Example 62

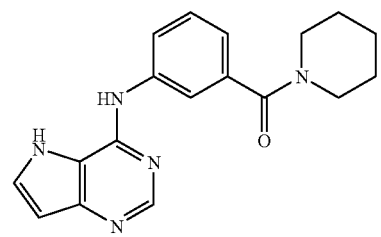

Production of N-[3-(piperidin-1-ylcarbonyl)phenyl]-5H-pyrrolo[3,2-d]pyrimidin-4-amine A mixture of 3-(5H-pyrrolo[3,2-d]pyrimidin-4-ylamino)benzoic acid (153 mg), piperidine (0.078 mL), 1-[3-(dimethylamino)propyl]-3-ethylcarbodiimide hydrochloride (173 mg) and N,N-dimethylformamide (10 mL) was stirred at room temperature for 2 hrs. Piperidine (0.078 mL) and 1-[3-(dimethylamino)propyl]-3-ethylcarbodiimide hydrochloride (173 mg) were added and the mixture was stirred for 1 hr. 1-Hydroxybenzotriazole (138 mg) was added, and the mixture was stirred for 3 days. Saturated brine was added to the reaction mixture and the mixture was extracted with ethyl acetate. The extract was washed with saturated brine and dried over anhydrous magnesium sulfate. The solvent was evaporated under reduced pressure and the obtained residue was purified by silica gel column chromatography (eluent, methanol:ethyl acetate=0:100→20:80). Diisopropyl ether was added and the precipitate was collected by filtration to give the title compound (78 mg) as a pale-brown powder.

$^1$H-NMR (CDCl$_3$) δ: 1.56 (2H, m), 1.73 (4H, m), 3.42 (2H, m), 3.83 (2H, m), 6.58 (1H, d, J=2.4 Hz), 6.90 (1H, d, J=7.5 Hz), 7.18-7.22 (1H, m), 7.23 (1H, s), 7.30 (1H, t, J=2.4 Hz), 7.88 (1H, d, J=8.3 Hz), 8.47 (1H, s), 8.70 (1H, s), 10.71 (1H, s).

Example 63

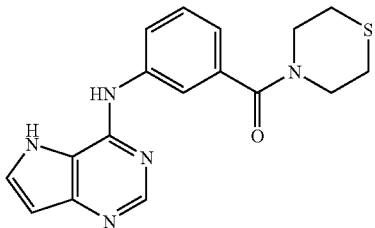

Production of N-[3-(thiomorpholin-4-ylcarbonyl)phenyl]-5H-pyrrolo[3,2-d]pyrimidin-4-amine A mixture of 3-(5H-pyrrolo[3,2-d]pyrimidin-4-ylamino)benzoic acid (153 mg), thiomorpholine (0.091 mL), 1-[3-(dimethylamino)propyl]-3-ethylcarbodiimide hydrochloride (173 mg) and N,N-dimethylformamide (10 mL) was stirred at room temperature for 2 hrs. Thiomorpholine (0.030 mL) and 1-[3-(dimethylamino)propyl]-3-ethylcarbodiimide hydrochloride (173 mg) were added and the mixture was stirred for 1 hr. 1-Hydroxybenzotriazole (138 mg) was added, and the mixture was stirred for 3 days. Saturated brine was added to the reaction mixture and the mixture was extracted with ethyl acetate. The extract was washed with saturated brine and dried over anhydrous magnesium sulfate. The solvent was evaporated under reduced pressure, and the obtained residue was purified by silica gel column chromatography (eluent, methanol:ethyl acetate=0:100→20:80). Diisopropyl ether was added and the precipitate was collected by filtration. The precipitate was dissolved in ethyl acetate containing methanol, washed with saturated brine and dried over anhydrous magnesium sulfate. The solvent was evaporated under reduced pressure, and diisopropyl ether was added to the obtained residue and the precipitate was collected by filtration to give the title compound (82 mg) as a pale-brown powder.

$^1$H-NMR (CDCl$_3$) δ: 2.65 (2H, m), 2.77 (2H, m), 3.78 (2H, m), 4.05 (2H, m), 6.59 (1H, d, J=3.0 Hz), 6.98 (1H, d, J=6.9 Hz), 7.33 (1H, d, J=7.8 Hz), 7.38 (1H, d, J=3.0 Hz), 7.53 (1H, s), 7.95 (1H, br), 8.48 (1H, s).

Example 64

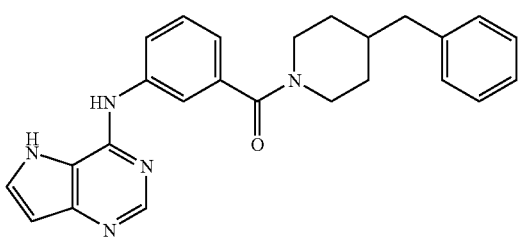

Production of N-{3-[(4-benzylpiperidin-1-yl)carbonyl]phenyl}-5H-pyrrolo[3,2-d]pyrimidin-4-amine A mixture of 3-(5H-pyrrolo[3,2-d]pyrimidin-4-ylamino)benzoic acid (153 mg), 4-benzylpiperidine (158 mg), 1-[3-(dimethylamino)propyl]-3-ethylcarbodiimide hydrochloride (173 mg), 1-hydroxybenzotriazole (138 mg) and N,N-dimethylformamide (10 mL) was stirred at room temperature for 3 hrs. The reaction mixture was concentrated under reduced pressure, water was added and extracted with ethyl acetate containing tetrahydrofuran. The extract was washed with saturated brine and dried over anhydrous magnesium sulfate. The solvent was evaporated under reduced pressure, and the obtained residue was purified by silica gel column chromatography (eluent, methanol:ethyl acetate=0:100→20:80). The obtained product was dissolved in ethyl acetate containing methanol and tetrahydrofuran, washed with aqueous sodium hydrogen carbonate solution and saturated brine and dried over anhydrous magnesium sulfate. The solvent was evaporated under reduced pressure, and diisopropyl ether was added to the obtained residue. The precipitate was collected by filtration to give the title compound (201 mg) as a pale-brown powder.

$^1$H-NMR (CDCl$_3$) δ: 1.10-2.00 (6H, m), 2.86 (2H, d, J=6.9 Hz), 2.75-3.05 (2H, m), 3.78-3.91 (1H, m), 4.68-4.82 (1H, m), 6.55 (1H, d, J=3.0 Hz), 6.90 (1H, d, J=7.5 Hz), 7.10-7.33 (7H, m), 7.40 (1H, s), 7.72 (1H, d, J=8.1 Hz), 8.45 (1H, s), 8.77 (1H, s), 10.83 (1H, s).

Example 65

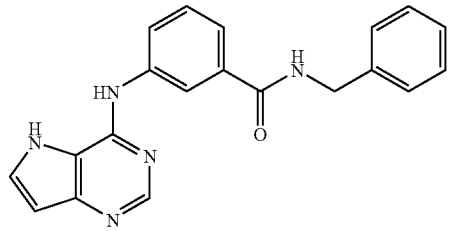

Production of N-benzyl-3-(5H-pyrrolo[3,2-d]pyrimidin-4-ylamino)benzamide

A mixture of 3-(5H-pyrrolo[3,2-d]pyrimidin-4-ylamino)benzoic acid (153 mg), benzylamine (96 mg), 1-[3-(dimethylamino)propyl]-3-ethylcarbodiimide hydrochloride (173 mg), 1-hydroxybenzotriazole (138 mg) and N,N-dimethylformamide (10 mL) was stirred at room temperature for 3 days. The reaction mixture was concentrated under reduced pressure, water was added and the mixture was extracted with ethyl acetate containing tetrahydrofuran. The extract was washed with saturated aqueous sodium hydrogen carbonate solution and saturated brine and dried over anhydrous magnesium sulfate. The solvent was evaporated under reduced pressure, and the obtained residue was purified by silica gel column chromatography (eluent, methanol:ethyl acetate=0:100→50:50). Ethyl acetate and diethyl ether were added and the precipitate was collected by filtration to give the title compound (128 mg) as a colorless powder.

$^1$H-NMR (DMSO-d$_6$) δ: 4.50 (2H, d, J=6.0 Hz), 6.49 (1H, m), 7.21-7.38 (5H, m), 7.46 (1H, t, J=8.0 Hz), 7.55 (1H, d,

J=8.1 Hz), 7.68 (1H, t, J=3.0 Hz), 8.19 (1H, s), 8.26 (1H, d, J=8.0 Hz), 8.37 (1H, s), 9.06 (1H, t, J=6.0 Hz), 9.41 (1H, s), 11.13 (1H, s).

Example 66

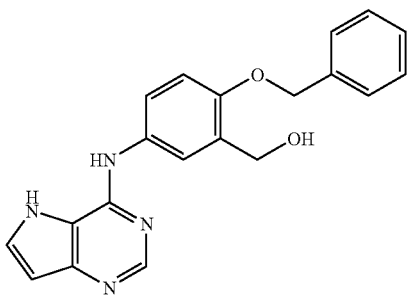

Production of [2-(benzyloxy)-5-(5H-pyrrolo[3,2-d]pyrimidin-4-ylamino)phenyl]methanol A mixture of 4-chloro-5H-pyrrolo[3,2-d]pyrimidine (307 mg), [5-amino-2-(benzyloxy)phenyl]methanol (459 mg) and N,N-dimethylformamide (10 mL) was stirred at 80° C. for 4 hrs. The reaction mixture was concentrated under reduced pressure, aqueous sodium hydrogen carbonate solution was added and the mixture was extracted with ethyl acetate containing tetrahydrofuran. The extract was washed with saturated brine and dried over anhydrous magnesium sulfate. The solvent was evaporated under reduced pressure, and the obtained residue was purified by silica gel column chromatography (eluent, methanol:ethyl acetate=0:100→30:70). Ethanol and ethyl acetate were added and the precipitate was collected by filtration to give the title compound (279 mg) as a brown powder.

$^1$H-NMR (DMSO-d$_6$) δ: 4.60 (2H, d, J=5.5 Hz), 5.12 (2H, s), 5.17 (1H, t, J=5.5 Hz), 6.45 (1H, m), 7.03 (1H, d, J=8.8 Hz), 7.29-7.51 (5H, m), 7.62 (1H, t, J=2.9 Hz), 7.65 (1H, d, J=2.7 Hz), 7.93 (1H, dd, J=8.8, 2.7 Hz), 8.29 (1H, s), 9.08 (1H, s), 11.05 (1H, s).

Example 67

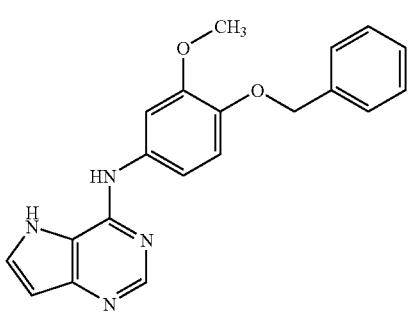

Production of N-[4-(benzyloxy)-3-methoxyphenyl]-5H-pyrrolo[3,2-d]pyrimidin-4-amine A mixture of 4-chloro-5H-pyrrolo[3,2-d]pyrimidine (200 mg), 4-(benzyloxy)-3-methoxyaniline (298 mg) and 1-methyl-2-pyrrolidone (5 mL) was stirred at 80° C. for 4 hrs. Methanol and activated carbon were added to the reaction mixture and the mixture was stirred. The activated carbon was filtered off, aqueous sodium hydrogen carbonate solution was added and the mixture was extracted with ethyl acetate. The extract was washed with saturated brine and dried over anhydrous magnesium sulfate. The solvent was evaporated under reduced pressure, and the obtained residue was purified by silica gel column chromatography (eluent, methanol:ethyl acetate=10:80→20:80) and recrystallized from methanol-ethyl acetate to give the title compound (269 mg) as a pale-gray powder.

$^1$H-NMR (DMSO-d$_6$) δ: 3.82 (3H, s), 5.06 (2H, s), 6.45 (1H, m), 7.03 (1H, d, J=8.9 Hz), 7.30-7.49 (6H, m), 7.51 (1H, d, J=2.5 Hz), 7.63 (1H, t, J=2.9 Hz), 8.30 (1H, s), 9.07 (1H, s), 11.06 (1H, s).

Example 68

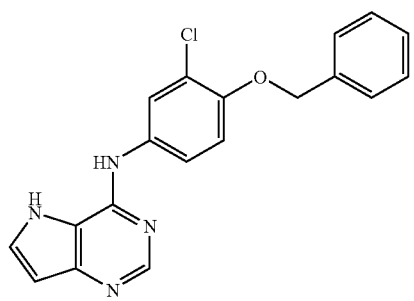

Production of N-[4-(benzyloxy)-3-chlorophenyl]-5H-pyrrolo[3,2-d]pyrimidin-4-amine A mixture of 4-chloro-5H-pyrrolo[3,2-d]pyrimidine (200 mg), 4-(benzyloxy)-3-chloroaniline (365 mg) and 1-methyl-2-pyrrolidone (3 mL) was stirred at 80° C. for 4 hrs. Methanol and activated carbon were added to the reaction mixture and the mixture was stirred. The activated carbon was filtered off, aqueous sodium hydrogen carbonate solution was added and the mixture was extracted with ethyl acetate. The extract was washed with water and saturated brine and dried over anhydrous magnesium sulfate. The solvent was evaporated under reduced pressure, and the obtained residue was purified by silica gel column chromatography (eluent, methanol:ethyl acetate=0:100→15:75) and recrystallized from ethanol-ethyl acetate to give the title compound (226 mg) as a pale-brown powder.

$^1$H-NMR (CDCl$_3$) δ: 5.15 (2H, s), 6.56 (1H, s), 6.98 (1H, d, J=8.9 Hz), 7.28-7.43 (4H, m), 7.48 (2H, d, J=7.5 Hz), 7.69 (1H, d, J=8.9 Hz), 7.80 (1H, d, J=2.6 Hz), 8.50 (1H, s), 8.63 (1H, s), 10.56 (1H, s).

Example 69

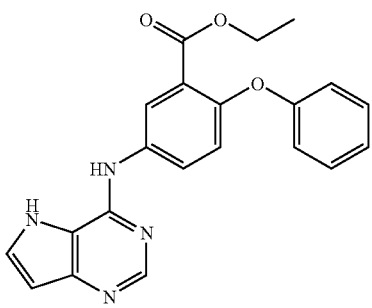

Production of ethyl 2-phenoxy-5-(5H-pyrrolo[3,2-d]pyrimidin-4-ylamino)benzoate A mixture of ethyl 4-chloro-5H-pyrrolo[3,2-d]pyrimidine (461 mg), 5-amino-2-phenoxybenzoate (926 mg) and 1-methyl-2-pyrrolidone (5 mL) was stirred at 80° C. for 2 hrs. Ethanol, water and activated carbon were added to the reaction mixture and the mixture was stirred. The activated carbon was filtered off, and the solvent was evaporated under reduced pressure. Aqueous sodium hydrogen carbonate solution was added to the residue and the mixture was extracted with ethyl acetate. The extract was washed with water and saturated brine and dried over anhydrous magnesium sulfate. The solvent was evaporated under reduced pressure, and the obtained residue was purified by silica gel column chromatography (eluent, methanol:ethyl acetate=0:100→20:80) and recrystallized from ethanol-ethyl acetate to give the title compound (572 mg) as a colorless powder.

$^1$H-NMR (CDCl$_3$) δ: 1.12 (3H, t, J=7.1 Hz), 4.19 (2H, q, J=7.1 Hz), 6.57 (1H, d, J=3.0 Hz), 6.84 (2H, d, J=7.7 Hz), 6.95 (1H, d, J=8.9 Hz), 7.00 (1H, t, J=7.3 Hz), 7.19-7.29 (2H, m), 7.34 (1H, d, J=3.0 Hz), 7.80 (1H, dd, J=8.9, 2.8 Hz), 8.00 (1H, d, J=2.8 Hz), 8.67 (1H, s), 8.87 (1H, s), 10.89 (1H, s).

Example 70

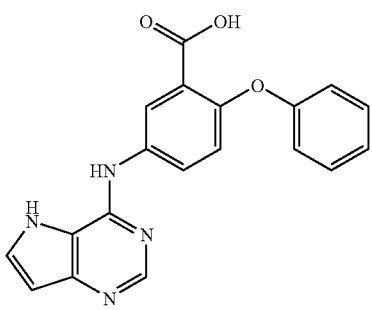

Production of 2-phenoxy-5-(5H-pyrrolo[3,2-d]pyrimidin-4-ylamino)benzoic acid A mixture of ethyl 2-phenoxy-5-(5H-pyrrolo[3,2-d]pyrimidin-4-ylamino)benzoate (899 mg), 1N aqueous sodium hydroxide solution (5 mL) and methanol (15 mL) was stirred at 60° C. for 1.5 hrs. To the reaction mixture was added 1N hydrochloric acid (5 mL), and methanol was evaporated under reduced pressure. The precipitated crystals were collected by filtration, and washed with water and acetone to give the title compound (768 mg) as a pale-brown powder.

$^1$H-NMR (DMSO-d$_6$) δ: 6.50 (1H, m), 6.89 (2H, d, J=7.7 Hz), 7.04 (1H, t, J=7.3 Hz), 7.12 (1H, d, J=8.9 Hz), 7.33 (2H, t, J=8.0 Hz), 7.69 (1H, t, J=2.9 Hz), 8.16 (1H, dd, J=8.9, 2.9 Hz), 8.31 (1H, d, J=2.9 Hz), 8.37 (1H, s), 9.46 (1H, s), 11.11 (1H, s), 12.95 (1H, br).

Example 71

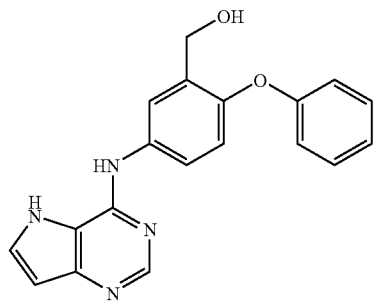

Production of [2-phenoxy-5-(5H-pyrrolo[3,2-d]pyrimidin-4-ylamino)phenyl]methanol To a solution of 2-phenoxy-5-(5H-pyrrolo[3,2-d]pyrimidin-4-ylamino)benzoic acid (173 mg) in N,N-dimethylformamide (5 mL) was added 1,1'-carbonyldiimidazole (97 mg) and the mixture was stirred at room temperature for 1 hr. Sodium borohydride (38 mg) was added to the reaction mixture at room temperature, and methanol (1 mL) was added dropwise. After stirring overnight at room temperature, water was added to the reaction mixture and the mixture was extracted with ethyl acetate. The extract was washed with water and saturated brine and dried over anhydrous magnesium sulfate. The solvent was evaporated under reduced pressure, and the obtained residue was purified by silica gel column chromatography (eluent, methanol:ethyl acetate=0:100→20:80) and crystallized from methanol-ethyl acetate, to give the title compound (44 mg) as a colorless powder.

$^1$H-NMR (DMSO-d$_6$) δ: 4.50 (2H, d, J=5.1 Hz), 5.28 (1H, t, J=255.1 Hz), 6.48 (1H, m), 6.90 (2H, d, J=7.7 Hz), 6.96 (1H, d, J=8.7 Hz), 7.06 (1H, t, J=7.3 Hz), 7.30-7.40 (2H, m), 7.66 (1H, t, J=2.9 Hz), 7.85 (1H, d, J=2.7 Hz), 8.04 (1H, dd, J=8.7, 2.7 Hz), 8.34 (1H, s), 9.28 (1H, s), 11.11 (1H, s).

Example 72

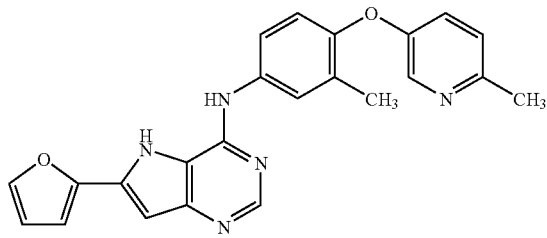

Production of 6-(2-furyl)-N-{3-methyl-4-[(6-methylpyridin-3-yl)oxy]phenyl}-5H-pyrrolo[3,2-d]pyrimidin-4-amine

(i) Production of 2-cyano-1-(2-furyl)vinyl 4-methylbenzenesulfonate

To a mixture of 3-(2-furyl)-3-oxopropanenitrile (5.29 g), p-toluenesulfonyl chloride (9.00 g) and dichloromethane (60 mL) was added dropwise triethylamine (5.99 g) under ice-cooling. After stirring under ice-cooling for 1.5 hrs, the mixture was diluted with dichloromethane (100 mL). The mixture was washed with water (150 mL), dried over anhydrous magnesium sulfate, and concentrated under reduced pressure. The residue was purified by silica gel column chromatography (eluent, hexane:methyl acetate=9:1→3:1) to give the title compound (10.48 g) as a mixture of (E)-form and (Z)-form (3:1).

$^1$H-NMR (CDCl$_3$) δ 2.47 (3/4H, s), 2.49 (9/4H, s), 5.27 (1/4H, s), 5.63 (3/4H, s), 6.47 (1/4H, m), 6.53 (3/4H, m), 6.86 (1/4H, d, J=3.6 Hz), 6.95 (3/4H, d, J=3.6 Hz), 7.38 (1/2H, d, J=7.8 Hz), 7.42 (3/2H, d, J=7.8 Hz), 7.51 (3/4H, m), 7.55 (1/4H, m), 7.83 (1/2H, d, J=7.8 Hz), 7.97 (3/2H, d, J=7.8 Hz).

(ii) Production of ethyl 3-amino-5-(2-furyl)-1H-pyrrole-2-carboxylate

To a solution of 2-cyano-1-(2-furyl)vinyl 4-methylbenzenesulfonate (10.48 g) and diethyl aminomalonate hydrochloride (7.67 g) in a mixed solvent of ethanol (120 mL)-tetrahydrofuran (64 mL) was added dropwise a solution (36.9 mL) of 20% sodium ethoxide in ethanol under ice-cooling. After stirring at room temperature for 12 hrs, the reaction mixture was poured into ice water (350 mL) and adjusted to pH 7 with 1N hydrochloric acid. The organic solvent was evaporated under reduced pressure, and the residue was extracted with ethyl acetate (150 mL×3). The organic layers were combined, washed with saturated brine (100 mL), and dried over anhydrous magnesium sulfate. After concentration under reduced pressure, the residue was purified by silica gel column chromatography (eluent, hexane:methyl acetate=3:1→1:1) and the obtained solid was recrystallized from ethyl acetate-hexane to give the title compound (2.66 g).

$^1$H-NMR (CDCl$_3$) δ 1.37 (3H, t, J=7.0 Hz), 4.34 (2H, q, J=7.0 Hz), 4.37 (2H, br s), 5.93 (1H, d, J=2.7 Hz), 6.45 (1H, dd, J=3.6, 1.8 Hz), 6.49 (1H, d, J=3.6 Hz), 7.41 (1H, d, J=1.8 Hz), 8.35 (1H, br s).

(iii) Production of 6-(2-furyl)-4,5-dihydro-3H-pyrrolo[3,2-d]pyrimidin-4-one To a solution of ethyl 3-amino-5-(2-furyl)-1H-pyrrole-2-carboxylate (2.58 g) in ethanol (35 mL) was added formamidine acetate (1.83 g), and the mixture was heated under reflux for 18 hrs. After cooling to room temperature, the precipitated solid was collected by filtration, washed with ethanol, and dried under reduced pressure at 60° C. to give the title compound (2.26 g).

$^1$H-NMR (DMSO-d$_6$) δ 6.58 (1H, d, J=2.1 Hz), 6.61 (1H, dd, J=3.5, 2.1 Hz), 7.08 (1H, m), 7.76 (1H, m), 7.80 (1H, d, J=3.5 Hz), 11.91 (1H, br s), 12.50 (1H, br s).

(iv) Production of 4-chloro-6-(2-furyl)-5H-pyrrolo[3,2-d]pyrimidine

A mixture of 6-(2-furyl)-4,5-dihydro-3H-pyrrolo[3,2-d]pyrimidin-4-one (2.20 g) and phosphoryl chloride (10.7 g) was stirred at 100° C. for 20 min, dioxane (30 mL) was added, and the mixture was stirred at 100° C. for 3 hrs. After concentration under reduced pressure, saturated aqueous sodium hydrogen carbonate was added to the residue, and the mixture was extracted with ethyl acetate-acetone (155 mL×4). The organic layers were combined, washed with saturated brine (100 mL), dried over anhydrous magnesium sulfate, and concentrated under reduced pressure. The residue was washed with ethyl acetate-diethyl ether, and dried under reduced pressure at 60° C. to give the title compound (2.19 g).

$^1$H-NMR (DMSO-d$_6$) δ 6.74 (1H, dd, J=3.6, 2.1 Hz), 6.95 (1H, d, J=1.8 Hz), 7.37 (1H, dd, J=3.6, 0.6 Hz), 7.95 (1H, dd, J=2.1, 0.6 Hz), 8.60 (1H, s), 12.71 (1H, br s).

(v) Production of 6-(2-furyl)-N-{3-methyl-4-[(6-methylpyridin-3-yl)oxy]phenyl}-5H-pyrrolo[3,2-d]pyrimidin-4-amine A mixture of 4-chloro-6-(2-furyl)-5H-pyrrolo[3,2-d]pyrimidine (110 mg), 3-methyl-4-[(6-methylpyridin-3-yl)oxy]aniline (161 mg) and 1-methyl-2-pyrrolidinone (2.5 mL) was stirred at 140° C. for 2 hrs, poured into water (10 mL) and adjusted to pH 8 with saturated aqueous sodium hydrogen carbonate. The mixture was extracted with ethyl acetate (25 mL×2) and the organic layers were combined and dried over anhydrous magnesium sulfate. After concentration under reduced pressure, the residue was subjected to silica gel column chromatography (eluent, hexane:ethyl acetate=1:1→0:1). The object fraction was concentrated under reduced pressure. Chloroform-diisopropyl ether was added to the residue, and the solid was collected by filtration and dried under reduced pressure at 60° C. to give the title compound (114 mg).

$^1$H-NMR (DMSO-d$_6$) δ 2.21 (3H, s), 2.48 (3H, s), 6.72 (1H, dd, J=3.3, 1.8 Hz), 6.78 (1H, d, J=1.8 Hz), 6.98 (1H, d, J=8.4 Hz), 7.02 (1H, d, J=3.6 Hz), 7.17 (1H, dd, J=8.4, 2.7 Hz), 7.22 (1H, d, J=8.4 Hz), 7.74 (1H, dd, J=8.4, 2.7 Hz), 7.80

(1H, d, J=2.1 Hz), 7.92 (1H, dd, J=1.8, 0.9 Hz), 8.16 (1H, dd, J=2.7, 0.9 Hz), 8.33 (1H, s), 9.17 (1H, br s), 11.67 (1H, br s).

Example 73

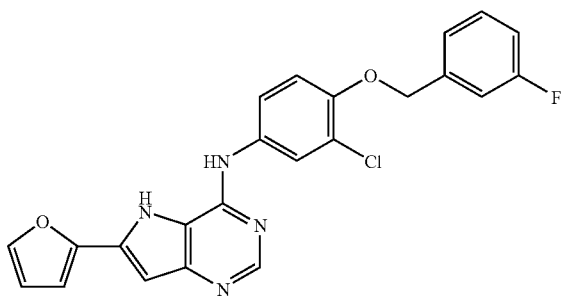

Production of N-{3-chloro-4-[(3-fluorobenzyl)oxy]phenyl}-6-(2-furyl)-5H-pyrrolo[3,2-d]pyrimidin-4-amine A mixture of 4-chloro-6-(2-furyl)-5H-pyrrolo[3,2-d]pyrimidine (110 mg), 3-chloro-4-[(3-fluorobenzyl)oxy]aniline (189 mg) and 1-methyl-2-pyrrolidinone (2.5 mL) was stirred at 140° C. for 2 hrs, poured into water (10 mL) and adjusted to pH 8 with saturated aqueous sodium hydrogen carbonate. The mixture was extracted with ethyl acetate (30 mL×2). The organic layers were combined and dried over anhydrous magnesium sulfate. After concentration under reduced pressure, the residue was subjected to silica gel column chromatography (eluent, hexane:ethyl acetate=4:1→1:1). The object fraction was concentrated under reduced pressure. Chloroform-diisopropyl ether was added to the residue, and the solid was collected by filtration and dried under reduced pressure at 60° C. to give the title compound (122 mg).

$^1$H-NMR (DMSO-$d_6$) δ 5.23 (2H, s), 6.71 (1H, dd, J=3.3, 2.1 Hz), 6.78 (1H, d, J=2.1 Hz), 7.02 (1H, d, J=3.3 Hz), 7.18 (1H, m), 7.25 (1H, d, J=9.0 Hz), 7.28-7.33 (2H, m), 7.46 (1H, m), 7.57 (1H, dd, J=9.0, 3.0 Hz), 7.92 (1H, d, J=1.8 Hz), 8.18 (1H, d, J=2.4 Hz), 8.33 (1H, s), 9.18 (1H, br s), 11.61 (1H, br s).

Example 74

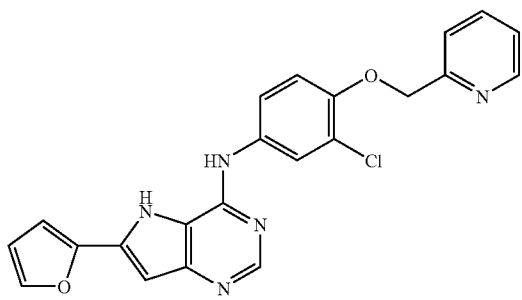

Production of N-[3-chloro-4-(pyridin-2-ylmethoxy)phenyl]-6-(2-furyl)-5H-pyrrolo[3,2-d]pyrimidin-4-amine A mixture of 4-chloro-6-(2-furyl)-5H-pyrrolo[3,2-d]pyrimidine (80 mg), 3-chloro-4-(pyridin-2-ylmethoxy)aniline (94 mg) and 1-methyl-2-pyrrolidinone (2.5 mL) was stirred at 140° C. for 2 hrs, poured into water (10 mL) and adjusted to pH 8 with saturated aqueous sodium hydrogen carbonate. The mixture was extracted with ethyl acetate (30 mL×2). The organic layers were combined and dried over anhydrous magnesium sulfate. After concentration under reduced pressure, the residue was subjected to silica gel column chromatography (eluent, hexane:ethyl acetate=1:1→0:1). The object fraction was concentrated under reduced pressure. Chloroform-diisopropyl ether was added to the residue, and the solid was collected by filtration and dried under reduced pressure at 60° C. to give the title compound (71 mg).

$^1$H-NMR (DMSO-$d_6$) δ 5.27 (2H, s), 6.72 (1H, m), 6.78 (1H, d, J=1.2 Hz), 7.02 (1H, d, J=3.3 Hz), 7.26 (1H, d, J=9.0 Hz), 7.36 (1H, m), 7.53-7.59 (2H, m), 7.81 (1H, d, J=8.1 Hz), 7.91 (1H, s), 8.21 (1H, d, J=2.4 Hz), 8.34 (1H, s), 8.59 (1H, d, J=5.1 Hz), 9.19 (1H, br s), 11.62 (1H, br s).

Example 75

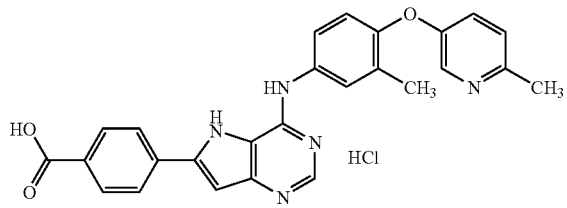

Production of 4-[4-({3-methyl-4-[(6-methylpyridin-3-yl)oxy]phenyl}amino)-5H-pyrrolo[3,2-d]pyrimidin-6-yl]benzoic acid hydrochloride (i) Production of methyl 4-(2-cyano-1-{[(4-methylphenyl)sulfonyl]oxy}vinyl)benzoate To a mixture of methyl 4-(cyanoacetyl)benzoate (10.29 g), p-toluenesulfonyl chloride (11.58 g) and dichloromethane (110 mL) was added dropwise triethylamine (7.68 g) under ice-cooling. After stirring under ice-cooling for 2.5 hrs, the mixture was diluted with dichloromethane (100 mL), washed with water (150 mL), dried over anhydrous magnesium sulfate, and concentrated under reduced pressure. The residue was purified by silica gel column chromatography (eluent, hexane:methyl acetate=9:1→1:1) to give the title compound (17.60 g) as a mixture of (E)-form and (Z)-form (6:5).

$^1$H-NMR (CDCl$_3$) δ 2.44 (18/11H, s), 2.47 (15/11H, s), 3.94 (18/11H, s), 3.95 (15/11H, s), 5.66 (6/11H, s), 5.68 (5/11H, s), 7.33 (12/11H, d, J=7.8 Hz), 7.38 (10/11H, d, J=7.8 Hz), 7.62-8.09 (6H, m).

(ii) Production of ethyl 3-amino-5-[4-(ethoxycarbonyl)phenyl]-1H-pyrrole-2-carboxylate To a suspension of methyl 4-(2-cyano-1-{[(4-methylphenyl)sulfonyl]oxy}vinyl)benzoate (17.5 g) and diethyl aminomalonate hydrochloride (10.36 g) in a mixed solvent of ethanol (165 mL)-tetrahydrofuran (80 mL) was added dropwise a solution (50 mL) of 20% sodium ethoxide in ethanol under ice-cooling. After stirring under ice-cooling for 1 hr, the mixture was stirred at room temperature for 21 hr. the reaction mixture was poured into ice water (400 mL) and adjusted to pH 7 with 1N hydrochloric acid. The organic solvent was evaporated under reduced pressure, and the residue was extracted with ethyl acetate (250 mL×3). The organic layers were combined, washed with saturated brine (150 mL), and dried over anhydrous magnesium sulfate. After concentration under reduced pressure, the residue was purified by silica gel column chromatography (eluent, hexane:ethyl acetate=2:1→1:1) and the obtained solid was recrystallized from ethyl acetate to give the title compound (4.76 g).

$^1$H-NMR (CDCl$_3$) δ 1.36-1.43 (6H, m), 4.31-4.42 (6H, m), 6.11 (1H, d, J=3.0 Hz), 7.55 (2H, d, J=8.4 Hz), 8.04 (2H, d, J=8.4 Hz), 8.40 (1H, br s).

(iii) Production of ethyl 4-(4-oxo-4,5-dihydro-3H-pyrrolo[3,2-d]pyrimidin-6-yl)benzoate A mixture of ethyl 3-amino-5-[4-(ethoxycarbonyl)phenyl]-1H-pyrrole-2-carboxylate (3.36 g), formamidine acetate (1.74 g) and ethanol (60 mL) was heated under reflux for 15 hrs. After cooling to room temperature, the precipitated solid was collected by filtration, washed with ethanol, and dried under reduced pressure at 60° C. to give the title compound (2.97 g).

$^1$H-NMR (DMSO-d$_6$) δ 1.34 (3H, t, J=7.1 Hz), 4.33 (2H, q, J=7.1 Hz), 7.04 (1H, s), 7.84 (1H, d, J=2.7 Hz), 8.00 (2H, d, J=8.1 Hz), 8.11 (2H, d, J=8.1 Hz), 11.97 (1H, br s), 12.64 (1H, br s).

(iv) Production of ethyl 4-(4-chloro-5H-pyrrolo[3,2-d]pyrimidin-6-yl)benzoate hydrochloride A mixture of ethyl 4-(4-oxo-4,5-dihydro-3H-pyrrolo[3,2-d]pyrimidin-6-yl)benzoate (2.97 g) and phosphoryl chloride (16.45 g) was stirred at 110° C. for 1 hr, dioxane (10 mL) was added and the mixture was heated under reflux for 4 hrs. After concentration under reduced pressure, ethanol (30 mL) was added to the residue and, after stirring at room temperature for 30 min, the precipitated solid was collected by filtration. The solid was washed with ethanol and dried under reduced pressure at 60° C. to give the title compound (3.34 g).

$^1$H-NMR (DMSO-d$_6$) δ 1.36 (3H, d, J=7.1 Hz), 4.36 (2H, q, J=7.1 Hz), 7.40 (1H, s), 8.09 (2H, d, J=8.7 Hz), 8.26 (2H, d, J=8.7 Hz), 8.67 (1H, s), 12.77 (1H, br s).

(v) Production of 4-[4-({3-methyl-4-[(6-methylpyridin-3-yl)oxy]phenyl}amino)-5H-pyrrolo[3,2-d]pyrimidin-6-yl]benzoic acid hydrochloride A mixture of ethyl 4-(4-chloro-5H-pyrrolo[3,2-d]pyrimidin-6-yl)benzoate hydrochloride (1.297 g), 3-methyl-4-[(6-methylpyridin-3-yl)oxy]aniline (1.00 g), diisopropylethylamine (0.834 g) and 1-methyl-2-pyrrolidinone (12.5 mL) was stirred at 140° C. for 3 hrs, poured into water (100 mL)-ethyl acetate (150 mL) and the precipitated solid was collected by filtration. The solid was washed with ethyl acetate and dried under reduced pressure at 60° C. The obtained solid was suspended in methanol (40 mL), and 1N aqueous sodium hydroxide solution (20 mL) was added. After stirring at room temperature for 12 hrs, the solvent was evaporated under reduced pressure, and the residue was adjusted to pH 2 with 1N hydrochloric acid. The precipitated solid was collected by filtration, washed with water and dried under reduced pressure at 60° C. to give the title compound (1.08 g).

$^1$H-NMR (DMSO-d$_6$) δ 2.21 (3H, s), 2.44 (3H, s), 6.98 (1H, d, J=9.0 Hz), 7.15 (1H, s), 7.17-7.25 (2H, m), 7.76 (1H, d, J=8.7 Hz), 7.85 (1H, s), 8.01-8.17 (5H, m), 8.48 (1H, s), 9.99 (1H, br s), 12.47 (1H, br s).

Example 76

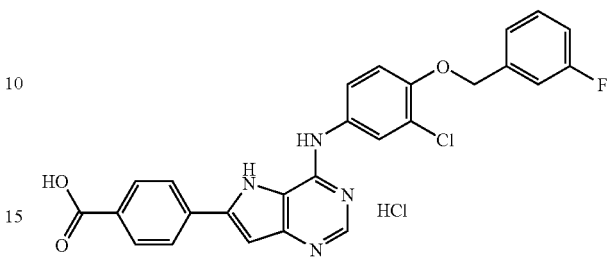

Production of 4-[4-({3-chloro-4-[(3-fluorobenzyl)oxy]phenyl}amino)-5H-pyrrolo[3,2-d]pyrimidin-6-yl]benzoic acid hydrochloride A mixture of ethyl 4-(4-chloro-5H-pyrrolo[3,2-d]pyrimidin-6-yl)benzoate hydrochloride (517 mg), 3-chloro-4-[(3-fluorobenzyl)oxy]aniline (462 mg) and 1-methyl-2-pyrrolidinone (8 mL) was stirred at 140° C. for 5 hrs, poured into water (40 mL), and adjusted to pH 8 with saturated aqueous sodium hydrogen carbonate. The precipitated solid was collected by filtration, washed with water and suspended in methanol (15 mL). After stirring at room temperature for 30 min, the solid was collected by filtration and dried under reduced pressure at 60° C. The obtained solid was suspended in ethanol (10 mL) and 1N aqueous sodium hydroxide solution (1.5 mL) was added. After stirring at room temperature for 6.5 hrs, and at 60° C. for 3.5 hrs, the mixture was cooled to room temperature. 1N Hydrochloric acid (155 mL) was added, and the precipitated solid was collected by filtration, washed with water and dried under reduced pressure at 60° C. to give the title compound (498 mg).

$^1$H-NMR (DMSO-d$_6$) δ 5.24 (2H, s), 7.12-7.35 (5H, m), 7.48 (1H, m), 7.70 (1H, d, J=8.7 Hz), 8.01-8.12 (4H, m), 8.27 (1H, s), 8.37 (1H, s), 9.65 (1H, br s), 12.15 (1H, br s).

Example 77

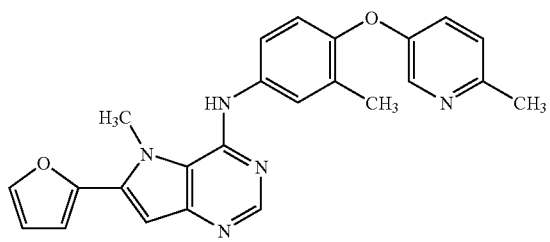

Production of 6-(2-furyl)-5-methyl-N-{3-methyl-4-[(6-methylpyridin-3-yl)oxy]phenyl}-5H-pyrrolo[3,2-d]pyrimidin-4-amine

(i) Production of 4-chloro-6-(2-furyl)-5-methyl-5H-pyrrolo[3,2-d]pyrimidine

To a solution of 4-chloro-6-(2-furyl)-5H-pyrrolo[3,2-d]pyrimidine (220 mg) in N,N-dimethylformamide (2.5 mL)

were added potassium carbonate (139 mg) and methyl iodide (0.25 mL) and the mixture was stirred at room temperature for 8 hrs. The mixture was poured into water (30 mL) and extracted with ethyl acetate (30 mL×3). The organic layers were combined and dried over anhydrous magnesium sulfate. After concentration under reduced pressure, the residue was subjected to silica gel column chromatography (eluent, hexane:ethyl acetate=4:1→0:1) to give the title compound (94 mg).

$^1$H-NMR (CDCl$_3$) δ 4.29 (3H, s), 6.62 (1H, dd, J=3.6, 1.8 Hz), 6.86 (1H, d, J=3.6 Hz), 6.94 (1H, s), 7.67 (1H, d, J=1.8 Hz), 8.68 (1H, s).

(ii) Production of 6-(2-furyl)-5-methyl-N-{3-methyl-4-[(6-methylpyridin-3-yl)oxy]phenyl}-5H-pyrrolo[3,2-d]pyrimidin-4-amine A mixture of 4-chloro-6-(2-furyl)-5-methyl-5H-pyrrolo[3,2-d]pyrimidine (92 mg), 3-methyl-4-[(6-methylpyridin-3-yl)oxy]aniline (102 mg) and 1-methyl-2-pyrrolidinone (2.5 mL) was stirred at 140° C. for 3.5 hrs, poured into water (10 mL) and adjusted to pH 8 with saturated aqueous sodium hydrogen carbonate. The mixture was extracted with ethyl acetate (25 mL×2), and the organic layers were combined and dried over anhydrous magnesium sulfate. After concentration under reduced pressure, the residue was subjected to silica gel column chromatography (eluent, hexane:ethyl acetate=1:1→0:1). The object fraction was concentrated under reduced pressure. Diethyl ether was added to the residue, and the solid was collected by filtration and dried under reduced pressure at 60° C. to give the title compound (105 mg).

$^1$H-NMR (DMSO-d$_6$) δ 2.17 (3H, s), 2.43 (3H, s), 4.12 (3H, s), 6.74 (1H, dd, J=3.6, 1.2 Hz), 6.76 (1H, s), 6.93 (1H, d, J=8.7 Hz), 7.05 (1H, d, J=3.6 Hz), 7.17 (1H, dd, J=8.7, 2.4 Hz), 7.23 (1H, d, J=8.7 Hz), 7.46 (1H, dd, J=8.7, 3.0 Hz), 7.52 (1H, d, J=2.4 Hz), 7.94 (1H, d, J=1.2 Hz), 8.16 (1H, d, J=3.0 Hz), 8.27 (1H, s), 8.71 (1H, br s).

Example 78 added and the mixture was stirred at room temperature for 1 day. The reaction mixture was poured into water (30 mL) and extracted with ethyl acetate (60 mL). The organic layer was dried over anhydrous magnesium sulfate and concentrated under reduced pressure. The residue was subjected to silica gel column chromatography (eluent, hexane:ethyl acetate=4:1→1:4) to give the title compound (76 mg).

$^1$H-NMR (CDCl$_3$) δ 1.09 (3H, t, J=6.9 Hz), 3.42 (2H, q, J=6.9 Hz), 3.82 (2H, t, J=6.3 Hz), 4.92 (2H, t, J=6.3 Hz), 6.60 (1H, dd, J=3.6, 2.1 Hz), 6.94 (1H, s), 6.98 (1H, d, J=3.6 Hz), 7.64 (1H, d, J=2.1 Hz), 8.68 (1H, s).

(ii) Production of 5-(2-ethoxyethyl)-6-(2-furyl)-N-{3-methyl-4-[(6-methylpyridin-3-yl)oxy]phenyl}-5H-pyrrolo[3,2-d]pyrimidin-4-amine A mixture of 4-chloro-5-(2-ethoxyethyl)-6-(2-furyl)-5H-pyrrolo[3,2-d]pyrimidine (76 mg), 3-methyl-4-[(6-methylpyridin-3-yl)oxy]aniline (67 mg) and 1-methyl-2-pyrrolidinone (1.5 mL) was stirred at 140° C. for 2 hrs, poured into water (8 mL) and adjusted to pH 8 with saturated aqueous sodium hydrogen carbonate. The mixture was extracted with ethyl acetate (20 mL×2) and the organic layers were combined and dried over anhydrous magnesium sulfate. After concentration under reduced pressure, the residue was subjected to silica gel column chromatography (eluent, hexane:ethyl acetate=1:1→0:1). The object fraction was concentrated under reduced pressure. Diisopropyl ether-hexane was added to the residue, and the solid was collected by filtration and dried under reduced pressure at 60° C. to give the title compound (78 mg).

$^1$H-NMR (DMSO-d$_6$) δ 1.08 (3H, t, J=6.9 Hz), 2.18 (3H, s), 2.43 (3H, s), 3.52 (2H, q, J=6.9 Hz), 3.95 (2H, t, J=4.4 Hz), 4.68 (2H, brt, J=4.4 Hz), 6.73 (1H, dd, J=3.6, 1.8 Hz), 6.84 (1H, s), 6.96 (1H, d, J=8.1 Hz), 7.01 (1H, d, J=3.6 Hz), 7.16 (1H, dd, J=8.4, 2.7 Hz), 7.22 (1H, d, J=8.4 Hz), 7.50-7.55 (2H, m), 7.93 (1H, d, J=1.8, Hz), 8.15 (1H, d, J=2.7 Hz), 8.31 (1H, s), 9.15 (1H, br s).

Example 79

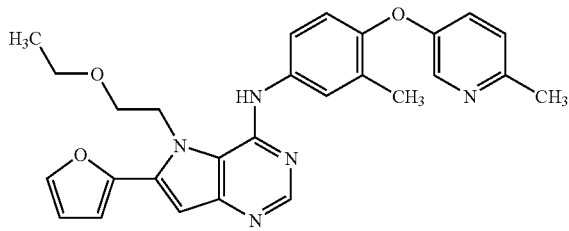

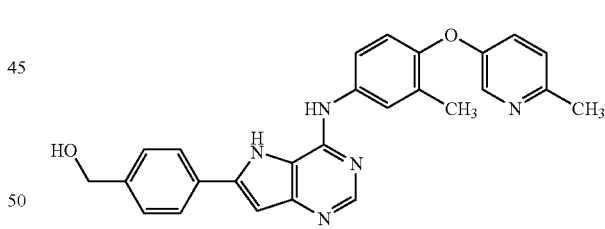

Production of 5-(2-ethoxyethyl)-6-(2-furyl)-N-{3-methyl-4-[(6-methylpyridin-3-yl)oxy]phenyl}-5H-pyrrolo[3,2-d]pyrimidin-4-amine (i) Production of 4-chloro-5-(2-ethoxyethyl)-6-(2-furyl)-5H-pyrrolo[3,2-d]pyrimidine To a solution of 4-chloro-6-(2-furyl)-5H-pyrrolo[3,2-d]pyrimidine (220 mg) in N,N-dimethylformamide (1.2 mL) was added cesium carbonate (489 mg) under ice-cooling, and the mixture was stirred under ice-cooling for 15 min. 2-Bromoethyl ethyl ether (0.169 mL) was added and the mixture was stirred at room temperature for 2 days. Cesium carbonate (326 mg) and 2-bromoethyl ethyl ether (0.113 mL) were Production of {4-[4-({3-methyl-4-[(6-methylpyridin-3-yl)oxy]phenyl}amino)-5H-pyrrolo[3,2-d]pyrimidin-6-yl]phenyl}methanol To a suspension of 4-[4-({3-methyl-4-[(6-methylpyridin-3-yl)oxy]phenyl}amino)-5H-pyrrolo[3,2-d]pyrimidin-6-yl]benzoic acid (122 mg) in tetrahydrofuran (10 mL) was added triethylamine (30.5 mg) and, after stirring at room temperature for 10 min, 1,1'-carbonyldiimidazole (49 mg) was added, and the mixture was stirred at room temperature for 13 hrs. Under ice-cooling, sodium borohydride (28 mg) was added, and methanol (2.5 mL) was further added. After stirring under ice-cooling for 2 hrs, water (1.5 mL) was added, and tetrahydrofuran and methanol were evaporated under reduced pressure. Water (20 mL) was added, and the mixture was extracted with ethyl acetate (30 mL)-tetrahydrofuran (15 mL). The organic layer was separated, and the aqueous layer was extracted with ethyl acetate (15 mL)-tetrahydrofuran (5 mL). The organic layers were combined and dried over anhydrous magnesium sulfate. After concentration under reduced pressure, the residue was subjected to silica gel column chromatography (eluent, ethyl acetate:methanol=99:1→9:1). The object fraction was concentrated under reduced pressure. The residue was recrystallized from methanol-ethyl acetate to give the title compound (65 mg).

¹H-NMR (DMSO-d₆) δ 2.21 (3H, s), 2.43 (3H, s), 4.57 (2H, d, J=4.8 Hz), 5.32 (1H, brt, J=4.8 Hz), 6.96 (1H, s), 6.99 (1H, d, J=8.4 Hz), 7.18 (1H, dd, J=8.7, 2.7 Hz), 7.23 (1H, d, J=8.7 Hz), 7.50 (2H, d, J=7.8 Hz), 7.74 (1H, dd, J=8.4, 2.7 Hz), 7.81-7.85 (3H, m), 8.16 (1H, d, J=2.7 Hz), 8.34 (1H, s), 9.09 (1H, br s), 11.56 (1H, br s).

Example 80

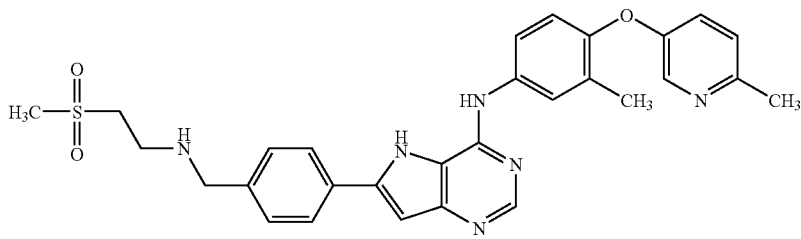

Production of N-{3-methyl-4-[(6-methylpyridin-3-yl)oxy]phenyl}-6-[4-({[2-(methylsulfonyl)ethyl]amino}methyl)phenyl]-5H-pyrrolo[3,2-d]pyrimidin-4-amine A mixture of {4-[4-({3-methyl-4-[(6-methylpyridin-3-yl)oxy]phenyl}amino)-5H-pyrrolo[3,2-d]pyrimidin-6-yl]phenyl}methanol (96 mg), manganese dioxide (1.0 g) and N,N-dimethylformamide (5 mL) was stirred at room temperature for 12 hrs. After celite filtration, the filtrate was concentrated under reduced pressure. The residue was subjected to silica gel column chromatography (eluent, ethyl acetate:methanol=100:0→9:1). A mixture of the obtained solid, methylsulfonylethylamine hydrochloride (27.5 mg), N,N-dimethylformamide (2 mL) and acetic acid (0.02 mL) was stirred at room temperature for 1 hr, and sodium triacetoxyborohydride (36.6 mg) was added. After stirring at room temperature for 4.5 hrs, saturated aqueous sodium hydrogen carbonate (10 mL) was added, and the mixture was extracted with ethyl acetate (25 mL×2). The organic layers were combined, dried over anhydrous magnesium sulfate, and concentrated under reduced pressure. The residue was subjected to silica gel column chromatography (ethyl acetate:methanol=10:0→9:1). The object fraction was concentrated under reduced pressure. Chloroform-diisopropyl ether was added to the residue, and the solid was collected by filtration and dried under reduced pressure at 60° C. to give the title compound (28 mg).

¹H-NMR (DMSO-d₆) δ 2.21 (3H, s), 2.44 (3H, s), 2.94 (2H, t, J=6.6 Hz), 3.00 (3H, s), 3.29 (2H, t, J=6.6 Hz), 3.78 (2H, s), 6.97 (1H, s), 7.00 (1H, d, J=8.7 Hz), 7.19 (1H, dd, J=8.4, 2.7 Hz), 7.24 (1H, d, J=8.4 Hz), 7.51 (2H, d, J=8.4 Hz), 7.77 (1H, dd, J=8.7, 2.4 Hz), 7.83-7.87 (3H, m), 8.18 (1H, d, J=2.4 Hz), 8.34 (1H, s), 9.23 (1H, br s), 11.73 (1H, br s).

Example 81

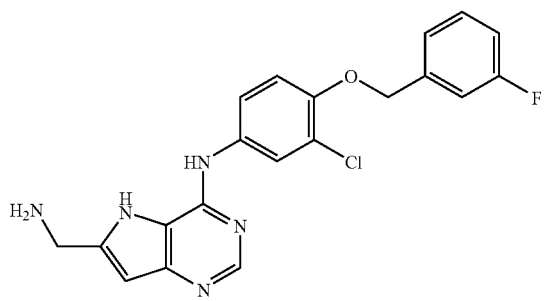

Production of 6-(aminomethyl)-N-{3-chloro-4-[(3-fluorobenzyl)oxy]phenyl}-5H-pyrrolo[3,2-d]pyrimidin-4-amine dihydrochloride (i) Production of N4-{3-chloro-4-[(3-fluorobenzyl)oxy]phenyl}-6-iodopyrimidine-4,5-diamine A solution of 5-amino-4,6-diiodopyrimidine (3.83 g) and 3-chloro-4-[(3-fluorobenzyl)oxy]aniline (2.78 g) in 1-methyl-2-pyrrolidone (30 mL) was stirred at 70° C. for 14 hrs. Water was added to the reaction system and the mixture was extracted with ethyl acetate. The organic layer was washed with water and saturated brine and dried over magnesium sulfate. After concentration under reduced pressure, the residue was separated and purified by column chromatography (eluent, ethyl acetate:hexane=1:4→2:3→1:1) to give the title compound (4.21 g) as brown powder crystals.

¹H-NMR (CDCl₃) δ: 3.47 (2H, br s), 5.13 (2H, s), 6.73 (1H, br s), 6.92 (1H, d, J=9.0 Hz), 6.96-7.04 (1H, m), 7.15-7.25 (2H, m), 7.31-7.38 (2H, m), 7.64 (1H, d, J=2.7 Hz), 8.04 (1H, s).

(ii) Production of tert-butyl 3-[5-amino-6-({3-chloro-4-[(3-fluorobenzyl)oxy]phenyl}amino)pyrimidin-4-yl]prop-2-ynylcarbamate To a solution of N4-{3-chloro-4-[(3-fluorobenzyl)oxy]phenyl}-6-iodopyrimidine-4,5-diamine (0.84 g) and tert-butyl prop-2-ynylcarbamae (0.36 g) in acetonitrile-triethylamine (20 mL-15 mL) were added bis(triphenylphosphine)palladium(II) dichloride (62.5 mg) and copper(I) iodide (20.3 mg) at room temperature, and the mixture was stirred at room temperature under an argon atmosphere for 6 hrs. After concentration under reduced pressure, the residue was separated and purified by column chromatography (eluent, ethyl acetate:hexane=1:1→ethyl acetate) to give the title compound (766.5 mg) as a brown solid.

$^1$H-NMR (DMSO-$d_6$) δ: 1.42 (9H, s), 4.06 (2H, d, J=5.4 Hz), 5.22 (2H, s), 5.45 (2H, br s), 7.13-7.23 (2H, m), 7.26-7.34 (2H, m), 7.42-7.51 (2H, m), 7.54-7.60 (1H, m), 7.95 (2H, s), 8.54 (1H, s).

(iii) Production of tert-butyl [4-({3-chloro-4-[(3-fluorobenzyl)oxy]phenyl}amino)-5H-pyrrolo[3,2-d]pyrimidin-6-yl]methylcarbamate A mixture of tert-butyl (3-[5-amino-6-({3-chloro-4-[(3-fluorobenzyl)oxy]phenyl}amino)pyrimidin-4-yl]prop-2-ynylcarbamate (720 mg) and copper(I) iodide (55.2 mg) in N,N-dimethylformamide (7.0 mL) was stirred at 80° C. for 12 hrs. After concentration under reduced pressure, the residue was separated and purified by column chromatography (basic silica gel, eluent, ethyl acetate→methanol:ethyl acetate=1:9) to give the title compound (604 mg) as pale-yellow powder crystals.

$^1$H-NMR (DMSO-$d_6$) δ: 1.42 (9H, s), 4.33 (2H, d, J=5.7 Hz), 5.22 (2H, s), 6.29 (1H, s), 7.14-7.35 (4H, m), 7.41-7.60 (3H, m), 8.16 (1H, d, J=2.7 Hz), 8.30 (1H, s), 9.29 (1H, s), 10.96 (1H, br s).

(iv) Production of 6-(aminomethyl)-N-{3-chloro-4-[(3-fluorobenzyl)oxy]phenyl}-5H-pyrrolo[3,2-d]pyrimidin-4-amine dihydrochloride To a solution of tert-butyl [4-({3-chloro-4-[(3-fluorobenzyl)oxy]phenyl}amino)-5H-pyrrolo[3,2-d]pyrimidin-6-yl]methylcarbamate (500 mg) in tetrahydrofuran (12 mL) was added 2N hydrochloric acid (6.0 mL) at room temperature. The mixture was stirred at 60° C. for 2 hrs, ethanol was added to the reaction system and the mixture was concentrated under reduced pressure. The resultant crystals were collected by filtration and washed with diisopropyl ether to give the title compound (481.4 mg) as pale-yellow powder crystals.

$^1$H-NMR (DMSO-$d_6$) δ: 4.28-4.39 (2H, m), 5.28 (2H, s), 6.89 (1H, s), 7.15-7.25 (1H, m), 7.29-7.40 (3H, m), 7.45-7.54 (1H, m), 7.73-7.80 (1H, m), 8.15 (1H, s), 8.48-8.65 (3H, m), 8.82 (1H, s).

Example 82

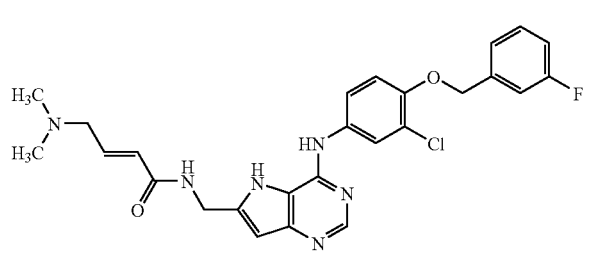

Production of (2E)-N-{[4-({3-chloro-4-[(3-fluorobenzyl)oxy]phenyl}amino)-5H-pyrrolo[3,2-d]pyrimidin-6-yl]methyl}-4-(dimethylamino)but-2-enamide A solution of 6-(aminomethyl)-N-{3-chloro-4-[(3-fluorobenzyl)oxy]phenyl}-5H-pyrrolo[3,2-d]pyrimidin-4-amine dihydrochloride (150 mg), (2E)-4-(dimethylamino)but-2-enoic acid hydrochloride (105 mg), 1-ethyl-3-(3-dimethylaminopropyl)carbodiimide hydrochloride (244 mg), 1-hydroxybenzotriazole monohydrate (196 mg) and triethylamine (0.30 mL) in N,N-dimethylformamide (5 mL) was stirred at room temperature for 2 days. Water was added to the reaction system and the mixture was extracted with ethyl acetate. The organic layer was washed with saturated brine, dried over magnesium sulfate and concentrated under reduced pressure, and the residue was separated and purified by column chromatography (basic silica gel, eluent, methanol:ethyl acetate=1:9→1:4) to give the title compound (104.2 mg) as pale-brown powder crystals.

$^1$H-NMR (DMSO-$d_6$) δ: 2.14 (6H, s), 3.00 (2H, d, J=6.1 Hz), 4.54 (2H, d, J=5.7 Hz), 5.21 (2H, s), 6.11 (1H, d, J=15.3 Hz), 6.35 (1H, s), 6.66 (1H, dt, J=15.3, 6.1 Hz), 7.12-7.34 (4H, m), 7.41-7.49 (1H, m), 7.53-7.60 (1H, m), 8.14 (1H, d, J=2.4 Hz), 8.29 (1H, s), 8.69 (1H, t, J=5.7 Hz), 9.34 (1H, br s), 10.99 (1H, br s).

Example 83

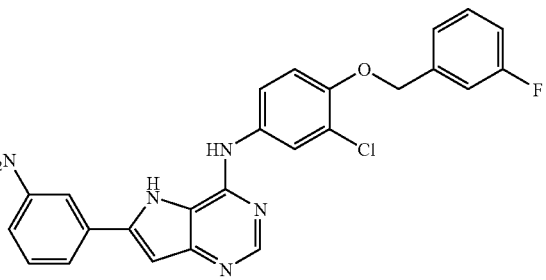

Production of 6-(3-aminophenyl)-N-{3-chloro-4-[(3-fluorobenzyl)oxy]phenyl}-5H-pyrrolo[3,2-d]pyrimidin-4-amine (i) Production of 6-[(3-aminophenyl)ethynyl]-N4-{3-chloro-4-[(3-fluorobenzyl)oxy]phenyl}pyrimidine-4,5-diamine The title compound (1.35 g) was obtained as brown powder crystals by the reaction in the same manner as in Example 81 (ii) using N4-{3-chloro-4-[(3-fluorobenzyl)oxy]phenyl}-6-iodopyrimidine-4,5-diamine (1.90 g), 3-aminophenylacetylene (0.41 mL), bis(triphenylphosphine)palladium(II) dichloride (102 mg), copper(I) iodide (27 mg), acetonitrile (24 mL) and triethylamine (18 mL).

$^1$H-NMR (CDCl$_3$) δ: 3.65-3.78 (4H, m), 5.15 (2H, s), 6.59 (1H, s), 6.73 (1H, d, J=8.1 Hz), 6.90-7.06 (4H, m), 7.14-7.41 (5H, m), 7.68 (1H, d, J=2.7 Hz), 8.35 (1H, s).

(ii) Production of 6-(3-aminophenyl)-N-{3-chloro-4-[(3-fluorobenzyl)oxy]phenyl}-5H-pyrrolo[3,2-d]pyrimidin-4-amine The title compound (673 mg) was obtained as brown powder crystals by the reaction in the same manner as in Example 81 (iii) using 6-[(3-aminophenyl)ethynyl]-N4-{3-chloro-4-[(3-fluorobenzyl)oxy]phenyl}pyrimidine-4,5-diamine (1.30 g), copper(I) iodide (54 mg) and N,N-dimethylformamide (7.0 mL).

$^1$H-NMR (DMSO-$d_6$) δ: 5.23 (2H, s), 5.31 (2H, s), 6.58-6.65 (1H, m), 6.75 (1H, s), 6.94-7.01 (2H, m), 7.13-7.34 (5H, m), 7.43-7.50 (1H, m), 7.57 (1H, dd, J=8.9, 2.6 Hz), 8.19 (1H, d, J=2.1 Hz), 8.32 (1H, s), 9.13 (1H, s), 11.40 (1H, s).

Example 84

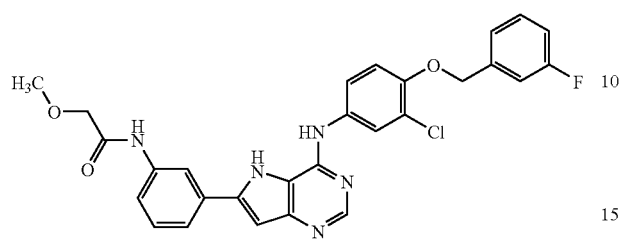

Production of N-{3-[4-({3-chloro-4-[(3-fluorobenzyl)oxy]phenyl}amino)-5H-pyrrolo[3,2-d]pyrimidin-6-yl]phenyl}-2-methoxyacetamide The title compound (42.9 mg) was obtained as pale-brown powder crystals by the reaction in the same manner as in Example 82 using 6-(3-aminophenyl)-N-{3-chloro-4-[(3-fluorobenzyl)oxy]phenyl}-5H-pyrrolo[3,2-d]pyrimidin-4-amine (80 mg), methoxyacetic acid (31 mg), 1-ethyl-3-(3-dimethylaminopropyl)carbodiimide hydrochloride (67 mg), 1-hydroxybenzotriazole monohydrate (54 mg), triethylamine (0.1 mL) and N,N-dimethylformamide (5 mL).

$^1$H-NMR (DMSO-$d_6$) δ: 3.42 (3H, s), 4.06 (2H, s), 5.24 (2H, s) 6.87 (1H, s), 7.13-7.36 (4H, m), 7.44-7.69 (5H, m), 8.19-8.26 (2H, m), 8.35 (1H, s), 9.25 (1H, s), 9.95 (1H, s), 11.56 (1H, s).

Example 85

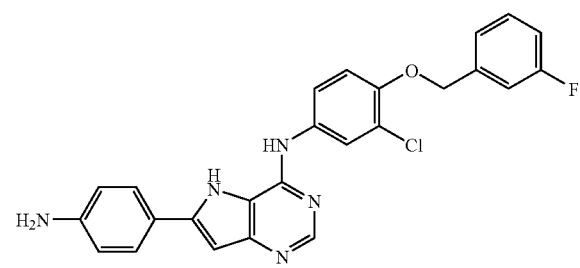

Production of 6-(4-aminophenyl)-N-{3-chloro-4-[(3-fluorobenzyl)oxy]phenyl}-5H-pyrrolo[3,2-d]pyrimidin-4-amine (i) Production of 6-[(4-aminophenyl)ethynyl]-N4-{3-chloro-4-[(3-fluorobenzyl)oxy]phenyl}pyrimidine-4,5-diamine The title compound (1.12 g) was obtained as a yellow solid by the reaction in the same manner as in Example 81 (ii) using N4-{3-chloro-4-[(3-fluorobenzyl)oxy]phenyl}-6-iodopyrimidine-4,5-diamine (1.50 g), 4-aminophenylacetylene (411 mg), bis(triphenylphosphine)palladium(II) dichloride (112 mg), copper(I) iodide (36.5 mg), acetonitrile (24 mL) and triethylamine (18 mL).

$^1$H-NMR (CDCl$_3$) δ: 3.68 (2H, br s), 3.94 (2H, br s), 5.14 (2H, s), 6.58 (1H, br s), 6.65 (2H, d, J=7.8 Hz), 6.95 (1H, d, J=9.0 Hz), 6.96-7.06 (1H, m), 7.19-7.43 (6H, m), 7.68 (1H, d, J=2.7 Hz), 8.34 (1H, s).

(ii) Production of 6-(4-aminophenyl)-N-{3-chloro-4-[(3-fluorobenzyl)oxy]phenyl}-5H-pyrrolo[3,2-d]pyrimidin-4-amine The title compound (768.6 mg) was obtained as yellow powder crystals by the reaction in the same manner as in Example 81 (iii) using 6-[(4-aminophenyl)ethynyl]-N4-{3-chloro-4-[(3-fluorobenzyl)oxy]phenyl}pyrimidine-4,5-diamine (1.11 g), copper(I) iodide (46 mg) and N,N-dimethylformamide (6.0 mL).

$^1$H-NMR (DMSO-$d_6$) δ: 5.22 (2H, s), 5.53 (2H, s), 6.65-6.70 (3H, m), 7.12-7.35 (4H, m), 7.42-7.61 (4H, m), 8.17 (1H, d, J=2.7 Hz), 8.28 (1H, s), 8.99 (1H, s), 11.21 (1H, br s).

Example 86

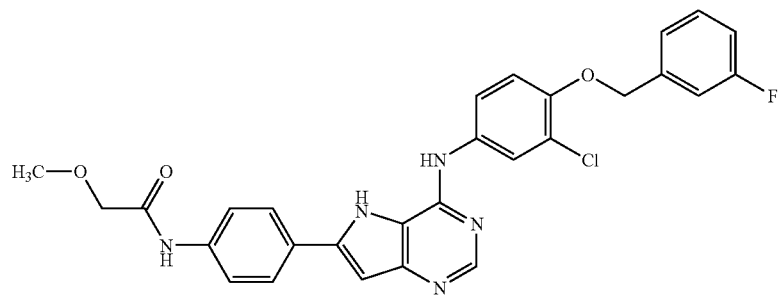

Production of N-{4-[4-({3-chloro-4-[(3-fluorobenzyl)oxy]phenyl}amino)-5H-pyrrolo[3,2-d]pyrimidin-6-yl]phenyl}-2-methoxyacetamide A solution of 6-(4-aminophenyl)-N-{3-chloro-4-[(3-fluorobenzyl)oxy]phenyl}-5H-pyrrolo[3,2-d]pyrimidin-4-amine (100 mg), methoxyacetic acid (29.4 mg), 1-ethyl-3-(3-dimethylaminopropyl)carbodiimide hydrochloride (94 mg), 1-hydroxybenzotriazole monohydrate (75 mg) and triethylamine (0.23 mL) in N,N-dimethylformamide (5 mL) was stirred at room temperature for 20 hrs. Methoxyacetic acid (29.4 mg), 1-ethyl-3-(3-dimethylaminopropyl)carbodiimide hydrochloride (94 mg) and 1-hydroxybenzotriazole monohydrate (75 mg) were added to the reaction system, and the mixture was further stirred for 24 hrs. Water was added to the reaction system and the mixture was extracted with ethyl acetate. The organic layer was washed with saturated brine, dried over magnesium sulfate and concentrated under reduced pressure, and the residue was separated and purified by column chromatography (basic silica gel, eluent, ethyl acetate→4 methanol:ethyl acetate=14:85) to give the title compound (63.5 mg) as pale-brown powder crystals.
$^1$H-NMR (DMSO-$d_6$) δ: 3.40 (3H, s), 4.04 (2H, s), 5.23 (2H, s), 6.90 (1H, s), 7.12-7.21 (1H, m), 7.23-7.35 (3H, s), 7.43-7.49 (1H, m), 7.52-7.60 (1H, m), 7.78-7.87 (4H, m), 8.19 (1H, d, J=1.8 Hz), 8.33 (1H, s), 9.07 (1H, s), 9.97 (1H, s), 11.45 (1H, s).

Example 87

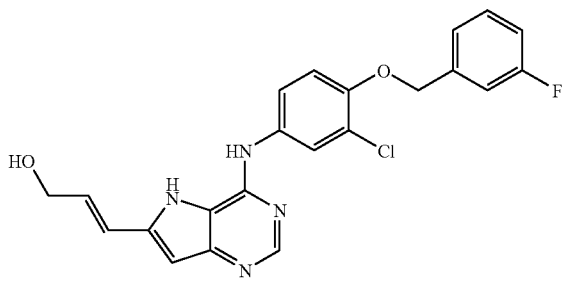

Production of (2E)-3-[4-({3-chloro-4-[(3-fluorobenzyl)oxy]phenyl}amino)-5H-pyrrolo[3,2-d]pyrimidin-6-yl]prop-2-en-1-ol (i) Production of (2E)-5-[5-amino-6-({3-chloro-4-[(3-fluorobenzyl)oxy]phenyl}amino)pyrimidin-4-yl]pent-2-en-4-yn-1-ol The title compound (188.2 mg) was obtained as a brown solid by the reaction in the same manner as in Example 81 (ii) using N4-{3-chloro-4-[(3-fluorobenzyl)oxy]phenyl}-6-iodopyrimidine-4,5-diamine (300 mg), 2-penten-4-yn-1-ol (58 mg), bis(triphenylphosphine)palladium(II) dichloride (22.5 mg), copper(I) iodide (7.3 mg), acetonitrile (6.0 mL) and triethylamine (4.5 mL).
$^1$H-NMR (DMSO-$d_6$) δ: 4.06-4.15 (2H, m), 5.06 (1H, t, J=5.4 Hz), 5.21 (2H, s), 5.45 (2H, br s), 5.98-6.07 (1H, m), 6.46-6.57 (1H, m), 7.12-7.34 (4H, m), 7.39-7.59 (2H, m), 7.92-7.99 (2H, m), 8.55 (1H, br s).

(ii) Production of (2E)-3-[4-({3-chloro-4-[(3-fluorobenzyl)oxy]phenyl}amino)-5H-pyrrolo[3,2-d]pyrimidin-6-yl]prop-2-en-1-ol The title compound (98 mg) was obtained as pale-yellow powder crystals by the reaction in the same manner as in Example 81 (iii) using (2E)-5-[5-amino-6-({3-chloro-4-[(3-fluorobenzyl)oxy]phenyl}amino)pyrimidin-4-yl]pent-2-en-4-yn-1-ol (170 mg), copper(I) iodide (7.6 mg) and N,N-dimethylformamide (1.5 mL).
$^1$H-NMR (DMSO-$d_6$) δ: 4.16-4.24 (2H, m), 5.02-5.09 (1H, m), 5.22 (2H, s), 6.40-6.52 (2H, m), 6.66 (1H, d, J=15.9 Hz), 7.13-7.34 (4H, m), 7.41-7.50 (1H, m), 7.52-7.60 (1H, m), 8.17 (1H, d, J=2.7 Hz), 8.29 (1H, s), 9.13 (1H, br s), 11.38 (1H, br s).

Example 88

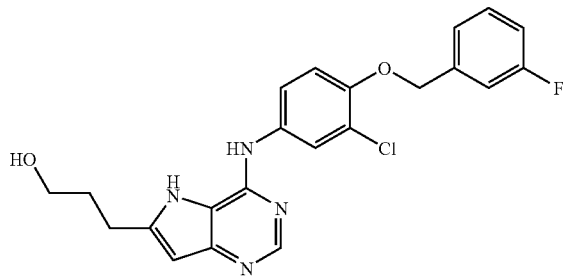

Production of 3-[4-({3-chloro-4-[(3-fluorobenzyl)oxy]phenyl}amino)-5H-pyrrolo[3,2-d]pyrimidin-6-yl]propan-1-ol (i) Production of 5-[5-amino-6-({3-chloro-4-[(3-fluorobenzyl)oxy]phenyl}amino)pyrimidin-4-yl]pent-4-yn-1-ol To a solution of N4-{3-chloro-4-[(3-fluorobenzyl)oxy]phenyl}-6-iodopyrimidine-4,5-diamine (300 mg) and 4-pentyn-1-ol (65 mg) in acetonitrile-triethylamine (6.0 mL-4.5 mL) were added bis(triphenylphosphine)palladium(II) dichloride (22.5 mg) and copper(I) iodide (7.3 mg) at room temperature, and the mixture was stirred at room temperature under an argon atmosphere for 24 hrs. 4-Pentyn-1-ol (65 mg), bis(triphenylphosphine)palladium(II) dichloride (22.5 mg) and copper(I) iodide (7.3 mg) were added to the reaction system and the mixture was stirred at 60° C. for 2 hrs. After concentration under reduced pressure, the residue was separated and purified by column chromatography (basic silica gel, eluent, ethyl acetate→methanol:ethyl acetate=1:19) to give the title compound (157.2 mg) as a yellow solid.
$^1$H-NMR (DMSO-$d_6$) δ: 1.66-1.79 (2H, m), 2.43-2.58 (2H, m), 3.53 (2H, q, J=5.4 Hz), 4.61 (1H, t, J=5.1 Hz), 5.20 (2H, s), 5.31 (2H, s), 7.11-7.21 (2H, m), 7.25-7.33 (2H, m), 7.39-7.50 (1H, m), 7.55 (1H, dd, J=9.0, 2.1 Hz), 7.92-7.94 (2H, m), 8.50 (1H, s).

(ii) Production of 3-[4-({3-chloro-4-[(3-fluorobenzyl)oxy]phenyl}amino)-5H-pyrrolo[3,2-d]pyrimidin-6-yl]propan-1-ol A mixture of 5-[5-amino-6-({3-chloro-4-[(3-fluorobenzyl)oxy]phenyl}amino)pyrimidin-4-yl]pent-4-yn-1-ol (140 mg) and copper(I) iodide (19 mg) in N,N-dimethylformamide (2.0 mL) was stirred at 80° C. for 5 hrs. After concentration under reduced pressure, and the residue was separated and purified by column chromatography (basic silica gel, eluent, ethyl acetate→methanol:ethyl acetate=15:85) to give the title compound (95.2 mg) as pale-brown powder crystals.

¹H-NMR (DMSO-d₆) δ: 1.79-1.91 (2H, m), 2.84 (2H, t, J=7.8 Hz), 3.44-3.52 (2H, m), 4.62-4.68 (1H, m), 5.22 (2H, s), 6.24 (1H, s), 7.13-7.35 (4H, m), 7.43-7.59 (2H, m), 8.17 (1H, d, J=2.7 Hz), 8.29 (1H, s), 9.01 (1H, br s), 10.94-11.05 (1H, m).

Example 89

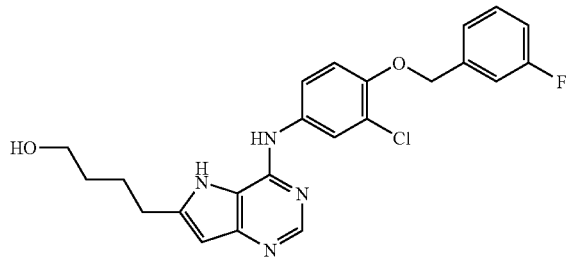

Production of 4-[4-({3-chloro-4-[(3-fluorobenzyl)oxy]phenyl}amino)-5H-pyrrolo[3,2-d]pyrimidin-6-yl]butan-1-ol (i) Production of 6-[5-amino-6-({3-chloro-4-[(3-fluorobenzyl)oxy]phenyl}amino)pyrimidin-4-yl]hex-5-yn-1-ol The title compound (242 mg) was obtained as a brown solid by the reaction in the same manner as in Example 81 (ii) using N4-{3-chloro-4-[(3-fluorobenzyl)oxy]phenyl}-6-iodopyrimidine-4, 5-diamine (300 mg), 5-hexyn-1-ol (94.2 mg), bis(triphenylphosphine)palladium(II) dichloride (22.5 mg), copper(I) iodide (7.3 mg), acetonitrile (6.0 mL) and triethylamine (4.5 mL).

¹H-NMR (DMSO-d₆) δ: 1.51-1.69 (4H, m), 2.39-2.58 (2H, m), 3.41-3.47 (2H, m), 4.46 (1H, t, J=4.8 Hz), 5.20 (2H, s), 5.28 (2H, br s), 7.12-7.22 (2H, m), 7.25-7.33 (2H, m), 7.41-7.49 (1H, m), 7.55 (1H, dd, J=8.6, 2.9 Hz), 7.89-7.96 (2H, m), 8.50 (1H, s).

(ii) Production of 4-[4-({3-chloro-4-[(3-fluorobenzyl)oxy]phenyl}amino)-5H-pyrrolo[3,2-d]pyrimidin-6-yl]butan-1-ol The title compound (109 mg) was obtained as pale-brown powder crystals by the reaction in the same manner as in Example 81 (iii) using 6-[5-amino-6-({3-chloro-4-[(3-fluorobenzyl) oxy]phenyl}amino)pyrimidin-4-yl]hex-5-yn-1-ol (220 mg), copper(I) iodide (9.5 mg) and N,N-dimethylformamide (4.0 mL).

¹H-NMR (DMSO-d₆) δ: 1.44-1.56 (2H, m), 1.67-1.81 (2H, m), 2.80 (2H, t, J=7.8 Hz), 3.45 (2H, t, J=6.0 Hz), 4.40-4.50 (1H, m), 5.21 (2H, s), 6.22 (1H, s), 7.12-7.32 (4H, m), 7.42-7.55 (2H, m), 8.15 (1H, d, J=2.7 Hz), 8.27 (1H, s), 8.98 (1H, s), 10.93 (1H, br s).

Example 90

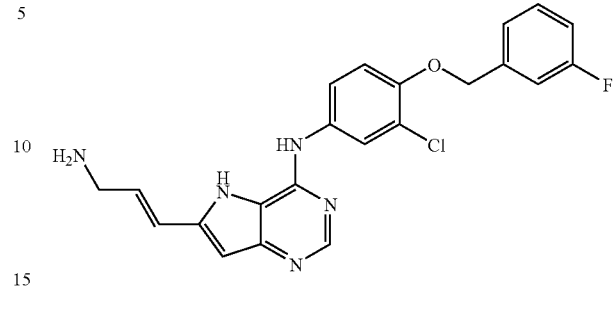

Production of 6-[(1E)-3-aminoprop-1-enyl]-N-{3-chloro-4-[(3-fluorobenzyl)oxy]phenyl}-5H-pyrrolo[3,2-d]pyrimidin-4-amine (i) Production of tert-butyl (2E)-5-[5-amino-6-({3-chloro-4-[(3-fluorobenzyl)oxy]phenyl}amino)pyrimidin-4-yl]pent-2-en-4-ynylcarbamate The title compound (373.8 mg) was obtained as a yellow solid by the reaction in the same manner as in Example 81 (ii) using N4-{3-chloro-4-[(3-fluorobenzyl)oxy]phenyl}-6-iodopyrimidine-4, 5-diamine (600 mg), tert-butyl pent-2-en-4-ynylcarbamate (0.26 g), bis(triphenylphosphine)palladium (II) dichloride (44.6 mg), copper(I) iodide (14.5 mg), acetonitrile (12 mL) and triethylamine (9 mL).

¹H-NMR (DMSO-d₆) δ: 1.40 (9H, s), 3.66-3.75 (2H, m), 5.21 (2H, s), 5.49 (2H, br s), 5.91 (1H, d, J=10.2 Hz), 6.30-6.42 (1H, m), 7.12-7.25 (3H, m), 7.27-7.36 (2H, m), 7.42-7.51 (1H, m), 7.54-7.62 (1H, m), 7.93-7.99 (2H, m), 8.58 (1H, s).

(ii) Production of tert-butyl (2E)-3-[4-({3-chloro-4-[(3-fluorobenzyl)oxy]phenyl}amino)-5H-pyrrolo[3,2-d]pyrimidin-6-yl]prop-2-enylcarbamate The title compound (189 mg) was obtained as pale-brown powder crystals by the reaction in the same manner as in Example 81 (iii) using tert-butyl (2E)-5-[5-amino-6-({3-chloro-4-[(3-fluorobenzyl)oxy]phenyl}amino)pyrimidin-4-yl]pent-2-en-4-ynylcarbamate (350 mg), copper(I) iodide (12.7 mg) and N,N-dimethylformamide (2.0 mL).

¹H-NMR (DMSO-d₆) δ: 1.41 (9H, s), 3.73-3.85 (2H, m), 5.23 (2H, s), 6.22-6.36 (1H, m), 6.48-6.62 (2H, m), 7.14-7.38 (5H, m), 7.42-7.50 (1H, m), 7.52-7.62 (1H, m), 8.18 (1H, s), 8.30 (1H, s), 9.06 (1H, br s), 11.29 (1H, br s).

(iii) Production of 6-[(1E)-3-aminoprop-1-enyl]-N-{3-chloro-4-[(3-fluorobenzyl)oxy]phenyl}-5H-pyrrolo[3,2-d]pyrimidin-4-amine To a solution of tert-butyl (2E)-3-[4-({3-chloro-4-[(3-fluorobenzyl) oxy]phenyl}amino)-5H-pyrrolo[3,2-d]pyrimidin-6-yl]prop-2-enylcarbamate (150 mg) in tetrahydrofuran (6.0 mL) was added 2N hydrochloric acid (3.0 mL) at room temperature and the mixture was stirred at 60° C. for 2 hrs. 1N Aqueous sodium hydroxide solution was added to alkalize the reaction system. After extraction with chloroform, the organic layer was dried over sodium sulfate and concentrated under reduced pressure. The resultant crystals were collected by filtration. The crystals were washed with diisopropyl ether to give the title compound (104 mg) as pale-brown powder crystals.

$^1$H-NMR (DMSO-d$_6$) δ: 3.42 (2H, d, J=4.2 Hz), 5.22 (2H, s), 6.41-6.50 (2H, m), 6.62 (1H, d, J=15.9 Hz), 7.12-7.35 (4H, m), 7.42-7.50 (1H, m), 7.57-7.60 (1H, m), 8.18 (1H, d, J=2.1 Hz), 8.28 (1H, s), 9.20 (1H, br s), 11.39 (1H, br s).

Example 91

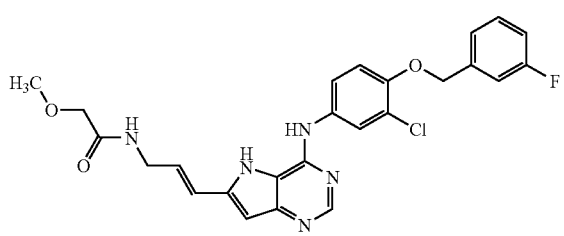

Production of N-{(2E)-3-[4-({3-chloro-4-[(3-fluorobenzyl) oxy]phenyl}amino)-5H-pyrrolo[3,2-d]pyrimidin-6-yl]prop-2-enyl}-2-methoxyacetamide The title compound (23.2 mg) was obtained as pale-brown powder crystals by the reaction in the same manner as in Example 82 using 6-[(1E)-3-aminoprop-1-enyl]-N-{3-chloro-4-[(3-fluorobenzyl)oxy]phenyl}-5H-pyrrolo[3,2-d]pyrimidin-4-amine (30 mg), methoxyacetic acid (14 mg), 1-ethyl-3-(3-dimethylaminopropyl) carbodiimide hydrochloride (55 mg), 1-hydroxybenzotriazole monohydrate (44 mg), triethylamine (0.1 mL) and N,N-dimethylformamide (5 mL).

$^1$H-NMR (DMSO-d$_6$) δ: 3.34 (3H, s), 3.87 (2H, s), 3.95 (2H, t, J=5.4 Hz), 5.21 (2H, s), 6.35 (1H, dt, J=16.2, 5.7 Hz), 6.47 (1H, s), 6.56 (1H, d, J=16.2 Hz), 7.12-7.32 (4H, m), 7.41-7.50 (1H, m), 7.62 (1H, dd, J=9.0. 2.7 Hz), 8.16-8.25 (2H, m), 8.28 (1H, s), 9.37-9.52 (1H, m), 11.67-11.84 (1H, m).

Example 92

Production of (2E)-N-{(2E)-3-[4-({3-chloro-4-[(3-fluorobenzyl) oxy]phenyl}amino)-5H-pyrrolo[3,2-d]pyrimidin-6-yl]prop-2-enyl}-4-(dimethylamino)but-2-enamide The title compound (25.6 mg) was obtained as pale-yellow powder crystals by the reaction in the same manner as in Example 82 using 6-[(1E)-3-aminoprop-1-enyl]-N-{3-chloro-4-[(3-fluorobenzyl)oxy]phenyl}-5H-pyrrolo[3,2-d]pyrimidin-4-amine (40 mg), (2E)-4-(dimethylamino)but-2-enoic acid hydrochloride (31 mg), 1-ethyl-3-(3-dimethylaminopropyl) carbodiimide hydrochloride (72 mg), 1-hydroxybenzotriazole monohydrate (58 mg), triethylamine (0.13 mL) and N,N-dimethylformamide (5 mL).

$^1$H-NMR (DMSO-d$_6$) δ: 2.15 (6H, s), 3.00 (2H, d, J=6.3 Hz), 3.97-4.06 (2H, m), 5.23 (2H, s), 6.10 (1H, d, J=15.3 Hz), 6.27-6.40 (1H, m), 6.51 (1H, s), 6.55-6.68 (2H, m), 7.14-7.36 (4H, m), 7.43-7.60 (2H, m), 8.17 (1H, d, J=2.7 Hz), 8.31 (1H, s), 8.41-8.45 (1H, m), 9.01 (1H, s), 11.22 (1H, s).

Example 93

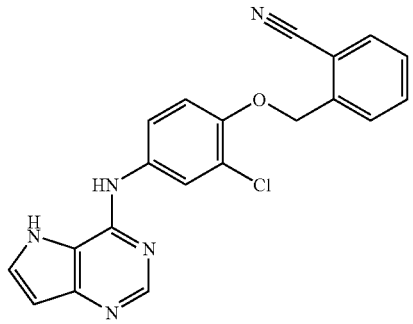

Production of 2-{[2-chloro-4-(5H-pyrrolo[3,2-d]pyrimidin-4-ylamino) phenoxy]methyl}benzonitrile The title compound (272 mg) was obtained by the reaction in the same manner as in Example 2 (ii) using 4-chloro-5H-pyrrolo[3,2-d.]pyrimidine (200 mg) and 2-[(4-amino-2-chlorophenoxy) methyl]benzonitrile (337 mg).

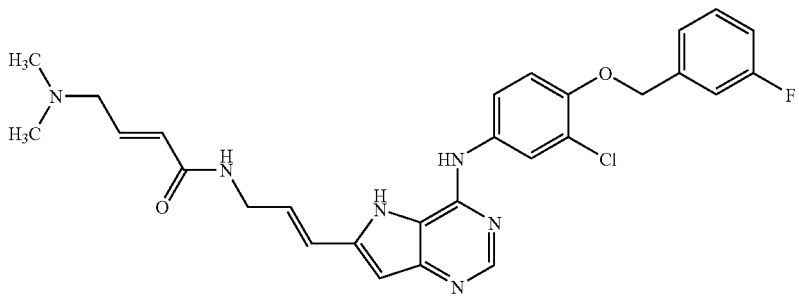

¹H-NMR (DMSO-d₆) δ 5.33 (2H, s), 6.49 (1H, s), 7.32 (1H, d, J=9.0 Hz), 7.57-7.68 (3H, m), 7.78-7.80 (2H, m), 7.94 (1H, d, J=8.1 Hz), 8.20 (1H, m), 8.36 (1H, s), 9.32 (1H, br s), 11.1 (1H, br s).

Example 94

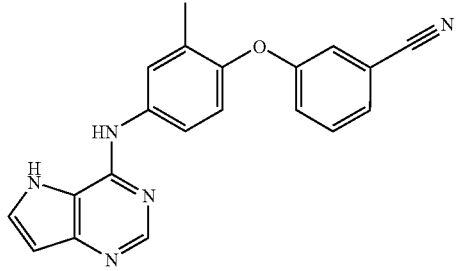

Production of 3-[2-methyl-4-(5H-pyrrolo[3,2-d]pyrimidin-4-ylamino) phenoxy]benzonitrile The title compound (338 mg) was obtained by the reaction in the same manner as in Example 2 (ii) using 4-chloro-5H-pyrrolo[3,2-d]pyrimidine (200 mg) and 3-(4-amino-2-methylphenoxy) benzonitrile (292 mg).

¹H-NMR (DMSO-d₆) δ 2.16 (3H, s), 6.49 (1H, s), 7.06 (1H, d, J=9.3 Hz), 7.21 (1H, m), 7.35 (1H, s), 7.51-7.59 (2H, m), 7.69 (1H, m), 7.80-7.83 (2H, m), 8.35 (1H, s), 9.26 (1H, s), 11.1 (1H, br s).

Example 95

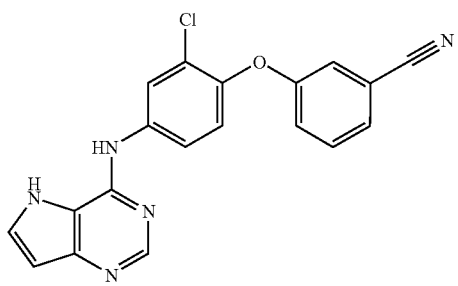

Production of 3-[2-chloro-4-(5H-pyrrolo[3,2-d]pyrimidin-4-ylamino) phenoxy]benzonitrile The title compound (230 mg) was obtained by the reaction in the same manner as in Example 2 (ii) using 4-chloro-5H-pyrrolo[3,2-d]pyrimidine (150 mg) and 3-(4-amino-2-chlorophenoxy) benzonitrile (219 mg).

¹H-NMR (DMSO-d₆) δ 6.53 (1H, s), 7.26 (1H, m), 7.32 (1H, d, J=8.7 Hz), 7.45 (1H, s), 7.58 (2H, d, J=5.7 Hz), 7.70-7.73 (2H, m), 8.41 (2H, s), 9.50 (1H, s), 11.1 (1H, br s).

Example 96

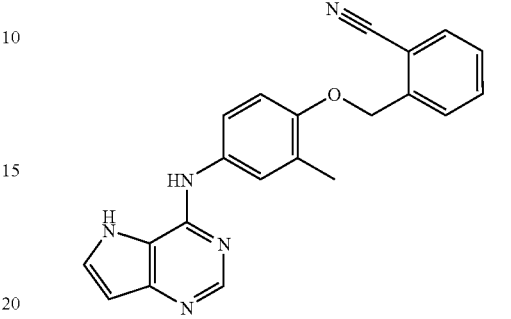

Production of 2-{[2-methyl-4-(5H-pyrrolo[3,2-d]pyrimidin-4-ylamino) phenoxy]methyl}benzonitrile The title compound (250 mg) was obtained by the reaction in the same manner as in Example 2 (ii) using 4-chloro-5H-pyrrolo[3,2-d]pyrimidine (200 mg) and 2-[(4-amino-2-methylphenoxy) methyl]benzonitrile (310 mg).

¹H-NMR (DMSO-d₆) δ 2.24 (3H, s), 5.26 (2H, s), 6.46 (1H, t, J=1.5 Hz), 7.08 (1H, d, J=9.0 Hz), 7.58-7.68 (4H, m), 7.78 (2H, d, J=4.2 Hz), 7.94 (1H, d, J=7.5 Hz), 8.29 (1H, s), 9.02 (1H, br s), 11.1 (1H, br s).

Example 97

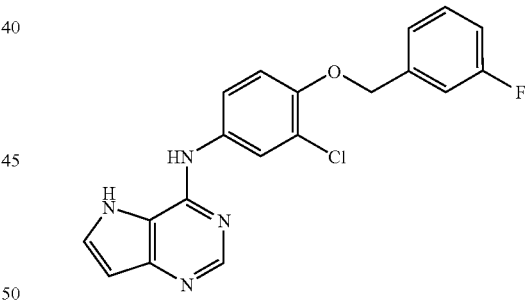

Production of N-{3-chloro-4-[(3-fluorobenzyl)oxy]phenyl}-1H-pyrazolo [4,3-d]pyrimidin-7-amine A mixture of 7-(methylthio)-1H-pyrazolo[4,3-d]pyrimidine (known compound from literature: *J. Am. Chem. Soc.*, 1956, 78, 2418) (150 mg), 3-chloro-4-[(3-fluorobenzyl)oxy] aniline (227 mg) and pyridine hydrochloride (156 mg) in 1-methyl-2-pyrrolidone (3 mL) was stirred at 120° C. for 10 hrs. After the completion of the reaction, the mixture was diluted with ethyl acetate and washed with saturated aqueous sodium hydrogen carbonate and saturated brine. The organic layer was concentrated under reduced pressure, and the residue was subjected to silica gel column chromatography (hexane/ethyl acetate=1/3→1/10) to give the title compound (220 mg, yield 61%) as a pale-yellow solid.

¹H-NMR (CDCl₃) δ 5.15 (2H, s), 6.96 (1H, d, J=8.7 Hz), 7.03 (1H, m), 7.20-7.26 (2H, m), 7.36 (1H, dt, J=5.7, 8.4 Hz), 7.71 (1H, dd, J=2.7, 9.0 Hz), 7.81 (1H, d, J=2.7 Hz), 8.14 (1H, s), 8.57 (1H, s).

Example 98

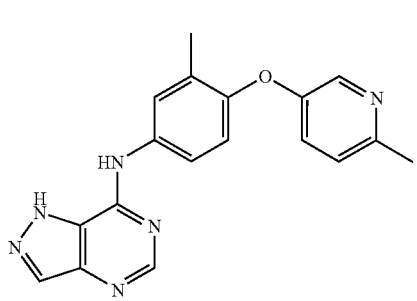

Production of N-{3-methyl-4-[(6-methylpyridin-3-yl)oxy]phenyl}-1H-pyrazolo[4,3-d]pyrimidin-7-amine The title compound (195 mg) was obtained as a brown solid by the reaction in the same manner as in Example 97 using 7-(methylthio)-1H-pyrazolo[4,3-d]pyrimidine (150 mg), 3-methyl-4-[(6-methylpyridin-3-yl)oxy]aniline (193 mg) and pyridine hydrochloride (156 mg).

¹H-NMR (CDCl₃) δ 2.13 (3H, s), 6.89 (1H, d, J=8.4 Hz), 7.11 (1H, d, J=8.1 Hz), 7.15 (1H, dd, J=2.7, 8.4 Hz), 7.50 (1H, dd, J=2.7, 9.0 Hz), 7.68 (1H, d, J=2.7 Hz), 8.14 (1H, s), 8.25 (1H, d, J=2.7 Hz), 8.58 (1H, s).

Example 99

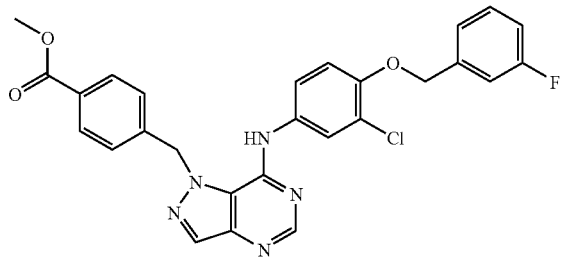

Production of methyl 4-{[7-({3-chloro-4-[(3-fluorobenzyl) oxy]phenyl}amino)-1H-pyrazolo[4,3-d]pyrimidin-1-yl]methyl}benzoate The title compound (45 mg) was obtained as a brown solid by the reaction in the same manner as in Example 97 using methyl 4-{[7-(methylthio)-1H-pyrazolo[4,3-d]pyrimidin-1-yl]methyl}benzoate (120 mg), 3-chloro-4-[(3-fluorobenzyl) oxy]aniline (87 mg) and pyridine hydrochloride (60 mg).

¹H-NMR (CDCl₃) δ 3.94 (3H, s), 5.11 (2H, s), 5.90 (2H, s), 6.34 (1H, br s), 6.85 (1H, d, J=8.7 Hz), 6.94 (1H, dd, J=2.7, 8.7 Hz), 7.01 (1H, m), 7.16-7.22 (2H, m), 7.32 (2H, d, J=8.7 Hz), 7.35 (1H, m), 8.14 (2H, d, J=8.7 Hz), 8.18 (1H, s), 8.51 (1H, s).

Example 100

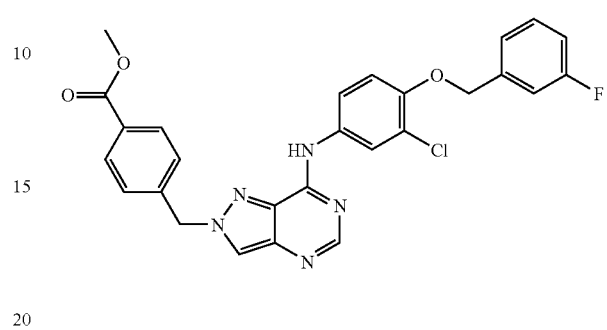

Production of methyl 4-{[7-({3-chloro-4-[(3-fluorobenzyl) oxy]phenyl}amino)-2H-pyrazolo[4,3-d]pyrimidin-2-yl]methyl}benzoate The title compound (140 mg) was obtained as a pale-yellow solid by the reaction in the same manner as in Example 97 using methyl 4-{[7-(methylthio)-2H-pyrazolo[4,3-d]pyrimidin-2-yl]methyl}benzoate (150 mg), 3-chloro-4-[(3-fluorobenzyl)oxy]aniline (109 mg) and pyridine hydrochloride (75 mg).

¹H-NMR (CDCl₃) δ 3.92 (3H, s), 5.16 (2H, s), 5.62 (2H, s), 6.97 (1H, d, J=8.8 Hz), 7.02 (1H, m), 7.18-7.42 (4H, m), 7.55-7.68 (2H, m), 8.00-8.08 (4H, m), 8.50 (1H, s).

Example 101

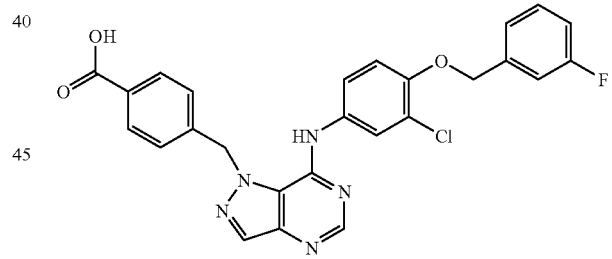

Production of 4-{[7-({3-chloro-4-[(3-fluorobenzyl) oxy]phenyl}amino)-1H-pyrazolo[4,3-d]pyrimidin-1-yl]methyl}benzoic acid To a solution of methyl 4-{[7-({3-chloro-4-[(3-fluorobenzyl) oxy]phenyl}amino)-1H-pyrazolo[4,3-d]pyrimidin-1-yl]methyl}benzoate (25 mg) in a mixed solvent of tetrahydrofuran/methanol (1:1, 1 mL) was added 1N aqueous sodium hydroxide solution (0.5 mL), and the mixture was stirred at room temperature for 1 hr. After the completion of the reaction, 1N aqueous hydrochloric acid solution (0.5 mL) and water (1 mL) were added under ice-cooling, and the mixture was stirred at room temperature for 1 hr. The resultant solid was collected by filtration, and washed with diisopropyl ether and dried to give the title compound (16 mg) as pale-yellow crystals.

¹H-NMR (DMSO-d₆) δ 5.24 (2H, s), 6.10 (2H, s), 7.13-7.31 (5H, m), 7.42-7.47 (2H, m), 7.70 (1H, m), 7.83-7.91 (2H, m), 8.27 (1H, s), 8.35 (1H, s), 8.81 (1H, s), 12.9 (1H, br s).

Example 102

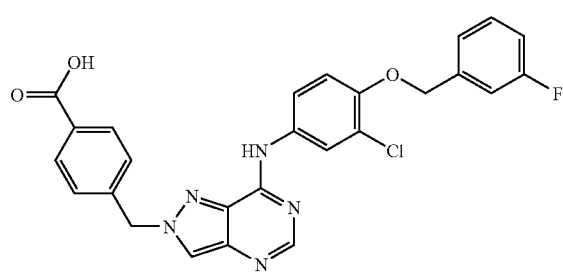

Production of 4-{[7-({3-chloro-4-[(3-fluorobenzyl)oxy]phenyl}amino)-2H-pyrazolo[4,3-d]pyrimidin-2-yl]methyl}benzoic acid The title compound (130 mg) was obtained as pale-yellow crystals by the reaction in the same manner as in Example 101 using methyl 4-{[7-({3-chloro-4-[(3-fluorobenzyl)oxy]phenyl}amino)-2H-pyrazolo[4,3-d]pyrimidin-2-yl]methyl}benzoate (150 mg) and 1N aqueous sodium hydroxide solution (6 mL).

¹H-NMR (DMSO-d₆) δ 5.26 (2H, s), 5.85 (2H, s), 7.15-7.32 (4H, m), 7.41 (2H, d, J=8.1 Hz), 7.45 (1H, m), 7.72 (1H, dd, J=2.4, 8.7 Hz), 7.94 (2H, d, J=8.1 Hz), 8.06 (1H, d, J=2.1 Hz), 8.65 (1H, s), 8.85 (1H, s), 11.4 (1H, br s).

Example 103

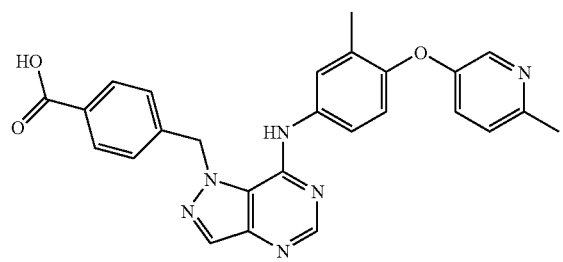

Production of 4-{[7-({3-methyl-4-[(6-methylpyridin-3-yl)oxy]phenyl}amino)-1H-pyrazolo[4,3-d]pyrimidin-1-yl]methyl}benzoic acid Methyl 4-{[7-({3-methyl-4-[(6-methylpyridin-3-yl)oxy]phenyl}amino)-1H-pyrazolo[4,3-d]pyrimidin-1-yl]methyl}benzoate was obtained as a mixture with 1-methyl-2-pyrrolidone by the reaction in the same manner as in Example 97 using methyl 4-{[7-(methylthio)-1H-pyrazolo[4,3-d]pyrimidin-1-yl]methyl}benzoate (120 mg), 3-methyl-4-[(6-methylpyridin-3-yl)oxy]aniline (87 mg) and pyridine hydrochloride (60 mg).

The title compound (20 mg) was obtained as yellow crystals by the reaction in the same manner as in Example 101 using the above-mentioned mixture and 1N aqueous sodium hydroxide solution (1 mL).

¹H-NMR (DMSO-d₆) δ 2.17 (3H, s), 2.43 (3H, s), 6.12 (2H, s), 6.91 (2H, d, J=8.7 Hz), 7.12-7.24 (4H, m), 7.38-7.47 (2H, m), 7.85 (2H, d, J=8.1 Hz), 8.16 (1H, d, J=2.4 Hz), 8.28 (1H, s), 8.35 (1H, s), 8.81 (1H, s).

Example 104

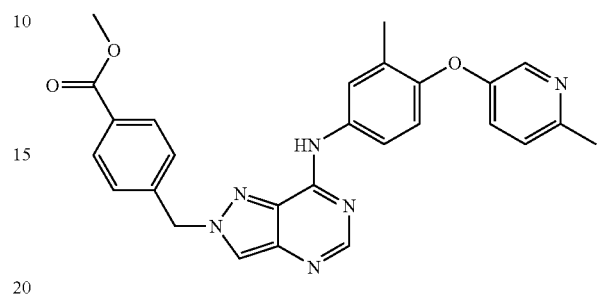

Production of methyl 4-{[7-({3-methyl-4-[(6-methylpyridin-3-yl)oxy]phenyl}amino)-2H-pyrazolo[4,3-d]pyrimidin-2-yl]methyl}benzoate The title compound (160 mg) was obtained as pale-yellow crystals by the reaction in the same manner as in Example 97 using methyl 4-{[7-(methylthio)-2H-pyrazolo[4,3-d]pyrimidin-2-yl]methyl}benzoate (150 mg), 3-methyl-4-[(6-methylpyridin-3-yl)oxy]aniline (93 mg) and pyridine hydrochloride (75 mg).

¹H-NMR (CDCl₃) δ 2.27 (3H, s), 2.52 (3H, s), 3.91 (3H, s), 5.60 (2H, s), 6.90 (1H, d, J=8.7 Hz), 7.08-7.09 (2H, m), 7.31 (1H, s), 7.66 (1H, dd, J=3.0, 9.0 Hz), 7.76 (1H, d, J=2.4 Hz), 7.86 (1H, m), 8.02 (2H, s), 8.04 (1H, s), 8.25 (1H, m), 8.51 (1H, s).

Example 105

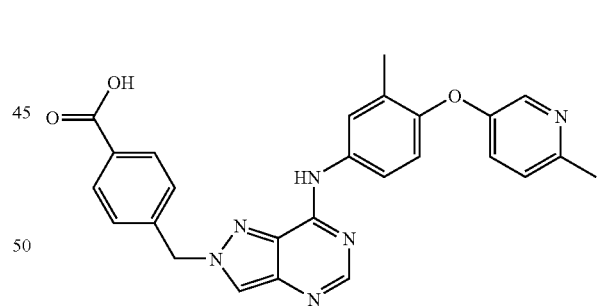

Production of 4-{[7-({3-methyl-4-[(6-methylpyridin-3-yl)oxy]phenyl}amino)-2H-pyrazolo[4,3-d]pyrimidin-2-yl]methyl}benzoic acid The title compound (120 mg) was obtained as white crystals by the reaction in the same manner as in Example 101 using methyl 4-{[7-({3-methyl-4-[(6-methylpyridin-3-yl)oxy]phenyl}amino)-2H-pyrazolo[4,3-d]pyrimidin-2-yl]methyl}benzoate (150 mg) and 1N aqueous sodium hydroxide solution (3 mL).

¹H-NMR (DMSO-d₆) δ 2.17 (3H, s), 2.43 (3H, s), 5.80 (2H, s), 6.93 (1H, d, J=8.7 Hz), 7.13-7.23 (2H, m), 7.37 (2H, d, J=7.8 Hz), 7.84 (1H, dd, J=2.1, 9.0 Hz), 7.92-7.97 (2H, m), 8.15 (1H, d, J=2.1 Hz), 8.32 (1H, s), 8.67 (1H, s), 10.09 (1H, s), 13.0 (1H, br s).

Example 106

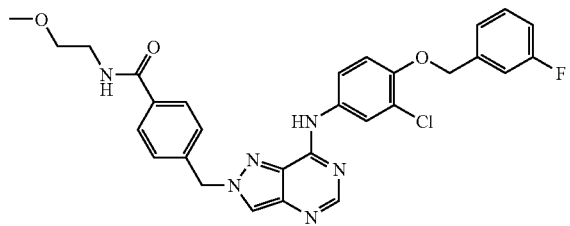

Production of 4-{[7-({3-chloro-4-[(3-fluorobenzyl)oxy]phenyl}amino)-2H-pyrazolo[4,3-d]pyrimidin-2-yl]methyl}-N-(2-methoxyethyl)benzamide A solution of 4-{[7-({3-chloro-4-[(3-fluorobenzyl)oxy]phenyl}amino)-2H-pyrazolo[4,3-d]pyrimidin-2-yl]methyl}benzoic acid (45 mg), 2-methoxyethylamine (9 mg), 1-hydroxybenzotriazole (18 mg), 1-[3-(dimethylamino)propyl]-3-ethylcarbodiimide hydrochloride (26 mg) and triethylamine (0.08 mL) in N,N-dimethylformamide (2 mL) was stirred at room temperature for 30 hrs. After the completion of the reaction, the reaction solution was concentrated under reduced pressure, and the residue was subjected to silica gel column chromatography (basic silica gel; ethyl acetate) to give the title compound (115 mg) as a pale-yellow solid.

$^1$H-NMR (CDCl$_3$) δ 3.38 (3H, s), 3.54-3.57 (2H, m), 3.63-3.68 (2H, m), 5.12 (2H, s), 5.60 (2H, s), 6.53 (1H, br s), 6.97 (1H, d, J=8.7 Hz), 7.02 (1H, m), 7.20-7.40 (3H, m), 7.31 (1H, d, J=8.4 Hz), 7.64 (1H, d, J=8.7 Hz), 7.65 (1H, d, J=8.4 Hz), 7.79 (1H, d, J=8.4 Hz), 8.00-8.01 (2H, m), 8.50 (1H, s).

Example 107

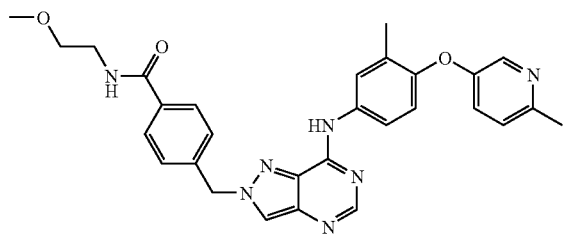

Production of N-(2-methoxyethyl)-4-{[7-({3-methyl-4-[(6-methylpyridin-3-yl)oxy]phenyl}amino)-2H-pyrazolo[4,3-d]pyrimidin-2-yl]methyl}benzamide The title compound (30 mg) was obtained as white crystals by the reaction in the same manner as in Example 106 using 4-{[7-({3-methyl-4-[(6-methylpyridin-3-yl)oxy]phenyl}amino)-2H-pyrazolo[4,3-d]pyrimidin-2-yl]methyl}benzoic acid (45 mg), 2-methoxyethylamine (10 mg), 1-hydroxybenzotriazole (20 mg), 1-[3-(dimethylamino)propyl]-3-ethylcarbodiimide hydrochloride (28 mg) and triethylamine (0.08 mL).

$^1$H-NMR (CDCl$_3$) δ 2.29 (3H, s), 2.53 (3H, s), 3.38 (3H, s), 3.54-3.57 (2H, m), 3.63-3.68 (2H, m), 5.62 (2H, s), 6.51 (1H, br s), 6.93 (1H, d, J=8.7 Hz), 7.09-7.10 (2H, m), 7.34 (2H, d, J=8.1 Hz), 7.62-7.69 (2H, m), 7.76 (1H, m), 7.80 (1H, d, J=8.1 Hz), 8.02 (1H, s), 8.26 (1H, m), 8.51 (1H, s).

Example 108

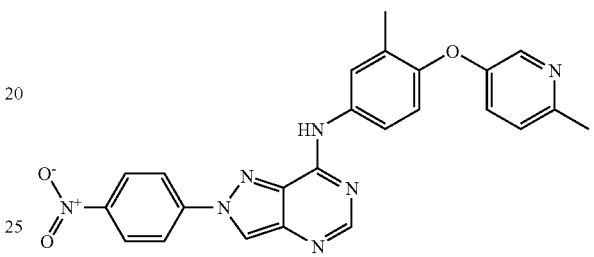

Production of N-{3-methyl-4-[(6-methylpyridin-3-yl)oxy]phenyl}-2-(4-nitrophenyl)-2H-pyrazolo[4,3-d]pyrimidin-7-amine (i) Production of 7-(methylthio)-2-(4-nitrophenyl)-2H-pyrazolo[4,3-d]pyrimidine To a solution of 7-(methylthio)-1H-pyrazolo[4,3-d]pyrimidine (500 mg) in N,N-dimethylformamide (10 mL) was added potassium tert-butoxide (405 mg) under ice-cooling, and the mixture was stirred at room temperature for 10 min. Subsequently, 1-fluoro-4-nitrobenzene (465 mg) was added, and the mixture was stirred at 70° C. for 30 min. After the completion of the reaction, water was added to the reaction mixture and the mixture was stirred at room temperature for 30 min. The resultant solid was collected by filtration, washed with diisopropyl ether and dried to give the title compound (860 mg) as brown crystals.

$^1$H-NMR (DMSO-d$_6$) δ 2.72 (3H, s), 8.39 (2H, d, J=8.7 Hz), 8.46 (2H, d, J=8.7 Hz), 8.76 (1H, s), 9.64 (1H, s).

(ii) Production of N-{3-methyl-4-[(6-methylpyridin-3-yl)oxy]phenyl}-2-(4-nitrophenyl)-2H-pyrazolo[4,3-d]pyrimidin-7-amine The title compound (667 mg) was obtained as a pale-yellow solid by the reaction in the same manner as in Example 97 using 7-(methylthio)-2-(4-nitrophenyl)-2H-pyrazolo[4,3-d]pyrimidine (430 mg), 3-methyl-4-[(6-methylpyridin-3-yl)oxy]aniline (321 mg) and pyridine hydrochloride (259 mg).

$^1$H-NMR (CDCl$_3$) δ 2.32 (3H, s), 2.54 (3H, s), 6.95 (1H, d, J=9.0 Hz), 7.07-7.15 (2H, m), 7.71 (1H, dd, J=2.7, 8.4 Hz), 7.80-7.81 (2H, m), 8.12 (2H, d, J=9.3 Hz), 8.25 (1H, dd, J=0.6, 2.7 Hz), 8.45 (2H, d, J=9.3 Hz), 8.55 (1H, s), 8.57 (1H, s).

Example 109

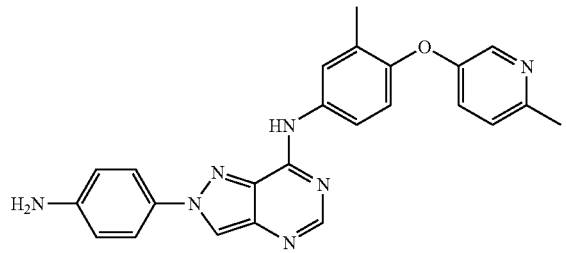

Production of 2-(4-aminophenyl)-N-{3-methyl-4-[(6-methylpyridin-3-yl)oxy]phenyl}-2H-pyrazolo[4,3-d]pyrimidin-7-amine To a solution of N-{3-methyl-4-[(6-methylpyridin-3-yl)oxy]phenyl}-2-(4-nitrophenyl)-2H-pyrazolo[4,3-d]pyrimidin-7-amine (200 mg) in a mixed solvent of ethanol/water (9:1, 6 mL) was added calcium chloride (90%, 28 mg) and the mixture was stirred at 100° C. for 10 min. Reduced iron (90%, 164 mg) was added at room temperature, and the mixture was stirred at 100° C. for 5 hrs. After the completion of the reaction, the reaction mixture was filtered (celite), and the filtrate was concentrated under reduced pressure. Water was added to the residue and the mixture was diluted with ethyl acetate and washed with water and saturated brine. The organic layer was dried over anhydrous magnesium sulfate, filtered and concentrated under reduced pressure. The residue was purified by silica gel column chromatography (ethyl acetate/methylene chloride=10/1) to give the title compound (140 mg) as a white solid.

$^1$H-NMR (DMSO-$d_6$) δ 2.20 (3H, s), 2.44 (3H, s), 5.55 (2H, s), 6.71-6.74 (2H, m), 6.95-6.98 (1H, m), 7.18-7.23 (2H, m), 7.73-7.76 (2H, m), 7.901 (1H, m), 8.03 (1H, br s), 8.18 (1H, br s), 8.34 (1H, br s), 8.94 (1H, br s), 10.05 (1H, br s).

Example 110

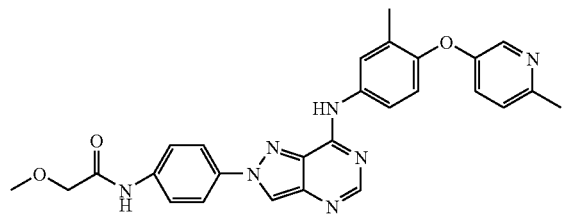

Production of 2-methoxy-N-{4-[7-({3-methyl-4-[(6-methylpyridin-3-yl)oxy]phenyl}amino)-2H-pyrazolo[4,3-d]pyrimidin-2-yl]phenyl}acetamide The title compound (64 mg) was obtained as white crystals by the reaction in the same manner as in Example 106 using 2-(4-aminophenyl)-N-{3-methyl-4-[(6-methylpyridin-3-yl)oxy]phenyl}-2H-pyrazolo[4,3-d]pyrimidin-7-amine (100 mg), methoxyacetic acid (30 mg), 1-hydroxybenzotriazole (48 mg), 1-[3-(dimethylamino)propyl]-3-ethylcarbodiimide hydrochloride (68 mg) and triethylamine (0.20 mL).

$^1$H-NMR (CDCl$_3$) δ 2.26 (3H, s), 2.53 (3H, s), 3.55 (3H, s), 4.07 (2H, s), 6.92 (1H, d, J=8.7 Hz), 7.12-7.25 (2H, m), 7.35-7.45 (3H, m), 7.70-7.83 (4H, m), 8.19 (1H, d, J=2.4 Hz), 8.44 (2H, s), 8.50 (1H, s).

Example 111

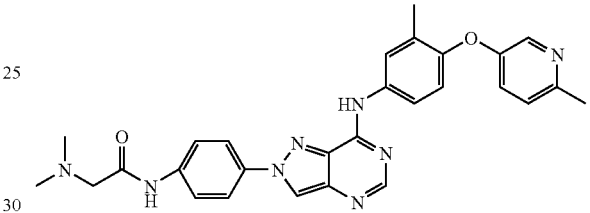

Production of 2-(N,N-dimethylamino)-N-{4-[7-({3-methyl-4-[(6-methylpyridin-3-yl)oxy]phenyl}amino)-2H-pyrazolo[4,3-d]pyrimidin-2-yl]phenyl}acetamide The title compound (60 mg) was obtained as white crystals by the reaction in the same manner as in Example 106 using 2-(4-aminophenyl)-N-{3-methyl-4-[(6-methylpyridin-3-yl)oxy]phenyl}-2H-pyrazolo[4,3-d]pyrimidin-7-amine (100 mg), N,N-dimethylglycine hydrochloride (46 mg), 1-hydroxybenzotriazole (48 mg), 1-[3-(dimethylamino)propyl]-3-ethylcarbodiimide hydrochloride (68 mg) and triethylamine (0.20 mL).

$^1$H-NMR (CDCl$_3$) δ 2.31 (3H, s), 2.43 (6H, s), 2.53 (3H, s), 3.14 (2H, s), 6.95 (1H, d, J=9.0 Hz), 7.09-7.11 (2H, m), 7.70-7.76 (2H, m), 7.81-7.85 (5H, m), 8.27 (1H, m), 8.43 (1H, s), 8.55 (1H, s), 9.35 (1H, br s).

Example 112

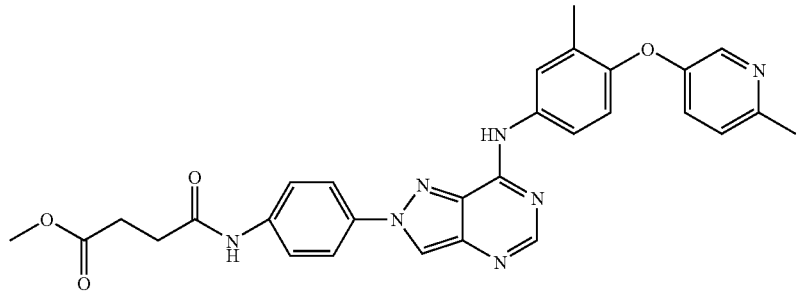

Production of methyl 4-({4-[7-({3-methyl-4-[(6-methylpyridin-3-yl)oxy]phenyl}amino)-2H-pyrazolo[4,3-d]pyrimidin-2-yl]phenyl}amino)-4-oxobutanoate The title compound (175 mg) was obtained as white crystals by the reaction in the same manner as in Example 106 using 2-(4-aminophenyl)-N-{3-methyl-4-[(6-methylpyridin-3-yl)oxy]phenyl}-2H-pyrazolo[4,3-d]pyrimidin-7-amine (150 mg), succinic acid monomethyl ester (66 mg), 1-hydroxybenzotriazole (72 mg), 1-[3-(dimethylamino)propyl]-3-ethylcarbodiimide hydrochloride (102 mg) and triethylamine (0.30 mL).

$^1$H-NMR (CDCl$_3$) δ 2.30 (3H, s), 2.53 (3H, s), 2.73-2.75 (2H, m), 2.79-2.81 (2H, m), 3.75 (3H, s), 6.94 (1H, d, J=8.7 Hz), 7.10-7.12 (2H, m), 7.69-7.74 (3H, m), 7.79-7.82 (4H, m), 8.08 (1H, br s), 8.27 (1H, dd, J=0.6, 2.4 Hz), 8.42 (1H, s), 8.53 (1H, s).

Example 113

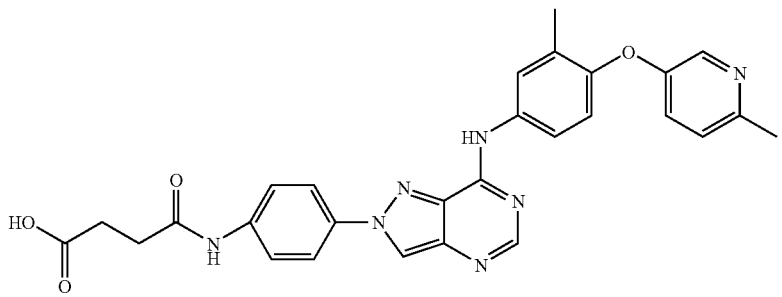

Production of 4-({4-[7-({3-methyl-4-[(6-methylpyridin-3-yl)oxy]phenyl}amino)-2H-pyrazolo[4,3-d]pyrimidin-2-yl]phenyl}amino)-4-oxobutanoic acid The title compound (98 mg) was obtained as white crystals by the reaction in the same manner as in Example 101 using methyl 4-({4-[7-({3-methyl-4-[(6-methylpyridin-3-yl)oxy]phenyl}amino)-2H-pyrazolo[4,3-d]pyrimidin-2-yl]phenyl}amino)-4-oxobutanoate (175 mg) and 1N aqueous sodium hydroxide solution (0.5 mL).

$^1$H-NMR (DMSO-d$_6$) δ 2.21 (3H, s), 2.44 (3H, s), 2.50-2.61 (4H, m), 6.97 (1H, d, J=8.4 Hz), 7.20-7.22 (2H, m), 7.81-7.93 (4H, m), 8.03-8.09 (3H, m), 8.18 (1H, m), 8.36 (1H, s), 9.13 (1H, s), 10.2 (1H, br s), 10.3 (1H, s).

Example 114

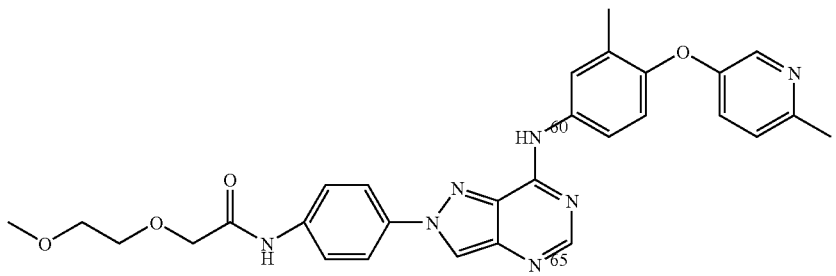

Production of 2-(2-methoxyethoxy)-N-{4-[7-({3-methyl-4-[(6-methylpyridin-3-yl)oxy]phenyl}amino)-2H-pyrazolo[4,3-d]pyrimidin-2-yl]phenyl}acetamide The title compound (88 mg) was obtained as white crystals by the reaction in the same manner as in Example 106 using 2-(4-aminophenyl)-N-{3-methyl-4-[(6-methylpyridin-3-yl)oxy]phenyl}-2H-pyrazolo[4,3-d]pyrimidin-7-amine (130 mg), (2-methoxyethoxy)acetic acid (58 mg), 1-hydroxybenzotriazole (62 mg), 1-[3-(dimethylamino)propyl]-3-ethylcarbodiimide hydrochloride (88 mg) and triethylamine (0.26 mL).

$^1$H-NMR (CDCl$_3$) δ 2.30 (3H, s), 2.53 (3H, s), 3.52 (3H, s), 3.63-3.66 (2H, m), 3.80-3.82 (2H, m), 4.16 (2H, s), 6.94 (1H, d, J=8.7 Hz), 7.07-7.10 (2H, m), 7.71 (1H, d, J=8.7 Hz), 7.80 (1H, m), 7.83 (4H, s), 8.27 (1H, s), 8.43 (1H, s), 8.54 (1H, s), 9.16 (1H, s).

Example 115

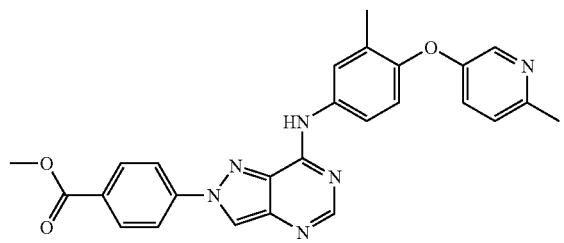

Production of methyl 4-[7-({3-methyl-4-[(6-methylpyridin-3-yl)oxy]phenyl}amino)-2H-pyrazolo[4,3-d]pyrimidin-2-yl]benzoate (i) Production of methyl 4-[7-(methylthio)-2H-pyrazolo[4,3-d]pyrimidin-2-yl]benzoate To a solution of 7-(methylthio)-1H-pyrazolo[4,3-d]pyrimidine (100 mg) and methyl 4-fluorobenzoate (102 mg) in 1-methyl-2-pyrrolidone (2 mL) was added potassium carbonate (125 mg), and the mixture was stirred at 120° C. for 3 hrs. After the completion of the reaction, water was added to the reaction mixture and the mixture was stirred at room temperature for 30 min. The resultant solid was collected by filtration, washed with diisopropyl ether and dried to give the title compound (90 mg) as yellow crystals.

$^1$H-NMR (CDCl$_3$) δ 2.76 (3H, s), 3.98 (3H, s), 8.04 (2H, d, J=8.4 Hz), 8.24 (2H, d, J=8.4 Hz), 8.63 (1H, s), 8.77 (1H, s).

(ii) Production of methyl 4-[7-({3-methyl-4-[(6-methylpyridin-3-yl)oxy]phenyl}amino)-2H-pyrazolo[4,3-d]pyrimidin-2-yl]benzoate The title compound (135 mg) was obtained as a pale-yellow solid by the reaction in the same manner as in Example 97 using methyl 4-[7-(methylthio)-2H-pyrazolo[4,3-d]pyrimidin-2-yl]benzoate (115 mg), 3-methyl-4-[(6-methylpyridin-3-yl)oxy]aniline (82 mg) and pyridine hydrochloride (66 mg).

$^1$H-NMR (CDCl$_3$) δ 2.32 (3H, s), 2.54 (3H, s), 3.99 (3H, s), 6.95 (1H, d, J=8.7 Hz), 7.10-7.12 (2H, m), 7.73 (1H, dd, J=2.7, 8.7 Hz), 7.81-7.82 (2H, m), 8.00 (2H, d, J=8.4 Hz), 8.26 (2H, d, J=8.4 Hz), 8.27 (1H, s), 8.55 (1H, s), 8.56 (1H, s).

Example 116

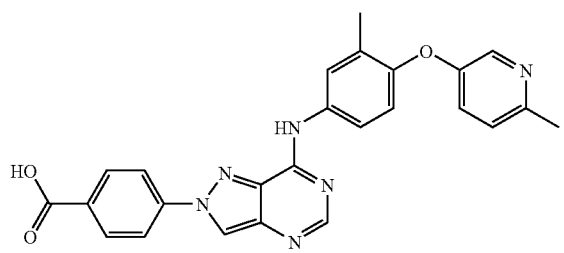

Production of 4-[7-({3-methyl-4-[(6-methylpyridin-3-yl)oxy]phenyl}amino)-2H-pyrazolo[4,3-d]pyrimidin-2-yl]benzoic acid The title compound (91 mg) was obtained as white crystals by the reaction in the same manner as in Example 101 using methyl 4-[7-({3-methyl-4-[(6-methylpyridin-3-yl)oxy]phenyl}amino)-2H-pyrazolo[4,3-d]pyrimidin-2-yl]benzoate (110 mg) and 1N aqueous sodium hydroxide solution (0.4 mL).

$^1$H-NMR (DMSO-d$_6$) δ 2.21 (3H, s), 2.44 (3H, s), 6.98 (1H, d, J=9.0 Hz), 7.21-7.26 (2H, m), 7.90 (1H, dd, J=2.7, 8.7 Hz), 8.03 (1H, m), 8.12-8.22 (6H, m), 8.38 (1H, s), 9.30 (1H, s), 10.3 (1H, br s).

Example 117

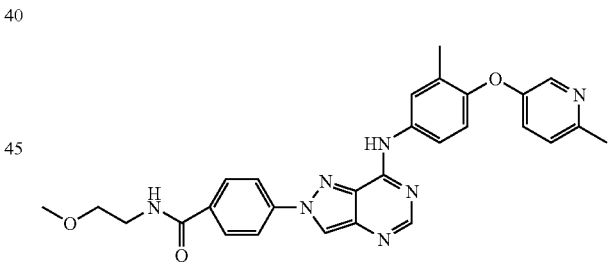

Production of N-(2-methoxyethyl)-4-[7-({3-methyl-4-[(6-methylpyridin-3-yl)oxy]phenyl}amino)-2H-pyrazolo[4,3-d]pyrimidin-2-yl]benzamide The title compound (63 mg) was obtained as white crystals by the reaction in the same manner as in Example 106 using 4-[7-({3-methyl-4-[(6-methylpyridin-3-yl)oxy]phenyl}amino)-2H-pyrazolo[4,3-d]pyrimidin-2-yl]benzoic acid (75 mg), 2-methoxyethylamine (17 mg), 1-hydroxybenzotriazole (34 mg), 1-[3-(dimethylamino)propyl]-3-ethylcarbodiimide hydrochloride (48 mg) and triethylamine (0.14 mL).

$^1$H-NMR (CDCl$_3$) δ 2.31 (3H, s), 2.54 (3H, s), 3.43 (3H, s), 3.60-3.63 (2H, m), 3.69-3.74 (2H, m), 6.61 (1H, br s), 6.96

(1H, d, J=8.7 Hz), 7.10-7.12 (2H, m), 7.72 (1H, dd, J=2.4, 8.4 Hz), 7.81 (1H, t, J=3.3 Hz), 8.00 (4H, s), 8.27 (1H, m), 8.53 (1H, s), 8.55 (1H, s).

Example 118

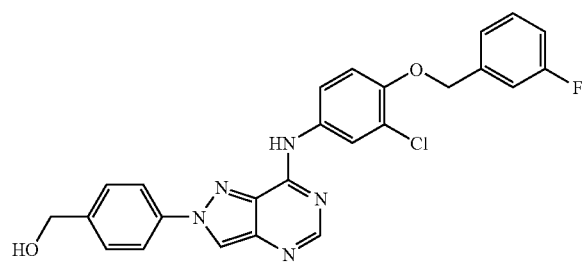

Production of {4-[7-({3-chloro-4-[(3-fluorobenzyl)oxy]phenyl}amino)-2H-pyrazolo[4,3-d]pyrimidin-2-yl]phenyl}methanol (i) Production of 4-[7-({3-chloro-4-[(3-fluorobenzyl)oxy]phenyl}amino)-2H-pyrazolo[4,3-d]pyrimidin-2-yl]benzaldehyde The title compound (60 mg) was obtained as pale-yellow crystals by the reaction in the same manner as in Example 115 (i) using N-{3-chloro-4-[(3-fluorobenzyl)oxy]phenyl}-1H-pyrazolo[4,3-d]pyrimidin-7-amine (100 mg) and 4-fluorobenzaldehyde (37 mg).

$^1$H-NMR (DMSO-d$_6$) δ 5.26 (2H, s), 7.16-7.35 (4H, m), 7.46 (1H, m), 7.93 (1H, dd, J=2.6, 8.8 Hz), 8.18 (2H, d, J=8.4 Hz), 8.30 (1H, d, J=2.2 Hz), 8.38-8.43 (3H, m), 9.40 (1H, s), 10.1 (1H, s), 10.3 (1H, s).

(ii) Production of {4-[7-({3-chloro-4-[(3-fluorobenzyl)oxy]phenyl}amino)-2H-pyrazolo[4,3-d]pyrimidin-2-yl]phenyl}methanol To a solution of 4-[7-({3-chloro-4-[(3-fluorobenzyl)oxy]phenyl}amino)-2H-pyrazolo[4,3-d]pyrimidin-2-yl]benzaldehyde (50 mg) in methanol (2 mL) was added sodium borohydride (2 mg) under ice-cooling, and the mixture was stirred for 30 min. After the completion of the reaction, the reaction solution was concentrated under reduced pressure, and the residue was subjected to silica gel column chromatography (tetrahydrofuran/ethyl acetate=1/1) to give the title compound (20 mg) as a white solid.

$^1$H-NMR (DMSO-d$_6$) δ 4.60 (2H, d, J=5.8 Hz), 5.25 (2H, s), 5.38 (1H, t, J=5.8 Hz), 7.16-7.35 (3H, m), 7.49 (1H, m), 7.56 (2H, d, J=8.8 Hz), 7.93 (1H, m), 8.09 (2H, d, J=8.8 Hz), 8.30 (1H, d, J=2.4 Hz), 8.38 (1H, s), 9.22 (1H, s), 10.2 (1H, s).

Example 119

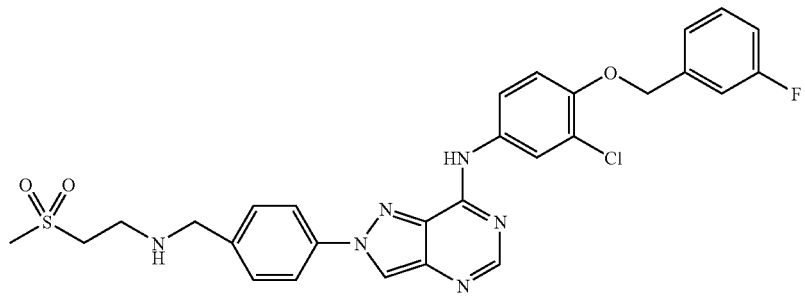

Production of N-{3-chloro-4-[(3-fluorobenzyl)oxy]phenyl}-2-[4-({[2-(methylsulfonyl)ethyl]amino}methyl)phenyl]-2H-pyrazolo[4,3-d]pyrimidin-7-amine To a solution of 4-[7-({3-chloro-4-[(3-fluorobenzyl)oxy]phenyl}amino)-2H-pyrazolo[4,3-d]pyrimidin-2-yl]benzaldehyde (80 mg) and 2-(methylsulfonyl)ethylamine hydrochloride (40 mg) in N,N-dimethylformamide (2 mL) was added acetic acid (0.02 mL), and the mixture was stirred at room temperature for 1 hr. Subsequently, sodium triacetoxyborohydride (54 mg) was added, and the mixture was stirred at the same temperature for 2 hrs. After the completion of the reaction, saturated aqueous sodium hydrogen carbonate was added, and the mixture was concentrated under reduced pressure. The residue was extracted with ethyl acetate, and the organic layer was washed with water and saturated brine and concentrated under reduced pressure. The residue was subjected to silica gel column chromatography (ethyl acetate/methanol=5/1) to give the title compound (70 mg) as a white solid.

$^1$H-NMR (CDCl$_3$) δ 3.02 (3H, s), 3.22 (4H, s), 3.92 (2H, s), 5.17 (2H, s), 6.98-7.04 (2H, m), 7.21-7.26 (3H, m), 7.36 (1H, m), 7.52 (2H, d, J=8.1 Hz), 7.68-7.71 (2H, m), 7.84 (2H, d, J=8.1 Hz), 8.05 (1H, d, J=2.4 Hz), 8.45 (1H, s), 8.54 (1H, s).

Example 120

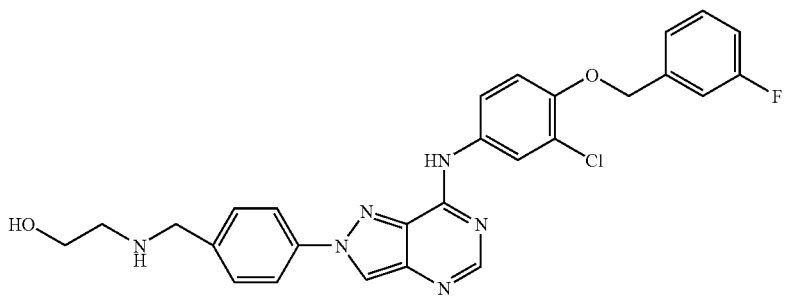

Production of 2-({4-[7-({3-chloro-4-[(3-fluorobenzyl)oxy]phenyl}amino)-2H-pyrazolo[4,3-d]pyrimidin-2-yl]benzyl}amino)ethanol The title compound (83 mg) was obtained as pale-yellow crystals by the reaction in the same manner as in Example 119 using 4-[7-({3-chloro-4-[(3-fluorobenzyl)oxy]phenyl}amino)-2H-pyrazolo[4,3-d]pyrimidin-2-yl]benzaldehyde (120 mg), ethanolamine (23 mg) and sodium triacetoxyborohydride (134 mg).

$^1$H-NMR (DMSO-$d_6$) δ 2.59 (2H, t, J=6.0 Hz), 3.48 (2H, m), 3.80 (2H, s), 4.51 (1H, br s), 5.25 (2H, s), 7.16-7.34 (5H, m), 7.46 (1H, m), 7.57 (2H, d, J=7.8 Hz), 7.91 (1H, dd, J=1.8, 9.0 Hz), 8.07 (2H, d, J=7.8 Hz), 8.30 (1H, d, J=1.8 Hz), 8.38 (1H, s), 9.21 (1H, s), 10.2 (1H, s).

Example 121

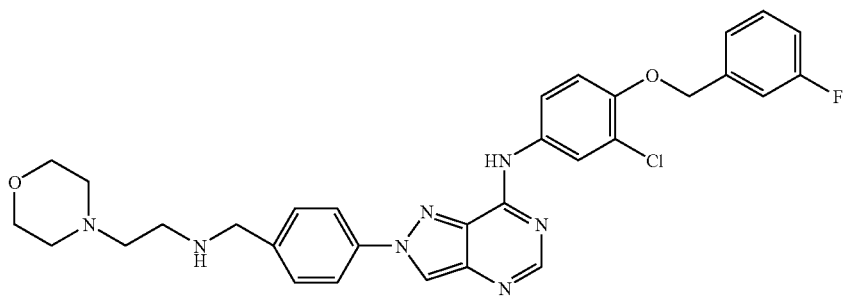

Production of N-{3-chloro-4-[(3-fluorobenzyl)oxy]phenyl}-2-(4-{[(2-morpholin-4-ylethyl)amino]methyl}phenyl)-2H-pyrazolo[4,3-d]pyrimidin-7-amine The title compound (68 mg) was obtained as pale-yellow crystals by the reaction in the same manner as in Example 119 using 4-[7-({3-chloro-4-[(3-fluorobenzyl)oxy]phenyl}amino)-2H-pyrazolo[4,3-d]pyrimidin-2-yl]benzaldehyde (80 mg), N-(2-aminoethyl) morpholine (33 mg) and sodium triacetoxyborohydride (54 mg).

$^1$H-NMR (CDCl$_3$) δ 2.44 (4H, t, J=4.5 Hz), 2.53 (2H, t, J=6.0 Hz), 2.74 (2H, t, J=6.0 Hz), 3.70 (4H, t, J=4.5 Hz), 3.91 (2H, s), 5.16 (2H, s), 6.98 (1H, d, J=8.7 Hz), 7.02 (1H, m), 7.19-7.25 (3H, m), 7.35 (1H, m), 7.52 (2H, d, J=8.7 Hz), 7.67-7.71 (2H, m), 7.82 (2H, d, J=8.7 Hz), 8.04 (1H, d, J=2.4 Hz), 8.43 (1H, s), 8.52 (1H, s).

Example 122

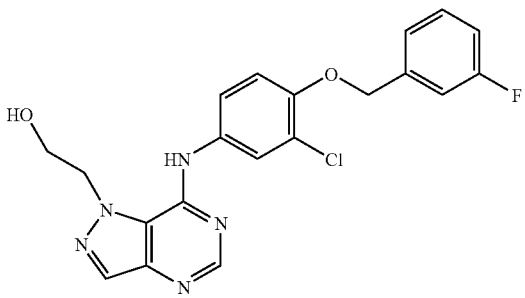

Production of 2-[7-({3-chloro-4-[(3-fluorobenzyl)oxy]phenyl}amino)-1H-pyrazolo[4,3-d]pyrimidin-1-yl]ethanol 2-[7-({3-Chloro-4-[(3-fluorobenzyl)oxy]phenyl}amino)-1H-pyrazolo[4,3-d]pyrimidin-1-yl]ethyl benzoate was obtained as a mixture with 1-methyl-2-pyrrolidone by the reaction in the same manner as in Example 97 using 2-[7-(methylthio)-1H-pyrazolo[4,3-d]pyrimidin-1-yl]ethyl benzoate (130 mg), 3-chloro-4-[(3-fluorobenzyl)oxy]aniline (104 mg) and pyridine hydrochloride (72 mg).

The title compound (60 mg) was obtained as a pale-yellow solid by the reaction in the same manner as in Example 101 using the above-mentioned mixture and 1N aqueous sodium hydroxide solution (0.2 mL).

$^1$H-NMR (DMSO-$d_6$) δ 3.87-3.93 (2H, m), 4.75 (2H, t, J=5.7 Hz), 5.24 (2H, s), 6.27 (1H, t, J=3.9 Hz), 7.13-7.32 (4H, m), 7.48 (1H, m), 7.55 (1H, dd, J=2.4, 9.3 Hz), 7.86 (1H, d, J=1.8 Hz), 8.17 (1H, s), 8.36 (1H, s), 9.85 (1H, s).

Example 123

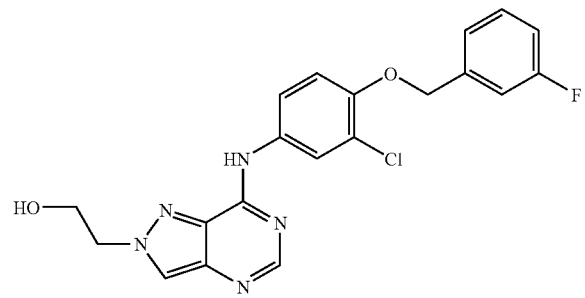

Production of 2-[7-({3-chloro-4-[(3-fluorobenzyl)oxy]phenyl}amino)-2H-pyrazolo[4,3-d]pyrimidin-2-yl]ethanol 2-[7-({3-Chloro-4-[(3-fluorobenzyl)oxy]phenyl}amino)-2H-pyrazolo[4,3-d]pyrimidin-2-yl]ethyl benzoate was obtained as a mixture with 1-methyl-2-pyrrolidone by the reaction in the same manner as in Example 97 using 2-[7-(methylthio)-2H-pyrazolo[4,3-d]pyrimidin-2-yl]ethyl benzoate (120 mg), 3-chloro-4-[(3-fluorobenzyl)oxy]aniline (96 mg) and pyridine hydrochloride (66 mg).

The title compound (86 mg) was obtained as a pale-yellow solid by the reaction in the same manner as in Example 101 using the above-mentioned mixture and 1N aqueous sodium hydroxide solution (0.2 mL).

$^1$H-NMR (DMSO-$d_6$) δ 3.88-3.93 (2H, m), 4.50 (2H, t, J=5.4 Hz), 5.04 (1H, t, J=5.7 Hz), 5.23 (2H, s), 7.14-7.32 (4H, m), 7.46 (1H, m), 7.88 (1H, dd, J=2.7, 9.0 Hz), 8.28 (1H, d, J=1.8 Hz), 8.31 (1H, s), 8.45 (1H, s), 10.12 (1H, s).

Example 124

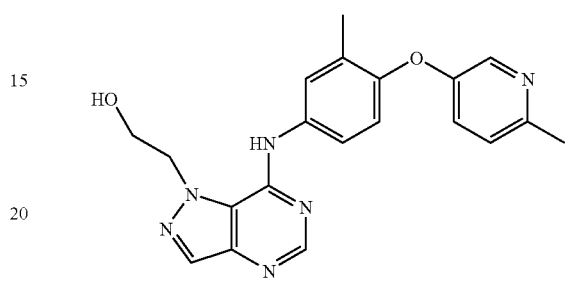

Production of 2-[7-({3-methyl-4-[(6-methylpyridin-3-yl)oxy]phenyl}amino)-1H-pyrazolo[4,3-d]pyrimidin-1-yl]ethanol 2-[7-({3-Methyl-4-[(6-methylpyridin-3-yl)oxy]phenyl}amino)-1H-pyrazolo[4,3-d]pyrimidin-1-yl]ethyl benzoate was obtained as a mixture with 1-methyl-2-pyrrolidone by the reaction in the same manner as in Example 101 using 2-[7-(methylthio)-1H-pyrazolo[4,3-d]pyrimidin-1-yl]ethyl benzoate (190 mg), 3-methyl-4-[(6-methylpyridin-3-yl)oxy]aniline (129 mg) and pyridine hydrochloride (105 mg).

The title compound (88 mg) was obtained as a pale-yellow solid by the reaction in the same manner as in Example 101 using the above-mentioned mixture and 1N aqueous sodium hydroxide solution (0.3 mL).

$^1$H-NMR (CDCl$_3$) δ 2.22 (3H, s), 2.48 (3H, s), 4.25 (2H, br s), 4.76 (2H, br s), 6.01 (1H, br s), 6.86 (1H, d, J=8.7 Hz), 7.08 (1H, d, J=8.7 Hz), 7.16 (1H, dd, J=3.0, 8.7 Hz), 7.45 (1H, dd, J=2.7, 8.7 Hz), 7.56 (1H, d, J=2.7 Hz), 8.05 (1H, d, J=3.0 Hz), 8.37 (1H, s), 9.88 (1H, s).

Example 125

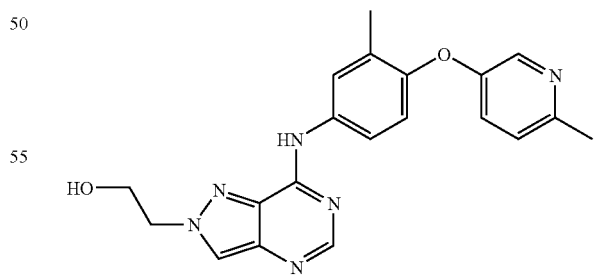

Production of 2-[7-({3-methyl-4-[(6-methylpyridin-3-yl)oxy]phenyl}amino)-2H-pyrazolo[4,3-d]pyrimidin-2-yl]ethanol 2-[7-({3-Methyl-4-[(6-methylpyridin-3-yl)oxy]phenyl}amino)-2H-pyrazolo[4,3-d]pyrimidin-2-yl]ethyl benzoate was obtained as a mixture with 1-methyl-2-pyrrolidone by the reaction in the same manner as in Example 97 using 2-[7-(methylthio)-2H-pyrazolo[4,3-d]pyrimidin-2-yl] ethyl benzoate (115 mg), 3-methyl-4-[(6-methylpyridin-3-yl)oxy]aniline (78 mg) and pyridine hydrochloride (63 mg).

The title compound (95 mg) was obtained as a pale-yellow solid by the reaction in the same manner as in Example 101 using the above-mentioned mixture and 1N aqueous sodium hydroxide solution (0.3 mL).

$^1$H-NMR (CDCl$_3$) δ 2.24 (3H, s), 2.52 (3H, s), 4.16 (2H, t, J=4.5 Hz), 4.26 (1H, br s), 4.50-4.53 (2H, m), 6.86 (1H, d, J=8.7 Hz), 7.05-7.12 (2H, m), 7.57-7.61 (2H, m), 7.69 (1H, d, J=2.7 Hz), 7.97 (1H, s), 8.23 (1H, m), 8.34 (1H, s).

Example 126

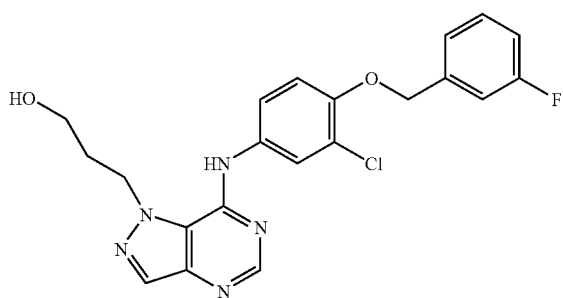

Production of 3-[7-({3-chloro-4-[(3-fluorobenzyl)oxy]phenyl}amino)-1H-pyrazolo[4,3-d]pyrimidin-1-yl]propanol The title compound (240 mg) was obtained as a pale-yellow solid by the reaction in the same manner as in Example 122 using 3-[7-(methylthio)-1H-pyrazolo[4,3-d]pyrimidin-1-yl]propyl benzoate (623 mg), 3-chloro-4-[(3-fluorobenzyl)oxy]aniline (477 mg) and pyridine hydrochloride (329 mg) and 1N aqueous sodium hydroxide solution (0.5 mL).

$^1$H-NMR (DMSO-d$_6$) δ 1.97-2.04 (2H, m), 3.25-3.28 (2H, m), 4.71 (2H, t, J=6.6 Hz), 5.27 (2H, s), 5.44 (1H, t, J=4.8 Hz), 7.16-7.34 (4H, m), 7.48 (1H, m), 7.57 (1H, dd, J=2.7, 9.0 Hz), 7.82 (1H, d, J=2.4 Hz), 8.19 (1H, s), 8.35 (1H, s), 9.22 (1H, s).

Example 127

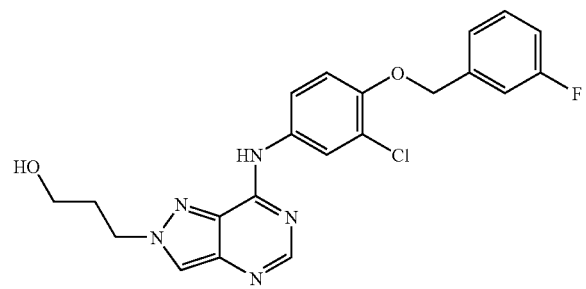

Production of 3-[7-({3-chloro-4-[(3-fluorobenzyl)oxy]phenyl}amino)-2H-pyrazolo[4,3-d]pyrimidin-2-yl]propanol The title compound (512 mg) was obtained as a pale-yellow solid by the reaction in the same manner as in Example 123 using 3-[7-(methylthio)-2H-pyrazolo[4,3-d]pyrimidin-2-yl]propyl benzoate (556 mg), 3-chloro-4-[(3-fluorobenzyl)oxy]aniline (426 mg), pyridine hydrochloride (293 mg) and 1N aqueous sodium hydroxide solution (10 mL).

$^1$H-NMR (DMSO-d$_6$) δ 2.06-2.13 (2H, m), 3.41-3.46 (2H, m), 4.53 (2H, t, J=6.9 Hz), 4.70 (1H, t, J=5.4 Hz), 5.24 (2H, s), 7.16-7.33 (4H, m), 7.46 (1H, m), 7.89 (1H, dd, J=2.4, 9.0 Hz), 8.28 (1H, d, J=2.4 Hz), 8.32 (1H, s), 8.51 (1H, s), 10.12 (1H, s).

Example 128

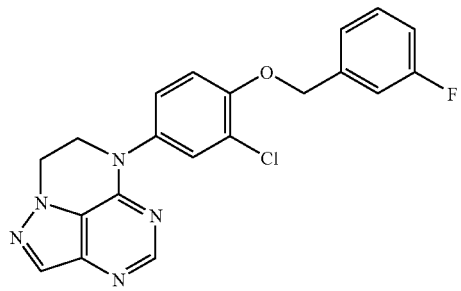

Production of 4-{3-chloro-4-[(3-fluorobenzyl)oxy]phenyl}-5,6-dihydro-4H-pyrazolo[4,5,1-de]pteridine A solution of 2-[7-({3-chloro-4-[(3-fluorobenzyl)oxy]phenyl}amino)-1H-pyrazolo[4,3-d]pyrimidin-1-yl]ethanol (40 mg), 1,1'-(azodicarbonyl)dipiperidine (48 mg) and tributylphosphine (40 mg) in tetrahydrofuran (2 mL) was stirred at room temperature for 15 hrs. After the completion of the reaction, water was added to the reaction mixture and the mixture was diluted with ethyl acetate and washed with saturated brine. The organic layer was dried over anhydrous magnesium sulfate, filtered and concentrated under reduced pressure. The residue was purified by silica gel column chromatography (hexane/ethyl acetate=4/1→1/4) to give the title compound (31 mg) as a white solid.

$^1$H-NMR (CDCl$_3$) δ 4.32 (2H, dd, J=5.0, 6.6 Hz), 4.62 (2H, dd, J=5.0, 6.6 Hz), 5.19 (2H, s), 7.04 (1H, d, J=9.2 Hz), 7.05 (1H, m), 7.18-7.26 (2H, m), 7.32-7.43 (2H, m), 7.55 (1H, d, J=2.6 Hz), 8.09 (1H, s), 8.51 (1H, s).

Example 129

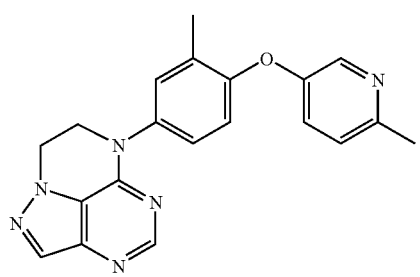

Production of 4-{3-methyl-4-[(6-methylpyridin-3-yl)oxy]phenyl}-5,6-dihydro-4H-pyrazolo[4,5,1-de]pteridine The title compound (21 mg) was obtained as a pale-yellow solid by the reaction in the same manner as in Example 128 using 2-[7-({3-methyl-4-[(6-methylpyridin-3-yl)oxy]phenyl}amino)-1H-pyrazolo[4,3-d]pyrimidin-1-yl]ethanol (30 mg), 1,1'-(azodicarbonyl)dipiperidine (40 mg) and tributylphosphine (32 mg).

$^1$H-NMR (CDCl$_3$) δ 2.34 (3H, s), 2.55 (3H, s), 4.36 (2H, t, J=5.7 Hz), 4.64 (2H, t, J=5.7 Hz), 6.92 (1H, d, J=8.4 Hz), 7.13 (1H, d, J=8.4 Hz), 7.20 (1H, dd, J=2.7, 8.4 Hz), 7.27 (1H, dd, J=2.4, 8.4 Hz), 7.41 (1H, d, J=2.4 Hz), 8.09 (1H, s), 8.30 (1H, d, J=2.7 Hz), 8.53 (1H, s).

Example 130

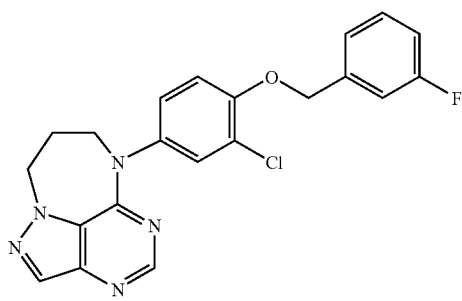

Production of 6-{3-chloro-4-[(3-fluorobenzyl)oxy]phenyl}-6,7,8,9-tetrahydro-1,3,5,6,9a-pentaazabenzo[cd]azulene The title compound (29 mg) was obtained as a pale-yellow solid by the reaction in the same manner as in Example 128 using 3-[7-({3-chloro-4-[(3-fluorobenzyl)oxy]phenyl}amino)-1H-pyrazolo[4,3-d]pyrimidin-1-yl]propanol (60 mg), 1,1'dipiperidine (70 mg) and tributylphosphine (57 mg).

$^1$H-NMR (CDCl$_3$) δ 2.49-2.56 (2H, m), 4.03 (2H, m), 4.62 (2H, t, J=5.7 Hz), 5.19 (2H, s), 7.02 (1H, d, J=8.7 Hz), 7.05 (1H, m), 7.15 (1H, dd, J=2.7, 9.0 Hz), 7.21-7.26 (2H, m), 7.35-7.42 (2H, m), 8.12 (1H, s), 8.37 (1H, s).

Example 131

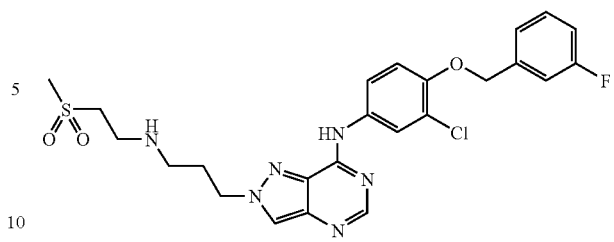

Production of N-{3-chloro-4-[(3-fluorobenzyl)oxy]phenyl}-2-(3-{[2-(methylsulfonyl)ethyl]amino}propyl)-2H-pyrazolo[4,3-d]pyrimidin-7-amine A solution of 3-[7-({3-chloro-4-[(3-fluorobenzyl)oxy]phenyl}amino)-2H-pyrazolo[4,3-d]pyrimidin-2-yl]propanol (50 mg), N-[2-(methylsulfonyl)ethyl]-2-nitrobenzenesulfonamide (47 mg), 1,1'-(azodicarbonyl)dipiperidine (59 mg) and tributylphosphine (47 mg) in tetrahydrofuran (2 mL) was stirred at room temperature for 4 hrs. After the completion of the reaction, water was added to the reaction mixture and the mixture was diluted with ethyl acetate and washed with saturated brine. The organic layer was dried over anhydrous magnesium sulfate, filtered and concentrated under reduced pressure. The residue was purified by silica gel column chromatography (ethyl acetate/methanol=4/1→1/4) to give N-{3-[7-({3-chloro-4-[(3-fluorobenzyl)oxy]phenyl}amino)-2H-pyrazolo[4,3-d]pyrimidin-2-yl]propyl}-N-[2-(methylsulfonyl)ethyl]-2-nitrobenzenesulfonamide. To a solution of this compound in tetrahydrofuran (2 mL) were added 2-mercaptoethanol (12 mg) and 1,8-diazabicyclo[5.4.0]undec-7-ene (23 mg), and the mixture was stirred at room temperature for 3 hrs. After the completion of the reaction, the reaction mixture was concentrated under reduced pressure, and the residue was purified by silica gel column chromatography (ethyl acetate/methanol=10/1) to give the title compound (34 mg) as a white solid.

$^1$H-NMR (CDCl$_3$) δ 2.05-2.14 (2H, m), 2.57 (2H, t, J=6.3 Hz), 3.08 (3H, s), 3.14-3.16 (2H, m), 3.22-3.26 (2H, m), 4.54 (2H, t, J=6.3 Hz), 5.16 (2H, s), 6.97 (1H, d, J=8.7 Hz), 7.02 (1H, m), 7.20-7.26 (3H, m), 7.36 (1H, dt, J=6.3, 7.8 Hz), 7.71 (1H, dd, J=2.7, 9.0 Hz), 7.99 (2H, s), 8.09 (1H, d, J=2.7 Hz), 8.49 (1H, s).

Example 132

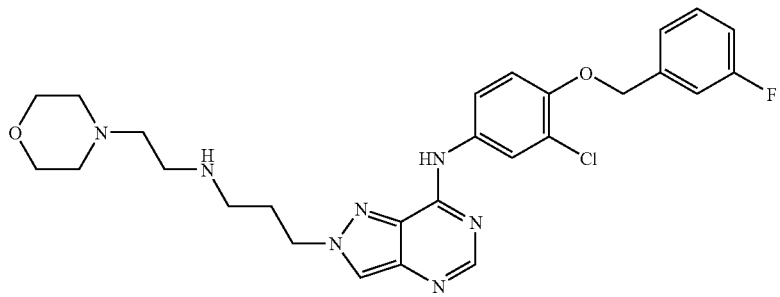

Production of N-{3-chloro-4-[(3-fluorobenzyl)oxy]phenyl}-2-{3-[(2-morpholin-4-ylethyl)amino]propyl}-2H-pyrazolo[4,3-d]pyrimidin-7-amine The title compound (32 mg) was obtained as a pale-yellow solid by the reaction in the same manner as in Example 131 using 3-[7-({3-chloro-4-[(3-fluorobenzyl)oxy]phenyl}amino)-2H-pyrazolo[4,3-d]pyrimidin-2-yl]propanol (60 mg), N-(2-morpholin-4-ylethyl)-2-nitrobenzenesulfonamide (53 mg), 1,1'-(azodicarbonyl)dipiperidine (71 mg), tributylphosphine (57 mg), 2-mercaptoethanol (12 mg) and 1,8-diazabicyclo[5.4.0]undec-7-ene (23 mg).

$^{1}$H-NMR (CDCl$_{3}$) δ 2.42-2.51 (8H, m), 2.59-2.72 (4H, m), 3.70 (4H, t, J=4.8 Hz), 4.51 (2H, t, J=6.8 Hz), 5.15 (2H, s), 6.97 (1H, d, J=8.8 Hz), 7.02 (1H, m), 7.19-7.26 (2H, m), 7.31-7.42 (2H, m), 7.66 (2H, m), 7.98 (1H, s), 8.01 (1H, d, J=2.8 Hz), 8.49 (1H, s).

Example 133

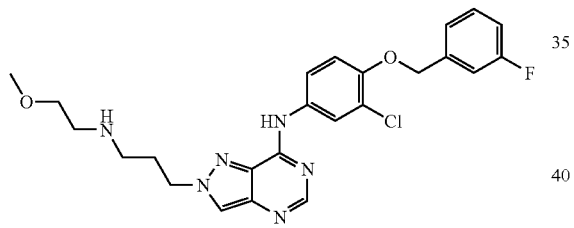

Production of N-{3-chloro-4-[(3-fluorobenzyl)oxy]phenyl}-2-{3-[(2-methoxyethyl)amino]propyl}-2H-pyrazolo[4,3-d]pyrimidin-7-amine The title compound (26 mg) was obtained as a pale-yellow solid by the reaction in the same manner as in Example 131 using 3-[7-({3-chloro-4-[(3-fluorobenzyl)oxy]phenyl}amino)-2H-pyrazolo[4,3-d]pyrimidin-2-yl]propanol (60 mg), N-(2-methoxyethyl)-2-nitrobenzenesulfonamide (44 mg), 1,1'-(azodicarbonyl)dipiperidine (71 mg), tributylphosphine (57 mg), 2-mercaptoethanol (12 mg) and 1,8-diazabicyclo[5.4.0]undec-7-ene (23 mg).

$^{1}$H-NMR (CDCl$_{3}$) δ 2.14-2.18 (2H, m), 2.61 (2H, t, J=6.6 Hz), 2.76 (2H, t, J=5.1 Hz), 3.37 (3H, s), 3.50 (2H, t, J=5.1 Hz), 4.52 (2H, t, J=6.6 Hz), 5.15 (2H, s), 6.97 (1H, d, J=9.0 Hz), 7.01 (1H, m), 7.18-7.26 (4H, m), 7.35 (1H, m), 7.58 (1H, br s), 7.65 (1H, dd, J=2.4, 8.7 Hz), 7.99-8.00 (2H, m), 8.48 (1H, s).

Example 134

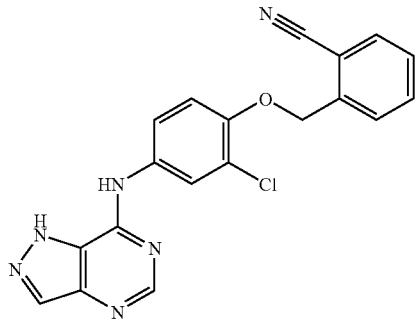

Production of 2-{[2-chloro-4-(1H-pyrazolo[4,3-d]pyrimidin-7-ylamino)phenoxy]methyl}benzonitrile The title compound (96 mg) was obtained as a pale-yellow solid by the reaction in the same manner as in Example 97 using 7-(methylthio)-1H-pyrazolo[4,3-d]pyrimidine (80 mg), 2-[(4-amino-2-chlorophenoxy)methyl]benzonitrile (125 mg) and pyridine hydrochloride (83 mg).

$^{1}$H-NMR (DMSO-d$_{6}$) δ 2.23 (3H, s), 5.26 (2H, s), 7.09 (1H, d, J=8.7 Hz), 7.54-7.77 (5H, m), 7.92 (1H, d, J=8.7 Hz), 8.20 (1H, br s), 8.34 (1H, br s), 9.45 (1H, br s), 12.8 (1H, br s).

Example 135

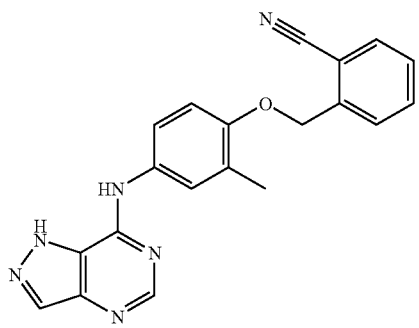

Production of 2-{[2-methyl-4-(1H-pyrazolo[4,3-d]pyrimidin-7-ylamino)phenoxy]methyl}benzonitrile The title compound (110 mg) was obtained as a pale-yellow solid by the reaction in the same manner as in Example 97 using 7-(methylthio)-1H-pyrazolo[4,3-d]pyrimidine (80 mg), 2-[(4-amino-2-methylphenoxy)methyl]benzonitrile (115 mg) and pyridine hydrochloride (83 mg).

$^{1}$H-NMR (DMSO-d$_{6}$) δ 2.23 (3H, s), 5.26 (2H, s), 7.09 (1H, d, J=8.7 Hz), 7.54-7.77 (5H, m), 7.92 (1H, d, J=8.7 Hz), 8.20 (1H, br s), 8.34 (1H, br s), 9.45 (1H, br s), 12.8 (1H, br s).

Example 136

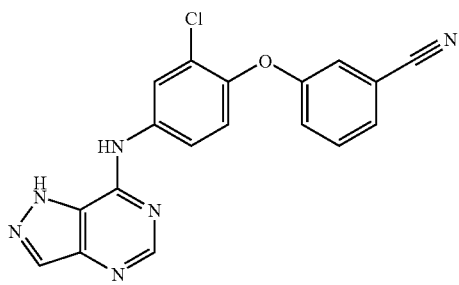

Production of 3-[2-chloro-4-(1H-pyrazolo[4,3-d]pyrimidin-7-ylamino)phenoxy]benzonitrile The title compound (89 mg) was obtained as a pale-yellow solid by the reaction in the same manner as in Example 97 using 7-(methylthio)-1H-pyrazolo[4,3-d]pyrimidine (80 mg), 3-(4-amino-2-chlorophenoxy)benzonitrile (117 mg) and pyridine hydrochloride (83 mg).

$^1$H-NMR (DMSO-$d_6$) δ 7.26-7.35 (2H, m), 7.46 (1H, m), 7.55-7.59 (2H, m), 7.89 (1H, m), 8.39 (1H, br s), 8.46 (2H, s), 10.16 (1H, br s), 12.6 (1H, br s).

Example 137

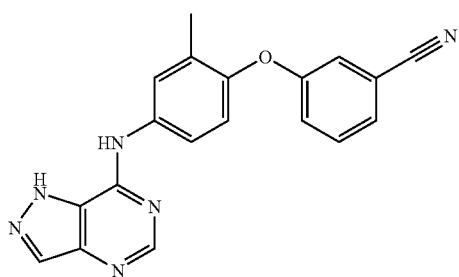

Production of 3-[2-methyl-4-(1H-pyrazolo[4,3-d]pyrimidin-7-ylamino)phenoxy]benzonitrile The title compound (98 mg) was obtained as a pale-yellow solid by the reaction in the same manner as in Example 97 using 7-(methylthio)-1H-pyrazolo[4,3-d]pyrimidine (80 mg), 3-(4-amino-2-methylphenoxy)benzonitrile (108 mg) and pyridine hydrochloride (83 mg).

$^1$H-NMR (DMSO-$d_6$) δ 2.18 (3H, s), 7.09 (1H, d, J=8.7 Hz), 7.24 (1H, m), 7.37 (1H, m), 7.53-7.59 (2H, m), 7.86 (1H, d, J=8.7 Hz), 7.93 (1H, br s), 8.32 (1H, br s), 8.42 (1H, br s), 9.85 (1H, br s), 12.2 (1H, br s).

Example 138

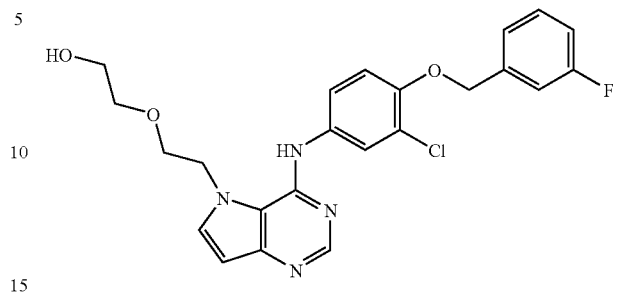

Production of 2-{2-[4-({3-chloro-4-[(3-fluorobenzyl)oxy]phenyl}amino)-5H-pyrrolo[3,2-d]pyrimidin-5-yl]ethoxy}ethanol (i) Production of 2-[2-(4-chloro-5H-pyrrolo[3,2-d]pyrimidin-5-yl)ethoxy]ethyl benzoate To a solution of 2,2'-oxydiethanol (2.12 g) in pyridine (20 mL) was added benzoic anhydride (4.52 g) by small portions under ice-cooling, and the reaction mixture was stirred while warming to room temperature for 18 hrs. Pyridine was evaporated under reduced pressure and the obtained residue was diluted with diethyl ether (20 mL). 5% Aqueous sodium hydrogen carbonate solution (100 mL) was added, and the mixture was extracted with diethyl ether (100 mL×3). The solvent was evaporated under reduced pressure, and the obtained residue was subjected to silica gel chromatography (eluent:hexane/ethyl acetate=95/5→40/60). The object fraction was concentrated under reduced pressure and dried to give 2-(2-hydroxyethoxy)ethyl benzoate (2.21 g). To a solution of the obtained 2-(2-hydroxyethoxy)ethyl benzoate (2.10 g) in dichloromethane (10 mL) were added 1-iodopyrrolidine-2,5-dione (2.70 g) and triphenylphosphine (3.14 g) by small portions under ice-cooling, and the mixture was stirred for 14 hrs. The reaction mixture was poured into 5% aqueous sodium hydrogen carbonate solution (100 mL), and extracted with ethyl acetate (120 mL×3). The organic layer was washed successively with water and saturated brine and dried over anhydrous magnesium sulfate. The solvent was evaporated under reduced pressure, and the obtained residue was subjected to silica gel chromatography (eluent:hexane/ethyl acetate=100/0→60/40). The object fraction was concentrated under reduced pressure and dried to give 2-(2-iodoethoxy) ethyl benzoate (2.05 g) as a colorless transparent oil.

To a suspension of 4-chloro-5H-pyrrolo[3,2-d]pyrimidine (0.659 g) in N,N-dimethylformamide (5.0 mL) was added cesium carbonate (3.13 g) under ice-cooling, and the reaction mixture was stirred while warming to room temperature for 15 min. To the reaction mixture was added 2-(2-iodoethoxy) ethyl benzoate (1.45 g) prepared above, and the mixture was stirred at room temperature for 15 hrs. The reaction mixture was poured into 5% aqueous sodium hydrogen carbonate solution (100 mL), and extracted with ethyl acetate (150 mL×3). The organic layer was washed successively with water and saturated brine and dried over anhydrous magnesium sulfate. The solvent was evaporated under reduced pressure, and the obtained residue was subjected to silica gel chromatography (eluent:hexane/ethyl acetate=95/5→60/40). The object fraction was concentrated under reduced pressure and dried to give the title compound (0.822 g) as a colorless transparent oil.

$^1$H-NMR (CDCl$_3$) δ 3.718 (2H, dt, J=3.0, 6.6 Hz), 3.887 (2H, t, J=5.1 Hz), 4.412 (2H, dt, J=3.0, 6.6 Hz), 4.680 (2H, t, J=5.1 Hz), 6.566 (1H, d, J=3.3 Hz), 7.404-7.462 (2H, m), 7.542-7.600 (2H, m), 7.944-7.982 (2H, m), 8.665 (1H, s).

(ii) Production of 2-{2-[4-({3-chloro-4-[(3-fluorobenzyl)oxy]phenyl}amino)-5H-pyrrolo[3,2-d]pyrimidin-5-yl]ethoxy}ethyl benzoate To a solution of 2-[2-(4-chloro-5H-pyrrolo[3,2-d]pyrimidin-5-yl)ethoxy]ethyl benzoate (802 mg) in 1-methyl-2-pyrrolidone (8.0 mL) was added 3-chloro-4-[(3-fluorobenzyl)oxy]aniline (745 mg), and the mixture was stirred in an oil bath at a temperature of 100° C. for 2 hrs. The reaction mixture was allowed to cool to room temperature, diluted with 5% aqueous sodium hydrogen carbonate solution (25 mL), and extracted with a mixed solvent (50 mL×3) of ethyl acetate/tetrahydrofuran (3/1). The solvent was evaporated under reduced pressure, and the obtained residue was subjected to basic silica gel chromatography (eluent:hexane/ethyl acetate=95/5→0/100). The object fraction was concentrated under reduced pressure and dried to give the title compound (1141 mg) as a yellow amorphous solid.

$^1$H-NMR (CDCl$_3$) δ 3.901-3.931 (2H, m), 4.036 (2H, t, J=4.2 Hz), 4.452-4.483 (2H, m), 4.540 (2H, t, J=4.2 Hz), 5.033 (2H, s), 6.590 (1H, d, J=3.0 Hz), 6.704 (1H, d, J=9.0 Hz), 7.005 (1H, td, J=1.8, 7.5 Hz), 7.164-7.372 (7H, m), 7.511 (1H, tt, J=1.8, 7.5 Hz), 7.679 (1H, d, J=3.0 Hz), 7.769 (1H, t, J=1.8 Hz), 7.788 (1H, t, J=0.6 Hz), 8.431 (1H, s), 8.511 (1H, s).

(iii) Production of 2-{2-[4-({3-chloro-4-[(3-fluorobenzyl)oxy]phenyl}amino)-5H-pyrrolo[3,2-d]pyrimidin-5-yl]ethoxy}ethanol To a solution of 2-{2-[4-({3-chloro-4-[(3-fluorobenzyl)oxy]phenyl}amino)-5H-pyrrolo[3,2-d]pyrimidin-5-yl]ethoxy}ethyl benzoate (760 mg) in tetrahydrofuran (7.0 mL) was added 1N aqueous sodium hydroxide solution (7.0 mL), and the mixture was stirred at room temperature for 14 hrs. 1N Hydrochloric acid (7.0 mL) was added to the reaction mixture, and the mixture was stirred at room temperature for 10 min. and extracted with a mixed solvent (100 mL×3) of ethyl acetate/tetrahydrofuran (1/1). The organic layer was washed successively with 5% aqueous sodium hydrogen carbonate and saturated brine and dried over anhydrous magnesium sulfate. The solvent was evaporated under reduced pressure, and the obtained residue was subjected to basic silica gel column chromatography (eluent:ethyl acetate/methanol=100/0→90/10). The object fraction was concentrated under reduced pressure. A mixed solvent of ethanol/isopropyl ether (1/4) was added to the residue, and the mixture was heated to 80° C. and then allowed to cool to room temperature. The resultant precipitate was collected by filtration and dried under reduced pressure to give the title compound (431 mg) as white powder crystals.

$^1$H-NMR (DMSO-d$_6$) δ 3.471-3.478 (4H, m), 3.817 (2H, t, J=4.6 Hz), 4.616 (2H, t, J=4.6 Hz), 4.681-4.712 (1H, m), 5.234 (2H, s), 6.480 (1H, d, J=3.2 Hz), 7.173-7.212 (2H, m), 7.289-7.339 (2H, m), 7.433-7.523 (2H, m), 7.641 (1H, d, J=3.2 Hz), 7.829 (1H, d, J=3.2 Hz), 8.271 (1H, s), 8.698 (1H, s)

melting point: 168-169° C. .

Example 139

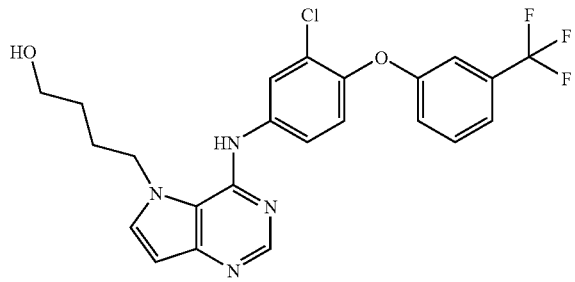

Production of 4-[4-({3-chloro-4-[3-(trifluoromethyl)phenoxy]phenyl}amino)-5H-pyrrolo[3,2-d]pyrimidin-5-yl]butan-1-ol (i) Production of 4-(4-chloro-5H-pyrrolo[3,2-d]pyrimidin-5-yl)butyl acetate To a suspension of 4-chloro-5H-pyrrolo[3,2-d]pyrimidine (0.768 g) in N,N-dimethylformamide (10 mL) was added cesium carbonate (2.01 g) under ice-cooling, and the reaction mixture was stirred while warming to room temperature for 15 min. 4-Bromobutyl acetate (1.26 g) was added dropwise to the reaction mixture, and the mixture was stirred at room temperature for 30 hrs. The reaction mixture was poured into 5% aqueous sodium hydrogen carbonate solution (80 mL), and extracted with ethyl acetate (100 mL×3). The organic layer was washed successively with water and saturated brine and dried over anhydrous magnesium sulfate. The solvent was evaporated under reduced pressure, and the obtained residue was subjected to silica gel chromatography (eluent: hexane/ethyl acetate=95/5→0/100). The object fraction was concentrated under reduced pressure and dried to give the title compound (1.084 g) as a colorless transparent oil.

$^1$H-NMR (CDCl$_3$) δ 1.636-1.730 (2H, m), 1.874-1.971 (2H, m), 2.047 (3H, s), 4.098 (2H, t, J=6.3 Hz), 4.512 (2H, t, J=6.3 Hz), 6.718 (1H, d, J=3.3 Hz), 7.482 (1H, d, J=3.3 Hz), 8.690 (1H, s).

(ii) Production of 4-[4-({3-chloro-4-[3-(trifluoromethyl)phenoxy]phenyl}amino)-5H-pyrrolo[3,2-d]pyrimidin-5-yl]butyl acetate To a solution of 4-(4-chloro-5H-pyrrolo[3,2-d]pyrimidin-5-yl)butyl acetate (302 mg) in isopropyl alcohol (2.24 mL) was added 3-chloro-4-[3-(trifluoromethyl)phenoxy]aniline (421 mg), and the mixture was stirred in an oil bath at a temperature of 100° C. for 3.5 hrs. The reaction mixture was allowed to cool to room temperature, 5% aqueous sodium hydrogen carbonate solution (35 mL) was added, and the mixture was extracted with ethyl acetate (50 mL×3). The organic layer was washed successively with water and saturated brine and dried over anhydrous magnesium sulfate. The solvent was evaporated under reduced pressure, and the obtained residue was subjected to basic silica gel chromatography (eluent:hexane/ethyl acetate=95/5→20/80). The object fraction was concentrated under reduced pressure and dried to give the title compound (293 mg) as a white powder.

¹H-NMR (CDCl₃) δ 1.624-1.714 (2H, m), 1.924-2.005 (2H, m), 2.005 (3H, s), 4.108 (2H, t, J=6.0 Hz), 4.342 (2H, t, J=6.0 Hz), 6.573 (1H, d, J=3.3 Hz), 7.054 (1H, s), 7.083-7.471 (7H, m), 7.793 (1H, d, J=3.3 Hz), 8.526 (1H, s).

(iii) Production of 4-[4-({3-chloro-4-[3-(trifluoromethyl)phenoxy]phenyl}amino)-5H-pyrrolo[3,2-d]pyrimidin-5-yl]butan-1-ol To a solution of 4-[4-({3-chloro-4-[3-(trifluoromethyl)phenoxy]phenyl}amino)-5H-pyrrolo[3,2-d]pyrimidin-5-yl]butyl acetate (281 mg) in tetrahydrofuran (4.0 mL) was added 1N aqueous sodium hydroxide solution (2.8 mL), and the mixture was stirred at room temperature for 4.5 hrs. 1N Aqueous hydrochloric acid solution (2.8 mL) was added, and the mixture was stirred for 15 min. The reaction mixture was poured into water (50 mL), and the mixture was extracted with ethyl acetate (50 mL×3). The organic layer was washed successively with 5% aqueous sodium hydrogen carbonate solution, water and saturated brine and dried over anhydrous magnesium sulfate. The solvent was evaporated under reduced pressure, and the obtained residue was subjected to basic silica gel chromatography (eluent:hexane/ethyl acetate=95/5→0/100). The object fraction was concentrated under reduced pressure and dried. Ethanol/diisopropyl ether (5/95) was added to the residue, and the mixture was stirred with heating to 80° C., allowed to cool to room temperature, and stood still. The resultant precipitate was collected by filtration. The obtained precipitate was washed with diisopropyl ether and dried under reduced pressure to give the title compound (214 mg) as white powder crystals.

¹H-NMR (DMSO-d₆) δ 1.240-1.331 (2H, m), 1.690-1.782 (2H, m), 3.324-3.361 (2H, m), 4.473 (1H, br s), 4.540 (2H, t, J=6.0 Hz), 6.492 (1H, d, J=3.0 Hz), 7.200-7.254 (2H, m), 7.303 (1H, d, J=9.0 Hz), 7.472 (1H, d, J=9.0 Hz), 7.621 (1H, t, J=9.0 Hz), 7.653-7.713 (2H, m), 7.970 (1H, s), 8.351 (1H, s), 8.632 (1H, s).

for 15 min. To the reaction mixture was added 2-iodoethyl benzoate (298 mg), and the mixture was stirred at room temperature for 15 hrs. The reaction mixture was poured into 5% aqueous sodium hydrogen carbonate solution (50 mL), and extracted with ethyl acetate (50 mL×3). The organic layer was washed successively with water and saturated brine and dried over anhydrous magnesium sulfate. The solvent was evaporated under reduced pressure, and the obtained residue was subjected to silica gel chromatography (eluent:hexane/ethyl acetate=95/5→60/40). The object fraction was concentrated under reduced pressure and dried to give 2-(4-chloro-5H-pyrrolo[3,2-d]pyrimidin-5-yl)ethyl benzoate (205 mg) as a colorless transparent oil.

The title compound (311 mg) was obtained as a yellow solid by the reaction in the same manner as in Example 42 (ii) using 3-(4-amino-2-chlorophenoxy)benzonitrile (211 mg) and a solution of 2-(4-chloro-5H-pyrrolo[3,2-d]pyrimidin-5-yl)ethyl benzoate (205 mg) in 1-methyl-2-pyrrolidone (1.3 mL).

¹H-NMR (CDCl₃) δ 4.693 (4H, s), 6.688 (1H, d, J=3.0 Hz), 7.086-7.497 (8H, m), 7.609-7.727 (2H, m), 7.962 (2H, d, J=6.9 Hz), 8.024 (2H, d, J=6.9 Hz), 8.569 (1H, s).

(ii) Production of 3-(2-chloro-4-{[5-(2-hydroxyethyl)-5H-pyrrolo[3,2-d]pyrimidin-4-yl]amino}phenoxy)benzonitrile The title compound (187 mg) was obtained as a pale-yellow powder by the reaction in the same manner as in Example 138 (iii) using 2-(4-{[3-chloro-4-(3-cyanophenoxy)phenyl]amino}-5H-pyrrolo[3,2-d]pyrimidin-5-yl)ethyl benzoate (310 mg).

¹H-NMR (DMSO-d₆) δ 3.977-3.990 (2H, m), 4.542 (2H, br s), 6.470 (1H, d, J=3.0 Hz), 7.162-7.24 (3H, m), 7.421-7.625 (3H, m), 7.645 (1H, d, J=7.2 Hz), 7.989 (1H, d, J=3.0 Hz), 8.078 (1H, d, J=3.0 Hz), 8.368 (1H, s), 10.10 (1H, br s).

Example 140

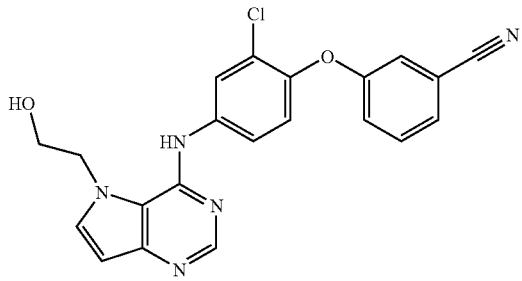

Production of 3-(2-chloro-4-{[5-(2-hydroxyethyl)-5H-pyrrolo[3,2-d]pyrimidin-4-yl]amino}phenoxy)benzonitrile (i) Production of 2-(4-{[3-chloro-4-(3-cyanophenoxy)phenyl]amino}-5H-pyrrolo[3,2-d]pyrimidin-5-yl)ethyl benzoate To a suspension of 4-chloro-5H-pyrrolo[3,2-d]pyrimidine (141 mg) in N,N-dimethylformamide (2.5 mL) was added cesium carbonate (358 mg) under ice-cooling, and the reaction mixture was stirred while warming to room temperature Example 141

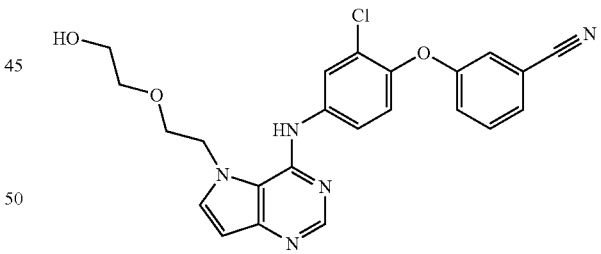

Production of 3-[2-chloro-4-({5-[2-(2-hydroxyethoxy)ethyl]-5H-pyrrolo[3,2-d]pyrimidin-4-yl}amino)phenoxy]benzonitrile (i) Production of 2-[2-(4-{[3-chloro-4-(3-cyanophenoxy)phenyl]amino}-5H-pyrrolo[3,2-d]pyrimidin-5-yl)ethoxy]ethyl benzoate The title compound (117 mg) was obtained as a pale brown solid by the reaction in the same manner as in Example 138 (ii) using 2-[2-(4-chloro-5H-pyrrolo[3,2-d]pyrimidin-5-yl)ethoxy]ethyl benzoate (130 mg) and 3-(4-amino-2-chlorophenoxy)benzonitrile (112 mg).

¹H-NMR (CDCl₃) δ 4.051-4.077 (2H, m), 4.206 (2H, t, J=4.2 Hz), 4.582-4.599 (2H, m), 4.610 (2H, t, J=4.2 Hz), 6.781 (1H, d, J=3.0 Hz), 6.904 (1H, d, J=9.0 Hz), 7.195 (1H, td, J=1.8, 7.5 Hz), 7.360-7.568 (7H, m), 7.709 (1H, tt, J=1.8, 7.5 Hz), 7.872 (1H, d, J=3.0 Hz), 7.975 (1H, t, J=1.8 Hz), 7.968 (1H, t, J=0.6 Hz), 8.531 (1H, s), 8.671 (1H, s).

(ii) Production of 3-[2-chloro-4-({5-[2-(2-hydroxyethoxy)ethyl]-5H-pyrrolo[3,2-d]pyrimidin-4-yl}amino)phenoxy]benzonitrile The title compound (52 mg) was obtained as a pale-yellow powder by the reaction in the same manner as in Example 138 (iii) using 2-[2-(4-{[3-chloro-4-(3-cyanophenoxy)phenyl]amino}-5H-pyrrolo[3,2-d]pyrimidin-5-yl)ethoxy]ethyl benzoate (92 mg).

¹H-NMR (DMSO-d₆) δ 3.578-3.693 (4H, m), 3.617 (2H, t, J=4.8 Hz), 4.515 (2H, t, J=4.8 Hz), 4.589-4.699 (1H, m), 6.378 (1H, d, J=3.0 Hz), 7.153-7.181 (3H, m), 7.411-7.461 (1H, m), 7.553-7.663 (2H, m), 7.840 (1H, d, J=3.2 Hz), 8.049 (1H, d, J=3.2 Hz), 8.377 (1H, s), 8.879 (1H, s).

Example 142

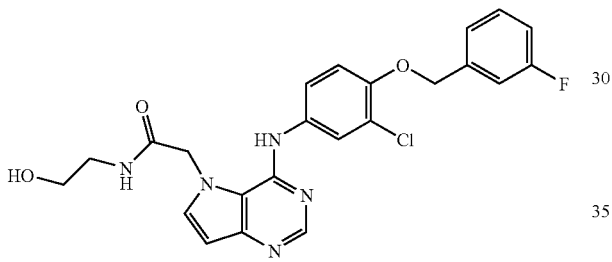

Production of 2-[4-({3-chloro-4-[(3-fluorobenzyl)oxy]phenyl}amino)-5H-pyrrolo[3,2-d]pyrimidin-5-yl]-N-(2-hydroxyethyl)acetamide (i) Production of ethyl [4-({3-chloro-4-[(3-fluorobenzyl)oxy]phenyl}amino)-5H-pyrrolo[3,2-d]pyrimidin-5-yl]acetate To a solution of ethyl (4-chloro-5H-pyrrolo[3,2-d]pyrimidin-5-yl)acetate (530 mg) in isopropyl alcohol (4.0 mL) was added 3-chloro-4-[(3-fluorobenzyl)oxy]aniline (695 mg), and the mixture was stirred in an oil bath at a temperature of 100° C. for 2.5 hrs. The reaction mixture was allowed to cool to room temperature, diluted with 5% aqueous sodium hydrogen carbonate solution (25 mL), and extracted with ethyl acetate (30 mL×3). The organic layer was washed successively with water and saturated brine and dried over anhydrous magnesium sulfate. The solvent was evaporated under reduced pressure, and the obtained residue was subjected to basic silica gel chromatography (eluent:hexane/ethyl acetate=95/5→20/80). The object fraction was concentrated under reduced pressure and dried to give the title compound (743 mg) as a white solid.

¹H-NMR (CDCl₃) δ 1.298-1.344 (3H, m), 4.338 (2H, q, J=7.2 Hz), 4.938 (2H, s), 5.132 (2H, s), 6.616 (1H, d, J=3.4 Hz), 6.935 (1H, d, J=8.8 Hz), 6.979-7.056 (1H, m), 7.190-7.263 (3H, m), 7.301-7.426 (2H, m), 7.638 (1H, t, J=2.4 Hz), 8.200 (1H, s), 8.499 (1H, br s).

(ii) Production of [4-({3-chloro-4-[(3-fluorobenzyl)oxy]phenyl}amino)-5H-pyrrolo[3,2-d]pyrimidin-5-yl]acetic acid The title compound (504 mg) was obtained as a pale-purple powder by the reaction in the same manner as in Example 46 using ethyl [4-({3-chloro-4-[(3-fluorobenzyl)oxy]phenyl}amino)-5H-pyrrolo[3,2-d]pyrimidin-5-yl]acetate (730 mg).

¹H-NMR (DMSO-d₆) δ 5.223 (2H, s), 5.282 (2H, s), 6.480 (1H, d, J=3.0 Hz), 7.137-7.525 (7H, m), 7.603 (1H, d, J=3.0 Hz), 7.666 (1H, d, J=3.0 Hz), 8.299 (1H, s).

(iii) Production of 2-[4-({3-chloro-4-[(3-fluorobenzyl)oxy]phenyl}amino)-5H-pyrrolo[3,2-d]pyrimidin-5-yl]-N-(2-hydroxyethyl)acetamide The title compound (39 mg) was obtained as a pale-yellow powder by the reaction in the same manner as in Example 36 using [4-({3-chloro-4-[(3-fluorobenzyl)oxy]phenyl}amino)-5H-pyrrolo[3,2-d]pyrimidin-5-yl]acetic acid (103 mg).

¹H-NMR (DMSO-d₆) δ 3.23 (2H, m), 3.46 (2H, m), 4.89 (1H, t, J=4.5 Hz), 5.04 (2H, s), 5.22 (2H, s), 6.48 (1H, d, J=3.0 Hz), 7.14-7.24 (2H, m), 7.29-7.33 (2H, m), 7.43-7.53 (2H, m), 7.56 (1H, d, J=3.0 Hz), 7.85 (1H, d, J=3.0 Hz), 8.29 (1H, s), 8.97 (1H, br s), 10.08 (1H, br s).

Example 143

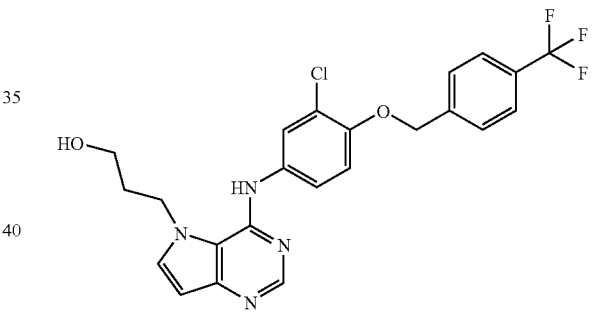

Production of 3-[4-({3-chloro-4-[3-(trifluoromethyl)phenoxy]phenyl}amino)-5H-pyrrolo[3,2-d]pyrimidin-5-yl]propan-1-ol To a solution of 3-(4-chloro-5H-pyrrolo[3,2-d]pyrimidin-5-yl)propan-1-ol (201 mg) synthesized in Example 53 (ii) in isopropyl alcohol (2.5 mL) was added 3-chloro-4-[3-(trifluoromethyl)phenoxy]aniline (381 mg), and the mixture was stirred in an oil bath at a temperature of 100° C. for 2.0 hrs. The reaction mixture was allowed to cool to room temperature, diluted with 5% aqueous sodium hydrogen carbonate solution (25 mL), and extracted with ethyl acetate (30 mL×3). The organic layer was washed successively with water and saturated brine and dried over anhydrous magnesium sulfate. The solvent was evaporated under reduced pressure, and the obtained residue was subjected to basic silica gel chromatography (eluent:hexane/ethyl acetate=95/5→20/80). The object fraction was concentrated under reduced pressure and dried. Ethanol/diisopropyl ether (1/9) was added to the residue, and the mixture was stirred with heating to 80° C., allowed to cool to room temperature, and stood still. The resultant precipitate was collected by filtration. The obtained precipitate was washed with diisopropyl ether and dried under reduced pressure to give the title compound (375 mg) as white powder crystals.

¹H-NMR (DMSO-d₆) δ 1.953 (2H, t, J=5.7 Hz), 3.380 (2H, t, J=5.7 Hz), 4.545 (2H, t, J=6.6 Hz), 5.372 (1H, br s), 6.527 (1H, d, J=3.0 Hz), 7.198-7.327 (3H, m), 7.470 (1H, d, J=7.5 Hz), 7.592-7.707 (3H, m), 7.981 (1H, d, J=3.0 Hz), 8.354 (1H, s), 9.038 (1H, br s).

Example 144

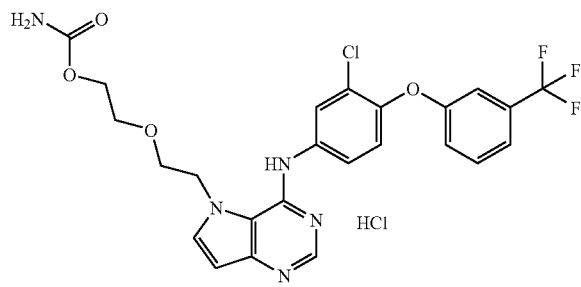

Production of 2-{2-[4-({3-chloro-4-[3-(trifluoromethyl)phenoxy]phenyl}amino)-5H-pyrrolo[3,2-d]pyrimidin-5-yl]ethoxy}ethyl carbamate hydrochloride To a solution of 2-{2-[4-({3-chloro-4-[3-(trifluoromethyl)phenoxy]phenyl}amino)-5H-pyrrolo[3,2-d]pyrimidin-5-yl]ethoxy}ethanol (84 mg) in a mixed solvent (1.0 mL) of toluene/dichloromethane (1/1) was added trichloroacetyl isocyanate (22 μL) under ice-cooling, and the mixture was stirred for 3 hrs. To the reaction mixture were added methanol (0.2 mL) and potassium carbonate (71 mg), and the mixture was stirred at room temperature for 12 hrs. The reaction mixture was poured into 5% aqueous sodium hydrogen carbonate solution (25 mL), and extracted with ethyl acetate (30 mL×3). The organic layer was washed successively with water and saturated brine and dried over anhydrous magnesium sulfate. The solvent was evaporated under reduced pressure, and the obtained residue was subjected to basic silica gel chromatography (eluent:ethyl acetate/methanol=100/0→95/5). The object fraction was concentrated under reduced pressure and dried to give 2-{2-[4-({3-chloro-4-[3-(trifluoromethyl)phenoxy]phenyl}amino)-5H-pyrrolo[3,2-d]pyrimidin-5-yl]ethoxy}ethyl carbamate (83 mg) as a colorless transparent oil. 4N Hydrochloric acid/ethyl acetate solution was added to the obtained colorless transparent oil. After stirring at room temperature for 3 hrs, the resultant precipitate was collected by filtration, washed with diisopropyl ether, ethyl acetate and ice water, and dried under reduced pressure at 60° C. to give the title compound (57 mg) as a pale-yellow powder.

¹H-NMR (DMSO-d₆) δ 3.57 (2H, t, J=3.0 Hz), 3.79 (2H, t, J=3.0 Hz), 3.96 (2H, t, J=6.0 Hz), 4.64 (2H, t, J=6.0 Hz), 6.48 (2H, br s), 6.56 (1H, s), 7.15-7.23 (2H, m), 7.30-7.34 (2H, m), 7.41 (1H, dd, J=3.0, 9.0 Hz), 7.47 (1H, dt, J=6.0, 9.0 Hz), 7.63 (1H, d, J=3.0 Hz), 7.82 (1H, s), 8.28 (1H, s), 8.56 (1H, s).

Example 145

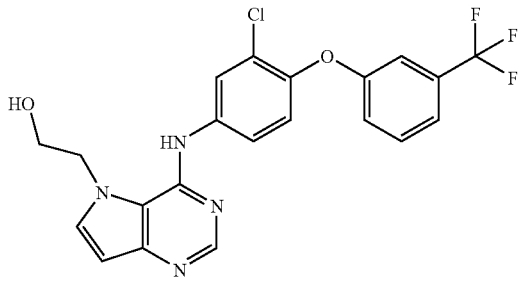

Production of 2-[4-({3-chloro-4-[3-(trifluoromethyl)phenoxy]phenyl}amino)-5H-pyrrolo[3,2-d]pyrimidin-5-yl]ethanol A mixture of 2-(4-chloro-5H-pyrrolo[3,2-d]pyrimidin-5-yl)ethyl benzoate (302 mg), 3-chloro-4-[3-(trifluoromethyl)phenoxy]aniline (288 mg) and 1-methyl-2-pyrrolidone (3 mL) was stirred at 120° C. for 2 hrs. Water and saturated aqueous sodium hydrogen carbonate solution were added to the reaction mixture and the mixture was extracted with ethyl acetate. The ethyl acetate layer was washed successively with water and saturated brine and dried over anhydrous magnesium sulfate. The solvent was evaporated under reduced pressure, and the obtained residue was subjected to silica gel column chromatography (eluent, ethyl acetate:hexane=20:80→100:0). The object fraction was concentrated under reduced pressure. Diethyl ether was added to the residue to allow crystallization, and diisopropyl ether was added, which was followed by filtration to give a white powder (286 mg). To a solution of this white powder (221 mg) in methanol (5 mL) was added 1N aqueous sodium hydroxide solution (0.8 mL), and the mixture was stirred at room temperature for 2 hrs. Water was added to the reaction mixture and the mixture was extracted with ethyl acetate. The ethyl acetate layer was washed with saturated brine and dried over anhydrous magnesium sulfate. The solvent was evaporated under reduced pressure, and ethyl acetate and diisopropyl ether were added to the obtained residue, which was followed by filtration to give the title compound (160 mg) as a white powder.

¹H-NMR (CDCl₃) δ 4.16 (2H, t, J=4.4 Hz), 4.38 (2H, t, J=4.4 Hz), 6.12 (1H, d, J=3.2 Hz), 6.97 (1H, d, J=3.2 Hz), 7.09 (1H, d, J=8.8 Hz), 7.10-7.17 (1H, m), 7.21 (1H, s), 7.32 (1H, d, J=7.7 Hz), 7.43 (1H, t, J=8.0 Hz), 7.52 (1H, dd, J=8.8, 2.6 Hz), 7.84 (1H, d, J=2.6 Hz), 8.24 (1H, s), 9.59 (1H, br s).

Example 146

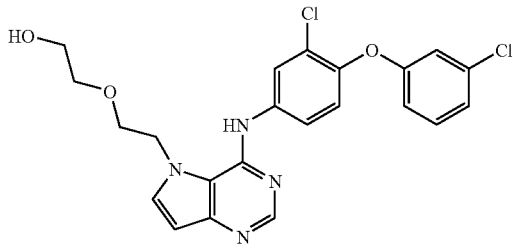

Production of 2-[2-(4-{[3-chloro-4-(3-chlorophenoxy)phenyl]amino}-5H-pyrrolo[3,2-d]pyrimidin-5-yl)ethoxy]ethanol A mixture of 2-[2-(4-chloro-5H-pyrrolo[3,2-d]pyrimidin-5-yl)ethoxy]ethyl benzoate (346 mg), 3-chloro-4-(3-chlorophenoxy)aniline (280 mg) and 1-methyl-2-pyrrolidone (3 mL) was stirred at 120° C. for 2 hrs. Water and saturated aqueous sodium hydrogen carbonate solution were added to the reaction mixture and the mixture was extracted with ethyl acetate. The ethyl acetate layer was washed successively with water and saturated brine and dried over anhydrous magnesium sulfate. The solvent was evaporated under reduced pressure, and the obtained residue was subjected to silica gel column chromatography (eluent, ethyl acetate:hexane=30:70→100:0). The object fraction was concentrated under reduced pressure. To a solution of the residue (431 mg) in methanol (10 mL) was added 1N aqueous sodium hydroxide solution (1 mL), and the mixture was stirred at room temperature for 4 hrs. Water was added to the reaction mixture and the mixture was extracted with ethyl acetate. The ethyl acetate layer was washed with saturated brine and dried over anhydrous magnesium sulfate. The solvent was evaporated under reduced pressure, and the obtained residue was crystallized from ethyl acetate-diethyl ether to give the title compound (312 mg) as a white powder.

$^1$H-NMR (CDCl$_3$) δ 2.05 (1H, br s), 3.71-3.84 (4H, m), 4.03 (2H, t, J=4.5 Hz), 4.57 (2H, t, J=4.5 Hz), 6.61 (1H, d, J=3.0 Hz), 6.83-6.88 (1H, m), 6.92 (1H, t, J=2.2 Hz), 7.01-7.06 (1H, m), 7.06 (1H, d, J=8.9 Hz), 7.19-7.27 (2H, m), 7.61 (1H, dd, J=8.9, 2.6 Hz), 7.89 (1H, d, J=2.6 Hz), 8.52 (1H, s), 8.82 (1H, br s).

Example 147

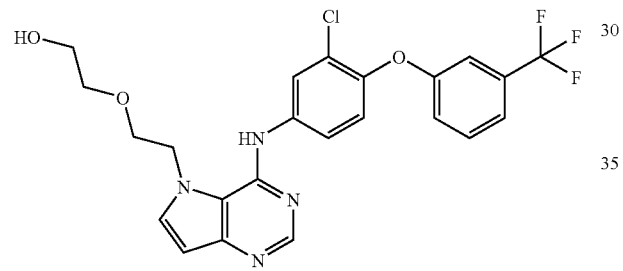

Production of 2-{2-[4-({3-chloro-4-[3-(trifluoromethyl)phenoxy]phenyl}amino)-5H-pyrrolo[3,2-d]pyrimidin-5-yl]ethoxy}ethanol A mixture of 2-[2-(4-chloro-5H-pyrrolo[3,2-d]pyrimidin-5-yl)ethoxy]ethyl benzoate (1.037 g), 3-chloro-4-[3-(trifluoromethyl)phenoxy]aniline (863 mg) and 1-methyl-2-pyrrolidone (10 mL) was stirred at 120° C. for 1.5 hrs. Water and saturated aqueous sodium hydrogen carbonate solution were added to the reaction mixture and the mixture was extracted with ethyl acetate. The ethyl acetate layer was washed successively with water and saturated brine and dried over anhydrous magnesium sulfate. The solvent was evaporated under reduced pressure, and the obtained residue was subjected to silica gel column chromatography (eluent, ethyl acetate:hexane=50:50→100:0). The object fraction was concentrated under reduced pressure. To a solution of the residue (1.420 g) in methanol (30 mL) was added 1N aqueous sodium hydroxide solution (3 mL), and the mixture was stirred at room temperature for 1 hr. The reaction mixture was concentrated under reduced pressure, water was added to the reaction mixture and the mixture was extracted with ethyl acetate. The ethyl acetate layer was washed with saturated brine and dried over anhydrous magnesium sulfate. The solvent was evaporated under reduced pressure, and the obtained residue was subjected to silica gel column chromatography (eluent, methanol:ethyl acetate=0:100→5:95). The object fraction was concentrated under reduced pressure. The precipitated crystals were collected by filtration, and washed with diethyl ether. The crude crystals were recrystallized from ethyl acetate-diisopropyl ether to give the title compound (933 mg) as a white powder.

$^1$H-NMR (CDCl$_3$) δ 1.94 (1H, br s), 3.71-3.85 (4H, m), 4.03 (2H, t, J=4.4 Hz), 4.57 (2H, t, J=4.4 Hz), 6.63 (1H, d, J=3.2 Hz), 7.07 (1H, d, J=8.9 Hz), 7.08-7.14 (1H, m), 7.19 (1H, s), 7.22 (1H, d, J=3.2 Hz), 7.31 (1H, d, J=7.7 Hz), 7.42 (1H, t, J=8.0 Hz), 7.63 (1H, dd, J=8.9, 2.6 Hz), 7.91 (1H, d, J=2.6 Hz), 8.52 (1H, s), 8.83 (1H, br s)

melting point: 130-132° C.

Example 148

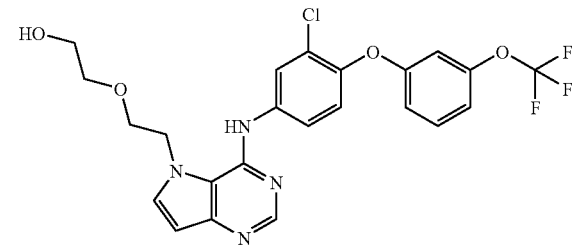

Production of 2-{2-[4-({3-chloro-4-[3-(trifluoromethoxy)phenoxy]phenyl}amino)-5H-pyrrolo[3,2-d]pyrimidin-5-yl]ethoxy}ethanol The title compound (293 mg) was obtained as a white powder by the reaction in the same manner as in Example 146 using 2-[2-(4-chloro-5H-pyrrolo[3,2-d]pyrimidin-5-yl)ethoxy]ethyl benzoate (346 mg), 3-chloro-4-[3-(trifluoromethoxy)phenoxy]aniline (334 mg) and 1-methyl-2-pyrrolidone (3 mL).

$^1$H-NMR (CDCl$_3$) δ 1.95 (1H, br s), 3.71-3.84 (4H, m), 4.03 (2H, t, J=4.5 Hz), 4.57 (2H, t, J=4.5 Hz), 6.62 (1H, d, J=3.2 Hz), 6.80-6.95 (3H, m), 7.08 (1H, d, J=8.8 Hz), 7.21 (1H, d, J=3.2 Hz), 7.30 (1H, t, J=8.2 Hz), 7.62 (1H, dd, J=8.8, 2.6 Hz), 7.90 (1H, d, J=2.6 Hz), 8.52 (1H, s), 8.82 (1H, br s).

Example 149

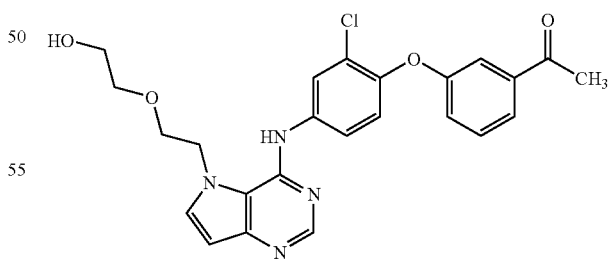

Production of 1-{3-[2-chloro-4-({5-[2-(2-hydroxyethoxy)ethyl]-5H-pyrrolo[3,2-d]pyrimidin-4-yl}amino)phenoxy]phenyl}ethanone The title compound (493 mg) was obtained as a white powder by the reaction in the same manner as in Example 146 using 2-[2-(4-chloro-5H-pyrrolo[3,2-d]pyrimidin-5-yl)ethoxy]ethyl benzoate (692 mg), 1-[3-(4-amino-2-chlorophenoxy)phenyl]ethanone (576 mg) and 1-methyl-2-pyrrolidone (5 mL).

¹H-NMR (CDCl₃) δ 1.97 (1H, br s), 2.58 (3H, s), 3.71-3.84 (4H, m), 4.03 (2H, t, J=4.4 Hz), 4.58 (2H, t, J=4.4 Hz), 6.63 (1H, d, J=3.2 Hz), 7.06 (1H, d, J=8.9 Hz), 7.15-7.20 (1H, m), 7.22 (1H, d, J=3.2 Hz), 7.41 (1H, t, J=7.9 Hz), 7.48-7.51 (1H, m), 7.61 (1H, dd, J=8.9, 2.6 Hz), 7.62-7.67 (1H, m), 7.90 (1H, d, J=2.6 Hz), 8.52 (1H, s), 8.80 (1H, br s).

Example 150

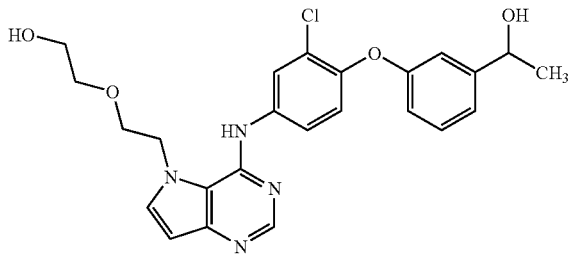

Production of 1-{3-[2-chloro-4-({5-[2-(2-hydroxyethoxy)ethyl]-5H-pyrrolo[3,2-d]pyrimidin-4-yl}amino)phenoxy]phenyl}ethanol To a solution of 1-{3-[2-chloro-4-({5-[2-(2-hydroxyethoxy)ethyl]-5H-pyrrolo[3,2-d]pyrimidin-4-yl}amino)phenoxy]phenyl}ethanone (233 mg) in methanol (5 mL) was added sodium borohydride (38 mg), and the mixture was stirred at room temperature for 2 hrs. Water was added to the reaction mixture and the mixture was extracted with ethyl acetate. The ethyl acetate layer was washed with saturated brine and dried over anhydrous magnesium sulfate. The solvent was evaporated under reduced pressure, and the obtained residue was crystallized from ethyl acetate-diethyl ether to give the title compound (225 mg) as a white powder.

¹H-NMR (CDCl₃) δ 2.47 (3H, d, J=6.4 Hz), 3.67-3.77 (4H, m), 4.00 (2H, t, J=4.4 Hz), 4.58 (2H, t, J=4.4 Hz), 4.84 (1H, q, J=6.4 Hz), 6.62 (1H, d, J=3.3 Hz), 6.85-6.90 (1H, m), 6.96-7.00 (1H, m), 7.01-7.09 (2H, m), 7.24-7.32 (2H, m), 7.52 (1H, dd, J=8.9, 2.6 Hz), 7.86 (1H, d, J=2.6 Hz), 8.45 (1H, s).

Example 151

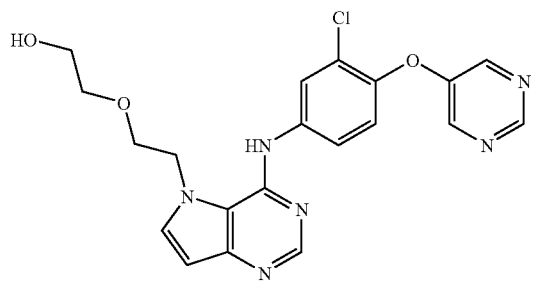

Production of 2-[2-(4-{[3-chloro-4-(pyrimidin-5-yloxy)phenyl]amino}-5H-pyrrolo[3,2-d]pyrimidin-5-yl)ethoxy]ethanol The title compound (63 mg) was obtained as a white powder by the reaction in the same manner as in Example 146 using 2-[2-(4-chloro-5H-pyrrolo[3,2-d]pyrimidin-5-yl)ethoxy]ethyl benzoate (346 mg), 3-chloro-4-(pyrimidin-5-yloxy)aniline (360 mg) and 1-methyl-2-pyrrolidone (3 mL).

¹H-NMR (CDCl₃) δ 2.08 (1H, br s), 3.72-3.84 (4H, m), 4.03 (2H, t, J=4.4 Hz), 4.58 (2H, t, J=4.4 Hz), 6.63 (1H, d, J=3.1 Hz), 7.12 (1H, d, J=8.7 Hz), 7.23 (1H, d, J=3.1 Hz), 7.67 (1H, dd, J=8.7, 2.6 Hz), 7.95 (1H, d, J=2.6 Hz), 8.43 (2H, s), 8.52 (1H, s), 8.89 (1H, br s), 8.94 (1H, s).

Example 152

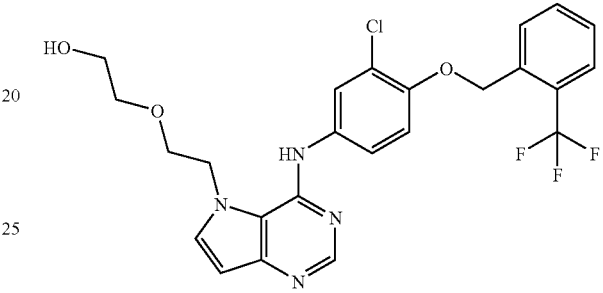

Production of 2-(2-{4-[(3-chloro-4-{[2-(trifluoromethyl)benzyl]oxy}phenyl)amino]-5H-pyrrolo[3,2-d]pyrimidin-5-yl}ethoxy)ethanol The title compound (276 mg) was obtained as a white powder by the reaction in the same manner as in Example 146 using 2-[2-(4-chloro-5H-pyrrolo[3,2-d]pyrimidin-5-yl)ethoxy]ethyl benzoate (277 mg), 3-chloro-4-{[2-(trifluoromethyl)benzyl]oxy}aniline (241 mg) and 1-methyl-2-pyrrolidone (3 mL).

¹H-NMR (CDCl₃) δ 2.02 (1H, br s), 3.68-3.81 (4H, m), 4.00 (2H, t, J=4.4 Hz), 4.53 (2H, t, J=4.4 Hz), 5.34 (2H, s), 6.58 (1H, d, J=3.2 Hz), 6.93 (1H, d, J=8.8 Hz), 7.17 (1H, d, J=3.2 Hz), 7.42 (1H, t, J=7.7 Hz), 7.49 (1H, dd, J=8.8, 2.6 Hz), 7.60 (1H, t, J=7.7 Hz), 7.69 (1H, d, J=7.7 Hz), 7.76 (1H, d, J=2.6 Hz), 7.89 (1H, d, J=7.7 Hz), 8.46 (1H, s), 8.57 (1H, br s).

Example 153

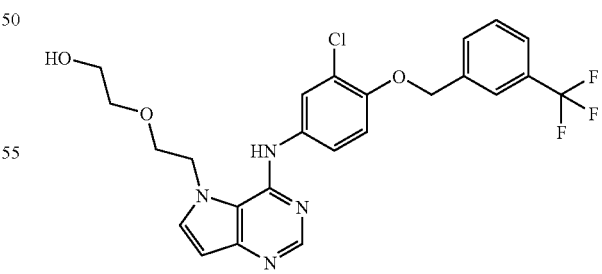

Production of 2-(2-{4-[(3-chloro-4-{[3-(trifluoromethyl)benzyl]oxy}phenyl)amino]-5H-pyrrolo[3,2-d]pyrimidin-5-yl}ethoxy)ethanol The title compound (393 mg) was obtained as a white powder by the reaction in the same manner as in Example 146 using 2-[2-(4-chloro-5H-pyrrolo[3,2-d]pyrimidin-5-yl)ethoxy]ethyl benzoate (346 mg), 3-chloro-4-{[3-(trifluoromethyl)benzyl]oxy}aniline (302 mg) and 1-methyl-2-pyrrolidone (3 mL).

$^1$H-NMR (CDCl$_3$) δ 2.03 (1H, br s), 3.68-3.80 (4H, m), 4.00 (2H, t, J=4.4 Hz), 4.54 (2H, t, J=4.4 Hz), 5.17 (2H, s), 6.59 (1H, d, J=3.1 Hz), 6.95 (1H, d, J=8.8 Hz), 7.17 (1H, d, J=3.1 Hz), 7.48-7.62 (3H, m), 7.66-7.76 (3H, m), 8.46 (1H, s), 8.58 (1H, br s).

Example 154

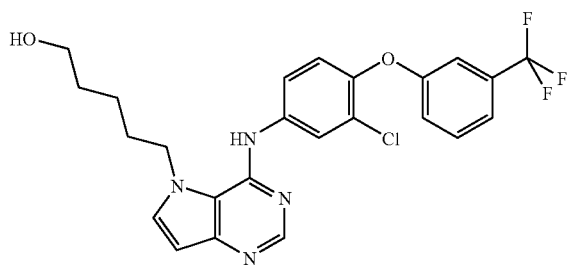

Production of 5-[4-({3-chloro-4-[3-(trifluoromethyl)phenoxy]phenyl}amino)-5H-pyrrolo[3,2-d]pyrimidin-5-yl]pentan-1-ol (i) Production of 5-(4-chloro-5H-pyrrolo[3,2-d]pyrimidin-5-yl)pentyl acetate A mixture of 4-chloro-5H-pyrrolo[3,2-d]pyrimidine (0.50 g), 5-bromopentyl acetate (0.71 mL), cesium carbonate (1.59 g) and N,N-dimethylformamide (5.0 mL) was stirred at 40° C. for 4 days. Water was added to the reaction system and the mixture was extracted with ethyl acetate. The organic layer was washed with water and saturated brine and dried over magnesium sulfate. After concentration under reduced pressure, the residue was separated and purified by silica gel column chromatography (eluent, ethyl acetate:hexane=1:3→6:4) to give the title compound (637 mg) as a white solid.

$^1$H-NMR (CDCl$_3$) δ: 1.33-1.46 (2H, m), 1.61-1.72 (2H, m), 1.84-1.97 (2H, m), 2.04 (3H, s), 4.05 (2H, t, J=6.6 Hz), 4.48 (2H, t, J=7.5 Hz), 6.71 (1H, d, J=3.3 Hz), 7.46 (1H, d, J=3.3 Hz), 8.69 (1H, s).

(ii) Production of 5-[4-({3-chloro-4-[3-(trifluoromethyl)phenoxy]phenyl}amino)-5H-pyrrolo[3,2-d]pyrimidin-5-yl]pentan-1-ol A solution of 5-(4-chloro-5H-pyrrolo[3,2-d]pyrimidin-5-yl)pentyl acetate (200 mg) and 3-chloro-4-[3-(trifluoromethyl)phenoxy]aniline (265 mg) in isopropyl alcohol (3.5 mL) was stirred at 80° C. for 14 hrs. 1N Aqueous sodium hydroxide solution (2.1 mL) was added at 0° C., and the mixture was stirred at room temperature for 1 hr. 1N Hydrochloric acid (2.0 mL) was added to the reaction system, and the mixture was extracted with ethyl acetate. The organic layer was washed with aqueous sodium hydrogen carbonate and saturated brine and dried over magnesium sulfate. After concentration under reduced pressure, the residue was separated and purified by silica gel column chromatography (eluent, ethyl acetate→ethyl acetate:methanol=1:19) to give a colorless solid. Recrystallization from ethyl acetate-hexane gave the title compound (275 mg) as colorless crystals.

$^1$H-NMR (CDCl$_3$) δ: 1.35 (1H, t, J=4.7 Hz), 1.50-1.69 (4H, m), 1.92-2.05 (2H, m), 3.63-3.71 (2H, m), 4.32 (2H, t, J=7.4 Hz), 6.59 (1H, d, J=3.3 Hz), 6.70 (1H, s), 7.08 (1H, d, J=8.7 Hz), 7.09-7.12 (1H, m), 7.15-7.27 (2H, m), 7.30-7.35 (1H, m), 7.40-7.43 (1H, m), 7.47 (1H, dd, J=8.7, 2.7 Hz), 7.82 (1H, d, J=2.7 Hz), 8.53 (1H, s).

Example 155

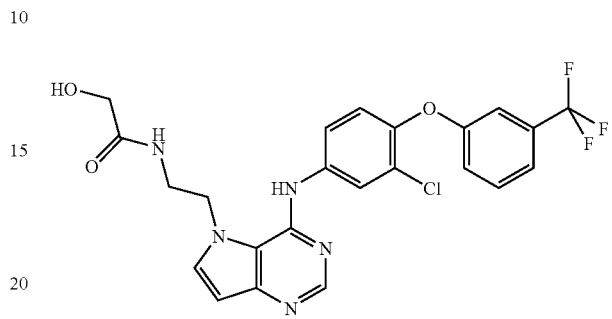

Production of N-{2-[4-({3-chloro-4-[3-(trifluoromethyl)phenoxy]phenyl}amino)-5H-pyrrolo[3,2-d]pyrimidin-5-yl]ethyl}-2-hydroxyacetamide (i) Production of tert-butyl [2-(4-chloro-5H-pyrrolo[3,2-d]pyrimidin-5-yl)ethyl]carbamate The title compound (687 mg) was obtained as a colorless solid by the reaction in the same manner as in Example 154 (i) using 4-chloro-5H-pyrrolo[3,2-d]pyrimidine (0.50 g), tert-butyl 2-bromoethylcarbamate (0.95 g), cesium carbonate (1.59 g) and N,N-dimethylformamide (10 ml).

$^1$H-NMR (CDCl$_3$) δ: 1.31-1.46 (9H, m), 3.55 (2H, dt, J=6.0, 6.0 Hz), 4.51-4.68 (3H, m), 6.74 (1H, d, J=3.2 Hz), 7.47 (1H, d, J=3.2 Hz), 8.71 (1H, s).

(ii) Production of tert-butyl {2-[4-({3-chloro-4-[3-(trifluoromethyl)phenoxy]phenyl}amino)-5H-pyrrolo[3,2-d]pyrimidin-5-yl]ethyl}carbamate A solution of tert-butyl [2-(4-chloro-5H-pyrrolo[3,2-d]pyrimidin-5-yl)ethyl]carbamate (712 mg) and 3-chloro-4-[3-(trifluoromethyl)phenoxy]aniline (830 mg) in isopropyl alcohol (7.1 mL) was stirred at 80° C. for 12 hrs. Aqueous sodium hydrogen carbonate was added to the reaction system and the mixture was extracted with ethyl acetate. The organic layer was washed with saturated brine and dried over magnesium sulfate. After concentration under reduced pressure, the residue was separated and purified by silica gel column chromatography (eluent, hexane:ethyl acetate=1:1→ethyl acetate) to give the title compound (1.12 g) as colorless crystals.

$^1$H-NMR (CDCl$_3$) δ: 1.49 (9H, s), 3.43-3.54 (2H, m), 4.43-4.51 (2H, m), 5.10 (1H, t, J=5.6 Hz), 6.60 (1H, d, J=3.3 Hz), 7.07 (1H, m), 7.09-7.14 (1H, m), 7.16-7.22 (2H, m), 7.25-7.30 (1H, m), 7.37-7.45 (1H, m), 7.89 (1H, dd, J=8.7, 2.4 Hz), 8.02 (1H, d, J=2.4 Hz), 8.50 (1H, s), 8.64 (1H, br s).

(iii) Production of 5-(2-aminoethyl)-N-{3-chloro-4-[3-(trifluoromethyl)phenoxy]phenyl}-5H-pyrrolo[3,2-d]pyrimidin-4-amine dihydrochloride A mixture of tert-butyl {2-[4-({3-chloro-4-[3-(trifluoromethyl)phenoxy]phenyl}amino)-5H-pyrrolo[3,2-d]pyrimidin-5-yl]ethyl}carbamate (1.12 g), 2N hydrochloric acid (15 mL)

and tetrahydrofuran (30 mL) was stirred at 60° C. for 20 hrs. The solvent was evaporated under reduced pressure, ethanol was added, and the mixture was further concentrated. The precipitated crystals were collected by filtration and the crystals were washed with ethyl acetate to give the title compound (1.07 g) as pale-yellow crystals.

$^1$H-NMR (DMSO-d$_6$) δ: 3.21-3.35 (2H, m), 4.92-5.02 (2H, m), 6.71-6.76 (1H, m), 7.24-7.32 (2H, m), 7.37 (1H, d, J=9.0 Hz), 7.50-7.56 (1H, m), 7.64-7.71 (2H, m), 7.91-7.97 (1H, m), 7.98-8.06 (1H, m), 8.13-8.26 (3H, m), 8.71 (1H, br s), 9.88-9.99 (1H, m).

(iv) Production of N-{2-[4-({3-chloro-4-[3-(trifluoromethyl)phenoxy]phenyl}amino)-5H-pyrrolo[3,2-d]pyrimidin-5-yl]ethyl}-2-hydroxyacetamide A mixture of 5-(2-aminoethyl)-N-{3-chloro-4-[3-(trifluoromethyl)phenoxy]phenyl}-5H-pyrrolo[3,2-d]pyrimidin-4-amine dihydrochloride (105 mg), glycolic acid (44 mg), 1-ethyl-3-(3-dimethylaminopropyl)carbodiimide hydrochloride (167 mg), 1-hydroxybenzotriazole monohydrate (133 mg), triethylamine (0.40 mL) and N,N-dimethylformamide (5.0 mL) was stirred at room temperature for 3 days. Water was added to the reaction system and the mixture was extracted with ethyl acetate. The organic layer was washed with water and saturated brine and dried over magnesium sulfate. After concentration under reduced pressure, the residue was separated and purified by basic silica gel column chromatography (eluent, ethyl acetate→methanol:ethyl acetate=1:9) to give the title compound (108 mg) as colorless crystals.

$^1$H-NMR (CDCl$_3$) δ: 2.93-3.09 (1H, m), 3.59-3.73 (2H, m), 4.24 (2H, s), 4.43-4.53 (2H, m), 6.59 (1H, d, J=3.3 Hz), 7.07 (1H, d, J=8.7 Hz), 7.09-7.46 (6H, m), 7.72 (1H, dd, J=8.7, 2.4 Hz), 8.06 (1H, d, J=2.4 Hz), 8.49 (1H, s), 8.57 (1H, s).

Example 156

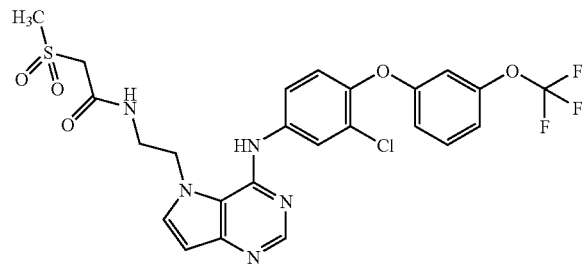

Production of N-{2-[4-({3-chloro-4-[3-(trifluoromethoxy)phenoxy]phenyl}amino)-5H-pyrrolo[3,2-d]pyrimidin-5-yl]ethyl}-2-(methylsulfonyl)acetamide (i) Production of tert-butyl {2-[4-({3-chloro-4-[3-(trifluoromethoxy)phenoxy]phenyl}amino)-5H-pyrrolo[3,2-d]pyrimidin-5-yl]ethyl}carbamate A solution of tert-butyl [2-(4-chloro-5H-pyrrolo[3,2-d]pyrimidin-5-yl)ethyl]carbamate (100 mg), 3-chloro-4-[3-(trifluoromethoxy)phenoxy]aniline (153 mg) in isopropyl alcohol (1.5 mL) was stirred at 80° C. for 12 hrs. Aqueous sodium hydrogen carbonate was added to the reaction system and the mixture was extracted with ethyl acetate. The organic layer was washed with saturated brine and dried over magnesium sulfate. After concentration under reduced pressure, the residue was separated and purified by silica gel column chromatography (eluent, hexane:ethyl acetate=11:1→ethyl acetate) to give the title compound (173 mg) as colorless crystals.

$^1$H-NMR (CDCl$_3$) δ: 1.50 (9H, s), 3.45-3.54 (2H, m), 4.43-4.52 (2H, m), 5.01-5.08 (1H, m), 6.61 (1H, d, J=3.0 Hz), 6.80-6.95 (3H, m), 7.09 (1H, d, J=8.7 Hz), 7.19 (1H, d, J=3.0 Hz), 7.29-7.34 (1H, m), 7.90 (1H, dd, J=8.7, 2.7 Hz), 8.03 (1H, d, J=2.7 Hz), 8.52 (1H, s), 8.62 (1H, br s).

(ii) Production of 5-(2-aminoethyl)-N-{3-chloro-4-[3-(trifluoromethoxy)phenoxy]phenyl}-5H-pyrrolo[3,2-d]pyrimidin-4-amine dihydrochloride A mixture of tert-butyl {2-[4-({3-chloro-4-[3-(trifluoromethoxy)phenoxy]phenyl}amino)-5H-pyrrolo[3,2-d]pyrimidin-5-yl]ethyl}carbamate (173 mg), 2N hydrochloric acid (2.5 mL) and tetrahydrofuran (5.0 mL) was stirred at 60° C. for 6 hrs. Ethanol was added to the reaction system. The solvent was evaporated under reduced pressure. Ethanol was added to the concentrate, and the mixture was further concentrated under reduced pressure. The residual crystals were collected by filtration and the crystals were washed with ethyl acetate to give the title compound (155 mg) as pale-yellow crystals.

$^1$H-NMR (DMSO-d$_6$) δ: 3.21-3.34 (2H, m), 4.89-5.00 (2H, m), 6.74 (1H, d, J=2.4 Hz), 6.94-7.01 (2H, m), 7.16 (1H, d, J=8.7 Hz), 7.36 (1H, d, J=9.0 Hz), 7.51-7.57 (1H, m), 7.62-7.69 (1H, m), 7.90-7.95 (1H, m), 7.99-8.05 (1H, m), 8.12-8.27 (3H, m), 8.71 (1H, s), 9.92 (1H, br s).

(iii) Production of N-{2-[4-({3-chloro-4-[3-(trifluoromethoxy)phenoxy]phenyl}amino)-5H-pyrrolo[3,2-d]pyrimidin-5-yl]ethyl}-2-(methylsulfonyl)acetamide A mixture of 5-(2-aminoethyl)-N-{3-chloro-4-[3-(trifluoromethoxy)phenoxy]phenyl}-5H-pyrrolo[3,2-d]pyrimidin-4-amine dihydrochloride (160 mg), 2-(methylsulfonyl)acetic acid (82.3 mg), 1-ethyl-3-(3-dimethylaminopropyl)carbodiimide hydrochloride (171 mg), 1-hydroxybenzotriazole monohydrate (137 mg), triethylamine (0.42 mL) and N,N-dimethylformamide (5.0 mL) was stirred at room temperature for 20 hrs. Water was added to the reaction system and the mixture was extracted with ethyl acetate. The organic layer was washed with water and saturated brine and dried over magnesium sulfate. After concentration under reduced pressure, the residue was separated and purified by basic silica gel column chromatography (eluent, ethyl acetate→ethyl acetate:methanol=4:1) and crystallization from ethanol-ethyl acetate-diisopropyl ether to give the title compound (112 mg) as pale-yellow crystals.

$^1$H-NMR (CDCl$_3$) δ: 3.12 (3H, s), 3.64-3.76 (2H, m), 3.99 (2H, s), 4.34-4.52 (2H, m), 6.62 (1H, d, J=3.0 Hz), 6.81-6.84 (1H, m), 6.86-6.95 (2H, m), 7.08 (1H, d, J=8.7 Hz), 7.17-7.24 (2H, m), 7.29-7.34 (1H, m), 7.76 (1H, dd, J=8.7, 2.7 Hz), 7.95 (1H, d, J=2.7 Hz), 8.18 (1H, s), 8.51 (1H, s).

melting point: 133-135° C.

Example 157

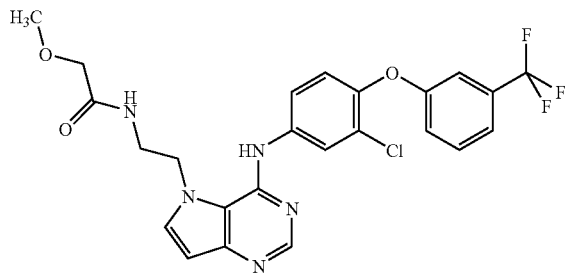

Production of N-{2-[4-({3-chloro-4-[3-(trifluoromethyl)phenoxy]phenyl}amino)-5H-pyrrolo[3,2-d]pyrimidin-5-yl]ethyl}-2-methoxyacetamide The title compound (120 mg) was obtained as colorless crystals by the reaction in the same manner as in Example 155 (iv) using 5-(2-aminoethyl)-N-{3-chloro-4-[3-(trifluoromethyl)phenoxy]phenyl}-5H-pyrrolo[3,2-d]pyrimidin-4-amine dihydrochloride (150 mg), methoxyacetic acid (52 mg), 1-ethyl-3-(3-dimethylaminopropyl)carbodiimide hydrochloride (166 mg), 1-hydroxybenzotriazole monohydrate (133 mg), triethylamine (0.40 mL) and N,N-dimethylformamide (5.0 mL).

$^1$H-NMR (CDCl$_3$) δ: 3.44 (3H, s), 3.60-3.71 (2H, m), 4.00 (2H, s), 4.44-4.53 (2H, m), 6.62 (1H, d, J=3.0 Hz), 7.02-7.15 (3H, m), 7.19 (1H, d, J=3.0 Hz), 7.22-7.35 (2H, m), 7.38-7.45 (1H, m), 7.74 (1H, dd, J=8.7, 2.4 Hz), 8.07 (1H, d, J=2.4 Hz), 8.52 (1H, s), 8.55 (1H, s).

Example 158

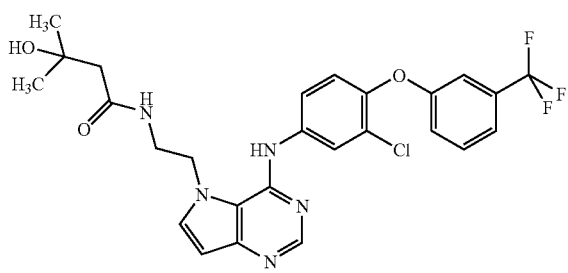

Production of N-{2-[4-({3-chloro-4-[3-(trifluoromethyl)phenoxy]phenyl}amino)-5H-pyrrolo[3,2-d]pyrimidin-5-yl]ethyl}-3-hydroxy-3-methylbutanamide A mixture of 5-(2-aminoethyl)-N-{3-chloro-4-[3-(trifluoromethyl)phenoxy]phenyl}-5H-pyrrolo[3,2-d]pyrimidin-4-amine dihydrochloride (150 mg), 3-hydroxy-3-methylbutyric acid (68 mg), 1-ethyl-3-(3-dimethylaminopropyl)carbodiimide hydrochloride (166 mg), 1-hydroxybenzotriazole monohydrate (133 mg), triethylamine (0.40 mL) and N,N-dimethylformamide (5.0 mL) was stirred at room temperature for 5 days. Water was added to the reaction system and the mixture was extracted with ethyl acetate. The organic layer was washed with water and saturated brine and dried over magnesium sulfate. After concentration under reduced pressure, the residue was separated and purified by basic silica gel column chromatography (eluent, ethyl acetate→ethyl acetate:methanol=9:1). Crystallization from ethyl acetate-diisopropyl ether gave the title compound (122 mg) as colorless crystals.

$^1$H-NMR (CDCl$_3$) δ: 1.33 (6H, s), 2.49 (2H, s), 2.65-2.77 (1H, m), 3.57-3.68 (2H, m), 4.44-4.53 (2H, m), 6.61 (1H, d, J=3.0 Hz), 6.93-7.01 (1H, m), 7.07 (1H, d, J=9.0 Hz), 7.09-7.15 (1H, m), 7.19 (1H, d, J=3.0 Hz), 7.23-7.35 (2H, m), 7.40-7.45 (1H, m), 7.77 (1H, dd, J=9.0, 2.7 Hz), 8.08 (1H, d, J=2.7 Hz), 8.52 (1H, s), 8.66 (1H, s).

melting point: 167-169° C.

Example 159

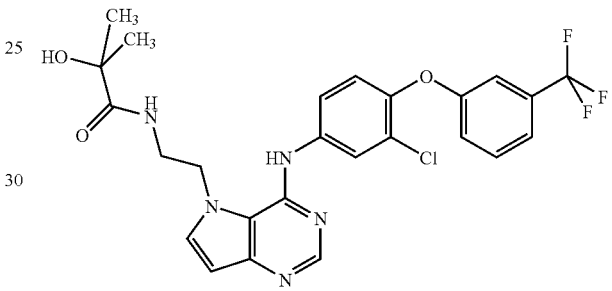

Production of N-{2-[4-({3-chloro-4-[3-(trifluoromethyl)phenoxy]phenyl}amino)-5H-pyrrolo[3,2-d]pyrimidin-5-yl]ethyl}-2-hydroxy-2-methylpropanamide To a suspension of 5-(2-aminoethyl)-N-{3-chloro-4-[3-(trifluoromethyl)phenoxy]phenyl}-5H-pyrrolo[3,2-d]pyrimidin-4-amine dihydrochloride (150 mg) and triethylamine (0.40 mL) in tetrahydrofuran (5.0 mL) was added 1-chlorocarbonyl-1-methylethyl acetate (0.12 mL) at room temperature. After stirring at room temperature for 3 days, aqueous sodium hydrogen carbonate was added, and the mixture was extracted with ethyl acetate. The organic layer was washed with saturated brine, dried over magnesium sulfate and concentrated under reduced pressure. To a solution of the residue in ethanol (3.0 mL) was added 1N aqueous sodium hydroxide solution (1.5 mL) at room temperature. After stirring at room temperature for 24 hrs, and the mixture was extracted with ethyl acetate. The organic layer was washed with saturated brine, dried over magnesium sulfate and concentrated under reduced pressure, and the residue was separated and purified by basic silica gel column chromatography (eluent, ethyl acetate→ethyl acetate:methanol=9:1) to give the title compound (133 mg) as colorless crystals.

$^1$H-NMR (CDCl$_3$) δ: 1.49 (6H, s), 2.12-2.27 (1H, m), 3.56-3.67 (2H, m), 4.42-4.52 (2H, m), 6.61 (1H, d, J=3.3 Hz), 7.06 (1H, d, J=9.0 Hz), 7.08-7.14 (1H, m), 7.15-7.43 (5H, m), 7.86 (1H, dd, J=9.0, 2.7 Hz), 8.10 (1H, d, J=2.7 Hz), 8.51 (1H, s), 8.72 (1H, s).

Example 160

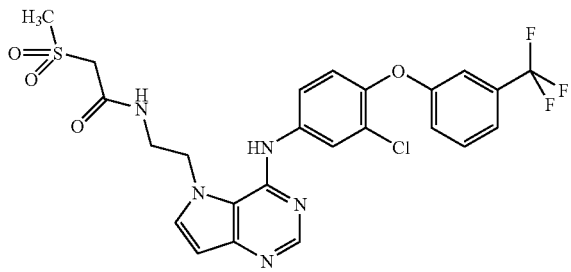

Production of N-{2-[4-({3-chloro-4-[3-(trifluoromethyl)phenoxy]phenyl}amino)-5H-pyrrolo[3,2-d]pyrimidin-5-yl]ethyl}-2-(methylsulfonyl)acetamide A mixture of 5-(2-aminoethyl)-N-{3-chloro-4-[3-(trifluoromethyl)phenoxy]phenyl}-5H-pyrrolo[3,2-d]pyrimidin-4-amine dihydrochloride (150 mg), 2-(methylsulfonyl)acetic acid (79.6 mg), 1-ethyl-3-(3-dimethylaminopropyl)carbodiimide hydrochloride (166 mg), 1-hydroxybenzotriazole monohydrate (133 mg), triethylamine (0.40 mL) and N,N-dimethylformamide (5.0 mL) was stirred at room temperature for 20 hrs. Water was added to the reaction system and the mixture was extracted with ethyl acetate. The organic layer was washed with water and saturated brine and dried over magnesium sulfate. After concentration under reduced pressure, the residue was separated and purified by basic silica gel column chromatography (eluent, ethyl acetate→ethyl acetate:methanol=4:1). Crystallization from ethyl acetate-diisopropyl ether gave the title compound (128 mg) as colorless powder crystals.

$^1$H-NMR (CDCl$_3$) δ: 3.12 (3H, s), 3.64-3.75 (2H, m), 3.98 (2H, s), 4.43-4.53 (2H, m), 6.62 (1H, d, J=3.0 Hz), 7.07 (1H, d, J=9.0 Hz), 7.09-7.15 (1H, m), 7.18-7.33 (4H, m), 7.40-7.45 (1H, m), 7.77 (1H, dd, J=9.0, 2.7 Hz), 7.96 (1H, d, J=2.7 Hz), 8.19 (1H, s), 8.51 (1H, s).

melting point: 177-178° C.

Example 161

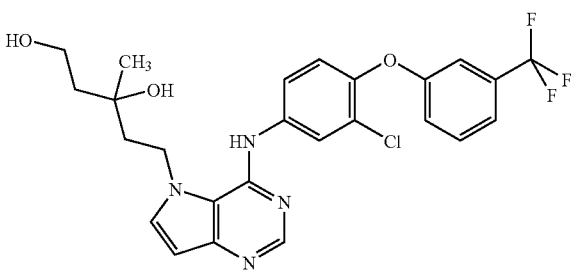

Production of 5-[4-({3-chloro-4-[3-(trifluoromethyl)phenoxy]phenyl}amino)-5H-pyrrolo[3,2-d]pyrimidin-5-yl]-3-methylpentane-1,3-diol (i) Production of 3,5-dihydroxy-3-methylpentyl benzoate A solution of 3-methyl-1,3,5-pentanetriol (21.9 g), benzoic anhydride (7.39 g), pyridine (4.0 mL) and 4-(N,N-dimethylamino)pyridine (0.39 g) in acetonitrile (200 mL) was stirred at room temperature for 2 days. After concentration under reduced pressure, water was added, and the mixture was extracted with ethyl acetate. The organic layer was washed with saturated brine, dried over magnesium sulfate and concentrated under reduced pressure, and the residue was separated and purified by silica gel column chromatography (eluent, hexane:ethyl acetate=1:1→ethyl acetate) to give the title compound (4.27 g) as a colorless oil.

$^1$H-NMR (CDCl$_3$) δ: 1.36 (3H, s), 1.72-1.81 (1H, m), 1.86-2.13 (3H, m), 2.47 (1H, t, J=4.7 Hz), 2.89 (1H, s), 3.85-4.02 (2H, m), 4.52 (2H, t, J=6.8 Hz), 7.42-7.48 (2H, m), 7.54-7.60 (1H, m), 8.00-8.04 (2H, m).

(ii) Production of 5-bromo-3-hydroxy-3-methylpentyl benzoate

To a solution of 3,5-dihydroxy-3-methylpentyl benzoate (1.0 g) and carbon tetrabromide (2.78 g) in tetrahydrofuran (30 mL) was added dropwise a solution of triphenylphosphine (2.20 g) in tetrahydrofuran (10 mL) under ice-cooling. After stirring at room temperature for 3 days, water was added, and the mixture was extracted with ethyl acetate. The organic layer was washed with saturated brine, dried over magnesium sulfate and concentrated under reduced pressure, and the residue was separated and purified by silica gel column chromatography (eluent, hexane:ethyl acetate=9:1→6:4) to give the title compound (979 mg) as a colorless oil.

$^1$H-NMR (CDCl$_3$) δ: 1.32 (3H, s), 1.78 (1H, s), 1.97-2.02 (2H, m), 2.11-2.23 (2H, m), 3.53 (2H, t, J=8.1 Hz), 4.51 (2H, t, J=6.5 Hz), 7.42-7.48 (2H, m), 7.55-7.60 (1H, m), 8.00-8.04 (2H, m).

(iii) Production of 5-(4-chloro-5H-pyrrolo[3,2-d]pyrimidin-5-yl)-3-hydroxy-3-methylpentyl benzoate The title compound (773 mg) was obtained as a colorless oil by the reaction in the same manner as in Example 154 (i) using 4-chloro-5H-pyrrolo[3,2-d]pyrimidine (400 mg), 5-bromo-3-hydroxy-3-methylpentyl benzoate (979 mg), cesium carbonate (0.94 g) and N,N-dimethylformamide (10 mL).

$^1$H-NMR (CDCl$_3$) δ: 1.41 (3H, s), 1.91 (1H, s), 2.01-2.13 (4H, m), 4.54 (2H, t, J=6.6 Hz), 4.59-4.76 (2H, m), 6.71 (1H, d, J=3.0 Hz), 7.40-7.46 (2H, m), 7.51 (1H, d, J=3.0 Hz), 7.54-7.60 (1H, m), 7.98-8.01 (2H, m), 8.69 (1H, s).

(iv) Production of 5-[4-({3-chloro-4-[3-(trifluoromethyl)phenoxy]phenyl}amino)-5H-pyrrolo[3,2-d]pyrimidin-5-yl]-3-methylpentane-1,3-diol The title compound (223 mg) was obtained as colorless crystals by the reaction in the same manner as in Example 154 (ii) using 5-(4-chloro-5H-pyrrolo[3,2-d]pyrimidin-5-yl)-3-hydroxy-3-methylpentyl benzoate (250 mg), 3-chloro-4-[3-(trifluoromethyl)phenoxy]aniline (230 mg), isopropyl alcohol (1.5 mL) and 1N aqueous sodium hydroxide solution (2.0 mL).

$^1$H-NMR (CDCl$_3$) δ: 1.35 (3H, s), 1.62-1.71 (1H, m), 1.89-2.22 (4H, m), 3.93-4.18 (2H, m), 4.54-4.65 (3H, m), 6.56 (1H, d, J=3.0 Hz), 7.04 (1H, d, J=8.7 Hz), 7.08-7.14 (1H, m), 7.19-7.25 (2H, m), 7.29-7.35 (1H, m), 7.39-7.44 (1H, m), 7.61 (1H, dd, J=8.7, 2.7 Hz), 7.93 (1H, d, J=2.7 Hz), 8.49 (1H, s), 8.52 (1H, br s).

Example 162

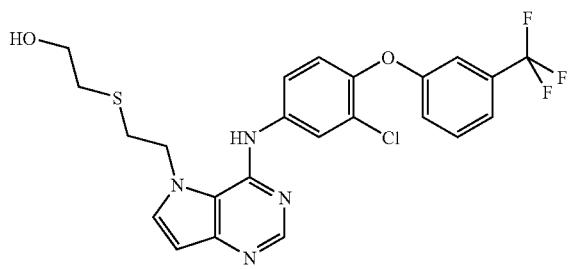

Production of 2-({2-[4-({3-chloro-4-[3-(trifluoromethyl)phenoxy]phenyl}amino)-5H-pyrrolo[3,2-d]pyrimidin-5-yl]ethyl}thio)ethanol (i) Production of 2-[(2-hydroxyethyl)thio]ethyl benzoate A solution of 2-mercaptoethanol (1.52 mL), 2-iodoethyl benzoate (6.00 g) and ethyldiisopropylamine (4.53 mL) in N,N-dimethylformamide (60 mL) was stirred at 40° C. for 3 days. Water was added to the reaction system and the mixture was extracted with ethyl acetate. The organic layer was washed with saturated brine, dried over magnesium sulfate and concentrated under reduced pressure. The residue was separated and purified by silica gel column chromatography (eluent, hexane:ethyl acetate=4:1→3:7) to give the title compound (3.77 g) as an orange oil.

$^1$H-NMR (CDCl$_3$) δ: 2.15 (1H, t, J=6.0 Hz), 2.83 (2H, t, J=5.9 Hz), 2.92 (2H, t, J=6.8 Hz), 3.79 (2H, dt, J=6.0, 6.0 Hz), 4.50 (2H, t, J=6.8 Hz), 7.43-7.48 (2H, m), 7.55-7.61 (1H, m), 8.03-8.08 (2H, m).

(ii) Production of 2-[(2-bromoethyl)thio]ethyl benzoate

The title compound (966 mg) was obtained as a colorless oil by the reaction in the same manner as in Example 161 (ii) using 2-[(2-hydroxyethyl)thio]ethyl benzoate (1.0 g), carbon tetrabromide (2.20 g), triphenylphosphine (1.74 g) and dichloromethane (50 mL).

$^1$H-NMR (CDCl$_3$) δ: 2.95 (2H, t, J=6.8 Hz), 3.02-3.08 (2H, m), 3.50-3.56 (2H, m), 4.49 (2H, t, J=6.8 Hz), 7.43-7.48 (2H, m), 7.55-7.61 (1H, m), 8.03-8.06 (2H, m).

(iii) Production of 2-{[2-(4-chloro-5H-pyrrolo[3,2-d]pyrimidin-5-yl)ethyl]thio}ethyl benzoate The title compound (790 mg) was obtained as a colorless oil by the reaction in the same manner as in Example 154 (i) using 4-chloro-5H-pyrrolo[3,2-d]pyrimidine (420 mg), 2-[(2-bromoethyl)thio]ethyl benzoate (966 mg), cesium carbonate (1.34 g) and N,N-dimethylformamide (4.2 mL).

$^1$H-NMR (CDCl$_3$) δ: 2.81 (2H, t, J=6.8 Hz), 3.08 (2H, t, J=6.9 Hz), 4.45 (2H, t, J=6.8 Hz), 4.69 (2H, t, J=6.9 Hz), 6.73 (1H, d, J=3.3 Hz), 7.39-7.46 (2H, m), 7.53-7.62 (2H, m), 7.96-8.06 (2H, m), 8.71 (1H, s).

(iv) Production of 2-({2-[4-({3-chloro-4-[3-(trifluoromethyl)phenoxy]phenyl}amino)-5H-pyrrolo[3,2-d]pyrimidin-5-yl]ethyl}thio)ethanol The title compound (420 mg) was obtained as colorless crystals by the reaction in the same manner as in Example 154 (ii) using 2-{[2-(4-chloro-5H-pyrrolo[3,2-d]pyrimidin-5-yl)ethyl]thio}ethyl benzoate (505 mg), 3-chloro-4-[3-(trifluoromethyl)phenoxy]aniline (480 mg), isopropyl alcohol (10 mL) and 1N aqueous sodium hydroxide solution (3.0 mL).

$^1$H-NMR (CDCl$_3$) δ: 1.92-2.00 (1H, m), 2.52 (2H, t, J=5.6 Hz), 3.13 (2H, t, J=6.5 Hz), 3.65-3.75 (2H, m), 4.61 (2H, t, J=6.5 Hz), 6.67 (1H, d, J=3.3 Hz), 7.08 (1H, d, J=8.7 Hz), 7.09-7.13 (1H, m), 7.18-7.23 (1H, m), 7.29 (1H, d, J=3.3 Hz), 7.32-7.35 (1H, m), 7.41-7.46 (1H, m), 7.51 (1H, dd, J=8.7, 2.7 Hz), 7.77 (1H, d, J=2.7 Hz), 7.80 (1H, s), 8.55 (1H, s).

Example 163

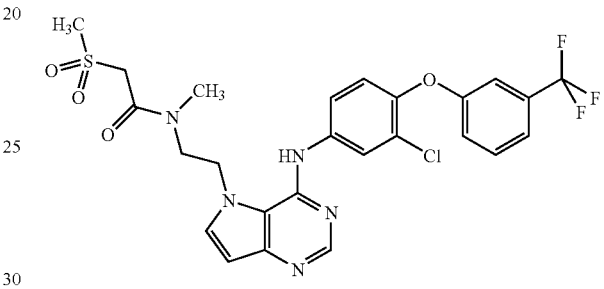

Production of N-{2-[4-({3-chloro-4-[3-(trifluoromethyl)phenoxy]phenyl}amino)-5H-pyrrolo[3,2-d]pyrimidin-5-yl]ethyl}-N-methyl-2-(methylsulfonyl)acetamide (i) Production of tert-butyl [2-(4-chloro-5H-pyrrolo[3,2-d]pyrimidin-5-yl)ethyl]methylcarbamate To a solution of 2-(methylamino)ethanol (1.00 g) in tetrahydrofuran (10 mL) was added di-tert-butyl dicarbonate (3.60 mL) at room temperature. After stirring at room temperature for 2 hrs, the mixture was concentrated under reduced pressure. To a solution of the residue and triethylamine (3.71 mL) in tetrahydrofuran (50 mL) was added dropwise methanesulfonyl chloride (1.55 mL) at 0° C., and the mixture was stirred at 0° C. for 1 hr. Aqueous sodium hydrogen carbonate was added to the reaction system and the mixture was extracted with ethyl acetate. The organic layer was washed with saturated brine, dried over magnesium sulfate and concentrated under reduced pressure to give a colorless oil.

The title compound (902 mg) was obtained as a pale-yellow oil by the reaction in the same manner as in Example 154 (i) using the obtained oil, 4-chloro-5H-pyrrolo[3,2-d]pyrimidine (1.34 g), cesium carbonate (5.69 g) and N,N-dimethylformamide (20 mL).

$^1$H-NMR (CDCl$_3$) δ: 1.12 (4.5H, s), 1.43 (4.5H, m), 2.55 (1.5H, s), 2.81 (1.5H, s), 3.58-3.60 (2H, m), 4.54-4.69 (2H, m), 6.73 (1H, d, J=3.0 Hz), 7.29-7.35 (0.5H, m), 7.38-7.46 (0.5H, m), 8.71 (1H, s).

(ii) Production of tert-butyl {2-[4-({3-chloro-4-[3-(trifluoromethyl)phenoxy]phenyl}amino)-5H-pyrrolo[3,2-d]pyrimidin-5-yl]ethyl}methylcarbamate The title compound (622 mg) was obtained as a colorless amorphous solid by the reaction in the same manner as in Example 155 (ii) using tert-butyl [2-(4-chloro-5H-pyrrolo[3,2-d]pyrimidin-5-yl)ethyl]methylcarbamate (450 mg), 3-chloro-4-[3-(trifluoromethyl)phenoxy]aniline (500 mg) and isopropyl alcohol (4.5 mL).

$^1$H-NMR (CDCl$_3$) δ: 1.51 (9H, s), 3.01 (3H, s), 3.51-3.59 (2H, m), 4.41-4.51 (2H, m), 6.60 (1H, d, J=3.0 Hz), 7.06 (1H, d, J=8.7 Hz), 7.08-7.13 (1H, m), 7.15-7.24 (2H, m), 7.30 (1H, d, J=8.4 Hz), 7.38-7.44 (1H, m), 7.85-7.93 (1H, m), 7.99-8.04 (1H, m), 8.50 (1H, s), 8.82 (1H, s).

(iii) Production of N-{3-chloro-4-[3-(trifluoromethyl)phenoxy]phenyl}-5-[2-(methylamino)ethyl]-5H-pyrrolo[3,2-d]pyrimidin-4-amine dihydrochloride The title compound (538 mg) was obtained as pale-yellow crystals by the reaction in the same manner as in Example 155 (iii) using tert-butyl {2-[4-({3-chloro-4-[3-(trifluoromethyl)phenoxy]phenyl}amino)-5H-pyrrolo[3,2-d]pyrimidin-5-yl]ethyl}methylcarbamate (622 mg), 2N hydrochloric acid (10 mL) and tetrahydrofuran (20 mL).

$^1$H-NMR (DMSO-d$_6$) δ: 2.54 (3H, t, J=5.3 Hz), 3.32-3.44 (2H, m), 5.01-5.15 (2H, m), 6.74 (1H, d, J=3.3 Hz), 7.22-7.27 (2H, m), 7.36 (1H, d, J=8.7 Hz), 7.51 (1H, d, J=8.4 Hz), 7.60-7.69 (2H, m), 7.91-7.96 (1H, m), 8.01-8.07 (1H, m), 8.72 (1H, s), 9.00-9.18 (2H, m), 10.06 (1H br s).

(iv) Production of N-{2-[4-({3-chloro-4-[3-(trifluoromethyl)phenoxy]phenyl}amino)-5H-pyrrolo[3,2-d]pyrimidin-5-yl]ethyl}-N-methyl-2-(methylsulfonyl)acetamide The title compound (131 mg) was obtained as colorless crystals by the reaction in the same manner as in Example 155 (iv) using N-{3-chloro-4-[3-(trifluoromethyl)phenoxy]phenyl}-5-[2-(methylamino)ethyl]-5H-pyrrolo[3,2-d]pyrimidin-4-amine dihydrochloride (170 mg), 2-(methylsulfonyl)acetic acid (88 mg), 1-ethyl-3-(3-dimethylaminopropyl)carbodiimide hydrochloride (183 mg), 1-hydroxybenzotriazole monohydrate (146 mg), triethylamine (0.44 mL) and N,N-dimethylformamide (5.0 mL).

$^1$H-NMR (CDCl$_3$) δ: 3.17 (3H, s), 3.34 (3H, s), 3.75-3.84 (2H, m), 4.18 (2H, s), 4.43-4.52 (2H, m), 6.64 (1H, d, J=3.0 Hz), 7.08 (1H, d, J=8.7 Hz), 7.10-7.16 (1H, m), 7.17-7.25 (2H, m), 7.32-7.37 (1H, m), 7.41-7.46 (1H, m), 7.86 (1H, dd, J=8.7, 2.7 Hz), 7.96 (1H, d, J=2.7 Hz), 8.46 (1H, s), 8.53 (1H, s).

Example 164

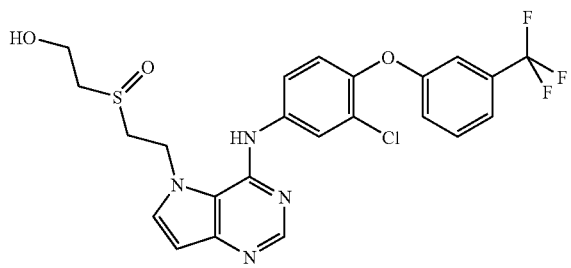

Production of 2-({2-[4-({3-chloro-4-[3-(trifluoromethyl)phenoxy]phenyl}amino)-5H-pyrrolo[3,2-d]pyrimidin-5-yl]ethyl}sulfinyl)ethanol To a solution of 2-({2-[4-({3-chloro-4-[3-(trifluoromethyl)phenoxy]phenyl}amino)-5H-pyrrolo[3,2-d]pyrimidin-5-yl]ethyl}thio)ethanol (100 mg) in dichloromethane (10 mL) was added dropwise a 70% solution of 3-chloroperbenzoic acid (58 mg) in dichloromethane (5.0 mL) at −78° C. The mixture was stirred at −78° C. for 1 hr, and aqueous sodium thiosulfate solution was added. After stirring at room temperature for 0.5 hr, the mixture was extracted with ethyl acetate. The organic layer was washed with saturated brine and dried over magnesium sulfate. After concentration under reduced pressure, the residue was separated and purified by silica gel column chromatography (eluent, ethyl acetate→ethyl acetate:methanol=4:1) to give the title compound (87 mg) as colorless crystals.

$^1$H-NMR (DMSO-d$_6$) δ: 2.78-3.01 (2H, m), 3.27-3.40 (1H, m), 3.42-3.58 (1H, m), 3.71-3.79 (2H, m), 4.80-4.90 (2H, m), 5.02-5.09 (1H, m), 6.58-6.63 (1H, m), 7.16-7.25 (2H, m), 7.27-7.31 (1H, m), 7.44-7.50 (1H, m), 7.59-7.64 (1H, m), 7.66-7.72 (1H, m), 7.74-7.82 (1H, m), 7.96-8.03 (1H, m), 8.37 (1H, s), 9.38 (1H, s).

Example 165

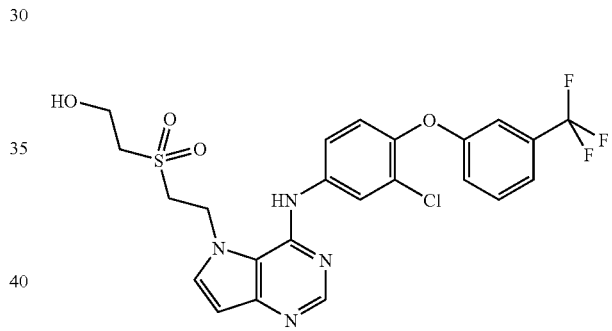

Production of 2-({2-[4-({3-chloro-4-[3-(trifluoromethyl)phenoxy]phenyl}amino)-5H-pyrrolo[3,2-d]pyrimidin-5-yl]ethyl}sulfonyl)ethanol To a solution of 2-({2-[4-({3-chloro-4-[3-(trifluoromethyl)phenoxy]phenyl}amino)-5H-pyrrolo[3,2-d]pyrimidin-5-yl]ethyl}thio)ethanol (150 mg), titanium tetraisopropoxide (43 μL), methanol (24 μL) and water (10 μL) in dichloromethane was stirred at room temperature for 30 min. 70% Aqueous tert-butyl hydroperoxide solution (0.12 mL) was added to the reaction system, and the mixture was stirred at room temperature for 2 days. An aqueous sodium thiosulfate solution was added to the reaction system, and the mixture was extracted with ethyl acetate. The organic layer was washed with saturated brine, dried over magnesium sulfate and concentrated under reduced pressure, and the residue was separated and purified by silica gel column chromatography (eluent, ethyl acetate→ethyl acetate:methanol=4:1) to give the title compound (118 mg) as colorless crystals.

$^1$H-NMR (DMSO-d$_6$) δ: 3.09-3.15 (2H, m), 3.62-3.75 (4H, m), 4.92-5.02 (2H, m), 5.09-5.15 (1H, m), 6.50-6.57 (1H, m), 7.16-7.32 (3H, m), 7.45-7.48 (1H, m), 7.58-7.74 (3H, m), 7.91-7.97 (1H, m), 8.37 (1H, br s), 8.69-8.79 (1H, m).

Example 166

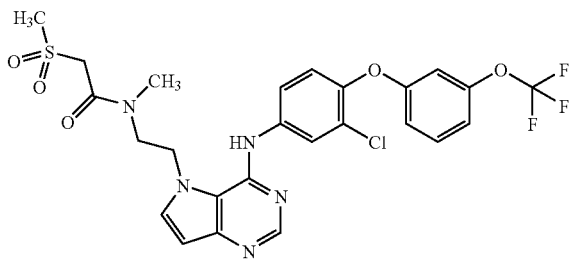

Production of N-{2-[4-({3-chloro-4-[3-(trifluoromethoxy)phenoxy]phenyl}amino)-5H-pyrrolo[3,2-d]pyrimidin-5-yl]ethyl}-N-methyl-2-(methylsulfonyl)acetamide (i) Production of tert-butyl {2-[4-({3-chloro-4-[3-(trifluoromethoxy)phenoxy]phenyl}amino)-5H-pyrrolo[3,2-d]pyrimidin-5-yl]ethyl}methylcarbamate The title compound (665 mg) was obtained as a colorless amorphous solid by the reaction in the same manner as in Example 155 (ii) using tert-butyl [2-(4-chloro-5H-pyrrolo[3,2-d]pyrimidin-5-yl)ethyl]methylcarbamate (463 mg), 3-chloro-4-[3-(trifluoromethoxy)phenoxy]aniline (679 mg) and isopropyl alcohol (5.0 mL).

$^1$H-NMR (CDCl$_3$) δ: 1.51 (9H, s), 3.01 (3H, s), 3.48-3.61 (2H, m), 4.42-4.50 (2H, m), 6.60 (1H, d, J=3.2 Hz), 6.80-6.83 (1H, m), 6.86-6.95 (2H, m), 7.08 (1H, d, J=8.7 Hz), 7.20 (1H, d, J=3.2 Hz), 7.28-7.33 (1H, m), 7.85-7.95 (1H, m), 7.99-8.05 (1H, m), 8.51 (1H, s), 8.81 (1H, br s).

(ii) Production of N-{3-chloro-4-[3-(trifluoromethoxy)phenoxy]phenyl}-5-[2-(methylamino)ethyl]-5H-pyrrolo[3,2-d]pyrimidin-4-amine dihydrochloride The title compound (557 mg) was obtained as pale-yellow crystals by the reaction in the same manner as in Example 155 (iii) using tert-butyl {2-[4-({3-chloro-4-[3-(trifluoromethoxy)phenoxy]phenyl}amino)-5H-pyrrolo[3,2-d]pyrimidin-5-yl]ethyl}methylcarbamate (665 mg), 2N hydrochloric acid (10 mL) and tetrahydrofuran (20 mL).

$^1$H-NMR (DMSO-d$_6$) δ: 2.52-2.66 (2H, m)), 3.29-3.45 (2H, m), 5.03-5.15 (2H, m), 6.75 (1H, d, J=3.0 Hz), 6.91-7.00 (2H, m), 7.11-7.18 (1H, m), 7.35 (1H, d, J=8.7 Hz), 7.51-7.57 (1H, m), 7.63-7.69 (1H, m), 7.91-7.96 (1H, m), 8.06 (1H, d, J=3.3 Hz), 8.73 (1H, s), 9.06-9.26 (2H, m), 10.11 (1H, br s).

(iii) Production of N-{2-[4-({3-chloro-4-[3-(trifluoromethoxy)phenoxy]phenyl}amino)-5H-pyrrolo[3,2-d]pyrimidin-5-yl]ethyl}-N-methyl-2-(methylsulfonyl)acetamide The title compound (147 mg) was obtained as colorless crystals by the reaction in the same manner as in Example 155 (iv) using N-{3-chloro-4-[3-(trifluoromethoxy)phenoxy]phenyl}-5-[2-(methylamino)ethyl]-5H-pyrrolo[3,2-d]pyrimidin-4-amine dihydrochloride (170 mg), 2-(methylsulfonyl)acetic acid (87 mg), 1-ethyl-3-(3-dimethylaminopropyl)carbodiimide hydrochloride (179 mg), 1-hydroxybenzotriazole monohydrate (143 mg), triethylamine (0.43 mL) and N,N-dimethylformamide (5.0 ml).

$^1$H-NMR (CDCl$_3$) δ: 3.17 (3H, s), 3.34 (3H, s), 3.75-3.84 (2H, m), 4.18 (2H, s), 4.43-4.52 (2H, m), 6.64 (1H, d, J=3.0 Hz), 7.08 (1H, d, J=8.7 Hz), 7.10-7.16 (1H, m), 7.17-7.25 (2H, m), 7.32-7.37 (1H, m), 7.41-7.46 (1H, m), 7.86 (1H, d, J=8.7, 2.7 Hz), 7.96 (1H, d, J=2.7 Hz), 8.46 (1H, s), 8.53 (1H, s).

Example 167

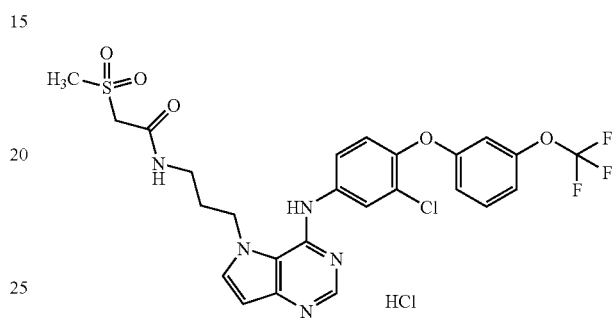

Production of N-{3-[4-({3-chloro-4-[3-(trifluoromethoxy)phenoxy]phenyl}amino)-5H-pyrrolo[3,2-d]pyrimidin-5-yl]propyl}-2-(methylsulfonyl)acetamide hydrochloride (i) Production of tert-butyl [3-(4-chloro-5H-pyrrolo[3,2-d]pyrimidin-5-yl)propyl]carbamate The title compound (1.04 g) was obtained as a colorless oil by the reaction in the same manner as in Example 154 (i) using 4-chloro-5H-pyrrolo[3,2-d]pyrimidine (500 mg), tert-butyl 3-bromopropylcarbamate (1.00 g), cesium carbonate (1.59 g) and N,N-dimethylacetamide (5.0 mL).

$^1$H-NMR (CDCl$_3$) δ: 1.46 (9H, s), 2.02-2.12 (2H, m), 3.13-3.25 (2H, m), 4.50-4.66 (3H, m), 6.78 (1H, d, J=3.0 Hz), 7.61-7.69 (1H, m), 8.71 (1H, s).

(ii) Production of tert-butyl {3-[4-({3-chloro-4-[3-(trifluoromethoxy)phenoxy]phenyl}amino)-5H-pyrrolo[3,2-d]pyrimidin-5-yl]propyl}carbamate The title compound (398 mg) was obtained as a colorless amorphous solid by the reaction in the same manner as in Example 155 (ii) using tert-butyl [3-(4-chloro-5H-pyrrolo[3,2-d]pyrimidin-5-yl)propyl]carbamate (546 mg), 3-chloro-4-[3-(trifluoromethoxy)phenoxy]aniline (640 mg) and isopropyl alcohol (10 mL)

$^1$H-NMR (CDCl$_3$) δ: 1.42 (9H, s), 2.10-2.21 (2H, m), 3.17-3.27 (2H, m), 4.40 (2H, t, J=7.5 Hz), 4.69-4.79 (1H, m), 6.62 (1H, d, J=3.0 Hz), 6.81 (1H, br s), 6.85-6.95 (2H, m), 7.04-7.13 (2H, m), 7.29-7.34 (2H, m), 7.54-7.60 (1H, m), 7.89 (1H, d, J=3.0 Hz), 8.52 (1H, s).

(iii) Production of 5-(3-aminopropyl)-N-{3-chloro-4-[3-(trifluoromethoxy)phenoxy]phenyl}-5H-pyrrolo[3,2-d]pyrimidin-4-amine dihydrochloride The title compound (355 mg) was obtained as colorless powder crystals by the reaction in the same manner as in Example 155 (iii) using tert-butyl {3-[4-({3-chloro-4-[3-(trifluoromethoxy)phenoxy]phenyl}amino)-5H-pyrrolo[3,2-d]pyrimidin-5-yl]propyl}carbamate (398 mg), 2N hydrochloric acid (10 mL) and tetrahydrofuran (20 ml).

$^1$H-NMR (DMSO-$d_6$) δ: 2.03-2.16 (2H, m), 2.61-2.75 (2H, m), 4.86 (2H, t, J=6.6 Hz), 6.70 (1H, d, J=3.0 Hz), 6.94-7.01 (2H, m), 7.11-7.19 (1H, m), 7.37 (1H, d, J=8.7 Hz), 7.52-7.58 (1H, m), 7.67 (1H, dd, J=8.7, 2.7 Hz), 7.95 (1H, d, J=2.1 Hz), 7.96-815 (4H, m), 8.72 (1H, s), 9.96 (1H, br s).

(iv) Production of N-{3-[4-({3-chloro-4-[3-(trifluoromethoxy)phenoxy]phenyl}amino)-5H-pyrrolo[3,2-d]pyrimidin-5-yl]propyl}-2-(methylsulfonyl)acetamide hydrochloride N-{3-[4-({3-Chloro-4-[3-(trifluoromethoxy)phenoxy]phenyl}amino)-5H-pyrrolo[3,2-d]pyrimidin-5-yl]propyl}-2-(methylsulfonyl)acetamide was obtained by the reaction in the same manner as in Example 155 (iv) using 5-(3-aminopropyl)-N-{3-chloro-4-[3-(trifluoromethoxy)phenyl}-5H-pyrrolo[3,2-d]pyrimidin-4-amine dihydrochloride (170 mg), 2-(methylsulfonyl)acetic acid (85.0 mg), 1-ethyl-3-(3-dimethylaminopropyl)carbodiimide hydrochloride (177 mg), 1-hydroxybenzotriazole monohydrate (141 mg), triethylamine (0.43 mL) and N,N-dimethylformamide (5.0 mL). To a solution of N-{3-[4-({3-chloro-4-[3-(trifluoromethoxy)phenoxy]phenyl}amino)-5H-pyrrolo[3,2-d]pyrimidin-5-yl]propyl}-2-(methylsulfonyl)acetamide in ethyl acetate (1.0 mL) was added 4N hydrochloric acid-ethyl acetate (0.50 mL) at room temperature, and the mixture was stirred at room temperature for 1 hr. After concentration under reduced pressure, diisopropyl ether was added, and the precipitated crystals were collected by filtration. The crystals were washed with diisopropyl ether to give the title compound (128 mg) as colorless powder crystals.

$^1$H-NMR (DMSO-$d_6$) δ: 1.88-2.00 (2H, m), 2.97-3.08 (2H, m), 3.11 (3H, s), 4.04 (2H, s), 4.63-4.72 (2H, m), 6.67 (1H, d, J=3.0 Hz), 6.94-7.01 (2H, m), 7.13-7.21 (1H, m), 7.36 (1H, d, J=9.0 Hz), 7.49-7.65 (2H, m), 7.91 (1H, d, J=2.4 Hz), 7.96 (1H, d, J=3.0 Hz), 8.45-8.52 (1H, m), 8.70 (1H, s), 9.67 (1H, br s).

Example 168 din-4-amine dihydrochloride (230 mg) and triethylamine (0.61 mL) in tetrahydrofuran (8.0 mL) was added 3-(methylthio)propionyl chloride (0.15 mL) under ice-cooling. After stirring at room temperature for 20 hrs, water was added, and the mixture was extracted with ethyl acetate. The organic layer was washed with saturated brine, dried over magnesium sulfate and concentrated under reduced pressure, and the residue was separated and purified by basic silica gel column chromatography (eluent, ethyl acetate→ethyl acetate:methanol=9:1) to give the title compound (133 mg) as colorless crystals.

$^1$H-NMR (CDCl$_3$) δ: 2.13 (3H, s), 2.59 (2H, t, J=6.9 Hz), 2.83 (2H, t, J=6.9 Hz), 3.57-3.69 (2H, m), 4.45-4.55 (2H, m), 6.39-6.47 (1H, m), 6.62 (1H, d, J=3.0 Hz), 7.08 (1H, d, J=8.7 Hz), 7.09-7.14 (1H, m), 7.20 (1H, d, J=3.0 Hz), 7.23-7.27 (1H, m), 7.29-7.34 (1H, m), 7.39-7.47 (1H, m), 7.83 (1H, dd, J=8.7, 2.7 Hz), 8.12 (1H, d, J=2.7 Hz), 8.523 (1H, s), 8.63 (1H, s).

(ii) Production of N-{2-[4-({3-chloro-4-[3-(trifluoromethyl)phenoxy]phenyl}amino)-5H-pyrrolo[3,2-d]pyrimidin-5-yl]ethyl}-3-(methylsulfonyl)propanamide The title compound (97 mg) was obtained as colorless crystals by the reaction in the same manner as in Example 165 using N-{2-[4-({3-chloro-4-[3-(trifluoromethyl)phenoxy]phenyl}amino)-5H-pyrrolo[3,2-d]pyrimidin-5-yl]ethyl}-3-(methylthio)propanamide (150 mg), titanium tetraisopropoxide (40.3 μL), methanol (22.2 μL), water (9.3 μL), 70% aqueous tert-butyl hydroperoxide solution (0.12 mL) and dichloromethane (8.0 mL).

$^1$H-NMR (DMSO-$d_6$) δ: 2.41-2.57 (2H, m), 2.95 (3H, s), 3.26 (2H, t, J=7.5 Hz), 3.35-3.45 (2H, m), 4.48-4.58 (2H, m), 6.51 (1H, d, J=3.0 Hz), 7.18-7.32 (3H, m), 7.43-7.50 (1H, m), 7.58-7.67 (2H, m), 7.73-7.82 (1H, m), 8.02-8.07 (1H, m), 8.34-8.45 (2H, m), 8.75 (1H, s).

Example 169

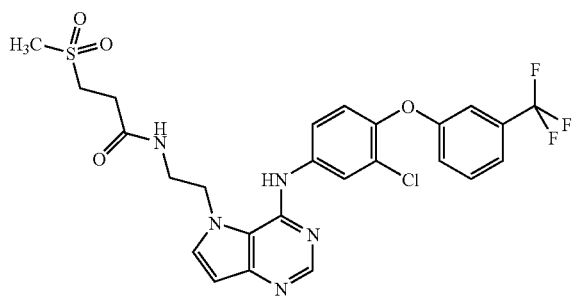

Production of N-{2-[4-({3-chloro-4-[3-(trifluoromethyl)phenoxy]phenyl}amino)-5H-pyrrolo[3,2-d]pyrimidin-5-yl]ethyl}-3-(methylsulfonyl)propanamide (i) Production of N-{2-[4-({3-chloro-4-[3-(trifluoromethyl)phenoxy]phenyl}amino)-5H-pyrrolo[3,2-d]pyrimidin-5-yl]ethyl}-3-(methylthio)propanamide To a mixture of 5-(2-aminoethyl)-N-{3-chloro-4-[3-(trifluoromethyl)phenoxy]phenyl}-5H-pyrrolo[3,2-d]pyrimi-

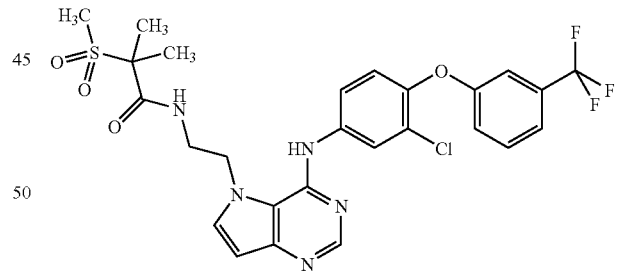

Production of N-{2-[4-({3-chloro-4-[3-(trifluoromethyl)phenoxy]phenyl}amino)-5H-pyrrolo[3,2-d]pyrimidin-5-yl]ethyl}-2-methyl-2-(methylsulfonyl)propanamide To a solution of 2-methyl-2-(methylsulfonyl)propanoic acid (115 mg) and N,N-dimethylformamide (catalytic amount) in tetrahydrofuran (5.0 mL) was added thionyl chloride (0.10 mL) at room temperature. After stirring at room temperature for 3 hrs, the mixture was concentrated under reduced pressure. A solution of the residue in tetrahydrofuran (10 mL) was added dropwise to a suspension of 5-(2-aminoethyl)-N-{3-chloro-4-[3-(trifluoromethyl)phenoxy]phenyl}-5H-pyrrolo[3,2-d]pyrimidin-4-amine dihydrochloride (180 mg) and triethylamine (0.48 mL) in tetrahydrofuran (10 mL) at room temperature. After stirring at room temperature for 20 hrs, water was added to the reaction system and the mixture was extracted with ethyl acetate. The organic layer was washed with saturated brine, dried over magnesium sulfate and concentrated under reduced pressure. The residue was separated and purified by basic silica gel column chromatography (eluent, ethyl acetate→ethyl acetate:methanol=9:1) to give the title compound (205 mg) as colorless crystals.

$^1$H-NMR (CDCl$_3$) δ: 1.70 (6H, s), 2.93 (3H, s), 3.63-3.73 (2H, m), 4.43-4.52 (2H, m), 6.64 (1H, d, J=3.3 Hz), 7.09 (1H, d, J=8.7 Hz), 7.10-7.16 (1H, m), 7.18-7.24 (2H, m), 7.27-7.35 (2H, m), 7.40-7.47 (1H, m), 7.90 (1H, dd, J=8.7, 2.7 Hz), 8.05 (1H, d, J=2.7 Hz), 8.38 (1H, s), 8.54 (1H, s)

melting point: 167-168° C.

Example 170

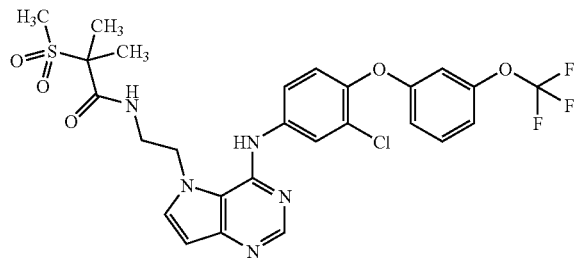

Production of N-{2-[4-({3-chloro-4-[3-(trifluoromethoxy)phenoxy]phenyl}amino)-5H-pyrrolo[3,2-d]pyrimidin-5-yl]ethyl}-2-methyl-2-(methylsulfonyl)propanamide To a solution of 2-methyl-2-(methylsulfonyl)propanoic acid (92 mg) and N,N-dimethylformamide (catalytic amount) in tetrahydrofuran (5.0 mL) was added thionyl chloride (80 μL) at room temperature. After stirring at room temperature for 3 hrs, the mixture was concentrated under reduced pressure. A solution of the residue in tetrahydrofuran-dichloromethane (10 mL-10 mL) was added dropwise to a suspension of 5-(2-aminoethyl)-N-{3-chloro-4-[3-(trifluoromethoxy)phenoxy]phenyl}-5H-pyrrolo[3,2-d]pyrimidin-4-amine dihydrochloride (150 mg) and triethylamine (0.39 mL) in tetrahydrofuran (10 mL) at room temperature. After stirring at room temperature for 20 hrs, aqueous sodium hydrogen carbonate was added to the reaction system and the mixture was extracted with ethyl acetate. The organic layer was washed with saturated brine, dried over magnesium sulfate and concentrated under reduced pressure. The residue was separated and purified by basic silica gel column chromatography (eluent, ethyl acetate→ethyl acetate:methanol=9:1) to give the title compound (108 mg) as pale-yellow crystals.

$^1$H-NMR (CDCl$_3$) δ: 1.70 (6H, s), 2.93 (3H, s), 3.62-3.73 (2H, m), 4.42-4.51 (2H, m), 6.64 (1H, d, J=3.3 Hz), 6.82-6.86 (1H, m), 6.88-6.96 (2H, m), 7.09 (1H, d, J=9.0 Hz), 7.21 (1H, d, J=3.3 Hz), 7.26-7.35 (2H, m), 7.89 (1H, dd, J=9.0, 2.6 Hz), 8.04 (1H, d, J=2.6 Hz), 8.37 (1H, s), 8.54 (1H, s).

Example 171

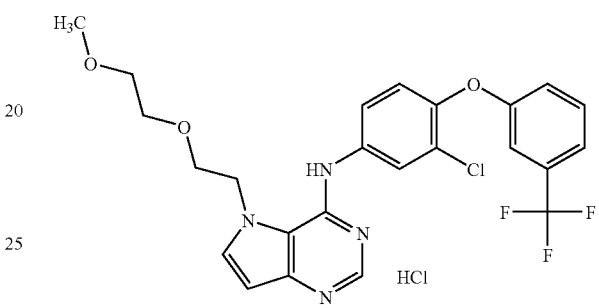

Production of N-{3-chloro-4-[3-(trifluoromethyl)phenoxy]phenyl}-5-[2-(2-methoxyethoxy)ethyl]-5H-pyrrolo[3,2-d]pyrimidin-4-amine hydrochloride 4-Chloro-5H-pyrrolo[3,2-d]pyrimidine (500 mg) was dissolved in N,N-dimethylformamide (10 mL), and potassium carbonate (830 mg) and 2-(2-methoxyethoxy)ethyl 4-methylbenzenesulfonate (920 mg) were added and the mixture was stirred at room temperature for 12 hrs. Saturated aqueous sodium hydrogen carbonate was added to the reaction mixture under ice-cooling, and the mixture was extracted with ethyl acetate. The organic layer was dried over magnesium sulfate and concentrated. The residue was purified by silica gel column chromatography (eluent, hexane:ethyl acetate=50:50→0:100). The obtained oil was dissolved in isopropyl alcohol (10 mL), and 3-chloro-4-[3-(trifluoromethyl)phenoxy]aniline was added. The mixture was stirred at 90° C. for 4 hrs, saturated aqueous sodium hydrogen carbonate was added to the reaction mixture under ice-cooling, and the mixture was extracted with ethyl acetate. The extract was dried over magnesium sulfate and concentrated. The residue was separated and purified by silica gel column chromatography (eluent, ethyl acetate:methanol=100:0→ethyl acetate:methanol=90:10), and crystallized from 4N hydrochloric acid-ethyl acetate solution/hexane to give the title compound (277 mg).

$^1$H-NMR (DMSO-d$_6$) δ: 3.06 (3H, s), 3.33-3.35 (2H, m), 3.55-3.61 (2H, m), 3.83-3.86 (2H, m), 4.83-4.86 (2H, m), 6.71 (1H, d, J=3 Hz), 7.24-7.72 (7H, m), 7.99-8.04 (2H, m), 8.77 (1H, s), 9.92 (1H, s).

Example 172

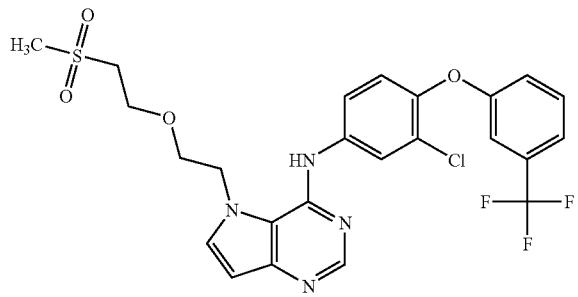

Production of N-{3-chloro-4-[3-(trifluoromethyl)phenoxy]phenyl}-5-{2-[2-(methylsulfonyl)ethoxy]ethyl}-5H-pyrrolo[3,2-d]pyrimidin-4-amine (i) Production of N-{3-chloro-4-[3-(trifluoromethyl)phenoxy]phenyl}-5-{2-[2-(methylthio)ethoxy]ethyl}-5H-pyrrolo[3,2-d]pyrimidin-4-amine The compound (150 mg) of Example 147 was dissolved in tetrahydrofuran (10 mL) and triethylamine (1.50 mL) and methanesulfonyl chloride (0.70 mL) were added under ice-cooling, and the mixture was stirred for 1 hr. Saturated aqueous sodium hydrogen carbonate was added to this reaction solution under ice-cooling, and the mixture was extracted with ethyl acetate. The extract was dried over magnesium sulfate and concentrated, and the residue was dissolved in a mixed solvent of N,N-dimethylformamide (5.0 mL) and tetrahydrofuran (4.0 mL). Sodium methanethiolate (180 mg) was added, and the mixture was stirred at room temperature for 1 hr. Saturated aqueous sodium hydrogen carbonate was added to the reaction mixture under ice-cooling, and the mixture was extracted with ethyl acetate. The extract was dried over magnesium sulfate and concentrated. The residue was separated and purified by silica gel column chromatography (eluent, ethyl acetate:methanol=100:0→ethyl acetate:methanol=90:10) to give the title compound (123 mg).

$^1$H-NMR (CDCl$_3$) δ: 2.02 (3H, s), 2.66-2.73 (2H, m), 3.74-3.78 (2H, m), 3.98-4.01 (2H, m), 4.55-4.58 (2H, m), 6.66 (1H, d, J=3 Hz), 7.07-7.63 (6H, m), 7.88 (1H, br s), 8.02 (1H, s), 8.55 (1H, s), 8.74 (1H, s).

(ii) Production of N-{3-chloro-4-[3-(trifluoromethyl)phenoxy]phenyl}-5-{2-[2-(methylsulfonyl)ethoxy]ethyl}-5H-pyrrolo[3,2-d]pyrimidin-4-amine N-{3-Chloro-4-[3-(trifluoromethyl)phenoxy]phenyl}-5-{2-[2-(methylthio)ethoxy]ethyl}-5H-pyrrolo[3,2-d]pyrimidin-4-amine (70.0 mg) was dissolved in dichloromethane (5.0 mL), titanium tetraisopropoxide (0.10 mL), methanol (0.50 mL) and 70% aqueous tert-butyl hydroperoxide solution (8.0 mL) were added, and the mixture was stirred at room temperature for 1 hr. Saturated aqueous sodium thiosulfate solution was added to the reaction mixture under ice-cooling, and the mixture was stirred at room temperature for 1 hr and extracted with dichloromethane. The extract was dried over magnesium sulfate and concentrated, and the residue was separated and purified by silica gel column chromatography (eluent, ethyl acetate:methanol=100:0→ethyl acetate:methanol=90:10). Crystallization from diethyl ether/ethyl acetate/hexane gave the title compound (62.5 mg).

$^1$H-NMR (CDCl$_3$) δ: 2.62 (3H, s), 4.57-4.61 (2H, m), 6.68 (1H, d, J=3 Hz), 4.16 (1H, m), 5.08 (2H, s), 5.55 (2H, s), 6.33 (1H, br s), 6.66 (1H, d, J=3 Hz), 7.09-7.60 (7H, m), 7.86 (1H, d, J=3 Hz), 8.11 (1H, s), 8.55 (1H, s).

Example 173

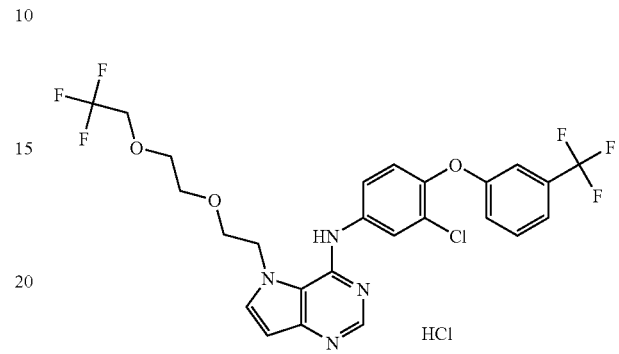

Production of N-{3-chloro-4-[3-(trifluoromethyl)phenoxy]phenyl}-5-{2-[2-(2,2,2-trifluoroethoxy)ethoxy]ethyl}-5H-pyrrolo[3,2-d]pyrimidin-4-amine hydrochloride The title compound (107 mg) was obtained as crystals by the reaction in the same manner as in Example 172 (i) using the compound (200 mg) of Example 147, sodium 2,2,2-trifluoroethanolate (1.20 g), tetrahydrofuran (7.0 mL) and N,N-dimethylformamide (10 mL) at a reaction temperature of 50° C., and crystallization from 4N hydrochloric acid-ethyl acetate solution/hexane.

$^1$H-NMR (DMSO-d$_6$) δ: 3.09 (4H, m), 3.30-3.39 (2H, m), 4.61 (2H, br s), 5.12 (2H, br s), 6.53 (1H, d, J=3 Hz), 7.20-8.56 (10H, m).

Example 174

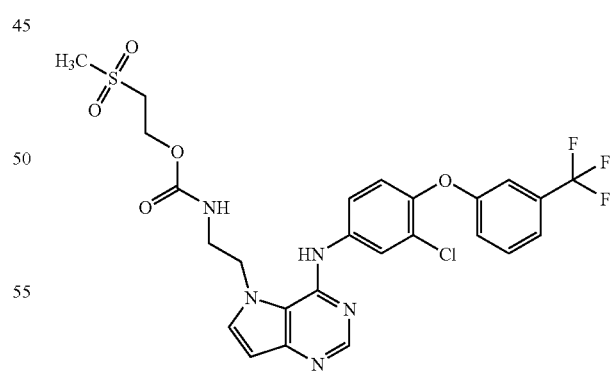

Production of 2-(methylsulfonyl)ethyl {2-[4-({3-chloro-4-[3-(trifluoromethyl)phenoxy]phenyl}amino)-5H-pyrrolo[3,2-d]pyrimidin-5-yl]ethyl}carbamate 5-(2-Aminoethyl)-N-{3-chloro-4-[3-(trifluoromethyl)phenoxy]phenyl}-5H-pyrrolo[3,2-d]pyrimidin-4-amine Example 175

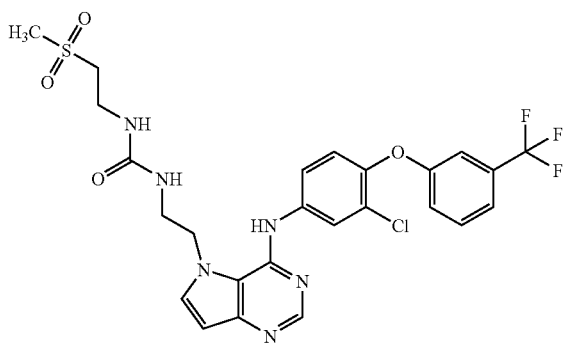

Production of N-{2-[4-({3-chloro-4-[3-(trifluoromethyl)phenoxy]phenyl}amino)-5H-pyrrolo[3,2-d]pyrimidin-5-yl]ethyl}-N'-[2-(methylsulfonyl)ethyl]urea 5-(2-Aminoethyl)-N-{3-chloro-4-[3-(trifluoromethyl)phenoxy]phenyl}-5H-pyrrolo[3,2-d]pyrimidin-4-amine dihydrochloride (54.1 mg) and triethylamine (0.7 mL) were dissolved in dichloromethane (10 mL), 1,1'-carbonylbis(1H-imidazole) was added, and the mixture was stirred at room temperature. After 1 hr, 2-(methylsulfonyl)ethanamine (1.0 mL) was added, and the mixture was further stirred for 1 hr. Saturated aqueous sodium hydrogen carbonate was added to the reaction mixture under ice-cooling, and the mixture was extracted with dichloromethane. The extract was dried over magnesium sulfate and concentrated, and the residue was separated and purified by silica gel column chromatography (eluent, ethyl acetate:methanol=100:0→ethyl acetate:methanol=90:10). crystallized from diethyl ether/ethyl acetate/hexane to give the title compound (37.6 mg).

$^1$H-NMR (CDCl$_3$) δ: 2.84 (3H, s), 3.11-3.17 (2H, m), 3.40-3.50 (2H, m), 3.66-3.72 (2H, m), 4.39-4.44 (2H, m), 5.55 (2H, m), 6.47 (1H, d, J=3 Hz), 7.00-7.39 (6H, m), 7.81-7.88 (1H, m), 7.99 (1H, m), 8.40 (1H, s), 8.73 (1H, s).

dihydrochloride (64.1 mg) and triethylamine (1.0 mL) were dissolved in dichloromethane (5.0 mL), 1-({[2-(methylsulfonyl)ethoxy]carbonyl}oxy)pyrrolidine-2,5-dione (45.6 mg) was added, and the mixture was stirred at room temperature for 2 hrs. Saturated aqueous sodium hydrogen carbonate was added to the reaction mixture under ice-cooling, and the mixture was extracted with ethyl acetate. The extract was dried over magnesium sulfate and concentrated, and the residue was separated and purified by silica gel column chromatography (eluent, ethyl acetate:methanol=100:0→ethyl acetate:methanol=95:5). Crystallization from diethyl ether/hexane gave the title compound (61.0 mg).

$^1$H-NMR (CDCl$_3$) δ: 3.10 (3H, s), 3.48-3.52 (2H, m), 3.70-3.75 (2H, m), 4.62-4.68 (2H, m), 4.75-4.79 (2H, m), 5.57 (1H, m), 6.78 (1H, d, J=3 Hz), 7.22-7.61 (6H, m), 7.92 (1H, m), 8.11 (1H, m), 8.20 (1H, s), 8.68 (1H, s).

Example 176

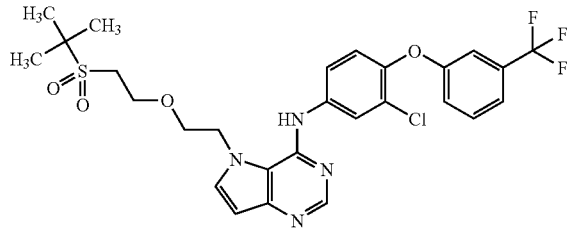

Production of 5-{2-[2-(tert-butylsulfonyl)ethoxy]ethyl}-N-{3-chloro-4-[3-(trifluoromethyl)phenoxy]phenyl}-5H-pyrrolo[3,2-d]pyrimidin-4-amine (i) Production of 5-{2-[2-(tert-butylthio)ethoxy]ethyl}-N-{3-chloro-4-[3-(trifluoromethyl)phenoxy]phenyl}-5H-pyrrolo[3,2-d]pyrimidin-4-amine 2-{2-[4-({3-Chloro-4-[3-(trifluoromethyl)phenoxy]phenyl}amino)-5H-pyrrolo[3,2-d]pyrimidin-5-yl]ethoxy}ethanol (150 mg) was dissolved in tetrahydrofuran (6.0 mL), and triethylamine (1.00 mL) and methanesulfonyl chloride (0.59 mL) were added under ice-cooling and the mixture was stirred for 1 hr. Saturated aqueous sodium hydrogen carbonate was added to this reaction solution under ice-cooling and the mixture was extracted with ethyl acetate. The extract was dried over magnesium sulfate and concentrated, and the residue was dissolved in a mixed solvent of N,N-dimethylformamide (4.0 mL) and tetrahydrofuran (6.0 mL). Sodium 2-methylpropane-2-thiolate (220 mg) was added, and the mixture was stirred at room temperature for 1 hr. Saturated aqueous sodium hydrogen carbonate was added to the reaction mixture under ice-cooling and the mixture was extracted with ethyl acetate. The extract was dried over magnesium sulfate and concentrated. The residue was separated and purified by silica gel column chromatography (eluent, ethyl acetate:methanol=100:0→ethyl acetate:methanol=90:10) to give the title compound (143 mg).

$^1$H-NMR (CDCl$_3$) δ: 1.23 (9H, s), 2.69-2.73 (2H, m), 3.73-3.78 (2H, m), 3.97-3.99 (2H, m), 4.54-4.57 (2H, m), 6.66 (1H, d, J=3 Hz), 7.07-7.45 (6H, m), 7.64-7.68 (1H, m), 7.89 (1H, d, J=3 Hz), 8.55 (1H, s), 8.77 (1H, s).

(ii) Production of 5-{2-[2-(tert-butylsulfonyl)ethoxy]ethyl}-N-{3-chloro-4-[3-(trifluoromethyl)phenoxy]phenyl}-5H-pyrrolo[3,2-d]pyrimidin-4-amine 5-{2-[2-(tert-Butylthio)ethoxy]ethyl}-N-{3-chloro-4-[3-(trifluoromethyl)phenoxy]phenyl}-5H-pyrrolo[3,2-d]pyrimidin-4-amine (140 mg) was dissolved in dichloromethane (5.0 mL), titanium tetraisopropoxide (0.90 mL), methanol (0.20 mL) and 70% aqueous tert-butyl hydroperoxide solution (7.0 mL) were added, and the mixture was stirred at room temperature for 1 hr. Saturated aqueous sodium thiosulfate solution was added to the reaction mixture under ice-cooling, and the mixture was stirred at room temperature for 1 hr and extracted with dichloromethane. The extract was dried over magnesium sulfate and concentrated, and the residue was separated and purified by silica gel column chromatography (eluent, ethyl acetate:methanol=100:0→ethyl acetate:methanol=90:10). Crystallization from diethyl ether/ethyl acetate/hexane gave the title compound (10.6 mg).

¹H-NMR (CDCl₃) δ: 1.24 (9H, s), 3.00-3.04 (2H, m), 3.97-4.08 (4H, m), 4.49-4.52 (2H, m), 6.59 (1H, d, J=3 Hz), 7.00-7.56 (7H, m), 7.84 (1H, d, J=3 Hz), 8.27 (1H, s), 8.48 (1H, s).

melting point: 79.5-81.5° C.

Example 177

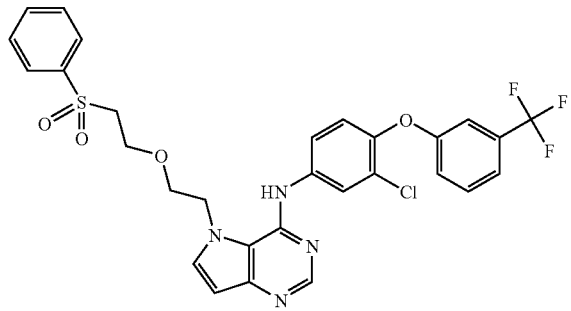

Production of N-{3-chloro-4-[3-(trifluoromethyl)phenoxy]phenyl}-5-{2-[2-(phenylsulfonyl)ethoxy]ethyl}-5H-pyrrolo[3,2-d]pyrimidin-4-amine (i) Production of N-{3-chloro-4-[3-(trifluoromethyl)phenoxy]phenyl}-5-{2-[2-(phenylthio)ethoxy]ethyl}-5H-pyrrolo[3,2-d]pyrimidin-4-amine The title compound (96.4 mg) was obtained by the reaction in the same manner as in Example 172 (i) using the compound (100 mg) of Example 147, sodium benzenethiolate (200 mg), tetrahydrofuran (5.0 mL) and N,N-dimethylformamide (4.0 mL).

¹H-NMR (CDCl₃) δ: 3.06-3.10 (2H, m), 3.75-3.79 (2H, m), 3.94-3.97 (2H, m), 4.52-4.55 (2H, m), 6.66 (1H, d, J=3 Hz), 7.01-7.56 (12H, m), 7.88 (1H, d, J=3 Hz), 8.56 (1H, s), 8.71 (1H, s).

(ii) Production of N-{3-chloro-4-[3-(trifluoromethyl)phenoxy]phenyl}-5-{2-[2-(phenylsulfonyl)ethoxy]ethyl}-5H-pyrrolo[3,2-d]pyrimidin-4-amine The title compound (7.2 mg) was obtained by the reaction in the same manner as in Example 172 (ii) using N-{3-chloro-4-[3-(trifluoromethyl)phenoxy]phenyl}-5-{2-[2-(phenylthio)ethoxy]ethyl}-5H-pyrrolo[3,2-d]pyrimidin-4-amine (60 mg), dichloromethane (5.0 mL), N,N-dimethylformamide (2.0 mL), titanium tetraisopropoxide (0.90 mL), methanol (0.20 mL) and 70% aqueous tert-butyl hydroperoxide solution (4.0 mL).

¹H-NMR (CDCl₃) δ: 3.23-3.27 (2H, m), 3.88-4.00 (4H, m), 4.42-4.45 (2H, m), 6.58 (1H, d, J=3 Hz), 7.00-7.70 (12H, m), 7.79 (1H, d, J=3 Hz), 8.13 (1H, s), 8.47 (1H, s).

Example 178

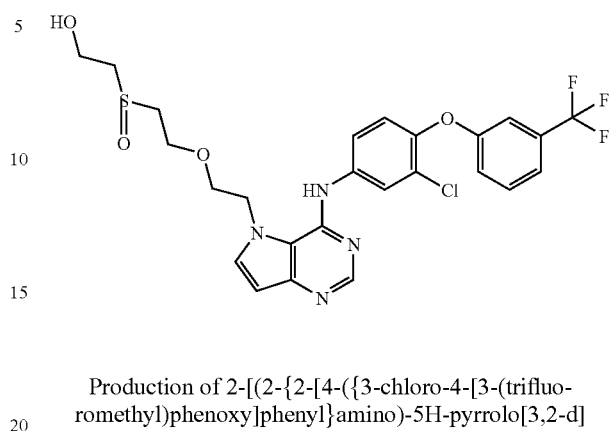

Production of 2-[(2-{2-[4-({3-chloro-4-[3-(trifluoromethyl)phenoxy]phenyl}amino)-5H-pyrrolo[3,2-d]pyrimidin-5-yl]ethoxy}ethyl)sulfinyl]ethanol The compound (120 mg) obtained by the reaction in the same manner as in Example 172 (i) using the compound (200 mg) of Example 147, sodium 2-hydroxyethanethiolate (2.02 g), tetrahydrofuran (6.0 mL) and N,N-dimethylformamide (5.0 mL) was dissolved in dichloromethane (7.0 mL). m-Chloroperbenzoic acid (110 mg) was added at −18° C. and the mixture was stirred for 5 hrs. Saturated aqueous sodium hydrogen carbonate was added to the reaction mixture under ice-cooling, and the mixture was extracted with dichloromethane. The extract was dried over magnesium sulfate and concentrated, and the residue was separated and purified by silica gel column chromatography (eluent, ethyl acetate:methanol=100:0→ethyl acetate:methanol=80:20). Crystallization from diethyl ether/ethyl acetate/hexane gave the title compound (97.0 mg).

¹H-NMR (CDCl₃) δ: 2.66-2.73 (2H, m), 2.90-2.98 (2H, m), 3.93-4.13 (6H, m), 4.56-4.62 (2H, m), 6.68 (1H, d, J=3 Hz), 7.08-7.59 (7H, m), 7.83 (1H, d, J=3 Hz), 8.37 (1H, m), 8.55 (1H, s).

Example 179

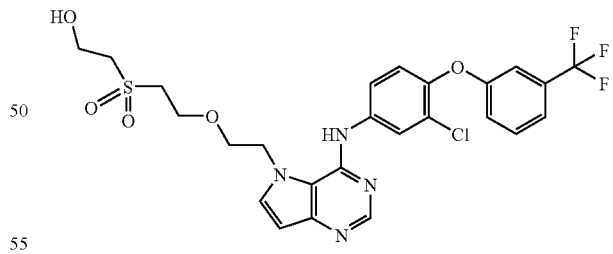

Production of 2-[(2-{2-[4-({3-chloro-4-[3-(trifluoromethyl)phenoxy]phenyl}amino)-5H-pyrrolo[3,2-d]pyrimidin-5-yl]ethoxy}ethyl)sulfonyl]ethanol The title compound (60.2 mg) was obtained as crystals by the reaction in the same manner as in Example 172 (ii) using the compound (87.0 mg) of Example 178, dichloromethane (4.0 mL), N,N-dimethylformamide (2.0 mL), titanium tetraisopropoxide (0.90 mL), methanol (0.50 mL) and 70% aqueous tert-butyl hydroperoxide solution (5.0 mL).

¹H-NMR (CDCl₃) δ: 2.78-2.82 (2H, m), 3.34-3.38 (2H, m), 3.79 (2H, m), 4.03-4.13 (4H, m), 4.57-4.60 (2H, m), 6.68 (1H, d, J=3 Hz), 7.07-7.57 (7H, m), 7.80 (1H, d, J=3 Hz), 8.23 (1H, m), 8.54 (1H, s).

Example 180

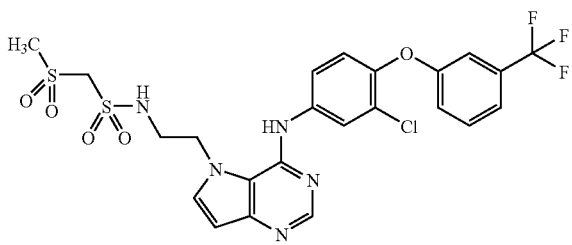

Production of N-{2-[4-({3-chloro-4-[3-(trifluoromethyl)phenoxy]phenyl}amino)-5H-pyrrolo[3,2-d]pyrimidin-5-yl]ethyl}-1-(methylsulfonyl)methanesulfonamide 5-(2-Aminoethyl)-N-{3-chloro-4-[3-(trifluoromethyl)phenoxy]phenyl}-5H-pyrrolo[3,2-d]pyrimidin-4-amine dihydrochloride (245 mg) and N-methylmorpholine (1.0 mL) were dissolved in dichloromethane (6.0 mL), (methylsulfonyl)methanesulfonyl chloride (0.40 mL) was added dropwise under ice-cooling, and the mixture was stirred for 1 hr. Saturated aqueous sodium hydrogen carbonate was added under ice-cooling, and the mixture was extracted with dichloromethane. The extract was dried over magnesium sulfate and concentrated, and the residue was separated and purified by silica gel column chromatography (eluent, ethyl acetate:methanol=100:0→ethyl acetate:methanol=80:20). Crystallization from diethyl ether/ethyl acetate to give the title compound (79.4 mg) as crystals.
¹H-NMR (CDCl₃) δ: 3.60 (3H, br s), 3.83-3.92 (4H, m), 4.82 (2H, br s), 6.68 (1H, d, J=3 Hz), 7.24-7.99 (8H, m), 8.73 (1H, s), 8.73 (1H, s), 9.72 (1H, s).

Example 181

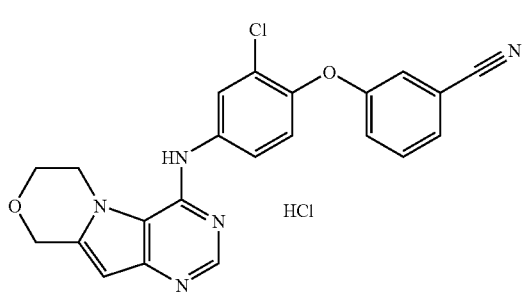

Production of 3-[2-chloro-4-(6,7-dihydro-9H-pyrimido[4',5':4,5]pyrrolo[2,1-c][1,4]oxazin-4-ylamino)phenoxy]benzonitrile hydrochloride (i) Production of 4-phenoxy-6,7-dihydro-9H-pyrimido[4',5':4,5]pyrrolo[2,1-c][1,4]oxazine The compound (130 mg) obtained in Example 21 (ii) was dissolved in N,N-dimethylformamide (2.16 mL), and cesium carbonate (1.05 g) and 1,2-dibromoethane (0.255 mL) were sequentially added. The mixture was stirred at room temperature for 16 hrs. The reaction mixture was diluted with ethyl acetate (30 mL), and washed with water (20 mL). The organic layer was separated, dried over magnesium sulfate and concentrated under reduced pressure. The residue was dissolved in N,N-dimethylformamide (1.08 mL), potassium t-butoxide (90.5 mg) was added, and the mixture was stirred at room temperature for 1 hr. Ethyl acetate (30 mL)/water (20 mL) was added, and the organic layer was dried over magnesium sulfate and concentrated under reduced pressure. The residue was purified by silica gel column chromatography (hexane/ethyl acetate=70/30→0/100) to give the title compound (76 mg).
¹H-NMR (CDCl₃) δ 4.20 (2H, t, J=5 Hz), 4.55 (2H, t, J=5 Hz), 5.06 (2H, s), 6.40 (1H, s), 7.2-7.5 (5H, m), 8.44 (1H, s).

(ii) Production of 3-[2-chloro-4-(6,7-dihydro-9H-pyrimido[4',5':4,5]pyrrolo[2,1-c][1,4]oxazin-4-ylamino)phenoxy]benzonitrile hydrochloride A mixture of 4-phenoxy-6,7-dihydro-9H-pyrimido[4',5':4,5]pyrrolo[2,1-c][1,4]oxazine (69 mg), 3-(4-amino-2-chlorophenoxy)benzonitrile (95 mg), pyridine hydrochloride (75 mg) and 1-methyl-2-pyrrolidone (1 mL) was stirred at 140° C. for 14 hrs. After the completion of the reaction, the mixture was diluted with ethyl acetate and washed with saturated aqueous sodium hydrogen carbonate and saturated brine. The organic layer was dried over magnesium sulfate. After concentration under reduced pressure, the residue was subjected to silica gel column chromatography (hexane/ethyl acetate=50/50→0/100). The obtained fractions were collected and concentrated, and the residue was dissolved in ethyl acetate (2 mL) and treated with 4N hydrochloric acid/ethyl acetate (0.13 mL) to give the title compound (81 mg) as hydrochloride crystals.
¹H-NMR (DMSO-d₆) δ 4.17 (2H, t, J=5 Hz), 4.75 (2H, m), 5.07 (2H, s), 6.55 (1H, s), 7.2-7.7 (6H, m), 7.94 (1H, m), 8.70 (1H, s), 9.91 (1H, br s).

Example 182

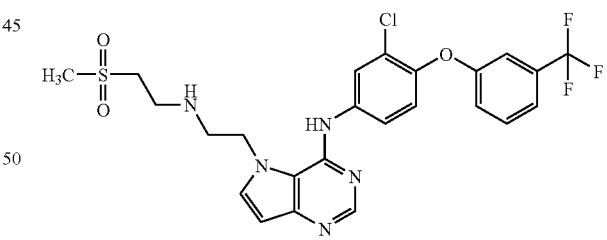

Production of N-{3-chloro-4-[3-(trifluoromethyl)phenoxy]phenyl}-5-(2-{[2-(methylsulfonyl)ethyl]amino}ethyl)-5H-pyrrolo[3,2-d]pyrimidin-4-amine (i) Production of 4-chloro-5-(2,2-diethoxyethyl)-5H-pyrrolo[3,2-d]pyrimidine 4-Chloro-5H-pyrrolo[3,2-d]pyrimidine (1 g) was dissolved in N,N-dimethylformamide (13 mL), cesium carbonate (6.37 g) and 2-bromo-1,1-diethoxyethane (2.94 mL) were sequentially added and the mixture was stirred at 80° C. for 4.5 hrs. The reaction mixture was diluted with ethyl acetate (100 mL), and washed with water (80 mL). The organic layer was separated, dried over magnesium sulfate and evaporated under reduced pressure. The residue was purified by silica gel column chromatography (hexane/ethyl acetate=50/50→0/100) to give the title compound (1.26 g) as a yellow oil.

$^1$H-NMR (CDCl$_3$) δ 1.14 (6H, t, J=6 Hz), 3.40 (2H, m), 3.72 (2H, m), 4.08 (1H, m), 4.56 (2H, d, J=5 Hz), 6.71 (1H, d, J=3 Hz), 7.55 (1H, d, J=3 Hz), 8.69 (1H, s).

(ii) Production of 4-phenoxy-5-(2,2-diethoxyethyl)-5H-pyrrolo[3,2-d]pyrimidine

A mixture of 4-chloro-5-(2,2-diethoxyethyl)-5H-pyrrolo[3,2-d]pyrimidine (1 g), phenol (420 mg), potassium carbonate (617 mg) and 1-methyl-2-pyrrolidone (6.74 mL) was stirred with heating at 140° C. for 6 hrs. The reaction mixture was diluted with ethyl acetate (100 mL), and washed with water (80 mL). The organic layer was separated, dried over magnesium sulfate and evaporated under reduced pressure. The residue was purified by silica gel column chromatography (hexane/ethyl acetate=90/10→40/60) to give the title compound (1.15 g) as a yellow oil.

$^1$H-NMR (CDCl$_3$) δ 1.13 (6H, t, J=7 Hz), 3.40 (2H, m), 3.69 (2H, m), 4.51 (2H, d, J=6 Hz), 4.76 (1H, t, J=6 Hz), 6.65 (1H, d, J=3 Hz), 7.2-7.5 (6H, m), 8.45 (1H, s).

(iii) Production of 2-(4-phenoxy-5H-pyrrolo[3,2-d]pyrimidin-5-yl)ethane-1,1-diol 4-Phenoxy-5-(2,2-diethoxyethyl)-5H-pyrrolo[3,2-d]pyrimidine (1.1 g) was dissolved in dichloromethane (4.53 mL)/trifluoroacetic acid (4.53 mL), and the mixture was stirred at room temperature for 16 hrs. The reaction mixture was concentrated under reduced pressure, and the residue was dissolved in ethyl acetate (100 mL). The mixture was washed with saturated aqueous sodium hydrogen carbonate (80 mL), and the organic layer was dried over magnesium sulfate and concentrated under reduced pressure to give the title compound (826 mg) as a white solid.

$^1$H-NMR (DMSO-d$_6$) δ 4.35 (2H, d, J=6 Hz), 5.17 (1H, t, J=6 Hz), 6.14 (2H, d, J=6 Hz), 6.59 (1H, d, J=3 Hz), 7.2-7.6 (5H, m), 7.75 (1H, d, J=3 Hz), 8.28 (1H, s).

(iv) Production of 2-(methylsulfonyl)-N-[2-(4-phenoxy-5H-pyrrolo[3,2-d]pyrimidin-5-yl)ethyl]ethanamine 2-(4-Phenoxy-5H-pyrrolo[3,2-d]pyrimidin-5-yl)ethane-1,1-diol (500 mg) and 2-(methylsulfonyl)ethylamine (341 mg) were dissolved in N,N-dimethylformamide (29 mL)/acetic acid (2.9 mL), and the mixture was stirred at room temperature for 1.5 hrs. Sodium triacetoxyborohydride (579 mg) was added, and the mixture was stirred at room temperature for 16 hrs. The reaction mixture was concentrated under reduced pressure, and the residue was purified by silica gel column chromatography (ethyl acetate/methanol=100/0→70/30) to give the title compound (508 mg) as a candy-like substance.

$^1$H-NMR (CDCl$_3$) δ 2.84 (3H, s), 3.0-3.2 (6H, m), 4.54 (2H, t, J=6 Hz), 6.66 (1H, d, J=3 Hz), 7.2-7.5 (6H, m), 8.45 (1H, s).

(v) Production of N-{3-chloro-4-[3-(trifluoromethyl)phenoxy]phenyl}-5-(2-{[2-(methylsulfonyl)ethyl]amino}ethyl)-5H-pyrrolo[3,2-d]pyrimidin-4-amine 2-(Methylsulfonyl)-N-[2-(4-phenoxy-5H-pyrrolo[3,2-d]pyrimidin-5-yl)ethyl]ethanamine (500 mg) was dissolved in tetrahydrofuran (5 mL), and di-tert-butyl dicarbonate (0.478 mL) and triethylamine (0.29 mL) were added, and the mixture was stirred at room temperature for 3 hrs. The reaction mixture was concentrated under reduced pressure, and the residue was purified by silica gel column chromatography (hexane/ethyl acetate=80/20→0/100). A mixture of a portion (243 mg) taken from the obtained residue (491 mg), 3-chloro-4-[3-(trifluoromethyl)phenoxy]aniline (228 mg), pyridine hydrochloride (183 mg) and phenol (406 mg) was stirred at 140° C. for 14 hrs. After the completion of the reaction, the mixture was diluted with dichloromethane (50 mL) and washed with saturated aqueous sodium hydrogen carbonate (30 mL). The organic layer was dried over magnesium sulfate. After concentration under reduced pressure, the residue was subjected to silica gel column chromatography (ethyl acetate/methanol=100/0→70/30) and crystallized from diisopropyl ether to give the title compound (123 mg).

$^1$H-NMR (DMSO-d$_6$) δ 2.88 (3H, s), 2.89 (2H, m), 2.99 (2H, m), 3.16 (2H, t, J=6 Hz), 4.50 (2H, m), 6.51 (1H, d, J=3 Hz), 7.22 (2H, m), 7.31 (1H, d, J=9 Hz), 7.46 (1H, d, J=8 Hz), 7.5-7.7 (3H, m), 8.04 (1H, d, J=2 Hz), 8.35 (1H, s).

Example 183

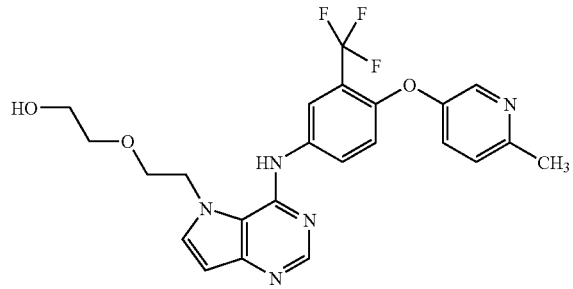

Production of 2-[2-(4-{[4-[(6-methylpyridin-3-yl)oxy]-3-(trifluoromethyl)phenyl]amino}-5H-pyrrolo[3,2-d]pyrimidin-5-yl)ethoxy]ethanol A mixture of 2-[2-(4-chloro-5H-pyrrolo[3,2-d]pyrimidin-5-yl)ethoxy]ethyl benzoate (150 mg), 4-[(6-methylpyridin-3-yl)oxy]-3-(trifluoromethyl)aniline (175 mg) and 1-methyl-2-pyrrolidone (0.863 mL) was stirred with heating at 140° C. for 2.5 hrs. The reaction mixture was diluted with ethyl acetate (80 mL) and washed with aqueous sodium hydrogen carbonate (30 mL). The organic layer was separated, dried over magnesium sulfate and evaporated under reduced pressure. The residue was purified by silica gel column chromatography (ethyl acetate/methanol=100/0→90/10). The object fraction was concentrated under reduced pressure. The obtained residue was dissolved in methanol (1.9 mL), 1N sodium hydroxide (0.433 mL) was added, and the mixture was stirred at room temperature for 1.5 hrs. 1N hydrochloric acid (0.433 mL) was added, and the mixture was diluted with ethyl acetate (80 mL) and washed with saturated brine (30 mL). The organic layer was dried over magnesium sulfate. After concentration under reduced pressure, the residue was subjected to silica gel column chromatography (ethyl acetate/methanol=100/0→90/10) and crystallized from diisopropyl ether to give the title compound (118 mg).

$^1$H-NMR (DMSO-d$_6$) δ 2.46 (3H, s), 3.47 (4H, br s), 3.82 (2H, m), 4.66 (3H, m), 6.51 (1H, d, J=3 Hz), 7.10 (1H, d, J=9

Hz), 7.31 (2H, m), 7.68 (1H, d, J=3 Hz), 7.90 (1H, dd, J=3 Hz, 9 Hz), 8.10 (1H, d, J=3 Hz), 8.24 (1H, d, J=3 Hz), 8.30 (1H, s), 8.99 (1H, br s).

Example 184

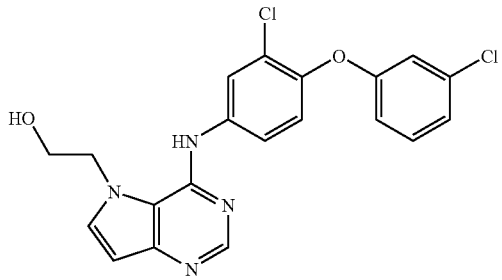

Production of 2-(4-{[3-chloro-4-(3-chlorophenoxy)phenyl]amino}-5H-pyrrolo[3,2-d]pyrimidin-5-yl)ethanol The title compound (81 mg) was obtained as colorless crystals by the reaction in the same manner as in Example 183 using 2-(4-chloro-5H-pyrrolo[3,2-d]pyrimidin-5-yl)ethyl benzoate (100 mg), 3-chloro-4-(3-chlorophenoxy)aniline (126 mg) and 1-methyl-2-pyrrolidone (0.66 mL).

$^1$H-NMR (DMSO-d$_6$) δ 3.87 (2H, m), 4.53 (2H, t, J=4.5 Hz), 6.31 (1H, br s), 6.51 (1H, d, J=3 Hz), 6.88 (1H, d, J=9 Hz), 6.95 (1H, s), 7.15 (1H, d, J=9 Hz), 7.28 (1H, d, J=9 Hz), 7.38 (1H, t, J=9 Hz), 7.60 (1H, dd, J=2 Hz, 9 Hz), 7.66 (1H, d, J=3 Hz), 7.97 (1H, d, J=2 Hz), 8.34 (1H, s), 9.89 (1H, br s).

Example 185

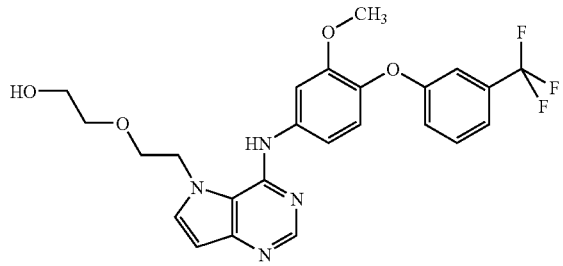

Production of 2-{2-[4-({3-methoxy-4-[3-(trifluoromethyl)phenoxy]phenyl}amino)-5H-pyrrolo[3,2-d]pyrimidin-5-yl]ethoxy}ethanol The title compound (80 mg) was obtained as colorless crystals by the reaction in the same manner as in Example 183 using 2-[2-(4-chloro-5H-pyrrolo[3,2-d]pyrimidin-5-yl)ethoxy]ethyl benzoate (150 mg), 3-methoxy-4-[3-(trifluoromethyl)phenoxy]aniline (185 mg) and 1-methyl-2-pyrrolidone (0.863 mL).

$^1$H-NMR (DMSO-d$_6$) δ 3.52 (4H, m), 3.74 (3H, s), 3.85 (2H, t, J=5 Hz), 4.65 (2H, t, J=5 Hz), 4.76 (1H, t, J=5 Hz), 6.51 (1H, d, J=3 Hz), 7.13 (3H, m), 7.35 (2H, m), 7.49 (1H, d, J=2 Hz), 7.55 (1H, t, J=8 Hz), 7.68 (1H, d, J=3 Hz), 8.32 (1H, s), 8.90 (1H, br s).

Example 186

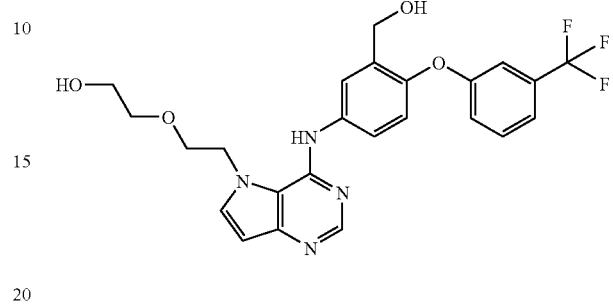

Production of 2-{2-[4-({3-(hydroxymethyl)-4-[3-(trifluoromethyl)phenoxy]phenyl}amino)-5H-pyrrolo[3,2-d]pyrimidin-5-yl]ethoxy}ethanol The title compound (175 mg) was obtained as colorless crystals by the reaction in the same manner as in Example 183 using 2-[2-(4-chloro-5H-pyrrolo[3,2-d]pyrimidin-5-yl)ethoxy]ethyl benzoate (150 mg), {5-amino-2-[3-(trifluoromethyl)phenoxy]phenyl}methanol (184 mg) and 1-methyl-2-pyrrolidone (0.863 mL).

$^1$H-NMR (DMSO-d$_6$) δ 3.52 (4H, m), 3.74 (3H, s), 3.85 (2H, t, J=5 Hz), 4.65 (2H, t, J=5 Hz), 4.76 (1H, t, J=5 Hz), 6.51 (1H, d, J=3 Hz), 7.13 (3H, m), 7.35 (2H, m), 7.49 (1H, d, J=2 Hz), 7.55 (1H, t, J=8 Hz), 7.68 (1H, d, J=3 Hz), 8.32 (1H, s), 8.90 (1H, br s).

Example 187

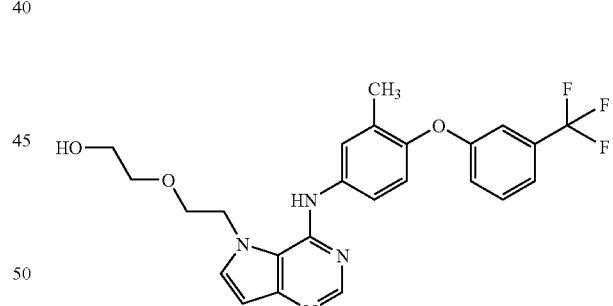

Production of 2-{2-[4-({3-methyl-4-[3-(trifluoromethyl)phenoxy]phenyl}amino)-5H-pyrrolo[3,2-d]pyrimidin-5-yl]ethoxy}ethanol The title compound (98 mg) was obtained as colorless crystals by the reaction in the same manner as in Example 183 using 2-[2-(4-chloro-5H-pyrrolo[3,2-d]pyrimidin-5-yl)ethoxy]ethyl benzoate (150 mg), 3-methyl-4-[3-(trifluoromethyl)phenoxy]aniline (174 mg) and 1-methyl-2-pyrrolidone (0.863 mL).

$^1$H-NMR (DMSO-d$_6$) δ 2.13 (3H, s), 3.51 (4H, m), 3.84 (2H, t, J=4.5 Hz), 4.63 (2H, t, J=4.5 Hz), 4.74 (1H, t, J=4.5

Hz), 6.49 (1H, d, J=3 Hz), 7.04 (1H, d, J=9 Hz), 7.16 (2H, m), 7.41 (1H, d, J=8 Hz), 7.5-7.7 (4H, m), 8.29 (1H, s), 8.83 (1H, br s).

Example 188

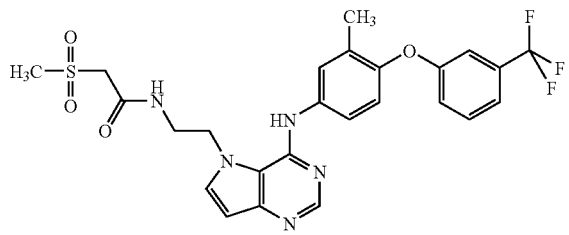

Production of 2-(methylsulfonyl)-N-{2-[4-({3-methyl-4-[3-(trifluoromethyl)phenoxy]phenyl}amino)-5H-pyrrolo[3,2-d]pyrimidin-5-yl]ethyl}acetamide (i) Production of tert-butyl {2-[4-({3-methyl-4-[3-(trifluoromethyl)phenoxy]phenyl}amino)-5H-pyrrolo[3,2-d]pyrimidin-5-yl]ethyl}carbamate A mixture of tert-butyl [2-(4-chloro-5H-pyrrolo[3,2-d]pyrimidin-5-yl)ethyl]carbamate (297 mg), 3-methyl-4-[3-(trifluoromethyl)phenoxy]aniline (401 mg) and isopropyl alcohol (2.97 mL) was stirred at 80° C. for 16 hrs. The reaction mixture was diluted with ethyl acetate (80 mL), and washed with aqueous sodium hydrogen carbonate (30 mL). The organic layer was separated, dried over magnesium sulfate and evaporated under reduced pressure. The residue was purified by silica gel column chromatography (hexane/ethyl acetate=90/10→0/100) to give the title compound (528 mg) as a white powder.
¹H-NMR (CDCl₃) δ 1.47 (9H, s), 2.21 (3H, s), 3.50 (2H, m), 4.46 (2H, m), 5.11 (1H, m), 6.58 (1H, d, J=3 Hz), 6.97 (1H, d, J=9 Hz), 7.0-7.2 (3H, m), 7.27 (1H, m), 7.39 (1H, t, J=8 Hz), 7.69 (2H, m), 8.45 (1H, br s), 8.50 (1H, s).

(ii) Production of 5-(2-aminoethyl)-N-{3-methyl-4-[3-(trifluoromethyl)phenoxy]phenyl}-5H-pyrrolo[3,2-d]pyrimidin-4-amine tert-Butyl {2-[4-({3-methyl-4-[3-(trifluoromethyl)phenoxy]phenyl}amino)-5H-pyrrolo[3,2-d]pyrimidin-5-yl]ethyl}carbamate (494 mg) was dissolved in dichloromethane (6.4 mL), trifluoroacetic acid (4.8 mL) was added, and the mixture was stirred at room temperature for 1 hr. The reaction mixture was concentrated under reduced pressure, and the residue was diluted with ethyl acetate (50 mL), and washed with aqueous sodium hydrogen carbonate (30 mL). The organic layer was separated, dried over magnesium sulfate and concentrated under reduced pressure to give the title compound (442 mg) as a powder.
¹H-NMR (CDCl₃) δ 2.20 (3H, s), 3.30 (2H, t, J=5 Hz), 4.46 (2H, t, J=5 Hz), 6.61 (1H, d, J=3 Hz), 6.95 (1H, d, J=9 Hz), 7.0-7.5 (6H, m), 7.51 (1H, d, J=3 Hz), 8.50 (1H, s).

(iii) Production of 2-(methylsulfonyl)-N-{2-[4-({3-methyl-4-[3-(trifluoromethyl)phenoxy]phenyl}amino)-5H-pyrrolo[3,2-d]pyrimidin-5-yl]ethyl}acetamide The title compound (89 mg) was obtained as colorless powder crystals by the reaction in the same manner as in Example 155 (iv) using 5-(2-aminoethyl)-N-{3-methyl-4-[3-(trifluoromethyl)phenoxy]phenyl}-5H-pyrrolo[3,2-d]pyrimidin-4-amine (196 mg), 2-(methylsulfonyl)acetic acid (64 mg), 1-ethyl-3-(3-dimethylaminopropyl)carbodiimide hydrochloride (133 mg), 1-hydroxybenzotriazole monohydrate (94 mg), triethylamine (0.319 mL) and N,N-dimethylformamide (5.0 mL).
¹H-NMR (DMSO-d₆) δ 2.14 (3H, s), 3.09 (3H, s), 3.45 (2H, m), 4.05 (2H, s), 4.56 (2H, t, J=7 Hz), 6.47 (1H, d, J=3 Hz), 7.04 (1H, d, J=9 Hz), 7.17 (2H, m), 7.47 (1H, m), 7.59 (4H, m), 8.29 (1H, s), 8.55 (1H, br s), 8.67 (1H, t, J=5.5 Hz).

Example 189

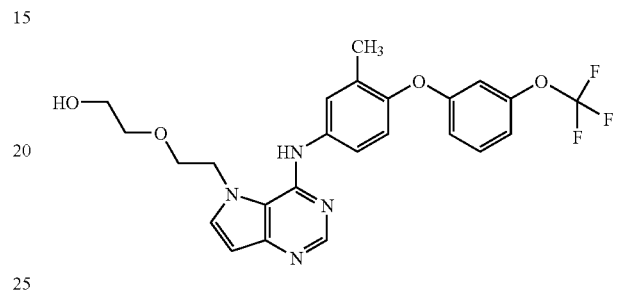

Production of 2-{2-[4-({3-methyl-4-[3-(trifluoromethoxy)phenoxy]phenyl}amino)-5H-pyrrolo[3,2-d]pyrimidin-5-yl]ethoxy}ethanol The title compound (128 mg) was obtained as colorless crystals by the reaction in the same manner as in Example 183 using 2-[2-(4-chloro-5H-pyrrolo[3,2-d]pyrimidin-5-yl)ethoxy]ethyl benzoate (150 mg), 3-methyl-4-[3-(trifluoromethoxy)phenoxy]aniline (184 mg) and 1-methyl-2-pyrrolidone (0.863 mL).
¹H-NMR (DMSO-d₆) δ 2.12 (3H, s), 3.51 (4H, m), 3.84 (2H, t, J=5 Hz), 4.63 (2H, t, J=5 Hz), 4.73 (1H, t, J=5 Hz), 6.49 (1H, d, J=3 Hz), 6.87 (2H, m), 7.04 (2H, m), 7.47 (1H, t, J=8 Hz), 7.59 (2H, m), 7.66 (1H, d, J=3 Hz), 8.29 (1H, s), 8.82 (1H, br s).

Example 190

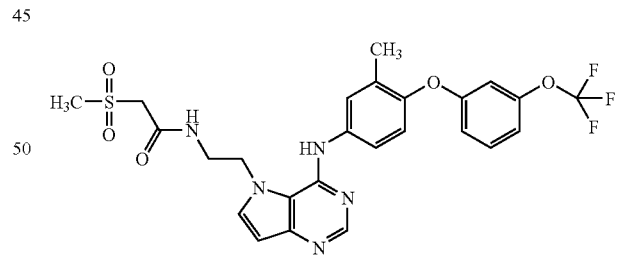

Production of 2-(methylsulfonyl)-N-{2-[4-({3-methyl-4-[3-(trifluoromethoxy)phenoxy] phenyl}amino)-5H-pyrrolo[3,2-d]pyrimidin-5-yl] ethyl}acetamide (i) Production of tert-butyl {2-[4-({3-methyl-4-[3-(trifluoromethoxy)phenoxy]phenyl}amino)-5H-pyrrolo[3,2-d]pyrimidin-5-yl]ethyl}carbamate tert-Butyl [2-(4-chloro-5H-pyrrolo[3,2-d]pyrimidin-5-yl) ethyl]carbamate (297 mg) and 3-methyl-4-[3-(trifluoromethoxy)phenoxy]aniline (425 mg) were dissolved in isopropyl alcohol (2.97 mL), and the mixture was stirred at 80° C. for 16 hrs. After cooling to room temperature, the mixture was diluted with ethyl acetate (60 mL), and washed with aqueous sodium hydrogen carbonate (30 mL). The organic layer was dried over magnesium sulfate and concentrated under reduced pressure. The residue was subjected to silica gel column chromatography (eluent, hexane:ethyl acetate=80:20→0:100) to give the title compound (563 mg) as a white powder.

$^1$H-NMR (CDCl$_3$) δ 1.47 (9H, s), 2.20 (3H, s), 3.49 (2H, m), 4.46 (2H, m), 5.08 (1H, m), 6.59 (1H, d, J=3 Hz), 6.78 (1H, m), 6.86 (2H, m), 6.97 (1H, m), 7.16 (1H, d, J=3 Hz), 7.27 (2H, m), 7.69 (2H, m), 8.43 (1H, br s), 8.50 (1H, s).

(ii) Production of 5-(2-aminoethyl)-N-{3-methyl-4-[3-(trifluoromethoxy)phenoxy]phenyl}-5H-pyrrolo[3,2-d]pyrimidin-4-amine tert-Butyl {2-[4-({3-methyl-4-[3-(trifluoromethoxy)phenoxy]phenyl}amino)-5H-pyrrolo[3,2-d]pyrimidin-5-yl]ethyl}carbamate (523 mg) was dissolved in dichloromethane (6.4 mL), trifluoroacetic acid (4.8 mL) was added, and the mixture was stirred at room temperature for 2 hrs. The reaction mixture was concentrated under reduced pressure, and the residue was diluted with ethyl acetate (50 mL), and washed with aqueous sodium hydrogen carbonate (40 mL). The organic layer was separated, dried over magnesium sulfate and concentrated under reduced pressure to give the title compound (420 mg) as a white powder.

$^1$H-NMR (CDCl$_3$) δ 2.20 (3H, s), 3.30 (2H, t, J=4.5 Hz), 4.46 (2H, t, J=4.5 Hz), 6.62 (1H, d, J=3 Hz), 6.85 (3H, m), 6.96 (1H, d, J=9 Hz), 7.19 (1H, d, J=3 Hz), 7.27 (1H, m), 7.44 (1H, dd, J=2 Hz, 9 Hz), 7.50 (1H, d, J=3 Hz), 8.50 (1H, s).

(iii) Production of 2-(methylsulfonyl)-N-{2-[4-({3-methyl-4-[3-(trifluoromethoxy)phenoxy]phenyl}amino)-5H-pyrrolo[3,2-d]pyrimidin-5-yl]ethyl}acetamide A solution of 5-(2-aminoethyl)-N-{3-methyl-4-[3-(trifluoromethoxy)phenoxy]phenyl}-5H-pyrrolo[3,2-d]pyrimidin-4-amine (174 mg), 2-(methylsulfonyl)acetic acid (54 mg), 1-ethyl-3-(3-dimethylaminopropyl)carbodiimide hydrochloride (112 mg), 1-hydroxybenzotriazole monohydrate (79 mg) and triethylamine (0.273 mL) in N,N-dimethylformamide (7.69 mL) was stirred at room temperature for 16 hrs. The reaction mixture was diluted with ethyl acetate (80 mL), and washed with water (60 mL). The organic layer was dried over magnesium sulfate and concentrated under reduced pressure. The residue was subjected to silica gel column chromatography (eluent, ethyl acetate:methanol=100:0→92:8), and crystallized from diisopropyl ether to give the title compound (92 mg) as colorless crystals.

$^1$H-NMR (DMSO-d$_6$) δ 2.14 (3H, s), 3.10 (3H, s), 3.46 (2H, q, J=6 Hz), 4.06 (2H, s), 4.56 (2H, t, J=6 Hz), 6.48 (1H, d, J=3 Hz), 6.89 (2H, m), 7.06 (2H, m), 7.48 (1H, t, J=8 Hz), 7.59 (3H, m), 8.30 (1H, s), 8.55 (1H, br s), 8.67 (1H, t, J=6 Hz).

melting point: 106-108° C.

Example 191

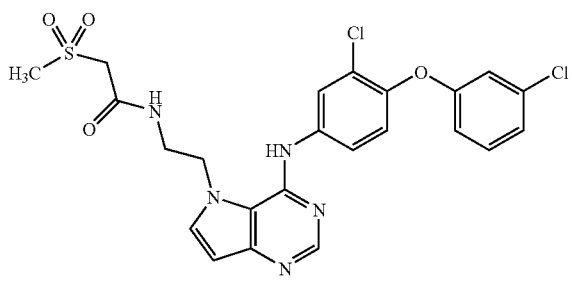

Production of N-[2-(4-{[3-chloro-4-(3-chlorophenoxy)phenyl]amino}-5H-pyrrolo[3,2-d]pyrimidin-5-yl)ethyl]-2-(methylsulfonyl)acetamide (i) Production of tert-butyl 2-(4-{[3-chloro-4-(3-chlorophenoxy)phenyl)amino)-5H-pyrrolo[3,2-d]pyrimidin-5-yl]ethylcarbamate A mixture of tert-butyl 2-(4-chloro-5H-pyrrolo[3,2-d]pyrimidin-5-yl)ethylcarbamate (1.19 g), 3-chloro-4-(3-chlorophenoxy)aniline (1.22 g) and isopropyl alcohol (12.0 mL) was stirred at 80° C. for 15 hrs. Under ice-cooling, aqueous sodium hydrogen carbonate was added, and the mixture was extracted with ethyl acetate. The organic layer was washed with brine, and dried over anhydrous magnesium sulfate. The solvent was concentrated under reduced pressure, and the residue was purified by silica gel chromatography (eluent: hexane/ethyl acetate=50/50→100/0), and washed with diisopropyl ether-hexane to give the title compound (1.69 g) as crystals.

$^1$H-NMR (CDCl$_3$) δ: 1.50 (9H, s), 3.4-3.6 (2H, m), 4.4-4.6 (2H, m), 5.0-5.1 (1H, m), 6.61 (1H, d, J=2.6 Hz), 6.85-7.05 (2H, m), 7.07 (2H, d, J=8.8 Hz), 7.18 (1H, d, J=2.6 Hz), 7.2-7.3 (1H, m), 7.85-7.95 (1H, m), 8.0-8.05 (1H, m), 8.52 (1H, s), 8.62 (1H, br s).

(ii) Production of 5-(2-aminoethyl)-N-[3-chloro-4-(3-chlorophenoxy)phenyl]-5H-pyrrolo[3,2-d]pyrimidin-4-amine dihydrochloride To a solution of tert-butyl 2-(4-{[3-chloro-4-(3-chlorophenoxy)phenyl]amino}-5H-pyrrolo[3,2-d]pyrimidin-5-yl)ethylcarbamate (1.69 g) in tetrahydrofuran (32 mL) was added 2N hydrochloric acid (16 mL). The reaction mixture was stirred at 65° C. for 18 hrs and concentrated. Ethanol was added, and the mixture was concentrated again. Ethyl acetate and diisopropyl ether were added to the residue, and the precipitate was collected by filtration and washed with diisopropyl ether to give the title compound (1.50 g) as crystals.

$^1$H-NMR (DMSO-d$_6$+CDCl$_3$) δ: 3.3-3.6 (4H, m), 5.0-5.15 (2H, m), 6.71 (1H, d, J=3.2 Hz), 6.9-7.0 (2H, m), 7.1-7.2 (1H, m), 7.22 (1H, d, J=8.8 Hz), 7.3-7.45 (1H, m), 7.6-7.7 (1H, m), 7.87 (1H, d, J=2.6 Hz), 8.05 (1H, d, J=2.4 Hz), 8.2-8.4 (2H, m), 8.71 (1H, s).

(iii) Production of N-[2-(4-{[3-chloro-4-(3-chlorophenoxy)phenyl]amino}-5H-pyrrolo[3,2-d]pyrimidin-5-yl)ethyl]-2-(methylsulfonyl)acetamide To a solution of 5-(2-aminoethyl)-N-[3-chloro-4-(3-chlorophenoxy)phenyl]-5H-pyrrolo[3,2-d]pyrimidin-4-amine dihydrochloride (200 mg), 2-(methylsulfonyl)acetic acid (113 mg) and 1-hydroxybenzotriazole (122 mg) in N,N-dimethylformamide (5.0 mL) were added a solution of triethylamine (419 mg) in N,N-dimethylformamide (1.25 mL) and 1-ethyl-3-(3-dimethylaminopropyl)carbodiimide hydrochloride (173 mg) under ice-cooling. After stirring the reaction mixture at room temperature for 16 hrs, water was added under ice-cooling, and the mixture was extracted twice with ethyl acetate. The organic layers were collected, dried over anhydrous magnesium sulfate and concentrated. The residue was purified by silica gel column chromatography (eluent: ethyl acetate/methanol=100/0→80/20), and recrystallized from ethanol-ethyl acetate-diisopropyl ether to give the title compound (151 mg) as crystals.

$^1$H-NMR (CDCl$_3$) δ: 3.13 (3H, s), 3.6-3.8 (2H, m), 3.99 (2H, s), 4.4-4.6 (2H, m), 6.62 (1H, d, J=3.4 Hz), 6.85-6.95 (2H, m), 7.0-7.1 (2H, m), 7.2-7.3 (2H, m), 7.7-7.8 (1H, m), 7.95-8.0 (1H, m), 8.19 (1H, s), 8.52 (1H, s).

melting point: 206-207° C.

Example 192

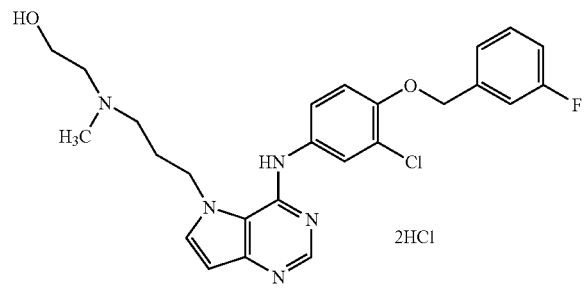

Production of 2-[{3-[4-({3-chloro-4-[(3-fluorobenzyl)oxy]phenyl}amino)-5H-pyrrolo[3,2-d]pyrimidin-5-yl]propyl}(methyl)amino]ethanol dihydrochloride (i) Production of 4-chloro-5-(3-chloropropyl)-5H-pyrrolo[3,2-d]pyrimidine To a solution of 4-chloro-5H-pyrrolo[3,2-d]pyrimidine (1.54 g) in N,N-dimethylformamide (20 mL) was added cesium carbonate (4.89 g) under ice-cooling, and the mixture was stirred under ice-cooling for 20 min. 1-Bromo-3-chloropropane (1.89 g) was added and the mixture was stirred under ice-cooling for 1 hr and at room temperature for 32 hrs. The reaction mixture was poured into water (40 mL), and the mixture was extracted with ethyl acetate (60 mL×2). The organic layers were combined, dried over anhydrous magnesium sulfate and concentrated under reduced pressure. The residue was purified by silica gel column chromatography (eluent, hexane:ethyl acetate=80:20→50:50) to give the title compound (1.87 g).

$^1$H-NMR (CDCl$_3$) δ: 2.35 (2H, m), 3.49 (2H, t, J=6.0 Hz), 4.69 (2H, t, J=6.6 Hz), 6.73 (1H, d, J=3.0 Hz), 7.56 (1H, d, J=3.0 Hz), 8.70 (1H, s).

(ii) Production of N-{3-chloro-4-[(3-fluorobenzyl)oxy]phenyl}-5-(3-chloropropyl)-5H-pyrrolo[3,2-d]pyrimidin-4-amine A mixture of 4-chloro-5-(3-chloropropyl)-5H-pyrrolo[3,2-d]pyrimidine (839 mg), 3-chloro-4-[(3-fluorobenzyl)oxy]aniline (1.10 g) and isopropyl alcohol (5 mL) was stirred at 80° C. for 1.5 hrs. The mixture was concentrated under reduced pressure, saturated aqueous sodium hydrogen carbonate (30 mL) was added to the residue, and the mixture was extracted with ethyl acetate (30 mL×3). The organic layers were combined, dried over anhydrous magnesium sulfate and concentrated under reduced pressure. The residue was purified by silica gel column chromatography (eluent, hexane:ethyl acetate=90:10→20:80) to give the title compound (1.19 g).

$^1$H-NMR (CDCl$_3$) δ: 2.36 (2H, m), 3.56 (2H, t, J=5.7 Hz), 4.47 (2H, t, J=6.9 Hz), 5.14 (2H, s), 6.60 (1H, d, J=3.3 Hz), 6.73 (1H, br s), 6.94 (1H, d, J=8.7 Hz), 7.02 (1H, m), 7.19-7.40 (5H, m), 7.65 (1H, d, J=3.3 Hz), 8.49 (1H, s).

(iii) Production of 2-[{3-[4-({3-chloro-4-[(3-fluorobenzyl)oxy]phenyl}amino)-5H-pyrrolo[3,2-d]pyrimidin-5-yl]propyl}(methyl)amino]ethanol dihydrochloride A mixture of N-{3-chloro-4-[(3-fluorobenzyl)oxy]phenyl}-5-(3-chloropropyl)-5H-pyrrolo[3,2-d]pyrimidin-4-amine (634 mg), 2-methylaminoethanol (534 mg) and N,N-dimethylformamide (5 mL) was stirred at room temperature for 64 hrs. After concentration under reduced pressure, saturated aqueous sodium hydrogen carbonate (10 mL) was added to the residue, and the mixture was extracted with ethyl acetate (55 mL×2). The organic layer was dried over anhydrous magnesium sulfate and concentrated under reduced pressure. The residue was purified by basic silica gel column chromatography (eluent, hexane:ethyl acetate=80:20→0:100). 4N Hydrogen chloride-ethyl acetate solution (10 mL) was added to the obtained amorphous solid and, after concentration under reduced pressure, the residue was recrystallized from ethanol-ethyl acetate to give the title compound (523 mg).

$^1$H-NMR (DMSO-d$_6$) δ: 2.16-2.32 (2H, m), 2.74 (3H, s), 2.94-3.40 (4H, m), 3.62-3.80 (2H, m), 4.74-4.84 (2H, m), 5.31 (2H, s), 6.69 (1H, m), 7.20 (1H, m), 7.29-7.36 (5H, m), 7.43-7.50 (2H, m), 7.71 (1H, m), 8.03 (1H, br s), 8.64 (1H, s), 9.84 (1H, br s), 10.12 (1H, br s).

Example 193

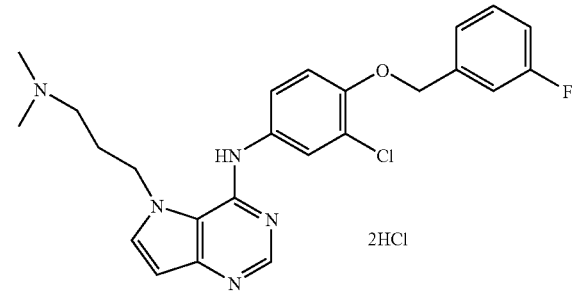

Production of N-{3-chloro-4-[(3-fluorobenzyl)oxy]phenyl}-5-[3-(dimethylamino)propyl]-5H-pyrrolo[3,2-d]pyrimidin-4-amine dihydrochloride N-{3-Chloro-4-[(3-fluorobenzyl)oxy]phenyl}-5-(3-chloropropyl)-5H-pyrrolo[3,2-d]pyrimidin-4-amine (560 mg) was dissolved in 2.0 M dimethylamine-tetrahydrofuran solution (5 mL), and the mixture was stirred at room temperature for 26 hrs. A 2.0 M dimethylamine-tetrahydrofuran solution (5 mL) was further added and the mixture was stirred at room temperature for 20 hrs. A 2.0 M dimethylamine-tetrahydrofuran solution (10 mL) was further added, and the mixture was stirred at room temperature for 24 hrs. After concentration of the reaction mixture under reduced pressure, saturated aqueous sodium hydrogen carbonate (20 mL) was added to the residue, and the mixture was extracted with ethyl acetate (35 mL×2). The organic layer was dried over anhydrous magnesium sulfate and concentrated under reduced pressure. The residue was purified by basic silica gel column chromatography (eluent, hexane:ethyl acetate=90:10→20:80), and 4N hydrogen chloride-ethyl acetate solution (10 mL) was added to the obtained amorphous solid. After concentration under reduced pressure, the residue was recrystallized from ethanol-ethyl acetate to give the title compound (428 mg).

$^1$H-NMR (DMSO-$d_6$) δ: 2.18-2.26 (2H, m), 2.70 (6H, s), 2.94-3.04 (2H, m), 4.77-4.84 (2H, m), 5.30 (2H, s), 6.67 (1H, m), 7.19 (1H, m), 7.28-7.34 (4H, m), 7.43-7.51 (2H, m), 7.71 (1H, m), 8.04 (1H, m), 8.63 (1H, s), 9.87 (1H, br s), 10.74 (1H, br s).

Example 194

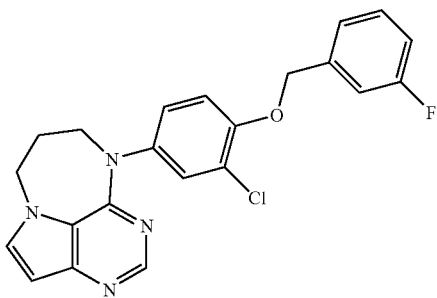

Production of 6-{3-chloro-4-[(3-fluorobenzyl)oxy]phenyl}-6,7,8,9-tetrahydro-3,5,6,9a-tetraazabenzo[cd]azulene A mixture of N-{3-chloro-4-[(3-fluorobenzyl)oxy]phenyl}-5-(3-chloropropyl)-5H-pyrrolo[3,2-d]pyrimidin-4-amine (839 mg), 3-chloro-4-[(3-fluorobenzyl)oxy]aniline (1.10 g) and 1-methyl-2-pyrrolidone (5 mL) was stirred at 140° C. for 1 hr. The reaction mixture was poured into water (10 mL) and adjusted to pH 8 with saturated aqueous sodium hydrogen carbonate. The mixture was extracted with ethyl acetate (40 mL×3), and the organic layers were combined and dried over anhydrous magnesium sulfate. After concentration under reduced pressure, the residue was subjected to silica gel column chromatography (eluent, hexane:ethyl acetate=60:40→50:50) and further subjected to basic silica gel column chromatography (eluent, hexane:ethyl acetate=80:20→0:100). The object fraction was concentrated under reduced pressure. Chloroform-diisopropyl ether was added to the residue, and the solid was collected by filtration and dried. Recrystallization from ethyl acetate gave the title compound (74.5 mg).

$^1$H-NMR (DMSO-$d_6$) δ: 2.31 (2H, m), 3.88 (2H, m), 4.31 (2H, m), 5.27 (2H, s), 6.47 (1H, d, J=3.0 Hz), 7.14-7.36 (5H, m), 7.42 (1H, d, J=2.4 Hz), 7.47 (1H, m), 7.65 (1H, d, J=3.0 Hz), 8.02 (1H, s).

Example 195

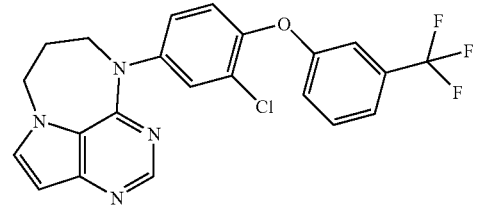

Production of 6-{3-chloro-4-[3-(trifluoromethyl)phenoxy]phenyl}-6,7,8,9-tetrahydro-3,5,6,9a-tetraazabenzo[cd]azulene (i) Production of 5-(3-chloropropyl)-N-{3-chloro-4-[3-(trifluoromethyl)phenoxy]phenyl}-5H-pyrrolo[3,2-d]pyrimidin-4-amine A mixture of 4-chloro-5-(3-chloropropyl)-5H-pyrrolo[3,2-d]pyrimidine (789 mg), 3-chloro-4-[3-(trifluoromethyl)phenoxy]aniline (1.09 g) and isopropyl alcohol (5 mL) was stirred at 80° C. for 4.5 hrs. The mixture was concentrated under reduced pressure, saturated aqueous sodium hydrogen carbonate (30 mL) was added to the residue, and the mixture was extracted with ethyl acetate (40 mL×3). The organic layers were combined, dried over anhydrous magnesium sulfate and concentrated under reduced pressure. The residue was purified by silica gel column chromatography (eluent, hexane:ethyl acetate=90:10→20:80) to give the title compound (1.46 g).

$^1$H-NMR (CDCl$_3$) δ: 2.39 (2H, m), 3.60 (2H, t, J=5.6 Hz), 4.53 (2H, t, J=6.9 Hz), 6.62 (1H, d, J=3.3 Hz), 6.96 (1H, br s), 7.07 (1H, d, J=8.7 Hz), 7.08-7.49 (6H, m), 7.87 (1H, m), 8.55 (1H, s).

(ii) Production of 6-{3-chloro-4-[3-(trifluoromethyl)phenoxy]phenyl}-6,7,8,9-tetrahydro-3,5,6,9a-tetraazabenzo[cd]azulene A mixture of 5-(3-chloropropyl)-N-{3-chloro-4-[3-(trifluoromethyl)phenoxy]phenyl}-5H-pyrrolo[3,2-d]pyrimidin-4-amine (470 mg), potassium carbonate (270 mg) and ethylene glycol (10 mL) was stirred at room temperature for 18.5 hrs, and at 60° C. for 4 hrs. The reaction mixture was poured into aqueous sodium hydrogen carbonate (20 mL), and the mixture was extracted with ethyl acetate (50 mL×2). The organic layers were combined, dried over anhydrous magnesium sulfate and concentrated under reduced pressure. The residue was purified by silica gel column chromatography (eluent, hexane:ethyl acetate=90:10→0:100), and the obtained solid was recrystallized from ethanol-water to give the title compound (116 mg).

$^1$H-NMR (DMSO-$d_6$) δ: 2.45 (2H, m), 3.99 (2H, t, J=4.8 Hz), 4.34 (2H, t, J=5.4 Hz), 6.65 (1H, d, J=3.0 Hz), 7.06 (1H, d, J=9.0 Hz), 7.16-7.22 (2H, m), 7.28 (1H, m), 7.33 (1H, d, J=3.0 Hz), 7.37 (1H, m), 7.42 (1H, d, J=2.4 Hz), 7.46 (1H, m), 8.36 (1H, s).

Example 196

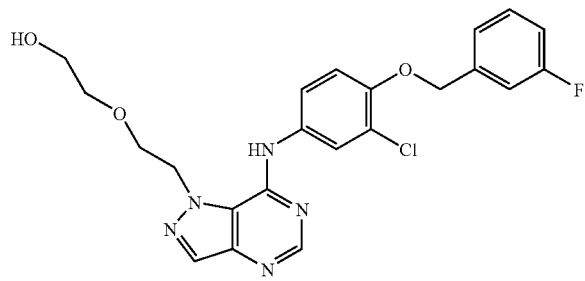

Production of 2-{2-[7-({3-chloro-4-[(3-fluorobenzyl)oxy]phenyl}amino)-1H-pyrazolo[4,3-d]pyrimidin-1-yl]ethoxy}ethanol (i) Production of 2-{2-[7-(methylthio)-1H-pyrazolo[4,3-d]pyrimidin-1-yl]ethoxy}ethyl benzoate A mixture of 7-(methylthio)-1H-pyrazolo[4,3-d]pyrimidine (747 mg), 2-{2-[(methylsulfonyl)oxy]ethoxy}ethyl benzoate (1.43 g), potassium carbonate (931 mg) and N,N-dimethylformamide (12 mL) was stirred at 60° C. for 4 hrs. The reaction mixture was poured into water (30 mL), and the mixture was extracted with ethyl acetate (50 mL×2). The organic layers were combined, washed with saturated brine and dried over anhydrous magnesium sulfate. After concentration under reduced pressure, the residue was purified by silica gel column chromatography (eluent, hexane:ethyl acetate=80:20→20:80), and further purified by basic silica gel column chromatography (eluent, hexane:ethyl acetate=90:10→40:60) to give the title compound (533 mg).
$^1$H-NMR (CDCl$_3$) δ: 2.67 (3H, s), 3.75 (2H, m), 4.01 (2H, m), 4.38 (2H, m), 4.87 (2H, t, J=5.8 Hz), 7.38-7.48 (3H, m), 7.91-7.95 (2H, m), 8.11 (1H, s), 8.71 (1H, s).

(ii) Production of 2-{2-[7-({3-chloro-4-[(3-fluorobenzyl)oxy]phenyl}amino)-1H-pyrazolo[4,3-d]pyrimidin-1-yl]ethoxy}ethanol A mixture of 2-{2-[7-(methylthio)-1H-pyrazolo[4,3-d]pyrimidin-1-yl]ethoxy}ethyl benzoate (200 mg), 3-chloro-4-[(3-fluorobenzyl)oxy]aniline (140 mg), pyridine hydrochloride (96 mg) and 1-methyl-2-pyrrolidone (5 mL) was stirred at 140° C. for 16.5 hrs. The reaction mixture was poured into saturated aqueous sodium hydrogen carbonate (30 mL), and extracted with ethyl acetate (30 mL×3). The organic layers were combined, washed with saturated brine and dried over anhydrous magnesium sulfate. After concentration under reduced pressure, the residue was subjected to silica gel column chromatography (eluent, hexane:ethyl acetate=90:10→20:80). The object fraction was concentrated under reduced pressure and the residue was dissolved in methanol (5 mL). 1N Aqueous sodium hydroxide solution (1 mL) was added and the mixture was stirred at room temperature for 11.5 hrs. After concentration of the reaction mixture under reduced pressure, water (30 mL) was added, and the mixture was extracted with ethyl acetate (45 mL×2). The organic layer was dried over anhydrous magnesium sulfate and concentrated under reduced pressure. The residue was purified by silica gel column chromatography (eluent, hexane:ethyl acetate=80:20→0:100) and recrystallized from ethanol-ethyl acetate to give the title compound (78 mg).
$^1$H-NMR (DMSO-d$_6$) δ: 3.30-3.55 (4H, m), 3.87 (2H, m), 4.67 (1H, m), 4.86 (2H, m), 5.26 (2H, s), 7.14-7.35 (4H, m), 7.46 (1H, m), 7.60 (1H, d, J=8.4 Hz), 7.92 (1H, m), 8.18 (1H, s), 8.35 (1H, s), 8.99 (1H, br s).

Example 197

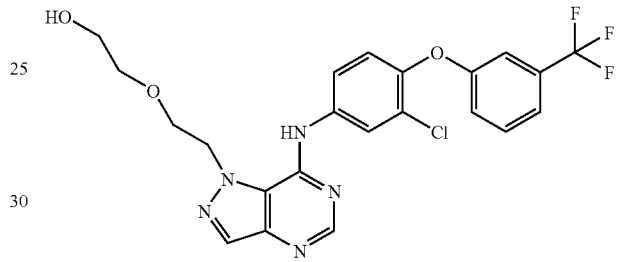

Production of 2-{2-[7-({3-chloro-4-[3-(trifluoromethyl)phenoxy]phenyl}amino)-1H-pyrazolo[4,3-d]pyrimidin-1-yl]ethoxy}ethanol A mixture of 2-{2-[7-(methylthio)-1H-pyrazolo[4,3-d]pyrimidin-1-yl]ethoxy}ethyl benzoate (328 mg), 3-chloro-4-[3-(trifluoromethyl)phenoxy]aniline (264 mg), pyridine hydrochloride (159 mg) and 1-methyl-2-pyrrolidone (7.5 mL) was stirred at 140° C. for 33.5 hrs. The reaction mixture was poured into saturated aqueous sodium hydrogen carbonate (15 mL), and extracted with ethyl acetate (35 mL×2). The organic layers were combined and dried over anhydrous magnesium sulfate. After concentration under reduced pressure, the residue was subjected to silica gel column chromatography (eluent, hexane:ethyl acetate=80:20→0:100). The object fraction was concentrated under reduced pressure and the residue was dissolved in methanol (5 mL). 1N Aqueous sodium hydroxide solution (1 mL) was added and the mixture was stirred at room temperature for 2 hrs. After concentration of the reaction mixture under reduced pressure, water (30 mL) was added, and the mixture was extracted with ethyl acetate (40 mL×2). The organic layer was dried over anhydrous magnesium sulfate and concentrated under reduced pressure. The residue was purified by silica gel column chromatography (eluent, hexane:ethyl acetate=80:20→0:100) and recrystallized from ethyl acetate-hexane to give the title compound (50 mg).
$^1$H-NMR (DMSO-d$_6$) δ: 3.40-3.55 (4H, m), 3.88 (2H, m), 4.68 (1H, m), 4.89 (2H, m), 7.20-7.24 (2H, m), 7.33 (1H, d, J=8.7 Hz), 7.47 (1H, d, J=7.5 Hz), 7.62 (1H, m), 7.77 (1H, m), 8.13 (1H, s), 8.22 (1H, s), 8.44 (1H, m), 9.23 (1H, br s).

Example 198

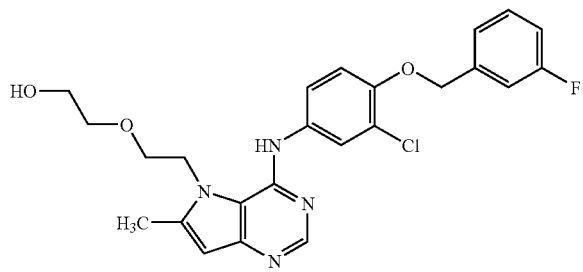

Production of 2-{2-[4-({3-chloro-4-[(3-fluorobenzyl)oxy]phenyl}amino)-6-methyl-5H-pyrrolo[3,2-d]pyrimidin-5-yl]ethoxy}ethanol (i) Production of 4-phenoxy-6-prop-1-yn-1-ylpyrimidin-5-amine 4-Iodo-6-phenoxypyrimidin-5-amine (5.00 g) was dissolved in a mixed solvent of N,N-dimethylformamide (100 mL)/triethylamine (50 mL), and 1-(trimethylsilyl)-1-propyne (3.3 mL), trans-dichlorobis(triphenylphosphine)palladium (II) (557.7 mg), triphenylphosphine (421.1 mg), copper(I) iodide (303.0 mg) and potassium fluoride (1.29 g) were sequentially added. The mixture was stirred at 60° C. under an argon stream for 16 hrs. The reaction mixture was treated with saturated aqueous sodium hydrogen carbonate solution and extracted with diethyl ether. The organic layer was washed with saturated brine, dried over anhydrous magnesium sulfate and concentrated under reduced pressure. The residue was separated and purified by silica gel column chromatography (eluent, hexane:ethyl acetate=80:20→50:50) to give the title compound (2.64 g) as a orange solid.

$^1$H-NMR (CDCl$_3$) δ: 2.19 (3H, s), 4.36 (2H, br s), 7.07-7.22 (2H, m), 7.22-7.34 (1H, m), 7.35-7.54 (2H, m), 8.08 (1H, s).

(ii) Production of 6-methyl-4-phenoxy-5H-pyrrolo[3,2-d]pyrimidine

4-Phenoxy-6-prop-1-yn-1-ylpyrimidin-5-amine (776.0 mg) was dissolved in tetrahydrofuran (30 mL) and cooled to 0° C. To this solution was added dropwise a 1.0 M solution (4 mL) of potassium tert-butoxide in tetrahydrofuran, and the mixture was stirred at room temperature for 30 min. Water was added to the reaction mixture, and the mixture was extracted with ethyl acetate. The organic layer was washed with saturated brine, dried over anhydrous magnesium sulfate and concentrated under reduced pressure. The residue was separated and purified by silica gel column chromatography (eluent, hexane:ethyl acetate=67:33→20:80) to give the title compound (578.6 mg) as a white solid.

$^1$H-NMR (CDCl$_3$) δ: 2.54 (3H, s), 6.44 (1H, q, J=1.0 Hz), 7.21-7.30 (3H, m), 7.41-7.48 (2H, m), 8.47 (1H, s), 8.55 (1H, br s).

(iii) Production of 2-[2-(6-methyl-4-phenoxy-5H-pyrrolo[3,2-d]pyrimidin-5-yl)ethoxy]ethyl benzoate 6-Methyl-4-phenoxy-5H-pyrrolo[3,2-d]pyrimidine (299.9 mg) and 2-{2-[(methylsulfonyl)oxy]ethoxy}ethyl benzoate (464.1 mg) were dissolved in N,N-dimethylformamide (7 mL), potassium carbonate (431 mg) was added, and the mixture was stirred at 60° C. for 21 hr. Water was added to the reaction mixture, and the mixture was extracted with ethyl acetate. The organic layer was washed with saturated brine, dried over anhydrous magnesium sulfate and concentrated under reduced pressure. The residue was separated and purified by silica gel column chromatography (eluent, hexane:ethyl acetate=80:20→20:80) to give the title compound (517.8 mg) as a yellow oil.

$^1$H-NMR (CDCl$_3$) δ: 2.50 (3H, s), 3.62-3.74 (2H, m), 3.92 (2H, t, J=5 Hz), 4.33-4.44 (2H, m), 4.57 (2H, t, J=5 Hz), 6.36 (1H, s), 7.15-7.34 (3H, m), 7.34-7.51 (4H, m), 7.51-7.65 (1H, m), 7.87-8.00 (2H, m), 8.40 (1H, s).

(iv) Production of 2-{2-[4-({3-chloro-4-[(3-fluorobenzyl)oxy]phenyl}amino)-6-methyl-5H-pyrrolo[3,2-d]pyrimidin-5-yl]ethoxy}ethyl benzoate A mixture of 2-[2-(6-methyl-4-phenoxy-5H-pyrrolo[3,2-d]pyrimidin-5-yl)ethoxy]ethyl benzoate (92.3 mg), 3-chloro-4-[(3-fluorobenzyl)oxy]aniline (86.3 mg), pyridine hydrochloride (81.6 mg) and phenol (156.1 mg) was stirred at 120° C. for 3 hrs, and at 140° C. for 5.5 hrs. Further, pyridine hydrochloride (77.6 mg) and phenol (188.7 mg) were added, and the mixture was stirred at 140° C. for 22.5 hrs. The reaction mixture was diluted with dichloromethane, washed with saturated brine, dried over anhydrous magnesium sulfate and concentrated under reduced pressure. The residue was separated and purified by basic silica gel column chromatography (eluent, hexane:ethyl acetate=50:50→0:100) to give the title compound (33.3 mg) as a purple oil.

$^1$H-NMR (CDCl$_3$) δ: 2.43 (3H, s), 3.88-3.97 (2H, m), 4.00 (2H, t, J=4.4 Hz), 4.42-4.55 (4H, m), 5.04 (2H, s), 6.38 (1H, s), 6.71 (1H, d, J=8.8 Hz), 6.93-7.09 (1H, m), 7.13-7.42 (6H, m), 7.46-7.58 (1H, m), 7.65 (1H, d, J=2.6 Hz), 7.74-7.85 (2H, m), 8.40 (1H, s), 8.48 (1H, s).

(v) Production of 2-{2-[4-({3-chloro-4-[(3-fluorobenzyl)oxy]phenyl}amino)-6-methyl-5H-pyrrolo[3,2-d]pyrimidin-5-yl]ethoxy}ethanol 2-{2-[4-({3-Chloro-4-[(3-fluorobenzyl)oxy]phenyl}amino)-6-methyl-5H-pyrrolo[3,2-d]pyrimidin-5-yl]ethoxy}ethyl benzoate (90.0 mg) was dissolved in methanol (1 mL), 1N aqueous sodium hydroxide solution (0.3 mL) was added, and the mixture was stirred at room temperature for 5 hrs. The reaction mixture was neutralized with 1N hydrochloric acid, and the mixture was extracted with ethyl acetate. The organic layer was washed with saturated brine, dried over anhydrous magnesium sulfate and concentrated under reduced pressure. The residue was separated and purified by basic silica gel column chromatography (eluent, hexane:ethyl acetate=33:67→0:100) to give the title compound (43.9 mg) as a pale-yellow powder.

$^1$H-NMR (DMSO-d$_6$) δ 2.45 (3H, s), 3.46-3.52 (4H, m), 3.82 (2H, t, J=4.7 Hz), 4.52 (2H, t, J=4.3 Hz), 4.64-4.80 (1H, m), 5.23 (2H, s), 6.30 (1H, s), 7.10-7.24 (2H, m), 7.26-7.38 (2H, m), 7.41-7.55 (2H, m), 7.82 (1H, d, J=2.8 Hz), 8.21 (1H, s), 8.68 (1H, s).

Example 199

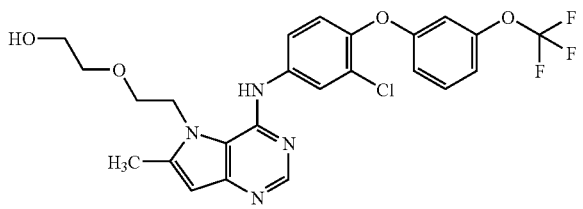

Production of 2-{2-[4-({3-chloro-4-[3-(trifluoromethoxy)phenoxy]phenyl}amino)-6-methyl-5H-pyrrolo[3,2-d]pyrimidin-5-yl]ethoxy}ethanol (i) Production of 2-{2-[4-({3-chloro-4-[3-(trifluoromethoxy)phenoxy]phenyl}amino)-5H-pyrrolo[3,2-d]pyrimidin-5-yl]ethoxy}ethyl benzoate The title compound (288.2 mg) was obtained as a pale pink oil by the reaction in the same manner as in Example 198 (iv) using 2-[2-(6-methyl-4-phenoxy-5H-pyrrolo[3,2-d]pyrimidin-5-yl)ethoxy]ethyl benzoate (271.0 mg), 3-chloro-4-[3-(trifluoromethoxy)phenoxy]aniline (297.3 mg), pyridine hydrochloride (235.0 mg) and phenol (497.9 mg).

$^1$H-NMR (CDCl$_3$) δ: 2.45 (3H, s), 3.92-4.00 (2H, m), 4.04 (2H, t, J=4.4 Hz), 4.45-4.55 (4H, m), 6.42 (1H, s), 6.75-6.85 (3H, m), 6.85-6.96 (2H, m), 7.19-7.37 (3H, m), 7.45-7.53 (1H, m), 7.75-7.82 (2H, m), 7.85 (1H, d, J=2.8 Hz), 8.46 (1H, s), 8.73 (1H, br s).

(ii) Production of 2-{2-[4-({3-chloro-4-[3-(trifluoromethoxy)phenoxy]phenyl}amino)-6-methyl-5H-pyrrolo[3,2-d]pyrimidin-5-yl]ethoxy}ethanol The title compound (119.1 mg) was obtained as a white powder by the reaction in the same manner as in Example 198 (v) using 2-{2-[4-({3-chloro-4-[3-(trifluoromethoxy)phenoxy]phenyl}amino)-5H-pyrrolo[3,2-d]pyrimidin-5-yl]ethoxy}ethyl benzoate (281.5 mg), 1N aqueous sodium hydroxide solution (0.6 mL) and methanol (2 mL).

$^1$H-NMR (DMSO-d$_6$) δ 2.47 (3H, s), 3.44-3.56 (4H, m), 3.81-3.89 (2H, m), 4.56 (2H, t, J=4.5 Hz), 4.71-4.79 (1H, m), 6.35 (1H, s), 6.88-6.95 (2H, m), 7.06-7.14 (1H, m), 7.26 (1H, d, J=9 Hz), 7.50 (1H, t, J=9 Hz), 7.66 (1H, dd, J=9 Hz, 2.5 Hz), 8.01 (1H, d, J=2.5 Hz), 8.30 (1H, s), 8.99 (1H, br s).

Example 200

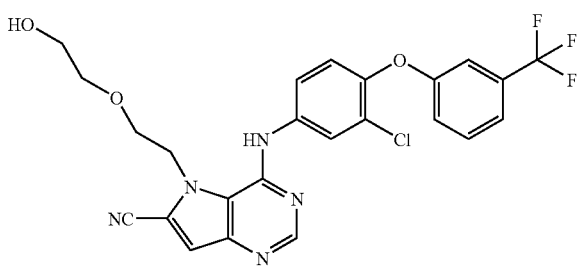

Production of 4-({3-chloro-4-[3-(trifluoromethyl)phenoxy]phenyl}amino)-5-[2-(2-hydroxyethoxy)ethyl]-5H-pyrrolo[3,2-d]pyrimidine-6-carbonitrile (i) Production of 4-(3,3-diethoxyprop-1-yn-1-yl)-6-phenoxypyrimidin-5-amine The title compound (6.20 g) was obtained as a brown oil by the reaction in the same manner as in Example 9 (iv) using 4-iodo-6-phenoxypyrimidin-5-amine (7.0 g), 3,3-diethoxyprop-1-yne (3.8 mL), trans-dichlorobis(triphenylphosphine)palladium(II) (783.3 mg), copper(I) iodide (255.2 mg) and acetonitrile (160 mL)/triethylamine (120 mL).

$^1$H-NMR (CDCl$_3$) δ: 1.29 (6H, t, J=7.2 Hz), 3.62-3.77 (2H, m), 3.77-3.91 (2H, m), 4.48 (2H, br s), 5.56 (1H, s), 7.14-7.21 (2H, m), 7.27-7.33 (1H, m), 7.39-7.50 (2H, m), 8.11 (1H, s).

(ii) Production of 6-(diethoxymethyl)-4-phenoxy-5H-pyrrolo[3,2-d]pyrimidine 4-(3,3-Diethoxyprop-1-yn-1-yl)-6-phenoxypyrimidin-5-amine (2.30 g) was dissolved in 1-methyl-2-pyrrolidone (7.5 mL), and the mixture was cooled to 0° C. A solution (7.6 mL) of potassium tert-butoxide in 1.0 M tetrahydrofuran was added dropwise to this solution, and the mixture was stirred at 0° C. for 30 min. and at room temperature for 1.5 hrs. Water was added to the reaction mixture and the mixture was extracted with ethyl acetate. The organic layer was washed with saturated brine, dried over anhydrous magnesium sulfate and concentrated under reduced pressure. The residue was separated and purified by silica gel column chromatography (eluent, hexane:ethyl acetate=90:10→50:50) to give the title compound (1.34 g) as a pale orange solid.

$^1$H-NMR (CDCl$_3$) δ: 1.29 (6H, t, J=7.1 Hz), 3.52-3.75 (4H, m), 5.78 (1H, s), 6.66 (1H, br d, J=2.2 Hz), 7.26-7.34 (3H, m), 7.42-7.52 (2H, m), 8.52 (1H, s), 8.95 (1H, br s).

(iii) Production of 4-phenoxy-5H-pyrrolo[3,2-d]pyrimidine-6-carbaldehyde 6-(Diethoxymethyl)-4-phenoxy-5H-pyrrolo[3,2-O]pyrimidine (3.15 g) was dissolved in tetrahydrofuran (40 mL), 1N hydrochloric acid (40 mL) was added, and the mixture was stirred at room temperature for 2 hrs. The reaction mixture was neutralized with 1N aqueous sodium hydroxide solution, and extracted with a mixed solvent of ethyl acetate/tetrahydrofuran=1/1. The organic layer was washed with saturated brine, dried over anhydrous magnesium sulfate and concentrated under reduced pressure. The precipitate was collected by filtration and dried to give the title compound (2.17 g) as a yellow powder.

$^1$H-NMR (DMSO-d$_6$) δ: 7.25-7.40 (3H, m), 7.43-7.58 (3H, m), 8.44 (1H, s), 10.06 (1H, s), 13.26 (1H, s).

(iv) Production of 4-phenoxy-5H-pyrrolo[3,2-d]pyrimidine-6-carboxylic acid

4-Phenoxy-5H-pyrrolo[3,2-d]pyrimidine-6-carbaldehyde (2.17 g) was dissolved in dimethyl sulfoxide (21 mL) and a solution of sodium dihydrogen phosphate (5.45 g) in water (14 mL) was added. A solution of sodium chlorite (2.06 g) in water (14 mL) was added dropwise to this solution, and the mixture was stirred for 2 hrs. Saturated aqueous sodium hydrogen carbonate solution was gradually added to the reaction mixture, and the pH of the solution was adjusted to 2-3 with 1N hydrochloric acid. The resultant precipitate was collected by filtration, washed with water and diisopropyl ether and dried to give the title compound (2.40 g) as a white powder.
¹H-NMR (DMSO-d₆) δ: 7.09 (1H, s), 7.23-7.36 (3H, m), 7.41-7.54 (2H, m), 8.36 (1H, s), 12.82 (1H, s).

(v) Production of 4-phenoxy-5H-pyrrolo[3,2-d]pyrimidine-6-carboxamide

Thionyl chloride (7 mL) was added to 4-phenoxy-5H-pyrrolo[3,2-d]pyrimidine-6-carboxylic acid (465.0 mg) and the mixture was stirred at 75° C. for 2 hrs. The reaction mixture was concentrated under reduced pressure and suspended in tetrahydrofuran (10 mL). The above-mentioned suspension was gradually added to aqueous ammonia (20 mL) and the precipitate was collected by filtration. The filtrate was extracted with a mixed solvent of ethyl acetate/tetrahydrofuran=1/1, washed with saturated brine, dried over anhydrous magnesium sulfate and concentrated under reduced pressure. The precipitate was collected by filtration, combined with the precipitate collected earlier by filtration and dried to give the title compound (427.4 mg) as a pale-yellow powder.
¹H-NMR (DMSO-d₆) δ: 7.25 (1H, s), 7.27-7.35 (3H, m), 7.39-7.57 (2H, m), 7.75 (1H, s), 8.17 (1H, s), 8.36 (1H, s), 12.58 (1H, s).

(vi) Production of 4-phenoxy-5H-pyrrolo[3,2-d]pyrimidine-6-carbonitrile

4-Phenoxy-5H-pyrrolo[3,2-d]pyrimidine-6-carboxamide (1.67 g) was suspended in phosphorus oxychloride (20 mL), and the suspension was stirred at 70° C. for 3 hrs. The reaction mixture was concentrated under reduced pressure, and the residue was dissolved in tetrahydrofuran (25 mL). Water and aqueous ammonia were added to the solution, and the mixture was extracted with a mixed solvent of ethyl acetate/tetrahydrofuran=1/1. The organic layer was washed with saturated brine, dried over anhydrous magnesium sulfate and concentrated under reduced pressure. The residue was separated and purified by silica gel column chromatography (eluent, hexane:ethyl acetate=90:10→67:33) to give the title compound (1.07 g) as a pale-yellow powder.
¹H-NMR (CDCl3) δ: 7.29-7.39 (3H, m), 7.46-7.55 (2H, m), 7.59 (1H, s), 8.47 (1H, s), 13.76 (1H, s).

(vii) Production of 2-{2-[4-({3-chloro-4-[3-(trifluoromethyl)phenoxy]phenyl}amino)-6-cyano-5H-pyrrolo[3,2-d]pyrimidin-5-yl]ethoxy}ethyl benzoate 4-Phenoxy-5H-pyrrolo[3,2-d]pyrimidine-6-carbonitrile (240.4 mg) was dissolved in N,N-dimethylformamide (5 mL), and 2-{2-[(methylsulfonyl)oxy]ethoxy}ethyl benzoate (354.1 mg) and potassium carbonate (354.8 mg) were added. The title compound (266.5 mg) was obtained as a colorless oil by the reaction in the same manner as in Example 198 (iii) using the mixture prepared above.
¹H-NMR (CDCl3) δ: 3.73-3.79 (2H, m), 3.96 (2H, t, J=4.9 Hz), 4.37-4.43 (2H, m), 4.83 (2H, t, J=4.9 Hz), 7.17 (1H, s), 7.18-7.23 (2H, m), 7.27-7.35 (1H, m), 7.36-7.49 (4H, m), 7.51-7.58 (1H, m), 7.85-7.92 (2H, m), 8.49 (1H, s).

(viii) Production of 2-{2-[4-({3-chloro-4-[3-(trifluoromethyl)phenoxy]phenyl}amino)-6-cyano-5H-pyrrolo[3,2-d]pyrimidin-5-yl]ethoxy}ethyl benzoate The title compound (282.6 mg) was obtained as a yellow oil by the reaction in the same manner as in Example 198 (iv) using 2-{2-[4-({3-chloro-4-[3-(trifluoromethyl)phenoxy]phenyl}amino)-6-cyano-5H-pyrrolo[3,2-d]pyrimidin-5-yl]ethoxy}ethyl benzoate (261.5 mg), 3-chloro-4-[3-(trifluoromethyl)phenoxy]aniline (264.4 mg), pyridine hydrochloride (221.6 mg) and phenol (461.6 mg).
¹H-NMR (CDCl₃) δ: 3.96-4.06 (2H, m), 4.16-4.22 (2H, m), 4.45-4.54 (2H, m), 4.68-4.79 (2H, m), 6.80 (1H, d, J=8.8 Hz), 7.01-7.09 (1H, m), 7.14-7.20 (1H, m), 7.24 (1H, s), 7.27-7.53 (6H, m), 7.68-7.76 (2H, m), 7.92 (1H, d, J=2.5 Hz), 8.53 (1H, s), 8.95 (1H, s).

(ix) Production of 4-({3-chloro-4-[3-(trifluoromethyl)phenoxy]phenyl}amino)-5-[2-(2-hydroxyethoxy)ethyl]-5H-pyrrolo[3,2-d]pyrimidine-6-carbonitrile The title compound (143.2 mg) was obtained as a white powder by the reaction in the same manner as in Example 198 (v) using 2-{2-[4-({3-chloro-4-[3-(trifluoromethyl)phenoxy]phenyl}amino)-6-cyano-5H-pyrrolo[3,2-d]pyrimidin-5-yl]ethoxy}ethyl benzoate (282.6 mg), 1N aqueous sodium hydroxide solution (0.6 mL) and methanol (3 mL).
¹H-NMR (CDCl₃) δ: 1.77 (1H, t, J=4.4 Hz), 3.74-3.88 (4H, m), 4.08-4.16 (2H, m), 4.70-4.80 (2H, m), 7.05-7.15 (2H, m), 7.16-7.21 (1H, m), 7.25 (1H, s), 7.30-7.36 (1H, m), 7.43 (1H, t, J=7.8 Hz), 7.67 (1H, dd, J=8.8 Hz, 2.8 Hz), 7.96 (1H, d, J=2.8 Hz), 8.58 (1H, s), 9.03 (1H, s).

Example 201

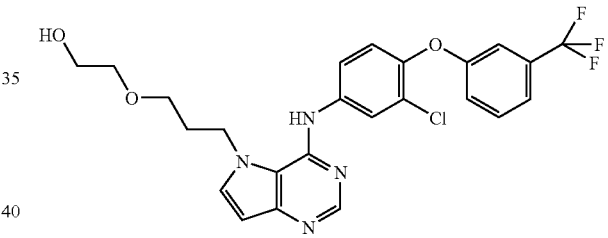

Production of 2-{3-[4-({3-chloro-4-[3-(trifluoromethyl)phenoxy]phenyl}amino)-5H-pyrrolo[3,2-d]pyrimidin-5-yl]propoxy}ethanol hydrochloride (i) Production of 3-[2-(tetrahydro-2H-pyran-2-yloxy)ethoxy]propyl methanesulfonate 60% Sodium hydride (8.05 g) was suspended in N,N-dimethylformamide (80 mL), and the suspension was cooled to 0° C. A solution of propane-1,3-diol (7.2 mL) in N,N-dimethylformamide (10 mL) was added dropwise, and the mixture was stirred at 0° C. for 1 hr. A solution of 2-(2-bromoethoxy)tetrahydro-2H-pyran (4.0 mL) in N,N-dimethylformamide (10 mL) was added dropwise to the reaction solution, and the mixture was stirred at 0° C. for 2 hrs. Saturated aqueous ammonium chloride solution was added to the reaction mixture, and the mixture was extracted with diethyl ether and ethyl acetate. The organic layer was washed with saturated brine, dried over anhydrous magnesium sulfate and concentrated under reduced pressure. The residue was dissolved in ethyl acetate (100 mL), and triethylamine (9 mL) and methanesulfonyl chloride (2.3 mL) were added. The mixture was stirred at room temperature for 3 hrs. Water was added to the reaction mixture and the mixture was extracted with ethyl acetate. The organic layer was washed with saturated brine, dried over anhydrous magnesium sulfate and concentrated under reduced pressure. The residue was separated and purified by silica gel column chromatography (eluent, hexane:ethyl acetate=80:20→20:80) to give the title compound (3.78 g) as a colorless oil.

$^1$H-NMR (CDCl$_3$) δ: 1.45-1.66 (4H, m), 1.66-1.92 (2H, m), 1.96-2.09 (2H, m), 3.02 (3H, s), 3.45-3.68 (6H, m), 3.81-3.94 (2H, m), 4.36 (2H, t, J=6.2 Hz), 4.62 (1H, dd, J=4.4 Hz, 2.7 Hz).

(ii) Production of 4-chloro-5-{3-[2-(tetrahydro-2H-pyran-2-yloxy)ethoxy]propyl}-5H-pyrrolo[3,2-d]pyrimidine 4-Chloro-5H-pyrrolo[3,2-d]pyrimidine (203.6 mg), 3-[2-(tetrahydro-2H-pyran-2-yloxy)ethoxy]propyl methanesulfonate (559.3 mg) was dissolved in N,N-dimethylformamide (4 mL), cesium carbonate (1.30 g) was added, and the mixture was stirred at 40° C. for 4.5 hrs. Water was added to the reaction mixture and the mixture was extracted with ethyl acetate. The organic layer was washed with saturated brine, dried over anhydrous magnesium sulfate and concentrated under reduced pressure. The residue was separated and purified by silica gel column chromatography (eluent, hexane: ethyl acetate=67:33→20:80) to give the title compound (380.2 mg) as a colorless oil.

$^1$H-NMR (CDCl$_3$) δ: 1.44-1.70 (4H, m), 1.70-1.95 (2H, m), 1.95-2.24 (2H, m), 3.23-3.43 (2H, m), 3.45-3.69 (2H, m), 3.78-4.02 (2H, m), 4.53-4.75 (3H, m), 6.69 (1H, d, J=3.3 Hz), 7.66 (1H, d, J=3.3 Hz), 8.69 (1H, s).

(iii) Production of 2-{3-[4-({3-chloro-4-[3-(trifluoromethyl)phenoxy]phenyl}amino)-5H-pyrrolo[3,2-d]pyrimidin-5-yl]propoxy}ethanol hydrochloride 4-Chloro-5-{3-[2-(tetrahydro-2H-pyran-2-yloxy)ethoxy]propyl}-5H-pyrrolo[3,2-d]pyrimidine (380.2 mg) was dissolved in isopropyl alcohol (7 mL), 3-chloro-4-[3-(trifluoromethyl)phenoxy]aniline (419.2 mg) was added, and the mixture was stirred at 80° C. for 18 hrs. Saturated aqueous sodium hydrogen carbonate solution was added to the reaction mixture and the mixture was extracted with ethyl acetate. The organic layer was washed with saturated brine, dried over anhydrous magnesium sulfate and concentrated under reduced pressure. The residue was separated and purified by silica gel column chromatography (eluent, hexane:ethyl acetate=50:50→0:100), and the mixture was dissolved in ethyl acetate (4 mL). 4N Hydrochloric acid-ethyl acetate (0.3 mL) was added to this solution, and the precipitate was collected by filtration, and dried to give the title compound (398.2 mg) as a white solid.

$^1$H-NMR (CDCl$_3$) δ: 1.86-2.02 (2H, m), 3.22 (2H, t, J=5.8 Hz), 3.27-3.40 (2H, m), 3.41-3.55 (2H, m), 4.53-4.69 (2H, m), 6.50 (1H, d, J=3.0 Hz), 7.16-7.26 (2H, m), 7.30 (1H, d, J=8.9 Hz), 7.47 (1H, d, J=7.7 Hz), 7.56-7.76 (2H, m), 7.97 (1H, s), 8.35 (1H, s), 8.61 (1H, s).

Example 202

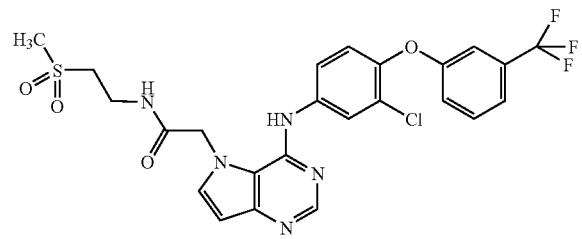

Production of 2-[4-({3-chloro-4-[3-(trifluoromethyl)phenoxy]phenyl}amino)-5H-pyrrolo[3,2-d]pyrimidin-5-yl]-N-[2-(methylsulfonyl)ethyl]acetamide

(i) Production of ethyl [4-({3-chloro-4-[3-(trifluoromethyl)phenoxy]phenyl}amino)-5H-pyrrolo[3,2-d]pyrimidin-5-yl]acetate The title compound (221.2 mg) was obtained as an orange oil by the reaction in the same manner as in Example 201 (iii) using ethyl (4-chloro-5H-pyrrolo[3,2-d]pyrimidin-5-yl)acetate (119.3 mg), 3-chloro-4-[3-(trifluoromethyl)phenoxy]aniline (171.3 mg) and isopropyl alcohol (3 mL).

$^1$H-NMR (CDCl$_3$) δ: 1.37 (3H, t, J=7 Hz), 4.37 (2H, q, J=7 Hz), 4.98 (2H, s), 6.66 (1H, d, J=3.3 Hz), 7.09 (1H, d, J=8.8 Hz), 7.09-7.14 (1H, m), 7.17-7.22 (1H, m), 7.24 (1H, d, J=3.3 Hz), 7.32 (1H, d, J=7.8 Hz), 7.42 (1H, t, J=7.8 Hz), 7.53 (1H, dd, J=8.8 Hz, 2.8 Hz), 7.83 (1H, d, J=2.8 Hz), 8.52-8.63 (2H, m)

(ii) Production of [4-({3-chloro-4-[3-(trifluoromethyl)phenoxy]phenyl}amino)-5H-pyrrolo[3,2-d]pyrimidin-5-yl]acetic acid Ethyl [4-({3-chloro-4-[3-(trifluoromethyl)phenoxy]phenyl}amino)-5H-pyrrolo[3,2-d]pyrimidin-5-yl]acetate (221.2 mg) was dissolved in a mixed solvent of tetrahydrofuran (1.5 mL)/ethanol (1.5 mL), 1N aqueous sodium hydroxide solution (0.6 mL) was added, and the mixture was stirred at room temperature for 30 min. The reaction mixture was adjusted to pH 2-3 with 1N hydrochloric acid and extracted with a mixed solvent of ethyl acetate/tetrahydrofuran=1/1. The organic layer was washed with saturated brine, dried over anhydrous magnesium sulfate and concentrated under reduced pressure. The residue was collected by filtration and dried to give the title compound (169.8 mg) as a yellow powder.

$^1$H-NMR (DMSO-d$_6$) δ: 5.62 (2H, s), 6.70 (1H, d, J=3.0 Hz), 7.22-7.31 (2H, m), 7.35 (1H, d, J=8.8 Hz), 7.51 (1H, d, J=8 Hz), 7.59 (1H, dd, J=8.8 Hz, 2.5 Hz), 7.65 (1H, t, J=8 Hz), 7.86 (1H, d, J=2.5 Hz), 7.95 (1H, d, J=3.0 Hz), 8.70 (1H, s), 9.99 (1H, s).

(iii) Production of 2-[4-({3-chloro-4-{3-(trifluoromethyl)phenoxy]phenyl}amino)-5H-pyrrolo[3,2-d]pyrimidin-5-yl]-N-[2-(methylsulfonyl)ethyl]acetamide

[4-({3-Chloro-4-[3-(trifluoromethyl)phenoxy]phenyl}amino)-5H-pyrrolo[3,2-d]pyrimidin-5-yl]acetic acid (149.3 mg) was dissolved in N,N-dimethylformamide (1.6 mL), 2-(methylsulfonyl)ethanamine (60.3 mg), 1H-1,2,3-benzotriazol-1-ol (67.8 mg), triethylamine (0.15 mL) and N-[3-(dimethylamino)propyl]-N'-ethylcarbodiimide hydrochloride (93.0 mg) were added, and the mixture was stirred at room temperature for 17 hrs. Moreover, 2-(methylsulfonyl)ethanamine (120.6 mg), 1H-1,2,3-benzotriazol-1-ol (134.6 mg), triethylamine (0.3 mL) and N-[3-(dimethylamino)propyl]-N'-ethylcarbodiimide hydrochloride (181.4 mg) were added, and the mixture was stirred at room temperature for 24 hrs. Water was added to the reaction mixture and the mixture was extracted with ethyl acetate. The organic layer was washed with saturated brine, dried over anhydrous magnesium sulfate and concentrated under reduced pressure. The residue was separated and purified by silica gel column chromatography (eluent, ethyl acetate:methanol=100:0→90:10), and basic silica gel column chromatography (eluent, hexane:ethyl acetate=33:67→0:100→ethyl acetate:methanol=90:10) to give the title compound (20.3 mg) as a white powder.

$^1$H-NMR (DMSO-d$_6$) δ: 2.98 (3H, s), 3.27 (2H, t, J=6.9 Hz), 3.50-3.61 (2H, m), 5.12 (2H, s), 6.54 (1H, d, J=3.0 Hz), 7.15-7.26 (2H, m), 7.33 (1H, d, J=8.8 Hz), 7.47 (1H, d, J=8.0 Hz), 7.56-7.68 (3H, m), 8.04 (1H, d, J=2.5 Hz), 8.38 (1H, s), 9.07 (1H, t, J=5.8 Hz), 9.97 (1H, s).

Example 203

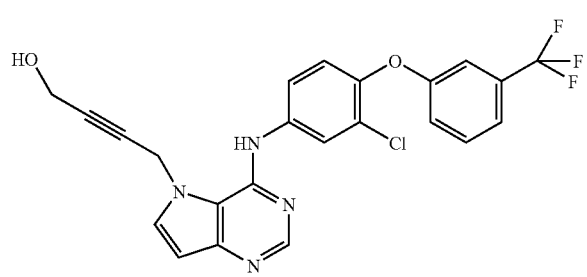

Production of 4-[4-({3-chloro-4-[3-(trifluoromethyl)phenoxy]phenyl}amino)-5H-pyrrolo[3,2-d]pyrimidin-5-yl]but-2-yn-1-ol (i) Production of 4-{[tert-butyl(dimethyl)silyl]oxy}but-2-yn-1-ol 60% Sodium hydride (1.39 g) was suspended in tetrahydrofuran (50 mL), and the suspension was cooled to 0° C., a solution of but-2-yne-1,4-diol (3.0 g) in tetrahydrofuran (20 mL) was added dropwise, and the mixture was stirred at room temperature for 1 hr. tert-Butyldimethylsilyl chloride (5.26 g) was added to the reaction mixture, and the mixture was stirred at room temperature for 24 hrs. Water was added to the reaction mixture and the mixture was extracted with diethyl ether. The organic layer was washed with saturated brine, dried over anhydrous magnesium sulfate and concentrated under reduced pressure. The residue was separated and purified by silica gel column chromatography (eluent, hexane:ethyl acetate=100:0→80:20) to give the title compound (1.48 g) as a colorless oil.

$^1$H-NMR (CDCl$_3$) δ: 0.12 (6H, s), 0.91 (9H, s), 1.60-1.66 (1H, m), 4.27-4.33 (2H, m), 4.36 (2H, t, J=1.8 Hz).

(ii) Production of 4-{[tert-butyl(dimethyl)silyl]oxy}but-2-yn-1-yl methanesulfonate 4-{[Tert-butyl(dimethyl)silyl]oxy}but-2-yn-1-ol (701.4 mg) was dissolved in ethyl acetate (15 mL), and the solution was cooled to 0° C. Triethylamine (1.1 mL) and methanesulfonyl chloride (0.3 mL) were added, and the mixture was stirred at 0° C. for 3 hrs. Water was added to the reaction mixture and the mixture was extracted with diethyl ether. The organic layer was washed with saturated brine, dried over anhydrous magnesium sulfate and concentrated under reduced pressure. The residue was separated and purified by silica gel column chromatography (eluent, hexane:ethyl acetate=90:10→50:50) to give the title compound (469.7 mg) as a colorless oil.

$^1$H-NMR (CDCl$_3$) δ: 0.12 (6H, s), 0.91 (9H, s), 3.12 (3H, s), 4.37 (2H, t, J=1.9 Hz), 4.89 (2H, t, J=1.9 Hz).

(iii) Production of 5-(4-{[tert-butyl(dimethyl)silyl]oxy}but-2-yn-1-yl)-4-chloro-5H-pyrrolo[3,2-d]pyrimidine The title compound (431.1 mg) was obtained as a yellow oil by the reaction in the same manner as in Example 201 (ii) using 4-chloro-5H-pyrrolo[3,2-d]pyrimidine (211.9 mg), 4-{[tert-butyl(dimethyl)silyl]oxy}but-2-yn-1-yl methanesulfonate (464.0 mg), cesium carbonate (672.7 mg) and N,N-dimethylformamide (5 mL).

$^1$H-NMR (CDCl$_3$) δ: 0.07 (6H, s), 0.87 (9H, s), 4.35 (2H, t, J=2 Hz), 5.33 (2H, t, J=2 Hz), 6.76 (1H, d, J=3.3 Hz), 7.69 (1H, d, J=3.3 Hz), 8.72 (1H, s).

(iv) Production of 4-[4-({3-chloro-4-[3-(trifluoromethyl)phenoxy]phenyl}amino)-5H-pyrrolo[3,2-d]pyrimidin-5-yl]but-2-yn-1-ol 5-(4-{[Tert-butyl(dimethyl)silyl]oxy}but-2-yn-1-yl)-4-chloro-5H-pyrrolo[3,2-d]pyrimidine (408.3 mg) was dissolved in isopropyl alcohol (7 mL), 3-chloro-4-[3-(trifluoromethyl)phenoxy]aniline (421.0 mg) was added, and the mixture was stirred at 80° C. for 6 hrs. Water was added to the reaction mixture and the mixture was extracted with ethyl acetate. The organic layer was washed with saturated brine, dried over anhydrous magnesium sulfate and concentrated under reduced pressure. The obtained oil was dissolved in tetrahydrofuran (6 mL), a 1.0 M solution (2 mL) of tetrabutylammonium fluoride in tetrahydrofuran was added, and the mixture was stirred at room temperature for 1 hr. To the reaction mixture was added saturated aqueous ammonium chloride solution and the mixture was extracted with ethyl acetate. The organic layer was washed with saturated brine, dried over anhydrous magnesium sulfate and concentrated under reduced pressure. The residue was separated and purified by silica gel column chromatography (eluent, hexane:ethyl acetate=67:33→20:80) and crystallized from hexane/ethyl acetate to give the title compound (425 mg) as white crystals.

$^1$H-NMR (CDCl$_3$) δ: 4.07-4.13 (1H, m), 4.45-4.52 (2H, m), 5.01-5.06 (2H, m), 6.44 (1H, d, J=3.3 Hz), 7.06-7.16 (3H, m), 7.18-7.22 (1H, m), 7.33 (1H, d, J=8 Hz), 7.43 (1H, t, J=8 Hz), 7.57 (1H, dd, J=8.8 Hz, 2.5 Hz), 7.82 (1H, s), 7.95 (1H, d, J=2.5 Hz), 8.40 (1H, s).

Example 204

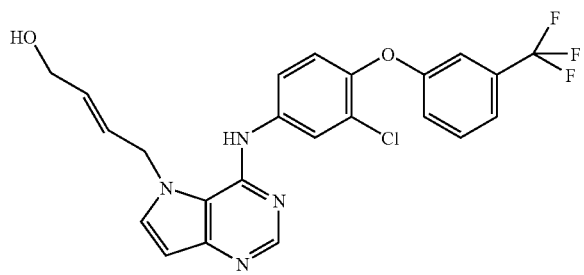

Production of (2E)-4-[4-({3-chloro-4-[3-(trifluoromethyl)phenoxy]phenyl}amino)-5H-pyrrolo[3,2-d]pyrimidin-5-yl]but-2-en-1-ol 70% Sodium bis(2-methoxyethoxy)aluminum hydride in toluene solution (0.8 mL) was dissolved in tetrahydrofuran (4 mL), and the solution was cooled to 0° C. A solution of 4-[4-({3-chloro-4-[3-(trifluoromethyl)phenoxy]phenyl}amino)-5H-pyrrolo[3,2-d]pyrimidin-5-yl]but-2-yn-1-ol (262.4 mg) in tetrahydrofuran (10 mL) was added dropwise, and the mixture was stirred at 0° C. for 2 hrs. To the reaction mixture was added 10% aqueous potassium carbonate solution and the mixture was extracted with ethyl acetate. The organic layer was washed with saturated brine, dried over anhydrous magnesium sulfate and concentrated under reduced pressure. The residue was separated and purified by silica gel column chromatography (eluent, hexane:ethyl acetate=33:67→0:100) and crystallized from hexane/ethyl acetate to give the title compound (195.9 mg) as white crystals.

$^1$H-NMR (DMSO-$d_6$) δ: 3.81-3.92 (2H, m), 4.75 (1H, t, J=5.5 Hz), 5.17 (2H, m), 5.56 (1H, br d, J=15 Hz), 5.80 (1H, br d, J=15 Hz), 6.53 (1H, d, J=3.0 Hz), 7.16-7.26 (2H, m), 7.30 (1H, d, J=8.8 Hz), 7.47 (1H, d, J=7.7 Hz), 7.57-7.74 (3H, m), 7.98 (1H, d, J=2.2 Hz), 8.36 (1H, s), 8.48 (1H, s).

Example 205

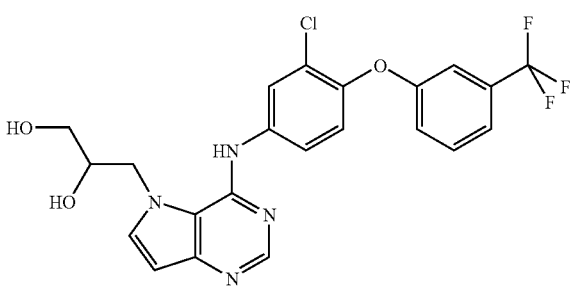

Production of 3-[4-({3-chloro-4-[3-(trifluoromethyl)phenoxy]phenyl}amino)-5H-pyrrolo[3,2-d]pyrimidin-5-yl]propane-1,2-diol (i) Production of 3-(4-chloro-5H-pyrrolo[3,2-d]pyrimidin-5-yl)propane-1,2-diyl dibenzoate A mixture of 4-chloro-5H-pyrrolo[3,2-d]pyrimidine (500 mg), 3-bromopropane-1,2-diyl dibenzoate (1.77 g), cesium carbonate (1.59 g) and N,N-dimethylformamide (6.5 mL) was stirred at 80° C. for 4 hrs. The reaction mixture was diluted with ethyl acetate (100 mL) and washed with water (80 mL). The organic layer was separated, dried over magnesium sulfate and concentrated under reduced pressure. The residue was purified by silica gel column chromatography (hexane/ethyl acetate=90/10→40/60) to give the title compound (401 mg) as a white powder.

$^1$H-NMR (CDCl$_3$) δ 4.58 (1H, dd, J=5 Hz, 12 Hz), 4.73 (1H, dd, J=5 Hz, 12 Hz), 4.84 (1H, dd, J=9 Hz, 15 Hz), 5.11 (1H, dd, J=15 Hz, 5 Hz), 5.84 (1H, m), 6.69 (1H, d, J=3 Hz), 7.3-7.7 (7H, m), 7.91 (2H, m), 8.02 (2H, m), 8.69 (1H, s).

(ii) Production of 3-[4-({3-chloro-4-[3-(trifluoromethyl)phenoxy]phenyl}amino)-5H-pyrrolo[3,2-d]pyrimidin-5-yl]propane-1,2-diol The title compound (180 mg) was obtained as colorless crystals by the method in the same manner as in Example 183 using 3-(4-chloro-5H-pyrrolo[3,2-d]pyrimidin-5-yl)propane-1,2-diyl dibenzoate (250 mg), 3-chloro-4-[3-(trifluoromethyl)phenoxy]aniline (280 mg) and 1-methyl-2-pyrrolidone (1.14 mL).

$^1$H-NMR (DMSO-$d_6$) δ 3.47 (2H, m), 3.94 (1H, m), 4.50 (2H, m), 5.18 (1H, br s), 6.52 (2H, d, J=3 Hz), 7.20 (2H, m), 7.33 (1H, d, J=9 Hz), 7.45 (1H, d, J=8 Hz), 7.64 (3H, m), 8.04 (1H, d, J=3 Hz), 8.35 (1H, s), 10.03 (1H, br s).

Example 206

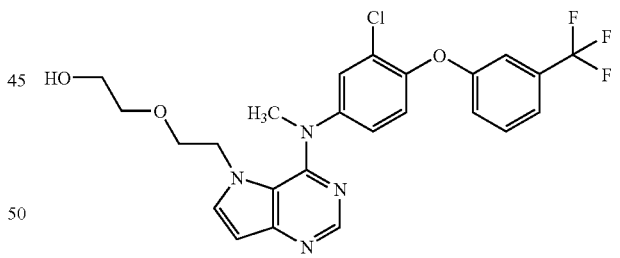

Production of 2-(2-{4-[{3-chloro-4-[3-(trifluoromethyl)phenoxy]phenyl}(methyl)amino]-5H-pyrrolo[3,2-d]pyrimidin-5-yl}ethoxy)ethanol The title compound (127 mg) was obtained by the method in the same manner as in Example 183 using 2-[2-(4-chloro-5H-pyrrolo[3,2-d]pyrimidin-5-yl)ethoxy]ethyl benzoate (150 mg), 3-chloro-N-methyl-4-[3-(trifluoromethyl)phenoxy]aniline (196 mg) and 1-methyl-2-pyrrolidone (0.863 mL).

$^1$H-NMR (CDCl$_3$) δ 3.38 (2H, t, J=4.5 Hz), 3.48 (2H, t, J=4.5 Hz), 3.58 (3H, s), 3.62 (2H, m), 4.00 (2H, t, J=5 Hz), 5.08 (1H, br s), 6.64 (1H, dd, J=3 Hz, 9 Hz), 6.70 (1H, d, J=3 Hz), 6.72 (1H, s), 6.97 (2H, m), 7.09 (2H, m), 7.40 (2H, m), 8.79 (1H, s).

Example 207

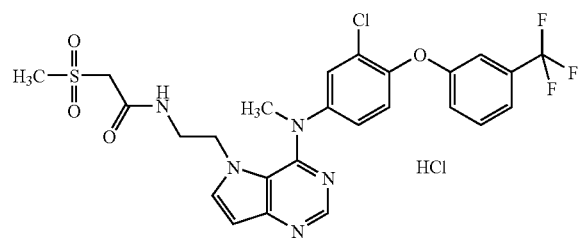

Production of N-(2-{4-[{3-chloro-4-[3-(trifluoromethyl)phenoxy]phenyl}(methyl)amino]-5H-pyrrolo[3,2-d]pyrimidin-5-yl}ethyl)-2-(methylsulfonyl)acetamide hydrochloride A mixture of tert-butyl [2-(4-chloro-5H-pyrrolo[3,2-d]pyrimidin-5-yl)ethyl]carbamate (297 mg), 3-chloro-N-methyl-4-[3-(trifluoromethyl)phenoxy]aniline (453 mg) and 1-methyl-2-pyrrolidone (1.99 mL) was stirred at 120° C. for 16 hrs. To the reaction mixture was added 2N hydrochloric acid (1 mL), and the mixture was stirred at 80° C. for 2.5 hrs. The reaction mixture was diluted with ethyl acetate (80 mL) and washed with aqueous sodium hydrogen carbonate (30 mL). The organic layer was separated, dried over magnesium sulfate and evaporated under reduced pressure. The residue, 2-(methylsulfonyl)acetic acid (207 mg), 1-ethyl-3-(3-dimethylaminopropyl)carbodiimide hydrochloride (429 mg), 1-hydroxybenzotriazole monohydrate (304 mg), triethylamine (0.697 mL) and N,N-dimethylformamide (7.69 mL) were reacted in the same manner as in Example 155 (iv). The obtained compound was treated with 4N hydrochloric acid/ethyl acetate to give the title compound (149 mg) as colorless crystals.

$^1$H-NMR (DMSO-$d_6$) δ 3.02 (3H, s), 3.20 (2H, s), 3.51 (2H, m), 3.71 (3H, s), 3.90 (2H, s), 6.72 (1H, d, J=3 Hz), 7.2-7.4 (4H, m), 7.52 (1H, d, J=8 Hz), 7.68 (2H, m), 7.86 (1H, d, J=2 Hz), 8.40 (1H, m), 8.94 (1H, s).

Example 208

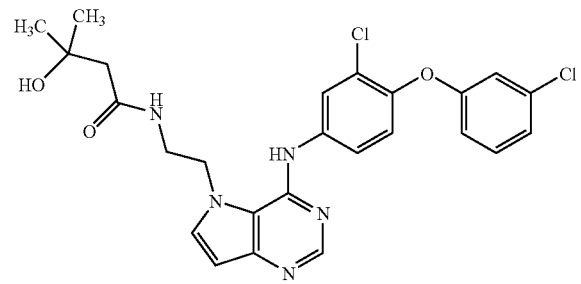

Production of N-[2-(4-{[3-chloro-4-(3-chlorophenoxy)phenyl]amino}-5H-pyrrolo[3,2-d]pyrimidin-5-yl)ethyl]-3-hydroxy-3-methylbutanamide The title compound (145 mg) was obtained as crystals by the reaction in the same manner as in Example 155 (iv) using 5-(2-aminoethyl)-N-[3-chloro-4-(3-chlorophenoxy)phenyl]-5H-pyrrolo[3,2-d]pyrimidin-4-amine dihydrochloride (200 mg) and 3-hydroxy-3-methylbutyric acid (104 mg).

$^1$H-NMR (CDCl$_3$) δ: 1.33 (6H, s), 2.49 (2H, s), 3.55-3.7 (2H, m), 4.4-4.55 (2H, m), 6.60 (1H, d, J=3.4 Hz), 6.85-7.1 (4H, m), 7.1-7.3 (2H, m), 7.7-7.8 (1H, m), 8.05 (1H, d, J=2.6 Hz), 8.52 (1H, s), 8.64 (1H, s).

Example 209

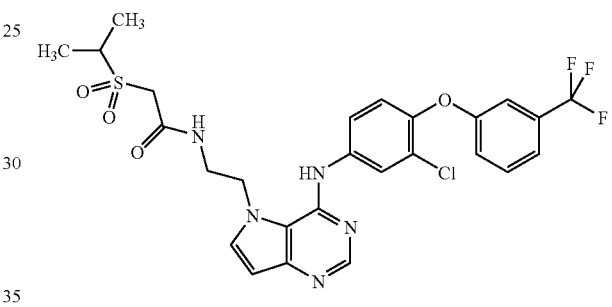

Production of N-{2-[4-({3-chloro-4-[3-(trifluoromethyl)phenoxy]phenyl}amino)-5H-pyrrolo[3,2-d]pyrimidin-5-yl]ethyl}-2-(isopropylsulfonyl)acetamide 5-(2-Aminoethyl)-N-{3-chloro-4-[3-(trifluoromethyl)phenoxy]phenyl}-5H-pyrrolo[3,2-d]pyrimidin-4-amine dihydrochloride (300 mg) and 4-methylmorpholine (3.0 mL) were dissolved in tetrahydrofuran (7.0 mL), chloroacetyl chloride (0.7 mL) was added, and the mixture was stirred at 0° C. for 2 hrs. To the reaction mixture was added saturated aqueous sodium hydrogen carbonate under ice-cooling and the mixture was extracted with ethyl acetate. The extract was dried over magnesium sulfate and concentrated, and the residue was dissolved in a mixed solvent of N,N-dimethylformamide (3.5 mL) and tetrahydrofuran (6.0 mL). To the mixture was added sodium 2-methylpropane-2-thiolate (180 mg), and the mixture was stirred at room temperature for 1 hr. To the reaction mixture was added saturated aqueous sodium hydrogen carbonate under ice-cooling and the mixture was extracted with ethyl acetate. The extract was dried over magnesium sulfate and concentrated, and the residue was separated and purified by silica gel column chromatography (eluent, ethyl acetate:methanol=100:0→ethyl acetate:methanol=90:10) to give an oil. The title compound (165 mg) was obtained as crystals by the reaction in the same manner as in Example 172 (ii) using the oil obtained above and titanium tetraisopropoxide (0.15 mL), methanol (0.52 mL) and 70% aqueous tert-butyl hydroperoxide solution (12.0 mL).

¹H-NMR (DMSO-d₆) δ: 1.24 (6H, d, J=6.8 Hz), 3.45-3.58 (3H, m), 4.03 (2H, s), 4.56 (2H, m), 6.52 (1H, m), 7.20-7.99 (8H, m), 8.35 (1H, s), 8.72 (1H, s).

Example 210

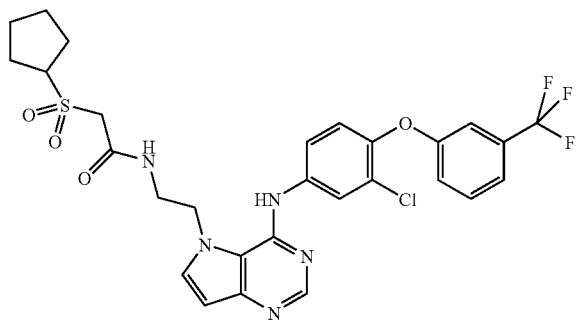

Production of N-{2-[4-({3-chloro-4-[3-(trifluoromethyl)phenoxy]phenyl}amino)-5H-pyrrolo[3,2-d]pyrimidin-5-yl]ethyl}-2-[(cyclopentyl)sulfonyl]acetamide The title compound (115 mg) was obtained as crystals by the reaction in the same manner as in Example 209 using 5-(2-aminoethyl)-N-{3-chloro-4-[3-(trifluoromethyl)phenoxy]phenyl}-5H-pyrrolo[3,2-d]pyrimidin-4-amine dihydrochloride (350 mg), 4-methylmorpholine (3.50 mL), chloroacetyl chloride (0.9 mL), sodium cyclopentanethiolate (890 mg), titanium tetraisopropoxide (0.25 mL), methanol (0.55 mL) and 70% aqueous tert-butyl hydroperoxide solution (15.0 mL).

¹H-NMR (DMSO-d₆) δ: 1.50-1.63 (4H, m), 1.89 (4H, m), 3.47 (2H, m), 3.79 (1H, m), 3.99 (2H, s), 4.56 (2H, m), 6.52 (1H, m), 7.20-7.99 (8H, m), 8.35 (1H, s), 8.72 (1H, s).

Example 211

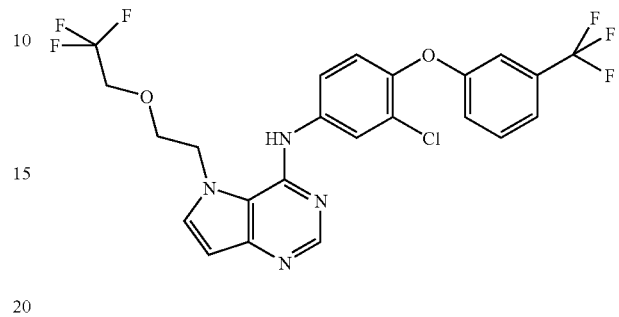

Production of N-{3-chloro-4-[3-(trifluoromethyl)phenoxy]phenyl}-5-[2-(2,2,2-trifluoroethoxy)ethyl]-5H-pyrrolo[3,2-d]pyrimidin-4-amine The title compound (175 mg) was obtained as crystals by the reaction in the same manner as in Example 171 using 4-chloro-5H-pyrrolo[3,2-d]pyrimidine (340 mg), potassium carbonate (530 mg) and 2-(2,2,2-trifluoroethoxy)ethyl methanesulfonate (550 mg).

¹H-NMR (DMSO-d₆) δ: 3.91-4.09 (4H, m), 3.73-3.76 (2H, m), 6.53 (1H, d, J=3 Hz), 7.21-7.92 (8H, m), 8.36 (1H, s), 8.62 (1H, s).

Example 212

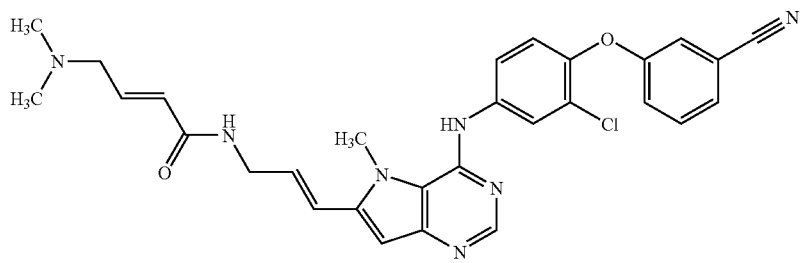

Production of (2E)-N-[(2E)-3-(4-{[3-chloro-4-(3-cyanophenoxy)phenyl]amino}-5-methyl-5H-pyrrolo[3,2-d]pyrimidin-6-yl)prop-2-en-1-yl]-4-(dimethylamino)but-2-enamide (i) Production of N-(4,6-diiodopyrimidin-5-yl)-2,2,2-trifluoro-N-methylacetamide 4,6-Diiodopyrimidin-5-amine (20 g) was dissolved in dichloromethane (200 mL), and trifluoroacetic anhydride (47.3 mL) and triethylamine (8.04 mL) were successively added dropwise. The mixture was stirred at room temperature for 1 hr, and the reaction mixture was concentrated under reduced pressure. The residue was dissolved in methanol (150 mL), and concentrated again under reduced pressure to give a colorless solid. The obtained solid was dissolved in N,N-dimethylformamide (106 mL), potassium carbonate (15.9 g) and iodomethane (10.8 mL) were added, and the mixture was stirred at room temperature for 16 hrs. The reaction mixture was diluted with diethyl ether (400 mL) and washed with water (400 mL). The organic layer was dried over magnesium sulfate and concentrated under reduced pressure to give the title compound (25.1 g) as a colorless solid.

$^1$H-NMR (CDCl$_3$) δ: 3.34 (2H, s), 3.48 (1H, s), 8.44 (1H, d, J=2 Hz).

(ii) Production of N-(4-{[3-chloro-4-(3-cyanophenoxy)phenyl]amino}-6-iodopyrimidin-5-yl)-2,2,2-trifluoro-N-methylacetamide N-(4,6-Diiodopyrimidin-5-yl)-2,2,2-trifluoro-N-methylacetamide (3 g) and 3-(4-amino-2-chlorophenoxy)benzonitrile (1.69 g) were dissolved in 1-methyl-2-pyrrolidone (11.4 mL), and the mixture was stirred with heating at 100° C. for 16 hrs. To the reaction mixture was added aqueous sodium hydrogen carbonate (80 mL) and the mixture was extracted with ethyl acetate (100 mL×2). The organic layer was washed with saturated brine (80 mL), dried over magnesium sulfate and concentrated under reduced pressure. The residue was purified by silica gel column chromatography (eluent, hexane:ethyl acetate=90:10→hexane:ethyl acetate=50:50) and crystallized from diisopropyl ether to give the title compound (1.67 g) as colorless crystals.

$^1$H-NMR (CDCl$_3$) δ: 3.39 (3H, s), 7.1-7.6 (6H, m), 7.90 (1H, d, J=3 Hz), 8.37 (1H, s).

(iii) Production of 3-(2-chloro-4-{[6-iodo-5-(methylamino)pyrimidin-4-yl]amino}phenoxy)benzonitrile To a solution of N-(4-{[3-chloro-4-(3-cyanophenoxy)phenyl]amino}-6-iodopyrimidin-5-yl)-2,2,2-trifluoro-N-methylacetamide (1.0 g) in isopropanol-tetrahydrofuran (5.0 mL-10 mL) was added sodium borohydride (70 mg) at room temperature. The mixture was stirred at room temperature for 1.5 hrs, and ethyl acetate was added. The mixture was washed with water and saturated brine and the organic layer was dried over magnesium sulfate. After concentration under reduced pressure, the residue was separated and purified by silica gel column chromatography (eluent, hexane:ethyl acetate=4:1→3:2) to give the title compound (755 mg) as a white amorphous solid.

$^1$H-NMR (CDCl$_3$) δ: 2.72 (3H, d, J=6.3 Hz), 2.86-2.98 (1H, m), 7.15-7.21 (3H, m), 7.31-7.45 (2H, m), 7.58 (1H, dd, J=9.0, 2.7 Hz), 7.73 (1H, br s), 7.99 (1H, d, J=2.7 Hz), 8.20 (1H, s).

(iv) Production of tert-butyl {(2E)-5-[6-{[3-chloro-4-(3-cyanophenoxy)phenyl]amino}-5-(methylamino)pyrimidin-4-yl]pent-2-en-4-yn-1-yl}carbamate The title compound (366 mg) was obtained as brown powder crystals by the reaction in the same manner as in Example 81 (ii) using 3-(2-chloro-4-{[6-iodo-5-(methylamino)pyrimidin-4-yl]amino}phenoxy)benzonitrile (755 mg), tert-butyl pent-2-en-4-ynylcarbamate (0.43 g), bis(triphenylphosphine)palladium(II) dichloride (55.5 mg), copper(I) iodide (18 mg), acetonitrile (16 mL) and triethylamine (12 mL).

$^1$H-NMR (CDCl$_3$) δ: 1.47 (9H, s), 2.78 (3H, d, J=6.3 Hz), 3.15-3.27 (1H, m), 3.84-3.95 (2H, m), 4.53-4.65 (1H, m), 5.84-5.93 (1H, m), 6.34-6.43 (1H, m), 7.09 (1H, d, J=8.7 Hz), 7.10-7.22 (2H, m), 7.32-7.44 (2H, m), 7.55 (1H, br s), 7.59 (1H, dd, J=8.7, 2.7 Hz), 7.99 (1H, d, J=2.7 Hz), 8.46 (1H, s).

(v) Production of tert-butyl [(2E)-3-(4-{[3-chloro-4-(3-cyanophenoxy)phenyl]amino}-5-methyl-5H-pyrrolo[3,2-d]pyrimidin-6-yl)prop-2-en-1-yl]carbamate The title compound (200 mg) was obtained as pale-yellow crystals by the reaction in the same manner as in Example 81 (iii) using tert-butyl {(2E)-5-[6-{[3-chloro-4-(3-cyanophenoxy)phenyl]amino}-5-(methylamino)pyrimidin-4-yl]pent-2-en-4-yn-1-yl}carbamate (366 mg), copper(I) iodide (13 mg) and N,N-dimethylformamide (4.0 mL).

$^1$H-NMR (CDCl$_3$) δ: 1.48 (9H, s), 3.92-4.03 (5H, m), 4.71-4.86 (1H, m), 6.31-6.45 (1H, m), 6.56 (1H, d, J=15.9 Hz), 6.67 (1H, s), 6.74 (1H, s), 7.06-7.22 (3H, m), 7.31-7.46 (3H, m), 7.75 (1H, d, J=2.7 Hz), 8.49 (1H, s).

(vi) Production of 3-[4-({6-[(1E)-3-aminoprop-1-en-1-yl]-5-methyl-5H-pyrrolo[3,2-d]pyrimidin-4-yl}amino)-2-chlorophenoxy]benzonitrile dihydrochloride The title compound (170 mg) was obtained as colorless crystals by the reaction in the same manner as in Example 81 (iv) using tert-butyl [(2E)-3-(4-{[3-chloro-4-(3-cyanophenoxy)phenyl]amino}-5-methyl-5H-pyrrolo[3,2-d]pyrimidin-6-yl)prop-2-en-1-yl]carbamate (190 mg), 2N hydrochloric acid (4.5 mL) and tetrahydrofuran (9.0 mL).

$^1$H-NMR (DMSO-d$_6$) δ: 3.75 (2H, t, J=5.3 Hz), 4.17 (3H, s), 6.62-6.72 (1H, m), 6.87 (1H, s), 7.13 (1H, d, J=16.5 Hz), 7.25-7.34 (2H, m), 7.43-7.46 (1H, m), 7.55-7.67 (3H, m), 7.93 (1H, d, J=2.4 Hz), 8.16-8.31 (3H, m), 8.64 (1H, s), 9.83 (1H, br s).

(vii) Production of (2E)-N-[(2E)-3-(4-{[3-chloro-4-(3-cyanophenoxy)phenyl]amino}-5-methyl-5H-pyrrolo[3,2-d]pyrimidin-6-yl)prop-2-en-1-yl]-4-(dimethylamino)but-2-enamide The title compound (74 mg) was obtained as pale-yellow crystals by the reaction in the same manner as in Example 82 using 3-[4-({6-[(1E)-3-aminoprop-1-en-1-yl]-5-methyl-5H-pyrrolo[3,2-d]pyrimidin-4-yl}amino)-2-chlorophenoxy]benzonitrile dihydrochloride (160 mg), (2E)-4-(dimethylamino)but-2-enoic acid hydrochloride (182 mg), 1-ethyl-3-(3-dimethylaminopropyl)carbodiimide hydrochloride (420 mg), 1-hydroxybenzotriazole monohydrate (340 mg), triethylamine (0.80 mL) and N,N-dimethylformamide (5.0 mL).

$^1$H-NMR (DMSO-d$_6$) δ: 2.15 (6H, s), 3.00 (2H, dd, J=6.0, 1.2 Hz), 3.95-4.08 (5H, m), 6.05-6.14 (1H, m), 6.42-6.53 (1H, m), 6.60 (1H, dt, J=15.6, 6.6 Hz), 6.72 (1H, s), 6.78 (1H, d, J=15.6 Hz), 7.20-7.28 (2H, m), 7.39-7.43 (1H, m), 7.53-7.59 (2H, m), 7.60-7.68 (1H, m), 7.68-7.92 (1H, m), 8.28 (1H, s), 8.32 (1H, t, J=5.4 Hz), 8.77 (1H, s).

Example 213

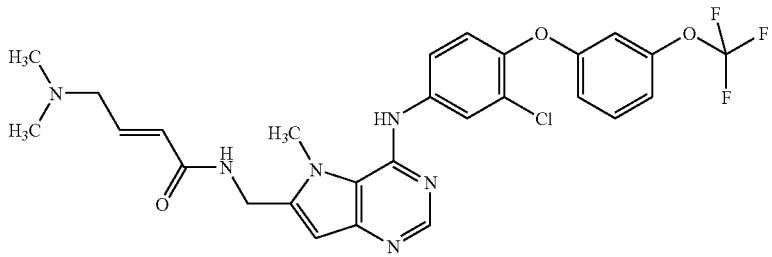

Production of (2E)-N-{[4-({3-chloro-4-[3-(trifluoromethoxy)phenoxy]phenyl}amino)-5-methyl-5H-pyrrolo[3,2-d]pyrimidin-6-yl]methyl}-4-(dimethylamino)but-2-enamide (i) Production of 4,6-diiodo-N-methylpyrimidin-5-amine To a solution of 4,6-diiodopyrimidin-5-amine (1.0 g) in tetrahydrofuran (10 mL) was added sodium hydride (60%, 138 mg) under ice-cooling. The mixture was stirred at room temperature for 30 min. To the reaction system was added dropwise a solution of methyl methanesulfonate (0.256 mL) in tetrahydrofuran (4.0 mL). The mixture was stirred at room temperature for 3 hrs and ethyl acetate was added. The mixture was washed with water and saturated brine and dried over magnesium sulfate. After concentration under reduced pressure, the residue was separated and purified by silica gel column chromatography (hexane:ethyl acetate=9:1→3:1) to give the title compound (600 mg) as pale-yellow crystals.

$^1$H-NMR (CDCl$_3$) δ: 3.02 (3H, d, J=5.7 Hz), 3.71-3.83 (1H, m), 8.04 (1H, s).

(ii) Production of N4-{3-chloro-4-[3-(trifluoromethoxy)phenoxy]phenyl}-6-iodo-N5-methylpyrimidine-4,5-diamine The title compound (552 mg) was obtained as pale-yellow crystals by the reaction in the same manner as in Example 212 (ii) using 4,6-diiodo-N-methylpyrimidin-5-amine (600 mg), 3-chloro-4-[3-(trifluoromethoxy)phenoxy]aniline (504 mg) and 1-methyl-2-pyrrolidone (10 mL).

$^1$H-NMR (DMSO-d$_6$) δ: 2.71 (3H, d, J=5.7 Hz), 2.87-2.98 (1H, m), 6.76-6.85 (2H, m), 6.90-6.96 (1H, m), 7.09 (1H, d, J=8.7 Hz), 7.29-7.34 (1H, m), 7.52-7.56 (1H, m), 7.70 (1H, br s), 7.96 (1H, d, J=1.5 Hz), 8.19 (1H, s).

(iii) Production of tert-butyl {[4-({3-chloro-4-[3-(trifluoromethoxy)phenoxy]phenyl}amino)-5-methyl-5H-pyrrolo[3,2-d]pyrimidin-6-yl]methyl}carbamate To a solution of N4-{3-chloro-4-[3-(trifluoromethoxy)phenoxy]phenyl}-6-iodo-N5-methylpyrimidine-4,5-diamine (1.53 g), tert-butyl prop-2-ynylcarbamate (0.67 g) and triethylamine (1.19 mL) in acetonitrile (28 mL) were added bis(triphenylphosphine)palladium(II) dichloride (100 mg) and copper(I) iodide (32.5 mg) at room temperature. Under an argon atmosphere, the mixture was stirred at room temperature for 4.5 hrs, heated at 50° C., and the mixture was stirred for 6 hrs. After concentration under reduced pressure, the residue was separated and purified by silica gel column chromatography (hexane:ethyl acetate=7:3→3:7→basic silica gel, hexane:ethyl acetate=1:1→ethyl acetate) to give the title compound (1.05 g) as colorless crystals.

$^1$H-NMR (CDCl$_3$) δ: 1.48 (9H, s), 4.04 (3H, s), 4.52 (2H, d, J=6.0 Hz), 4.83-4.95 (1H, m), 6.49 (1H, s), 6.76-6.96 (4H, m), 7.08 (1H, d, J=8.7 Hz), 7.31 (1H, t, J=8.3 Hz), 7.43 (1H, dd, J=8.3 Hz), 7.78 (1H, d, J=2.4 Hz), 8.48 (1H, s).

(iv) Production of 6-(aminomethyl)-N-{3-chloro-4-[3-(trifluoromethoxy)phenoxy]phenyl}-5-methyl-5H-pyrrolo[3,2-d]pyrimidin-4-amine dihydrochloride The title compound (1.01 g) was obtained as pale-yellow crystals by the reaction in the same manner as in Example 81 (iv) using tert-butyl {[4-({3-chloro-4-[3-(trifluoromethoxy)phenoxy]phenyl}amino)-5-methyl-5H-pyrrolo[3,2-d]pyrimidin-6-yl]methyl}carbamate (1.05 g), 2N hydrochloric acid (20 mL) and tetrahydrofuran (40 mL).

$^1$H-NMR (DMSO-d$_6$) δ: 4.18 (3H, s), 4.39-4.48 (2H, m), 6.89 (1H, s), 6.94-6.99 (2H, m), 7.15 (1H, d, J=9.0 Hz), 7.35 (1H, d, J=8.7 Hz), 7.50-7.56 (1H, m), 7.67 (1H, dd, J=9.0, 2.4 Hz), 7.94 (1H, d, J=2.4 Hz), 8.72 (1H, s), 8.77-8.92 (3H, m), 10.04 (1H, br s).

(v) Production of (2E)-N-{[4-({3-chloro-4-[3-(trifluoromethoxy)phenoxy]phenyl}amino)-5-methyl-5H-pyrrolo[3,2-d]pyrimidin-6-yl]methyl}-4-(dimethylamino)but-2-enamide The title compound (105 mg) was obtained as colorless crystals by the reaction in the same manner as in Example 82 using 6-(aminomethyl)-N-{3-chloro-4-[3-(trifluoromethoxy)phenoxy]phenyl}-5-methyl-5H-pyrrolo[3,2-d]pyrimidin-4-amine dihydrochloride (200 mg), (2E)-4-(dimethylamino)but-2-enoic acid hydrochloride (124 mg), 1-ethyl-3-(3-dimethylaminopropyl)carbodiimide hydrochloride (214 mg), 1-hydroxybenzotriazole monohydrate (171 mg), triethylamine (0.52 mL) and N,N-dimethylformamide (5.0 mL).

$^1$H-NMR (CDCl$_3$) δ: 2.14 (6H, s), 3.00 (2H, d, J=6.3 Hz), 4.00 (3H, s), 4.58 (2H, d, J=5.4 Hz), 6.11 (1H, d, J=15.3 Hz), 6.39 (1H, s), 6.58-6.68 (1H, m), 6.87-6.95 (2H, m), 7.04-7.11 (1H, m), 7.25 (1H, d, J=8.7 Hz), 7.45-7.51 (1H, m), 7.60-7.68 (1H, m), 7.91 (1H, d, J=2.7 Hz), 8.28 (1H, s), 8.54-8.61 (1H, m), 8.71 (1H, s).

Example 214

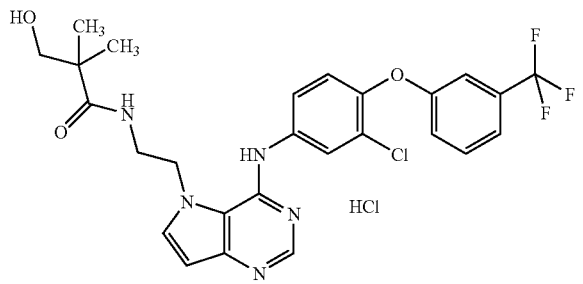

Production of N-{2-[4-({3-chloro-4-[3-(trifluoromethyl)phenoxy]phenyl}amino)-5H-pyrrolo[3,2-d]pyrimidin-5-yl]ethyl}-3-hydroxy-2,2-dimethylpropanamide hydrochloride A solution of 5-(2-aminoethyl)-N-{3-chloro-4-[3-(trifluoromethyl)phenoxy]phenyl}-5H-pyrrolo[3,2-d]pyrimidin-4-amine dihydrochloride (150 mg), 3-hydroxy-2,2-dimethylpropanoic acid (68 mg), 1-ethyl-3-(3-dimethylaminopropyl)carbodiimide hydrochloride (166 mg), 1-hydroxybenzotriazole monohydrate (132 mg) and triethylamine (0.40 mL) in N,N-dimethylformamide (5.0 mL) was stirred at room temperature for 20 hrs. Water was added to the reaction system and the mixture was extracted with ethyl acetate. The organic layer was washed with water and saturated brine and dried over magnesium sulfate. After concentration under reduced pressure, the residue was separated and purified by basic silica gel column chromatography (eluent, ethyl acetate→methanol:ethyl acetate=15:85). After concentration under reduced pressure, ethyl acetate (2.0 mL) and 4N hydrochloric acid/ethyl acetate (0.5 mL) were added, and the mixture was stirred at room temperature for 15 hrs. After concentration under reduced pressure, the precipitated crystals were collected by filtration. To a solution of the collected crystals in ethanol (2.0 mL) was added 1N aqueous sodium hydroxide solution at room temperature, and the mixture was stirred for 2 days. The mixture was concentrated under reduced pressure and a solution of the residue in ethyl acetate was washed with water and saturated brine and dried over magnesium sulfate. After concentration under reduced pressure, 4N hydrochloric acid/ethyl acetate (0.5 mL) was added to a solution of the residue in ethyl acetate (1.0 mL). After concentration under reduced pressure, the precipitated crystals were collected by filtration. The crystals were washed with diisopropyl ether to give the title compound (119 mg) as colorless crystals.

$^1$H-NMR (DMSO-$d_6$) δ: 0.96 (6H, s), 3.23-3.52 (4H, m), 4.56-4.68 (2H, m), 6.64 (1H, d, J=3.0 Hz), 7.23-7.30 (2H, m), 7.38 (1H, d, J=8.4 Hz), 7.52 (1H, d, J=8.1 Hz), 7.61-7.69 (1H, m), 7.72-7.80 (1H, m), 7.85-7.92 (2H, m), 8.00-8.03 (1H, m), 8.70 (1H, s), 9.95-10.06 (1H, m).

Example 215

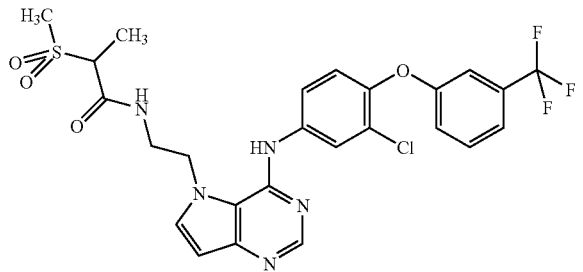

Production of N-{2-[4-({3-chloro-4-[3-(trifluoromethyl)phenoxy]phenyl}amino)-5H-pyrrolo[3,2-d]pyrimidin-5-yl]ethyl}-2-(methylsulfonyl)propanamide To a mixture of 5-(2-aminoethyl)-N-{3-chloro-4-[3-(trifluoromethyl)phenoxy]phenyl}-5H-pyrrolo[3,2-d]pyrimidin-4-amine dihydrochloride (150 mg), triethylamine (0.39 mL) and tetrahydrofuran (5.0 mL) was added 2-chloropropionyl chloride (54 µL) at room temperature. The mixture was stirred at room temperature for 3 days, water was added and the mixture was extracted with ethyl acetate. The organic layer was washed with saturated brine and dried over magnesium sulfate. After concentration under reduced pressure, sodium methanesulfinate (85 mg) and pyridine (67 µL) were added to a solution of the residue in N,N-dimethylformamide (5.0 mL), and the mixture was stirred at 70° C. for 2 days. Water was added to the reaction system and the mixture was extracted with ethyl acetate. The organic layer was washed with saturated brine and dried over magnesium sulfate. After concentration under reduced pressure, the residue was separated and purified by basic silica gel column chromatography (eluent, ethyl acetate→ethyl acetate:methanol=9:1) and recrystallized from ethyl acetate-diisopropyl ether to give the title compound (114 mg) as colorless crystals.

$^1$H-NMR (CDCl$_3$) δ: 1.71 (3H, d, J=7.2 Hz), 2.98 (3H, s), 3.63-3.75 (2H, m), 3.81 (1H, q, J=7.2 Hz), 4.44-4.55 (2H, m), 6.64 (1H, d, J=3.0 Hz), 7.09 (1H, d, J=8.7 Hz), 7.11-7.18 (2H, m), 7.19-7.25 (2H, m), 7.30-7.36 (1H, m), 7.40-7.47 (1H, m), 7.85 (1H, dd, J=8.7, 2.7 Hz), 8.01 (1H, d, J=2.7 Hz), 8.30 (1H, s), 8.54 (1H, s).

Example 216

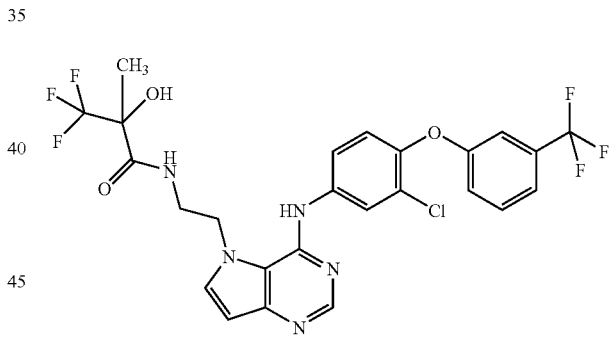

Production of N-{2-[4-({3-chloro-4-[3-(trifluoromethyl)phenoxy]phenyl}amino)-5H-pyrrolo[3,2-d]pyrimidin-5-yl]ethyl}-3,3,3-trifluoro-2-hydroxy-2-methylpropanamide The title compound (128 mg) was obtained as colorless crystals by the reaction in the same manner as in Example 155 (iv) using 5-(2-aminoethyl)-N-{3-chloro-4-[3-(trifluoromethyl)phenoxy]phenyl}-5H-pyrrolo[3,2-d]pyrimidin-4-amine dihydrochloride (150 mg), 2-hydroxy-2-(trifluoromethyl)propionic acid (88.2 mg), 1-ethyl-3-(3-dimethylaminopropyl)carbodiimide hydrochloride (160 mg), 1-hydroxybenzotriazole monohydrate (128 mg), triethylamine (0.39 mL) and N,N-dimethylformamide (5.0 mL).

$^1$H-NMR (CDCl$_3$) δ: 1.68 (3H, s), 3.65-3.77 (2H, m), 3.80-3.89 (1H, m), 4.43-4.57 (2H, m), 6.63 (1H, d, J=3.0 Hz), 7.08 (1H, d, J=8.7 Hz), 7.11-7.16 (1H, m), 7.19-7.28 (3H, m), 7.30-7.36 (1H, m), 7.40-7.43 (1H, m), 7.79 (1H, dd, J=8.7, 2.4 Hz), 8.08 (1H, d, J=2.4 Hz), 8.31 (1H, s), 8.53 (1H, s).

Example 217

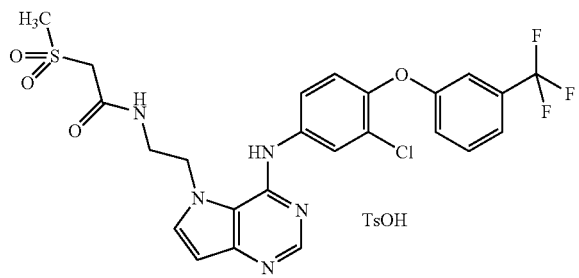

Production of N-{2-[4-({3-chloro-4-[3-(trifluoromethyl)phenoxy]phenyl}amino)-5H-pyrrolo[3,2-d]pyrimidin-5-yl]ethyl}-2-(methylsulfonyl)acetamide 4-methylbenzenesulfonate To a solution of N-{2-[4-({3-chloro-4-[3-(trifluoromethyl)phenoxy]phenyl}amino)-5H-pyrrolo[3,2-d]pyrimidin-5-yl]ethyl}-2-(methylsulfonyl)acetamide (150 mg) in ethyl acetate (10 mL) was added 4-methylbenzenesulfonic acid monohydrate (55.4 mg) at room temperature. The mixture was stirred at room temperature for 20 hrs, and the solvent was evaporated under reduced pressure. The precipitated crystals were collected by filtration and washed with ethyl acetate and diisopropyl ether to give the title compound (150.3 mg) as colorless crystals.

$^1$H-NMR (DMSO-$d_6$) δ: 2.29 (3H, s), 3.07 (3H, s), 3.44-3.60 (2H, m), 4.06 (2H, s), 4.61-4.70 (2H, m), 6.66 (1H, d, J=3.0 Hz), 7.11 (2H, d, J=8.4 Hz), 7.22-7.28 (2H, m), 7.38 (1H, d, J=8.7 Hz), 7.47 (2H, d, J=8.4 Hz), 7.50-7.55 (1H, m), 7.62-7.72 (2H, m), 7.89-7.96 (2H, m), 8.65-8.74 (2H, m), 9.70-9.80 (1H, m).

Example 218

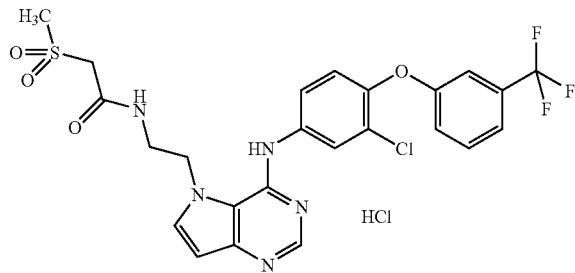

Production of N-{2-[4-({3-chloro-4-[3-(trifluoromethyl)phenoxy]phenyl}amino)-5H-pyrrolo[3,2-d]pyrimidin-5-yl]ethyl}-2-(methylsulfonyl)acetamide hydrochloride The title compound (147 mg) was obtained as colorless crystals in the same manner as in Example 217 using N-{2-[4-({3-chloro-4-[3-(trifluoromethyl)phenoxy]phenyl}amino)-5H-pyrrolo[3,2-d]pyrimidin-5-yl]ethyl}-2-(methylsulfonyl)acetamide (150 mg), 4N hydrochloric acid/ethyl acetate (0.13 mL) and ethyl acetate (10 mL).

$^1$H-NMR (DMSO-$d_6$) δ: 3.06 (3H, s), 3.35-3.59 (2H, m), 4.07 (2H, s), 4.63-4.74 (2H, m), 6.67 (1H, d, J=3.0 Hz), 7.25-7.30 (2H, m), 7.38 (1H, d, J=8.7 Hz), 7.51-7.54 (1H, m), 7.62-7.72 (2H, m), 7.92-7.99 (2H, m), 8.70-8.79 (2H, m), 9.78-9.89 (1H, m).

Example 219

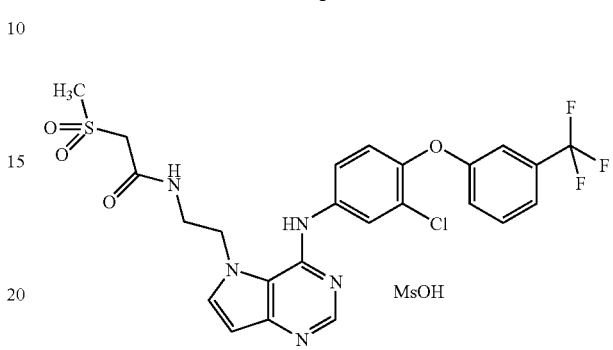

Production of N-{2-[4-({3-chloro-4-[3-(trifluoromethyl)phenoxy]phenyl}amino)-5H-pyrrolo[3,2-d]pyrimidin-5-yl]ethyl}-2-(methylsulfonyl)acetamide methanesulfonate The title compound (1.14 g) was obtained as colorless crystals in the same manner as in Example 217 using N-{2-[4-({3-chloro-4-[3-(trifluoromethyl)phenoxy]phenyl}amino)-5H-pyrrolo[3,2-d]pyrimidin-5-yl]ethyl}-2-(methylsulfonyl)acetamide (1.0 g), methanesulfonic acid (0.126 mL) and ethyl acetate (50 mL).

$^1$H-NMR (DMSO-$d_6$) δ: 2.30 (3H, s), 3.06 (3H, s), 3.47-3.61 (2H, m), 4.06 (2H, s), 4.63-4.72 (2H, m), 6.67 (1H, d, J=3.3 Hz), 7.23-7.29 (2H, m), 7.37-7.40 (2H, m), 7.63-7.73 (2H, m), 7.91-7.98 (2H, m), 8.68-8.78 (2H, m), 9.80 (1H, br s).

Example 220

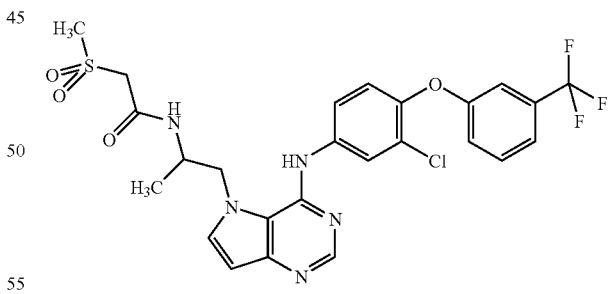

Production of N-{2-[4-({3-chloro-4-[3-(trifluoromethyl)phenoxy]phenyl}amino)-5H-pyrrolo[3,2-d]pyrimidin-5-yl]-1-methylethyl}-2-(methylsulfonyl)acetamide (i) Production of tert-butyl [2-(4-chloro-5H-pyrrolo[3,2-d]pyrimidin-5-yl)-1-methylethyl]carbamate To a solution of 2-aminopropan-1-ol (1.0 g) in tetrahydrofuran (50 mL) was added di-tert-butyl dicarbonate (3.1 mL) at room temperature. The mixture was stirred at room temperature for 3 days and concentrated under reduced pressure. To a solution of the residue and triethylamine (3.7 mL) in tetrahydrofuran (30 mL) was added methanesulfonyl chloride (1.54 mL) under ice-cooling, and the mixture was stirred at 30 min. To the reaction system was added aqueous sodium hydrogen carbonate and the mixture was extracted with ethyl acetate. The organic layer was washed with saturated brine and dried over magnesium sulfate. After concentration under reduced pressure, 4-chloro-5H-pyrrolo[3,2-d]pyrimidine (1.02 g), cesium carbonate (6.49 g) and N,N-dimethylformamide (10 mL) were added to the residue, and the mixture was stirred at 40° C. for 3 days. Water was added to the reaction system and the mixture was extracted with ethyl acetate. The organic layer was washed with water and saturated brine and dried over magnesium sulfate. After concentration under reduced pressure, the residue was separated and purified by silica gel column chromatography (hexane:ethyl acetate=3:1→2:3) to give the title compound (1.16 g) as a pale-yellow oil.

$^1$H-NMR (CDCl$_3$) δ: 0.93-1.35 (12H, m), 4.02-4.18 (1.5H, m), 4.39-4.53 (1.5H, m), 4.57-4.70 (1H, m), 6.74 (1H, d, J=3.0 Hz), 7.50 (1H, d, J=3.0 Hz), 8.71 (1H, s).

(ii) Production of 5-(2-aminopropyl)-N-{3-chloro-4-[3-(trifluoromethyl)phenoxy]phenyl}-5H-pyrrolo[3,2-d]pyrimidin-4-amine dihydrochloride A solution of tert-butyl [2-(4-chloro-5H-pyrrolo[3,2-d]pyrimidin-5-yl)-1-methylethyl]carbamate (350 mg) and 3-chloro-4-[3-(trifluoromethyl)phenoxy]aniline (423 mg) in 1-methyl-2-pyrrolidone (3.5 mL) was stirred at 120° C. for 4 hrs. After cooling to room temperature, triethylamine (0.24 mL) and di-tert-butyl dicarbonate (0.13 mL) were added, and the mixture was stirred for 20 hrs. Water was added to the reaction system and the mixture was extracted with ethyl acetate. The organic layer was washed with water and saturated brine and dried over magnesium sulfate. The residue was separated and purified by silica gel column chromatography (hexane:ethyl acetate=19:1→3:2→ethyl acetate) to give a brown solid. To a solution of the obtained solid in tetrahydrofuran (20 mL) was added 2N hydrochloric acid (10 mL) at room temperature, and the mixture was stirred at 60° C. for 20 hrs. After concentration under reduced pressure, ethanol was added and the mixture was further concentrated. To the residue was added diisopropyl ether, and the precipitated crystals were collected by filtration. The crystals were washed with diisopropyl ether to give the title compound (225 mg) as pale-yellow crystals.

$^1$H-NMR (DMSO-d$_6$) δ: 1.17 (3H, d, J=6.6 Hz), 3.35-3.77 (1H, m), 4.75-4.89 (1H, m), 4.98-5.09 (1H, m), 6.75 (1H, d, J=2.7 Hz), 7.23-7.30 (2H, m), 7.37 (1H, d, J=8.7 Hz), 7.52-7.54 (1H, m), 7.64-7.69 (2H, m), 7.89-7.97 (1H, m), 8.04-8.10 (1H, m), 8.24-8.43 (3H, m), 8.74 (1H, s), 10.04 (1H, br s).

(iii) Production of N-{2-[4-({3-chloro-4-[3-(trifluoromethyl)phenoxy]phenyl}amino)-5H-pyrrolo[3,2-d]pyrimidin-5-yl]-1-methylethyl}-2-(methylsulfonyl)acetamide The title compound (34 mg) was obtained as colorless crystals by the reaction in the same manner as in Example 155 (iv) using 5-(2-aminopropyl)-N-{3-chloro-4-[3-(trifluoromethyl)phenoxy]phenyl}-5H-pyrrolo[3,2-d]pyrimidin-4-amine dihydrochloride (150 mg), 2-(methylsulfonyl)acetic acid (77 mg), 1-ethyl-3-(3-dimethylaminopropyl)carbodiimide hydrochloride (160 mg), 1-hydroxybenzotriazole monohydrate (128 mg), triethylamine (0.39 mL) and N,N-dimethylformamide (5.0 mL).

$^1$H-NMR (CDCl$_3$) δ: 1.28 (3H, d, J=6.6 Hz), 3.14 (3H, s), 3.71-3.80 (1H, m), 4.00 (2H, s), 4.12-4.26 (1H, m), 4.98-5.04 (1H, m), 6.62 (1H, d, J=3.3 Hz), 6.82-6.88 (1H, m), 7.07 (1H, d, J=8.7 Hz), 7.12-7.24 (3H, m), 7.30-7.35 (1H, m), 7.41-7.49 (1H, m), 7.79 (1H, dd, J=8.7, 2.7 Hz), 7.95 (1H, d, J=2.7 Hz), 8.52 (1H, s), 8.54 (1H, br s).

Example 221

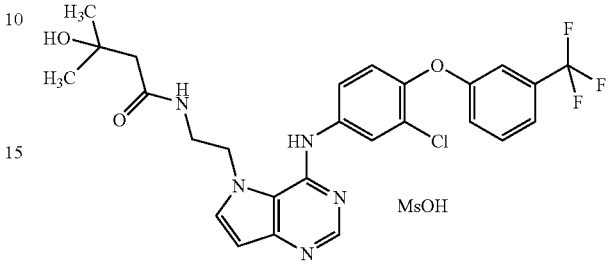

Production of N-{2-[4-({3-chloro-4-[3-(trifluoromethyl)phenoxy]phenyl}amino)-5H-pyrrolo[3,2-d]pyrimidin-5-yl]ethyl}-3-hydroxy-3-methylbutanamide methanesulfonate To a solution of N-{2-[4-({3-chloro-4-[3-(trifluoromethyl)phenoxy]phenyl}amino)-5H-pyrrolo[3,2-d]pyrimidin-5-yl]ethyl}-3-hydroxy-3-methylbutanamide (200 mg) in ethyl acetate (10 mL) was added methanesulfonic acid (26 μL) at room temperature. The mixture was stirred at room temperature for 1 hr and concentrated under reduced pressure. To the residue were added ethanol and ethyl acetate, and the precipitated crystals were collected by filtration to give the title compound (223 mg) as colorless crystals.

$^1$H-NMR (DMSO-d$_6$) δ: 1.12 (6H, s), 2.21 (2H, s), 2.29 (3H, s), 3.41-3.54 (2H, m), 4.56-4.68 (2H, m), 6.66 (1H, d, J=3.3 Hz), 7.26-7.28 (2H, m), 7.37 (1H, d, J=9.0 Hz), 7.51-7.54 (1H, m), 7.61-7.75 (2H, m), 7.95-8.03 (2H, m), 8.31-8.40 (1H, m), 8.72 (1H, s), 10.11-10.19 (1H, m).

Example 222

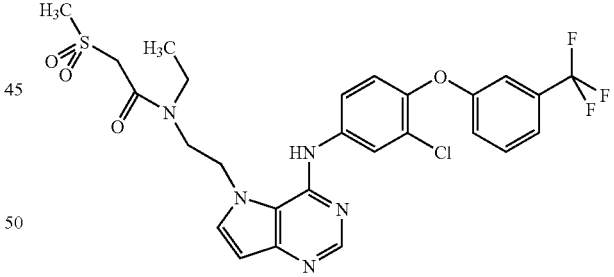

Production of N-{2-[4-({3-chloro-4-[3-(trifluoromethyl)phenoxy]phenyl}amino)-5H-pyrrolo[3,2-d]pyrimidin-5-yl]ethyl}-N-ethyl-2-(methylsulfonyl)acetamide (i) Production of tert-butyl [2-(4-chloro-5H-pyrrolo[3,2-d]pyrimidin-5-yl)ethyl]ethylcarbamate The title compound (630 mg) was obtained as a pale-yellow oil by the reaction in the same manner as in Example 163 (i) using 2-(ethylamino)ethanol (1.00 g), di-tert-butyl dicarbonate (2.58 mL), tetrahydrofuran (100 mL), methanesulfonyl chloride (1.30 mL), triethylamine (3.12 mL), tetrahydrofuran (50 mL), 4-chloro-5H-pyrrolo[3,2-d]pyrimidine (0.86 g), cesium carbonate (7.5 g) and N,N-dimethylformamide (20 mL).

¹H-NMR (CDCl₃) δ: 0.84-1.48 (12H, m), 2.80-2.93 (1H, m), 3.07-3.22 (1H, m), 3.51-3.67 (2H, m), 4.52-4.72 (2H, m), 6.73 (1H, d, J=3.3 Hz), 7.29-7.47 (1H, m), 8.71 (1H, s).

(ii) Production of tert-butyl {2-[4-({3-chloro-4-[3-(trifluoromethyl)phenoxy]phenyl}amino)-5H-pyrrolo[3,2-d]pyrimidin-5-yl]ethyl}ethylcarbamate The title compound (950 mg) was obtained as a colorless solid by the reaction in the same manner as in Example 155 (ii) using tert-butyl [2-(4-chloro-5H-pyrrolo[3,2-d]pyrimidin-5-yl)ethyl]ethylcarbamate (630 mg), 3-chloro-4-[3-(trifluoromethyl)phenoxy]aniline (725 mg) and isopropyl alcohol (6.0 mL).

¹H-NMR (CDCl₃) δ: 1.18 (3H, t, J=7.2 Hz), 1.52 (9H, s), 3.35 (2H, q, J=7.2 Hz), 3.49-3.58 (2H, m), 4.41-4.51 (2H, m), 6.60 (1H, d, J=3.0 Hz), 7.07 (1H, d, J=9.0 Hz), 7.09-7.15 (1H, m), 7.18-7.22 (2H, m), 7.29-7.33 (1H, m), 7.39-7.45 (1H, m), 7.93 (1H, d, J=9.0, 2.4 Hz), 8.04 (1H, d, J=2.4 Hz), 8.51 (1H, s), 8.92 (1H, br s).

(iii) Production of N-{3-chloro-4-[3-(trifluoromethyl)phenoxy]phenyl}-5-[2-(ethylamino)ethyl]-5H-pyrrolo[3,2-d]pyrimidin-4-amine dihydrochloride The title compound (861 mg) was obtained as pale-yellow crystals by the reaction in the same manner as in Example 155 (iii) using tert-butyl {2-[4-({3-chloro-4-[3-(trifluoromethyl)phenoxy]phenyl}amino)-5H-pyrrolo[3,2-d]pyrimidin-5-yl]ethyl}ethylcarbamate (950 mg), 2N hydrochloric acid (5.0 mL) and tetrahydrofuran (10 mL).

¹H-NMR (DMSO-d₆) δ: 1.18 (3H, t, J=7.5 Hz), 2.89-3.02 (2H, m), 3.33-3.47 (2H, m), 5.03-5.12 (2H, m), 6.72-6.77 (1H, m), 7.22-7.29 (2H, m), 7.37 (1H, d, J=9.0 Hz), 7.51-7.54 (1H, m), 7.61-7.71 (2H, m), 7.91-7.98 (1H, m), 8.04-8.10 (1H, m), 8.72 (1H, s), 9.05-9.21 (2H, m), 9.95-10.05 (1H, m).

(iv) Production of N-{2-[4-({3-chloro-4-[3-(trifluoromethyl)phenoxy]phenyl}amino)-5H-pyrrolo[3,2-d]pyrimidin-5-yl]ethyl}-N-ethyl-2-(methylsulfonyl)acetamide The title compound (94 mg) was obtained as colorless crystals by the reaction in the same manner as in Example 155 (iv) using N-{3-chloro-4-[3-(trifluoromethyl)phenoxy]phenyl}-5-[2-(ethylamino)ethyl]-5H-pyrrolo[3,2-d]pyrimidin-4-amine dihydrochloride (150 mg), 2-(methylsulfonyl)acetic acid (76 mg), 1-ethyl-3-(3-dimethylaminopropyl)carbodiimide hydrochloride (158 mg), 1-hydroxybenzotriazole monohydrate (126 mg), triethylamine (0.38 mL) and N,N-dimethylformamide (5.0 mL).

¹H-NMR (CDCl₃) δ: 1.36 (3H, t, J=7.2 Hz), 3.20 (3H, s), 3.61 (2H, q, J=7.2 Hz), 3.71-3.80 (2H, m), 4.15 (2H, s), 4.45-4.53 (2H, m), 6.64 (1H, d, J=3.3 Hz), 7.08 (1H, d, J=8.7 Hz), 7.10-7.17 (1H, m), 7.19-7.23 (2H, m), 7.30-7.35 (1H, m), 7.40-7.46 (1H, m), 7.89 (1H, dd, J=8.7, 2.7 Hz), 7.96 (1H, d, J=2.7 Hz), 8.53 (1H, s), 8.60 (1H, s).

Example 223

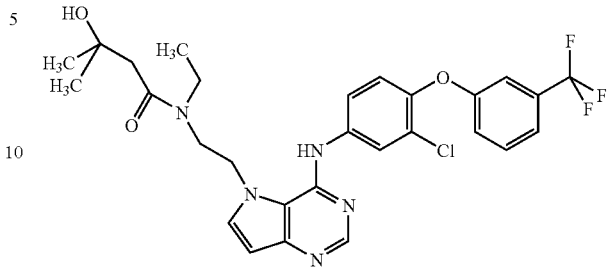

Production of N-{2-[4-({3-chloro-4-[3-(trifluoromethyl)phenoxy]phenyl}amino)-5H-pyrrolo[3,2-d]pyrimidin-5-yl]ethyl}-N-ethyl-3-hydroxy-3-methylbutanamide The title compound (106 mg) was obtained as colorless crystals by the reaction in the same manner as in Example 155 (iv) using N-{3-chloro-4-[3-(trifluoromethyl)phenoxy]phenyl}-5-[2-(ethylamino)ethyl]-5H-pyrrolo[3,2-d]pyrimidin-4-amine dihydrochloride (150 mg), 3-hydroxy-3-methylbutyric acid (64.6 mg), 1-ethyl-3-(3-dimethylaminopropyl)carbodiimide hydrochloride (157 mg), 1-hydroxybenzotriazole monohydrate (125 mg), triethylamine (0.38 mL) and N,N-dimethylformamide (5.0 mL).

¹H-NMR (CDCl₃) δ: 1.29 (3H, t, J=7.2 Hz), 1.34 (6H, s), 2.56 (2H, s), 3.47 (2H, q, J=7.2 Hz), 3.65-3.75 (2H, m), 4.42-4.52 (3H, m), 6.62 (1H, d, J=3.0 Hz), 7.08 (1H, d, J=8.7 Hz), 7.10-7.15 (1H, m), 7.20 (1H, d, J=3.0 Hz), 7.24-7.33 (2H, m), 7.39-7.46 (1H, m), 7.72 (1H, dd, J=8.7, 2.4 Hz), 8.03 (1H, d, J=2.4 Hz), 8.50 (1H, s), 8.81 (1H, s).

Example 224

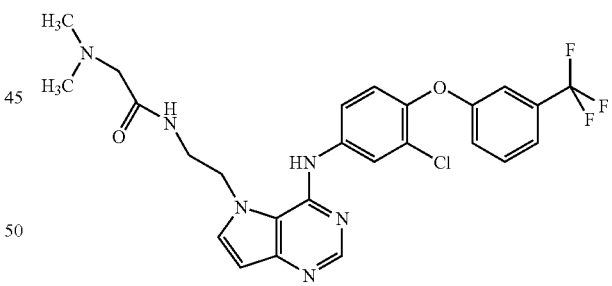

Production of N-{2-[4-({3-chloro-4-[3-(trifluoromethyl)phenoxy]phenyl}amino)-5H-pyrrolo[3,2-d]pyrimidin-5-yl]ethyl}-2-(dimethylamino)acetamide The title compound (84 mg) was obtained as colorless crystals by the reaction in the same manner as in Example 155 (iv) using 5-(2-aminoethyl)-N-{3-chloro-4-[3-(trifluoromethyl)phenoxy]phenyl}-5H-pyrrolo[3,2-d]pyrimidin-4-amine dihydrochloride (150 mg), N,N-dimethylglycine (59.4 mg), 1-ethyl-3-(3-dimethylaminopropyl)carbodiimide hydrochloride (166 mg), 1-hydroxybenzotriazole monohydrate (132 mg), triethylamine (0.40 mL) and N,N-dimethylformamide (5.0 mL).

$^1$H-NMR (CDCl$_3$) δ: 2.29 (6H, s), 3.05 (2H, s), 3.58-3.70 (2H, m), 4.45-4.54 (2H, m), 6.63 (1H, d, J=3.0 Hz), 7.08 (1H, d, J=9.0 Hz), 7.10-7.15 (1H, m), 7.20 (1H, d, J=3.0 Hz), 7.23-7.34 (2H, m), 7.36-7.45 (1H, m), 7.70-7.79 (2H, m), 8.10 (1H, d, J=2.7 Hz), 8.52 (1H, s), 8.63 (1H, s).

Example 225

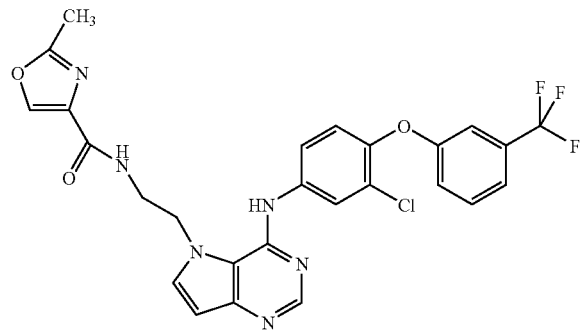

Production of N-{2-[4-({3-chloro-4-[3-(trifluoromethyl)phenoxy]phenyl}amino)-5H-pyrrolo[3,2-d]pyrimidin-5-yl]ethyl}-2-methyl-1,3-oxazole-4-carboxamide The title compound (112.1 mg) was obtained as colorless crystals by the reaction in the same manner as in Example 155 (iv) using 5-(2-aminoethyl)-N-{3-chloro-4-[3-(trifluoromethyl)phenoxy]phenyl}-5H-pyrrolo[3,2-d]pyrimidin-4-amine dihydrochloride (210 mg), 2-methyl-1,3-oxazole-4-carboxylic acid (210 mg), 1-ethyl-3-(3-dimethylaminopropyl)carbodiimide hydrochloride (560 mg), 1-hydroxybenzotriazole monohydrate (100 mg), triethylamine (2.0 mL) and tetrahydrofuran (10 mL).

$^1$H-NMR (DMSO-d$_6$) δ 2.41 (3H, s), 3.56 (2H, m), 4.67 (2H, m), 6.53 (1H, d, J=3 Hz), 7.21-7.91 (8H, m), 8.30 (1H, s), 8.42 (2H, m), 8.87 (1H, br s).

Example 226

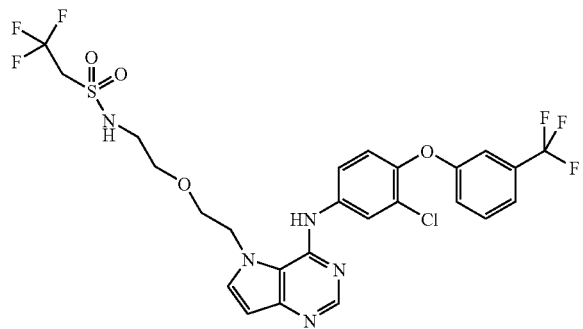

Production of N-(2-{2-[4-({3-chloro-4-[3-(trifluoromethyl)phenoxy]phenyl}amino)-5H-pyrrolo[3,2-d]pyrimidin-5-yl]ethoxy}ethyl)-2,2,2-trifluoroethanesulfonamide (i) Production of 2-(2-{2-[4-({3-chloro-4-[3-(trifluoromethyl)phenoxy]phenyl}amino)-5H-pyrrolo[3,2-d]pyrimidin-5-yl]ethoxy}ethyl)-1H-isoindole-1,3(2H)-dione The title compound (5.20 g) was obtained by the reaction in the same manner as in Example 172 (i) using 2-{2-[4-({3-chloro-4-[3-(trifluoromethyl)phenoxy]phenyl}amino)-5H-pyrrolo[3,2-d]pyrimidin-5-yl]ethoxy}ethanol (4.00 g), tetrahydrofuran (25 mL), triethylamine (13.0 mL), methanesulfonyl chloride (7.25 mL), potassium phthalimide (4.51 g), tetrahydrofuran (60 mL) and N,N-dimethylformamide (50 mL).

$^1$H-NMR (DMSO-d$_6$) δ 3.69 (4H, s), 3.83 (2H, m), 4.61 (2H, m), 6.33 (1H, m), 7.13-7.23 (3H, m), 7.42-7.95 (9H, m), 8.24 (1H, s), 8.75 (1H, s).

(ii) Production of N-(2-{2-[4-({3-chloro-4-[3-(trifluoromethyl)phenoxy]phenyl}amino)-5H-pyrrolo[3,2-d]pyrimidin-5-yl]ethoxy}ethyl)-2,2,2-trifluoroethanesulfonamide 2-(2-{2-[4-({3-Chloro-4-[3-(trifluoromethyl)phenoxy]phenyl}amino)-5H-pyrrolo[3,2-d]pyrimidin-5-yl]ethoxy}ethyl)-1H-isoindole-1,3(2H)-dione (100 mg) was dissolved in ethanol (2.0 mL), hydrazine monohydrate (0.45 mL) was added, and the mixture was stirred for 1 hr. To the reaction mixture was added saturated aqueous sodium hydrogen carbonate under ice-cooling, and the mixture was extracted with ethyl acetate. The extract was dried over magnesium sulfate and concentrated, and the residue was separated and purified by basic silica gel column chromatography (eluent, ethyl acetate:methanol=100:0→ethyl acetate:methanol=95:5). The obtained oil was dissolved in tetrahydrofuran (5.0 mL). N-Methylmorpholine (2.0 mL) was added, 2,2,2-trifluoroethanesulfonyl chloride (0.10 mL) was added dropwise under ice-cooling, and the mixture was stirred for 1 hr. Under ice-cooling, saturated aqueous sodium hydrogen carbonate was added, and the mixture was extracted with dichloromethane. The extract was dried over magnesium sulfate and concentrated, and the residue was separated and purified by silica gel column chromatography (eluent, ethyl acetate:methanol=100:0→ethyl acetate:methanol=80:20). Crystallization from diethyl ether/ethyl acetate gave the title compound (36.0 mg) as crystals.

$^1$H-NMR (DMSO-d$_6$) δ 3.10 (2H, m), 3.47 (2H, m), 3.79 (2H, m), 4.30 (2H, m), 4.68 (2H, m), 6.52 (1H, m), 7.20-8.02 (9H, m), 8.35 (1H, s), 8.79 (1H, s).

Example 227

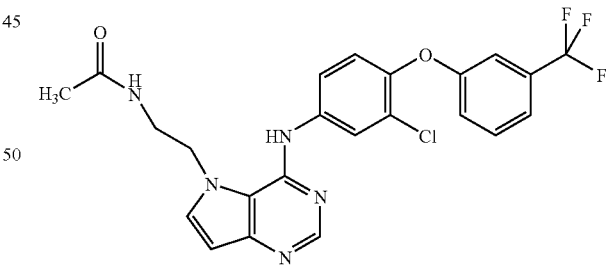

Production of N-{2-[4-({3-chloro-4-[3-(trifluoromethyl)phenoxy]phenyl}amino)-5H-pyrrolo[3,2-d]pyrimidin-5-yl]ethyl}acetamide The title compound (62.1 mg) was obtained as colorless crystals by the reaction in the same manner as in Example 155 (iv) using 5-(2-aminoethyl)-N-{3-chloro-4-[3-(trifluoromethyl)phenoxy]phenyl}-5H-pyrrolo[3,2-d]pyrimidin-4-amine dihydrochloride (270 mg), acetic acid (0.20 mL), 1-ethyl-3-(3-dimethylaminopropyl)carbodiimide hydrochloride (500 mg), 1-hydroxybenzotriazole monohydrate (100 mg), triethylamine (2.0 mL) and tetrahydrofuran (10 mL).

¹H-NMR (DMSO-d₆) δ 1.79 (3H, s), 3.37 (2H, m), 4.51 (2H, m), 6.51 (1H, d, J=3 Hz), 7.20-7.81 (7H, m), 8.06 (1H, m), 8.26 (1H, m), 8.34 (1H, s), 8.81 (1H, s).

Example 228

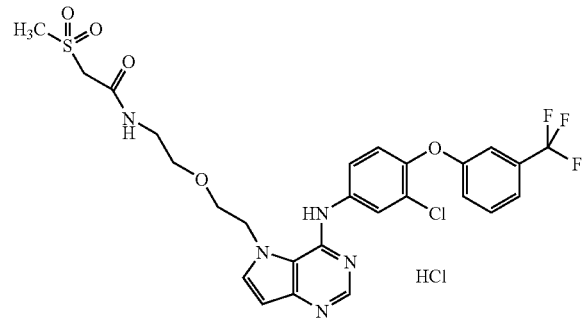

Production of N-(2-{2-[4-({3-chloro-4-[3-(trifluoromethyl)phenoxy]phenyl}amino)-5H-pyrrolo[3,2-d]pyrimidin-5-yl]ethoxy}ethyl)-2-(methylsulfonyl)acetamide hydrochloride 2-(2-{2-[4-({3-Chloro-4-[3-(trifluoromethyl)phenoxy]phenyl}amino)-5H-pyrrolo[3,2-d]pyrimidin-5-yl]ethoxy}ethyl)-1H-isoindole-1,3(2H)-dione (600 mg) was dissolved in ethanol (30 mL), hydrazine monohydrate (8.0 mL) was added, and the mixture was stirred for 1 hr. To the reaction mixture was added saturated aqueous sodium hydrogen carbonate under ice-cooling and the mixture was extracted with ethyl acetate. The extract was dried over magnesium sulfate and concentrated, and the residue was separated and purified by basic silica gel column chromatography (eluent, ethyl acetate:methanol=100:0→ethyl acetate:methanol=95:5). The title compound (312 mg) was obtained as colorless crystals by the reaction in the same manner as in Example 155 (iv) using the obtained oil, 2-(methylsulfonyl)acetic acid (500 mg), 1-ethyl-3-(3-dimethylaminopropyl)carbodiimide hydrochloride (1.50 g), 1-hydroxybenzotriazole monohydrate (200 mg), triethylamine (2.0 mL) and tetrahydrofuran (20 mL).

¹H-NMR (DMSO-d₆) δ 3.06 (3H, s), 3.16-3.47 (4H, m), 3.81 (2H, m), 3.98 (2H, s), 4.86 (2H, s), 6.70 (1H, m), 7.25-7.68 (6H, m), 7.97-8.01 (2H, m), 8.44 (1H, m), 8.75 (1H, s), 9.90 (1H, s).

Example 229

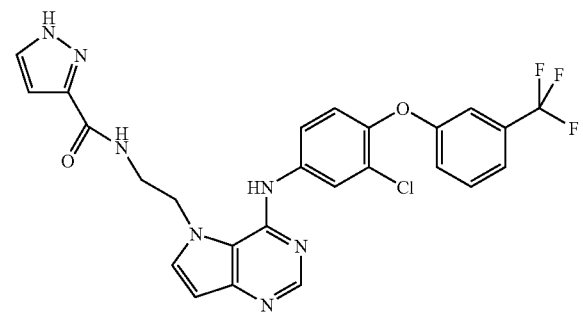

Production of N-{2-[4-({3-chloro-4-[3-(trifluoromethyl)phenoxy]phenyl}amino)-5H-pyrrolo[3,2-d]pyrimidin-5-yl]ethyl}-1H-pyrazole-3-carboxamide The title compound (67.0 mg) was obtained as colorless crystals by the reaction in the same manner as in Example 155 (iv) using 5-(2-aminoethyl)-N-{3-chloro-4-[3-(trifluoromethyl)phenoxy]phenyl}-5H-pyrrolo[3,2-d]pyrimidin-4-amine dihydrochloride (250 mg), 1H-pyrazole-3-carboxylic acid (210 mg), 1-ethyl-3-(3-dimethylaminopropyl)carbodiimide hydrochloride (500 mg), 1-hydroxybenzotriazole monohydrate (100 mg), triethylamine (2.0 mL) and tetrahydrofuran (15 mL).

¹H-NMR (DMSO-d₆) δ 3.58 (2H, m), 4.64 (2H, m), 6.49 (1H, m), 6.57 (1H, s), 7.21-7.79 (8H, m), 8.01 (1H, s), 8.33 (1H, s), 8.49 (1H, m), 8.77 (1H, s), 13.25 (1H, s).

Example 230

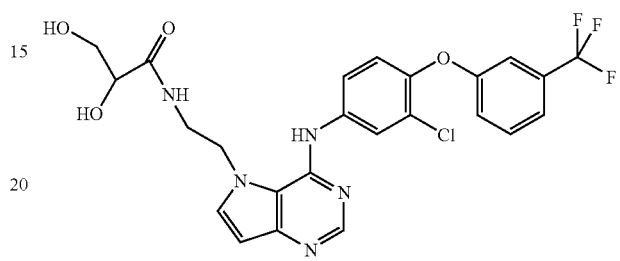

Production of (2R)—N-{2-[4-({3-chloro-4-[3-(trifluoromethyl)phenoxy]phenyl}amino)-5H-pyrrolo[3,2-d]pyrimidin-5-yl]ethyl}-2,3-dihydroxypropanamide The title compound (197.3 mg) was obtained as colorless crystals by the reaction in the same manner as in Example 155 (iv) using 5-(2-aminoethyl)-N-{3-chloro-4-[3-(trifluoromethyl)phenoxy]phenyl}-5H-pyrrolo[3,2-d]pyrimidin-4-amine dihydrochloride (350 mg), (2R)-2,3-dihydroxypropanoic acid (400 mg), 1-ethyl-3-(3-dimethylaminopropyl)carbodiimide hydrochloride (2.70 g), 1-hydroxybenzotriazole monohydrate (1.0 g), triethylamine (2.0 mL) and tetrahydrofuran (10 mL).

¹H-NMR (DMSO-d₆) δ 3.33-3.58 (4H, m), 3.87 (1H, m), 4.53 (2H, m), 4.69 (1H, m), 5.62 (1H, d, J=5 Hz), 6.48 (1H, d, J=3 Hz), 7.20-7.81 (7H, m), 8.05 (1H, d, J=2 Hz), 8.14 (1H, m), 8.34 (1H, s), 8.77 (1H, s).

Example 231

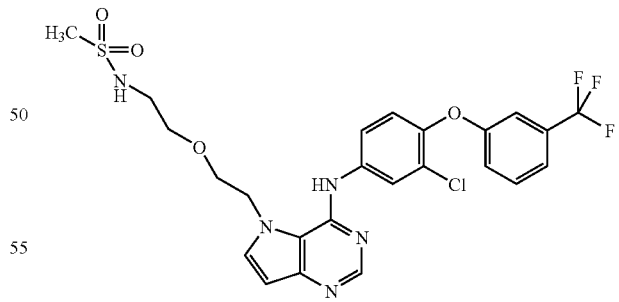

Production of N-(2-{2-[4-({3-chloro-4-[3-(trifluoromethyl)phenoxy]phenyl}amino)-5H-pyrrolo[3,2-d]pyrimidin-5-yl]ethoxy}ethyl)methanesulfonamide The title compound (18.2 mg) was obtained as colorless crystals by the reaction in the same manner as in Example 226 (ii) using 2-(2-{2-[4-({3-chloro-4-[3-(trifluoromethyl)phenoxy]phenyl}amino)-5H-pyrrolo[3,2-d]pyrimidin-5-yl]

ethoxy}ethyl)-1H-isoindole-1,3(2H)-dione (200 mg), hydrazine monohydrate (1.50 mL), methanesulfonyl chloride (0.70 mL), N-methylmorpholine (1.20 mL), ethanol (7.0 mL) and tetrahydrofuran (10 mL).

$^1$H-NMR (DMSO-$d_6$) δ 2.78 (3H, s), 3.04 (2H, m), 3.48 (2H, m), 3.79 (2H, m), 4.68 (2H, m), 6.52 (1H, d, J=3 Hz), 7.03-7.70 (8H, m), 8.02 (1H, s), 8.35 (1H, s), 8.81 (1H, s).

Example 232

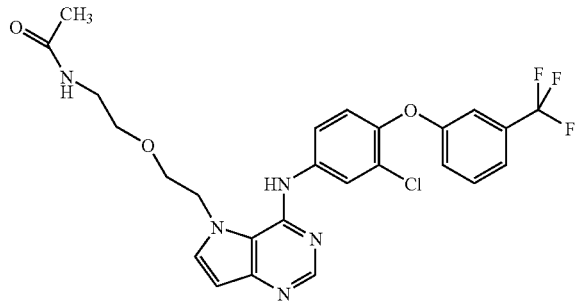

Production of N-(2-{2-[4-({3-chloro-4-[3-(trifluoromethyl)phenoxy]phenyl}amino)-5H-pyrrolo[3,2-d]pyrimidin-5-yl]ethoxy}ethyl)acetamide 2-(2-{2-[4-({3-Chloro-4-[3-(trifluoromethyl)phenoxy]phenyl}amino)-5H-pyrrolo[3,2-d]pyrimidin-5-yl]ethoxy}ethyl)-1H-isoindole-1,3(2H)-dione (200 mg) was dissolved in ethanol (5.0 mL), hydrazine monohydrate (3.0 mL) was added, and the mixture was stirred for 1 hr. To the reaction mixture was added saturated aqueous sodium hydrogen carbonate under ice-cooling and the mixture was extracted with ethyl acetate. The extract was dried over magnesium sulfate and concentrated, and the residue was separated and purified by basic silica gel column chromatography (eluent, ethyl acetate:methanol=100:0→ethyl acetate:methanol=95:5). The title compound (146.0 mg) was obtained as colorless crystals by the reaction in the same manner as in Example 180 using the obtained oil, acetic anhydride (1.0 mL), N-methylmorpholine (1.0 mL) and tetrahydrofuran (5.0 mL).

$^1$H-NMR (DMSO-$d_6$) δ 1.69 (3H, s), 3.12 (2H, m), 3.44 (2H, m), 3.79 (2H, m), 4.66 (2H, m), 6.52 (1H, d, J=3 Hz), 7.20-7.78 (8H, m), 8.00 (1H, s), 8.36 (1H, s), 8.85 (1H, s).

Example 233

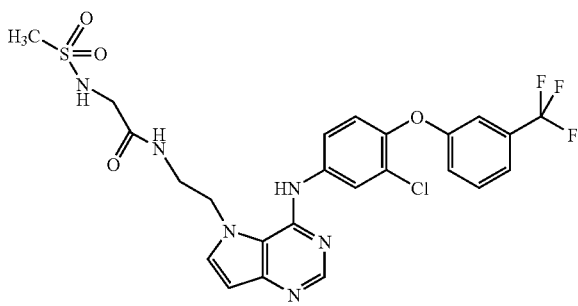

Production of N-{2-[4-({3-chloro-4-[3-(trifluoromethyl)phenoxy]phenyl}amino)-5H-pyrrolo[3,2-d]pyrimidin-5-yl]ethyl}-N2-(methylsulfonyl)glycinamide Using 5-(2-aminoethyl)-N-{3-chloro-4-[3-(trifluoromethyl)phenoxy]phenyl}-5H-pyrrolo[3,2-d]pyrimidin-4-amine dihydrochloride (450 mg), N-(tert-butoxy carbonyl) glycine (500 mg), 1-ethyl-3-(3-dimethylaminopropyl) carbodiimide hydrochloride (960 mg), 1-hydroxybenzotriazole monohydrate (300 mg), triethylamine (4.0 mL) and tetrahydrofuran (25 mL), the reaction was performed in the same manner as in Example 155 (iv). The obtained compound was dissolved in methanol (5.0 mL), 4N hydrochloric acid/ethyl acetate (8 mL) was added, and the mixture was stirred for 5 hrs. 8N Aqueous sodium hydroxide solution (8 mL) and water (10 mL) were added and the mixture was extracted with dichloromethane. The extract was dried over magnesium sulfate and concentrated, and the residue was dissolved in tetrahydrofuran (5.0 mL). N-Methylmorpholine (1.0 mL) was added, methanesulfonyl chloride (0.70 mL) was added dropwise under ice-cooling, and the mixture was stirred for 1 hr. Under ice-cooling, saturated aqueous sodium hydrogen carbonate was added and the mixture was extracted with dichloromethane. The extract was dried over magnesium sulfate and concentrated, and the residue was separated and purified by silica gel column chromatography (eluent, ethyl acetate:methanol=100:0→ethyl acetate:methanol=80:20), and crystallized from diethyl ether/ethyl acetate to give the title compound (47.9 mg) as crystals.

$^1$H-NMR (DMSO-$d_6$) δ 2.89 (3H, s), 3.46 (2H, m), 3.58 (2H, m), 4.54 (2H, m), 6.51 (1H, d, J=3 Hz), 7.20-7.78 (8H, m), 8.02 (1H, s), 8.27 (1H, m), 8.36 (1H, s), 8.77 (1H, s).

Example 234

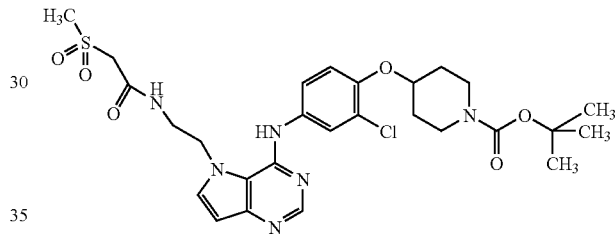

Production of tert-butyl 4-(2-chloro-4-{[5-(2-{[(methylsulfonyl)acetyl]amino}ethyl)-5H-pyrrolo[3,2-d]pyrimidin-4-yl]amino}phenoxy)piperidine-1-carboxylate (i) Production of N-[2-(4-chloro-5H-pyrrolo[3,2-d]pyrimidin-5-yl)ethyl]-2-(methylsulfonyl)acetamide tert-Butyl [2-(4-chloro-5H-pyrrolo[3,2-d]pyrimidin-5-yl)ethyl]carbamate (300 mg) was dissolved in trifluoroacetic acid (5.0 mL), and the mixture was stirred for 15 min. Toluene (5 mL) was added, the solvent was evaporated, and the residue was separated and purified by basic silica gel column chromatography (eluent, ethyl acetate:methanol=100:0→ethyl acetate:methanol=75:25). The title compound (64.0 mg) as colorless crystals were obtained by the reaction in the same manner as in Example 155 (iv) using obtained oil, 1-ethyl-3-(3-dimethylaminopropyl)carbodiimide hydrochloride (2.50 g), triethylamine (2.0 mL), 2-(methylsulfonyl)acetic acid (180 mg) and tetrahydrofuran (10 mL).

$^1$H-NMR (DMSO-$d_6$) δ 3.07 (3H, s), 3.57 (2H, m), 4.00 (2H, s), 4.57 (2H, m), 6.74 (1H, d, J=3 Hz), 7.92 (1H, d, J=3 Hz), 8.49 (1H, m), 8.63 (1H, s).

(ii) Production of tert-butyl 4-(2-chloro-4-{[5-(2-{[(methylsulfonyl)acetyl]amino}ethyl)-5H-pyrrolo[3,2-d]pyrimidin-4-yl]amino}phenoxy)piperidine-1-carboxylate The title compound (24.0 mg) was obtained as colorless crystals by the reaction in the same manner as in Example 155

(ii) using N-[2-(4-chloro-5H-pyrrolo[3,2-d]pyrimidin-5-yl)ethyl]-2-(methylsulfonyl)acetamide (60.0 mg) and tert-butyl 4-(4-amino-2-chlorophenoxy)piperidine-1-carboxylate (160 mg).

$^1$H-NMR (DMSO-$d_6$) δ 1.41 (9H, s), 1.50-1.70 (2H, m), 1.81-1.95 (2H, m), 3.10 (3H, s), 3.22-3.60 (6H, m), 4.04 (2H, s), 4.45-4.65 (3H, m), 6.47 (1H, d, J=3 Hz), 7.23 (1H, d, J=9 Hz), 7.55-7.58 (2H, m), 7.75 (1H, d, J=3 Hz), 8.27 (1H, s), 8.48 (1H, s), 8.66 (1H, m).

Example 235

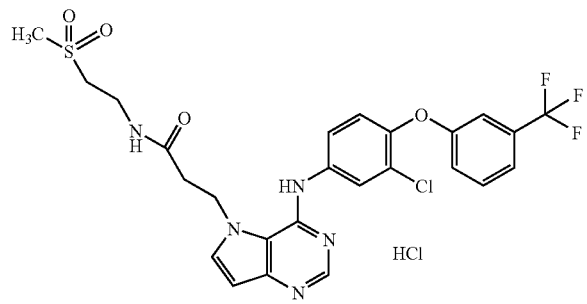

Production of 3-[4-({3-chloro-4-[3-(trifluoromethyl)phenoxy]phenyl}amino)-5H-pyrrolo[3,2-d]pyrimidin-5-yl]-N-[2-(methylsulfonyl)ethyl]propanamide hydrochloride (i) Production of ethyl 3-(4-chloro-5H-pyrrolo[3,2-d]pyrimidin-5-yl)propanoate 4-Chloro-5H-pyrrolo[3,2-d]pyrimidine (303 mg) was dissolved in N,N-dimethylformamide (9 mL), ethyl acrylate (0.3 mL) and potassium carbonate (538 mg) were sequentially added, and the mixture was stirred at room temperature for 7.5 hrs. Ethyl acrylate (0.2 mL) was added, and the mixture was stirred for 16 hrs. Ethyl acrylate (0.3 mL) and potassium carbonate (526 mg) were further added, and the mixture was stirred for 6 hrs. The reaction mixture was treated with saturated aqueous ammonium chloride solution and the mixture was extracted with ethyl acetate. The organic layer was washed with saturated brine, dried over anhydrous magnesium sulfate and concentrated under reduced pressure. The residue was separated and purified by silica gel column chromatography (eluent, hexane:ethyl acetate=66:34→20:80) to give the title compound (404 mg) as a colorless oil.

$^1$H-NMR (CDCl$_3$) δ: 1.22 (3H, t, J=7.1 Hz), 2.92 (2H, t, J=6.3 Hz), 4.13 (2H, q, J=7.1 Hz), 4.80 (2H, t, J=6.3 Hz), 6.70 (1H, d, J=3.3 Hz), 7.61 (1H, d, J=3.3 Hz), 8.71 (1H, s).

(ii) Production of ethyl 3-[4-({3-chloro-4-[3-(trifluoromethyl)phenoxy]phenyl}amino)-5H-pyrrolo[3,2-d]pyrimidin-5-yl]propanoate The title compound (687 mg) was obtained as a pale-yellow oil by the reaction in the same manner as in Example 201 (iii) using ethyl 3-(4-chloro-5H-pyrrolo[3,2-d]pyrimidin-5-yl)propanoate (404 mg), isopropyl alcohol (10 mL) and 3-chloro-4-[3-(trifluoromethyl)phenoxy]aniline (555 mg).

$^1$H-NMR (CDCl$_3$) δ: 1.26 (3H, t, J=7 Hz), 2.99-3.10 (2H, m), 4.24 (2H, q, J=7 Hz), 4.53-4.65 (2H, m), 6.69 (1H, d, J=3.3 Hz), 7.06-7.17 (2H, m), 7.18-7.24 (1H, m), 7.27-7.35 (2H, m), 7.43 (1H, t, J=7.9 Hz), 7.65 (1H, dd, J=8.8 Hz, 2.6 Hz), 7.92 (1H, d, J=2.6 Hz), 8.54 (1H, s), 9.14 (1H, s).

(iii) Production of 3-[4-({3-chloro-4-[3-(trifluoromethyl)phenoxy]phenyl}amino)-5H-pyrrolo[3,2-d]pyrimidin-5-yl]propanoic acid The title compound (595 mg) was obtained as a pale-yellow powder by the reaction in the same manner as in Example 202 (ii) using a mixed solvent of ethyl 3-[4-({3-chloro-4-[3-(trifluoromethyl)phenoxy]phenyl}amino)-5H-pyrrolo[3,2-d]pyrimidin-5-yl]propanoate (683 mg), 1N aqueous sodium hydroxide solution (2 mL) and tetrahydrofuran (6 mL)/ethanol (6 mL).

$^1$H-NMR (DMSO-$d_6$) δ: 2.84 (2H, t, J=6.4 Hz), 4.69 (2H, t, J=6.4 Hz), 6.52 (1H, d, J=3.0 Hz), 7.14-7.29 (2H, m), 7.32 (1H, d, J=8.9 Hz), 7.47 (1H, d, J=7.7 Hz), 7.56-7.80 (3H, m), 7.94 (1H, s), 8.35 (1H, s), 9.10 (1H, s), 12.72 (1H, s).

(iv) Production of 3-[4-({3-chloro-4-[3-(trifluoromethyl)phenoxy]phenyl}amino)-5H-pyrrolo[3,2-d]pyrimidin-5-yl]-N-[2-(methylsulfonyl)ethyl]propanamide hydrochloride 3-[4-({3-Chloro-4-[3-(trifluoromethyl)phenoxy]phenyl}amino)-5H-pyrrolo[3,2-d]pyrimidin-5-yl]-N-[2-(methylsulfonyl)ethyl]propanamide (140 mg) was obtained by the reaction in the same manner as in Example 202 (iii) using 3-[4-({3-chloro-4-[3-(trifluoromethyl)phenoxy]phenyl}amino)-5H-pyrrolo[3,2-d]pyrimidin-5-yl]propanoic acid (199 mg), 2-(methylsulfonyl)ethanamine (106 mg), 1-hydroxybenzotriazole monohydrate (84.7 mg), N-[3-(dimethylamino)propyl]-N'-ethylcarbodiimide hydrochloride (128.6 mg), triethylamine (0.1 mL) and N,N-dimethylformamide (2 mL). The obtained 3-[4-({3-chloro-4-[3-(trifluoromethyl)phenoxy]phenyl}amino)-5H-pyrrolo[3,2-d]pyrimidin-5-yl]-N-[2-(methylsulfonyl)ethyl]propanamide was dissolved in ethyl acetate (2 mL), 4N hydrochloric acid-ethyl acetate (0.1 mL) was added, and the precipitate was collected by filtration and dried to give the title compound (119 mg) as a white powder.

$^1$H-NMR (DMSO-$d_6$) δ: 2.82-2.90 (2H, m), 2.91 (3H, s), 3.18 (2H, t, J=6.6 Hz), 3.40-3.51 (2H, m), 4.72-4.83 (2H, m), 6.70 (1H, d, J=3.0 Hz), 7.23-7.32 (2H, m), 7.41 (1H, d, J=8.8 Hz), 7.52 (1H, d, J=7.7 Hz), 7.66 (1H, t, J=7.7 Hz), 7.74 (1H, dd, J=8.8 Hz, 2.5 Hz), 8.01-8.08 (2H, m), 8.67 (1H, t, J=5.6 Hz), 8.76 (1H, s), 10.80 (1H, s).

Example 236

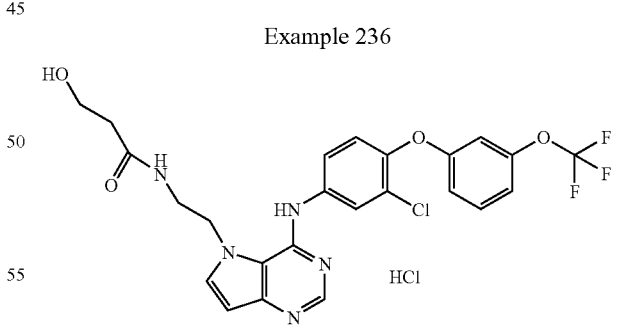

Production of N-{2-[4-({3-chloro-4-[3-(trifluoromethoxy)phenoxy]phenyl}amino)-5H-pyrrolo[3,2-d]pyrimidin-5-yl]ethyl}-3-hydroxypropanamide hydrochloride N-{2-[4-({3-Chloro-4-[3-(trifluoromethoxy)phenoxy]phenyl}amino)-5H-pyrrolo[3,2-d]pyrimidin-5-yl]ethyl}-3-hydroxypropanamide was obtained by the reaction in the same manner as in Example 202 (iii) using 5-(2-aminoethyl)-N-{3-chloro-4-[3-(trifluoromethoxy)phenoxy]phenyl}-5H-pyrrolo[3,2-d]pyrimidin-4-amine dihydrochloride (303 mg), 3.6M aqueous solution (0.25 mL) of 3-hydroxypropanoic acid, 1-hydroxybenzotriazole monohydrate (231 mg), N-[3-(dimethylamino)propyl]-N-ethylcarbodiimide hydrochloride (322 mg), triethylamine (0.8 mL) and N,N-dimethylformamide (3 mL). The obtained N-{2-[4-({3-chloro-4-[3-(trifluoromethoxy)phenoxy]phenyl}amino)-5H-pyrrolo[3,2-d]pyrimidin-5-yl]ethyl}-3-hydroxypropanamide was dissolved in ethyl acetate (2 mL), 4N hydrochloric acid-ethyl acetate (0.1 mL) was added, and the obtained product was crystallized from ethyl acetate to give the title compound (80.9 mg) as white crystals.

$^1$H-NMR (DMSO-$d_6$) δ: 2.21 (2H, t, J=6.5 Hz), 3.39-3.51 (2H, m), 3.54 (2H, t, J=6.5 Hz), 4.67 (2H, t, J=7.0 Hz), 6.68 (1H, t, J=3.0 Hz), 6.94-7.04 (2H, m), 7.16 (1H, d, J=8.3 Hz), 7.36 (1H, d, J=8.8 Hz), 7.54 (1H, t, J=8.3 Hz), 7.72 (1H, dd, J=8.8 Hz, 2.6 Hz), 7.93-8.04 (2H, m), 8.36 (1H, t, J=5.8 Hz), 8.74 (1H, s), 10.23 (1H, s).

Example 237

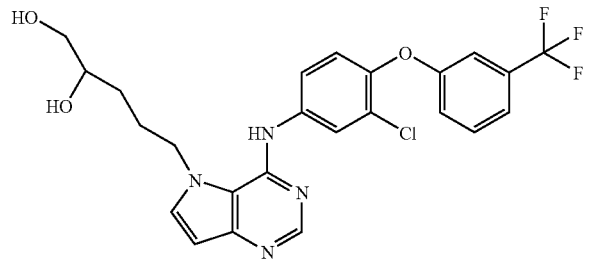

Production of 5-[4-({3-chloro-4-[3-(trifluoromethyl)phenoxy]phenyl}amino)-5H-pyrrolo[3,2-d]pyrimidin-5-yl]pentane-1,2-diol (i) Production of 3-(2,2-dimethyl-1,3-dioxolan-4-yl)propan-1-ol Pentane-1,2,5-triol (5.00 g) was dissolved in acetone (150 mL), 2,2-dimethoxypropane (10.5 mL) and 4-methylbenzenesulfonic acid (794 mg) were added, and the mixture was stirred at room temperature for 1.5 hrs. The reaction mixture was concentrated under reduced pressure, and the residue was separated and purified by silica gel column chromatography (eluent, hexane:ethyl acetate=80:20→50:50) to give the title compound (3.79 g) as a colorless oil.

$^1$H-NMR (CDCl$_3$) δ: 1.37 (3H, s), 1.42 (3H, s), 1.57-1.77 (4H, m), 2.05 (1H, br s), 3.53 (1H, t, J=7.3 Hz), 3.60-3.77 (2H, m), 4.00-4.21 (2H, m).

(ii) Production of 3-(2,2-dimethyl-1,3-dioxolan-4-yl)propyl methanesulfonate

The title compound (2.13 g) was obtained as a colorless oil by the reaction in the same manner as in Example 203 (ii) using 3-(2,2-dimethyl-1,3-dioxolan-4-yl)propan-1-ol (2.30 g), methanesulfonyl chloride (0.8 mL), triethylamine (3.0 mL) and ethyl acetate (50 mL).

$^1$H-NMR (CDCl$_3$) δ: 1.35 (3H, s), 1.41 (3H, s), 1.62-1.73 (2H, m), 1.75-2.02 (2H, m), 3.02 (3H, m), 3.50-3.57 (1H, m), 4.02-4.17 (2H, m), 4.21-4.36 (2H, m).

(iii) Production of 4-chloro-5-[3-(2,2-dimethyl-1,3-dioxolan-4-yl)propyl]-5H-pyrrolo[3,2-d]pyrimidine The title compound (176 mg) was obtained as a white powder by the reaction in the same manner as in Example 201 (ii) using 4-chloro-5H-pyrrolo[3,2-d]pyrimidine (151 mg), 3-(2,2-dimethyl-1,3-dioxolan-4-yl)propyl methanesulfonate (319 mg), cesium carbonate (574 mg) and N,N-dimethylformamide (1.5 mL).

$^1$H-NMR (CDCl$_3$) δ: 1.34 (3H, s), 1.40 (3H, s), 1.53-1.73 (2H, m), 1.80-2.13 (2H, m), 3.47-3.53 (1H, m), 3.97-4.18 (2H, m), 4.41-4.70 (2H, m), 6.72 (1H, d, J=3.3 Hz), 7.51 (1H, d, J=3.3 Hz), 8.70 (1H, s).

(iv) Production of 5-[4-({3-chloro-4-[3-(trifluoromethyl)phenoxy]phenyl}amino)-5H-pyrrolo[3,2-d]pyrimidin-5-yl]pentane-1,2-diol The crude product was obtained by the reaction in the same manner as in Example 201 (iii) using 4-chloro-5-[3-(2,2-dimethyl-1,3-dioxolan-4-yl)propyl]-5H-pyrrolo[3,2-d]pyrimidine (171 mg), 3-chloro-4-[3-(trifluoromethyl)phenoxy]aniline (195 mg) and isopropyl alcohol (3.5 mL). The crude product was dissolved in methanol (1 mL), 1N hydrochloric acid (0.5 mL) was added, and the mixture was stirred at room temperature for 3.5 hrs. The reaction mixture was treated with 1N aqueous sodium hydroxide solution, extracted with ethyl acetate, washed with saturated brine, dried over anhydrous magnesium sulfate and concentrated under reduced pressure. The residue was separated and purified by silica gel column chromatography (eluent, ethyl acetate:methanol=100:0→95:5) to give the title compound (179 mg) as white crystals.

$^1$H-NMR (DMSO-$d_6$) δ: 1.03-1.41 (2H, m), 1.61-1.93 (2H, m), 3.08-3.28 (2H, m), 3.28-3.43 (1H, m), 4.44 (1H, t, J=5.5 Hz), 4.47-4.59 (3H, m), 6.49 (1H, d, J=3.0 Hz), 7.17-7.27 (2H, m), 7.30 (1H, d, J=9.1 Hz), 7.47 (1H, d, J=8.5 Hz), 7.57-7.74 (3H, m), 7.97 (1H, d, J=2.4 Hz), 8.34 (1H, s), 8.61 (1H, s).

Example 238

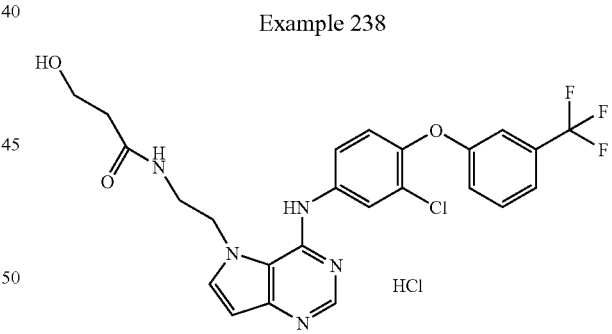

Production of N-{2-[4-({3-chloro-4-[3-(trifluoromethyl)phenoxy]phenyl}amino)-5H-pyrrolo[3,2-d]pyrimidin-5-yl]ethyl}-3-hydroxypropanamide hydrochloride N-{2-[4-({3-Chloro-4-[3-(trifluoromethyl)phenoxy]phenyl}amino)-5H-pyrrolo[3,2-d]pyrimidin-5-yl]ethyl}-3-hydroxypropanamide was obtained by the reaction in the same manner as in Example 202 (iii) using 5-(2-aminoethyl)-N-{3-chloro-4-[3-(trifluoromethyl)phenoxy]phenyl}-5H-pyrrolo[3,2-d]pyrimidin-4-amine dihydrochloride (300 mg), 3.6 M aqueous solution (0.25 mL) of 3-hydroxypropanoic acid, 1-hydroxybenzotriazole monohydrate (231 mg), N-[3-

(dimethylamino)propyl]-N-ethylcarbodiimide hydrochloride (330 mg), triethylamine (0.8 mL) and N,N-dimethylformamide (3 mL). The obtained N-{2-[4-({3-chloro-4-[3-(trifluoromethyl)phenoxy]phenyl}amino)-5H-pyrrolo[3,2-d]pyrimidin-5-yl]ethyl}-3-hydroxypropanamide was dissolved in ethyl acetate (2 mL), and 4N hydrochloric acid-ethyl acetate (0.1 mL) was added. The obtained product was recrystallized from ethyl acetate to give the title compound (63.1 mg) as a white powder.

$^1$H-NMR (DMSO-d$_6$) δ: 2.22 (2H, t, J=6.5 Hz), 3.39-3.52 (2H, m), 3.55 (2H, t, J=6.5 Hz), 4.65 (2H, t, J=6.7 Hz), 6.67 (1H, d, J=3.0 Hz), 7.24-7.32 (2H, m), 7.37 (1H, d, J=8.8 Hz), 7.53 (1H, d, J=8.0 Hz), 7.66 (1H, t, J=8.0 Hz), 7.72 (1H, dd, J=8.8 Hz, 2.5 Hz), 7.96-8.01 (2H, m), 8.34 (1H, t, J=5.8 Hz), 8.74 (1H, s), 10.17 (1H, s).

Example 239

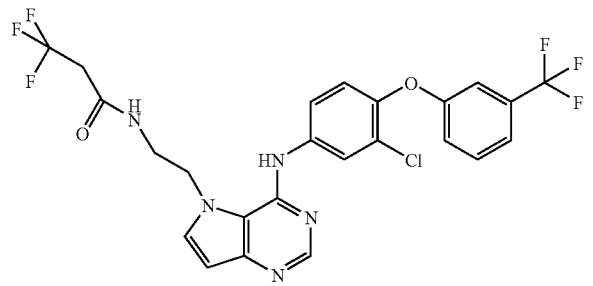

Production of N-{2-[4-({3-chloro-4-[3-(trifluoromethyl)phenoxy]phenyl}amino)-5H-pyrrolo[3,2-d]pyrimidin-5-yl]ethyl}-3,3,3-trifluoropropanamide The title compound (64.0 mg) was obtained as yellow crystals by the reaction in the same manner as in Example 202 (iii) using 5-(2-aminoethyl)-N-{3-chloro-4-[3-(trifluoromethyl)phenoxy]phenyl}-5H-pyrrolo[3,2-d]pyrimidin-4-amine dihydrochloride (150 mg), 3,3,3-trifluoropropanoic acid (0.06 mL), 1-hydroxybenzotriazole monohydrate (142 mg), N-[3-(dimethylamino)propyl]-N-ethylcarbodiimide hydrochloride (200 mg), triethylamine (0.4 mL) and N,N-dimethylformamide (1.5 mL) and crystallization from diisopropyl ether.

$^1$H-NMR (DMSO-d$_6$) δ: 3.19 (2H, q, J=11.2 Hz) 3.43 (2H, m), 4.58 (2H, t, J=6.4 Hz), 6.52 (1H, d, J=3.0 Hz), 7.18-7.26 (2H, m), 7.30 (1H, d, J=9 Hz), 7.47 (1H, d, J=7.5 Hz), 7.57-7.67 (2H, m), 7.76 (1H, dd, J=9 Hz, 2.5 Hz), 8.00 (1H, d, J=2.5 Hz), 8.36 (1H, s), 8.50 (1H, t, J=5.3 Hz), 8.72 (1H, s).

Example 240

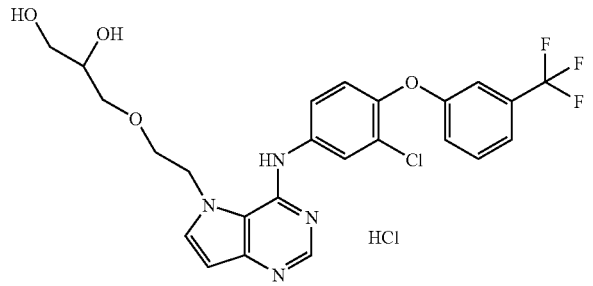

Production of 3-{2-[4-({3-chloro-4-[3-(trifluoromethyl)phenoxy]phenyl}amino)-5H-pyrrolo[3,2-d]pyrimidin-5-yl]ethoxy}propane-1,2-diol hydrochloride (i) Production of tert-butyl {2-[(2,2-dimethyl-1,3-dioxolan-4-yl)methoxy]ethoxy}dimethylsilane 60% Sodium hydride (890 mg) was suspended in N,N-dimethylformamide (60 mL), and the suspension was cooled to 0° C. (2,2-Dimethyl-1,3-dioxolan-4-yl)methanol (2.3 mL) was added dropwise and the mixture was stirred at 0° C. for 1 hr. To the reaction mixture was added (2-bromoethoxy)(tert-butyl)dimethylsilane (3 mL), and the mixture was stirred at 0° C. for 2 hrs. To the reaction mixture was added saturated aqueous ammonium chloride solution, and the mixture was extracted with ethyl acetate. The organic layer was washed with saturated brine, dried over anhydrous magnesium sulfate and concentrated under reduced pressure. The residue was separated and purified by silica gel column chromatography (eluent, hexane:ethyl acetate=100:0→90:10) to give the title compound (1.04 g) as a yellow oil.

$^1$H-NMR (CDCl$_3$) δ: 0.06 (6H, s), 0.89 (9H, s), 1.36 (3H, s), 1.42 (3H, s), 3.47-3.63 (4H, m) 3.71-3.79 (3H, m), 4.06 (1H, dd, J=8.2 Hz, 6.3 Hz), 4.20-4.35 (1H, m).

(ii) Production of 2-[(2,2-dimethyl-1,3-dioxolan-4-yl)methoxy]ethyl methanesulfonate tert-Butyl{2-[(2,2-dimethyl-1,3-dioxolan-4-yl)methoxy]ethoxy}dimethylsilane (1.03 g) was dissolved in tetrahydrofuran (20 mL), a 1.0 M solution (4 mL) of tetrabutylammonium fluoride in tetrahydrofuran was added, and the mixture was stirred at room temperature for 1 hr. To the reaction mixture was added saturated aqueous ammonium chloride solution, and the mixture was extracted with ethyl acetate. The organic layer was washed with saturated brine, dried over anhydrous magnesium sulfate and concentrated under reduced pressure. The residue was dissolved in ethyl acetate (20 mL) and subjected the reaction similar to that in Example 203 (ii) using methanesulfonyl chloride (0.3 mL) and triethylamine (2 mL) to give the title compound (857 mg) as a yellow oil.

$^1$H-NMR (CDCl$_3$) δ: 1.36 (3H, s), 1.42 (3H, s), 3.07 (3H, s), 3.56 (1H, d, J=1.4 Hz), 3.58 (1H, d, J=1.9 Hz), 3.73 (1H, dd, J=8.3 Hz, 6.3 Hz), 3.77-3.82 (2H, m), 4.06 (1H, dd, J=8.3 Hz, 6.3 Hz), 4.24-4.33 (1H, m), 4.35-4.41 (2H, m).

(iii) Production of 4-chloro-5-{2-[(2,2-dimethyl-1,3-dioxolan-4-yl)methoxy]ethyl}-5H-pyrrolo[3,2-d]pyrimidine The title compound (298 mg) was obtained as a colorless oil by the reaction in the same manner as in Example 201 (ii) using 4-chloro-5H-pyrrolo[3,2-d]pyrimidine (152 mg), 2-[(2,2-dimethyl-1,3-dioxolan-4-yl)methoxy]ethyl methanesulfonate (327 mg), cesium carbonate (576 mg) and N,N-dimethylformamide (1.5 mL).

$^1$H-NMR (CDCl$_3$) δ: 1.33 (3H, s), 1.38 (3H, s), 3.37-3.50 (2H, m), 3.59 (1H, dd, J=8.3 Hz, 6.6 Hz), 3.87 (2H, dt, J=5.1 Hz, 2.2 Hz), 3.96 (1H, dd, J=8.3 Hz, 6.6 Hz), 4.11-4.22 (1H, m), 4.66-4.72 (2H, m), 6.71 (1H, d, J=3 Hz), 7.57 (1H, d, J=3 Hz), 8.70 (1H, s).

(iv) Production of 3-{2-[4-({3-chloro-4-[3-(trifluoromethyl)phenoxy]phenyl}amino)-5H-pyrrolo[3,2-d]pyrimidin-5-yl]ethoxy}propane-1,2-diol hydrochloride 3-{2-[4-({3-Chloro-4-[3-(trifluoromethyl)phenoxy]phenyl}amino)-5H-pyrrolo[3,2-d]pyrimidin-5-yl]ethoxy}propane-1,2-diol was obtained by the reaction in the same manner as in Example 237 (iv) using 4-chloro-5-{2-[(2,2-dimethyl-1,3-dioxolan-4-yl)methoxy]ethyl}-5H-pyrrolo[3,2-d]pyrimidine (295 mg), 3-chloro-4-[3-(trifluoromethyl)phenoxy]aniline (359 mg) and isopropyl alcohol (6 mL). The obtained 3-{2-[4-({3-chloro-4-[3-(trifluoromethyl)phenoxy]phenyl}amino)-5H-pyrrolo[3,2-O]pyrimidin-5-yl]ethoxy}propane-1,2-diol was dissolved in ethyl acetate (6 mL), 4N hydrochloric acid-ethyl acetate (0.2 mL) was added, and the mixture was concentrated under reduced pressure. The residue was crystallized from ethyl acetate to give the title compound (360 mg) as a white powder.

$^1$H-NMR (DMSO-$d_6$) δ: 3.10-3.26 (2H, m), 3.31-3.42 (1H, m), 3.42-3.56 (2H, m), 3.78-3.89 (2H, m), 4.77-4.89 (2H, m), 6.71 (1H, d, J=3.0 Hz), 7.22-7.31 (2H, m), 7.36 (1H, d, J=8.8 Hz), 7.52 (1H, d, J=7.7 Hz), 7.60-7.73 (2H, m), 7.96-8.06 (2H, m), 8.75 (1H, s), 9.96 (1H, s).

Example 241

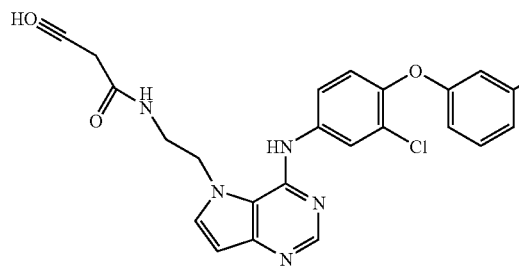

Production of N-{2-[4-({3-chloro-4-[3-(trifluoromethyl)phenoxy]phenyl}amino)-5H-pyrrolo[3,2-d]pyrimidin-5-yl]ethyl}-2-cyanoacetamide The title compound (104 mg) was obtained as a yellow powder by the reaction in the same manner as in Example 202 (iii) using 5-(2-aminoethyl)-N-{3-chloro-4-[3-(trifluoromethyl)phenoxy]phenyl}-5H-pyrrolo[3,2-d]pyrimidin-4-amine dihydrochloride (201 mg), cyanoacetic acid (65.9 mg), 1-hydroxybenzotriazole monohydrate (215 mg), N-[3-(dimethylamino)propyl]-N-ethylcarbodiimide hydrochloride (300 mg), triethylamine (0.55 mL) and N,N-dimethylformamide (2.0 mL) and crystallization from diisopropyl ether.

$^1$H-NMR (DMSO-$d_6$) δ: 3.36-3.47 (2H, m), 3.56 (2H, s), 4.58 (2H, t, J=6.3 Hz), 6.52 (1H, d, J=3.3 Hz), 7.18-7.28 (2H, m), 7.31 (1H, d, J=8.8 Hz), 7.47 (1H, d, J=7.7 Hz), 7.56-7.68 (2H, m), 7.73 (1H, dd, J=8.8 Hz, 2.5 Hz), 7.99 (1H, d, J=2.5 Hz), 8.36 (1H, s), 8.44 (1H, t, J=5.8 Hz), 8.67 (1H, s).

Example 242

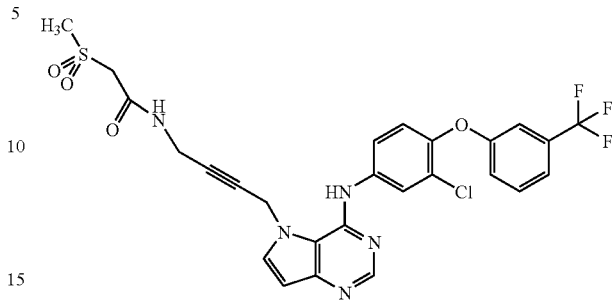

Production of N-{4-[4-({3-chloro-4-[3-(trifluoromethyl)phenoxy]phenyl}amino)-5H-pyrrolo[3,2-d]pyrimidin-5-yl]but-2-yn-1-yl}-2-(methylsulfonyl)acetamide (i) Production of tert-butyl (4-chlorobut-2-yn-1-yl)carbamate 4-Chlorobut-2-yn-1-amine hydrochloride (10.5 g) was dissolved in a mixed solvent of water (200 mL)/methanol (40 mL), di-tert-butyl dicarbonate (19 mL) was added, and the mixture was stirred at room temperature for 2 hrs. In this case, the reaction solution was maintained at pH 10-11 with 4N aqueous sodium hydroxide solution. Water was added to the reaction mixture and the mixture was extracted with ethyl acetate. The organic layer was washed with saturated brine, dried over anhydrous magnesium sulfate and concentrated under reduced pressure. The residue was separated and purified by silica gel column chromatography (eluent, hexane:ethyl acetate=100:0→80:20) to give the title compound (14.5 g) as a pale-yellow oil.

$^1$H-NMR (CDCl$_3$) δ: 1.45 (9H, s), 3.89-4.06 (2H, m), 4.14 (2H, t, J=2.1 Hz), 4.71 (1H, br s).

(ii) Production of tert-butyl [4-(4-chloro-5H-pyrrolo[3,2-d]pyrimidin-5-yl)but-2-yn-1-yl]carbamate A mixture of 4-chloro-5H-pyrrolo[3,2-d]pyrimidine (1.51 g), tert-butyl (4-chlorobut-2-yn-1-yl)carbamate (2.60 g), cesium carbonate (4.80 g) and N,N-dimethylformamide (15 mL) was stirred at room temperature for 2 hrs. Water was added to the reaction mixture and the mixture was extracted with ethyl acetate. The organic layer was washed with saturated brine, dried over anhydrous magnesium sulfate and concentrated under reduced pressure. The residue was separated and purified by silica gel column chromatography (eluent, hexane:ethyl acetate=80:20→33:67) to give the title compound (2.61 g) as an orange oil.

$^1$H-NMR (CDCl$_3$) δ: 1.44 (9H, s), 3.87-4.05 (2H, m), 4.71 (1H, s), 5.29 (2H, t, J=2.1 Hz), 6.76 (1H, d, J=3.3 Hz), 7.70 (1H, d, J=3.3 Hz), 8.72 (1H, s).

(iii) Production of tert-butyl {4-[4-({3-chloro-4-[3-(trifluoromethyl)phenoxy]phenyl}amino)-5H-pyrrolo[3,2-d]pyrimidin-5-yl]but-2-yn-1-yl}carbamate The title compound (1.86 g) was obtained as a colorless powder by the reaction in the same manner as in Example 201 (iii) using tert-butyl [4-(4-chloro-5H-pyrrolo[3,2-d]pyrimidin-5-yl)but-2-yn-1-yl]carbamate (1.32 g), 3-chloro-4-[3-(trifluoromethyl)phenoxy]aniline (1.43 g) and isopropyl alcohol (25 mL) and crystallization from hexane/diisopropyl ether.

$^1$H-NMR (CDCl$_3$) δ: 1.39 (9H, s), 4.03-4.08 (2H, m), 4.80 (1H, br s), 5.08 (2H, t, J=2.1 Hz), 6.60 (1H, d, J=3.3 Hz), 7.09 (1H, d, J=8.8 Hz), 7.10-7.15 (1H, m), 7.18-7.23 (2H, m), 7.33 (1H, d, J=7.8 Hz), 7.43 (1H, t, J=7.8 Hz), 7.51 (1H, dd, J=8.8 Hz, 2.5 Hz), 7.68 (1H, s), 7.97 (1H, d, J=2.5 Hz), 8.56 (1H, s).

(iv) Production of 5-(4-aminobut-2-yn-1-yl)-N-{3-chloro-4-[3-(trifluoromethyl)phenoxy]phenyl}-5H-pyrrolo[3,2-d]pyrimidin-4-amine dihydrochloride tert-Butyl {4-[4-({3-chloro-4-[3-(trifluoromethyl)phenoxy]phenyl}amino)-5H-pyrrolo[3,2-d]pyrimidin-5-yl]but-2-yn-1-yl}carbamate (1.90 g) was dissolved in tetrahydrofuran (35 mL), 2N hydrochloric acid (18 mL) was added, and the mixture was stirred at 60° C. for 16 hrs. To the reaction mixture was added ethanol, and the mixture was concentrated under reduced pressure. The residue was crystallized from ethyl acetate to give the title compound (802 mg) as a white powder.

$^1$H-NMR (DMSO-d$_6$) δ: 3.71-3.84 (2H, m), 5.97 (2H, s), 6.74 (1H, d, J=3 Hz), 7.23-7.32 (2H, m), 7.36 (1H, d, J=8.8 Hz), 7.52 (1H, d, J=8.0 Hz), 7.66 (1H, t, J=8.0 Hz), 7.76 (1H, dd, J=8.8 Hz, 2.5 Hz), 8.05 (1H, d, J=2.5 Hz), 8.21 (1H, d, J=3 Hz), 8.42-8.60 (3H, m), 8.76 (1H, s), 10.49 (1H, s).

(v) Production of N-{4-[4-({3-chloro-4-[3-(trifluoromethyl)phenoxy]phenyl}amino)-5H-pyrrolo[3,2-d]pyrimidin-5-yl]but-2-yn-1-yl}-2-(methylsulfonyl)acetamide The title compound (55.8 mg) was obtained as a pale-yellow powder by the reaction in the same manner as in Example 202 (iii) using 5-(4-aminobut-2-yn-1-yl)-N-{3-chloro-4-[3-(trifluoromethyl)phenoxy]phenyl}-5H-pyrrolo[3,2-d]pyrimidin-4-amine dihydrochloride (204 mg), methanesulfonylacetic acid (102 mg), 1-hydroxybenzotriazole monohydrate (204 mg), N-[3-(dimethylamino)propyl]-N-ethylcarbodiimide hydrochloride (287 mg), triethylamine (0.5 mL) and N,N-dimethylformamide (2 mL) and crystallization from diisopropyl ether/ethyl acetate.

$^1$H-NMR (DMSO-d$_6$) δ: 3.07 (3H, s), 3.92-4.00 (2H, m), 4.02 (2H, s), 5.50 (2H, s), 6.55 (1H, d, J=3 Hz), 7.18-7.28 (2H, m), 7.32 (1H, d, J=9.1 Hz), 7.48 (1H, d, J=7.1 Hz), 7.57-7.70 (2H, m), 7.76 (1H, d, J=3 Hz), 8.02 (1H, d, J=2.5 Hz), 8.39 (1H, s), 8.62 (1H, s), 8.77 (1H, t, J=5.5 Hz).

Example 243

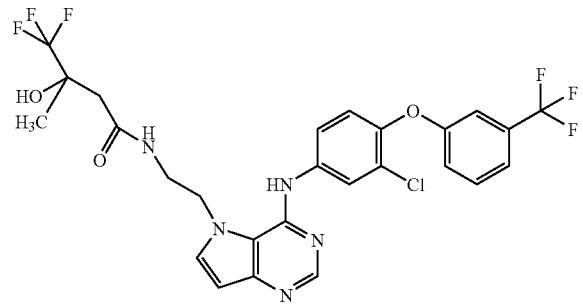

Production of N-{2-[4-({3-chloro-4-[3-(trifluoromethyl)phenoxy]phenyl}amino)-5H-pyrrolo[3,2-d]pyrimidin-5-yl]ethyl}-4,4,4-trifluoro-3-hydroxy-3-methylbutanamide The title compound (104 mg) was obtained as white crystals by the reaction in the same manner as in Example 202 (iii) using 5-(2-aminoethyl)-N-{3-chloro-4-[3-(trifluoromethyl)phenoxy]phenyl}-5H-pyrrolo[3,2-d]pyrimidin-4-amine dihydrochloride (201 mg), 4,4,4-trifluoro-3-hydroxy-3-methylbutanoic acid (131 mg), 1-hydroxybenzotriazole monohydrate (159 mg), N-[3-(dimethylamino)propyl]-N-ethylcarbodiimide hydrochloride (372 mg), triethylamine (0.55 mL) and tetrahydrofuran (2 mL) and crystallization from diisopropyl ether/ethyl acetate.

$^1$H-NMR (DMSO-d$_6$) δ: 1.36 (3H, s), 2.26-2.48 (2H, m), 3.36-3.56 (2H, m), 4.53 (2H, t, J=6.7 Hz), 6.18 (1H, s), 6.51 (1H, d, J=3.0 Hz), 7.15-7.26 (2H, m), 7.30 (1H, d, J=8.8 Hz), 7.47 (1H, d, J=8.0 Hz), 7.56-7.72 (2H, m), 7.81 (1H, dd, J=8.8 Hz, 2.5 Hz), 8.04 (1H, d, J=2.5 Hz), 8.35 (1H, s), 8.42 (1H, t, J=5.9 Hz), 8.83 (1H, s).

Example 244

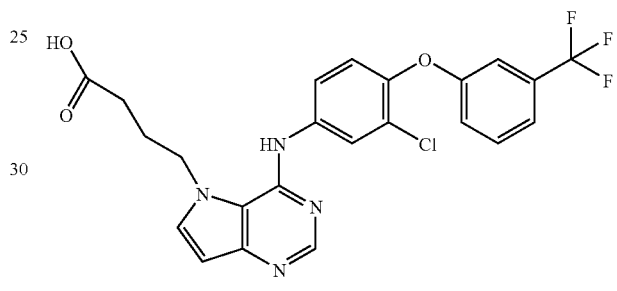

Production of 4-[4-({3-chloro-4-[3-(trifluoromethyl)phenoxy]phenyl}amino)-5H-pyrrolo[3,2-d]pyrimidin-5-yl]butanoic acid (i) Production of ethyl 4-(4-chloro-5H-pyrrolo[3,2-d]pyrimidin-5-yl)butanoate The title compound (1.70 g) was obtained as a yellow oil by the reaction in the same manner as in Example 201 (ii) using 4-chloro-5H-pyrrolo[3,2-d]pyrimidine (1.01 g), ethyl 4-bromobutanoate (1.2 mL), cesium carbonate (3.23 g) and N,N-dimethylformamide (10 mL).

$^1$H-NMR (CDCl$_3$) δ: 1.25 (3H, t, J=7 Hz), 2.09-2.44 (4H, m), 4.13 (2H, q, J=7 Hz), 4.56 (2H, t, J=7.0 Hz), 6.73 (1H, d, J=3 Hz), 7.50 (1H, d, J=3 Hz), 8.71 (1H, s).

(ii) Production of ethyl 4-[4-({3-chloro-4-[3-(trifluoromethyl)phenoxy]phenyl}amino)-5H-pyrrolo[3,2-d]pyrimidin-5-yl]butanoate The title compound (2.69 g) was obtained as a yellow solid by the reaction in the same manner as in Example 201 (iii) using ethyl 4-(4-chloro-5H-pyrrolo[3,2-d]pyrimidin-5-yl)butanoate (1.70 g), 3-chloro-4-[3-(trifluoromethyl)phenoxy]aniline (2.19 g) and isopropyl alcohol (35 mL).

$^1$H-NMR (CDCl$_3$) δ: 1.31 (3H, t, J=7.2 Hz), 2.12-2.27 (2H, m), 2.50-2.61 (2H, m), 4.24 (2H, q, J=7.2 Hz), 4.34-4.48 (2H, m), 6.60 (1H, d, J=3.3 Hz), 7.08 (1H, d, J=8.0 Hz), 7.11-7.17 (1H, m), 7.19-7.25 (2H, m), 7.32 (1H, d, J=8.0 Hz), 7.43 (1H, t, J=8.0 Hz), 7.82 (1H, dd, J=8.8 Hz, 2.6 Hz), 8.00 (1H, d, J=2.6 Hz), 8.16 (1H, s), 8.52 (1H, s).

(iii) Production of 4-[4-({3-chloro-4-[3-(trifluoromethyl)phenoxy]phenyl}amino)-5H-pyrrolo[3,2-d]pyrimidin-5-yl]butanoic acid The title compound (2.02 g) was obtained as a white solid by the reaction in the same manner as in Example 202 (ii) using ethyl 4-[4-({3-chloro-4-[3-(trifluoromethyl)phenoxy]phenyl}amino)-5H-pyrrolo[3,2-d]pyrimidin-5-yl]butanoate (2.69 g), 1N aqueous sodium hydroxide solution (7 mL) and a mixed solvent of tetrahydrofuran (20 mL)/ethanol (20 mL).

$^1$H-NMR (DMSO-$d_6$) δ: 1.87-2.00 (2H, m), 2.20 (2H, t, J=6.9 Hz), 4.52 (2H, t, J=7.6 Hz), 6.50 (1H, d, J=3.0 Hz), 7.17-7.28 (2H, m), 7.30 (1H, d, J=8.8 Hz), 7.47 (1H, d, J=7.7 Hz), 7.57-7.76 (3H, m), 7.99 (1H, d, J=2.5 Hz), 8.34 (1H, s), 8.61 (1H, s), 12.33 (1H, s).

Example 245

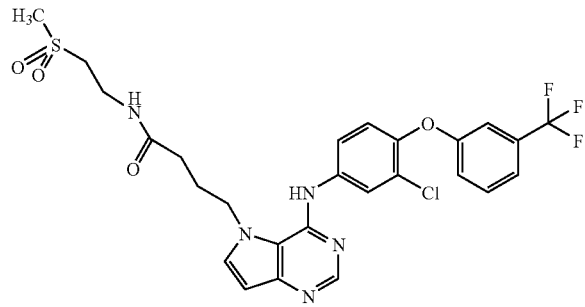

Production of 4-[4-({3-chloro-4-[3-(trifluoromethyl)phenoxy]phenyl}amino)-5H-pyrrolo[3,2-d]pyrimidin-5-yl]-N-[2-(methylsulfonyl)ethyl]butanamide The title compound (142 mg) was obtained as white crystals by the reaction in the same manner as in Example 202 (iii) using 4-[4-({3-chloro-4-[3-(trifluoromethyl)phenoxy]phenyl}amino)-5H-pyrrolo[3,2-d]pyrimidin-5-yl]butanoic acid (250 mg), 2-(methylsulfonyl)ethanamine (128 mg), 1-hydroxybenzotriazole monohydrate (114 mg), N-[3-(dimethylamino)propyl]-N-ethylcarbodiimide hydrochloride (492 mg), triethylamine (0.15 mL) and a mixed solvent of tetrahydrofuran (1.5 mL)/N,N-dimethylformamide (1.5 mL) and crystallization from ethyl acetate.

$^1$H-NMR (DMSO-$d_6$) δ: 1.90-2.03 (2H, m), 2.08-2.19 (2H, m), 2.97 (3H, s), 3.20-3.30 (2H, m), 3.40-3.52 (2H, m), 4.49 (2H, t, J=7.2 Hz), 6.50 (1H, d, J=3 Hz), 7.17-7.24 (1H, m), 7.24-7.27 (1H, m), 7.30 (1H, d, J=9 Hz), 7.47 (1H, d, J=8 Hz), 7.62 (1H, t, J=8 Hz), 7.67 (1H, d, J=3 Hz), 7.82 (1H, dd, J=9 Hz, 2.5 Hz), 8.09 (1H, d, J=2.5 Hz), 8.29 (1H, t, J=5.6 Hz), 8.34 (1H, s), 8.79 (1H, s).

Example 246

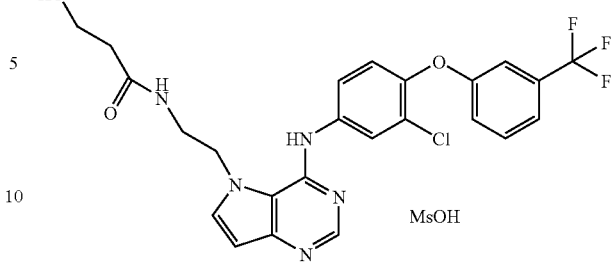

Production of N-{2-[4-({3-chloro-4-[3-(trifluoromethyl)phenoxy]phenyl}amino)-5H-pyrrolo[3,2-d]pyrimidin-5-yl]ethyl}-3-hydroxypropanamide methanesulfonate N-{2-[4-({3-Chloro-4-[3-(trifluoromethyl)phenoxy]phenyl}amino)-5H-pyrrolo[3,2-d]pyrimidin-5-yl]ethyl}-3-hydroxypropanamide was obtained by the reaction in the same manner as in Example 202 (iii) using 5-(2-aminoethyl)-N-{3-chloro-4-[3-(trifluoromethyl)phenoxy]phenyl}-5H-pyrrolo[3,2-d]pyrimidin-4-amine dihydrochloride (3.50 g), a 3.6 M aqueous solution (5.6 mL) of 3-hydroxypropanoic acid, 1-hydroxybenzotriazole monohydrate (4.56 g), N-[3-(dimethylamino)propyl]-N-ethylcarbodiimide hydrochloride (10.1 g), triethylamine (10 mL) and a mixed solvent of tetrahydrofuran (17 mL)/N,N-dimethylformamide (17 mL). The obtained N-{2-[4-({3-chloro-4-[3-(trifluoromethyl)phenoxy]phenyl}amino)-5H-pyrrolo[3,2-d]pyrimidin-5-yl]ethyl}-3-hydroxypropanamide was dissolved in ethyl acetate (50 mL), methanesulfonic acid (0.155 mL) was added, and the mixture was stirred for 2 hrs. The reaction mixture was concentrated under reduced pressure and recrystallized from ethyl acetate to give the title compound (1.04 g) as white crystals.

$^1$H-NMR (DMSO-$d_6$) δ: 2.22 (2H, t, J=6.3 Hz), 2.31 (3H, s), 3.41-3.51 (4H, m), 3.56 (2H, t, J=6.5 Hz), 6.67 (1H, d, J=3.0 Hz), 7.25-7.32 (2H, m), 7.37 (1H, d, J=8.8 Hz), 7.50-7.56 (1H, m), 7.62-7.74 (2H, m), 7.98 (1H, d, J=2.8 Hz), 8.33 (1H, t, J=5.5 Hz), 8.75 (1H, s), 10.11 (1H, s).

Example 247

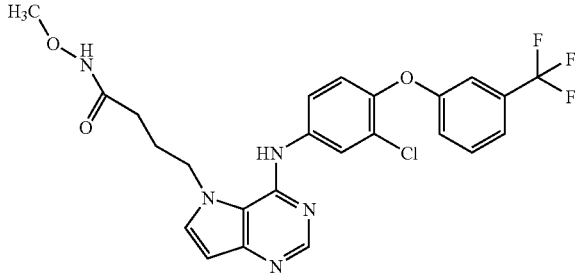

Production of 4-[4-({3-chloro-4-[3-(trifluoromethyl)phenoxy]phenyl}amino)-5H-pyrrolo[3,2-d]pyrimidin-5-yl]-N-methoxybutanamide The title compound (98.1 mg) was obtained as white crystals by the reaction in the same manner as in Example 202 (iii) using 4-[4-({3-chloro-4-[3-(trifluoromethyl)phenoxy]phenyl}amino)-5H-pyrrolo[3,2-d]pyrimidin-5-yl]butanoic acid (252 mg), O-methylhydroxylamine hydrochloride (85 mg), 1-hydroxybenzotriazole monohydrate (105 mg), N-[3-(dimethylamino)propyl]-N-ethylcarbodiimide hydrochloride (484 mg), triethylamine (0.7 mL) and a mixed solvent of tetrahydrofuran (1 mL)/N,N-dimethylformamide (1 mL).

$^1$H-NMR (DMSO-d$_6$) δ: 1.92-1.99 (4H, m), 3.55 (3H, s), 4.46-4.56 (2H, m), 6.51 (1H, d, J=2.8 Hz), 7.18-7.27 (2H, m), 7.30 (1H, d, J=8.8 Hz), 7.47 (1H, d, J=7.7 Hz), 7.58-7.69 (2H, m), 7.74-7.81 (1H, m), 8.03 (1H, s), 8.34 (1H, s), 8.75 (1H, br s), 11.02 (1H, br s).

Example 248

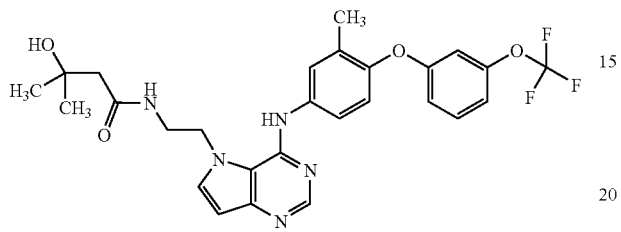

Production of 3-hydroxy-3-methyl-N-{2-[4-({3-methyl-4-[3-(trifluoromethoxy)phenoxy]phenyl}amino)-5H-pyrrolo[3,2-d]pyrimidin-5-yl]ethyl}butanamide The title compound (203 mg) was obtained as colorless powder crystals by the reaction in the same manner as in Example 155 (iv) using 5-(2-aminoethyl)-N-{3-methyl-4-[3-(trifluoromethoxy)phenoxy]phenyl}-5H-pyrrolo[3,2-d]pyrimidin-4-amine (238 mg), 3-hydroxy-3-methylbutanoic acid (0.0865 mL), 1-ethyl-3-(3-dimethylaminopropyl)carbodiimide hydrochloride (154 mg), 1-hydroxybenzotriazole monohydrate (109 mg), triethylamine (0.374 mL) and N,N-dimethylformamide (10.5 mL).

$^1$H-NMR (DMSO-d$_6$) δ 1.13 (6H, s), 2.12 (3H, s), 2.21 (2H, s), 3.41 (2H, m), 4.51 (2H, t, J=6 Hz), 4.70 (1H, s), 6.47 (1H, d, J=3 Hz), 6.88 (2H, m), 7.04 (2H, m), 7.47 (1H, t, J=8 Hz), 7.61 (1H, d, J=3 Hz), 7.65 (2H, m), 8.28 (2H, m), 8.73 (1H, br s).

Example 249

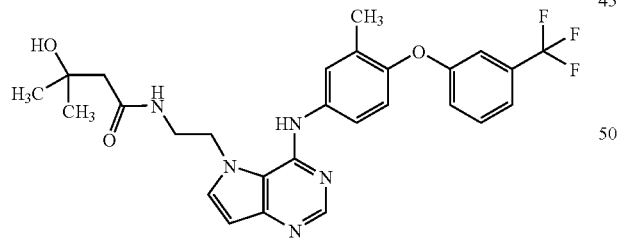

Production of 3-hydroxy-3-methyl-N-{2-[4-({3-methyl-4-[3-(trifluoromethyl)phenoxy]phenyl}amino)-5H-pyrrolo[3,2-d]pyrimidin-5-yl]ethyl}butanamide (i) Production of 5-(2-aminoethyl)-N-{3-methyl-4-[3-(trifluoromethyl)phenoxy]phenyl}-5H-pyrrolo[3,2-d]pyrimidin-4-amine dihydrochloride tert-Butyl {2-[4-({3-methyl-4-[3-(trifluoromethyl)phenoxy]phenyl}amino)-5H-pyrrolo[3,2-d]pyrimidin-5-yl]ethyl}carbamate (2.9 g) obtained in Example 188 (i) was dissolved in tetrahydrofuran (80 mL)/2N hydrochloric acid (40 mL), and the mixture was stirred at 60° C. for 16 hrs. The reaction mixture was concentrated under reduced pressure, ethanol (80 mL) was added to the residue and the mixture was concentrated again under reduced pressure. Ethyl acetate was added to the residue and the solid was collected by filtration and dried under reduced pressure to give the title compound (2.58 g) as a solid powder.

$^1$H-NMR (DMSO-d$_6$) δ 2.20 (3H, s), 3.29 (2H, m), 5.06 (2H, m), 6.73 (1H, d, J=3 Hz), 7.11 (1H, d, J=9 Hz), 7.22 (2H, m), 7.48 (2H, m), 7.61 (2H, m), 8.08 (1H, d, J=3 Hz), 8.42 (3H, br s), 8.70 (1H, s), 10.04 (1H, br s).

(ii) Production of 3-hydroxy-3-methyl-N-{2-[4-({3-methyl-4-[3-(trifluoromethyl)phenoxy]phenyl}amino)-5H-pyrrolo[3,2-d]pyrimidin-5-yl]ethyl}butanamide The title compound (203 mg) was obtained as colorless powder crystals by the reaction in the same manner as in Example 155 (iv) using 5-(2-aminoethyl)-N-{3-methyl-4-[3-(trifluoromethyl)phenoxy]phenyl}-5H-pyrrolo[3,2-d]pyrimidin-4-amine dihydrochloride (200 mg), 3-hydroxy-3-methylbutanoic acid (0.0644 mL), 1-ethyl-3-(3-dimethylaminopropyl)carbodiimide hydrochloride (115 mg), 1-hydroxybenzotriazole monohydrate (81 mg), triethylamine (0.279 mL) and N,N-dimethylformamide (7.82 mL).

$^1$H-NMR (DMSO-d$_6$) δ 1.13 (6H, s), 2.13 (3H, s), 2.21 (2H, s), 3.42 (2H, m), 4.52 (2H, t, J=7 Hz), 4.69 (1H, s), 6.47 (1H, d, J=3 Hz), 7.03 (1H, m), 7.18 (2H, m), 7.42 (1H, d, J=8 Hz), 7.5-7.7 (4H, m), 8.26 (2H, m), 8.73 (1H, br s).

Example 250

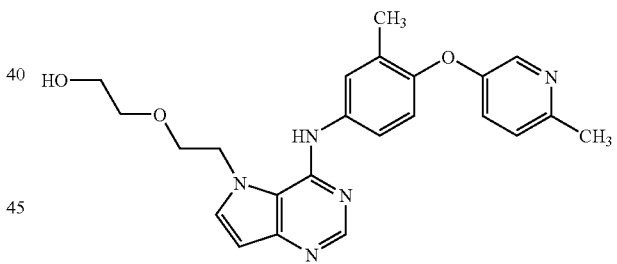

Production of 2-{2-[4-({3-methyl-4-[(6-methylpyridin-3-yl)oxy]phenyl}amino)-5H-pyrrolo[3,2-d]pyrimidin-5-yl]ethoxy}ethanol The title compound (132 mg) was obtained colorless crystals by the method in the same manner as in Example 183 using 2-[2-(4-chloro-5H-pyrrolo[3,2-d]pyrimidin-5-yl)ethoxy]ethyl benzoate (150 mg), 3-methyl-4-[(6-methylpyridin-3-yl)oxy]aniline (139 mg) and 1-methyl-2-pyrrolidone (0.863 mL).

$^1$H-NMR (DMSO-d$_6$) δ 2.17 (3H, s), 2.43 (3H, s), 3.51 (4H, br s), 3.84 (2H, t, J=4.5 Hz), 4.63 (2H, t, J=4.5 Hz), 4.73 (1H, t, J=4.5 Hz), 6.49 (1H, d, J=3 Hz), 6.93 (1H, d, J=8 Hz), 7.16 (1H, dd, J=9 Hz, 3 Hz), 7.23 (1H, d, J=8 Hz), 7.56 (2H, m), 7.65 (1H, d, J=3 Hz), 8.17 (1H, d, J=3 Hz), 8.28 (1H, s), 8.78 (1H, br s).

Example 251

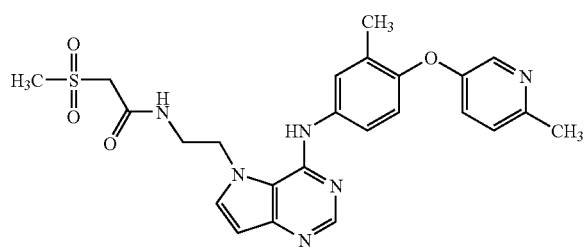

Production of N-{2-[4-({3-methyl-4-[(6-methylpyridin-3-yl)oxy]phenyl}amino)-5H-pyrrolo[3,2-d]pyrimidin-5-yl]ethyl}-2-(methylsulfonyl)acetamide (i) Production of tert-butyl {2-[4-({3-methyl-4-[(6-methylpyridin-3-yl)oxy]phenyl}amino)-5H-pyrrolo[3,2-d]pyrimidin-5-yl]ethyl}carbamate The title compound (799 mg) was obtained as a white powder by the method in the same manner as in Example 188 (i) using tert-butyl [2-(4-chloro-5H-pyrrolo[3,2-d]pyrimidin-5-yl)ethyl]carbamate (500 mg), 3-methyl-4-[(6-methylpyridin-3-yl)oxy]aniline (542 mg) and isopropyl alcohol (5 mL).

$^1$H-NMR (CDCl$_3$) δ 1.47 (9H, s), 2.24 (3H, s), 2.52 (3H, s), 3.49 (2H, m), 4.46 (2H, m), 5.18 (1H, m), 6.58 (1H, d, J=3 Hz), 6.89 (1H, d, J=9 Hz), 7.0-7.2 (3H, m), 7.65 (2H, m), 8.27 (1H, d, J=2 Hz), 8.41 (1H, br s), 8.48 (1H, s).

(ii) Production of 5-(2-aminoethyl)-N-{3-methyl-4-[(6-methylpyridin-3-yl)oxy]phenyl}-5H-pyrrolo[3,2-d]pyrimidin-4-amine trihydrochloride tert-Butyl {2-[4-({3-methyl-4-[(6-methylpyridin-3-yl)oxy]phenyl}amino)-5H-pyrrolo[3,2-d]pyrimidin-5-yl]ethyl}carbamate (790 mg) was dissolved in tetrahydrofuran (24 mL)/2N hydrochloric acid (12 mL), and the mixture was stirred at 60° C. for 16 hrs. The reaction mixture was concentrated under reduced pressure, ethanol (30 mL) was added to the residue and the mixture was concentrated again under reduced pressure. Ethyl acetate was added to the residue and the solid was collected by filtration and dried under reduced pressure to give the title compound (701 mg) as a solid powder.

$^1$H-NMR (DMSO-d$_6$) δ 2.23 (3H, s), 2.68 (3H, s), 3.29 (2H, m), 5.11 (2H, m), 6.74 (1H, d, J=3 Hz), 7.16 (1H, d, J=8 Hz), 7.52 (1H, d, J=9 Hz), 7.62 (1H, s), 7.80 (1H, m), 7.96 (1H, m), 8.10 (1H, m), 8.37 (1H, d, J=3 Hz), 8.51 (3H, br s), 8.71 (1H, s).

(iii) Production of N-{2-[4-({3-methyl-4-[(6-methylpyridin-3-yl)oxy]phenyl}amino)-5H-pyrrolo[3,2-d]pyrimidin-5-yl]ethyl}-2-(methylsulfonyl)acetamide The title compound (205 mg) was obtained as colorless powder crystals by the reaction in the same manner as in Example 155 (iv) using 5-(2-aminoethyl)-N-{3-methyl-4-[(6-methylpyridin-3-yl)oxy]phenyl}-5H-pyrrolo[3,2-d]pyrimidin-4-amine trihydrochloride (250 mg), 2-(methylsulfonyl)acetic acid (107 mg), 1-ethyl-3-(3-dimethylaminopropyl)carbodiimide hydrochloride (149 mg), 1-hydroxybenzotriazole monohydrate (105 mg), triethylamine (0.360 mL) and N,N-dimethylformamide (10 mL).

$^1$H-NMR (DMSO-d$_6$) δ 2.17 (3H, s), 2.44 (3H, s), 3.34 (3H, s), 3.45 (2H, q, J=6 Hz), 4.05 (2H, s), 4.55 (2H, t, J=6 Hz), 6.47 (1H, d, J=3 Hz), 6.94 (1H, d, J=9 Hz), 7.1-7.3 (2H, m), 7.55 (3H, m), 8.18 (1H, d, J=3 Hz), 8.28 (1H, s), 8.51 (1H, br s), 8.67 (1H, t, J=5 Hz).

Example 252

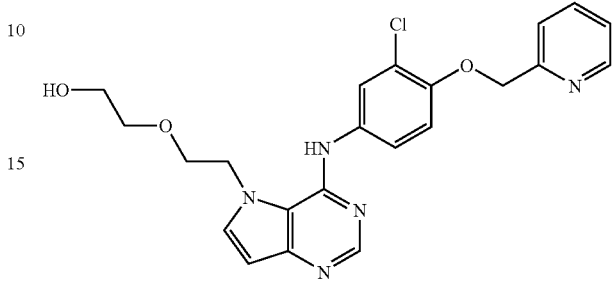

Production of 2-[2-(4-{[3-chloro-4-(pyridin-2-ylmethoxy)phenyl]amino}-5H-pyrrolo[3,2-d]pyrimidin-5-yl)ethoxy]ethanol The title compound (149 mg) was obtained as colorless crystals by the method in the same manner as in Example 183 using 2-[2-(4-chloro-5H-pyrrolo[3,2-d]pyrimidin-5-yl)ethoxy]ethyl benzoate (150 mg), 3-chloro-4-(pyridin-2-ylmethoxy)aniline (152 mg) and 1-methyl-2-pyrrolidone (0.863 mL).

$^1$H-NMR (DMSO-d$_6$) δ 3.47 (4H, m), 3.81 (2H, t, J=4.5 Hz), 4.61 (2H, t, J=4.5 Hz), 4.70 (1H, t, J=4.5 Hz), 5.27 (2H, s), 6.48 (1H, d, J=3 Hz), 7.20 (1H, d, J=9 Hz), 7.37 (1H, dd, J=7 Hz, 4.5 Hz), 7.49 (1H, dd, J=9 Hz, 3 Hz), 7.58 (1H, d, J=8 Hz), 7.64 (1H, d, J=3 Hz), 7.84 (1H, d, J=3 Hz), 7.88 (1H, m), 8.27 (1H, s), 8.59 (1H, dd, J=3 Hz, 1 Hz), 8.70 (1H, br s).

Example 253

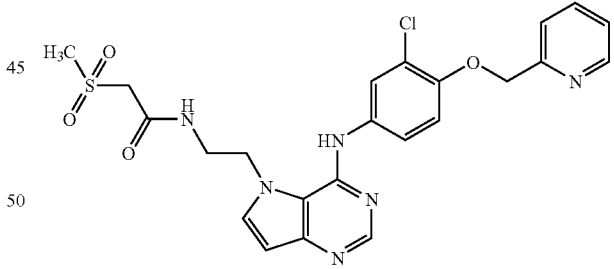

Production of N-[2-(4-{[3-chloro-4-(pyridin-2-ylmethoxy)phenyl]amino}-5H-pyrrolo[3,2-d]pyrimidin-5-yl)ethyl]-2-(methylsulfonyl)acetamide (i) Production of tert-butyl [2-(4-{[3-chloro-4-(pyridin-2-ylmethoxy)phenyl]amino}-5H-pyrrolo[3,2-d]pyrimidin-5-yl)ethyl]carbamate The title compound (812 mg) was obtained as a white powder by the method in the same manner as in Example 188 (i) using tert-butyl [2-(4-chloro-5H-pyrrolo[3,2-d]pyrimidin- 5-yl)ethyl]carbamate (500 mg), 3-chloro-4-(pyridin-2-yl-methoxy)aniline (594 mg) and isopropyl alcohol (5 mL).

$^1$H-NMR (CDCl$_3$) δ 1.48 (9H, s), 3.46 (2H, m), 4.43 (2H, m), 5.19 (1H, t, J=5 Hz), 5.29 (2H, s), 6.56 (1H, d, J=3 Hz), 6.98 (1H, d, J=9 Hz), 7.14 (1H, d, J=3 Hz), 7.2-7.3 (2H, m), 7.6-7.8 (3H, m), 7.87 (1H, d, J=3 Hz), 8.46 (1H, s), 8.51 (1H, br s), 8.59 (1H, m).

(ii) Production of 5-(2-aminoethyl)-N-[3-chloro-4-(pyridin-2-ylmethoxy)phenyl]-5H-pyrrolo[3,2-d]pyrimidin-4-amine trihydrochloride tert-Butyl [2-(4-{[3-chloro-4-(pyridin-2-ylmethoxy)phenyl]amino}-5H-pyrrolo[3,2-d]pyrimidin-5-yl)ethyl]carbamate (790 mg) was dissolved in tetrahydrofuran (24 mL)/2N hydrochloric acid (12 mL), and the mixture was stirred at 60° C. for 16 hrs. The reaction mixture was concentrated under reduced pressure, ethanol (30 mL) was added to the residue and the mixture was concentrated again under reduced pressure. Ethyl acetate was added to the residue and the solid was collected by filtration and dried under reduced pressure to give the title compound (826 mg) as a solid powder.

$^1$H-NMR (DMSO-d$_6$) δ 3.29 (2H, m), 5.07 (2H, m), 5.49 (2H, s), 6.73 (1H, dd, J=3 Hz, 1 Hz), 7.34 (1H, d, J=9 Hz), 7.52 (1H, dd, J=9 Hz, 3 Hz), 7.68 (1H, m), 7.74 (1H, d, J=2 Hz), 7.85 (1H, m), 8.09 (1H, d, J=3 Hz), 8.24 (1H, m), 8.47 (3H, br s), 8.69 (1H, s), 8.77 (1H, m), 10.19 (1H, br s).

(iii) Production of N-[2-(4-{[3-chloro-4-(pyridin-2-ylmethoxy)phenyl]amino}-5H-pyrrolo[3,2-d]pyrimidin-5-yl)ethyl]-2-(methylsulfonyl)acetamide The title compound (182 mg) was obtained as colorless powder crystals by the reaction in the same manner as in Example 155 (iv) using 5-(2-aminoethyl)-N-[3-chloro-4-(pyridin-2-ylmethoxy)phenyl]-5H-pyrrolo[3,2-d]pyrimidin-4-amine trihydrochloride (261 mg), 2-(methylsulfonyl)acetic acid (107 mg), 1-ethyl-3-(3-dimethylaminopropyl)carbodiimide hydrochloride (149 mg), 1-hydroxybenzotriazole monohydrate (105 mg), triethylamine (0.360 mL) and N,N-dimethylformamide (10 mL).

$^1$H-NMR (DMSO-d$_6$) δ 3.10 (3H, s), 3.44 (2H, q, J=6 Hz), 4.06 (2H, s), 4.53 (2H, t, J=6 Hz), 5.28 (2H, s), 6.46 (1H, d, J=3 Hz), 7.22 (1H, d, J=9 Hz), 7.37 (1H, dd, J=8 Hz, 6 Hz), 7.57 (3H, m), 7.78 (1H, d, J=2 Hz), 7.89 (1H, dt, J=2 Hz, 8 Hz), 8.26 (1H, s), 8.49 (1H, br s), 8.60 (1H, d, J=5 Hz), 8.67 (1H, t, J=6 Hz).

Example 254

Production of tert-butyl (2S,4R)-4-hydroxy-2-[({2-[4-({3-methyl-4-[3-(trifluoromethyl)phenoxy]phenyl}amino)-5H-pyrrolo[3,2-d]pyrimidin-5-yl]ethyl}amino)carbonyl]pyrrolidine-1-carboxylate The title compound (310 mg) was obtained as a colorless powder by the reaction in the same manner as in Example 155 (iv) using 5-(2-aminoethyl)-N-{3-methyl-4-[3-(trifluoromethyl)phenoxy]phenyl}-5H-pyrrolo[3,2-d]pyrimidin-4-amine dihydrochloride (300 mg), (4R)-1-(tert-butoxycarbonyl)-4-hydroxy-L-proline (118 mg), 1-ethyl-3-(3-dimethylaminopropyl)carbodiimide hydrochloride (172 mg), 1-hydroxybenzotriazole monohydrate (122 mg), triethylamine (0.418 mL) and N,N-dimethylformamide (11.73 mL).

$^1$H-NMR (CDCl$_3$) δ 1.43 (9H, s), 1.9-2.1 (2H, m), 2.22 (3H, s), (1H, br s), 3.44 (2H, m), 3.61 (2H, m), 4.44 (4H, m), (1H, d, J=3 Hz), 6.94 (1H, d, J=9 Hz), 7.10 (1H, m), (2H, m), 7.27 (2H, m), 7.39 (1H, d, J=8 Hz), 7.65 (1H, d, J=9 Hz), 7.73 (1H, m), 8.39 (1H, br s), 8.48 (1H, s).

Example 255

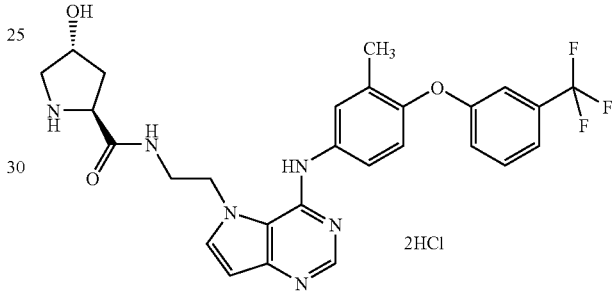

Production of (4R)-4-hydroxy-N-{2-[4-({3-methyl-4-[3-(trifluoromethyl)phenoxy]phenyl}amino)-5H-pyrrolo[3,2-d]pyrimidin-5-yl]ethyl}-L-prolinamide dihydrochloride tert-Butyl (2S,4R)-4-hydroxy-2-[({2-[4-({3-methyl-4-[3-(trifluoromethyl)phenoxy]phenyl}amino)-5H-pyrrolo[3,2-d]pyrimidin-5-yl]ethyl}amino)carbonyl]pyrrolidine-1-carboxylate (230 mg) was dissolved in dichloromethane (2.39 mL), trifluoroacetic acid (1.79 mL) was added, and the mixture was stirred at room temperature for 2 hrs. The reaction mixture was concentrated under reduced pressure, and the residue was dissolved in ethyl acetate/tetrahydrofuran (1:1,

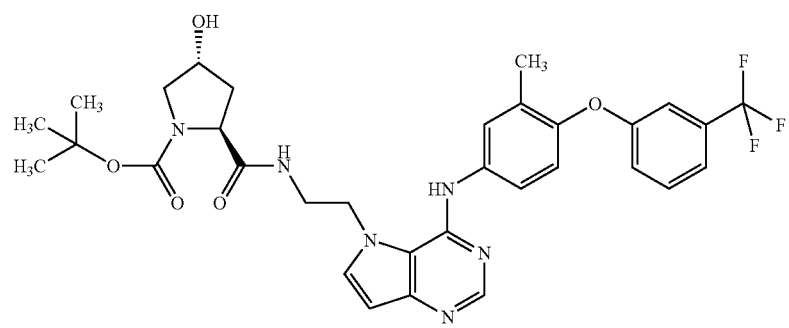

50 mL). The organic layer was washed with saturated aqueous sodium hydrogen carbonate (30 mL), dried over magnesium sulfate and concentrated under reduced pressure. The residue was subjected to basic silica gel chromatography (ethyl acetate/methanol=100/0→80/20). The fractions containing the title compound were collected and concentrated under reduced pressure. The residue was dissolved in ethyl acetate, 4N hydrochloric acid (0.252 mL) was added, and the mixture was crystallized to give the title compound (136 mg).

$^1$H-NMR (DMSO-d$_6$) δ 1.66 (1H, m), 2.14 (1H, m), 2.21 (3H, s), 3.04 (1H, m), 3.23 (1H, m), 3.49 (3H, m), 3.67 (1H, m), 4.16 (2H, m), 4.36 (1H, m), 4.83 (2H, m), 5.55 (1H, br s), 6.66 (1H, d, J=3 Hz), 7.13 (1H, d, J=9 Hz), 7.23 (2H, m), 7.49 (2H, m), 7.61 (2H, m), 7.94 (1H, m), 8.56 (1H, m), 8.68 (1H, s), 8.95 (1H, m), 10.02 (2H, m).

Example 256

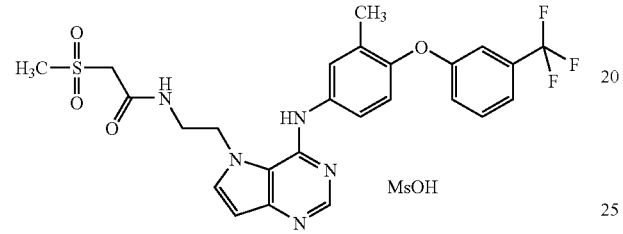

Production of 2-(methylsulfonyl)-N-{2-[4-({3-methyl-4-[3-(trifluoromethyl)phenoxy]phenyl}amino)-5H-pyrrolo[3,2-d]pyrimidin-5-yl]ethyl}acetamide methanesulfonate 2-(Methylsulfonyl)-N-{2-[4-({3-methyl-4-[3-(trifluoromethyl)phenoxy]phenyl}amino)-5H-pyrrolo[3,2-d]pyrimidin-5-yl]ethyl}acetamide (680 mg) was dissolved in ethyl acetate (3.4 mL), methanesulfonic acid (0.0887 mL) was added at 50° C., and the mixture was stirred for 10 min. and further stirred at room temperature for 2 hrs. The precipitated crystals were collected by filtration and washed with diisopropyl ether to give the title compound (797 mg) as colorless crystals.

$^1$H-NMR (DMSO-d$_6$) δ 2.20 (3H, s), 2.31 (3H, s), 3.05 (3H, s), 3.55 (2H, q, J=6 Hz), 4.06 (2H, s), 4.68 (2H, t, J=6 Hz), 6.65 (1H, d, J=3 Hz), 7.13 (1H, d, J=9 Hz), 7.23 (2H, m), 7.49 (2H, m), 7.62 (2H, m), 7.91 (1H, d, J=3 Hz), 8.70 (2H, m), 9.84 (1H, br s).

Example 257

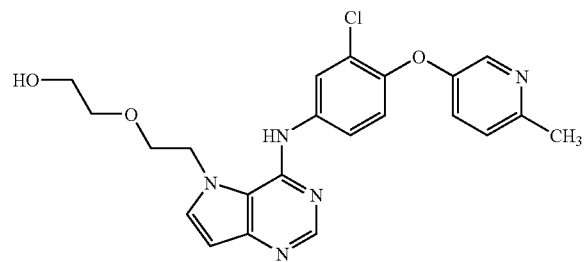

Production of 2-{2-[4-({3-chloro-4-[(6-methylpyridin-3-yl)oxy]phenyl}amino)-5H-pyrrolo[3,2-d]pyrimidin-5-yl]ethoxy}ethanol The title compound (133 mg) was obtained as colorless crystals by the method in the same manner as in Example 183 using 2-[2-(4-chloro-5H-pyrrolo[3,2-d]pyrimidin-5-yl)ethoxy]ethyl benzoate (150 mg), 3-chloro-4-[(6-methylpyridin-3-yl)oxy]aniline (152 mg) and 1-methyl-2-pyrrolidone (0.863 mL).

$^1$H-NMR (DMSO-d$_6$) δ 2.44 (3H, s), 3.48 (4H, m), 3.83 (2H, t, J=4.5 Hz), 4.64 (2H, t, J=4.5 Hz), 4.71 (1H, t, J=4.5 Hz), 6.52 (1H, d, J=3 Hz), 7.18 (1H, d, J=9 Hz), 7.24 (2H, m), 7.62 (1H, dd, J=9 Hz, 2 Hz), 7.69 (1H, d, J=3 Hz), 8.00 (1H, d, J=2 Hz), 8.20 (1H, d, J=1 Hz), 8.34 (1H, s), 8.96 (1H, br s).

Example 258

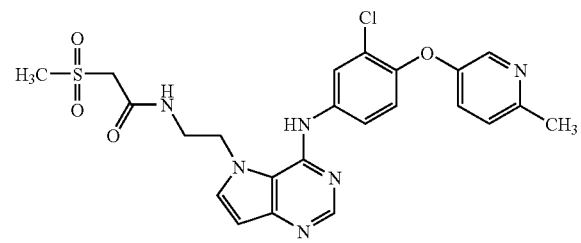

Production of N-{2-[4-({3-chloro-4-[(6-methylpyridin-3-yl)oxy]phenyl}amino)-5H-pyrrolo[3,2-d]pyrimidin-5-yl]ethyl}-2-(methylsulfonyl)acetamide (i) Production of tert-butyl {2-[4-({3-chloro-4-[(6-methylpyridin-3-yl)oxy]phenyl}amino)-5H-pyrrolo[3,2-d]pyrimidin-5-yl]ethyl}carbamate The title compound (673 mg) was obtained as a white powder by the method in the same manner as in Example 188 (i) using tert-butyl [2-(4-chloro-5H-pyrrolo[3,2-d]pyrimidin-5-yl)ethyl]carbamate (500 mg), 3-chloro-4-[(6-methylpyridin-3-yl)oxy]aniline (594 mg) and isopropyl alcohol (5 mL).

$^1$H-NMR (CDCl$_3$) δ 1.49 (9H, s), 2.53 (3H, s), 3.48 (2H, m), 4.46 (2H, m), 5.26 (1H, t, J=6 Hz), 6.59 (1H, d, J=3 Hz), 7.01 (1H, d, J=9 Hz), 7.09 (1H, d, J=8 Hz), 7.18 (2H, m), 7.85 (1H, dd, J=9 Hz, 3 Hz), 8.00 (1H, d, J=3 Hz), 8.30 (1H, d, J=3 Hz), 8.50 (1H, s), 8.63 (1H, br s).

(ii) Production of 5-(2-aminoethyl)-N-{3-chloro-4-[(6-methylpyridin-3-yl)oxy]phenyl}-5H-pyrrolo[3,2-d]pyrimidin-4-amine trihydrochloride tert-Butyl {2-[4-({3-chloro-4-[(6-methylpyridin-3-yl)oxy]phenyl}amino)-5H-pyrrolo[3,2-d]pyrimidin-5-yl]ethyl}carbamate (643 mg) was dissolved in tetrahydrofuran (19.5 mL)/2N hydrochloric acid (9.75 mL), and the mixture was stirred at 60° C. for 16 hrs. The reaction mixture was concentrated under reduced pressure, ethanol (50 mL) was added to the residue and the mixture was concentrated again under reduced pressure. Ethyl acetate was added to the residue and the solid was collected by filtration and dried under reduced pressure to give the title compound (646 mg) as a solid powder.

$^1$H-NMR (DMSO-d$_6$) δ 2.68 (3H, d, J=6 Hz), 3.30 (2H, m), 5.14 (2H, m), 6.77 (1H, d, J=3 Hz), 7.40 (1H, m), 7.6-7.9 (2H, m), 8.00 (2H, m), 8.12 (1H, m), 8.52 (4H, m), 8.77 (1H, s), 10.50 (1H, m).

(iii) Production of N-{2-[4-({3-chloro-4-[(6-methylpyridin-3-yl)oxy]phenyl}amino)-5H-pyrrolo[3,2-d]pyrimidin-5-yl]ethyl}-2-(methylsulfonyl)acetamide The title compound (230 mg) was obtained as colorless powder crystals by the reaction in the same manner as in Example 155 (iv) using 5-(2-aminoethyl)-N-{3-chloro-4-[(6-methylpyridin-3-yl)oxy]phenyl}-5H-pyrrolo[3,2-d]pyrimidin-4-amine trihydrochloride (261 mg), 2-(methylsulfonyl)acetic acid (107 mg), 1-ethyl-3-(3-dimethylaminopropyl)carbodiimide hydrochloride (149 mg), 1-hydroxybenzotriazole monohydrate (105 mg), triethylamine (0.360 mL) and N,N-dimethylformamide (10 mL).

$^1$H-NMR (DMSO-$d_6$) δ 2.45 (3H, s), 3.10 (3H, s), 3.45 (2H, q, J=6 Hz), 4.04 (2H, s), 4.56 (2H, t, J=6 Hz), 6.50 (1H, d, J=3 Hz), 7.18 (1H, d, J=9 Hz), 7.25 (1H, d, J=2 Hz), 7.62 (1H, d, J=3 Hz), 7.70 (1H, dd, J=9 Hz, 3 Hz), 7.95 (1H, d, J=2 Hz), 8.22 (1H, m), 8.34 (1H, s), 8.67 (2H, m).

Example 259

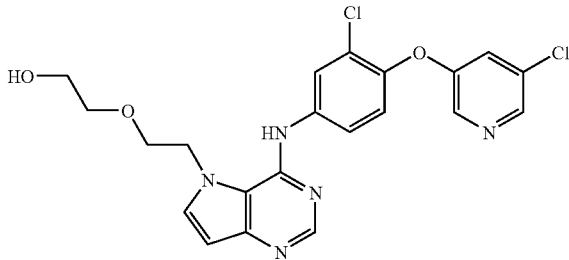

Production of 2-{2-[4-({3-chloro-4-[(5-chloropyridin-3-yl)oxy]phenyl}amino)-5H-pyrrolo[3,2-d]pyrimidin-5-yl]ethoxy}ethanol The title compound (145 mg) was obtained as colorless crystals by the method in the same manner as in Example 183 using 2-[2-(4-chloro-5H-pyrrolo[3,2-d]pyrimidin-5-yl)ethoxy]ethyl benzoate (150 mg), 3-chloro-4-[(5-chloropyridin-3-yl)oxy]aniline (165 mg) and 1-methyl-2-pyrrolidone (0.863 mL).

$^1$H-NMR (DMSO-$d_6$) δ 3.49 (4H, m), 3.84 (2H, t, J=4.5 Hz), 4.65 (2H, t, J=4.5 Hz), 4.72 (1H, t, J=4.5 Hz), 6.53 (1H, d, J=3 Hz), 7.33 (1H, d, J=9 Hz), 7.49 (1H, m), 7.69 (2H, m), 8.04 (1H, d, J=2 Hz), 8.32 (1H, d, J=2 Hz), 8.36 (1H, s), 8.40 (1H, d, J=2 Hz), 9.02 (1H, br s).

Example 260

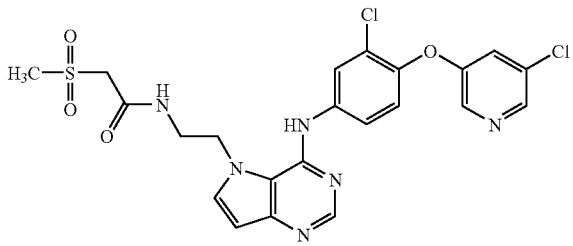

Production of N-{2-[4-({3-chloro-4-[(5-chloropyridin-3-yl)oxy]phenyl}amino)-5H-pyrrolo[3,2-d]pyrimidin-5-yl]ethyl}-2-(methylsulfonyl)acetamide (i) Production of tert-butyl {2-[4-({3-chloro-4-[(5-chloropyridin-3-yl)oxy]phenyl}amino)-5H-pyrrolo[3,2-d]pyrimidin-5-yl]ethyl}carbamate The title compound (769 mg) was obtained as a white powder by the method in the same manner as in Example 188 (i) using tert-butyl [2-(4-chloro-5H-pyrrolo[3,2-d]pyrimidin-5-yl)ethyl]carbamate (500 mg), 3-chloro-4-[(5-chloropyridin-3-yl)oxy]aniline (643 mg) and isopropyl alcohol (5 mL).

$^1$H-NMR (CDCl$_3$) δ 1.50 (9H, s), 3.49 (2H, m), 4.48 (2H, m), 5.21 (1H, t, J=6 Hz), 6.60 (1H, d, J=3 Hz), 7.11 (1H, d, J=9 Hz) 7.21 (2H, m), 7.94 (1H, dd, J=9 Hz, 3 Hz), 8.06 (1H, d, J=3 Hz), 8.29 (2H, m), 8.53 (1H, s), 8.69 (1H, br s).

(ii) Production of 5-(2-aminoethyl)-N-{3-chloro-4-[(5-chloropyridin-3-yl)oxy]phenyl}-5H-pyrrolo[3,2-d]pyrimidin-4-amine trihydrochloride tert-Butyl {2-[4-({3-chloro-4-[(5-chloropyridin-3-yl)oxy]phenyl}amino)-5H-pyrrolo[3,2-d]pyrimidin-5-yl]ethyl}carbamate (700 mg) was dissolved in tetrahydrofuran (19.5 mL)/2N hydrochloric acid (9.75 mL), and the mixture was stirred at 60° C. for 16 hrs. The reaction mixture was concentrated under reduced pressure, ethanol (50 mL) was added to the residue and the mixture was concentrated again under reduced pressure. Ethyl acetate was added to the residue and the solid was collected by filtration and dried under reduced pressure to give the title compound (663 mg) as a solid powder.

$^1$H-NMR (DMSO-$d_6$) δ 3.30 (2H, m), 5.09 (2H, m), 6.77 (1H, d, J=3 Hz), 7.40 (1H, d, J=9 Hz), 7.61 (1H, m), 7.69 (1H, dd, J=9 Hz, 2 Hz), 7.96 (1H, d, J=2 Hz), 8.12 (1H, d, J=3 Hz), 8.35 (1H, d, J=2 Hz), 8.40 (3H, s), 8.46 (1H, d, J=2 Hz), 8.77 (1H, s), 10.36 (1H, m).

(iii) Production of N-{2-[4-({3-chloropyridin-3-yl)oxy]phenyl}amino)-5H-pyrrolo[3,2-d]pyrimidin-5-yl]ethyl}-2-(methylsulfonyl)acetamide The title compound (255 mg) was obtained as colorless powder crystals by the reaction in the same manner as in Example 155 (iv) using 5-(2-aminoethyl)-N-{3-chloro-4-[(5-chloropyridin-3-yl)oxy]phenyl}-5H-pyrrolo[3,2-d]pyrimidin-4-amine trihydrochloride (271 mg), 2-(methylsulfonyl)acetic acid (107 mg), 1-ethyl-3-(3-dimethylaminopropyl)carbodiimide hydrochloride (149 mg), 1-hydroxybenzotriazole monohydrate (105 mg), triethylamine (0.360 mL) and N,N-dimethylformamide (10 mL).

$^1$H-NMR (DMSO-$d_6$) δ 3.09 (3H, s), 3.45 (2H, m), 4.04 (2H, s), 4.56 (2H, t, J=6 Hz), 6.50 (1H, d, J=3 Hz), 7.34 (1H, d, J=9 Hz), 7.50 (1H, m), 7.63 (1H, d, J=3 Hz), 7.76 (1H, dd, J=9 Hz, 2 Hz), 7.99 (1H, d, J=3 Hz), 8.32 (1H, d, J=2 Hz), 8.35 (1H, s), 8.40 (1H, d, J=2 Hz), 8.66 (1H, m), 8.73 (1H, br s).

Example 261

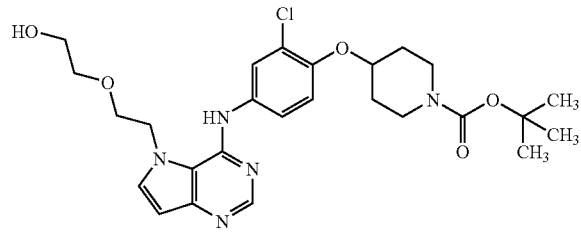

Production of tert-butyl 4-[2-chloro-4-({5-[2-(2-hydroxyethoxy)ethyl]-5H-pyrrolo[3,2-d]pyrimidin-4-yl}amino)phenoxy]piperidine-1-carboxylate (i) Production of tert-butyl 4-{4-[(5-{2-[2-(benzoyloxy)ethoxy]ethyl}-5H-pyrrolo[3,2-d]pyrimidin-4-yl)amino]-2-chlorophenoxy}piperidine-1-carboxylate A mixture of 2-[2-(4-chloro-5H-pyrrolo[3,2-d]pyrimidin-5-yl)ethoxy]ethyl benzoate (3.46 g), tert-butyl 4-(4-amino-2- chlorophenoxy)piperidine-1-carboxylate (3.27 g) and isopropyl alcohol (50 mL) was stirred at 80° C. overnight. The reaction mixture was concentrated under reduced pressure, water and saturated aqueous sodium hydrogen carbonate solution were added, and the mixture was extracted with ethyl acetate. The ethyl acetate layer was washed with saturated brine and dried over anhydrous magnesium sulfate. The solvent was evaporated under reduced pressure and the obtained residue was subjected to silica gel column chromatography (eluent, methanol:ethyl acetate=0:100→10:90). The object fraction was concentrated under reduced pressure. The residue was crystallized from ethyl acetate-diisopropyl ether to give the title compound (4.70 g) as a white powder.

$^1$H-NMR (CDCl$_3$) δ 1.48 (9H, s), 1.71-1.92 (4H, m), 3.33-3.45 (2H, m), 3.62-3.73 (2H, m), 3.90-3.97 (2H, m), 4.05 (2H, t, J=4.4 Hz), 4.29-4.39 (1H, m), 4.46-4.52 (2H, m), 4.56 (2H, t, J=4.4 Hz), 6.61 (1H, d, J=3.3 Hz), 6.72 (1H, d, J=8.7 Hz), 7.19 (1H, d, J=3.3 Hz), 7.29 (1H, dd, J=8.7, 2.7 Hz), 7.33-7.40 (2H, m), 7.50-7.57 (1H, m), 7.69 (1H, d, J=2.7 Hz), 7.78-7.83 (2H, m), 8.47 (1H, s), 8.55 (1H, br s).

(ii) Production of tert-butyl 4-[2-chloro-4-({5-[2-(2-hydroxyethoxy)ethyl]-5H-pyrrolo[3,2-d]pyrimidin-4-yl}amino)phenoxy]piperidine-1-carboxylate tert-Butyl 4-{4-[(5-{2-[2-(benzoyloxy)ethoxy]ethyl}-5H-pyrrolo[3,2-d]pyrimidin-4-yl)amino]-2-chlorophenoxy}piperidine-1-carboxylate (636 mg) was dissolved in a mixed solvent of methanol (10 mL) and tetrahydrofuran (10 mL), 1N aqueous sodium hydroxide solution (2 mL) was added, and the mixture was stirred overnight at room temperature. Water was added to the reaction mixture and the mixture was extracted with ethyl acetate. The ethyl acetate layer was washed with saturated brine and dried over anhydrous magnesium sulfate. The solvent was evaporated under reduced pressure and the obtained residue was subjected to basic silica gel column chromatography (eluent, methanol:ethyl acetate=0:100→10:90). The object fraction was concentrated under reduced pressure. The solvent was evaporated under reduced pressure and the obtained residue was crystallized from ethyl acetate-diethyl ether to give the title compound (498 mg) as a white powder.

$^1$H-NMR (CDCl$_3$) δ 1.47 (9H, s), 1.75-1.96 (4H, m), 2.27 (1H, br s), 3.33-3.45 (2H, m), 3.63-3.82 (6H, m), 4.00 (2H, t, J=4.5 Hz), 4.39-4.47 (1H, m), 4.54 (2H, t, J=4.5 Hz), 6.58 (1H, d, J=3.3 Hz), 6.95 (1H, d, J=8.8 Hz), 7.17 (1H, d, J=3.3 Hz), 7.52 (1H, dd, J=8.8, 2.7 Hz), 7.70 (1H, d, J=2.7 Hz), 8.46 (1H, s), 8.60 (1H, br s).

Example 262

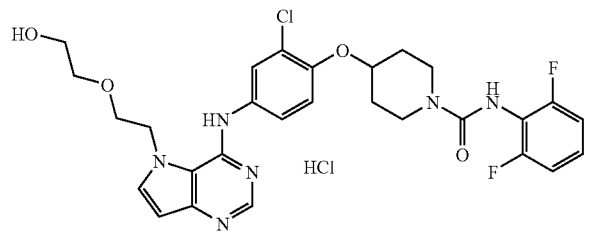

Production of 4-[2-chloro-4-({5-[2-(2-hydroxyethoxy)ethyl]-5H-pyrrolo[3,2-d]pyrimidin-4-yl}amino)phenoxy]-N-(2,6-difluorophenyl)piperidine-1-carboxamide hydrochloride (i) Production of 2-[2-(4-{[3-chloro-4-(piperidin-4-yloxy)phenyl]amino}-5H-pyrrolo[3,2-d]pyrimidin-5-yl)ethoxy]ethyl benzoate dihydrochloride 4N Hydrochloric acid/ethyl acetate solution (20 mL) and ethanol (10 mL) were added to tert-butyl 4-{4-[(5-{2-[2-(benzoyloxy)ethoxy]ethyl}-5H-pyrrolo[3,2-d]pyrimidin-4-yl)amino]-2-chlorophenoxy}piperidine-1-carboxylate (3.82 g), and the mixture was stirred at room temperature for 5 hrs. The reaction mixture was concentrated under reduced pressure, and the obtained residue was crystallized from ethanol-ethyl acetate to give the title compound (3.68 g) as a white powder.

$^1$H-NMR (DMSO-d$_6$) δ 1.85-2.00 (2H, m), 2.07-2.21 (2H, m), 3.02-3.28 (4H, m), 3.77 (2H, m), 3.88 (2H, m), 4.29 (2H, m), 4.70-4.79 (1H, m), 4.89 (2H, m), 6.60 (1H, d, J=3.0 Hz), 7.25 (1H, d, J=8.7 Hz), 7.42-7.51 (3H, m), 7.61-7.73 (4H, m), 7.98 (1H, d, J=3.0 Hz), 8.57 (1H, s), 9.20-9.50 (2H, m), 9.85 (1H, br s).

(ii) Production of 4-[2-chloro-4-({5-[2-(2-hydroxyethoxy)ethyl]-5H-pyrrolo[3,2-d]pyrimidin-4-yl}amino)phenoxy]-N-(2,6-difluorophenyl)piperidine-1-carboxamide hydrochloride To a mixture of 2-[2-(4-{[3-chloro-4-(piperidin-4-yloxy)phenyl]amino}-5H-pyrrolo[3,2-d]pyrimidin-5-yl)ethoxy]ethyl benzoate dihydrochloride (305 mg), 10% aqueous sodium carbonate solution (10 mL), ethyl acetate (15 mL) and tetrahydrofuran (5 mL) was added 2,6-difluorophenyl isocyanate (93 mg) with vigorous stirring. The mixture was stirred at room temperature for 2 hrs, water was added and the mixture was extracted with ethyl acetate. The ethyl acetate layer was washed with saturated brine and dried over anhydrous magnesium sulfate. The solvent was evaporated under reduced pressure and the obtained residue was dissolved in methanol (8 mL) and tetrahydrofuran (2 mL). 1N Aqueous sodium hydroxide solution (1 mL) was added, and the mixture was stirred at room temperature for 3 hrs. Water was added to the reaction mixture and the mixture was extracted with ethyl acetate. The ethyl acetate layer was washed with saturated brine and dried over anhydrous magnesium sulfate. The solvent was evaporated under reduced pressure and the obtained residue was subjected to basic silica gel column chromatography (eluent, methanol:ethyl acetate=0:100→15:85). The object fraction was concentrated under reduced pressure. The residue was dissolved in ethyl acetate-ethanol, and 1N hydrochloric acid/ethyl acetate solution (0.5 mL) was added. The solvent was evaporated under reduced pressure and the obtained residue was crystallized from ethanol-ethyl acetate to give the title compound (202 mg) as a white powder.

$^1$H-NMR (DMSO-d$_6$) δ 1.60-1.75 (2H, m), 1.91-2.04 (2H, m), 3.20-3.55 (6H, m), 3.68-3.81 (2H, m), 3.84 (2H, m), 4.72-4.85 (3H, m), 6.67 (1H, d, J=3.0 Hz), 7.06-7.17 (2H, m), 7.23-7.32 (1H, m), 7.35 (1H, d, J=8.9 Hz), 7.51 (1H, dd, J=8.9, 2.5 Hz), 7.77 (1H, d, J=2.5 Hz), 7.99 (1H, d, J=3.0 Hz), 8.34 (1H, s), 8.68 (1H, s), 9.79 (1H, br s).

Example 263

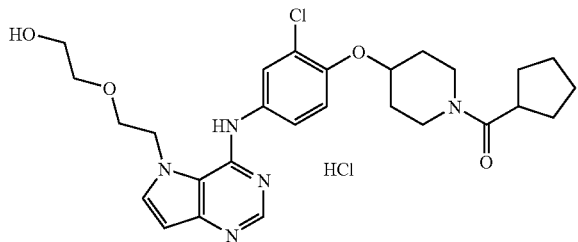

Production of 2-(2-{4-[(3-chloro-4-{[1-(cyclopentyl-carbonyl)piperidin-4-yl]oxy}phenyl)amino]-5H-pyrrolo[3,2-d]pyrimidin-5-yl}ethoxy)ethanol hydrochloride The title compound (207 mg) was obtained as a white powder by the method in the same manner as in Example 262 (ii) using 2-[2-(4-{[3-chloro-4-(piperidin-4-yloxy)phenyl]amino}-5H-pyrrolo[3,2-d]pyrimidin-5-yl)ethoxy]ethyl benzoate dihydrochloride (305 mg), 10% aqueous sodium carbonate solution (10 mL), ethyl acetate (15 mL), tetrahydrofuran (5 mL) and cyclopentanecarbonyl chloride (80 mg).

$^1$H-NMR (DMSO-$d_6$) δ 1.45-2.06 (12H, m), 2.95-3.08 (1H, m), 3.30-3.55 (6H, m), 3.69-3.80 (2H, m), 3.83 (2H, t, J=4.4 Hz), 4.70-4.85 (3H, m), 6.67 (1H, d, J=3.0 Hz), 7.34 (1H, d, J=9.0 Hz), 7.50 (1H, dd, J=9.0, 2.7 Hz), 7.76 (1H, d, J=2.7 Hz), 7.99 (1H, d, J=3.0 Hz), 8.68 (1H, s), 9.82 (1H, br s).

Example 264

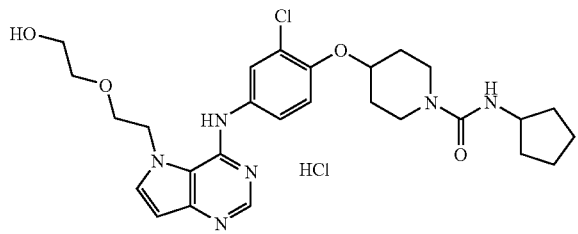

Production of 4-[2-chloro-4-({5-[2-(2-hydroxy-ethoxy)ethyl]-5H-pyrrolo[3,2-d]pyrimidin-4-yl}amino)phenoxy]-N-cyclopentylpiperidine-1-carboxamide hydrochloride To a solution of 1,1'-carbonylbis(1H-imidazole) (162 mg) in tetrahydrofuran (5 mL) was added a solution of cyclopentylamine (85 mg) in tetrahydrofuran (1 mL), and the mixture was stirred at room temperature for 1 hr. A solution of 2-[2-(4-{[3-chloro-4-(piperidin-4-yloxy)phenyl]amino}-5H-pyrrolo[3,2-d]pyrimidin-5-yl)ethoxy]ethyl benzoate dihydrochloride (305 mg) and triethylamine (0.153 mL) in tetrahydrofuran (1 mL) was added, and the mixture was stirred overnight at room temperature. Water was added to the reaction mixture and the mixture was extracted with ethyl acetate. The ethyl acetate layer was washed with saturated brine and dried over anhydrous magnesium sulfate. The solvent was evaporated under reduced pressure and the obtained residue was dissolved in methanol (8 mL) and tetrahydrofuran (2 mL). 1N Aqueous sodium hydroxide solution (1 mL) was added, and the mixture was stirred overnight at room temperature. Water was added to the reaction mixture and the mixture was extracted with ethyl acetate. The ethyl acetate layer was washed with saturated brine and dried over anhydrous magnesium sulfate. The solvent was evaporated under reduced pressure and the obtained residue was subjected to basic silica gel column chromatography (eluent, methanol:ethyl acetate=0:100→10:90). The object fraction was concentrated under reduced pressure. The residue was dissolved in ethyl acetate-ethanol, and 1N hydrochloric acid/ethyl acetate solution (0.5 mL) was added. The solvent was evaporated under reduced pressure and the obtained residue was crystallized from ethanol-ethyl acetate to give the title compound (188 mg) as a white powder.

$^1$H-NMR (DMSO-$d_6$) δ 1.30-1.95 (12H, m), 3.15-3.27 (2H, m), 3.40-3.50 (4H, m), 3.55-3.67 (2H, m), 3.83 (2H, t, J=4.6 Hz), 3.82-3.98 (1H, m), 4.62-4.72 (1H, m), 4.80 (2H, m), 6.30 (1H, d, J=6.4 Hz), 6.67 (1H, d, J=3.0 Hz), 7.32 (1H, d, J=9.0 Hz), 7.50 (1H, dd, J=9.0, 2.6 Hz), 7.75 (1H, d, J=2.6 Hz), 7.99 (1H, d, J=3.0 Hz), 8.68 (1H, s), 9.82 (1H, br s).

Example 265

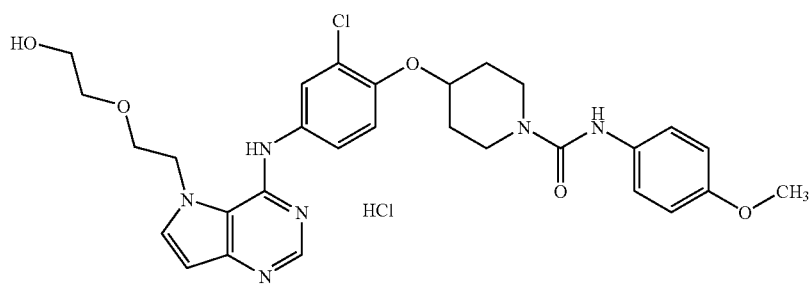

Production of 4-[2-chloro-4-({5-[2-(2-hydroxy-ethoxy)ethyl]-5H-pyrrolo[3,2-d]pyrimidin-4-yl}amino)phenoxy]-N-(4-methoxyphenyl)piperidine-1-carboxamide hydrochloride The title compound (209 mg) was obtained as a white powder by the method in the same manner as in Example 262 (ii) using 2-[2-(4-{[3-chloro-4-(piperidin-4-yloxy)phenyl]amino}-5H-pyrrolo[3,2-d]pyrimidin-5-yl)ethoxy]ethyl benzoate dihydrochloride (305 mg), 10% aqueous sodium carbonate solution (10 mL), ethyl acetate (15 mL), tetrahydrofuran (5 mL) and 4-methoxyphenyl isocyanate (75 mg).

$^1$H-NMR (DMSO-$d_6$) δ 1.60-1.75 (2H, m), 1.90-2.03 (2H, m), 3.34-3.51 (6H, m), 3.68-3.80 (2H, m), 3.70 (3H, s), 3.84 (2H, t, J=4.5 Hz), 4.70-4.85 (3H, m), 6.68 (1H, d, J=3.2 Hz), 6.82 (2H, d, J=9.1 Hz), 7.31-7.40 (3H, m), 7.51 (1H, dd, J=8.9, 2.6 Hz), 7.77 (1H, d, J=2.6 Hz), 7.99 (1H, d, J=3.2 Hz), 8.44 (1H, br s), 8.68 (1H, s), 9.81 (1H, br s).

Example 266

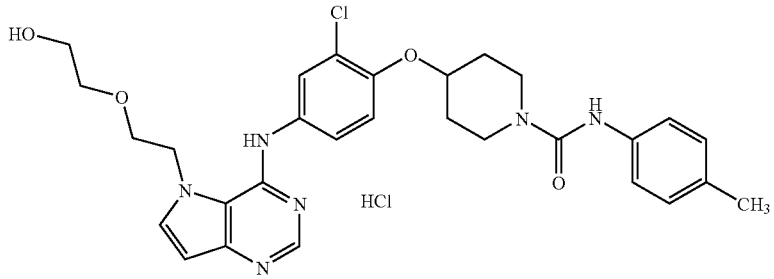

Production of 4-[2-chloro-4-({5-[2-(2-hydroxy-ethoxy)ethyl]-5H-pyrrolo[3,2-d]pyrimidin-4-yl}amino)phenoxy]-N-(4-methylphenyl)piperidine-1-carboxamide hydrochloride The title compound (190 mg) was obtained as a white powder by the method in the same manner as in Example 262 (ii) using 2-[2-(4-{[3-chloro-4-(piperidin-4-yloxy)phenyl]amino}-5H-pyrrolo[3,2-d]pyrimidin-5-yl)ethoxy]ethyl benzoate dihydrochloride (305 mg), 10% aqueous sodium carbonate solution (10 mL), ethyl acetate (15 mL), tetrahydrofuran (5 mL) and 4-methylphenyl isocyanate (67 mg).

$^1$H-NMR (DMSO-$d_6$) δ 1.60-1.75 (2H, m), 1.90-2.03 (2H, m), 2.23 (3H, s), 3.34-3.51 (6H, m), 3.69-3.80 (2H, m), 3.84 (2H, t, J=4.5 Hz), 4.69-4.84 (3H, m), 6.67 (1H, d, J=3.0 Hz), 7.03 (2H, d, J=8.5 Hz), 7.31-7.39 (3H, m), 7.51 (1H, dd, J=8.9, 2.7 Hz), 7.76 (1H, d, J=2.7 Hz), 7.99 (1H, d, J=3.0 Hz), 8.50 (1H, br s), 8.68 (1H, s), 9.82 (1H, br s).

Example 267

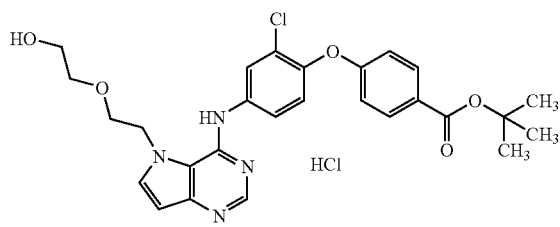

Production of tert-butyl 4-[2-chloro-4-({5-[2-(2-hydroxyethoxy)ethyl]-5H-pyrrolo[3,2-d]pyrimidin-4-yl}amino)phenoxy]benzoate hydrochloride (i) Production of tert-butyl 4-{4-[(5-{2-[2-(benzoyloxy)ethoxy]ethyl}-5H-pyrrolo[3,2-d]pyrimidin-4-yl)amino]-2-chlorophenoxy}benzoate A mixture of 2-[2-(4-chloro-5H-pyrrolo[3,2-d]pyrimidin-5-yl)ethoxy]ethyl benzoate (1.46 g), tert-butyl 4-(4-amino-2-chlorophenoxy)benzoate (1.35 g) and isopropyl alcohol (30 mL) was stirred at 80° C. overnight. The reaction mixture was concentrated under reduced pressure, water and saturated aqueous sodium hydrogen carbonate solution were added, and the mixture was extracted with ethyl acetate. The ethyl acetate layer was washed with saturated brine and dried over anhydrous magnesium sulfate. The solvent was evaporated under reduced pressure and the obtained residue was subjected to silica gel column chromatography (eluent, ethyl acetate). The object fraction was concentrated under reduced pressure and the residue was crystallized from ethyl acetate-diethyl ether to give the title compound (1.54 g) as a white powder.

$^1$H-NMR (CDCl$_3$) δ 1.59 (9H, s), 3.93-3.99 (2H, m), 4.05-4.11 (2H, m), 4.46-4.52 (2H, m), 4.55-4.61 (2H, m), 6.64 (1H, d, J=3.2 Hz), 6.82-6.90 (3H, m), 7.22 (1H, d, J=3.2 Hz), 7.30-7.40 (3H, m), 7.47-7.54 (1H, m), 7.76-7.81 (2H, m), 7.90 (1H, d, J=2.6 Hz), 7.94 (2H, d, J=9.1 Hz), 8.51 (1H, s), 8.78 (1H, br s).

(ii) Production of tert-butyl 4-[2-chloro-4-({5-[2-(2-hydroxyethoxy)ethyl]-5H-pyrrolo[3,2-d]pyrimidin-4-yl}amino)phenoxy]benzoate hydrochloride tert-Butyl 4-{4-[(5-{2-[2-(benzoyloxy)ethoxy]ethyl}-5H-pyrrolo[3,2-d]pyrimidin-4-yl)amino]-2-chlorophenoxy}benzoate (189 mg) was dissolved in a mixed solvent of methanol (5 mL) and tetrahydrofuran (1 mL), 1N aqueous sodium hydroxide solution (0.6 mL) was added, and the mixture was stirred overnight at room temperature. Water was added to the reaction mixture and the mixture was extracted with ethyl acetate. The ethyl acetate layer was washed with saturated brine and dried over anhydrous magnesium sulfate. The solvent was evaporated under reduced pressure and the obtained residue was subjected to basic silica gel column chromatography (eluent, methanol:ethyl acetate=0:100→10:90). The object fraction was concentrated under reduced pressure. The residue was dissolved in ethyl acetate-ethanol, and 1N hydrochloric acid/ethyl acetate solution (0.3 mL) was added. The solvent was evaporated under reduced pressure and the obtained residue was crystallized from ethanol-ethyl acetate to give the title compound (163 mg) as a white powder.

$^1$H-NMR (DMSO-$d_6$) δ 1.54 (9H, s), 3.41-3.52 (4H, m), 3.85 (2H, m), 4.84 (2H, m), 6.71 (1H, d, J=3.2 Hz), 7.02 (2H, d, J=8.9 Hz), 7.36 (1H, d, J=8.9 Hz), 7.69 (1H, dd, J=8.9, 2.4

Hz), 7.93 (2H, d, J=8.9 Hz), 8.00 (1H, d, J=2.4 Hz), 8.04 (1H, d, J=3.2 Hz), 8.75 (1H, s), 10.00 (1H, br s).

Example 268

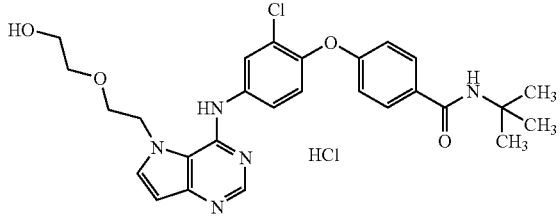

Production of N-(tert-butyl)-4-[2-chloro-4-({5-[2-(2-hydroxyethoxy)ethyl]-5H-pyrrolo[3,2-d]pyrimidin-4-yl}amino)phenoxy]benzamide hydrochloride (i) Production of 4-{4-[(5-{2-[2-(benzoyloxy)ethoxy]ethyl}-5H-pyrrolo[3,2-d]pyrimidin-4-yl)amino]-2-chlorophenoxy}benzoic acid hydrochloride Trifluoroacetic acid (10 mL) was added to tert-butyl 4-{4-[(5-{2-[2-(benzoyloxy)ethoxy]ethyl}-5H-pyrrolo[3,2-d]pyrimidin-4-yl)amino]-2-chlorophenoxy}benzoate (1.26 g), and the mixture was stirred at room temperature for 3 hrs. The reaction mixture was concentrated under reduced pressure, 4N hydrochloric acid/ethyl acetate solution was added, and the mixture was concentrated again under reduced pressure. The obtained residue was crystallized from ethyl acetate to give the title compound (1.16 g) as a white powder.
$^1$H-NMR (DMSO-$d_6$) δ 3.76-3.83 (2H, m), 3.92 (2H, t, J=4.4 Hz), 4.26-4.34 (2H, m), 4.89 (2H, m), 6.63 (1H, d, J=3.4 Hz), 6.98 (2H, d, J=8.8 Hz), 7.27 (1H, d, J=8.8 Hz), 7.41-7.50 (2H, m), 7.55-7.73 (4H, m), 7.92-8.03 (4H, m), 8.66 (1H, s), 9.91 (1H, br).

(ii) Production of N-(tert-butyl)-4-[2-chloro-4-({5-[2-(2-hydroxyethoxy)ethyl]-5H-pyrrolo[3,2-d]pyrimidin-4-yl}amino)phenoxy]benzamide hydrochloride A mixture of 4-{4-[(5-{2-[2-(benzoyloxy)ethoxy]ethyl}-5H-pyrrolo[3,2-d]pyrimidin-4-yl)amino]-2-chlorophenoxy}benzoic acid hydrochloride (183 mg), 2-methylpropan-2-amine (0.038 mL), 1-ethyl-3-(3-dimethylaminopropyl)carbodiimide hydrochloride (69 mg), 1-hydroxybenzotriazole monohydrate (55 mg), triethylamine (0.050 mL) and N,N-dimethylformamide (3 mL) was stirred overnight at room temperature. Water was added to the reaction mixture and the mixture was extracted with ethyl acetate. The ethyl acetate layer was washed with saturated brine and dried over anhydrous magnesium sulfate. The solvent was evaporated under reduced pressure and the obtained residue was subjected to silica gel column chromatography (eluent, methanol:ethyl acetate=0:100→10:90). The object fraction was concentrated under reduced pressure. The residue was dissolved in a mixed solvent of methanol (5 mL) and tetrahydrofuran (1 mL), 1N aqueous sodium hydroxide solution (0.6 mL) was added and the mixture was stirred at room temperature for 3 days. Water was added to the reaction mixture and the mixture was extracted with ethyl acetate. The ethyl acetate layer was washed with saturated brine and dried over anhydrous magnesium sulfate. The solvent was evaporated under reduced pressure and the obtained residue was subjected to basic silica gel column chromatography (eluent, methanol:ethyl acetate=0:100→10:90). The object fraction was concentrated under reduced pressure. The residue was dissolved in ethyl acetate-ethanol, and 1N hydrochloric acid/ethyl acetate solution (0.3 mL) was added. The solvent was evaporated under reduced pressure and the obtained residue was crystallized from ethanol-ethyl acetate to give the title compound (118 mg) as a white powder.
$^1$H-NMR (DMSO-$d_6$) δ 1.37 (9H, s), 3.41-3.52 (4H, m), 3.85 (2H, m), 4.84 (2H, m), 6.71 (1H, d, J=3.2 Hz), 6.97 (2H, d, J=8.8 Hz), 7.29 (1H, d, J=8.8 Hz), 7.67 (1H, dd, J=8.8, 2.5 Hz), 7.72 (1H, s), 7.85 (2H, d, J=8.8 Hz), 7.99 (1H, d, J=2.5 Hz), 8.04 (1H, d, J=3.2 Hz), 8.75 (1H, s), 10.00 (1H, br s).

Example 269

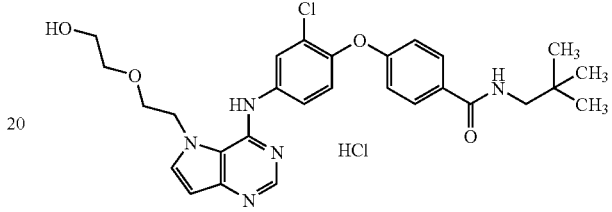

Production of 4-[2-chloro-4-({5-[2-(2-hydroxyethoxy)ethyl]-5H-pyrrolo[3,2-d]pyrimidin-4-yl}amino)phenoxy]-N-(2,2-dimethylpropyl)benzamide The title compound (140 mg) was obtained as a white powder by the method in the same manner as in Example 268 (ii) using 4-{4-[(5-{2-[2-(benzoyloxy)ethoxy]ethyl}-5H-pyrrolo[3,2-d]pyrimidin-4-yl)amino]-2-chlorophenoxy}benzoic acid hydrochloride (183 mg), neopentylamine (0.042 mL), 1-ethyl-3-(3-dimethylaminopropyl)carbodiimide hydrochloride (69 mg), 1-hydroxybenzotriazole monohydrate (55 mg), triethylamine (0.050 mL), N,N-dimethylformamide (3 mL), methanol (5 mL), tetrahydrofuran (1 mL) and 1N aqueous sodium hydroxide solution (0.6 mL).
$^1$H-NMR (DMSO-$d_6$) δ 0.90 (9H, s), 3.10 (2H, d, J=6.4 Hz), 3.42-3.52 (4H, m), 3.86 (2H, t, J=4.6 Hz), 4.83 (2H, t, J=4.6 Hz), 6.71 (1H, d, J=2.9 Hz), 7.01 (2H, d, J=8.5 Hz), 7.32 (1H, d, J=8.8 Hz), 7.66 (1H, dd, J=8.8, 2.2 Hz), 7.91 (2H, d, J=8.5 Hz), 7.99 (1H, d, J=2.2 Hz), 8.03 (1H, d, J=2.9 Hz), 8.32 (1H, t, J=6.4 Hz), 8.75 (1H, s), 9.95 (1H, br s).

Example 270

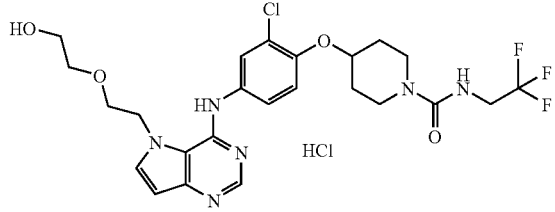

Production of 4-[2-chloro-4-({5-[2-(2-hydroxyethoxy)ethyl]-5H-pyrrolo[3,2-d]pyrimidin-4-yl}amino)phenoxy]-N-(2,2,2-trifluoroethyl)piperidine-1-carboxamide hydrochloride The title compound (101 mg) was obtained as a white powder by the method in the same manner as in Example 264 using 1,1'-carbonylbis(1H-imidazole) (97 mg), 2,2,2-trifluoroethylamine (0.048 mL), 2-[2-(4-{[3-chloro-4-(piperidin-4-yloxy)phenyl]amino}-5H-pyrrolo[3,2-d]pyrimidin-5-yl)ethoxy]ethyl benzoate dihydrochloride (244 mg), triethylamine (0.123 mL) and 1N aqueous sodium hydroxide solution (0.6 mL).

¹H-NMR (DMSO-d₆) δ 1.53-1.68 (2H, m), 1.84-1.98 (2H, m), 3.25-3.70 (8H, m), 3.77-3.92 (4H, m), 4.66-4.77 (1H, m), 4.79 (2H, t, J=4.8 Hz), 6.67 (1H, d, J=3.1 Hz), 7.23 (1H, t, J=6.2 Hz), 7.33 (1H, d, J=9.0 Hz), 7.50 (1H, dd, J=9.0, 2.6 Hz), 7.76 (1H, d, J=2.6 Hz), 7.99 (1H, d, J=3.1 Hz), 8.68 (1H, s), 9.78 (1H, br s).

Example 271

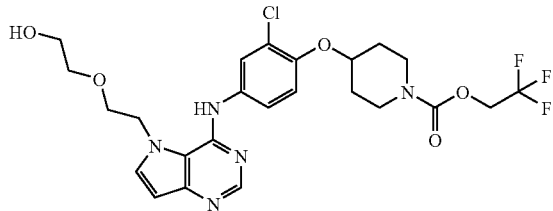

Production of 2,2,2-trifluoroethyl 4-[2-chloro-4-({5-[2-(2-hydroxyethoxy)ethyl]-5H-pyrrolo[3,2-d]pyrimidin-4-yl}amino)phenoxy]piperidine-1-carboxylate hydrochloride The title compound (135 mg) was obtained as a white powder by the method in the same manner as in Example 264 using 1,1'-carbonylbis(1H-imidazole) (97 mg), 2,2,2-trifluoroethanol (0.044 mL), 2-[2-(4-{[3-chloro-4-(piperidin-4-yloxy)phenyl]amino}-5H-pyrrolo[3,2-d]pyrimidin-5-yl)ethoxy]ethyl benzoate dihydrochloride (244 mg), triethylamine (0.123 mL) and 1N aqueous sodium hydroxide solution (0.6 mL).

¹H-NMR (DMSO-d₆) δ 1.62-1.77 (2H, m), 1.89-2.02 (2H, m), 3.38-3.52 (6H, m), 3.58-3.73 (2H, m), 3.83 (2H, t, J=4.7 Hz), 4.67-4.85 (5H, m), 6.68 (1H, d, J=2.9 Hz), 7.34 (1H, d, J=9.0 Hz), 7.51 (1H, dd, J=9.0, 2.5 Hz), 7.76 (1H, d, J=2.5 Hz), 7.99 (1H, d, J=2.9 Hz), 8.68 (1H, s), 9.82 (1H, br s).

Example 272

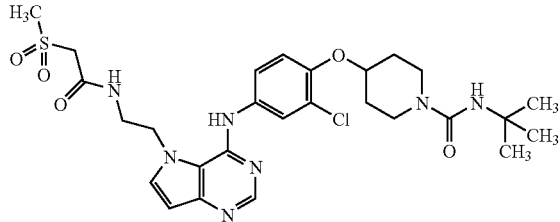

Production of N-(tert-butyl)-4-(2-chloro-4-{[5-(2-{[(methylsulfonyl)acetyl]amino}ethyl)-5H-pyrrolo[3,2-d]pyrimidin-4-yl]amino}phenoxy)piperidine-1-carboxamide tert-Butyl 4-(2-chloro-4-{[5-(2-{[(methylsulfonyl)acetyl]amino}ethyl)-5H-pyrrolo[3,2-d]pyrimidin-4-yl]amino}phenoxy)piperidine-1-carboxylate (120.0 mg) was dissolved in methanol (4.0 mL), 4N hydrochloric acid/ethyl acetate (5 mL) was added, and the mixture was stirred for 5 hrs. 8N Aqueous sodium hydroxide solution (5 mL) and water (10 mL) were added, and the mixture was extracted with dichloromethane. The extract was dried over magnesium sulfate and concentrated. The residue was added to the reaction system, wherein 1,1'-carbonylbis(1H-imidazole) (48.5 mg) and 2-methylpropan-2-amine (22.0 mg) were dissolved in tetrahydrofuran (5.0 mL), and the mixture was stirred for 1 hr. Triethylamine (1.0 mL) was further added dropwise and the mixture was stirred for 1 hr. Under ice-cooling, saturated aqueous sodium hydrogen carbonate was added, and the mixture was extracted with dichloromethane. The extract was dried over magnesium sulfate and concentrated, and the residue was separated and purified by silica gel column chromatography (eluent, ethyl acetate:methanol=100:0→ethyl acetate:methanol=80:20). Crystallization from diethyl ether/ethyl acetate gave the title compound (17.9 mg) as crystals.

¹H-NMR (DMSO-d₆) δ 1.26 (9H, s), 1.50-1.70 (2H, m), 1.81-1.95 (2H, m), 3.10 (3H, s), 3.11-3.65 (6H, m), 4.05 (2H, s), 4.45-4.65 (3H, m), 5.82 (1H, s), 6.47 (1H, d, J=3 Hz), 7.22 (1H, d, J=9 Hz), 7.55-7.58 (2H, m), 7.75 (1H, d, J=3 Hz), 8.27 (1H, s), 8.48 (1H, s), 8.66 (1H, m).

Example 273

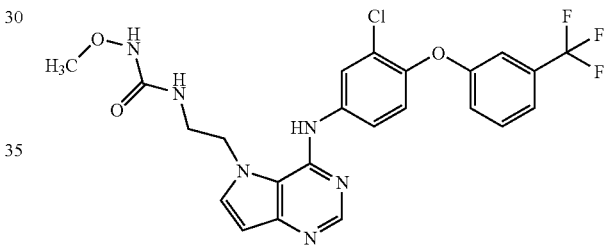

Production of N-{2-[4-({3-chloro-4-[3-(trifluoromethyl)phenoxy]phenyl}amino)-5H-pyrrolo[3,2-d]pyrimidin-5-yl]ethyl}-N'-methoxyurea To a solution of N,N'-carbonyldiimidazole (187 mg) in N,N-dimethylformamide (2 mL) were added O-methylhydroxylamine hydrochloride (96 mg) and triethylamine (0.27 mL) under ice-cooling, and the mixture was stirred at room temperature for 30 min. A solution of 5-(2-aminoethyl)-N-{3-chloro-4-[3-(trifluoromethyl)phenoxy]phenyl}-5H-pyrrolo[3,2-d]pyrimidin-4-amine dihydrochloride (200 mg) in N,N-dimethylformamide (5 mL) was added. The reaction mixture was stirred at room temperature for 22 hrs, aqueous sodium hydrogen carbonate and brine were added under ice-cooling, and the mixture was extracted twice with ethyl acetate. The organic layers were collected, dried over anhydrous magnesium sulfate and concentrated. The residue was purified by silica gel column chromatography (eluent, ethyl acetate:methanol=100:0→80:20) and further recrystallized from ethyl acetate/diisopropyl ether to give the title compound (116 mg) as crystals.

¹H-NMR (CDCl₃) δ: 3.6-3.7 (2H, m), 3.70 (3H, s), 4.5-4.6 (2H, m), 6.14 (1H, br s), 6.63 (1H, d, J=3.0 Hz), 7.05 (1H, d, J=9.0 Hz), 7.1-7.5 (5H, m), 7.65-7.75 (1H, m), 8.02 (1H, d, J=2.7 Hz), 8.46 (1H, s), 8.52 (1H, s).

Example 274

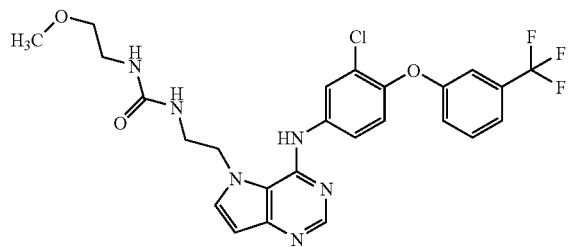

Production of N-{2-[4-({3-chloro-4-[3-(trifluoromethyl)phenoxy]phenyl}amino)-5H-pyrrolo[3,2-d]pyrimidin-5-yl]ethyl}-N'-(2-methoxyethyl)urea The title compound (147 mg) was obtained as a powder by the reaction in the same manner as in Example 273 using 5-(2-aminoethyl)-N-{3-chloro-4-[3-(trifluoromethyl)phenoxy]phenyl}-5H-pyrrolo[3,2-d]pyrimidin-4-amine dihydrochloride (200 mg), 2-methoxyethylamine (87 mg) and N,N-dimethylformamide (3 mL).

$^1$H-NMR (DMSO-$d_6$) δ: 3.05-3.15 (2H, m), 3.12 (3H, s), 3.2-3.5 (4H, m), 4.55-4.65 (2H, m), 6.42 (1H, br s), 6.56 (1H, br s), 6.68 (1H, d, J=1.8 Hz), 7.25-7.35 (2H, m), 7.36 (1H, d, J=8.7 Hz), 7.52 (1H, d, J=8.1 Hz), 7.64 (1H, d, J=9.0 Hz), 7.76 (1H, d, J=9.0 Hz), 7.95-8.05 (2H, m), 8.75 (1H, s), 9.12 (1H, s).

Example 275

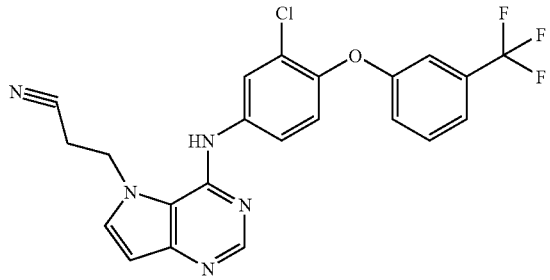

Production of 3-[4-({3-chloro-4-[3-(trifluoromethyl)phenoxy]phenyl}amino)-5H-pyrrolo[3,2-d]pyrimidin-5-yl]propanenitrile The title compound (2.02 g) was obtained as a powder by the reaction in the same manner as in Example 171 using 4-chloro-5H-pyrrolo[3,2-d]pyrimidine (3.07 g), N,N-dimethylformamide (30 mL), potassium carbonate (4.15 g), 3-bromopropionitrile (3.48 g), 3-chloro-4-[3-(trifluoromethyl)phenoxy]aniline (2.26 g) and isopropyl alcohol (20 mL).

$^1$H-NMR (DMSO-$d_6$) δ: 3.01 (2H, t, J=6.4 Hz), 4.83 (2H, t, J=6.4 Hz), 6.58 (1H, s), 7.2-7.3 (2H, m), 7.31 (1H, d, J=8.4 Hz), 7.47 (1H, d, J=7.5 Hz), 7.55-7.7 (2H, m), 7.7-7.8 (1H, m), 7.87 (1H, s), 8.37 (1H, s), 8.76 (1H, s).

Example 276

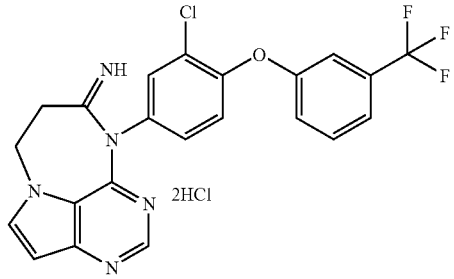

Production of 6-{3-chloro-4-[3-(trifluoromethyl)phenoxy]phenyl}-8,9-dihydro-3,5,6,9a-tetraazabenzo[cd]azulen-7(6H)-imine dihydrochloride 12N Hydrogen chloride/ethanol (3 mL) was added to 3-[4-({3-chloro-4-[3-(trifluoromethyl)phenoxy]phenyl}amino)-5H-pyrrolo[3,2-d]pyrimidin-5-yl]propanenitrile (200 mg) under ice-cooling, and the mixture was stirred at 0° C. for 2 hrs. The reaction mixture was concentrated and the residue was washed with ethyl acetate and diisopropyl ether to give the title compound (161 mg) as a powder.

$^1$H-NMR (DMSO-$d_6$) δ: 3.55-3.65 (2H, m), 4.7-4.8 (2H, m), 6.75-6.8 (1H, m), 7.4-7.5 (2H, m), 7.5-7.6 (2H, m), 7.65-7.75 (1H, m), 7.94 (1H, s), 8.05-8.1 (1H, m), 8.59 (1H, s), 9.37 (1H, s), 11.29 (1H, s).

Example 277

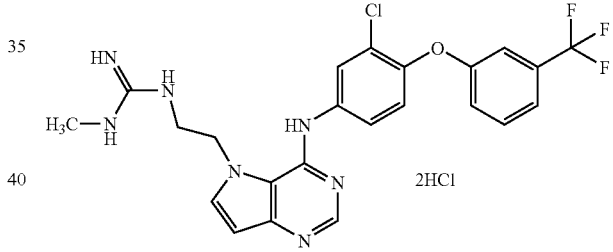

Production of N-{2-[4-({3-chloro-4-[3-(trifluoromethyl)phenoxy]phenyl}amino)-5H-pyrrolo[3,2-d]pyrimidin-5-yl]ethyl}-N'-methylguanidine dihydrochloride To a solution of N-methyl-N,N'-bis(tert-butoxy carbonyl)-1H-pyrazole-1-carboxamidine (138 mg) and ethyldiisopropylamine (0.16 mL) in acetonitrile (4 mL) was added 5-(2-aminoethyl)-N-{3-chloro-4-[3-(trifluoromethyl)phenoxy]phenyl}-5H-pyrrolo[3,2-d]pyrimidin-4-amine dihydrochloride (200 mg), and the mixture was stirred at room temperature for 4 days. Under ice-cooling, water was added, and the mixture was extracted with ethyl acetate. The extract was washed with brine, dried over anhydrous magnesium sulfate and concentrated. The residue was purified by silica gel column chromatography (eluent, ethyl acetate:hexane=80:20→100:0). The obtained product was dissolved in ethyl acetate, 4N hydrochloric acid/ethyl acetate was added, and the mixture was stirred at room temperature for 22 hrs. The precipitate was collected by filtration, and washed with ethyl acetate and diisopropyl ether to give the title compound (98 mg) as a powder.

¹H-NMR (DMSO-d₆) δ: 2.57 (3H, d, J=3.3 Hz), 3.5-3.7 (2H, m), 4.8-4.9 (2H, m), 6.72 (1H, s), 7.25-7.3 (2H, m), 7.38 (1H, d, J=9.0 Hz), 7.4-7.6 (3H, m), 7.6-7.75 (3H, m), 8.01 (2H, d, J=8.1 Hz), 8.75 (1H, s), 10.15 (1H, s).

Example 278

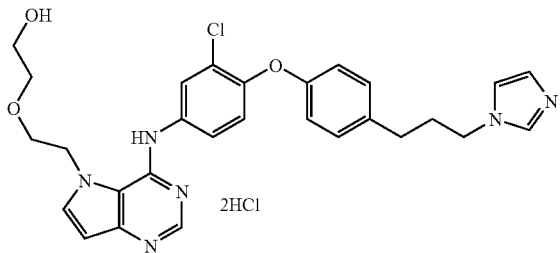

Production of 2-(2-{4-[(3-chloro-4-{4-[3-(1H-imidazol-1-yl)propyl]phenoxy}phenyl)amino]-5H-pyrrolo[3,2-d]pyrimidin-5-yl}ethoxy)ethanol dihydrochloride (i) Production of 3-chloro-4-{4-[3-(1H-imidazol-1-yl)propyl]phenoxy}nitrobenzene To a solution of 4-[3-(1H-imidazol-1-yl)propyl]phenol (405 mg) and 3-chloro-4-fluoronitrobenzene (370 mg) in N,N-dimethylformamide (4 mL) was added potassium carbonate (415 mg), and the mixture was stirred at room temperature for 16 hrs. Under ice-cooling, water was added and the mixture was extracted with ethyl acetate. The extract was washed with brine, dried over anhydrous magnesium sulfate and concentrated. The residue was purified by basic silica gel column chromatography (eluent, ethyl acetate:hexane=80:20→100:0) to give the title compound (669 mg) as an oil.

¹H-NMR (CDCl₃) δ: 2.1-2.25 (2H, m), 2.65 (2H, t, J=7.6 Hz), 3.98 (2H, t, J=6.9 Hz), 6.86 (1H, d, J=9.0 Hz), 6.93 (1H, s), 7.02 (1H, d, J=8.6 Hz), 7.09 (1H, s), 7.21 (1H, d, J=8.6 Hz), 7.47 (1H, s), 8.04 (1H, dd, J=9.0, 2.7 Hz), 8.38 (1H, d, J=2.7 Hz).

(ii) Production of 3-chloro-4-{4-[3-(1H-imidazol-1-yl)propyl]phenoxy}aniline

To a solution of 3-chloro-4-{4-[3-(1H-imidazol-1-yl)propyl]phenoxy}nitrobenzene (669 mg) in methanol (7 mL) was added 5% Pt/C (140 mg), and the mixture was stirred under hydrogen atmosphere at room temperature for 16 hrs. 5% Pt/C was filtered off and the filtrate was concentrated. The residue was purified by basic silica gel column chromatography (eluent, ethyl acetate:hexane=80:20→100:0) and further washed with diethyl ether and hexane to give the title compound (277 mg) as a powder.

¹H-NMR (CDCl₃) δ: 2.09 (2H, quintet, J=7.2 Hz), 2.56 (2H, t, J=7.2 Hz), 3.67 (2H, br s), 3.93 (2H, t, J=7.2 Hz), 6.56 (1H, dd, J=8.4, 2.7 Hz), 6.75-6.95 (5H, m), 7.0-7.1 (3H, m), 7.45 (1H, s).

(iii) Production of 2-(2-{4-[(3-chloro-4-{4-[3-(1H-imidazol-1-yl)propyl]phenoxy}phenyl)amino]-5H-pyrrolo[3,2-d]pyrimidin-5-yl}ethoxy)ethanol dihydrochloride The title compound (99 mg) was obtained as a powder by the reaction in the same manner as in Example 138 (ii) and (iii) using 2-[2-(4-chloro-5H-pyrrolo[3,2-d]pyrimidin-5-yl)ethoxy]ethyl benzoate (207 mg), 3-chloro-4-{4-[3-(1H-imidazol-1-yl)propyl]phenoxy}aniline (197 mg) and tetrahydrofuran (4 mL).

¹H-NMR (DMSO-d₆) δ: 2.1-2.3 (2H, m), 2.5-2.7 (2H, m), 3.4-3.6 (2H, m), 3.8-3.9 (2H, m), 4.23 (2H, t, J=6.8 Hz), 4.87 (2H, s), 6.71 (1H, d, J=2.4 Hz), 6.92 (2H, d, J=8.1 Hz), 7.14 (1H, d, J=8.1 Hz), 7.25 (2H, d, J=8.4 Hz), 7.6-7.7 (1H, m), 7.70 (1H, s), 7.83 (1H, s), 7.94 (1H, s), 8.04 (1H, d, J=3.0 Hz), 8.73 (1H, s), 9.22 (1H, s).

Example 279

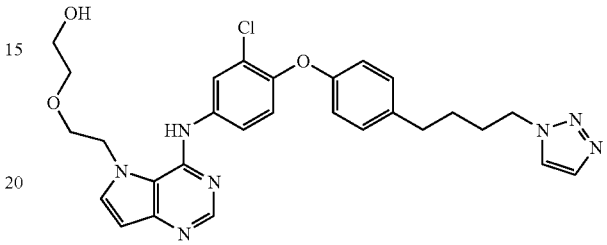

Production of 2-(2-{4-[(3-chloro-4-{4-[4-(1H-1,2,3-triazol-1-yl)butyl]phenoxy}phenyl)amino]-5H-pyrrolo[3,2-d]pyrimidin-5-yl}ethoxy)ethanol (i) Production of 3-chloro-4-{4-[4-(1H-1,2,3-triazol-1-yl)butyl]phenoxy}nitrobenzene The title compound (721 mg) was obtained as an oil by the reaction in the same manner as in Example 278 (i) using 4-[4-(1H-1,2,3-triazol-1-yl)butyl]phenol (435 mg), 3-chloro-4-fluoronitrobenzene (370 mg) and N,N-dimethylformamide (4 mL).

¹H-NMR (CDCl₃) δ: 1.6-1.75 (2H, m), 1.9-2.05 (2H, m), 2.68 (2H, t, J=7.4 Hz), 4.43 (2H, t, J=7.2 Hz), 6.85 (1H, d, J=9.2 Hz), 7.00 (2H, d, J=8.8 Hz), 7.21 (2H, d, J=8.8 Hz), 7.53 (1H, s), 7.72 (1H, s), 8.04 (1H, dd, J=2.6, 9.2 Hz), 8.37 (1H, d, J=2.6 Hz).

(ii) Production of 3-chloro-4-{4-[4-(1H-1,2,3-triazol-1-yl)butyl]phenoxy}aniline The title compound (626 mg) was obtained as an oil by the reaction in the same manner as in Example 278 (ii) using 3-chloro-4-{4-[4-(1H-1,2,3-triazol-1-yl)butyl]phenoxy}nitrobenzene (711 mg) and ethyl acetate (10 mL).

¹H-NMR (CDCl₃) δ: 1.55-1.7 (2H, m), 1.8-2.0 (2H, m), 2.60 (2H, t, J=7.5 Hz), 3.65 (2H, br s), 4.39 (2H, t, J=7.2 Hz), 6.55 (1H, dd, J=8.7, 2.7 Hz), 6.75-6.85 (3H, m), 6.87 (1H, d, J=8.4 Hz), 7.04 (2H, d, J=8.4 Hz), 7.49 (1H, d, J=1.0 Hz), 7.69 (1H, d, J=1.0 Hz).

(iii) Production of 2-(2-{4-[(3-chloro-4-{4-[4-(1H-1,2,3-triazol-1-yl)butyl]phenoxy}phenyl)amino]-5H-pyrrolo[3,2-d]pyrimidin-5-yl}ethoxy)ethanol The title compound (293 mg) was obtained as a powder by the reaction in the same manner as in Example 139 (ii) and (iii) using 2-[2-(4-chloro-5H-pyrrolo[3,2-d]pyrimidin-5-yl)ethoxy]ethyl benzoate (346 mg), 3-chloro-4-{4-[4-(1H-1,2,3-triazol-1-yl)butyl]phenoxy}aniline (405 mg) and isopropyl alcohol (5 mL).

¹H-NMR (DMSO-d₆) δ: 1.55-1.7 (2H, m), 1.85-2.0 (2H, m), 2.62 (2H, t, J=7.2 Hz), 3.7-3.75 (2H, m), 3.75-3.8 (2H, m), 4.02 (2H, t, J=4.2 Hz), 4.39 (2H, t, J=6.9 Hz), 4.56 (2H, t, J=4.2 Hz), 6.63 (1H, d, J=3.0 Hz), 6.88 (2H, d, J=8.7 Hz), 6.98 (1H, d, J=8.4 Hz), 7.08 (2H, d, J=8.7 Hz), 7.21 (1H, d, J=3.3 Hz), 7.50 (1H, s), 7.54 (1H, dd, J=8.7, 2.7 Hz), 7.87 (1H, d, J=2.7 Hz), 7.69 (1H, s), 8.51 (1H, s), 8.73 (1H, s).

Example 280

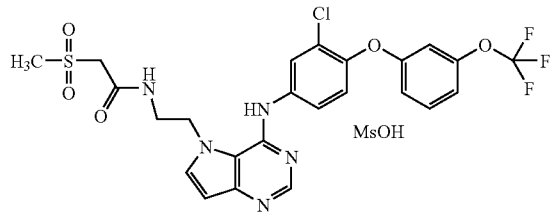

Production of 2-(methylsulfonyl)-N-{2-[4-({3-methyl-4-[3-(trifluoromethoxy)phenoxy]phenyl}amino)-5H-pyrrolo[3,2-d]pyrimidin-5-yl]ethyl}acetamide methanesulfonate The title compound (1.0 g) was obtained as colorless crystals by the reaction in the same manner as in Example 256 using 2-(methylsulfonyl)-N-{2-[4-({3-methyl-4-[3-(trifluoromethoxy)phenoxy]phenyl}amino)-5H-pyrrolo[3,2-d]pyrimidin-5-yl]ethyl}acetamide (900 mg), ethyl acetate (4.5 mL) and methanesulfonic acid (0.114 mL).

$^1$H-NMR (DMSO-$d_6$) δ 2.19 (3H, s), 2.32 (3H, s), 3.05 (3H, s), 3.55 (2H, q, J=6 Hz), 4.06 (2H, s), 4.68 (2H, t, J=6 Hz), 6.65 (1H, d, J=3 Hz), 6.93 (2H, m), 7.12 (2H, m), 7.4-7.6 (3H, m), 7.92 (1H, d, J=3 Hz), 8.70 (2H, m), 9.84 (1H, br s).

Formulation Example 1

Amount Per Tablet

| | | |
|---|---|---|
| (1) Compound obtained in Example 39 | 10.0 mg |
| (2) Lactose | 60.0 mg |
| (3) Corn starch | 35.0 mg |
| (4) Gelatin | 3.0 mg |
| (5) Magnesium stearate | 2.0 mg |

A mixture of 10.0 mg of the compound obtained in Example 39, 60.0 mg of lactose and 35.0 mg of corn starch is granulated through a 1 mm-mesh sieve using 0.03 ml of a 10% by weight aqueous solution of gelatin (3.0 mg of gelatin), after which the granules are dried at 40° C. and filtered again. The granules obtained are mixed with 2.0 mg of magnesium stearate and compressed. The core tablets obtained are coated with a sugar coat comprising a suspension of sucrose, titanium dioxide, talc and gum arabic and polished with beeswax to yield sugar-coated tablets.

Formulation Example 2

Dose Per Tablet

| | | |
|---|---|---|
| (1) Compound obtained in Example 39 | 10.0 mg |
| (2) Lactose | 70.0 mg |
| (3) Corn starch | 50.0 mg |
| (4) Soluble starch | 7.0 mg |
| (5) Magnesium stearate | 3.0 mg |

10.0 mg of the compound obtained in Example 39 and 3.0 mg of magnesium stearate are granulated using 0.07 ml of an aqueous solution of soluble starch (7.0 mg of soluble starch), after which these granules are dried and mixed with 70.0 mg of lactose and 50.0 mg of corn starch. This mixture is compressed to yield tablets.

Experimental Example 1A

Cloning of Human HER2 Gene and Preparation of Recombinant Baculovirus

Human HER2 gene was cloned by RT-PCR using total RNA prepared from MCF7 cells as a template. The primer used for RT-PCR was prepared from nucleotide sequence (Genbank Accession M11730) information of HER2 gene by adding a nucleotide sequence encoding flag peptide and a restriction enzyme recognition sequence to a nucleotide sequence (2176-3918 of Genbank Accession M11730) encoding the HER2 intracellular domain region, so that the protein contains an N-terminal Flag tag. The primer nucleotide sequence is shown below.

HER2-U:
(SEQ ID NO: 1)
5'-AATTAAGTCGACATGGACTACAAAGACGATGACGACAAGCGACGGCA

GCAGAAGATCCGGAAGTAC-3'
and

HER2-L:
(SEQ ID NO: 2)
5'-AATTAAGCATGCTCACACTGGCACGTCCAGACCCAGGTACTC-3'

The RT reaction was conducted using SuperScript First-Strand Synthesis System for RT-PCR (Invitrogen) and the PCR reaction was conducted using a KOD-plus kit (TOYOBO). The obtained PCR product was electrophoresed on agarose gel (1%), the DNA fragment amplified by PCR was recovered from the gel, and then digested with restriction enzymes Sal I and Sph I. The DNA treated with the restriction enzymes was electrophoresed on agarose gel (1%), and the obtained DNA fragment was recovered and ligated to plasmid pFASTBAC1 (Invitrogen) digested with restriction enzymes Sal I and Sph I to give expression plasmid pFB-HER2. The nucleotide sequence of the insertion fragment was confirmed and found to be identical with the nucleotide sequence (2176-3918 of Genbank Accession M11730) of HER2 intracellular domain. Furthermore, using BAC-TO-BAC Baculovirus Expression System (Invitrogen), recombinant baculovirus BAC-HER2 was prepared.

Experimental Example 1B

Preparation of HER2 Intracellular Domain Protein

SF-21 cells were sown at 1×10⁶ cells/mL to Sf-900II SFM medium (1 L, Invitrogen) containing 10% fetal bovine serum (trace), 50 mg/L gentamicin (Invitrogen) and 0.1% Pluronic F-68 (Invitrogen), and shaking culture was performed using a 2 L volume Erlenmeyer flask at 27° C., 100 rpm. After culturing for 24 hrs, recombinant baculovirus BAC-HER2 (13.4 mL) was added, and the mixture was further cultured for 3 days. The culture medium was centrifuged at 2,000 rpm for 5 min. to give virus-infected cells. The infected cells were washed with a phosphate buffered saline (Invitrogen), centrifuged under the same conditions, and the cells were preserved at −80° C. The cryopreserved cells were thawed in ice, suspended in buffer A (50 mM Tris buffer (30 mL, pH 7.4) containing 20% glycerol, 0.15 M NaCl) supplemented with Complete Protease Inhibitor (Boehringer), and ruptured 3 times with a Polytron homogenizer (Kinematica) at 20,000 rpm for 30 sec. The rupture medium was clarified by centrifugation at 40,000 rpm for 30 min. and filtered with a 0.45 µm filter. The filtrate was passed through a column packed with Anti-FLAG M2 Affinity Gel (4 mL, Sigma) at a flow rate of about 0.5 mL/min. The column was washed with buffer A, and eluted with buffer A containing 100 µg/mL of FLAG peptide. The eluate was concentrated with Vivaspin 20 (Vivascience) having a molecular weight cut off of 30K. The concentrate was purified by gel filtration using HiLoad Superdex 200 pg 16/60 (Amersham Bioscience) equilibrated with buffer A. The fractions containing HER2 intracellular domain were collected, glycerol was added to the final concentration of 50% and cryopreserved at −80° C.

Experimental Example 1C

Determination of HER2 Kinase Inhibitory Activity

A test compound dissolved in dimethyl sulfoxide (DMSO) was diluted with a buffer for kinase reaction (50 mM Tris-HCl (pH7.5), 5 mM MgCl$_2$, 5 mM MnCl$_2$, 2 mM dithiothreitol, 0.01% Tween-20). To this compound solution (10 µL) was added a buffer for kinase reaction (20 µL) containing 5 µg/mL of HER2 intracellular domain obtained in Experimental Example 1B and 12.5 µg/mL of polypeptide substrate poly-Glu:Tyr (4:1) (Sigma). To the obtained mixture was added 20 µL of ATP solution (1.25 µM ATP, 0.05 µCi [γ-$^{32}$P]ATP), the mixture was allowed to react at 25° C. for 10 min. and the reaction was quenched with 50 µL of 20% TCA solution. The reaction solution was allowed to stand at 4° C. for 20 min., and the acid insoluble fraction was transferred to GF/C filter (PerkinElmer) using cell harvester (PerkinElmer) and washed with 250 mM phosphoric acid solution. After washing, the plate was dried at 45° C. for 60 min., and 35 µL of MicroScinti 0 (PerkinElmer) was added. The radioactivity was measured using TopCount (PerkinElmer). HER2 kinase inhibitory rate (%) of the test compound was calculated by the following formula:

Inhibitory rate (%)=(1−(count of test compound−blank)÷(control−blank))×100

The count of the solution reacted without addition of the compound was used as a "control", and the count of the solution without the compound and HER2 intracellular domain was used as a "blank". The results of the inhibitory rate of the compounds are shown in Table 1.

From the foregoing, it was shown that the compounds of the present invention strongly inhibited the activity of HER2 kinase.

TABLE 1

| Example No. (compound No.) | Inhibitory rate (%) at 1.0 µM |
|---|---|
| 13 | 94.9 |
| 38 | 95.9 |
| 39 | 96.1 |
| 158 | 87.0 |
| 190 | 95.9 |
| 191 | 100 |

Experimental Example 2A

Cloning of Human EGF Receptor Gene and Preparation of Recombinant Baculovirus Human EGF receptor gene was cloned by RT-PCR using total RNA prepared from A431 cells as a template. The primer for RT-PCR was prepared from nucleotide sequence (Genbank Accession XM__167493) information of EGF receptor gene by adding a nucleotide sequence encoding flag peptide and a restriction enzyme recognition sequence to a nucleotide sequence (2182-3810 of Genbank Accession XM__167493) encoding EGF receptor intracellular domain region, so that the protein contains an N-terminal Flag tag. The primer nucleotide sequence is shown below.

```
EGFR-U:
                                       (SEQ ID NO: 3)
5'-AATTAAGTCGACATGGACTACAAAGACGATGACGACCGAAGGCGCCA
CATCGTTCGGAAGCGCACG-3'
and EGFR-L:
                                       (SEQ ID NO: 4)
5'-AATTAAGCATGCTCATGCTCCAATAAATTCACTGCTTTGTGG-3'
```

The RT reaction was conducted using SuperScript First-Strand Synthesis System for RT-PCR (Invitrogen) and the PCR reaction was conducted using a KOD-plus kit (TOYOBO). The obtained PCR product was electrophoresed on agarose gel (1%), the DNA fragment amplified by PCR was recovered from the gel, and then digested with restriction enzymes Sal I and Sph I. The DNA treated with the restriction enzymes was electrophoresed on agarose gel (1%), and the obtained DNA fragment was recovered and ligated to plasmid pFASTBAC1 (Invitrogen) digested with restriction enzymes Sal I and Sph I to give expression plasmid pFB-EGFR. The nucleotide sequence of insertion fragment was confirmed and found to be identical with the nucleotide sequence (2182-3810 of Genbank Accession XM__167493) of EGFR intracellular domain. Furthermore, using BAC-TO-BAC Baculovirus Expression System (Invitrogen), virus stock BAC-EGFR of recombinant baculovirus was prepared.

Experimental Example 2B

Preparation of EGF Receptor Intracellular Domain Protein

SF-21 cells were sown at 1×10⁶ cells/mL to Sf-900II SFM medium (1 L, Invitrogen) containing 10% fetal bovine serum (trace), 50 mg/L gentamicin (Invitrogen) and 0.1% Pluronic F-68 (Invitrogen), and shaking culture was performed using a 2 L volume Erlenmeyer flask at 27° C., 100 rpm. After culturing for 24 hrs, recombinant baculovirus BAC-EGFR (13.4 mL) was added, and the mixture was further cultured for 3 days. The culture medium was centrifuged at 2,000 rpm for 5 min. to give virus-infected cells. The infected cells were washed with a phosphate buffered saline (Invitrogen), centrifuged under the same conditions, and the cells were preserved at −80° C. The cryopreserved cells were thawed in ice, suspended in buffer A (50 mM Tris buffer (30 mL, pH7.4) containing 20% glycerol, 0.15 M NaCl) supplemented with Complete Protease Inhibitor (Boehringer), and ruptured 3 times with a Polytron homogenizer (Kinematica) at 20,000 rpm for 30 sec. The ruptured medium was clarified by centrifugation at 40,000 rpm for 30 min. and filtered with a 0.45 µm filter. The filtrate was passed through a column packed with Anti-FLAG M2 Affinity Gel (4 mL, Sigma) at a flow rate of about 0.5 mL/min. The column was washed with buffer A, and eluted with buffer A containing 100 µg/mL of FLAG peptide. The eluate was concentrated with Vivaspin 20 (Vivascience) having a molecular weight cut off of 30K. The buffer of this concentrate was exchanged using NAPE 25 column (Amersham Bioscience) equilibrated with buffer A. The fractions containing EGF receptor intracellular domain protein were collected, glycerol was added to the final concentration of 50% and cryopreserved at −80° C.

Experimental Example 2C

Determination of EGF Receptor Kinase Inhibitory Activity

A test compound dissolved in dimethyl sulfoxide (DMSO) was diluted with a buffer (50 mM Tris-HCl (pH 7.5), 5 mM MgCl$_2$, 5 mM MnCl$_2$, 2 mM dithiothreitol, 0.01% Tween-20). To this compound solution (5 µL) was added a buffer (10 µL) containing 250 ng/mL of EGF receptor intracellular domain protein and 250 ng/mL of biotin labeled polypeptide biotinyl-poly-Glu:Tyr (4:1) (CIS bio International). To the obtained mixture was added a buffer (10 µL) containing ATP (5 µM), the mixture was allowed to react at 25° C. for 10 min. and the reaction was quenched with 25 µL of a stop solution (100 mM EDTA disodium salt, 62.5 mM HEPES buffer (pH 7.4), 250 mM NaCl, 0.1% bovine serum albumin, 10 µg/mL AlphaScreen assay streptavidin donor beads (Streptavidin Donor beads: PerkinElmer), 10 µg/mL AlphaScreen assay anti-phosphotyrosine recognition antibody PY-100 binding acceptor beads (Anti-phosphotyrosine (P-Tyr-100) Acceptor beads: PerkinElmer)). The reaction solution was allowed to stand at 25° C. for 16 hrs, and the cells were counted using a plate reader Fusion™ (PerkinElmer). The kinase inhibitory rate (%) of the test compound was calculated by the following formula:

Inhibitory rate (%)=(1−(count of test compound− blank)÷(control−blank))×100

The count of the solution reacted without addition of the compound was used as a "control", and the count of the solution without the compound and ATP was used as a "blank". The results of the inhibitory rate of the compounds are shown in Table 2.

From the foregoing, it was shown that the compounds of the present invention strongly inhibited the activity of EGF receptor kinase.

TABLE 2

| Example No. (compound No.) | Inhibitory rate (%) at 1.0 µM |
|---|---|
| 22 | 98.5 |
| 41 | 98.9 |
| 92 | 98.0 |
| 138 | 99.0 |
| 147 | 96.0 |
| 160 | 97.0 |

Experimental Example 3

Inhibitory Action on Breast Cancer Cell BT-474 Proliferation In Vitro

A suspension of human breast cancer cell BT-474 (100 µl (6,000 cells)) were sown to a 96-well microplate and cultured in an incubator (37° C., 5% carbon dioxide). On the following day, 100 µl of a solution of each test compound, which was previously diluted 2-fold, was added, and the cells were cultured for 5 days. After the culture medium containing the test compound was removed, the cells were washed and fixed with 50% trichloroacetic acid, after which a 0.4% (w/v) SRB solution (dissolved in 1% acetic acid) was added to fix and stain the cell protein (Skehan et al., Journal of the National Cancer Institute, Vol. 82, pp. 1107-1112, 1990). After washing with a 1% acetic acid solution, 100 µl of an extract (10 mM Tris solution) was added to extract the pigment, and absorbance was measured at an absorption wavelength of 550 nm to quantify the amount of cells as protein content. Taking as 100% the protein content for the control group, which received no test compound solution, the ratio of the residual protein content for each treatment group was determined, and the compound concentration required to achieve 50% suppression of the residual cell content relative to the control (IC$_{50}$ value) was calculated. The results are shown in Table 3.

TABLE 3

| Example No. (compound No.) | IC$_{50}$ (nM) |
|---|---|
| 82 | <100 |
| 92 | <100 |
| 169 | <100 |
| 176 | <100 |

INDUSTRIAL APPLICABILITY

According to the present invention, pyrrolo[3,2-d]pyrimidine and pyrazolo[4,3-d]pyrimidine compounds, a production method thereof and use thereof are provided. These fused pyrimidine compounds have a superior tyrosine kinase inhibitory action, are low toxic, and are sufficiently satisfactory as pharmaceutical products.

This application is based on patent application Nos. 165050/2004 and 58231/2005 filed in Japan, the contents of which are hereby incorporated by reference.

The invention claimed is:
1. A compound represented by a formula:

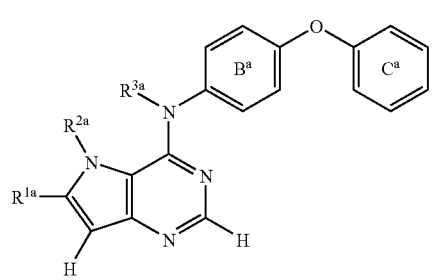

(Ia)

wherein $R^{1a}$ is a hydrogen atom,
$R^{2a}$ is a $C_{1-8}$ alkyl group, a $C_{2-8}$ alkenyl group or a $C_{2-8}$ alkynyl group, each of which is substituted by substituent(s) selected from
(a) hydroxy,
(b) optionally halogenated $C_{1-4}$ alkyloxy,
(c) —O—$(CH_2)_n$—OH,
(d) —O—$(CH_2)_n$—O—CO—$NH_2$,
(e) —O—$(CH_2)_n$—O—$C_{1-4}$ alkyl,
(f) —O—$(CH_2)_n$—$SO_2$-(optionally halogenated $C_{1-4}$ alkyl),
(g) —O—$(CH_2)_n$—$SO_2$—$C_{6-18}$ aryl,
(h) —O—$(CH_2)_n$—$SO_2$—$(CH_2)_n$—OH,
(i) —O—$(CH_2)_n$—$NR^8$—$SO_2$-(optionally halogenated $C_{1-4}$ alkyl),
(j) —CO—$NR^8$—$(CH_2)_n$—OH,
(k) —CO—$NR^8$—$(CH_2)_n$—$SO_2$-(optionally halogenated $C_{1-4}$ alkyl), (l) —NR⁶R⁷,
(m) —NR⁸—(CH$_2$)$_n$—OH,
(n) —NR⁸—(CH$_2$)$_n$—SO$_2$—C$_{1-4}$ alkyl,
(o) —NR⁸—CO—(CH$_2$)$_n$—OH,
(p) —NR⁸—CO—(CH$_2$)$_n$—O—C$_{1-4}$ alkyl,
(q) —NR⁸—CO—(CH$_2$)$_n$—SO-(optionally halogenated C$_{1-4}$ alkyl),
(r) —NR⁸—CO—(CH$_2$)$_n$—SO$_2$-(optionally halogenated C$_{1-4}$ alkyl),
(s) —NR⁸—CO—(CH$_2$)$_n$—SO$_2$—C$_{3-8}$ cycloalkyl,
(t) —NR⁸—CO$_2$—(CH$_2$)$_n$—SO$_2$—C$_{1-4}$ alkyl,
(u) —NR⁸—CO—NH—(CH$_2$)$_n$—SO$_2$—C$_{1-4}$ alkyl,
(v) —NR⁸—SO$_2$—(CH$_2$)$_n$—SO$_2$—C$_{1-4}$ alkyl,
(w) —S—(CH$_2$)$_n$—OH,
(x) —SO—(CH$_2$)$_n$—OH,
(y) —SO$_2$—(CH$_2$)$_n$—OH, and
(z) —NR⁸—CO-(optionally substituted heterocyclic group), (wherein said heterocyclic group is a 5- to 8-membered heterocyclic group having 1 to 3 hetero atoms selected from the group consisting of a nitrogen atom, an oxygen atom and an optionally oxidized sulfur atom, which is optionally substituted by substituents selected from the group consisting of hydroxy, C$_{1-4}$ alkyl, optionally oxidized C$_{1-4}$ alkylthio, —CO—C$_{1-4}$ alkyl, —CO—NH—C$_{1-4}$ alkyl, —CONH$_2$, —SO$_2$—C$_{1-4}$ alkyl, —SO$_2$—NH—C$_{1-4}$ alkyl, and —SO$_2$NH$_2$), wherein n is an integer of 1 to 4, R⁶ and R⁷ are the same or different and each is a hydrogen atom or a C$_{1-4}$ alkyl group, R⁸ is a hydrogen atom or a C$_{1-4}$ alkyl group, and (CH$_2$)$_n$ is optionally substituted by C$_{1-4}$ alkyl or hydroxy, R$^{3a}$ is a hydrogen atom or a C$_{1-6}$ alkyl group, B$^a$ is 1,4-phenylene group optionally substituted by 1 to 4 substituents selected from the group consisting of halogen and optionally halogenated C$_{1-4}$ alkyl, and C$^a$ is a phenyl group substituted by 1 to 5 substituents selected from the group consisting of (i) halogen, (ii) optionally halogenated C$_{1-4}$ alkyl, (iii) hydroxy-C$_{1-4}$ alkyl, (iv) a 5- to 8-membered heterocycle-C$_{1-4}$ alkyl, wherein said 5- to 8-membered heterocycle has 1 to 3 hetero atoms selected from the group consisting of a nitrogen atom, an oxygen atom, and an optionally oxidized sulfur atom, (v) optionally halogenated C$_{1-4}$ alkyloxy, (vi) cyano, and (vii) carbamoyl optionally substituted by C$_{1-8}$ alkyl or a salt thereof.

2. A pharmaceutical composition comprising a compound of claim 1 or a salt thereof, and a pharmaceutically acceptable carrier.

\* \* \* \* \*

UNITED STATES PATENT AND TRADEMARK OFFICE
CERTIFICATE OF CORRECTION

PATENT NO.        : 8,178,543 B2
APPLICATION NO.   : 12/172631
DATED             : May 15, 2012
INVENTOR(S)       : Ishikawa et al.

It is certified that error appears in the above-identified patent and that said Letters Patent is hereby corrected as shown below:

Column 349, line 3 from the bottom: "by substituents" should read --by one or more substituents--

Signed and Sealed this
Thirtieth Day of October, 2012

David J. Kappos
*Director of the United States Patent and Trademark Office*

SEQUENCE LISTING

<160> NUMBER OF SEQ ID NOS: 4

<210> SEQ ID NO 1
<211> LENGTH: 66
<212> TYPE: DNA
<213> ORGANISM: Artificial
<220> FEATURE:
<223> OTHER INFORMATION: primer for cloning human HER2 gene

<400> SEQUENCE: 1
aattaagtcg acatggacta caaagacgat gacgacaagc gacggcagca gaagatccgg     60
aagtac                                                               66

<210> SEQ ID NO 2
<211> LENGTH: 42
<212> TYPE: DNA
<213> ORGANISM: Artificial
<220> FEATURE:
<223> OTHER INFORMATION: primer for cloning human HER2 gene

<400> SEQUENCE: 2
aattaagcat gctcacactg gcacgtccag acccaggtac tc                       42

<210> SEQ ID NO 3
<211> LENGTH: 66
<212> TYPE: DNA
<213> ORGANISM: Artificial
<220> FEATURE:
<223> OTHER INFORMATION: primer for cloning human EGFR gene

<400> SEQUENCE: 3
aattaagtcg acatggacta caaagacgat gacgaccgaa ggcgccacat cgttcggaag     60
cgcacg                                                               66

<210> SEQ ID NO 4
<211> LENGTH: 42
<212> TYPE: DNA
<213> ORGANISM: Artificial
<220> FEATURE:
<223> OTHER INFORMATION: primer for cloning human EGFR gene

<400> SEQUENCE: 4
aattaagcat gctcatgctc aataaattc actgctttgt gg                        42